United States Patent
Sanches et al.

(10) Patent No.: US 12,286,489 B2
(45) Date of Patent: Apr. 29, 2025

(54) MODIFIED ANTIGEN BINDING POLYPEPTIDE CONSTRUCTS AND USES THEREOF

(71) Applicant: ZYMEWORKS BC INC., Vancouver (CA)

(72) Inventors: Mario Sanches, Vancouver (CA); Thomas Spreter Von Kreudenstein, Vancouver (CA); Dunja Urosev, Vancouver (CA); Stacey A. L. Tom-Yew, Vancouver (CA); Adam Louis Corper, Vancouver (CA); Igor Edmondo Paolo D'Angelo, Vancouver (CA); Yang-Chieh Chou, Vancouver (CA); Surjit Bhimarao Dixit, Vancouver (CA)

(73) Assignee: Zymeworks BC, Inc., Vancouver (CA)

( * ) Notice: Subject to any disclaimer, the term of this patent is extended or adjusted under 35 U.S.C. 154(b) by 468 days.

(21) Appl. No.: 17/652,557

(22) Filed: Feb. 25, 2022

(65) Prior Publication Data
US 2022/0251242 A1 Aug. 11, 2022

Related U.S. Application Data

(62) Division of application No. 15/314,496, filed as application No. PCT/IB2015/054107 on May 29, 2015, now Pat. No. 11,306,156.

(60) Provisional application No. 62/154,055, filed on Apr. 28, 2015, provisional application No. 62/003,663, filed on May 28, 2014.

(51) Int. Cl.
| | |
|---|---|
| *C07K 16/46* | (2006.01) |
| *C07K 16/28* | (2006.01) |
| *C07K 16/32* | (2006.01) |
| *C07K 16/36* | (2006.01) |

(52) U.S. Cl.
CPC ........ *C07K 16/468* (2013.01); *C07K 16/2863* (2013.01); *C07K 16/32* (2013.01); *C07K 16/36* (2013.01); *C07K 2317/21* (2013.01); *C07K 2317/24* (2013.01); *C07K 2317/31* (2013.01); *C07K 2317/51* (2013.01); *C07K 2317/52* (2013.01); *C07K 2317/522* (2013.01); *C07K 2317/55* (2013.01); *C07K 2317/56* (2013.01); *C07K 2317/92* (2013.01); *C07K 2317/94* (2013.01)

(58) Field of Classification Search
CPC .......................... C07K 2317/50; C07K 2317/52
USPC ..................................................... 424/136.1
See application file for complete search history.

(56) References Cited

U.S. PATENT DOCUMENTS

| | | | |
|---|---|---|---|
| 5,731,168 | A | 3/1998 | Carter et al. |
| 5,807,706 | A | 9/1998 | Carter et al. |
| 5,821,333 | A | 10/1998 | Carter et al. |
| 6,809,185 | B1 | 10/2004 | Schoonjans et al. |
| 7,183,076 | B2 | 2/2007 | Arathoon et al. |
| 7,642,228 | B2 | 1/2010 | Carter et al. |
| 7,695,936 | B2 | 4/2010 | Carter et al. |
| 7,951,917 | B1 | 5/2011 | Arathoon et al. |
| 8,501,185 | B2 | 8/2013 | Heitner Hansen et al. |
| 8,592,562 | B2 | 11/2013 | Kannan et al. |
| 9,499,634 | B2 | 11/2016 | Dixit et al. |
| 9,527,927 | B2 | 12/2016 | Chowdhury et al. |
| 9,562,109 | B2 | 2/2017 | Von Kreudenstein et al. |
| 9,574,010 | B2 | 2/2017 | Spreter Von et al. |
| 9,708,388 | B2 | 7/2017 | Dutalys |
| 9,771,573 | B2 | 9/2017 | Ohrn et al. |
| 9,914,785 | B2 | 3/2018 | Corper et al. |

(Continued)

FOREIGN PATENT DOCUMENTS

| | | |
|---|---|---|
| CN | 1176659 | 3/1998 |
| CN | 102153650 | 7/2012 |

(Continued)

OTHER PUBLICATIONS

U.S. Appl. No. 13/927,065, Final Office Action mailed on Feb. 22, 2016, 6 pages.
U.S. Appl. No. 13/927,065, Non-Final Office Action mailed on Oct. 7, 2015, 10 pages.
U.S. Appl. No. 13/927,065, Notice of Allowance mailed on Aug. 26, 2016, 7 pages.
U.S. Appl. No. 13/927,065, Restriction Requirement mailed on Apr. 15, 2015, 9 pages.
U.S. Appl. No. 14/092,804, Final Office Action mailed on Dec. 29, 2016, 46 pages.
U.S. Appl. No. 14/092,804, Non-Final Office Action mailed on Sep. 10, 2015, 33 pages.

(Continued)

*Primary Examiner* — Lynn A Bristol
(74) *Attorney, Agent, or Firm* — Kilpatrick Townsend & Stockton LLP

(57) ABSTRACT

The present invention provides heterodimer pairs that can comprise a first heterodimer and a second heterodimer wherein each heterodimer comprises an immunoglobulin heavy chain or fragment thereof and an immunoglobulin light chain or fragment thereof. At least one of the heterodimers can comprise one or more amino acid modifications in the $C_{H1}$ and/or $C_L$ domains, one or more amino acid modifications in the $V_H$ and/or $V_L$ domains, or a combination thereof. The modified amino acid(s) can be part of the interface between the light chain and heavy chain and are typically modified to create preferential pairing between each heavy chain and a desired light chain such that when the two heavy chains and two light chains of the heterodimer pair are co-expressed in a cell, the heavy chain of the first heterodimer preferentially pairs with one of the light chains rather than the other. Likewise, the heavy chain of the second heterodimer typically preferentially pairs with the second light chain rather than first.

40 Claims, 27 Drawing Sheets

Specification includes a Sequence Listing.

(56) References Cited

U.S. PATENT DOCUMENTS

| | | |
|---|---|---|
| 10,077,298 B2 * | 9/2018 | Corper ................. A61P 9/14 |
| 11,078,296 B2 | 8/2021 | Corper |
| 11,161,915 B2 | 11/2021 | Urosev et al. |
| 11,286,293 B2 * | 3/2022 | Corper ............. C07K 16/2863 |
| 11,306,156 B2 | 4/2022 | Sanches |
| 2003/0003502 A1 | 1/2003 | Jardetzky et al. |
| 2003/0129659 A1 | 7/2003 | Whelihan et al. |
| 2005/0069549 A1 | 3/2005 | Herman |
| 2006/0160184 A1 | 7/2006 | Hoogenboom |
| 2007/0196363 A1 | 8/2007 | Arathoon et al. |
| 2007/0274985 A1 | 11/2007 | Dubel et al. |
| 2008/0050370 A1 | 2/2008 | Glaser et al. |
| 2009/0162360 A1 | 6/2009 | Klein et al. |
| 2009/0182127 A1 | 7/2009 | Kjaergaard et al. |
| 2009/0232811 A1 | 9/2009 | Klein et al. |
| 2009/0263392 A1 | 10/2009 | Igawa et al. |
| 2010/0015133 A1 | 1/2010 | Igawa et al. |
| 2010/0075326 A1 | 3/2010 | Jin et al. |
| 2010/0105874 A1 | 4/2010 | Schuurman et al. |
| 2010/0256338 A1 | 10/2010 | Brinkmann et al. |
| 2010/0286374 A1 | 11/2010 | Kannan et al. |
| 2010/0322934 A1 | 12/2010 | Imhof-Jung et al. |
| 2010/0322935 A1 | 12/2010 | Croasdale et al. |
| 2010/0331527 A1 | 12/2010 | Davis et al. |
| 2011/0008345 A1 | 1/2011 | Ashman et al. |
| 2011/0275787 A1 | 11/2011 | Kufer et al. |
| 2011/0287009 A1 | 11/2011 | Scheer et al. |
| 2011/0293613 A1 | 12/2011 | Brinkmann et al. |
| 2012/0143580 A1 | 6/2012 | Constantine et al. |
| 2012/0149876 A1 | 6/2012 | Von Kreudenstein et al. |
| 2012/0244578 A1 | 9/2012 | Kannan et al. |
| 2013/0078249 A1 | 3/2013 | Ast et al. |
| 2013/0195849 A1 | 8/2013 | Spreter Von et al. |
| 2013/0336973 A1 | 12/2013 | Spreter Von et al. |
| 2014/0051835 A1 | 2/2014 | Dixit et al. |
| 2014/0072581 A1 | 3/2014 | Dixit et al. |
| 2014/0154254 A1 | 6/2014 | Kannan et al. |
| 2014/0187753 A1 | 7/2014 | Blein et al. |
| 2014/0200331 A1 | 7/2014 | Corper et al. |
| 2014/0370020 A1 | 12/2014 | Kuramochi et al. |
| 2015/0211001 A1 | 7/2015 | Ohrn et al. |
| 2015/0284470 A1 | 10/2015 | Spreter Von et al. |
| 2015/0307594 A1 | 10/2015 | Corper et al. |
| 2016/0257763 A1 | 9/2016 | Von Kreudenstein et al. |
| 2018/0179296 A1 | 6/2018 | Corper et al. |
| 2019/0085055 A1 | 3/2019 | Corper et al. |
| 2019/0338048 A1 | 11/2019 | Urosev et al. |

FOREIGN PATENT DOCUMENTS

| | | |
|---|---|---|
| CN | 104114579 | 10/2014 |
| CN | 108283001 A | 7/2018 |
| EP | 1870459 | 12/2007 |
| EP | 2543680 | 1/2013 |
| EP | 2647707 | 10/2013 |
| JP | 2012512894 A | 6/2012 |
| JP | 2012525149 A | 10/2012 |
| JP | 2018162253 A | 10/2018 |
| WO | 9404690 | 3/1994 |
| WO | 9627011 | 9/1996 |
| WO | 2006106905 | 10/2006 |
| WO | 2007110205 | 10/2007 |
| WO | 2008131242 | 10/2008 |
| WO | 2009089004 | 7/2009 |
| WO | 2010085682 | 7/2010 |
| WO | 2010115553 | 10/2010 |
| WO | 2011028952 | 3/2011 |
| WO | 2011063348 | 5/2011 |
| WO | 2011119484 | 9/2011 |
| WO | 2011131746 | 10/2011 |
| WO | 2011143545 | 11/2011 |
| WO | 2011133886 | 12/2011 |
| WO | 2011147982 | 12/2011 |
| WO | 2012006635 | 1/2012 |
| WO | 2012020096 | 2/2012 |
| WO | 2012023053 | 2/2012 |
| WO | 2012058768 | 5/2012 |
| WO | 2012073985 | 6/2012 |
| WO | 2012131555 | 10/2012 |
| WO | 2012143523 | 10/2012 |
| WO | 2013002362 | 1/2013 |
| WO | 2013005194 | 1/2013 |
| WO | 2013063702 | 5/2013 |
| WO | 2013096291 | 6/2013 |
| WO | 2013166594 | 11/2013 |
| WO | 2014004586 | 1/2014 |
| WO | 2014012082 | 1/2014 |
| WO | 2014018572 | 1/2014 |
| WO | 2014005784 | 4/2014 |
| WO | 2014081955 | 5/2014 |
| WO | WO 2014082179 | * 5/2014 |
| WO | 2014124326 | 8/2014 |
| WO | 2014150973 | 9/2014 |
| WO | 20140150973 | 9/2014 |
| WO | 2014182970 | 11/2014 |
| WO | 2015006749 | 1/2015 |
| WO | 2015173756 | 11/2015 |
| WO | 2015181805 | 12/2015 |
| WO | 2016026943 | 2/2016 |
| WO | 2016172485 | 10/2016 |
| WO | 2017059551 | 4/2017 |

OTHER PUBLICATIONS

U.S. Appl. No. 14/092,804, Notice of Allowance mailed on Nov. 1, 2017, 10 pages.
U.S. Appl. No. 14/092,804, Restriction Requirement dated May 12, 2016.
U.S. Appl. No. 14/092,804, Restriction Requirement mailed on Jun. 18, 2015, 5 pages.
U.S. Appl. No. 14/432,153, Non-Final Office Action mailed on Oct. 27, 2016, 10 pages.
U.S. Appl. No. 14/432,153, Corrected Notice of Allowability mailed on Aug. 18, 2017, 7 pages.
U.S. Appl. No. 14/432,153, Notice of Allowance mailed on May 15, 2017, 8 pages.
U.S. Appl. No. 14/432,153, Restriction Requirement mailed on Jun. 30, 2016, 7 pages.
U.S. Appl. No. 14/648,222, Notice of Allowance mailed on May 8, 2018, 74 pages.
U.S. Appl. No. 14/648,222, Final Office Action mailed on Dec. 29, 2017, 12 pages.
U.S. Appl. No. 14/648,222, Non-Final Office Action mailed on May 16, 2017, 43 pages.
U.S. Appl. No. 14/648,222, Restriction Requirement mailed on May 9, 2016, 14 pages.
U.S. Appl. No. 14/648,222, Restriction Requirement mailed on Dec. 2, 2016, 33 pages.
U.S. Appl. No. 15/355,019, Non-Final Action issued Jul. 21, 2017.
U.S. Appl. No. 15/355,019, Notice of Allowance issued Nov. 17, 2017.
U.S. Appl. No. 15/355,019: Non-Final Office Action dated Jan. 8, 2019, 5 pages.
U.S. Appl. No. 15/355,019, Notice of Allowance dated Jul. 29, 2019.
U.S. Appl. No. 15/765,574, Restriction Requirement dated Sep. 10, 2019.
U.S. Appl. No. 15/765,574, Office Action dated Dec. 27, 2019.
U.S. Appl. No. 15/765,574, Notice of Allowance dated Sep. 2, 2020.
U.S. Appl. No. 15/896,170, Final Office Action dated May 18, 2020.
U.S. Appl. No. 15/896,170 Restriction Requirement dated Jun. 26, 2019.
U.S. Appl. No. 15/896,170 Office Action dated Sep. 18, 2019.
U.S. Appl. No. 16/122,417 Restriction Requirement dated Mar. 6, 2020.
U.S. Appl. No. 16/122,417 Office Action dated Jun. 19, 2020.
Atwell et al., Stable Heterodimers From Remodeling the Domain Interface of a Homodimer Using a Phage Display Library, Journal of Molecular Biology, vol. 270, No. 1, Jul. 4, 1997, pp. 26-35.

(56) References Cited

OTHER PUBLICATIONS

Barthelemy et al., Comprehensive Analysis of the Factors Contributing to the Stability and Solubility of Autonomous Human Vh Domains, J. Bioi. Chem., vol. 283, No. 6, Feb. 2008, pp. 3639-3654.
Beck et al., Strategies and Challenges for the Next Generation of Therapeutic Antibodies, Nature Reviews Immunology, vol. 10, No. 5, May 2010, pp. 345-352.
Bell et al., Differential Tumor-targeting Abilities of Three Single-domain Antibody Formats, Cancer Letters, vol. 289, No. 1, 2010, pp. 81-90.
Bolon et al., Specificity Versus Stability in Computational Protein Design, Proceedings of the National Academy of Sciences, vol. 102, No. 36, Sep. 6, 2005, pp. 12724-12749.
Carter et al., Humanization Of An Anti-p185HER2 Antibody For Human Cancer Therapy, Proc. Natl. Acad. Sci. USA, vol. 89, No. 10, 1992, pp. 4285-4289.
Carter, Introduction to Current and Future Protein Therapeutics: a Protein Engineering Perspective, Experimental Cell Research, vol. 317, No. 9, May 15, 2011, pp. 1261-1269.
Chames et al., Therapeutic Antibodies: Successes, Limitations and Hopes for the Future, British Journal of Pharmacology, vol. 157, No. 2, 2009, pp. 220-223.
Chen, et al., "Preferential Germline Usage and VH/VL Pairing Observed in Human Antibodies Selected by mRNA display", *Protein Engineering, Design 7 Selection : Peds*, Sep. 2015, vol. 28, No. 10, pp. 427-435.
Colman, Effects of Amino Acid Sequence Changes on Antibody-antigen Interactions, Research in Immunology, vol. 145, No. 1, Jan. 1994, pp. 33-36.
Coloma et al., Design and Production of Novel Tetravalent Bispecific Antibodies, Nature Biotechnology, vol. 15, No. 2, Feb. 1997, pp. 159-163.
Dall'Acqua et al., Contribution of Domain Interface Residues to the Stability of Antibody CH3 Domain Homodimers, Biochemistry, American Chemical Society, vol. 37, No. 26, Jun. 30, 1998, pp. 9266-9273.
Davis et al., SEEDbodies: Fusion Proteins Based on Strand-exchange Engineered Domain (SEED) CH3 Heterodimers in an Fc Analogue Platform for Asymmetric Binders or Immunofusions and Bispecific Antibodies, Protein Engineering, Design & Selection, vol. 23, No. 4, Feb. 4, 2010, pp. 195-202.
Demarest et al., Antibody Therapeutics, Antibody Engineering, and the Merits of Protein Stability, Current Opinion in Drug Discovery and Development vol. 11, No. 5, Sep. 2008, pp. 675-687.
Demarest et al., Optimization of the Antibody CH3 Domain by Residue Frequency Analysis of IgG Sequences, Journal of Molecular Biology, vol. 335, No. 1, Jan. 2, 2004, pp. 41-48.
Fischer, N., et al., Exploiting light chains for the scalable generation and platform purification or native human bispecific IgG. Nature Communications, Feb. 12, 2015; 6(6113):1-12.
Gramer, M. J., et al., Production of stable bispecific lgG1 by controlled Fab-arm exchange. mAbs, Nov./Dec. 2013; 5(6):962-973.
Gunasekaran et al., Enhancing Antibody Fc Heterodimer Formation Through Electrostatic Steering Effects: Applications to Bispecific Molecules and Monovalent IgG mailed on J. Biol. Chem., vol. 285, No. 25, Jun. 18, 2010, pp. 19637-19646.
Hamel et al., The Role of the VL- and VH-Segments in the Preferential Reassociation of Immunoglobulin Subunits, Molecular Immunology, vol. 23, No. 5, May 23, 1986, pp. 503-510.
Head, et al., 'Relative Stabilities of IgG1 and IgG4 Fab Domains Influence of the Light Heavy interchain disulfide bond arthiture', *Protein Science*, Jul. 2012, 21(9), pp. 1315-1322.
Holt et al., Domain Antibodies: Proteins for Therapy, Trends In Biotechnology vol. 21, No. 11, Nov. 2003, pp. 484-490.
Huang et al., A De Novo Designed Protein Protein Interface, Protein Science, vol. 16, No. 12, 2007, pp. 2770-2774.
Igawa et al., VH/VL Interface Engineering to Promote Selective Expression and Inhibit Conformational Isomerization of Thrombopoietin Receptor Against Single-chain Diabody, Protein Engineering, Design & Selection, vol. 23, No. 8, Aug. 2010, pp. 667-677.
Jackman et al., Development of a Two-part Strategy to Identify a Therapeutic Human Bispecific Antibody That Inhibits IgE Receptor Signaling, J Biol Chem., vol. 285, No. 27, Jul. 2, 2010, pp. 20850-20859.
Jordan et al., Structural Understanding of Stabilization Patterns in Engineered Bispecific Ig-like Antibody Molecules, proteins: structure. Function. And bioinformatics, vol. 77, No. 4, Dec. 1, 2009, pp. 832-841.
Kabat, E.A., et al., 'Sequences of proteins of Immunological Interest', . Diae publishing, 5th Ed., vol. 1, 1991, NIH Publication 91-3242 (pp. 647-657, 661-669).
Klein et al., Progress in Overcoming the Chain Association Issue in Bispecific Heterodimeric LgG Antibodies, Mabs, vol. 4, No. 6, Nov. 2012, pp. 653-663.
Labrijin, A.F., et al., Efficient generation of stable bispecific IgG1 by controlled Fab-arm exchange. PNAS. Mar. 26, 2016;110(13):5145-5150.
Lewis et al., Generation of Bispecific IgG Antibodies by Structure-Based Design of an Orthogonal Fab Interface, Nature Biotechnology, vol. 32, No. 2, Jan. 26, 2014, pp. 191-198.
Lindhofer et al., Preferential Species-restricted Heavy/light Chain Pairing in Rat/mouse Quadromas. Implications for a Single-step Purification of Bispecific Antibodies, The Journal of Immunology, vol. 155, No. 1, Jul. 1, 1995, pp. 219-225.
Liu, Zhi, et al., "A Novel Antibody Engineering Strategy for Making Monovalent Bispecific Heterodimeric IgG Antibodies by Electrostatic Steering Mechanism", Journal of Biological Chemistry, vol. 290, No. 12, Mar. 2015, pp. 7535-7562.
Lu et al., Fab-scFv Fusion Protein: an Efficient Approach to Production of Bispecific Antibody Fragments mailed on Journal of Immunological Methods, vol. 267, No. 2, 2002, pp. 213-226.
MacCallum et al., Antibody-antigen Interactions: Contact Analysis and Binding Site Topography, Journal of Molecular Biology, vol. 262, No. 5, Oct. 1996, pp. 732-745.
Marqusee et al., Helix Stabilization by Glu- . . . Lys+ Salt Sridges in Short Septides of De Novo Design, Proc Natl Acad Sci U S A., vol. 84, No. 24, 1987, pp. 8898-8902.
McCann et al., Peptide Tags for Labeling Membrane Proteins in Live Cells with Multiple Fluorophores, Bio Techniques, vol. 38, No. 6, Jun. 2005, pp. 945-951.
Merchant et al., An Efficient Route to Human Bispecific IgG, Nature Biotechnology, vol. 16, No. 7, Jul. 16, 1998, pp. 677-681.
Merk et al., Cell-Free Expression of Two single-Chain Monoclonal Antibodies against Lysozyme: Effect of Domain Arrangement on the Expression, J. Biochem., vol. 125, Dec. 31, 1999, pp. 328-333.
Miller et al., Stability Engineering of scFvs for the Development of Bispecific and Multivalent Antibodies, Protein Engineering. Design and selection, Oxford Journal, vol. 23, No. 7., Jul. 1, 2010, pp. 549-557.
Milstein et al., Hybrid Hybridomas and Their Use in Immunohistochemistry, Nature, vol. 305, No. 6, Oct. 6, 1983, pp. 537-540.
Moore et al., A Novel Bispecific Antibody Format Enables Simultaneous Bivalent and Monovalent Co-engagement of Distinct Target Antigens, mAbs, vol. 3, No. 6, 2011, pp. 546-557.
Omidfar et al., Single Domain Antibodies: a New Concept for Epidermal Growth Factor Receptor and EGFRvIII Targeting, DNA Cell Biol., vol. 31, No. 6, 2012, pp. 1015-1026.
International Application No. PCT/IB2015/054107, International Preliminary Report on Patentability.
Padlan, E.A., et al., Antibody Fab assembly: the interface residues between CH1 and CL. Mol Immunol. Sep. 1986; 23(9):951-960.
Portolano et al., Lack of Promiscuity in Autoantigen-Specific H and L Chain Combinations as Revealed by Human H and L Chain "Roulette", J Immunol., vol. 150, No. 3, Feb. 1, 1993, pp. 880-887.
Presta, et al., Engineering Therapeutic Antibodies for Improved Function, Biochem. Soc. Trans., vol. 30, No. 4, Aug. 2002, pp. 487-490.
Ridgway et al., Knobs-into-Holes' Engineering of Antibody CH3 Domains for Heavy Chain Heterodimerization, Protein Engineering, vol. 9, No. 7, Jul. 1996, pp. 617-621.

(56) References Cited

OTHER PUBLICATIONS

Robinson et al., Targeting ErbB2 and ErbB3 With a Bispecific Single-chain Fv Enhances 1-5 Targeting Selectivity and Induces a Therapeutic Effect in Vitro, Br. J. Cancer, vol. 99, Oct. 7, 2008, pp. 1415-1425.
Rudikoff et al., Single Amino Acid Substitution altering Antigen-binding Specificity, Proc. Natl Acad Sci., vol. 79,No. 6, 1982, pp. 1979-1983.
Schaefer, W., et al., Immunoglobulin domain crossover as a generic approach for the production of bispcific IgG antibodied. PNAS, Jul. 5, 2011; 108(27):11187-11192.
Schlatter et al., On the Optimal ratio of Heavy to Light Chain Genes for Efficient Recombinant Antibody Production by CHO Cells, Biotechnology Progress, vol. 21, No. 1, Jan.-Feb. 2005, pp. 122-133.
Segal et al., Introduction: Bispecific Antibodies, Journal of Immunological Methods, vol. 248, No. 1-2, Feb. 1, 2001, pp. 1-6.
Spreter Von Kreudenstein, T., et al., Protein engineering and the use of molecular modeling and simulation: the case of heterodimeric Fc engineering. Methods. Jan. 1, 2014; 65(1):77-94.
Stanglmaier et al., Bi20 (fBTA05), a Novel Trifunctional Bispecific Antibody (Anti-CD20 X Anti-CD3), Mediates Efficient Killing of B-cell Lymphoma Cells Even With Very Low CD20 Expression Levels, International Journal of Cancer, vol. 123, 2008, pp. 1181-1189.
Strop, P. J., et al., Generating Bispecific Human IgG1 and IgG2 Antibodies from any Antibody Pair. J Mol Biol., Jul. 13, 2012; 420(3):204-219.
Suresh et al., Bispecific Monoclonal Antibodies From Hybrid Hybridomas, Methods in Enzymology, vol. 121, 1986, pp. 210-228.
Traunecker et al., Bispecific Single Chain Molecules (Janusins) Target Cytotoxic Lymphocytes on HIV Infected Cells, EMBO Journal, vol. 10, No. 12, Dec. 1991, pp. 3655-3699.
Troise et al., Differential Binding of Human Immunoagents and Herceptin to the ErbB2 Receptor, FEBS Journal, vol. 275, No. 20, 2008, pp. 4967-4979.
Tu et al., Generation and Characterization of Chimeric Antibodies against NS3, NS4, NS5, and Core Antigens of Hepatitis C Virus, Clinical & Vaccine Immnology, Jun. 2010, pp. 1040-1047.
Vitetta et al., Considering Therapeutic Antibodies, Immunology, Science, 2006, vol. 313, No. 5785, 2006, pp. 308-309.
Von Kreudenstein et al., Improving biophysical properties of a bispecific antibody scaffold to aid developability, vol. 5, No. 5, Sep./Oct. 2013, pp. 646-654.
Von Kreudenstein et al., Protein Engineering and The Use of Molecular Modeling and Simulation: The Case of Heterodimeric Fc Engineering, Methods, vol. 65, No. 1, Jan. 1, 2014, pp. 77-94.
Wiens et al., Mutation of a Single Conserved Residue in VH Complementarity-determining Region 2 Results in a Severe Ig Secretion Defect., J Immunology, vol. 167, No. 4, Aug. 2001, pp. 2179-2186.
Woods et al., LC-MS Characterization and Purity Assessment of a Prototype Bispecific Antibody, MABS, vol. 5, No. 5, Sep. 1, 2013, pp. 711-722.
Wu et al., Humanization of a Murine Monoclonal Antibody by Simultaneous Optimization of Framework and CDR Residues, Journal of Molecular Biology, vol. 294, Nov. 1999, pp. 151-162.
Zhu et al., Remodeling Domain Interfaces to Enhance Heterodimer Formation, Protein Science, vol. 6, No. 4, Apr. 1997, pp. 781-788.
Edwards, et all, J Mol Biology, 334(1); 2003.
Lloyd, et al, Protein Engineering, Design & Selection 22: 159-168, 2009.
Briney et al., Nature 566: 393 (Year: 2019).
Piche-Nicholas etal., MABS 10(1): 81-94 (Year: 2018).
Spiess et al., Molecular Immunology 67: 95-106 (Year: 2015).
U.S. Appl. No. 17/343,198; Non-Final Office Action dated Sep. 27, 2023.
RU2020112916, "Office Action", Sep. 1, 2023, 27 pages.
JP2022-186638, "Office Action", Oct. 25, 2023, 4 pages.
Berry, et al., "Substitution of Cysteine for Selenocysteine in Type I Iodothyronine Deiodinase Reduces the Catalytic Efficiency of the Protein but Enhances Its Translation", Endocrinology, vol. 131, No. 4, Oct. 1992, pp. 1848-1852.
Chen, et al., "Fusion Protein Linkers: Property, Design and Functionality", Advanced Drug Delivery Reviews, vol. 65, No. 10, Oct. 15, 2013, pp. 1357-1369.
Halin, et al., "Synergistic Therapeutic Effects of a Tumor Targeting Antibody Fragment, Fused to Interleukin 12 and to Tumor Necrosis Factor Alpha", Cancer Research, vol. 63, No. 12, Jun. 15, 2003, pp. 3202-3210.
Lund, et al., "Oligosaccharide-Protein Interactions in IgG can Modulate Recognition by Fcγ Receptors", The FASEB Journal, vol. 9, No. 1, Jan. 1995, pp. 115-119.
Maeda, et al., "Engineering of Functional Chimeric Protein Gvargula Luciferase", Analytical biochemistry, vol. 249, No. 2, Jul. 1997, pp. 147-152.
Mariuzza, et al., "The Structural Basis of Antigen-Antibody Recognition", Annual Review of Biophysics and Biophysical Chemistry, vol. 16, Jun. 1987, pp. 139-159.
Pan, et al., "Blocking Neuropilin-1 Function Has an Additive Effect with Anti-VEGF to Inhibit Tumor Growth", Cancer Cell, vol. 11, No. 1, Jan. 2007, pp. 53-67.
Riechmann, et al., "Reshaping Human Antibodies for Therapy", Nature, vol. 332, No. 6162, Mar. 24, 1988, pp. 323-327.
Su, et al., "The Role of Antibody Vk Framework 3 Region Towards Antigen Binding: Effects on Recombinant Production and Protein L Binding", Scientific Reports, vol. 7, No. 1, Jun. 2017, pp. 1-7.
Vajdos, et al., "Comprehensive Functional Maps of the Antigen-Binding Site of an Anti-ErbB2 Antibody Obtained with Shotgun Scanning Mutagenesis", Journal of Molecular Biology, vol. 320, No. 2, Jul. 5, 2002, pp. 415-428.
Singer et al., Genes and genomes; Two vols. V. 1, Moscow, "Mir", 1998, p. 63.

* cited by examiner

```
            FR1                              CDR1        FR2              CDR2                  FR3
D3H44   EVQLVESGGGLVQPGGSLRLSCAASGFNI       KE---YYMH   WVRQAPGKGLEWVG   LIDP---EQGNTIYDPKFQD   RATISADNSKNTAYLQMNSLRAEDTAVYYCAR
        ********************************    *   *       **************   *                      ****  **  ************************

VH1     QVQLVQSGAEVKKPGASVKVSCKASGYTF       TG---YYMH   WVRQAPGQGLEWMG   WINP--NSGGTNYAQKFQG    RVTMTRDTSISTAYMELSRLRSDDTAVYYCAR
VH2     QITLKESGPTLVKPTQTLTLTCTFSGFSL       STSGVGVG    WIRQPPGKALEWLA   LIY----WNDDKRYSPSLKS   RLTITKDTSKNQVVLTMTNMDPVDTATYYCAHR
VH3     EVQLVESGGGLVQPGGSLRLSCAASGFTF       SS---YWMS   WVRQAPGKGLEWVA   NIKQ--DGSEKYYVDSVKG    RFTISRDNAKNSLYLQMNSLRAEDTAVYYCAR
VH4     QVQLQESGPGLVKPSGTLSLTCAVSGGSI       SSS-NWWS    WVRQPPGKGLEWIG   EIY---HSGSTNYNPSLKS    RVTISVDKSKNQFSLKLSSVTAADTAVYYCAR
VH5     EVQLVQSGAEVKKPGESLKISCKGSGYSF       TS---YWIG   WVRQMPGKGLEWMG   IIYP--GDSDTRYSPSFQG    QVTISADKSISTAYLQWSSLKASDTAMYYCAR
VH6     QVQLQQSGPGLVKPSQTLSLTCAISGDSV       SSNSAAWN    WIRQSPSRGLEWLG   RTYYR-SKWYNDYAVSVKS    RITINPDTSKNQFSLQLNSVTPEDTAVYYCAR
VH7     QVQLVQSGSELKKPGASVKVSCKASGYTF       TS---YAMN   WVRQAPGQGLEWMG   WINT--NTGNPTYAQGFTG    RFVFSLDTSVSTAYLQICSLKAEDTAVYYCAR
```

```
            CDR3
D3H44   --DTAAYFDYWGQGTLVTVSS
        **    ******  ******

IGHJ1*01    ----AEYFQHWGQGTLVTVSS
IGHJ2*01    ---YWYFDLWGRGTLVTVSS
IGHJ3*02    ------DAFDIWGQGTMVTVSS
IGHJ4*01    -------YFDYWGQGTLVTVSS
IGHJ5*02    ----NWFDPWGQGTLVTVSS
IGHJ6*01    YYYYYGMDVWGQGTTVTVSS
```

FIG. 1B

VL (kappa)

```
         FR1                        CDR1         FR2              CDR2      FR3                              CDR3
D3H44    DIQMTQSPSSLSASVGDRVTITC    RASRDIKS-----YLN    WYQQKPGKAPKVLIY    YATSLAE    GVPSRFSGSGSGTDYTLTISSLQPEDFATYYC    LQHGESP
         **********************    ***     ***         **********     Y    *  **     *******************************      *

VKI      DIQMTQSPSSLSASVGDRVTISC    RASQSISS-----YLN    WYQQKPGKAPKLLIY    AASSLQS    GVPSRFSGSGSGTDFTLTISSLQPEDFATYYC    QQSYSTP
VKII     DIVMTQTPLSLPVTPGEPASISC    RSSQSLLDSDDGNTYLD   WYLQKPGQSPQLLIY    TLSYRAS    GVPDRFSGSGSGTDFTLKISRVEAEDVGVYYC    MQRIEFP
VKIII    EIVLTQSPGTLSLSPGERATLSC    RASQSVSS-----YLA    WYQQKPGQAPRLLIY    GASSRAT    GIPDRFSGSGSGTDFTLTISRLEPEDFAVYYC    QQYGSSP
VKIV     DIVMTQSPDSLAVSLGERATINC    KSSQSVLYSSNNKNYLA   WYQQKPGQPPKLLIY    WASTRES    GVPDRFSGSGSGTDFTLTISSLQAEDVAVYYC    QQYYSTP
VKV      ETTLTQSPAFMSATPGDKVNISC    KASQDIDD-----DMN    WYQQKPGEAAIFIIQ    EATTLVP    GIPPRFSGSGYGTDFTLTINNIESEDAAYFC    LQHDNFP
VKVI     EIVLTQSPDFQSVTPKEKVTITC    RASQSIGS-----SLH    WYQQKPDQSPKLLIK    YASQSFS    GVPSRFSGSGSGTDFTLTINSLEAEDAATYYC    HQSSSLP
```

```
         CDR3
D3H44    WTFGQGTKVEIK
         ***********

IGKJ1*01  WTFGQGTKVEIK
IGKJ2*01  YTFGQGTKLEIK
IGKJ3*01  FTFGPGTKVDIK
IGKJ4*01  LTFGGGTKVEIK
IGKJ5*01  ITFGQGTRLEIK
```

FIG. 1C

VL (lambda)

| | FR1 | CDR1 | FR2 | CDR2 | FR3 | CDR3 |
|---|---|---|---|---|---|---|
| D3H44 | DIQMTQSPSSLSASVGDRVTITC | R-AS-RDIKS--YLN | WYQQKPGKAPKVLIY | YATS------LAE | GVPSRFSGSG---SGTDYTLTISSLQPEDFATYYC | LQHGESP---- |
| | ** * | **** * | * | ******* | * | ** *** ** ** *** | * |
| VLI | QSVLTQPPS--VSEAPRQRVTISC | SGSS--SNIGNNAVN | WYQQLPGKAPKLLIY | YDDL-------LPS | GVSDRFSGSK---SGTSASLAISGLQSEDEADYYC | AAWDDSLNG--- |
| VLII | QSALTQPPS--ASGSPGQSVTISC | TGTSSDVGGYNYVS | WYQQHPGKAPKLMIY | EVSK-------RPS | GVPDRFSGSK---SGNTASLTVSGLQAEDEADYYC | SSYAGSNNF--- |
| VLIII | QSELTQPPS--VSVSPGQTASITC | SGDK----LGDKYAC | WYQQKPGQSPVLVIY | QDSK-------RPS | GIPERFSGSN---SGNTATLTISGTQAMDEADYYC | QAWDSSTA---- |
| VLIV | LPVLTQPPS--ASALLGASIKLTC | TLSS---EHSTYTIE | WYQQKPGRSPQYIMK | VKSDGSH-SKGD | GIPDRFMGSS--SGADRYLTFSNLQSDDEAEYHC | GESHTIDGQVG |
| VLV | QPVLTQPPS--SSASPGESARLTC | TLPSDINVGSYNIY | WYQQKPGSPPRYLLN | YYSDSDK-GQGS | GVPSRFSGSKDASANTGILLISGLQSEDEADYYC | MIWPSNAS--- |
| VLVI | NFMLTQPHS--VSESPGKTVTISC | TRSS--GSIASNYVQ | WYQQRPGSSPTTVIY | EDNQ-------RPS | GVPDRFSGSIDSSSNSASLTISGLKTEDEADYYC | QSYDSSN---- |
| VLVII | QTVVTQEPS--LTVSPGGTVTLTC | ASSTGAVTSGYYPN | WFQQKPGQAPRALIY | STSN-------KHS | WTPARFSGSLLG---GKAALTLSGVQPEDEAEYYC | LLYYGGAQ--- |
| VLVIII | QTVVTQEPS--FSVSPGGTVTLTC | GLSSGSVSTSGYYPS | WYQQTPGQAPRTLIY | STNT-------RSS | GVPDRFSGSILG---NKAALTITGAQADDESDYYC | VLYMGSGI--- |
| VLIX | QPVLTQPPS--ASALGASVTLTC | TLSS---GYSNYKVD | WYQQRPGKGPRFVMR | VGTGGIVGSKGD | GIPDRFSVLG---SGLNRYLTIKNIQEEDESDYHC | GADHGSGSNFV |
| VLX | QAGLTQPPS--VSKGLRQTATLTC | TGNS--NNVGNQGAA | WLQQHQGHPPKLLSY | RNMN-------RPS | GISERLSASR---SGNTASLTITGLQPEDEADYYC | SAWDSSLSA--- |

| | CDR3 | |
|---|---|---|
| D3H44 | WTFGQGTKVEIK | |
| | ** ***** | |
| IGLJ1*01 | YVFGTGTKVTVL | |
| IGLJ2*01 | VVFGGGTKLTVL | |
| IGLJ3*01 | VVFGGGTKLTVL | |
| IGLJ4*01 | FVFGGGTQLIIL | |
| IGLJ5*01 | WVFGEGTELTVL | |
| IGLJ6*01 | NVFGSGTKVTVL | |
| IGLJ7*01 | AVFGGGTQLTVL | |

```
D3H44      ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV(EPKSCDKTHT)
           ****************************************************************************************************
IGHG1*01   ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV
IGHG1*03   ..................................................................................................:R:
IGHG3*06   ..................................................................................................:R:
IGHG3*18   ............:C:R:...................................................:T:.........................:R:
IGHG3*17   ............:C:R:.............................................Y:....:T:.........................:R:
IGHG2*04   ............:C:R:..:ES:........................................:NF:.:T:..:D:....................:T:
IGHG4*01   ............:C:R:..:ES:...............................................:K::T:..:D:................:R:
IGHG2*03   ............:C:R:..:ES:........................................:NF:.:T:..:D:....................:T:
IGHG2*02   ............:C:R:..:ES:.....................................:T:.:NF:.:T:..:D:....................:T:
```

: identical residues to that of IGHG1*01

FIG. 1E

CL (kappa)

```
D3H44    RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC
         ****************************************************************************************************
IGKC*01  RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC
IGKC*04  ....................................................................L...............................
IGKC*05  ....................................................................N...............................
IGKC*02  ............................................................E...........................G...........
IGKC*03  ............................................................E.......................................
                                                               R
```

: identical residues to that of IGKC*01

CL (lambda)

```
D3H44    RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC-
          ***  ***  *****  **                ***    *                ****              *   *   *     *          **
IGλC1    --PKANPTVTLFPPSSEELQANKATLVCLISDFYPGAVTVAWKADGSPVKAGVETTKPSKQS-NNKYAASSYLSLTPEQWKSHRSYSCQVTHEG--STVEKTVAPTECS
IGλC7    Q:::A:S:::::::::::::::::::::::::::::::::::::::::::::::::::T:::::::::::::::::::::::::::::::::---:::::::::::
IGλC2    :::A:S:::::::::::::::::::::::::::::::::::::::::::::::::::S::::::::::::::::::::::::::::::::::---:::::::::::
IGλC3    :::A:S::::::::::::::::::::::::::::::K:::::::::::::::::::::::::::::::::::K:::::::::::::::::::---:::::::::::
IGλC6    Q:::A:S:::::::::::::::::::::::::::::::::::::::::::::::::NT:::::::::::::::::::::::::::::A:::::---:::::::::::
```

: identical residues to that of IGλC1

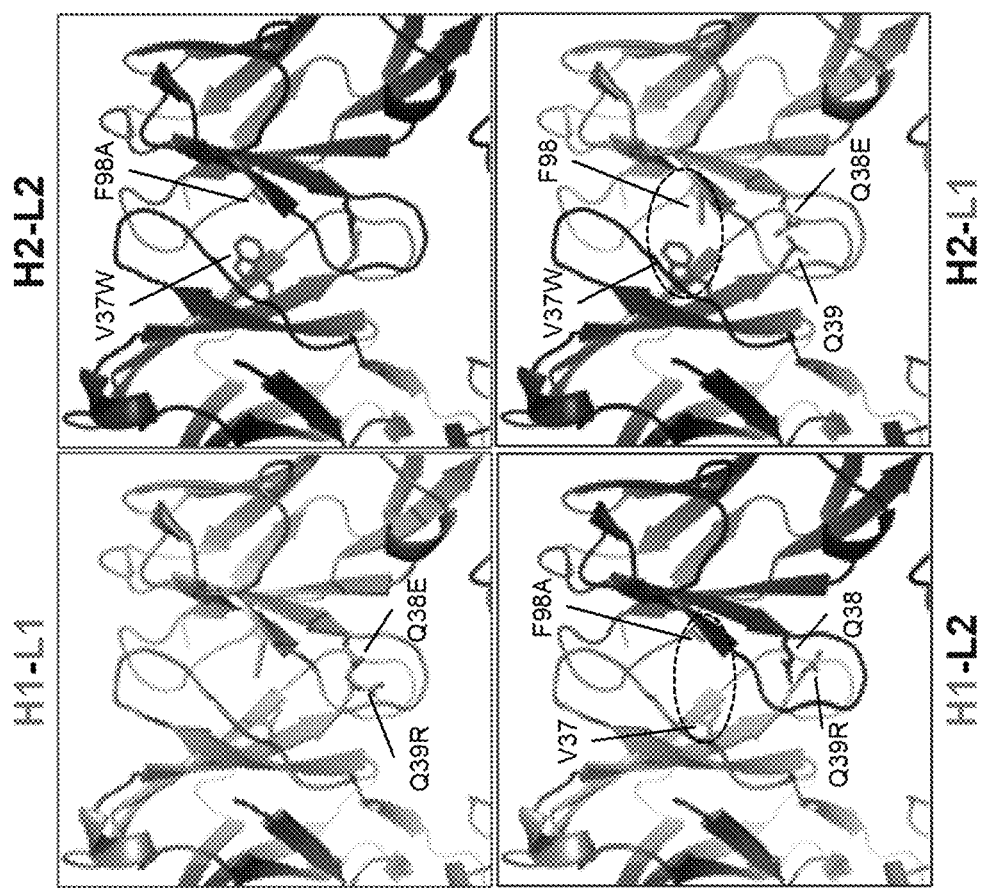
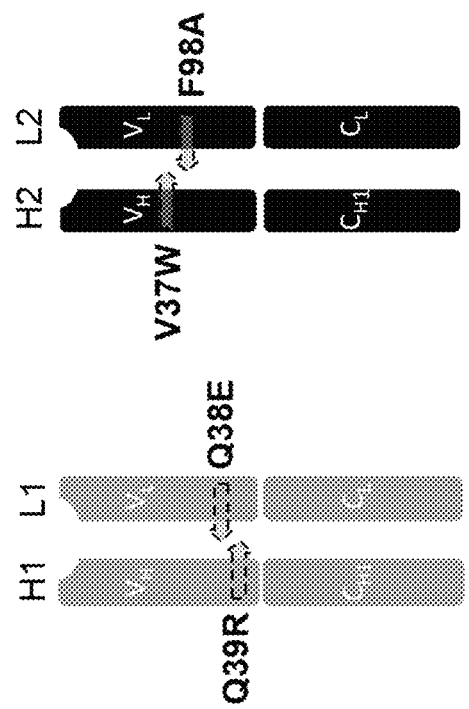
FIG. 3

Assay Requirements:

Engineering Goal: H1-L1 + H2-L2 + H1-L2 + H2-L1

→

Assay Requirement: Quantification of
H1-L1 : H1-L2 and H2-L2 : H2-L1
ratios

→

Simplified Assay: Separate Quantification of
1. H1 + L1 + L2 ⇒ H1-L1 + H1-L2
2. H2 + L2 + L1 ⇒ H2-L2 + H2-L1

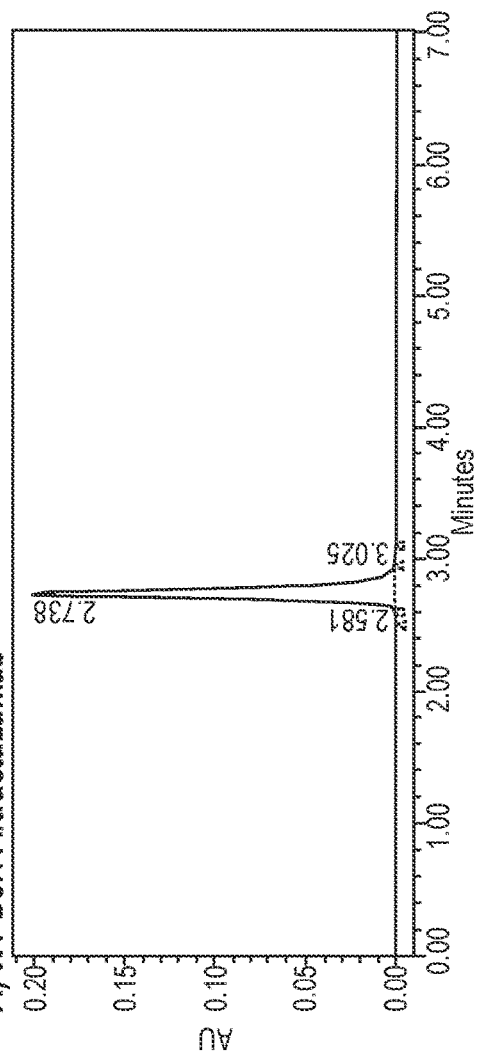
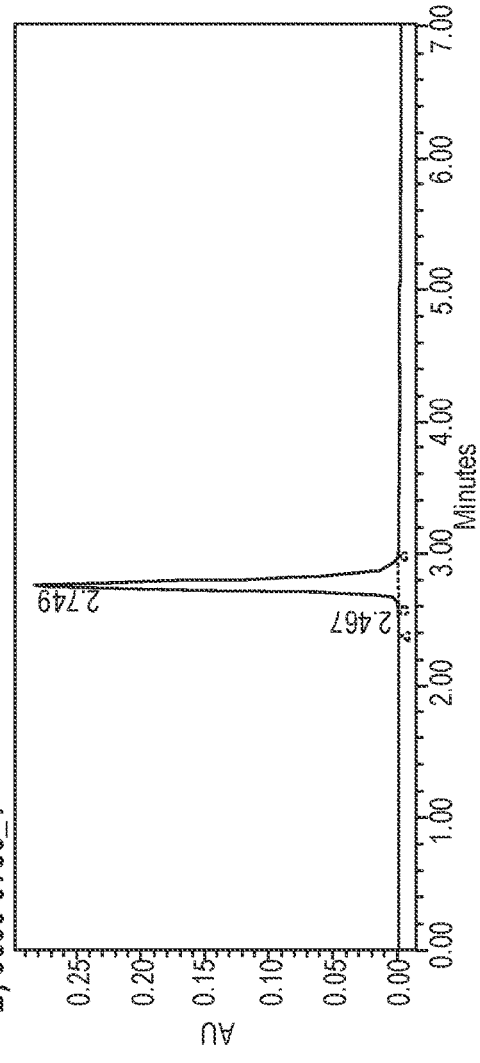

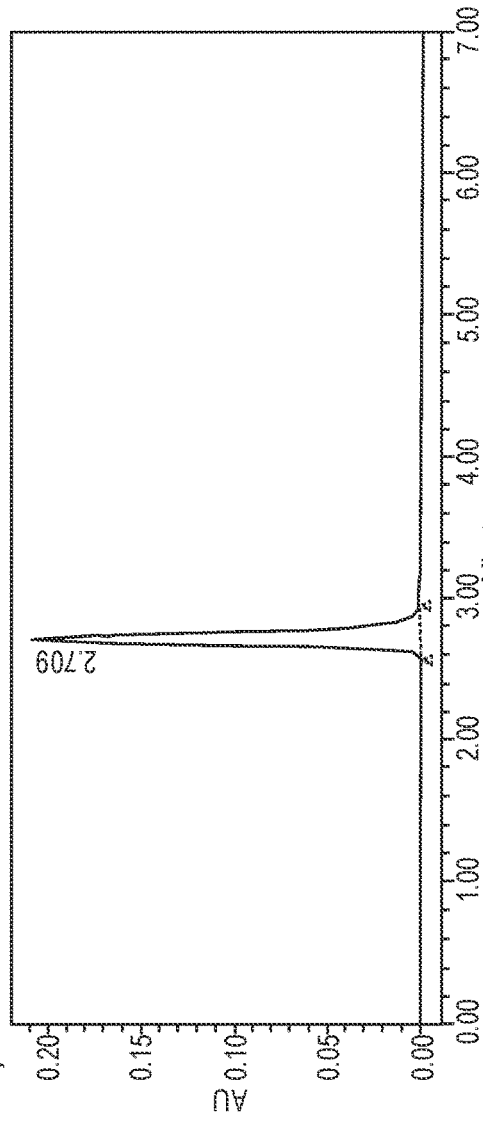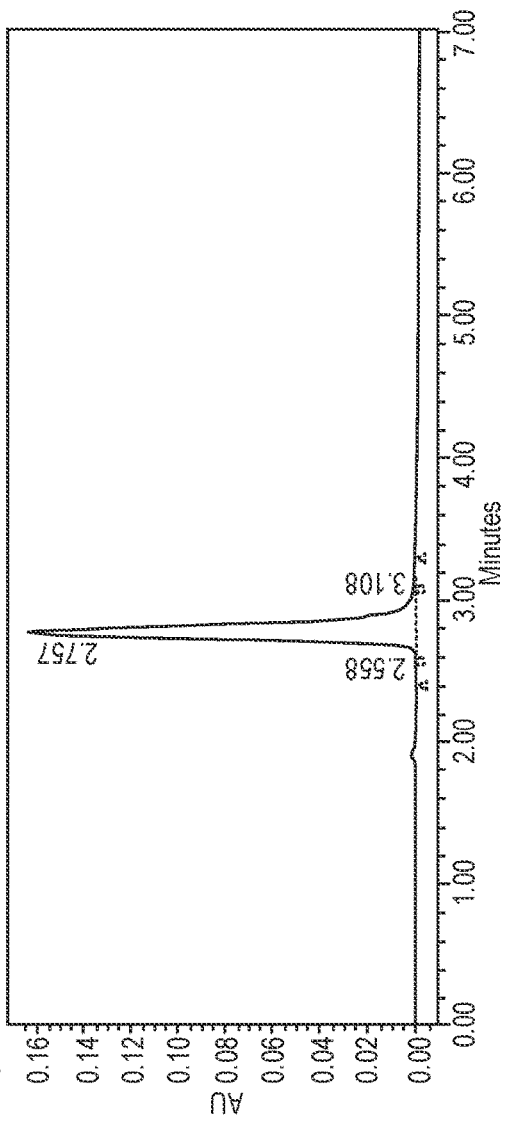

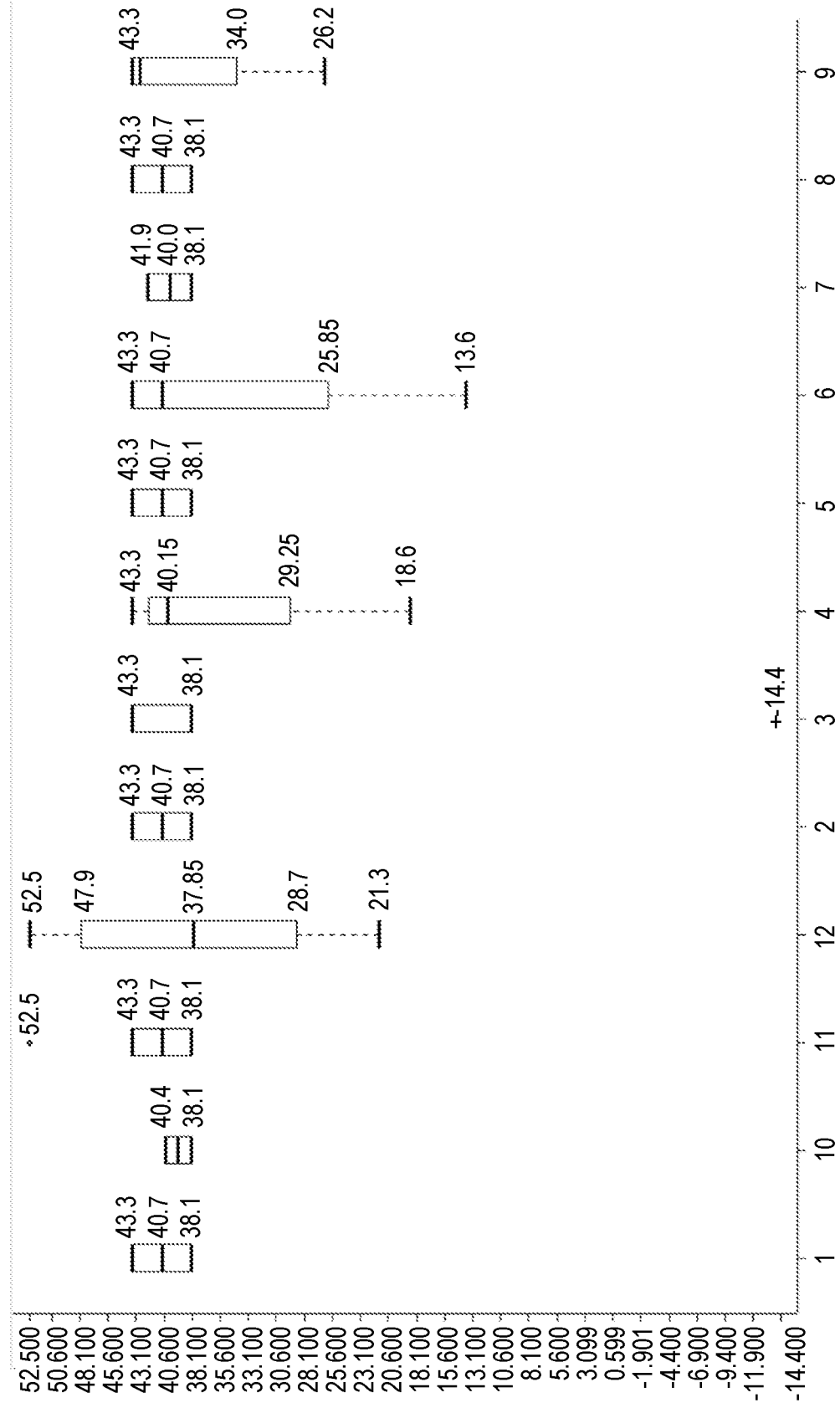

MODIFIED ANTIGEN BINDING POLYPEPTIDE CONSTRUCTS AND USES THEREOF

CROSS REFERENCE TO RELATED APPLICATIONS

This application is a divisional of U.S. patent application Ser. No. 15/314,496, filed Nov. 28, 2016, which is a U.S. National Phase of International Patent Application No.: PCT/IB2015/054107, filed May 29, 2015, which claims the benefit of priority to U.S. Provisional Application No. 62/003,663, filed May 28, 2014, and U.S. Provisional Application No. 62/154,055, filed Apr. 28, 2015, which applications are incorporated herein by reference in their entirety for all purposes.

This application is related to PCT/CA2013/050914, filed Nov. 28, 2013, U.S. Provisional Application No. 61/730,906, filed Nov. 28, 2012, U.S. Provisional Application No. 61/761,641, filed Feb. 6, 2013, U.S. Provisional Application No. 61/818,874, filed May 2, 2013, and U.S. Provisional Application No. 61/869,200, filed Aug. 23, 2013, the entire disclosure of each of which is hereby incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Jan. 29, 2019, is named ZYME023US SeqList_ST25 Amended_SL.txt and is 27,012 bytes in size.

BACKGROUND

Bi-specific antibodies are capable of binding to two different epitopes. The epitopes can be on the same antigen, or each epitope can be on a different antigen. This feature of bi-specific antibodies makes them an attractive tool for various therapeutic applications where there is a therapeutic benefit to targeting or recruiting more than one molecule in the treatment of disease. One of the approaches to form bi-specific antibody would involve concomitant expression of two unique antibody heavy chains and two unique antibody light chains. Correctly forming bi-specific antibodies in a format that is similar to wild-type remains a challenge, since antibody heavy chains have evolved to bind antibody light chains in a relatively promiscuous manner. As a result of this promiscuous pairing, concomitant expression of two antibody heavy chains and two antibody light chains naturally leads to a scrambling of heavy chain-light chain pairings. This mispairing remains a major challenge for the generation of bi-specific therapeutics, where homogeneous pairing is an essential requirement for good manufacturability and biological efficacy.

Several approaches have been described to prepare bi-specific antibodies in which specific antibody light chains or fragment pair with specific antibody heavy chains or fragments. A review of various approaches to address this problem can be found in Klein et al., (2012) mAbs 4:6, 1-11. International Patent Application No. PCT/EP2011/056388 (WO 2011/131746) describes an in vitro method for generating a heterodimeric protein in which asymmetrical mutations are introduced into the CH3 regions of two monospecific starting proteins in order to drive directional "Fab-arm" or "half-molecule" exchange between two monospecific IgG4- or IgG4-like antibodies upon incubation under reducing conditions.

Schaefer et al. (Roche Diagnostics GmbH), describe a method to assemble two heavy and two light chains, derived from two existing antibodies, into human bivalent bi-specific IgG antibodies without use of artificial linkers (PNAS (2011) 108(27): 11187-11192). The method involves exchanging heavy chain and light chain domains within the antigen-binding fragment (Fab) of one half of the bi-specific antibody.

Strop et al. (Rinat-Pfizer Inc.), describe a method of producing stable bi-specific antibodies by expressing and purifying two antibodies of interest separately, and then mixing them together under specified redox conditions (J. Mol. Biol. (2012) 420:204-19).

Zhu et al. (Genentech) have engineered mutations in the VL/VH interface of a diabody construct consisting of variant domain antibody fragments completely devoid of constant domains, and generated a heterodimeric diabody (Protein Science (1997) 6:781-788). Similarly, Igawa et al. (Chugai) have also engineered mutations in the VL/VH interface of a single-chain diabody to promote selective expression and inhibit conformational isomerization of the diabody (Protein Engineering, Design & Selection (2010) 23:667-677).

US Patent Publication No. 2009/0182127 (Novo Nordisk, Inc.) describes the generation of bi-specific antibodies by modifying amino acid residues at the Fc interface and at the CH1:CL interface of light-heavy chain pairs that reduce the ability of the light chain of one pair to interact with the heavy chain of the other pair.

US Patent Publication No. 2014/0370020 (Chugai), describes regulating the association between the CH1 and CL regions of an antibody by substituting amino acids that exist on the interface between these regions with charged amino acids.

SUMMARY

Described herein is an isolated antigen binding polypeptide construct comprising at least a first heterodimer and a second heterodimer, the first heterodimer comprising a first immunoglobulin heavy chain polypeptide sequence (H1), and a first immunoglobulin light chain polypeptide sequence (L1); and the second heterodimer comprising a second immunoglobulin heavy chain polypeptide sequence (H2), and a second immunoglobulin light chain polypeptide sequence (L2), wherein at least one of the H1 or L1 sequences of the first heterodimer is distinct from the corresponding H2 or L2 sequence of the second heterodimer, and wherein H1 and H2 each comprise at least a heavy chain variable domain ($V_H$ domain) and a heavy chain constant domain ($C_{H1}$ domain); L1 and L2 each comprise at least a light chain variable domain ($V_L$ domain) and a light chain constant domain ($C_L$ domain); and at least one of H1, H2, L1 and L2 comprises at least one amino acid modification of at least one constant domain and/or at least one variable domain, wherein H1 preferentially pairs with L1 as compared to L2 and H2 preferentially pairs with L2 as compared to L1.

In some aspects, the construct further comprises a heterodimeric Fc, the Fc comprising at least two $C_{H3}$ sequences, wherein the Fc is coupled, with or without one or more linkers, to the first heterodimer and the second heterodimer, wherein the dimerized $C_{H3}$ sequences have a melting temperature (Tm) of about 68° C. or higher as measured by differential scanning calorimetry (DSC), and wherein the construct is bispecific.

In some aspects, the at least one amino acid modification is selected from at least one amino acid modification shown in the Tables or Examples.

In some aspects, H1 pairs preferentially with L1 as compared to L2, and H2 pairs preferentially with L2 as compared to L1, when H1, H2, L1 and L2 are co-expressed in a cell or a mammalian cell, or when H1, H2, L1 and L2 are co-expressed in a cell-free expression system, or when H1, H2, L1 and L2 are co-produced, or when H1, H2, L1 and L2 are co-produced via a redox production method.

In some aspects, at least one of H1, H2, L1 and L2 comprises at least one amino acid modification of a $V_H$ and/or $V_L$ domain and at least one amino acid modification of a $C_{H1}$ and/or CL domain such that H1 pairs preferentially with L1 as compared to L2, and/or H2 pairs preferentially with L2 as compared to L1.

In some aspects, if H1 comprises at least one amino acid modification in the $C_{H1}$ domain, then at least one of L1 and L2 comprise at least one amino acid modification in the $C_L$ domain; and/or if H1 comprises at least one amino acid modification in the $V_H$ domain, then at least one of L1 and L2 comprise at least one amino acid modification in the $V_L$ domain.

In some aspects, H1, L1, H2, and/or L2 comprises at least 1, 2, 3, 4, 5, 6, 7, 8, 9, or 10 amino acid mutations. In some aspects, at least one of H1, H2, L1 and L2 comprises at least 2, 3, 4, 5, 6, 7, 8, 9, or 10 amino acid modifications of at least one constant domain and/or at least one variable domain.

In some aspects, when both L1 and L2 are co-expressed with at least one of H1 and H2, the relative pairing of the at least one of H1-L1 and H2-L2 heterodimer pair to that of the respective corresponding H1-L2 or H2-L1 heterodimer pair is greater than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%, and wherein the relative pairing of the modified H1-L1 or H2-L2 heterodimer pair is greater than the respective relative pairing observed in the corresponding H1-L1 or H2-L2 heterodimer pair without the at least one amino acid modification.

In some aspects, the thermal stability as measured by the melting temperature (Tm) as measured by DSF of at least one of the first and second heterodimers is within about 0, 1, 2, 3, 4, 5, 6, 7, 8, 9, or 10° C. of the Tm of the corresponding heterodimer without the at least one amino acid modification. In some aspects, the thermal stability as measured by the melting temperature (Tm) as measured by DSF of each heterodimer comprising at least one amino acid modification is within about 0, 1, 2, 3, 4, 5, 6, 7, 8, 9, or 10° C. of the Tm of the corresponding heterodimer without the at least one amino acid modification. In some embodiments, the thermal stability as measured by the melting temperature (Tm) as measured by DSF of each heterodimer comprising at least one amino acid modification is within about 0, 1, 2, or 3° C. of the Tm of the corresponding heterodimer without the at least one amino acid modification.

In some aspects, the affinity of each heterodimer for the antigen to which it binds is within about 1, 2, 3, 4, 5, 6, 7, 8, 9, 10-fold of the affinity of the respective unmodified heterodimer for the same antigen as measured by surface plasmon resonance (SPR) or FACS.

In some aspects, at least one of H1 and L1 comprises at least one domain comprising at least one amino acid modification resulting in greater steric complementarity of amino acids when H1 pairs with L1 as compared to L2. In some aspects, at least one of H2 and L2 comprises at least one domain comprising at least one amino acid modification resulting in greater steric complementarity of amino acids when H2 pairs with L2 as compared to L1. In some aspects, at least one of H1 and L1 comprises at least one domain comprising at least one amino acid modification resulting in greater electrostatic complementarity between charged amino acids when H1 pairs with L1 as compared to L2. In some aspects, at least one of H2 and L2 comprises at least one domain comprising at least one amino acid modification resulting in greater electrostatic complementarity between charged amino acids when H2 pairs with L2 as compared to L1.

In some aspects, the at least one amino acid modification of is a set of mutations shown in at least one of the Tables or Examples.

In some aspects, the construct further comprises an Fc comprising at least two CH3 sequences, wherein the Fc is coupled, with or without one or more linkers, to the first heterodimer and the second heterodimer.

In some aspects, the Fc is a human Fc, a human IgG1 Fc, a human IgA Fc, a human IgG Fc, a human IgD Fc, a human IgE Fc, a human IgM Fc, a human IgG2 Fc, a human IgG3 Fc, or a human IgG4 Fc. In some aspects, the Fc is a heterodimeric Fc. In some aspects, the Fc comprises one or more modifications in at least one of the $C_{H3}$ sequences. In some aspects, the dimerized $C_{H3}$ sequences have a melting temperature (Tm) as measured by DSC of about 68, 69, 70, 71, 72, 73, 74, 75, 76, 77, 77.5, 78, 79, 80, 81, 82, 83, 84, or 85° C. or higher. In some aspects, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when produced; or wherein the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed or when expressed via a single cell. In some aspects, the Fc comprises one or more modifications in at least one of the $C_{H3}$ sequences that promote the formation of a heterodimeric Fc with stability comparable to a wild-type homodimeric Fc. In some aspects, the Fc further comprises at least one $C_{H2}$ sequence. In some aspects, the $C_{H2}$ sequence(s) of the Fc comprises one or more modifications. In some aspects, the Fc comprises one or more modifications to promote selective binding of Fc-gamma receptors.

In some embodiments, the Fc comprises:
  i) a heterodimeric IgG1 Fc having the modifications L351Y_F405A_Y407V in the first Fc polypeptide, and the modifications T366L_K392M_T394W in the second Fc polypeptide;
  ii) a heterodimeric IgG1 Fc having the modifications L351Y_F405A_Y407V in the first Fc polypeptide, and the modifications T366L_K392L_T394W in the second Fc polypeptide;
  iii) a heterodimeric IgG1 Fc having the modifications T350V_L351Y_F405A_Y407V in the first Fc polypeptide, and the modifications T350V_T366L_K392L_T394W in the second Fc polypeptide;
  iv) a heterodimeric IgG1 Fc having the modifications T350V_L351Y_F405A_Y407V in the first Fc polypeptide, and the modifications T350V_T366L_K392M_T394W in the second Fc polypeptide; or
  v) a heterodimeric IgG1 Fc having the modifications T350V_L351Y_S400E_F405A_Y407V in the first Fc polypeptide, and the modifications T350V_T366L_N390R_K392M_T394W in the second Fc polypeptide.

In some aspects, the Fc is coupled to the heterodimers by one or more linkers, or wherein the Fc is coupled to H1 and H2 by one or more linkers. In some aspects, the one or more linkers are one or more polypeptide linkers. In some aspects, the one or more linkers comprises one or more antibody hinge regions. In some aspects, the one or more linkers comprises one or more IgG1 hinge regions. In some aspects, the one or more linkers comprises one or more modifications. In some aspects, the one or more modifications to the one or more linkers promote selective binding of Fc-gamma receptors.

In some aspects, the at least one amino acid modification is at least one amino acid mutation or wherein the at least one amino acid modification is at least one amino acid substitution.

In some aspects, the sequences of each of H1, H2, L1, and L2 are derived from human sequences.

In some aspects, the construct is multispecific or bispecific. In some aspects, the construct is multivalent or bivalent.

In some aspects, the heterodimers described herein preferentially pair to form a bi-specific antibody. For example, in some embodiments, the heavy chain polypeptide sequences H1 and H2 comprise a full length heavy chain sequence comprising a heavy chain constant domain ($C_{H1}$ domain), a $C_{H2}$ domain, and a $C_{H3}$ domain. In some embodiments, the percentage of the correctly paired heavy and light chains in the bi-specific antibody (e.g., H1-L1:H2-L2) is greater than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

Also described herein is an isolated polynucleotide or set of isolated polynucleotides comprising at least one sequence that encodes a construct or a heavy chain or light chain described herein. In some aspects, the polynucleotide or set of polynucleotides is cDNA.

Also described herein is a vector or set of vectors comprising one or more of the polynucleotides or sets of polynucleotides described herein. In some aspects, the vector or set of vectors is selected from the group consisting of a plasmid, a multi-cistronic vector, a viral vector, a non-episomal mammalian vector, an expression vector, and a recombinant expression vector.

Also described herein is an isolated cell comprising a polynucleotide or set of polynucleotides described herein or a vector or set of vectors described herein. In some aspects, the cell is a hybridoma, a Chinese Hamster Ovary (CHO) cell, or a HEK293 cell.

Also described herein is a pharmaceutical composition comprising a construct described herein and a pharmaceutically acceptable carrier. In some aspects, the composition further comprises one or more substances selected from the group consisting of a buffer, an antioxidant, a low molecular weight molecule, a drug, a protein, an amino acid, a carbohydrate, a lipid, a chelating agent, a stabilizer, and an excipient.

Also described herein is a use of a construct described herein or a pharmaceutical composition described herein for the treatment of a disease or disorder or cancer or vascular disease in a subject or in the manufacture of a medicine.

Also described herein is a method of treatment of a subject having a disease or disorder or cancer or vascular disease comprising administering to the subject a construct described herein or a composition described herein.

Also described herein is a method of obtaining a construct described herein from a host cell culture, the method comprising the steps of: (a) obtaining a host cell culture comprising at least one host cell comprising one or more nucleic acid sequences encoding the construct; and (b) recovering the construct from the host cell culture.

Also described herein is a method of obtaining a construct described herein comprising the steps of: (a) obtaining H1, L1, H2, and L2; (b) allowing H1 to pair preferentially with L1 as compared to L2 and H2 to pair preferentially with L2 as compared to L1; and (c) obtaining the construct.

Also described herein is a method of preparing a construct described herein comprising: obtaining a polynucleotide or set of polynucleotides encoding at least one construct; determining the optimal ratios of each of the polynucleotide or set of polynucleotides for introduction into at least one host cell, wherein the optimal ratios are determined by assessing the amount of H1-L1 and H2-L2 heterodimer pairs formed upon expression of H1, L1, H2, and L2 as compared to mispaired H1-L2 and H2-L1 heterodimer pairs formed upon expression of H1, L1, H2, and L2; selecting a preferred optimal ratio, wherein transfection of at least one host cell with the preferred optimal ratio of the polynucleotide or set of polynucleotides results in expression of the construct; transfecting the at least one host cell with the optimal ratio of the polynucleotide or set of polynucleotides; and culturing the at least one host cell to express the construct.

In some aspects, selecting the optimal ratio is assessed by transfection in a transient transfection system. In some aspects, transfection of the at least one host cell with the preferred optimal ratio of the polynucleotide or set of polynucleotides results in optimal expression of the construct. In some aspects, the construct comprises an Fc comprising at least two $C_{H3}$ sequences, wherein the Fc is coupled, with or without one or more linkers, to the first heterodimer and the second heterodimer. In some aspects, the Fc is a heterodimer, optionally comprising one or more amino acid modifications.

Also described herein is a computer-readable storage medium storing a dataset comprising data representing complementary mutations in a first heterodimer comprising a first immunoglobulin heavy chain polypeptide sequence (H1) and a first immunoglobulin light chain polypeptide sequence (L1); and a second heterodimer comprising a second immunoglobulin heavy chain polypeptide sequence (H2) and a second immunoglobulin light chain polypeptide sequence (L2), wherein H1 and H2 each comprise at least a heavy chain variable domain ($V_H$ domain) and a heavy chain constant domain ($C_{H1}$ domain); wherein L1 and L2 each comprise at least a light chain variable domain ($V_L$ domain) and a light chain constant domain ($C_L$ domain), and wherein the dataset of complementary mutations comprises data representing those mutations listed in the Tables or Examples or a subset of those mutations; and computer executable code for determining the likelihood that H1 will pair preferentially with L1 as compared to L2 and/or H2 will pair preferentially with L2 as compared to L1.

Also described herein is a computer implemented method for determining preferential pairing, comprising: obtaining a dataset comprising data representing complementary mutations in a first heterodimer comprising a first immunoglobulin heavy chain polypeptide sequence (H1) and a first immunoglobulin light chain polypeptide sequence (L1); and a second heterodimer comprising a second immunoglobulin heavy chain polypeptide sequence (H2) and a second immunoglobulin light chain polypeptide sequence (L2), wherein H1 and H2 each comprise at least a heavy chain variable domain ($V_H$ domain) and a heavy chain constant domain ($C_{H1}$ domain); wherein L1 and L2 each comprise at least a light chain variable domain ($V_L$ domain) and a light chain constant domain ($C_L$ domain), and wherein the dataset of complementary mutations comprises data representing those mutations listed in the Tables or Examples or a subset of those mutations; and determining, by a computer processor, the likelihood that H1 will pair preferentially with L1 as compared to L2 and/or H2 will pair preferentially with L2 as compared to L1. In some aspects, the method further comprises producing a construct described herein.

Also described herein is a method of producing a bi-specific antigen binding polypeptide construct, said bi-specific construct comprising a first heterodimer comprising a first immunoglobulin heavy chain polypeptide sequence (H1), and a first immunoglobulin light chain polypeptide sequence (L1) from a first mono-specific antigen binding polypeptide; and a second heterodimer comprising a second immunoglobulin heavy chain polypeptide sequence (H2), and a second immunoglobulin light chain polypeptide sequence (L2) from a second mono-specific antigen binding polypeptide, wherein H1 and H2 each comprise at least a heavy chain variable domain ($V_H$ domain) and a heavy chain constant domain ($C_{H1}$ domain); wherein L1 and L2 each comprise at least a light chain variable domain ($V_L$ domain) and a light chain constant domain ($C_L$ domain), the method comprising: introducing one or more complementary mutations from the dataset described herein into the first heterodimer and/or the second heterodimer; and co-expressing the first heterodimer and the second heterodimer in at least one host cell to produce an expression product comprising the bi-specific construct.

In some aspects, the method further comprises determining the amount of the bi-specific construct in the expression product relative to other polypeptide products to select a preferred subset of complementary mutations. In some aspects, the bi-specific construct is produced with a purity of greater than 70% (e.g., greater than 75%, 80%, 85%, 90%, 91%, 92%, 93%, 94%, 95%, 96%, 97%, 98%, or 99%) compared to the other polypeptide products. In some aspects, the dataset is a dataset described herein. In some aspects, the method further comprises the step of adding additional amino acid modifications to at least one of H1, H2, L1, or L2 to increase the purity of the bi-specific construct compared to the other polypeptide products. In some aspects, the construct comprises an Fc comprising at least two $C_{H3}$ sequences, wherein the Fc is coupled, with or without one or more linkers, to the first heterodimer and the second heterodimer. In some aspects, the Fc is a heterodimer, optionally comprising one or more amino acid modifications. In some aspects, the antigen binding polypeptide is an antibody, a Fab, or a scFv.

In some embodiments of the construct, H1 and/or H2 comprises at least one or a set of amino acid modifications at L124, K145, D146, Q179, and S186, and L1 and/or L2 comprises at least one or a set of amino acid modifications at Q124, S131, V133, Q160, S176, T178, and T180. For example, in some embodiments, H1 and/or H2 comprises at least one or a set of amino acid modifications selected from L124R, L124E, K145M, K145T, D146N, Q179E, Q179K, S186R, and S186K, and L1 and/or L2 comprises at least one or a set of amino acid modifications selected from Q124E, S131R, S131K, V133G, Q160E, S176R, S176D, T178D, T178E, and T180E. In some embodiments, H1 comprises amino acid modifications selected from the group consisting of L124E, K145M, K145T, and Q179E, or a combination thereof; L1 comprises amino acid modifications selected from the group consisting of S131R, S131K, V133G, and S176R, or a combination thereof; H2 comprises amino acid modifications selected from the group consisting of L124R, D146N, Q179K, S186R, and S186K, or a combination thereof; and L2 comprises amino acid modifications selected from the group consisting of Q124E, V133G, Q160E, S176D, T178D, T178E, and T180E, or a combination thereof. In some embodiments, H1 comprises the amino acid modifications L124E, K145T, and Q179E; L1 comprises the amino acid modifications S131K, V133G, and S176R; H2 comprises the amino acid modifications L124R and S186R; and L2 comprises the amino acid modifications V133G, S176D, and T178D.

In some embodiments of the construct, H1 and/or H2 comprises at least one or a set of amino acid modifications at L124, L143, K145, D146, Q179, and S186; and L1 and/or L2 comprises at least one or a set of amino acid modifications at Q124, V133, Q160, S176, T178, and T180. In some embodiments, H1 and/or H2 comprises at least one or a set of amino acid modifications selected from L124E, L124R, L143E, L143D, K145T, K145M, D146N, Q179K, S186R, and S186K; and L1 and/or L2 comprises at least one or a set of amino acid modifications selected from Q124K, Q124E, V133G, Q160K, S176R, S176D, T178E, T178K, T178R, T178D, and T180E. In some embodiments, H1 comprises amino acid modifications selected from the group consisting of L124E, L143E, L143D, K145T, and K145M, or combinations thereof; L1 comprises amino acid modifications selected from the group consisting of Q124K, V133G, Q160K, S176R, T178K, and T178R, or combinations thereof; H2 comprises amino acid modifications selected from the group consisting of L124R, D146N, Q179K, S186R, and S186K, or combinations thereof; and L2 comprises amino acid modifications selected from the group consisting of Q124E, V133G, S176D, T178E, T178D, and T180E, or combinations thereof. In some embodiments, H1 comprises the amino acid modifications L124E, L143E, and K145T; L1 comprises the amino acid modifications Q124K, V133G, and S176R; H2 comprises the amino acid modifications L124R and Q179K; and L2 comprises the amino acid modifications V133G, S176D, and T178E. In some embodiments, H1 comprises the amino acid modifications L124E, L143E, and K145T; L1 comprises the amino acid modifications Q124K, V133G, and S176R; H2 comprises the amino acid modifications L124R and S186R; and L2 comprises the amino acid modifications V133G, S176D, and T178D.

In some embodiments of the construct, H1 and/or H2 comprises at least one or a set of amino acid modifications at Q39, L45, L124, L143, F122, and H172, and L1 and/or L2 comprises at least one or a set of amino acid modifications at Q38, P44, Q124, S131, V133, N137, S174, S176, and T178. In some embodiments, H1 and/or H2 comprises at least one or a set of amino acid modifications selected from Q39E, Q39R, L45P, F122C, L124E, L124R, L143F, H172T, and H172R; and L1 and/or L2 comprises at least one or a set of amino acid modifications selected from Q38R, Q38E, P44F, Q124C, S131T, S131E, V133G, N137K, S174R, S176R, S176K, S176D, T178Y, and T178D. In some embodiments, H1 comprises amino acid modifications selected from the group consisting of Q39E, L45P, F122C, L124E, L143F, H172T, and H172R or combinations thereof; L1 comprises amino acid modifications selected from the group consisting of Q38R, P44F, Q124C, S131T, V133G, N137K, S174R, S176R, S176K, and T178Y, or combinations thereof; H2 comprises amino acid modifications selected from the group consisting of Q39R, L124R, and H172R, or combinations thereof; and L2 comprises amino acid modifications selected from the group consisting of Q38E, S131E, V133G, S176D, and T178D, or combinations thereof. In some embodiments, H1 comprises the amino acid modifications Q39E and L124E; L1 comprises the amino acid modifications Q38R, V133G, and S176R; H2 comprises the amino acid modifications Q39R and L124R; and L2 comprises the amino acid modifications Q38E, V133G, and S176D. In some embodiments, H1 comprises the amino acid modifications L45P and L124E; L1 comprises the amino acid modifications P44F, V133G, and S176R; H2 comprises the amino acid modification L124R; and L2 comprises the amino acid modifications V133G, S176D, and T178D. In some embodiments, H1 comprises the amino acid modifications L124E and L143F; L1 comprises the amino acid modifications V133G, and S176R; H2 comprises the amino acid modification L124R; and L2 comprises the amino acid modifications V133G, S176D, and T178D. In some embodiments, H1 comprises the amino acid modifications F122C and L124E; L1 comprises the amino acid modifications Q124C, V133G, and S176R; H2 comprises the amino acid modification L124R; and L2 comprises the amino acid modifications V133G and S176D. In some embodiments, H1 comprises the amino acid modifications L124E and H172T; L1 comprises the amino acid modifications V133G, N137K, S174R, and S176R; H2 comprises the amino acid modification L124R and H172R; and L2 comprises the amino acid modifications V133G, S176D, and T178D.

In some embodiments of the construct, H1 and/or H2 comprises at least one or a set of amino acid modifications at L124, A125, H172, and K228, and L1 and/or L2 comprises at least one or a set of amino acid modifications at S121, V133, N137, S174, S176, and T178. In some embodiments, H1 and/or H2 comprises at least one or a set of amino acid modifications selected from L124E, L124R, A125S, A125R, H172R, H172T, and K228D; and (ii) L1 and/or L2 comprises at least one or a set of amino acid modifications selected from S121K, V133G, N137K, S174R, S176K, S176R, S176D, and T178D. In some embodiments, H1 comprises amino acid modifications selected from the group consisting of L124E, A125S, H172R, and K228D or combinations thereof; L1 comprises amino acid modifications selected from the group consisting of S121K, V133G, and S176R, or combinations thereof; H2 comprises amino acid modifications selected from the group consisting of L124R, A125R, and H172T, or combinations thereof; and L2 comprises amino acid modifications selected from the group consisting of V133G, N137K, S174R, S176D, and T178D, or combinations thereof. In some embodiments, H1 comprises the amino acid modifications L124E and K228D; L1 comprises the amino acid modifications S121K, V133G, and S176R; H2 comprises the amino acid modifications L124R and A125R; and L2 comprises the amino acid modifications V133G and S176D. In some embodiments, H1 comprises the amino acid modifications L124E and H172R; L1 comprises the amino acid modifications V133G and S176R; H2 comprises the amino acid modifications L124R and H172T; and L2 comprises the amino acid modifications V133G, S174R, and S176D.

In some embodiments of the construct, H1 and/or H2 comprises at least one or a set of amino acid modifications at L124, A139, and V190, and L1 and/or L2 comprises at least one or a set of amino acid modifications at F116, V133, L135, and S176. In some embodiments, H1 and/or H2 comprises at least one or a set of amino acid modifications selected from L124E, L124R, A139W, A139G, and V190A; and L1 and/or L2 comprises at least one or a set of amino acid modifications selected from F116A, V133G, L135V, L135W, S176R, and S176D. In some embodiments, H1 comprises amino acid modifications selected from the group consisting of L124E and A139W, or combinations thereof; L1 comprises amino acid modifications selected from the group consisting of F116A, V133G, L135V, and S176R, or combinations thereof; H2 comprises amino acid modifications selected from the group consisting of L124R, A139G, and V190A, or combinations thereof; and L2 comprises amino acid modifications selected from the group consisting of V133G, L135W, and S176D, or combinations thereof. In some embodiments, H1 comprises the amino acid modifications L124E and A139W; L1 comprises the amino acid modifications F116A, V133G, L135V, and S176R; H2 comprises the amino acid modifications L124R, A139G, and V190A; and L2 comprises the amino acid modifications V133G, L135W, and S176D.

In some embodiments of the construct, H1 and/or H2 comprises at least one or a set of amino acid modifications at Q39, L45, K145, H172, Q179 and S186, and L1 and/or L2 comprises at least one or a set of amino acid modifications at Q38, P44, Q124, S131, Q160, T180 and C214. In some embodiments, H1 and/or H2 comprises at least one or a set of amino acid modifications selected from Q39E, Q39R, L45P, K145T, H172R, Q179E and S186R; and L1 and/or L2 comprises at least one or a set of amino acid modifications selected from Q38R, Q38E, P44F, Q124E, S131K, Q160E, T180E and C214S. In some embodiments, H1 comprises amino acid modifications selected from the group consisting of Q39E, L45P, K145T, H172R, and Q179E, or combinations thereof; L1 comprises amino acid modifications selected from the group consisting of Q38R, P44F, and S131K, or combinations thereof; H2 comprises amino acid modifications selected from the group consisting of Q39R, H172R, and S186R, or combinations thereof; and L2 comprises amino acid modifications selected from the group consisting of Q38E, Q124E, Q160E, T180E and C214S, or combinations thereof. In some embodiments, H1 comprises the amino acid modifications Q39E, K145T, and Q179E; L1 comprises the amino acid modifications Q38R and S131K; H2 comprises the amino acid modifications Q39R and S186R; and L2 comprises the amino acid modifications Q38E, Q124E, Q160E, and T180E. In some embodiments, H1 comprises the amino acid modifications L45P, K145T, H172R, and Q179E; L1 comprises the amino acid modifications P44F and S131K; H2 comprises the amino acid modifications H172R and S186R; and L2 comprises the amino acid modifications Q124E, Q160E, and T180E.

In some embodiments of the construct, H1 and/or H2 comprises at least one or a set of amino acid modifications at A139, L143, K145, Q179 and V190, and L1 and/or L2 comprises at least one or a set of amino acid modifications at F116, Q124, L135, Q160, T178, and T180. In some embodiments, H1 and/or H2 comprises at least one or a set of amino acid modifications selected from A139W, A139G, L143E, K145T, Q179E, Q179K, and V190A; and L1 and/or L2 comprises at least one or a set of amino acid modifications selected from F116A, Q124R, Q124E, L135V, L135W, Q160E, T178R, and T180E. In some embodiments, H1 comprises amino acid modifications selected from the group consisting of A139W, L143E, K145T, and Q179E, or combinations thereof; L1 comprises amino acid modifications selected from the group consisting of F116A, Q124R, L135V, and T178R, or combinations thereof; H2 comprises amino acid modifications selected from the group consisting of A139G, Q179K, and V190A, or combinations thereof; and L2 comprises amino acid modifications selected from the group consisting of Q124E, L135W, Q160E, and T180E, or combinations thereof. In some embodiments, H1 comprises the amino acid modifications A139W, L143E, K145T, and Q179E; L1 comprises the amino acid modifications F116A, Q124R, L135V, and T178R; H2 comprises the amino acid modification Q179K; and L2 comprises the amino acid modifications Q124E, L135W, Q160E, and T180E.

In some embodiments of the construct, H1 and/or H2 comprises at least one or a set of amino acid modifications at Q39, L143, K145, D146, H172, and Q179, and L1 and/or L2 comprises at least one or a set of amino acid modifications at Q38, Q124, Q160, T178, and T180. In some embodiments, H1 and/or H2 comprises at least one or a set of amino acid modifications selected from Q39E, Q39R, L143E, K145T, D146G, H172R, Q179E, and Q179K; and L1 and/or L2 comprises at least one or a set of amino acid modifications selected from Q38R, Q38E, Q124R, Q124E, Q160K, Q160E, T178R, and T180E. In some embodiments, H1 comprises amino acid modifications selected from the group consisting of Q39E, L143E, K145T, H172R, and Q179E, or combinations thereof; L1 comprises amino acid modifications selected from the group consisting of Q38R, Q124R, Q160K, and T178R, or combinations thereof; H2 comprises amino acid modifications selected from the group consisting of Q39R, H172R, and Q179K, or combinations thereof; and L2 comprises amino acid modifications selected from the group consisting of Q38E, Q124E, D146G, Q160E, and T180E, or combinations thereof. In some embodiments, H1 comprises the amino acid modifications Q39E, L143E, K145T, and Q179E; L1 comprises the amino acid modifications Q38R, Q124R, Q160K, and T178R; H2 comprises the amino acid modifications Q39R, H172R, and Q179K; and L2 comprises the amino acid modifications Q38E, Q124E, Q160E, and T180E.

In some embodiments of the construct, H1 and/or H2 comprises at least one or a set of amino acid modifications at L45, L143, K145, D146, H172, and Q179, and L1 and/or L2 comprises at least one or a set of amino acid modifications at Q38, P44, Q124, N137, Q160, S174, T178, T180, and C214. In some embodiments, H1 and/or H2 comprises at least one or a set of amino acid modifications selected from L45P, L143E, K145T, D146G, H172R, H172T, Q179E, and Q179K; and (ii) L1 and/or L2 comprises at least one or a set of amino acid modifications selected from Q38E, P44F, Q124R, Q124E, N137K, Q160K, Q160E, S174R, T178R, T180E, and C214S. In some embodiments, H1 comprises amino acid modifications selected from the group consisting of L45P, L143E, K145T, H172R, and Q179E, or combinations thereof; L1 comprises amino acid modifications selected from the group consisting of P44F, Q124R, Q160K, and T178R, or combinations thereof; H2 comprises amino acid modifications selected from the group consisting of D146G, H172R, H172T, and Q179K, or combinations thereof; and L2 comprises amino acid modifications selected from the group consisting of Q38E, Q124E, N137K, Q160E, S174R, T180E, and C214S, or combinations thereof. In some embodiments, H1 comprises the amino acid modifications L45P, L143E, and K145T; L1 comprises the amino acid modifications P44F, Q124R, Q160K, and T178R; H2 comprises the amino acid modifications D146G and Q179K; and L2 comprises the amino acid modifications Q38E, Q124E, Q160E, and T180E. In some embodiments, H1 comprises the amino acid modifications L143E, K145T, and H172R; L1 comprises the amino acid modifications Q124R, Q160K, and T178R; H2 comprises the amino acid modifications H172T and Q179K; and L2 comprises the amino acid modifications Q124E, Q160E, N137K, S174R, and T180E.

In some embodiments of the construct, H1 and/or H2 comprises at least one or a set of amino acid modifications at L124, L143, K145, and Q179, and L1 and/or L2 comprises at least one or a set of amino acid modifications at Q124, S131, V133, S176, T178, and T180. In some embodiments, H1 and/or H2 comprises at least one or a set of amino acid modifications selected from L124W, L124A, L143E, L143F, K145T, Q179E, and Q179K; and L1 and/or L2 comprises at least one or a set of amino acid modifications selected from Q124R, Q124K, Q124E, S131K, V133A, V133W, S176T, T178R, T178L, T178E, and T180E. In some embodiments, H1 comprises amino acid modifications selected from the group consisting of L124W, L143E, K145T, and Q179E, or combinations thereof; L1 comprises amino acid modifications selected from the group consisting of Q124R, Q124K, S131K, V133A, S176T, T178R, and T178L, or combinations thereof; H2 comprises amino acid modifications selected from the group consisting of L124A, L143F, and Q179K, or combinations thereof; and L2 comprises amino acid modifications selected from the group consisting of Q124E, V133W, S176T, T178L, T178E, and T180E, or combinations thereof. In some embodiments, H1 comprises the amino acid modifications L124W, L143E, K145T, and Q179E; L1 comprises the amino acid modifications Q124R, V133A, S176T, and T178R; H2 comprises the amino acid modifications L124A, L143F, and Q179K; and L2 comprises the amino acid modifications Q124E, V133W, S176T, T178L, and T180E.

In some embodiments of the construct, H1 and/or H2 comprises at least one or a set of amino acid modifications at A139, L143, K145, Q179, and S186, and L1 and/or L2 comprises at least one or a set of amino acid modifications at F116, Q124, V133, Q160, T178, and T180. In some embodiments, H1 and/or H2 comprises at least one or a set of amino acid modifications selected from A139C, L143E, L143D, L143R, L143K, K145T, Q179E, Q179D, Q179R, Q179K, S186K, S186R; and L1 and/or L2 comprises at least one or a set of amino acid modifications selected from F116C, Q124R, Q124K, Q124E, V133E, V133D, Q160K, Q160E, T178R, T178K, T178E, and T180E. In some embodiments, H1 comprises amino acid modifications selected from the group consisting of A139C, L143E, L143D, K145T, Q179E, and Q179D, or combinations thereof; L1 comprises amino acid modifications selected from the group consisting of F116C, Q124R, Q124K, Q160K, T178R, and T178K, or combinations thereof; H2 comprises amino acid modifications selected from the group consisting of L143R, L143K, Q179R, Q179K, S186K, and S186R, or combinations thereof; and L2 comprises amino acid modifications selected from the group consisting of Q124E, V133E, V133D, Q160E, T178E, and T180E, or combinations thereof. In some embodiments, H1 comprises the amino acid modifications A139C, L143E, K145T, and Q179E; L1 comprises the amino acid modifications F116C, Q124R, and T178R; H2 comprises the amino acid modification Q179K; and L2 comprises the amino acid modifications Q124E, Q160E, and T180E. In some embodiments, H1 comprises the amino acid modifications L143E, K145T, and Q179E; L1 comprises the amino acid modifications Q124R and T178R; H2 comprises the amino acid modification S186K; and L2 comprises the amino acid modifications Q124E, Q160E, and T178E. In some embodiments, H1 comprises the amino acid modifications L143E, K145T, and Q179E; L1 comprises the amino acid modifications Q124R and T178R; H2 comprises the amino acid modification L143R; and L2 comprises the amino acid modifications Q124E and V133E.

In some embodiments of the construct, H1 and/or H2 comprises at least one or a set of amino acid modifications at L124, L143, K145, D146, Q179, S186, and S188, and L1 and/or L2 comprises at least one or a set of amino acid modifications at Q124, S131, V133, Q160, S176, T178, and T180. In some embodiments, H1 and/or H2 comprises at least one or a set of amino acid modifications selected from L124A, L143A, L143R, L143E, L143K, K145T, D146G, Q179R, Q179E, Q179K, S186R, S186K, and S188L; and L1 and/or L2 comprises at least one or a set of amino acid modifications selected from Q124R, Q124E, S131E, S131T, V133Y, V133W, V133E, V133D, Q160E, Q160K, Q160M, S176L, T178R, T178E, T178F, T178Y, and T180E. In some embodiments, H1 comprises amino acid modifications selected from the group consisting of L143E, K145T, Q179E, and S188L, or combinations thereof; L1 comprises amino acid modifications selected from the group consisting of Q124R, Q160K, and T178R, or combinations thereof; H2 comprises amino acid modifications selected from the group consisting of L124A, L143A, L143R, L143K, D146G, Q179R, Q179K, S186R, and S186K, or combinations thereof; and L2 comprises amino acid modifications selected from the group consisting of Q124E, S131E, S131T, V133Y, V133W, V133E, V133D, Q160E, Q160M, S176L, T178E, T178F, T178Y, and T180E, or combinations thereof. In some embodiments, H1 comprises the amino acid modifications L143E, K145T, Q179E, and S188L; L1 comprises the amino acid modifications Q124R and T178R; H2 comprises the amino acid modification S186K; and L2 comprises the amino acid modifications Q124E, S176L, and T180E. In some embodiments, H1 comprises the amino acid modifications L143E, K145T, Q179E, and S188L; L1 comprises the amino acid modifications Q124R and T178R; H2 comprises the amino acid modification S186K; and L2 comprises the amino acid modifications Q124E, S131T, T178Y, and T180E. In some embodiments, H1 comprises the amino acid modifications L143E and K145T; L1 comprises the amino acid modifications Q124R, Q160K, and T178R; H2 comprises the amino acid modification S186K; and L2 comprises the amino acid modifications S131E. In some embodiments, H1 comprises the amino acid modifications L143E and K145T; L1 comprises the amino acid modification Q124R; H2 comprises the amino acid modification L143R; and L2 comprises the amino acid modifications Q124E and V133E.

In some embodiments of the construct, H1 comprises at least one or a set of amino acid modifications at F122 and C233, and L1 comprises at least one or a set of amino acid modifications at Q124 and C214. In some embodiments, H1 comprises at least one or a set of amino acid modifications selected from F122C and C233S; and L1 comprises at least one or a set of amino acid modifications selected from Q124C and C214S. In some embodiments, H1 comprises amino acid modifications selected from the group consisting of F122C and C233S, or combinations thereof; L1 comprises amino acid modifications selected from the group consisting of Q124C and C214S, or combinations thereof; H2 comprises a wild-type or unmodified amino acid sequence; and L2 comprises a wild-type or unmodified amino acid sequence. In some embodiments, H1 comprises the amino acid modifications F122C and C233S; L1 comprises the amino acid modifications Q124C and C214S; H2 comprises a wild-type or unmodified amino acid sequence; and L2 comprises a wild-type or unmodified amino acid sequence.

In some embodiments, the construct comprises amino acid modifications selected from SMCA designs 9561-9095_1, 9561-9095_2, 9121-9373_1, 9121-9373_2, 9116-9349_1, 9116-9349_2, 9134-9521_1, 9134-9521_2, 9286-9402_1, 9286-9402_2, 9667-9830_1, 9667-9830_2, 9696-9848_1, 9696-9848_2, 9060-9756_1, 9060-9756_2, 9682-9740_1, 9682-9740_2, 9049-9759_1, 9049-9759_2, 9820-9823_1, and 9820-9823_2 of the Tables herein. In some embodiments, the construct comprises amino acid modifications selected from SMCA designs 9327-6054_1, 9815-9825_1, 9815-9825_2, 9587-9735_1, 9587-9735_2, 3522_1, 3522_2, 3519_1, and 3519_2 of the Tables herein.

In some embodiments, H1 and/or H2 does not comprise an amino acid modification at position Q179. In some embodiments, H1 does not comprise the amino acid modification Q179E and/or H2 does not comprise the amino acid modification Q179K. In some embodiments, L1 does not comprise an amino acid modification at position S131. In one embodiment, L1 does not comprise the amino acid modification S131K. In some embodiments, L2 does not comprise an amino acid modification at position T180. In one embodiment, L2 does not comprise the amino acid modification T180E. In some embodiments, the construct does not comprise a combination of amino acid modifications wherein H1 comprises Q179E, L1 comprises S131K, H2 comprises Q179K, and L2 comprises T180E.

In some embodiments, H1 does not comprise an amino acid modification at position Q39 and/or Q179. In some embodiments, H1 does not comprise the amino acid modification Q39E and/or Q179E. In some embodiments, L1 does not comprise an amino acid modification at position Q160. In one embodiment, L1 does not comprise the amino acid modification Q160K. In some embodiments, H2 does not comprise an amino acid modification at position Q179. In one embodiment, H2 does not comprise the amino acid modification Q179K. In some embodiments, L2 does not comprise an amino acid modification at position Q38, Q160, and/or T180. In one embodiment, L2 does not comprise the amino acid modifications Q38E, Q160E, and/or T180E. In some embodiments, the construct does not comprise a combination of amino acid modifications wherein H1 comprises Q39E and/or Q179E, L1 comprises Q160K, H2 comprises Q179K, and L2 comprises Q38E, Q160E and/or T180E. For example, in some embodiments, the construct does not comprise a combination of amino acid modifications wherein: (i) H1 comprises Q179E, L1 comprises Q160K, H2 comprises Q179K, and L2 comprises Q160E and T180E; (ii) H1 comprises Q39E and Q179E, L1 comprises Q160K, H2 comprises Q179K, and L2 comprises Q38E, Q160E and T180E; or (iii) H1 comprises Q39E, L1 comprises Q160K, H2 comprises Q179K, and L2 comprises Q38E, Q160E and T180E.

In some embodiments, H1 does not comprise an amino acid modification at position Q179. In some embodiments, H1 does not comprise the amino acid modification Q179K or Q179E. In some embodiments, L1 does not comprise an amino acid modification at position Q160 and/or T180. In one embodiment, L1 does not comprise the amino acid modification Q160E, Q160K, and/or T180E. In some embodiments, H2 does not comprise an amino acid modification at position Q179. In one embodiments, H2 does not comprise the amino acid modification Q179K or Q179E. In some embodiments, L2 does not comprise an amino acid modification at position Q160 and/or T180. In one embodiment, L2 does not comprise the amino acid modifications Q160K, Q160E, and/or T180E. In some embodiments, the construct does not comprise a combination of amino acid modifications wherein H1 comprises Q179K or Q179E, L1 comprises Q160E, Q160K, and/or T180E, H2 comprises Q179K or Q179E, and L2 comprises Q160K, Q160E, and/or T180E.

In some embodiments, H1 and/or H2 does not comprise an amino acid modification at position Q179. In some embodiments, H1 does not comprise the amino acid modification Q179K and/or H2 does not comprise the amino acid modification Q179E. In some embodiments, L1 does not comprise an amino acid modification at position T180. In one embodiment, L1 does not comprise the amino acid modification T180E. In some embodiments, L2 does not comprise an amino acid modification at position S131. In one embodiment, L2 does not comprise the amino acid modification S131K. In some embodiments, the construct does not comprise a combination of amino acid modifications wherein H1 comprises Q179K, L1 comprises T180E, H2 comprises Q179E, and L2 comprises S131K.

In some embodiments, H1 does not comprise an amino acid modification at position Q179. In some embodiments, H1 does not comprise the amino acid modification Q179E. In some embodiments, L1 does not comprise an amino acid modification at position Q160. In one embodiment, L1 does not comprise the amino acid modification Q160K. In some embodiments, H2 does not comprise an amino acid modification at position Q179. In one embodiment, H2 does not comprise the amino acid modification Q179K. In some embodiments, L2 does not comprise an amino acid modification at position T180. In one embodiment, L2 does not comprise the amino acid modification T180E. In some embodiments, the construct does not comprise a combination of amino acid modifications wherein H1 comprises Q179E, L1 comprises Q160K, H2 comprises Q179K, and L2 comprises T180E.

In some embodiments, H1 does not comprise an amino acid modification at position A139. In some embodiments, H1 does not comprise the amino acid modification A139C. In some embodiments, L1 does not comprise an amino acid modification at position F116. In one embodiment, L1 does not comprise the amino acid modification F116C. In some embodiments, the construct does not comprise a combination of amino acid modifications wherein H1 comprises A139C and L1 comprises F116C.

In some embodiments, the construct does not comprise native disulfide linkages between the heavy and light chains. For example, in some embodiments, the cysteine at position 214 of L1 and/or L2 is modified to another amino acid. In some embodiments, L1 and/or L2 comprises the amino acid modification C214S. In some embodiments, the cysteine at position 233 of H1 and/or H2 is modified to another amino acid. In one embodiment, H1 and/or H2 comprises the amino acid modification C233S.

The embodiments described herein are applicable to constructs in the Fab format and full antibody format.

BRIEF DESCRIPTION OF THE FIGURES

FIG. 1A-E depicts D3H44 heavy chain and light chain amino acid sequences aligned against canonical human germline sequences for Variable, Constant and J-region segments (Notations in figures: * sequence identity). FIG. 1A depicts Human VH germline subgroups (one representative sequence is displayed for each family; SEQ ID Nos 14-21 and 62-67). Sequence identity based on an alignment of D3H44 against VH3 and IGHJ3*02. FIG. 1B depicts Human kappa VL germline subgroups (one representative sequence is displayed from each family; SEQ ID Nos 22-28 and 68-72). Sequence identity based on an alignment of D3H44 against VKI and IGKJ1*01. FIG. 1C depicts Human lambda VL germline subgroups (one representative sequence is displayed from each family; SEQ ID Nos. 29-39 and 73-79). Sequence identity based on an alignment of D3H44 against VL1 and IGLJ1*01. FIG. 1D depicts human CH1 allele sequences (SEQ ID Nos. 40-49). FIG. 1E depicts Human kappa (SEQ ID Nos. 50-55) and lambda allele sequences (SEQ ID Nos. 56-61).

FIG. 3 depicts an exemplary set of H1, L1, H2, L2 chains which have been designed such that H1 preferentially pairs with L1 over L2 and H2 preferentially pairs with L2 over L1. A cartoon representation of the 3D crystal structure of the variable region heavy and light chain interface is presented. The mutations introduced at the interface achieve electrostatic and steric complementarity for the preferentially forming obligate pairs H1-L1 and H2-L2, respectively. On the other hand, there is unfavorable steric and electrostatic mismatch in the incorrect pair that would result in reduced pairing propensity for the mismatched pair as well as reduced stability.

FIGS. 10A-10F. shows representative UPLC-SEC profiles for WT heterodimeric as well as engineered heterodimeric antibodies. FIGS. 10A and 10B refers to D3H44/trastuzumab WT and 9060-9756_1, respectively. FIGS. 10C and 10D refers to D3H44/Cetuximab WT and 9820-9823_1, respectively. FIGS. 10E and 10F refers to trastuzumab/cetuximab WT and 9696-9848_1, respectively.

FIGS. 11a-11h depict box plots of the changes in the % of the correctly paired Fab component over all mispaired Fab components utilizing the same heavy chain (H1:L1 over all H1 species with respect to wild type for D3H44/trastuzumab and D3H44/cetuximab; the change of H2:L2 over all H2 species with respect to wild type for trastuzumab/cetuximab) as well as changes in the percentage of the desired bispecific antibody with respect to wild type, for engineered bispecific antibody samples per cluster. Changes in the % of the correctly paired Fab component over all mispaired Fab components utilizing the same heavy chain vs cluster are shown for each system in a) D3H44/trastuzumab, c) D3H44/cetuximab and e) trastuzumab/cetuximab. Changes in the percentage of the desired bispecific antibody with respect to wild type vs cluster are shown for each system in b) D3H44/trastuzumab, d) D3H44/cetuximab and f) trastuzumab/cetuximab. Across all bispecific systems, changes in the % of the correctly paired Fab component over all mispaired Fab components utilizing the same heavy chain vs cluster are shown in FIG. 11g and changes in the percentage of the desired bispecific antibody with respect to wild type vs cluster are shown in FIG. 11h. Note that the values reported also include estimated changes for engineered bispecific antibody samples where the corresponding wild type constructs were not assessed by SMCA.

DETAILED DESCRIPTION

Figure 2:
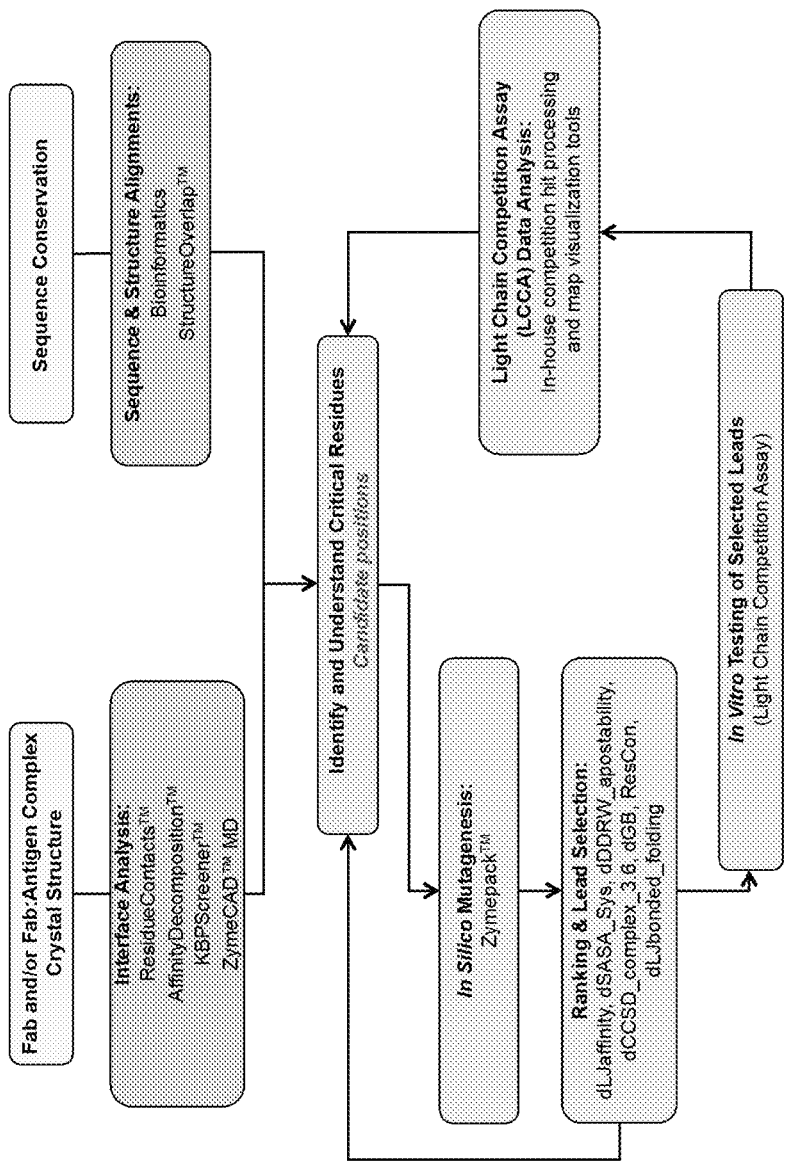
FIG. 2 depicts a flowchart for identifying critical interface residues and for computational modeling of designs with preferential heavy-light chain pairing.

Provided herein are antigen binding polypeptide constructs (also referred to as heterodimer pairs) which can comprise a first heterodimer and a second heterodimer wherein each heterodimer comprises an immunoglobulin heavy chain or fragment thereof and an immunoglobulin light chain. Both of the heterodimers can comprise one or more amino acid modifications in the immunoglobulin heavy chain constant domain 1 (CH1) and one or more amino acid modifications in the immunoglobulin light chain constant domain (CL); one or more amino acid modifications in the immunoglobulin heavy chain variable domain (VH) and one or more amino acid modifications in the immunoglobulin light chain variable domain (VL); or a combination of the preceding amino acid modifications to both the constant and variable domains of the heavy and light chains. The amino acids that are modified are typically part of the interface between the light chain and heavy chain and are modified to create preferential pairing between each heavy chain and the desired light chain such that the heavy chain of the first heterodimer preferentially pairs with one of the light chains rather than the other. Likewise, the heavy chain of the second heterodimer can preferentially pair with the second light chain rather than first.

As noted above, specific combinations of the amino acid modifications described herein promote preferential pairing of heavy chains with specific light chains, thus enabling bi-specific monoclonal antibody (Mab) expression to occur with negligible or limited mispairing, and minimizing the need to purify the desired heterodimers from undesired, or mispaired products. The heterodimers can exhibit comparable thermal stability to heterodimers that do not include the amino acid modifications, and can also demonstrate binding affinity for antigen that is comparable to heterodimers that do not include the amino acid modifications. The designs of the first and second heterodimers, can be used to create bi-specific antibodies targeting two different therapeutic targets or targeting two distinct epitopes (overlapping or non-overlapping) within the same antigen.

Also provided herein are methods of preparing the heterodimer pairs.

Definitions

Unless defined otherwise, all technical and scientific terms used herein have the same meaning as is commonly understood by one of skill in the art to which the claimed subject matter belongs. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise.

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, "about" means 10% of the indicated range, value, sequence, or structure, unless otherwise indicated. It should be understood that the terms "a" and "an" as used herein refer to "one or more" of the enumerated components unless otherwise indicated or dictated by its context. The use of the alternative (e.g., "or") should be understood to mean either one, both, or any combination thereof of the alternatives. As used herein, the terms "include" and "comprise" are used synonymously. In addition, it should be understood that the individual single chain polypeptides or immunoglobulin constructs derived from various combinations of the structures and substituents described herein are disclosed by the present application to the same extent as if each single chain polypeptide or heterodimer were set forth individually. Thus, selection of particular components to form individual single chain polypeptides or heterodimers is within the scope of the present disclosure The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

In the present application, amino acid names and atom names (e.g. N, O, C, etc.) are used as defined by the Protein DataBank (PDB) (www.pdb.org), which is based on the IUPAC nomenclature (IUPAC Nomenclature and Symbolism for Amino Acids and Peptides (residue names, atom names etc.), Eur. J. Biochem., 138, 9-37 (1984) together with their corrections in Eur. J. Biochem., 152, 1 (1985). The term "amino acid residue" is primarily intended to indicate an amino acid residue contained in the group consisting of the 20 naturally occurring amino acids, i.e. alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "nucleotide sequence" or "nucleic acid sequence" is intended to indicate a consecutive stretch of two or more nucleotide molecules. The nucleotide sequence can be of genomic, cDNA, RNA, semisynthetic or synthetic origin, or any combination thereof.

"Cell", "host cell", "cell line" and "cell culture" are used interchangeably herein and all such terms should be understood to include progeny resulting from growth or culturing of a cell. "Transformation" and "transfection" are used interchangeably to refer to the process of introducing a nucleic acid sequence into a cell.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as alanine, ornithine, etc.; and chemically synthesized compounds having properties known in the art to be characteristic of amino acids. Examples of non-naturally occurring amino acids include, but are not limited to, —methyl amino acids (e.g. methyl alanine), D-amino acids, histidine-like amino acids (e.g., 2-amino-histidine, hydroxy-histidine, homohistidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids, substituted amino acids, or one or more D-amino acids into the proteins of the present invention can be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

Amino acids are referred to herein by either their commonly known three letter symbols or by the one-letter symbols recommended by the IUPAC-IUB Biochemical Nomenclature Commission. Nucleotides, likewise, can be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the invention.

Conservative substitution tables providing functionally similar amino acids are known to those of ordinary skill in the art. The following eight groups each contain amino acids that are conservative substitutions for one another:

Alanine (A), Glycine (G);
Aspartic acid (D), Glutamic acid (E);
Asparagine (N), Glutamine (Q);
Arginine (R), Lysine (K);
Isoleucine (I), Leucine (L), Methionine (M), Valine (V);
Phenylalanine (F), Tyrosine (Y), Tryptophan (W);
Serine (S), Threonine (T); and
Cysteine (C), Methionine (M)

(see, e.g., Creighton, Proteins: Structures and Molecular Properties (W H Freeman & Co.; 2nd edition (December 1993).

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., at least about 50%, 55%, 60%, 65%, 70%, 75%, 80%, 85%, 90%, 91%, 92%, 93%, 94%, 95%, 96%, 97%, 98%, or 99% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, can be obtained by a process comprising the steps of screening a library under stringent hybridization conditions with a labeled probe having a polynucleotide sequence of the invention or a fragment thereof, and isolating full-length cDNA and genomic clones containing said polynucleotide sequence. Such hybridization techniques are well known to the skilled artisan.

A derivative, or a variant of a polypeptide is said to share "homology" or be "homologous" with the peptide if the amino acid sequences of the derivative or variant has at least 50% identity with a 100 amino acid sequence from the original peptide. In certain embodiments, the derivative or variant is at least 75% the same as that of either the peptide or a fragment of the peptide having the same number of amino acid residues as the derivative. In certain embodiments, the derivative or variant is at least 85% the same as that of either the peptide or a fragment of the peptide having the same number of amino acid residues as the derivative. In certain embodiments, the amino acid sequence of the derivative is at least 90% the same as the peptide or a fragment of the peptide having the same number of amino acid residues as the derivative. In some embodiments, the amino acid sequence of the derivative is at least 95% the same as the peptide or a fragment of the peptide having the same number of amino acid residues as the derivative. In certain embodiments, the derivative or variant is at least 99% the same as that of either the peptide or a fragment of the peptide having the same number of amino acid residues as the derivative.

As used herein, an "isolated" polypeptide or construct means a construct or polypeptide that has been identified and separated and/or recovered from a component of its natural cell culture environment. Contaminant components of its natural environment are materials that would typically interfere with diagnostic or therapeutic uses for the heteromultimer, and can include enzymes, hormones, and other proteinaceous or non-proteinaceous solutes.

In certain embodiments, as used herein, "isolated" antigen-binding polypeptide constructs described herein comprise heterodimer pairs or "isolated" heterodimer pairs that comprise a heterodimer or heterodimer pair that has been identified and separated and/or recovered from a component of its natural cell culture environment. Contaminant components of its natural environment are materials that would interfere with diagnostic or therapeutic uses for the heterodimer or antigen-binding polypeptide constructs, and can include enzymes, hormones, and other proteinaceous or non-proteinaceous solutes.

The heterodimers and antigen-binding polypeptide constructs and heterodimer pairs are generally purified to substantial homogeneity. The phrases "substantially homogeneous", "substantially homogeneous form" and "substantial homogeneity" are used to indicate that the product is substantially devoid of by-products originated from undesired polypeptide combinations (e.g. homodimers). In this context, the species of interest is the heterodimer comprising H1 and L1 (H1-L1), or H2 and L2 (H2-L2). Contaminants include heterodimers comprising H1 and L2 (H1-L2), or H2 and L1 (H2-L1) or homodimers comprising H1 and L1 or H2 and L2 (regardless of whether the Fab portion is correctly paired or mispaired). Expressed in terms of purity, substantial homogeneity means that the amount of by-products does not exceed 10%, for example is below 5%, below 1%, or below 0.5% of the total LC-MS intensity from all species present in the mixture, wherein the percentages reflect results from Mass Spectrometric analysis.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

Terms understood by those in the art of antibody technology are each given the meaning acquired in the art, unless expressly defined differently herein. Antibodies are known to have variable regions, a hinge region, and constant domains. Immunoglobulin structure and function are reviewed, for example, in Harlow et al, Eds., Antibodies: A Laboratory Manual, Chapter 14 (Cold Spring Harbor Laboratory, Cold Spring Harbor, 1988).

As used herein, the terms "antibody" and "immunoglobulin" or "antigen binding polypeptide construct" are used interchangeably. An "antigen binding polypeptide construct" refers to a polypeptide substantially encoded by an immunoglobulin gene or immunoglobulin genes, or one or more fragments thereof, which specifically bind an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin isotypes, IgG, IgM, IgA, IgD, and IgE, respectively. Further, the antibody can belong to one of a number of subtypes, for instance, the IgG can belong to the IgG1, IgG2, IgG3, or IgG4 subclasses.

An exemplary immunoglobulin (antibody) structural unit is composed of two pairs of polypeptide chains, each pair having one "light" (about 25 kD) and one "heavy" chain (about 50-70 kD). The term "light chain" includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains. The term "heavy chain" includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the $C_{H3}$ being closest to the carboxy-terminus of the polypeptide. Heavy chains can be of any isotype, including IgG (including IgG1, IgG2, IgG3 and IgG4 subclasses), IgA (including IgA1 and IgA2 subclasses), IgM and IgE. The term "variable region" or "variable domain" refers to a portion of the light and/or heavy chains of an antibody generally responsible for antigen recognition, typically including approximately the amino-terminal 120 to 130 amino acids in the heavy chain (VH) and about 100 to 110 amino terminal amino acids in the light chain (VL). A "complementarity determining region" or "CDR" is an amino acid sequence that contributes to antigen binding specificity and affinity. "Framework" regions (FR) can aid in maintaining the proper conformation of the CDRs to promote binding between the antigen binding region and an antigen. Structurally, framework regions can be located in antibodies between CDRs. The variable regions typically exhibit the same general structure of relatively conserved framework regions (FR) joined by three hyper variable regions, CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3, and FR4. The assignment of amino acids to each domain is typically in accordance with the definitions of Kabat Sequences of Proteins of Immunological Interest (National Institutes of Health, Bethesda, Md. (1987 and 1991)), unless stated otherwise. In certain embodiments, the antigen-binding polypeptide constructs comprise at least one immunoglobulin domain from IgG, IgM, IgA, IgD, or IgE connected to a therapeutic polypeptide. In some embodiments, the immunoglobulin domain comprised in an antigen-binding polypeptide construct provided herein, is from an immunoglobulin-based construct such as a diabody, or a nanobody. In certain embodiments, the antigen-binding polypeptide constructs described herein comprise at least one immunoglobulin domain from a heavy chain antibody such as a camelid antibody. In certain embodiments, the antigen-binding polypeptide constructs provided herein comprise at least one immunoglobulin domain from a mammalian antibody such as a bovine antibody, a human antibody, a camelid antibody (single domain and non-single domain), a rodent antibody, humanized antibody, a non-humanized antibody, a mouse antibody, or any chimeric antibody. In certain embodiments, the antigen-binding polypeptide constructs provided herein comprise at least one immunoglobulin domain from an antibody generated from a synthetic library.

A "bi-specific," "dual-specific" or "bifunctional" antigen binding protein or antibody is a hybrid antigen binding protein having two different antigen binding sites. Bispecific antigen binding proteins and antibodies are a species of multispecific antigen binding protein antibody. The two binding sites of a bispecific antigen binding protein or antibody will bind to two different epitopes, which can reside on the same or different molecular targets. A "multispecific antigen binding protein" or "multispecific antibody" is one that targets more than one antigen or epitope. A "bivalent antigen binding protein" or "bivalent antibody" comprises two antigen binding sites. In some instances, the two binding sites have the same antigen specificities. Bivalent antigen binding proteins and bivalent antibodies can be bispecific, see, infra. A bivalent antibody other than a "multispecific" or "multifunctional" antibody, in certain embodiments, typically is understood to have each of its binding sites identical.

The term "preferential pairing" is used herein to describe the pairing pattern of a first polypeptide with a second polypeptide, e.g., an immunoglobulin heavy chain with an immunoglobulin light chain in the antigen-binding polypeptide constructs and heterodimer pairs described herein. As such, "preferential pairing" refers to the preferred pairing of a first polypeptide with a second polypeptide when one or more additional, distinct polypeptides are present at the same time as the pairing occurs between the first and second polypeptide. Typically preferential pairing occurs as a result of the modification (e.g., amino acid modification) of one or both of the first and second polypeptide. Typically preferential pairing results in the paired first and second polypeptide being the most abundant dimer present after pairing occurs. It is known in the art that an immunoglobulin heavy chain (H1) will if co-expressed with two different immunoglobulin light chains (L1 and L2), statistically pair equally with both light chains, resulting in an approximate 50:50 mixture of H1 paired with L1 and H1 paired with L2. In this context, "preferential pairing" would occur between, for example, H1 and L1, if the amount of the H1-L1 heavy chain-light chain heterodimer was greater than the amount of the H1-L2 heterodimer when H1 is co-expressed with both L1 and L2. Thus, in this case, H1 preferentially pairs with L1 relative to L2.

However, in the context of wild-type bispecific antibodies generated from two starting antibody systems, it is also known in the art that in some cases there is an inherent bias where the light chain of one antibody system preferentially pairs with the heavy chains of both antibody systems. Thus, when determining the strength of a design in the context of a bispecific antigen-binding construct, it may be necessary to assess the degree of pairing with the design compared to the degree of pairing in the wild-type system. Thus, in one embodiment, a design is considered to show preferential pairing if the amount of desired bispecific antibody is greater than the amount of desired bispecific antibody obtained in wild-type systems. In another embodiment, a design is considered to show preferential pairing if the amount of pairing in the weaker arm of the antibody, is greater than that seen in the wild-type system.

Antibody heavy chains pair with antibody light chains and meet or contact one another at one or more "interfaces." The "interface" includes one or more "contact" amino acid residues in a first polypeptide that interact with one or more "contact" amino acid residues of a second polypeptide. For example, an interface exists between the CH3 polypeptide sequences of a dimerized CH3 domain, between the CH1 domain of the heavy chain and CL domain of the light chain, and between the VH domain of the heavy chain and the VL domain of the light chain. The "interface" can be derived from an IgG antibody and for example, from a human IgG1 antibody.

The term "amino acid modifications" as used herein includes, but is not limited to, amino acid mutations, insertions, deletions, substitutions, chemical modifications, physical modifications, and rearrangements.

Antigen Binding Polypeptide Constructs and Heterodimer Pairs

The antigen-binding polypeptide constructs described herein can comprise a first heterodimer and a second heterodimer; each heterodimer obtained by pairing an immunoglobulin heavy chain with an immunoglobulin light chain. The structure and organization of the constant and variable domains of immunoglobulin heavy and light chains are well known in the art. Immunoglobulin heavy chains typically comprise one variable (VH) domain, and three constant domains, CH1, CH2, and CH3. Immunoglobulin light chains typically comprise one variable (VL) domain and one constant (CL) domain. Various modifications to these typical formats can be made.

The antigen-binding polypeptide constructs and heterodimer pairs described herein can comprise a first heterodimer and a second heterodimer, each heterodimer comprising an immunoglobulin/antibody heavy chain or fragment thereof having at least a VH and CH1 domain, and an immunoglobulin/antibody light chain having a VL domain and a CL domain. In one embodiment, both heterodimers of the heterodimer pair and antigen-binding polypeptide constructs comprise a full-length immunoglobulin heavy chain. In another embodiment, both heterodimers of the heterodimer pair or antigen-binding polypeptide constructs comprise a fragment of the immunoglobulin heavy chain that includes at least a VH and a CH1 domain. In one embodiment, both heterodimers of the heterodimer pair comprise an amino terminal fragment of the immunoglobulin heavy chain that comprises at least a VH and a CH1 domain. In another embodiment, both heterodimers of the heterodimer pair comprise a carboxy terminal fragment of the immunoglobulin heavy chain that comprises at least a VH and a CH1 domain.

Each heterodimer of the heterodimer pair can bind specifically to an antigen or epitope. In one embodiment, the immunoglobulin heavy chain and the immunoglobulin light chain of each heterodimer is derived or engineered from a known antibody, for example a therapeutic antibody. A therapeutic antibody is one that is effective in treating a disease or disorder in a mammal with or predisposed to the disease or disorder. Suitable therapeutic antibodies from which each heterodimer can be derived include, but are not limited to abagovomab, adalimumab, alemtuzumab, aurograb, bapineuzumab, basiliximab, belimumab, bevacizumab, briakinumab, canakinumab, catumaxomab, certolizumab pegol, cetuximab, daclizumab, denosumab, efalizumab, galiximab, gemtuzumab ozogamicin, golimumab, ibritumomab tiuxetan, infliximab, ipilimumab, lumiliximab, mepolizumab, motavizumab, muromonab, mycograb, natalizumab, nimotuzumab, ocrelizumab, ofatumumab, omalizumab, palivizumab, panitumumab, pertuzumab, ranibizumab, reslizumab, rituximab, teplizumab, tocilizumab/atlizumab, tositumomab, trastuzumab, Proxinium™, Rencarex™, ustekinumab, and zalutumumab.

In one embodiment, the immunoglobulin heavy chain and/or the immunoglobulin light chain of each heterodimer are derived or engineered from an antibody that binds a molecule including, but not limited to, the following list of proteins, as well as subunits, domains, motifs and epitopes belonging to the following list of proteins: renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VII, factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors such as, for example, EGFR, VEGFR; interferons such as alpha interferon (alpha-IFN), beta interferon (beta-IFN) and gamma interferon (gamma-IFN); protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor; platelet-derived growth factor (PDGF); fibroblast growth factor such as AFGF and PFGF; epidermal growth factor (EGF); transforming growth factor (TGF) such as TGF-alpha and TGF-beta, including TGF-1, TGF-2, TGF-3, TGF-4, or TGF-5; insulin-like growth factor-I and -II (IGF-I and IGF-II); des (1-3)-IGF-I (brain IGF-I), insulin-like growth factor binding proteins; CD proteins such as CD2, CD3, CD4, CD8, CD11a, CD14, CD18, CD19, CD20, CD22, CD23, CD25, CD33, CD34, CD40, CD40L, CD52, CD63, CD64, CD80 and CD147; erythropoietin; osteoinductive factors; immunotoxins; a bone morphogenetic protein (BMP); an interferon such as interferon-alpha, -beta, and -gamma; colony stimulating factors (CSFs), such as M-CSF, GM-CSF, and G-CSF; interleukins (ILs), e.g., IL-1 to IL-13; TNF-alpha, superoxide dismutase; T-cell receptors; surface membrane proteins; decay accelerating factor; viral antigen such as, for example, a portion of the AIDS envelope, e.g., gp120; transport proteins; homing receptors; addressins; regulatory proteins; cell adhesion molecules such as LFA-1, Mac 1, p150.95, VLA-4, ICAM-1, ICAM-3 and VCAM, a4/p7 integrin, and (Xv/p3 integrin including either a or subunits thereof, integrin alpha subunits such as CD49a, CD49b, CD49c, CD49d, CD49e, CD49f, alpha7, alpha8, alpha9, alphaD, CD11a, CD11b, CD51, CD11c, CD41, alphaIIb, alphaIELb; integrin beta subunits such as, CD29, CD 18, CD61, CD104, beta5, beta6, beta7 and beta8; Integrin subunit combinations including but not limited to, alphaVbeta3, alphaVbeta5 and alpha4beta7; a member of an apoptosis pathway; IgE; blood group antigens; flk2/flt3 receptor; obesity (OB) receptor; mp1 receptor; CTLA-4; protein C; an Eph receptor such as EphA2, EphA4, EphB2, etc.; a Human Leukocyte Antigen (HLA) such as HLA-DR; complement proteins such as complement receptor CR1, C1Rq and other complement factors such as C3, and C5; a glycoprotein receptor such as GpIb.alpha., GPIIb/IIIa and CD200; and fragments of any of the above-listed polypeptides.

In an embodiment, the immunoglobulin heavy and/or light chains of each heterodimer are derived or engineered from antibodies that specifically bind cancer antigens including, but not limited to, ALK receptor (pleiotrophin receptor), pleiotrophin, KS 1/4 pan-carcinoma antigen; ovarian carcinoma antigen (CA125); prostatic acid phosphate; prostate specific antigen (PSA); melanoma-associated antigen p97; melanoma antigen gp75; high molecular weight melanoma antigen (HMW-MAA); prostate specific membrane antigen; carcinoembryonic antigen (CEA); polymorphic epithelial mucin antigen; human milk fat globule antigen; colorectal tumor-associated antigens such as: CEA, TAG-72, C017-1A, GICA 19-9, CTA-1 and LEA; Burkitt's lymphoma antigen-38.13; CD19; human B-lymphoma antigen-CD20; CD33; melanoma specific antigens such as ganglioside GD2, ganglioside GD3, ganglioside GM2 and ganglioside GM3; tumor-specific transplantation type cell-surface antigen (TSTA); virally-induced tumor antigens including T-antigen, DNA tumor viruses and Envelope antigens of RNA tumor viruses; oncofetal antigen-alpha-fetoprotein such as CEA of colon, 514 oncofetal trophoblast glycoprotein and bladder tumor oncofetal antigen; differentiation antigen such as human lung carcinoma antigens L6 and L20; antigens of fibrosarcoma; human leukemia T cell antigen-Gp37; neoglycoprotein; sphingolipids; breast cancer antigens such as EGFR (Epidermal growth factor receptor); NY-BR-16; NY-BR-16 and HER2 antigen (p185HER2); polymorphic epithelial mucin (PEM); malignant human lymphocyte antigen-APO-1; differentiation antigen such as I antigen found in fetal erythrocytes; primary endoderm I antigen found in adult erythrocytes; preimplantation embryos; I(Ma) found in gastric adenocarcinomas; M18, M39 found in breast epithelium; SSEA-1 found in myeloid cells; VEP8; VEP9; Myl; Va4-D5; D156-22 found in colorectal cancer; TRA-1-85 (blood group H); SCP-1 found in testis and ovarian cancer; C14 found in colonic adenocarcinoma; F3 found in lung adenocarcinoma; AH6 found in gastric cancer; Y hapten; Ley found in embryonal carcinoma cells; TL5 (blood group A); EGF receptor found in A431 cells; E1 series (blood group B) found in pancreatic cancer; FC10.2 found in embryonal carcinoma cells; gastric adenocarcinoma antigen; CO-514 (blood group Lea) found in Adenocarcinoma; NS-10 found in adenocarcinomas; CO-43 (blood group Leb); G49 found in EGF receptor of A431 cells; MH2 (blood group ALeb/Ley) found in colonic adenocarcinoma; 19.9 found in colon cancer; gastric cancer mucins; T5A7 found in myeloid cells; R24 found in melanoma; 4.2, GD3, D1.1, OFA-1, GM2, OFA-2, GD2, and M1:22:25:8 found in embryonal carcinoma cells and SSEA-3 and SSEA-4 found in 4 to 8-cell stage embryos; Cutaneous Tcell Lymphoma antigen; MART-1 antigen; Sialy Tn (STn) antigen; Colon cancer antigen NY-CO-45; Lung cancer antigen NY-LU-12 valiant A; Adenocarcinoma antigen ART1; Paraneoplastic associated brain-testis-cancer antigen (onconeuronal antigen MA2; paraneoplastic neuronal antigen); Neuro-oncological ventral antigen 2 (NOVA2); Hepatocellular carcinoma antigen gene 520; TUMOR-ASSOCIATED ANTIGEN CO-029; Tumor-associated antigens MAGE-C1 (cancer/testis antigen CT7), MAGE-B1 (MAGE-XP antigen), MAGE-B2 (DAM6), MAGE-2, MAGE-4-a, MAGE-4-b and MAGE-X2; Cancer-Testis Antigen (NY-EOS-1) and fragments of any of the above-listed polypeptides.

Human antibodies can be grouped into isotypes including IgG, IgA, IgE, IgM, and IgD. In one embodiment, an Fc is derived from an IgG isotype. In another embodiment, an Fc is derived from an IgA isotype. In another embodiment, an Fc is derived from an IgE isotype. In another embodiment, an Fc is derived from an IgM isotype. In another embodiment, an Fc is derived from an IgD isotype.

Human IgG antibodies can also be divided into the subclasses IgG1, IgG2, IgG3, and IgG4. Thus, in some embodiments, it is contemplated an Fc can be derived from an IgG1, IgG2, IgG3, or IgG4 subclass of antibodies.

Each heterodimer of the heterodimer pair can bind specifically to an epitope or antigen. In one embodiment, each heterodimer of the heterodimer pair binds to the same epitope. In another embodiment, the first heterodimer of the heterodimer pair specifically binds to an epitope on one antigen and the second heterodimer of the heterodimer pair binds specifically to a different epitope on the same antigen. In another embodiment, the first heterodimer of the heterodimer pair specifically binds to an epitope on a first antigen, and the second heterodimer of the heterodimer pair specifically binds to an epitope on a second antigen that is different from the first antigen. For example, in one embodiment, the first heterodimer binds specifically to Tissue Factor, while the second heterodimer binds specifically to antigen Her2(ErbB2), or vice-versa. In an alternative embodiment, the first heterodimer binds specifically to Tissue Factor, while the second heterodimer binds specifically to EGFR, or vice-versa. In yet another embodiment, the first heterodimer binds specifically to EGFR, while the second heterodimer binds specifically to antigen Her2, or vice-versa. In another embodiment, the first heterodimer binds specifically to a molecule or cancer antigen described above. In another embodiment, the second heterodimer binds specifically to a molecule or cancer antigen described above.

As indicated above, in some embodiments, the immunoglobulin heavy chain and the immunoglobulin light chain of each heterodimer are derived or engineered from a known therapeutic antibody, or from an antibody that binds various target molecules or cancer antigens. The amino acid and nucleotide sequences of numerous such molecules are readily available (see for example, GENBANK®: AJ308087.1 (Humanized anti-human tissue factor antibody D3H44 light chain variable region and CL domain); GENBANK®: AJ308086.1 (humanized anti-human tissue factor antibody D3H44 heavy chain variable region and CH1 domain); GENBANK®: HC359025.1 (Pertuzumab Fab light chain gene module); GENBANK®: HC359024.1 (Pertuzumab Fab heavy chain gene module); GENBANK®: GM685465.1 (Antibody Trastuzumab (=HERCEPTIN®)—wildtype; light chain); GENBANK®: GM685463.1 (Antibody Trastuzumab (=HERCEPTIN®)—wildtype; heavy chain); GENBANK®: GM685466.1 (Antibody Trastuzumab (=HERCEPTIN®)—GC-optimized light chain); and GENBANK®: GM685464.1 (Antibody Trastuzumab (=HERCEPTIN®)—GC-optimized heavy chain. The sequences of each of the GENBANK® numbers described herein are available from the NCBI website as of Nov. 28, 2012 and are each incorporated by reference in its entirety for all purposes. Amino acid and nucleotide sequences for cetuximab are also known in the art, see for example the Drug Bank website supported by Canadian Institutes of Health Research, Alberta Innovates—Health Solutions, and by The Metabolomics Innovation Centre (TMIC), Accession No. DB00002.

In some aspects, an isolated antigen-binding polypeptide construct comprises an amino acid sequence that is at least 80, 85, 90, 91, 92, 93, 94, 95, 96, 97, 98, 99, or 100% identical to an amino acid sequence or fragment thereof set forth in the Tables or accession numbers disclosed herein. In some aspects, an isolated antigen-binding polypeptide construct comprises an amino acid sequence encoded by a polynucleotide that is at least 80, 85, 90, 91, 92, 93, 94, 95, 96, 97, 98, 99, or 100% identical to a nucleotide sequence or fragment thereof set forth in the Tables or accession numbers disclosed herein.

Amino Acid Modifications to Immunoglobulin Heavy and Light Chains

At least one of the heterodimers of a heterodimer pair can comprise one or more amino acid modifications to their immunoglobulin heavy and/or immunoglobulin light chains such that the heavy chain of the first heterodimer preferentially pairs with one of the light chains rather than the other. Likewise, the heavy chain of the second heterodimer can preferentially pair with the second light chain rather than the first. This preferential pairing of one heavy chain with one of two light chains can be based on design sets comprising one immunoglobulin heavy chain and two immunoglobulin light chains (referred to as an LCCA design set) where the immunoglobulin heavy chain preferentially pairs with one of the two immunoglobulin light chains over the other when the immunoglobulin heavy chain is co-expressed with both immunoglobulin light chains. Thus, a LCCA design set can comprise one immunoglobulin heavy chain, a first immunoglobulin light chain and a second immunoglobulin light chain.

In one embodiment, the one or more amino acid modifications comprise one or more amino acid substitutions.

In one embodiment, the preferential pairing demonstrated in the LCCA design set is established by modifying one or more amino acids that are part of the interface between the light chain and heavy chain. In one embodiment, the preferential pairing demonstrated in the LCCA design set is established by modifying one or more amino acids in at least one of the CH1 domain of the immunoglobulin heavy chain, the CL domain of a first immunoglobulin light chain and the CL domain of the second immunoglobulin light chain.

In one embodiment the one or amino acid modifications are limited to the conserved framework residues of the variable (VH, VL) and constant (CH1, CL) domains as indicated by the Kabat numbering of residues. For example, Almagro [Frontiers In Bioscience (2008) 13: 1619-1633] provides a definition of the framework residues on the basis of Kabat, Chotia, and IMGT numbering schemes.

In one embodiment, at least one of the heterodimers comprises one or more mutations introduced in the immunoglobulin heavy and immunoglobulin light chains that are complementary to each other. Complementarity at the heavy and light chain interface can be achieved on the basis of steric and hydrophobic contacts, electrostatic/charge interactions or a combination of the variety of interactions. The complementarity between protein surfaces is broadly described in the literature in terms of lock and key fit, knob into hole, protrusion and cavity, donor and acceptor etc., all implying the nature of structural and chemical match between the two interacting surfaces. In one embodiment, at least one of the heterodimers comprises one or more mutations where the mutations introduced in the immunoglobulin heavy and immunoglobulin light chains introduce a new hydrogen bond across the light and heavy chain at the interface. In one embodiment, at least one of the heterodimers comprises one or more mutations where the mutations introduced in the immunoglobulin heavy and immunoglobulin light chains introduce a new salt bridge across the light and heavy chain at the interface.

Non-limiting examples of suitable LCCA design sets are described in the Examples, Tables, and Figures. In one embodiment, the LCCA design set comprises an immunoglobulin heavy chain with at least one amino acid modification in the CH1 domain, a first immunoglobulin light chain with at least one amino acid modification in the CL domain, and a second immunoglobulin light chain without any amino acid modifications in the CL domain. In another embodiment, the LCCA design set comprises an immunoglobulin heavy chain with at least one amino acid modification in the CH1 domain, a first immunoglobulin light chain with at least one amino acid modification in the CL domain, and a second immunoglobulin light chain with at least one amino acid modification in the CL domain. In another embodiment, the LCCA design set comprises an immunoglobulin heavy chain with at least one amino acid modification in the CH1 domain, a first immunoglobulin light chain with at least two amino acid modifications in the CL domain, and a second immunoglobulin light chain with at least two amino acid modifications in the CL domain. In another embodiment, the LCCA design set comprises an immunoglobulin heavy chain with at least one amino acid modification in the CH1 domain, a first immunoglobulin light chain with at least two amino acid modifications in the CL domain, and a second immunoglobulin light chain with at least one amino acid modification in the CL domain.

In one embodiment, the LCCA design set comprises an immunoglobulin heavy chain with no amino acid modifications in the CH1 domain, a first immunoglobulin light chain with no amino acid modifications in the CL domain, and a second immunoglobulin light chain with at least one amino acid modification in the CL domain. In one embodiment, the LCCA design set comprises an immunoglobulin heavy chain with no amino acid modifications in the CH1 domain, a first immunoglobulin light chain with no amino acid modifications in the CL domain, and a second immunoglobulin light chain with at least two amino acid modifications in the CL domain.

In one embodiment, the LCCA design set comprises an immunoglobulin heavy chain with at least two amino acid modifications in the CH1 domain, a first immunoglobulin light chain with no amino acid modifications in the CL domain, and a second immunoglobulin light chain with at least one amino acid modification in the CL domain. In one embodiment, the LCCA design set comprises an immunoglobulin heavy chain with at least two amino acid modifications in the CH1 domain, a first immunoglobulin light chain with at least one amino acid modifications in the CL domain, and a second immunoglobulin light chain with at least one amino acid modification in the CL domain. In one embodiment, the LCCA design set comprises an immunoglobulin heavy chain with at least two amino acid modifications in the CH1 domain, a first immunoglobulin light chain with at least one amino acid modification in the CL domain, and a second immunoglobulin light chain with at least two amino acid modifications in the CL domain. In one embodiment, the LCCA design set comprises an immunoglobulin heavy chain with at least two amino acid modifications in the CH1 domain, a first immunoglobulin light chain with at least two amino acid modifications in the CL domain, and a second immunoglobulin light chain with at least two amino acid modifications in the CL domain. In one embodiment, the LCCA design set comprises an immunoglobulin heavy chain with at least two amino acid modifications in the CH1 domain, a first immunoglobulin light chain with at least three amino acid modifications in the CL domain, and a second immunoglobulin light chain with at least two amino acid modifications in the CL domain.

In one embodiment, the LCCA design set comprises an immunoglobulin heavy chain with at least three amino acid modifications in the CH1 domain, a first immunoglobulin light chain with no amino acid modifications in the CL domain, and a second immunoglobulin light chain with at least one amino acid modifications in the CL domain. In one embodiment, the LCCA design set comprises an immunoglobulin heavy chain with at least three amino acid modifications in the CH1 domain, a first immunoglobulin light chain with at least one amino acid modification in the CL domain, and a second immunoglobulin light chain with at least one amino acid modification in the CL domain. In one embodiment, the LCCA design set comprises an immunoglobulin heavy chain with at least three amino acid modifications in the CH1 domain, a first immunoglobulin light chain with at least three amino acid modifications in the CL domain, and a second immunoglobulin light chain with at least two amino acid modifications in the CL domain. In one embodiment, the LCCA design set comprises an immunoglobulin heavy chain with at least three amino acid modifications in the CH1 domain, a first immunoglobulin light chain with at least four amino acid modifications in the CL domain, and a second immunoglobulin light chain with at least three amino acid modifications in the CL domain.

In one embodiment, the preferential pairing demonstrated in the LCCA design set is established by modifying one or more amino acids in at least one of the VH domain of the immunoglobulin heavy chain, the VL domain of a first immunoglobulin light chain and the VL domain of the second immunoglobulin light chain. Non-limiting examples of suitable LCCA design sets are shown in Tables and Examples below.

In one embodiment, the LCCA design set comprises an immunoglobulin heavy chain with no amino acid modifications in the VH domain, a first immunoglobulin light chain with no amino acid modifications in the VL domain, and a second immunoglobulin light chain with at least one amino acid modification in the VL domain. In one embodiment, the LCCA design set comprises an immunoglobulin heavy chain with no amino acid modifications in the VH domain, a first immunoglobulin light chain with no amino acid modifications in the VL domain, and a second immunoglobulin light chain with at least two amino acid modifications in the VL domain.

In one embodiment, the LCCA design set comprises an immunoglobulin heavy chain with at least one amino acid modification in the VH domain, a first immunoglobulin light chain with no amino acid modifications in the VL domain, and a second immunoglobulin light chain with at least one amino acid modification in the VL domain. In one embodiment, the LCCA design set comprises an immunoglobulin heavy chain with at least one amino acid modification in the VH domain, a first immunoglobulin light chain with at least one amino acid modification in the VL domain, and a second immunoglobulin light chain with at least one amino acid modification in the VL domain. In one embodiment, the LCCA design set comprises an immunoglobulin heavy chain with at least one amino acid modification in the VH domain, a first immunoglobulin light chain with at least two amino acid modifications in the VL domain, and a second immunoglobulin light chain with at least two amino acid modifications in the VL domain.

In one embodiment, the LCCA design set comprises an immunoglobulin heavy chain with at least two amino acid modifications in the VH domain, a first immunoglobulin light chain with no amino acid modifications in the VL domain, and a second immunoglobulin light chain with at least one amino acid modiflan in the VL domain. In one embodiment, the LCCA design set comprises an immunoglobulin heavy chain with at least two amino acid modifications in the VH domain, a first immunoglobulin light chain with at least two amino acid modifications in the VL domain, and a second immunoglobulin light chain with at least one amino acid modification in the VL domain. In one embodiment, the LCCA design set comprises an immunoglobulin heavy chain with at least two amino acid modifications in the VH domain, a first immunoglobulin light chain with at least one amino acid modification in the VL domain, and a second immunoglobulin light chain with at least one amino acid modification in the VL domain.

In one embodiment, the LCCA design sets can be combined to provide a combination comprising two distinct immunoglobulin heavy chains (H1 and H2) and two distinct immunoglobulin light chains (L1 and L2), where H1 preferentially pairs with L1 and H2 preferentially pairs with L2 when H1, H2, L1, and L2 are co-expressed.

In some embodiments, the amino acid modifications described herein are in the context of a bi-specific antibody construct. For example, the design sets described herein can be incorporated into full length immunoglobulin heavy chains such that the full length heavy chains preferentially pair with the immunoglobulin light chains. In some embodiments, the full length immunoglobulin heavy chains contain amino acid modifications that promote dimerization in the Fc region, as described in the Examples.

Transferability of Specific Amino Acid Modifications Identified Herein to Other Antibodies:

Although the specific amino acid modifications to immunoglobulin heavy and light chains identified above have been described with respect to the D3H44 anti-tissue factor extracellular domain antibody, Trastuzumab, and Cetuximab immunoglobulin heavy and light chains, it is contemplated and demonstrated herein (see Examples, Figures, and Tables) that these amino acid modifications are transferable to other immunoglobulin heavy and light chains, resulting in similar patterns of preferential pairing of one immunoglobulin heavy chain with one of the two immunoglobulin light chains in view of the following.

The VH:VL and CH1:CL interface residues in the interface between immunoglobulin heavy and light chains are relatively well conserved (Padlan et al., 1986, Mol. Immunol. 23(9): 951-960). This sequence conservation, a result of evolutionary constraints, increases the likelihood that functionally active antibody binding domains will be formed during combinatorial pairing of light and heavy chains. As a result of this sequence conservation, it follows that sequence modifications in the specific examples noted above for D3H44, which drive preferential pairing, could transfer to other heavy and light chain pair heterodimers with approximately equivalent results being obtained with respect to preferential pairing, since this region displays high sequence conservation across antibodies; Further, when sequence differences do occur, these usually lie distal to the CH1:CL interface. This is particularly the case for the CH1 and CL domains. There is, however, some sequence variability at the antigen-binding site with respect to CDR (complementarity-determining regions) loop residues (and length), particularly for CDR-H3. Thus, in one embodiment, the heterodimer pairs described herein comprise heterodimers where at least one heterodimer comprises one or more amino acid modifications in the VH and/or VL domains that lie distal to the CDR loops when the amino acid sequence of the antigen-binding site is significantly different from that of the D3H44 antibody. In another embodiment, the heterodimer pairs described herein comprise heterodimers where at least one heterodimer comprises one or more amino acid modifications in the VH and/or VL domains that lie proximal or distal to the CDR loops, when the amino acid sequence of the antigen-binding site is substantially the same as that of the D3H44 antibody.

In one embodiment, the amino acid modifications described herein are transferable to the immunoglobulin heavy and light chains of antibodies based on human or humanized IgG1/κ. Non-limiting examples of such IgG1/κ chains include Ofatumumab (for human) or Trastuzumab, Pertuzumab or Bevacizumab (for humanized).

In another embodiment, the amino acid modifications described herein are transferable to the immunoglobulin heavy and light chains of antibodies utilizing commonly used VH and VL subgroups. Non-limiting examples of such antibodies include Pertuzumab.

In one embodiment, the amino acid modifications described herein are transferable to the immunoglobulin heavy and light chains of antibodies having a framework close to germline. Examples of such antibodies include Obinutuzumab.

In one embodiment, the amino acid modifications described herein are transferable to the immunoglobulin heavy and light chains of antibodies having a VH:VL interdomain angle close to the average observed for heavy and light chain pairs. An example of this type of antibody includes, but is not limited to Pertuzumab. In another embodiment, the amino acid modifications described herein are transferable to the immunoglobulin heavy and light chains of antibodies having canonical CL and CH1 domains. Suitable examples of such antibodies include, but are not limited to Trastuzumab.

In some embodiments, certain subsets of the amino acid modifications described herein are utilized in variant domains in antigen binding constructs provided above.

The Examples, Figures, and Tables demonstrate that amino acid modifications (e.g., within one or more Fab fragments comprising a variable region and a constant region) are transferable to other immunoglobulin heavy and light chains, resulting in similar patterns of preferential pairing of one immunoglobulin heavy chain with one of the two immunoglobulin light chains.

Preferential Pairing

As described above, at least one heterodimer of the antigen binding construct/heterodimer pairs described herein can comprise one or more amino acid modifications to their immunoglobulin heavy and/or immunoglobulin light chains such that the heavy chain of the one heterodimer, for example H1, preferentially pairs with one of the light chains, for example L1, rather than the other light chain, L2, and the heavy chain of the other heterodimer, H2, preferentially pairs with the light chain, L2, rather than the light chain L1. In other words, the desired, preferential pairing is considered to be between H1 and L1, and between H2 and L2. Preferential pairing between, for example, H1 and L1 is considered to occur if the yield of the H1-L1 heterodimer is greater than the yield of the mispaired H1-L2 heterodimer when H1 is combined with L1 and L2, relative to the respective pairing of corresponding H1/L1 pair to H2/L2 pair without the one or more amino acid modifications. Likewise, preferential pairing between H2 and L2 is considered to occur if the yield of the H2-L2 heterodimer is greater than the yield of the mispaired H2-L1 heterodimer when H2 is combined with L1 and L2, relative to the respective pairing of corresponding H1-L1 pair to H2-L2 pair without the one or more amino acid modifications. In this context, an heterodimer comprising H1 and L1 (H1-L1), or H2 and L2 (H2-L2), is referred to herein as a preferentially paired, correctly paired, obligate pair, or desired heterodimer, while a heterodimer comprising H1 and L2 (H1-L2), or H2 and L1 (H2-L1), is referred to herein as a mispaired heterodimer. The set of mutations corresponding to the two heavy chains and the two light chains meant to achieve selective pairing of H1-L1 and H2-L2 is referred to as a design set.

Thus, in one embodiment, when one immunoglobulin heavy chain of a heterodimer is co-expressed with two immunoglobulin light chains, the relative yield of the desired heterodimer is greater than 55%. In another embodiment, when one immunoglobulin heavy chain of a heterodimer is co-expressed with two immunoglobulin light chains, the relative yield of the desired heterodimer is greater than 60%. In another embodiment, when one immunoglobulin heavy chain of a heterodimer is co-expressed with two immunoglobulin light chains, the relative yield of the desired heterodimer is greater than 70%. In another embodiment, when one immunoglobulin heavy chain of a heterodimer is co-expressed with two immunoglobulin light chains, the relative yield of the desired heterodimer is greater than 80%. In another embodiment, when one immunoglobulin heavy chain of a heterodimer is co-expressed with two immunoglobulin light chains, the relative yield of the desired heterodimer is greater than 90%. In another embodiment, when one immunoglobulin heavy chain of a heterodimer is co-expressed with two immunoglobulin light chains, the relative yield of the desired heterodimer is greater than 95%.

In the above example, preferential pairing between H1-L1 is considered to occur if the amount of the desired H1-L1 heterodimer is greater than the amount of the mispaired H1-L2 heterodimer when H1 is co-expressed with L1 and L2. Similarly, preferential pairing between H2-L2 is considered to occur if the amount of the desired H2-L2 heterodimer is greater than the amount of the mispaired H2-L2 heterodimer when H2 is co-expressed with L1 and L2. Thus, in one embodiment, when one immunoglobulin heavy chain of a heterodimer is co-expressed with two immunoglobulin light chains, the ratio of the desired heterodimer to the mispaired heterodimer is greater than 1.25:1. In one embodiment, when one immunoglobulin heavy chain of a heterodimer is co-expressed with two immunoglobulin light chains, the ratio of the desired heterodimer to the mispaired heterodimer is greater than 1.5:1. In another embodiment, when one immunoglobulin heavy chain of a heterodimer is co-expressed with two immunoglobulin light chains, the ratio of the desired heterodimer to the mispaired heterodimer is greater than 2:1. In another embodiment, when one immunoglobulin heavy chain of a heterodimer is co-expressed with two immunoglobulin light chains, the ratio of the desired heterodimer to the mispaired heterodimer is greater than 3:1. In another embodiment, when one immunoglobulin heavy chain of a heterodimer is co-expressed with two immunoglobulin light chains, the ratio of the desired heterodimer to the mispaired heterodimer is greater than 5:1. In another embodiment, when one immunoglobulin heavy chain of a heterodimer is co-expressed with two immunoglobulin light chains, the ratio of the desired heterodimer to the mispaired heterodimer is greater than 10:1. In another embodiment, when one immunoglobulin heavy chain of a heterodimer is co-expressed with two immunoglobulin light chains, the ratio of the desired heterodimer to the mispaired heterodimer is greater than 25:1. In another embodiment, when one immunoglobulin heavy chain of a heterodimer is co-expressed with two immunoglobulin light chains, the ratio of the desired heterodimer to the mispaired heterodimer is greater than 50:1.

In some embodiments, the heterodimers described herein preferentially pair to form a bi-specific antibody. In some embodiments, the construct comprises a heterodimer that preferentially pairs to form a bi-specific antibody selected from D3H44/trastuzumab, D3H44/cetuximab, and trastuzumab/cetuximab. In some embodiments, the bi-specific antibodies comprise the amino acid modifications described in Tables 28a-28c.

In some embodiments, two full-length heavy chain constructs are co-expressed with two unique light chain constructs, yielding ten possible antibody species: H1-L1:H1-L1, H1-L2:H1-L2, H1-L1:H1-L2, H2-L1:H2-L1, H2-L2:H2-L2, H2-L1:H2-L2, H1-L1:H2-L1, H1-L2:H2-L2, H1-L2:H2-L1 and H1-L1:H2-L2. The H1-L1:H2-L2 species is considered the correctly paired bispecific antibody species. In some embodiments, the DNA ratios are selected to yield the greatest amount of the correctly paired bispecific antibody species. For example, in some embodiments, the ratio of H1:H2:L1:L2 is 15:15:53:17. In some embodiments, the ratio of H1:H2:L1:L2 is 15:15:17:53.

In some embodiments, the percentage of the correctly paired bispecific species is at least 40%, 45%, 50%, 55%, 60%, 65%, 70%, 75%, 80%, 85%, 90%, 91%, 92%, 93%, 94%, 95%, 96%, 97%, 98%, 99%, or 100% relative to all species (see, e.g., Tables 29a-29c and 30a-30c). In some embodiments, the percentage of correctly paired bispecific species is greater than the percentage of correctly paired bispecific species obtained by co-expressing a corresponding wild-type H1, H2, L1 and L2 without the amino acid modifications described in Tables 28a-28c. In some embodiments, the percentage of correctly paired bispecific species is increased by at least 5%, 10%, 15%, 20%, 30%, 40%, 50%, 60%, 70%, or 75% compared to the percentage of correctly paired bispecific species obtained by co-expressing wild-type H1, H2, L1 and L2 without the amino acid modifications described in Tables 28a-28c.

Thermal Stability of Heterodimers

In addition to promoting preferential pairing, the amino acid substitutions were selected such that the mutations would not destabilize the Fab heterodimers. Thus, in most cases, the stability measurements of the Fab heterodimers were very close to that of the wild-type Fab (e.g., within 3° C. of the wild-type Fab).

Thus, in some embodiments, each heterodimer of the heterodimer pair described herein has a thermal stability that is comparable to that of a heterodimer comprising the same immunoglobulin heavy and light chains but without the amino acid modifications to the CH1, CL, VH, or VL domains described herein. In one embodiment, thermal stability is determined by measurement of melting temperature, or Tm. Thus, in one embodiment, the thermal stability of a heterodimer described herein is within about 10° C. of that of a heterodimer comprising the same immunoglobulin heavy and light chains without the amino acid modifications to the CH1, CL, VH, or VL domains described herein. Thus, in one embodiment, the thermal stability of a heterodimer described herein is within about 5° C. of that of a heterodimer comprising the same immunoglobulin heavy and light chains without the amino acid modifications to the CH1, CL, VH, or VL domains described herein. In another embodiment, the thermal stability of a heterodimer described herein is within about 3° C. of that of a heterodimer comprising the same immunoglobulin heavy and light chains without the amino acid modifications to the CH1, CL, VH, or VL domains described herein. In another embodiment, the thermal stability of a heterodimer described herein is within about 2° C. of that of a heterodimer comprising the same immunoglobulin heavy and light chains without the amino acid modifications to the CH1, CL, VH, or VL domains described herein. In another embodiment, the thermal stability of a heterodimer described herein is within about 1.5° C. of that of a heterodimer comprising the same immunoglobulin heavy and light chains without the amino acid modifications to the CH1, CL, VH, or VL domains described herein. In another embodiment, the thermal stability of a heterodimer described herein is within about 1° C. of that of a heterodimer comprising the same immunoglobulin heavy and light chains without the amino acid modifications to the CH1, CL, VH, or VL domains described herein. In another embodiment, the thermal stability of a heterodimer described herein is within about 0.5° C. of that of a heterodimer comprising the same immunoglobulin heavy and light chains without the amino acid modifications to the CH1, CL, VH, or VL domains described herein. In another embodiment, the thermal stability of a heterodimer described herein is within about 0.25° C. of that of a heterodimer comprising the same immunoglobulin heavy and light chains without the amino acid modifications to the CH1, CL, VH, or VL domains described herein.

Furthermore, in some embodiments, the thermal stability of a heterodimer described herein is surprisingly improved (i.e., increased) relative to that of a heterodimer comprising the same immunoglobulin heavy and light chains without the amino acid modifications to the CH1, CL, VH, or VL domains described herein. Thus, in one embodiment, the thermal stability of a heterodimer described herein is increased by about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 3.0, 3.1, 3.2, 3.3, 3.4, 3.5, 3.6, 3.7, 3.8, 3.9, 4.0, 4.5, 5.0° C. or more compared to a heterodimer comprising the same immunoglobulin heavy and light chains without the amino acid modifications to the CH1, CL, VH, or VL domains described herein.

Affinity of Heterodimers for Antigen

In one embodiment, each heterodimer of the heterodimer pair has an affinity for its respective antigen that is the same or comparable to that of a heterodimer comprising the same immunoglobulin heavy and light chains but without the amino acid modifications to the CH1, CL, VH, or VL domains described herein. In one embodiment, a heterodimer of the heterodimer pair has an affinity for its respective antigen that is within about 50 fold of that of a heterodimer comprising the same immunoglobulin heavy and light chains without the amino acid modifications to the CH1, CL, VH, or VL domains described herein. In one embodiment, a heterodimer of the heterodimer pair has an affinity for its respective antigen that is within about 25 fold of that of a heterodimer comprising the same immunoglobulin heavy and light chains without the amino acid modifications to the CH1, CL, VH, or VL domains described herein. In one embodiment, a heterodimer of the heterodimer pair has an affinity for its respective antigen that is within about 10 fold of that of a heterodimer comprising the same immunoglobulin heavy and light chains without the amino acid modifications to the CH1, CL, VH, or VL domains described herein. In another embodiment, a heterodimer of the heterodimer pair has an affinity for its respective antigen that is within about 5 fold of that of a heterodimer comprising the same immunoglobulin heavy and light chains without the amino acid modifications to the CH1, CL, VH, or VL domains described herein. In another embodiment, a heterodimer of the heterodimer pair has an affinity for its respective antigen that is within about 2.5 fold of that of a heterodimer comprising the same immunoglobulin heavy and light chains without the amino acid modifications to the CH1, CL, VH, or VL domains described herein. In another embodiment, a heterodimer of the heterodimer pair has an affinity for its respective antigen that is within about 2 fold of that of a heterodimer comprising the same immunoglobulin heavy and light chains without the amino acid modifications to the CH1, CL, VH, or VL domains described herein. In another embodiment, a heterodimer of the heterodimer pair has an affinity for its respective antigen that is within about 1.5 fold of that of a heterodimer comprising the same immunoglobulin heavy and light chains without the amino acid modifications to the CH1, CL, VH, or VL domains described herein. In another embodiment, a heterodimer of the heterodimer pair has an affinity for its respective antigen that is about the same as that of a heterodimer comprising the same immunoglobulin heavy and light chains without the amino acid modifications to the CH1, CL, VH, or VL domains described herein.

Additional Optional Modifications

In one embodiment, the immunoglobulin heavy and light chains of the heterodimer pairs described herein can be further modified (i.e., by the covalent attachment of various types of molecules) such that covalent attachment does not interfere with the preferential pairing between heavy chain and light chains or affect the ability of the heterodimer to bind to its antigen, or affect its stability. Such modification include, for example, but not by way of limitation, glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to, specific chemical cleavage, acetylation, formylation, metabolic synthesis of tunicamycin, etc.

In another embodiment, the immunoglobulin heavy and light chains of the heterodimer pairs described herein can be conjugated (directly or indirectly) to a therapeutic agent or drug moiety that modifies a given biological response. Therapeutic agents or drug moieties are not to be construed as limited to classical chemical therapeutic agents. For example, the drug moiety can be a protein or polypeptide possessing a desired biological activity. Such proteins can include, for example, a toxin such as abrin, ricin A, Onconase (or another cytotoxic RNase), pseudomonas exotoxin, cholera toxin, or diphtheria toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (see, International Publication No. WO 97/33899), AIM II (see, International Publication No. WO 97/34911), Fas Ligand (Takahashi et al., 1994, J. Immunol., 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Moreover, in an alternate embodiment, an antibody can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N",N"-tetraacetic acid (DOTA) which can be attached to the antibody via a linker molecule. Such linker molecules are commonly known in the art and described in Denardo et al., 1998, Clin Cancer Res. 4:2483; Peterson et al., 1999, Bioconjug. Chem. 10:553; and Zimmerman et al., 1999, Nucl. Med. Biol. 26:943.

In some embodiments, the immunoglobulin heavy and light chains of the heterodimer are expressed as fusion proteins comprising a tag to facilitate purification and/or testing etc. As referred to herein, a "tag" is any added series of amino acids which are provided in a protein at either the C-terminus, the N-terminus, or internally that contributes to the identification or purification of the protein. Suitable tags include but are not limited to tags known to those skilled in the art to be useful in purification and/or testing such as albumin binding domain (ABD), His tag, FLAG™ tag, glutathione-s-transferase, haemaglutinin (HA) and maltose binding protein. Such tagged proteins can also be engineered to comprise a cleavage site, such as a thrombin, enterokinase or factor X cleavage site, for ease of removal, of the tag before, during or after purification.

In some embodiments, one or more of the cysteine residues at the bottom of the Fab domain in the light (position 214, Kabat numbering) and heavy (position 233, Kabat numbering) chain that form an interchain disulphide bond can be modified to serine or alanine or a non-cysteine or a distinct amino acid.

It is contemplated that additional amino acid modifications can be made to the immunoglobulin heavy chains in order to increase the level of preferential pairing, and/or the thermal stability of the heterodimer pairs. For example, additional amino acid modifications can be made to the immunoglobulin heavy chain Fc domain in order to drive preferential pairing between heterodimer pairs relative to homodimer pairs. Such amino acid modifications are known in the art and include, for example, those described, in US Patent Publication No. 2012/0149876. Alternatively, alternate strategies for driving preferential pairing between heterodimer pairs relative to homodimer pairs such as, for example, "knobs into holes", charged residues with ionic interactions, and strand-exchange engineered domain (SEED) technologies can also be employed. The latter strategies have been described in the art and are reviewed in Klein et al, supra. Further discussion of Fc domains follows below.

Fc Domains

In embodiments where the antigen-binding polypeptide construct comprises full-length immunoglobulin heavy chains, the construct will comprise an Fc. In some aspects, the Fc comprises at least one or two CH3 domain sequences.

In some aspects, where the antigen-binding polypeptide construct comprises heterodimers that comprise only the Fab region of the heavy chain, the Fc is coupled, with or without one or more linkers, to a first heterodimer and/or a second heterodimer. In some aspects, the Fc is a human Fc. In some aspects, the Fc is a human IgG or IgG1 Fc. In some aspects, the Fc is a heterodimeric Fc. In some aspects, the Fc comprises at least one or two CH2 domain sequences.

In some aspects, the Fc comprises one or more modifications in at least one of the $C_{H3}$ domain sequences. In some aspects, the Fc comprises one or more modifications in at least one of the $C_{H2}$ domain sequences. In some aspects, an Fc is a single polypeptide. In some aspects, an Fc is multiple peptides, e.g., two polypeptides.

In some aspects, the Fc comprises one or more modifications in at least one of the $C_{H3}$ sequences. In some aspects, the Fc comprises one or more modifications in at least one of the $C_{H2}$ sequences. In some aspects, an Fc is a single polypeptide. In some aspects, an Fc is multiple peptides, e.g., two polypeptides.

In some aspects, Fc is an Fc described in patent applications PCT/CA2011/001238, filed Nov. 4, 2011 or PCT/CA2012/050780, filed Nov. 2, 2012, the entire disclosure of each of which is hereby incorporated by reference in its entirety for all purposes.

acids at the same respective amino acid position on each sequence; or modification of both amino acids on each sequence at the same respective position on each of the first and second CH3 sequences. The first and second CH3 sequence of a heterodimeric Fc can comprise one or more than one asymmetric amino acid modification.

Table X provides the amino acid sequence of the human IgG1 Fc sequence, corresponding to amino acids 231 to 447 of the full-length human IgG1 heavy chain. The CH3 sequence comprises amino acid 341-447 of the full-length human IgG1 heavy chain.

Typically an Fc can include two contiguous heavy chain sequences (A and B) that are capable of dimerizing. In some aspects, one or both sequences of an Fc include one or more mutations or modifications at the following locations: L351, F405, Y407, T366, K392, T394, T350, S400, and/or N390, using EU numbering. In some aspects, an Fc includes a mutant sequence shown in Table X. In some aspects, an Fc includes the mutations of Variant 1 A-B. In some aspects, an Fc includes the mutations of Variant 2 A-B. In some aspects, an Fc includes the mutations of Variant 3 A-B. In some aspects, an Fc includes the mutations of Variant 4 A-B. In some aspects, an Fc includes the mutations of Variant 5 A-B.

TABLE X

| Human IgG1 Fc sequence 231-447 (EU-numbering) | APELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKAL PAPIEKTISKAKGQPREPQVYTLPPSRDELTKNQVSLTCLVKGFYPSDI AVEWESNGQPENNYKTTPPVLDSDGSFFLYSKLTVDKSRWQQGNVFSCS VMHEALHNHYTQKSLSLSPGK (SEQ ID NO. 13) | |
|---|---|---|

| Variant IgG1 Fc sequence (231-447) | Chain | Mutations |
|---|---|---|
| 1 | A | L351Y_F405A_Y407V |
| 1 | B | T366L_K392M_T394W |
| 2 | A | L351Y_F405A_Y407V |
| 2 | B | T366L_K392L_1394W |
| 3 | A | T350V_L351Y_F405A_Y407V |
| 3 | B | T350V_T366L_K392L_T394W |
| 4 | A | T350V_L351Y_F405A_Y407V |
| 4 | B | T350V_T366L_K392M_T394W |
| 5 | A | T350V_L351Y_S400E_F405A_Y407V |
| 5 | B | T350V_T366L_N390R_K392M_T394W |

In some aspects, a construct described herein comprises a heterodimeric Fc comprising a modified CH3 domain that has been asymmetrically modified. The heterodimeric Fc can comprise two heavy chain constant domain polypeptides: a first heavy chain polypeptide and a second heavy chain polypeptide, which can be used interchangeably provided that Fc comprises one first heavy chain polypeptide and one second heavy chain polypeptide. Generally, the first heavy chain polypeptide comprises a first CH3 sequence and the second heavy chain polypeptide comprises a second CH3 sequence.

Two CH3 sequences that comprise one or more amino acid modifications introduced in an asymmetric fashion generally results in a heterodimeric Fc, rather than a homodimer, when the two CH3 sequences dimerize. As used herein, "asymmetric amino acid modifications" refers to any modification where an amino acid at a specific position on a first CH3 sequence is different from the amino acid on a second CH3 sequence at the same position, and the first and second CH3 sequence preferentially pair to form a heterodimer, rather than a homodimer. This heterodimerization can be a result of modification of only one of the two amino The first and second CH3 sequences can comprise amino acid mutations as described herein, with reference to amino acids 231 to 447 of the full-length human IgG1 heavy chain. In one embodiment, the heterodimeric Fc comprises a modified CH3 domain with a first CH3 sequence having amino acid modifications at positions F405 and Y407, and a second CH3 sequence having amino acid modifications at position T394. In one embodiment, the heterodimeric Fc comprises a modified CH3 domain with a first CH3 sequence having one or more amino acid modifications selected from L351Y, F405A, and Y407V, and the second CH3 sequence having one or more amino acid modifications selected from T366L, T366I, K392L, K392M, and T394W.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, and one of the first or second CH3 sequences further comprising amino acid modifications at position Q347, and the other CH3 sequence further comprising amino acid modification at position K360. In another embodiment, a heterodimeric Fc comprises a modified CH3 domain with a first CH3 sequence having amino acid modifications at positions L351, F405 and Y407, and a second CH3 sequence having amino acid modifications at position T366, K392, and T394, one of the first or second CH3 sequences further comprising amino acid modifications at position Q347, and the other CH3 sequence further comprising amino acid modification at position K360, and one or both of said CH3 sequences further comprise the amino acid modification T350V.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394 and one of said first and second CH3 sequences further comprising amino acid modification of D399R or D399K and the other CH3 sequence comprising one or more of T411E, T411D, K409E, K409D, K392E and K392D. In another embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, one of said first and second CH3 sequences further comprises amino acid modification of D399R or D399K and the other CH3 sequence comprising one or more of T411E, T411 D, K409E, K409D, K392E and K392D, and one or both of said CH3 sequences further comprise the amino acid modification T350V.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, wherein one or both of said CH3 sequences further comprise the amino acid modification of T350V.

In one embodiment, a heterodimeric Fc comprises a modified CH3 domain comprising the following amino acid modifications, where "A" represents the amino acid modifications to the first CH3 sequence, and "B" represents the amino acid modifications to the second CH3 sequence:
A:L351 Y_F405A_Y407V, B:T366L_K392M_T394W,
A:L351 Y_F405A_Y407V, B:T366L_K392L_T394W,
A:T350V_L351Y_F405A_Y407V,
B:T350V_T366L_K392L_T394W,
A:T350V_L351Y_F405A_Y407V,
B:T350V_T366L_K392M_T394W,
A:T350V_L351Y_S400E_F405A_Y407V, and/or
B:T350V_T366L_N390R_K392M_T394W.

The one or more asymmetric amino acid modifications can promote the formation of a heterodimeric Fc in which the heterodimeric CH3 domain has a stability that is comparable to a wild-type homodimeric CH3 domain. In an embodiment, the one or more asymmetric amino acid modifications promote the formation of a heterodimeric Fc domain in which the heterodimeric Fc domain has a stability that is comparable to a wild-type homodimeric Fc domain. In an embodiment, the one or more asymmetric amino acid modifications promote the formation of a heterodimeric Fc domain in which the heterodimeric Fc domain has a stability observed via the melting temperature (Tm) in a differential scanning calorimetry study, and where the melting temperature is within 4° C. of that observed for the corresponding symmetric wild-type homodimeric Fc domain. In some aspects, the Fc comprises one or more modifications in at least one of the CH3 sequences that promote the formation of a heterodimeric [0169] Fc with stability comparable to a wild-type homodimeric Fc.

In one embodiment, the stability of the CH3 domain can be assessed by measuring the melting temperature of the CH3 domain, for example by differential scanning calorimetry (DSC). Thus, in a further embodiment, the CH3 domain has a melting temperature of about 68° C. or higher. In another embodiment, the CH3 domain has a melting temperature of about 70° C. or higher. In another embodiment, the CH3 domain has a melting temperature of about 72° C. or higher. In another embodiment, the CH3 domain has a melting temperature of about 73° C. or higher. In another embodiment, the CH3 domain has a melting temperature of about 75° C. or higher. In another embodiment, the CH3 domain has a melting temperature of about 78° C. or higher. In some aspects, the dimerized CH3 sequences have a melting temperature (Tm) of about 68, 69, 70, 71, 72, 73, 74, 75, 76, 77, 77.5, 78, 79, 80, 81, 82, 83, 84, or 85° C. or higher.

In some embodiments, a heterodimeric Fc comprising modified CH3 sequences can be formed with a purity of at least about 75% as compared to homodimeric Fc in the expressed product. In another embodiment, the heterodimeric Fc is formed with a purity greater than about 80%. In another embodiment, the heterodimeric Fc is formed with a purity greater than about 85%. In another embodiment, the heterodimeric Fc is formed with a purity greater than about 90%. In another embodiment, the heterodimeric Fc is formed with a purity greater than about 95%. In another embodiment, the heterodimeric Fc is formed with a purity greater than about 97%. In some aspects, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed. In some aspects, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed via a single cell.

Additional methods for modifying monomeric Fc polypeptides to promote heterodimeric Fc formation are described in International Patent Publication No. WO 96/027011 (knobs into holes), in Gunasekaran et al. (Gunasekaran K. et al. (2010) J Biol Chem. 285, 19637-46, electrostatic design to achieve selective heterodimerization), in Davis et al. (Davis, J H. et al. (2010) Prot Eng Des Sel; 23(4): 195-202, strand exchange engineered domain (SEED) technology), and in Labrijn et al [Efficient generation of stable bispecific IgG1 by controlled Fab-arm exchange. Labrijn A F, Meesters J I, de Goeij B E, van den Bremer E T, Neijssen J, van Kampen M D, Strumane K, Verploegen S, Kundu A, Gramer M J, van Berkel P H, van de Winkel J G, Schuurman J, Parren P W. Proc Natl Acad Sci USA. 2013 Mar. 26; 110(13):5145-50.

In some embodiments an isolated construct described herein comprises an antigen binding construct which binds an antigen; and a dimeric Fc polypeptide construct that has superior biophysical properties like stability and ease of manufacture relative to an antigen binding construct which does not include the same Fc polypeptide. A number of mutations in the heavy chain sequence of the Fc are known in the art for selectively altering the affinity of the antibody Fc for the different Fcgamma receptors. In some aspects, the Fc comprises one or more modifications to promote selective binding of Fc-gamma receptors.

The CH2 domain is amino acid 231-340 of the sequence shown in Table X. Exemplary mutations are listed below:
S298A/E333A/K334A, S298A/E333:A1K334A1K326A (Lu Y, Vernes J M, Chiang N, et al. J Immunol Methods. 2011 February 28; 365(1-2):132-41); F243L/R292P/Y300L/

V3051/P396L, F243L/R292P/Y300L/L235V/P396L (Stavenhagen J B, Gorlatov S, Tuaillon N, et al. Cancer Res. 2007 Sep. 15; 67(18):8882-90; Nordstrom J L, Gorlatov S, Zhang W, et al, Breast Cancer Res. 2011 Nov. 30; 13(6): R123); F243L (Stewart R, Thom G. Levens M, et al. Protein Eng Des Sel. 2011 September; 24(9):671-8.), S298A/E333A/K334A (Shields R L, Namenuk A K, Hong K, et al. J Biol Chem. 2001 Mar. 2; 276(9):6591-604); S239D/I332E/A330L, S239D/I332E (Lazar G A, Dang W, Karki S, et al. Proc Natl Acad Sci USA. 2006 Mar. 14; 103(11):4005-10); S239D/S267E, S267E/L328F (Chu S Y, Vostiar I, Karki S, et al. Mol Immunol. 2008 September; 45(15):3926-33); S239D/D265S/S298A/I332E, S239E/S298A/K326A/A327H, G237F/S298A/A330L/I332E, S239D/I332E/S298A, S239D/K326E/A330L/I332E/S298A, G236A/S239D/D 270L/I332E, S239E/S267E/H268D, L234F/S267E/N325L, G237F/V266L/S267D and other mutations listed in WO2011/120134 and WO2011/120135, herein incorporated by reference. *Therapeutic Antibody Engineering* (by William R. Strohl and Lila M. Strohl, Woodhead Publishing series in Biomedicine No 11, ISBN 1 907568 37 9, October 2012) lists mutations on page 283.

In some embodiments a CH2 domain comprises one or more asymmetric amino acid modifications. In some embodiments a CH2 domain comprises one or more asymmetric amino acid modifications to promote selective binding of a FcγR. In some embodiments the CH2 domain allows for separation and purification of an isolated construct described herein.

FcRn Binding and PK Parameters

As is known in the art, binding to FcRn recycles endocytosed antibody from the endosome back to the bloodstream (Raghavan et al., 1996, Annu Rev Cell Dev Biol 12:181-220; Ghetie et al., 2000, Annu Rev Immunol 18:739-766). This process, coupled with preclusion of kidney filtration due to the large size of the full-length molecule, results in favorable antibody serum half-lives ranging from one to three weeks. Binding of Fc to FcRn also plays a key role in antibody transport. Thus, in one embodiment, the constructs of the invention are able to bind FcRn.

Additional Modifications to Improve Effector Function.

In some embodiments a construct described herein can be modified to improve its effector function. Such modifications are known in the art and include afucosylation, or engineering of the affinity of the Fc portion of antibodies towards an activating receptor, mainly FCGR3a for ADCC, and towards C1q for CDC. The following Table Y summarizes various designs reported in the literature for effector function engineering.

TABLE Y

| Reference | Mutations | Effect |
|---|---|---|
| Lu, 2011, Ferrara 2011, Mizushima 2011 | Afucosylated | Increased ADCC |
| Lu, 2011 | S298A/E333A/K334A | Increased ADCC |
| Lu, 2011 | S298A/E333A/K334A/K326A | Increased ADCC |
| Stavenhagen, 2007 | F243L/R292P/Y300L/V305I/P396L | Increased ADCC |
| Nordstrom, 2011 | F243L/R292P/Y300L/L235V/P396L | Increased ADCC |
| Stewart, 2011 | F243L | Increased ADCC |
| Shields, 2001 | S298A/E333A/K334A | Increased ADCC |

TABLE Y-continued

| Reference | Mutations | Effect |
|---|---|---|
| Lazar, 2006 | S239D/I332E/A330L | Increased ADCC |
| Lazar, 2006 | S239D/I332E | Increased ADCC |
| Bowles, 2006 | AME-D, not specified mutations | Increased ADCC |
| Heider, 2011 | 37.1, mutations not disclosed | Increased ADCC |
| Moore, 2010 | S267E/H268F/S324T | Increased CDC |

Thus, in one embodiment, a construct described herein can include a dimeric Fc that comprises one or more amino acid modifications as noted in the above table that confer improved effector function. In another embodiment, the construct can be afucosylated to improve effector function.

Linkers

The constructs described herein can include one or more heterodimers described herein operatively coupled to an Fc described herein. In some aspects, Fc is coupled to the one or more heterodimers with or without one or more linkers. In some aspects, Fc is directly coupled to the one or more heterodimers. In some aspects, Fc is coupled to the one or more heterodimers by one or more linkers. In some aspects, Fc is coupled to the heavy chain of each heterodimer by a linker.

In some aspects, the one or more linkers are one or more polypeptide linkers. In some aspects, the one or more linkers comprise one or more antibody hinge regions. In some aspects, the one or more linkers comprise one or more IgG1 hinge regions.

Methods of Preparing Heterodimer Pairs

As described above, the heterodimer pairs described herein can comprise a first heterodimer and a second heterodimer, each heterodimer comprising an immunoglobulin heavy chain or fragment thereof having at least a VH and CH1 domain, and an immunoglobulin light chain having a VL domain and a CL domain. The immunoglobulin heavy chains and immunoglobulin light chains of the heterodimer can readily be prepared using recombinant DNA technology known in the art. Standard techniques such as, for example, those described in Sambrook and Russell, Molecular Cloning: A Laboratory Manual (Cold Spring Harbor Laboratory Press, Cold Spring Harbor, N.Y., 3rd ed., 2001); Sambrook et al., Molecular Cloning: A Laboratory Manual (Cold Spring Harbor Laboratory Press, Cold Spring Harbor, N.Y., 2nd ed., 1989); Short Protocols in Molecular Biology (Ausubel et al., John Wiley and Sons, New York, 4th ed., 1999); and Glick and Pasternak, Molecular Biotechnology: Principles and Applications of Recombinant DNA (ASM Press, Washington, D.C., 2nd ed., 1998) can be used for recombinant nucleic acid methods, nucleic acid synthesis, cell culture, transgene incorporation, and recombinant protein expression. Alternatively, the heterodimers and heterodimer pairs described herein can be chemically synthesized.

The nucleic acid and amino acid sequences of the immunoglobulin heavy and light chains of the antibodies from which the heterodimers are derived are either known in the art or can be readily determined using nucleic acid and/or protein sequencing methods. Methods of genetically fusing the tags described herein to the immunoglobulin heavy and/or light chains are known in the art, and some are described below and in the Examples.

For example, methods of expressing and co-expressing immunoglobulin heavy and light chains in a host cell are well known in the art. In addition, methods of tagging heavy chains and/or light chains using recombinant DNA technology are also well known in the art. Expression vectors and host cells suitable for expression of the heavy and light chains are also well known in the art as described below.

Bispecific antibody production methods that do not rely on the use only a single clonal or transient cell line expressing all four chains are known in the art (Gramer, et al. (2013) mAbs 5, 962; Strop et al. (2012) J Mol Biol 420, 204.). These methods rely on a post production arm exchange under redox conditions of the two pairs of light and heavy chain involved in the formation of bispecific antibody (Redox production). In this approach the H1:L1 and H2:L2 pairs can be expressed in two different cell lines to independently produce the two Fab arms. Subsequently, the two Fab arms are mixed under select redox conditions to achieve re-association of the two unique heavy chain H1 and H2 to form the bispecific antibody comprising L1:H1:H2:L2 chains. One can envision the use of the library/dataset of designs described herein in the production of bispecific antibodies using the Redox production method or modified versions of that method.

In certain embodiments, cell-free protein expression systems are utilized to co-express polypeptides (e.g., heavy and light chain polypeptides) without the use of living cells. Instead, all components needed to transcribe DNA to RNA and translate the RNA to protein (e.g. ribosomes, tRNAs, enzymes, cofactors, amino acids) are provided in solution for use in vitro. In certain embodiments, the in vitro expression requires (1) the genetic template (mRNA or DNA) encoding the heavy and light chain polypeptides and (2) a reaction solution containing the necessary transcriptional and translational molecular machinery. In certain embodiments, cell extracts substantially supply components of the reaction solution, for instance: RNA polymerases for mRNA transcription, ribosomes for polypeptide translation, tRNA, amino acids, enzymatic cofactors, an energy source, and cellular components essential for proper protein folding. Cell-free protein expression systems can be prepared using lysates derived from bacterial cells, yeast cells, insect cells, plant cells, mammalian cells, human cells or combinations thereof. Such cell lysates can provide the correct composition and proportion of enzymes and building blocks required for translation. In some embodiments, cell membranes are removed to leave only the cytosolic and organelle components of the cell.

Several cell-free protein expression systems are known in the art as reviewed in Carlson et al. (2012) Biotechnol. Adv. 30:1185-1194. For example, cell-free protein expression systems are available based on prokaryotic or eukaryotic cells. Examples of prokaryotic cell-free expression systems include those from *E. coli*. Eukaryotic cell-free protein expression systems are available based on extracts from rabbit reticulocytes, wheat germ, and insect cells, for example. Such prokaryotic and eukaryotic cell-free protein expression systems are commercially available from companies such as Roche, INVITROGEN™, QIAGEN©, and Novagen. One skilled in the art would readily be able to select suitable cell-free protein expression systems that would produce polypeptides (e.g., heavy chain and light chain polypeptides) that are capable of pairing with each other. Further, the cell-free protein expression system can also be supplemented with chaperones (e.g. BiP) and isomerases (e.g. disulphide isomerase) to improve the efficiency of IgG folding.

In some embodiments, cell-free expression systems are utilized to co-express the heavy and light chain polypeptides from DNA templates (transcription and translation) or mRNA templates (translation only).

Vectors and Host Cells

Recombinant expression of heavy and light chains requires construction of an expression vector containing a polynucleotide that encodes the heavy or light chain (e.g., antibody, or fusion protein). Once a polynucleotide encoding the heavy or light chain has been obtained, the vector for the production of the heavy or light chain can be produced by recombinant DNA technology using techniques well known in the art. Thus, methods for preparing a protein by expressing a polynucleotide containing the heavy or light chain encoding nucleotide sequence are described herein. Methods that are well known to those skilled in the art can be used to construct expression vectors containing heavy or light chain coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding heavy or light chains, operably linked to a promoter.

The expression vector is transferred to a host cell by conventional techniques and the transfected cells are then cultured by conventional techniques to produce the modified heavy or light chains for use in the method of the invention. In specific embodiments the heavy and light chains for use in the method are co-expressed in the host cell for expression of the entire immunoglobulin molecule, as detailed below.

A variety of host-expression vector systems can be utilized to express the modified heavy and light chains. Such host-expression systems represent vehicles by which the coding sequences of interest can be produced and subsequently purified, but also represent cells which can, when transformed or transfected with the appropriate nucleotide coding sequences, express the modified heavy and light chains in situ. These include but are not limited to microorganisms such as bacteria (e.g., *E. coli* and *B. subtilis*) transformed with recombinant bacteriophage DNA, plasmid DNA or cosmid DNA expression vectors containing the modified heavy and light chain coding sequences; yeast (e.g., *Saccharomyces pichia*) transformed with recombinant yeast expression vectors containing modified heavy and light chain coding sequences; insect cell systems infected with recombinant virus expression vectors (e.g., baculovirus) containing modified heavy and light chain coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing modified heavy and light chain coding sequences; or mammalian cell systems (e.g., COS, CHO, BHK, HEK-293, NSO, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In certain embodiments, bacterial cells such as *Escherichia coli*, or eukaryotic cells, are used for the expression of modified heavy and light chains, which is a recombinant antibody or fusion protein molecules. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In a specific embodiment, the expression of nucleotide sequences encoding the immunoglobulin heavy and light chains of each heterodimer is regulated by a constitutive promoter, inducible promoter or tissue specific promoter.

In mammalian host cells, a number of viral-based expression systems can be utilized. In cases where an adenovirus is used as an expression vector, the modified heavy and light chain coding sequences of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the modified heavy and light chains in infected hosts (e.g., see Logan & Shenk, 1984, Proc. Natl. Acad. Sci. USA 81:355-359). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, Methods in Enzymol. 153:516-544).

The expression of the immunoglobulin heavy and light chains of the heterodimers can be controlled by any promoter or enhancer element known in the art. Promoters which can be used to control the expression of the gene encoding modified heavy and light chains (e.g., antibody or fusion protein) include, but are not limited to, the SV40 early promoter region (Bemoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78.1441-1445), the regulatory sequences of the metallothionein gene (Brinster et al., 1982, Nature 296:39-42), the tetracycline (Tet) promoter (Gossen et al., 1995, Proc. Nat. Acad. Sci. USA 89:5547-5551); prokaryotic expression vectors such as the β-lactamase promoter (Villa-Kamaroff et al, 1978, Proc. Natl. Acad. Sci. U.S.A. 75:3727-3731), or the tac promoter (DeBoer et al., 1983, Proc. Natl. Acad. Sci. U.S.A. 80:21-25; see also "Useful proteins from recombinant bacteria" in Scientific American, 1980, 242:74-94); plant expression vectors comprising the nopaline synthetase promoter region (Herrera-Estrella et al., Nature 303:209-213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286); neuronal-specific enolase (NSE) which is active in neuronal cells (Morelli et al., 1999, Gen. Virol. 80:571-83); brain-derived neurotrophic factor (BDNF) gene control region which is active in neuronal cells (Tabuchi et al., 1998, Biochem. Biophysic. Res. Com. 253:818-823); glial fibrillary acidic protein (GFAP) promoter which is active in astrocytes (Gomes et al., 1999, Braz J Med Biol Res 32(5): 619-631; Morelli et al., 1999, Gen. Virol. 80:571-83) and gonadotropic releasing hormone gene control region which is active in the hypothalamus (Mason et al., 1986, Science 234:1372-1378).

In addition, a host cell strain can be chosen which modulates the expression of the inserted sequences, or modifies and processes the gene product in the specific fashion desired. Expression from certain promoters can be elevated in the presence of certain inducers; thus, expression of the genetically engineered fusion protein can be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells that possess the cellular machinery for proper processing of the primary transcript (e.g., glycosylation, and phosphorylation) of the gene product can be used. Such mammalian host cells include, but are not limited to, CHO, VERY, BHK, Hela, COS, MDCK, HEK-293, 3T3, W138, NSO, and in particular, neuronal cell lines such as, for example, SK-N-AS, SK-N-FI, SK-N-DZ human neuroblastomas (Sugimoto et al., 1984, J. Natl. Cancer Inst. 73: 51-57), SK-N-SH human neuroblastoma (Biochim. Biophys. Acta, 1982, 704: 450-460), Daoy human cerebellar medulloblastoma (He et al., 1992, Cancer Res. 52: 1144-1148) DBTRG-05MG glioblastoma cells (Kruse et al., 1992, In Vitro Cell. Dev. Biol. 28A: 609-614), IMR-32 human neuroblastoma (Cancer Res., 1970, 30: 2110-2118), 1321 N1 human astrocytoma (Proc. Natl. Acad. Sci. USA, 1977, 74: 4816), MOG-G-CCM human astrocytoma (Br. J. Cancer, 1984, 49: 269), U87MG human glioblastoma-astrocytoma (Acta Pathol. Microbiol. Scand., 1968, 74: 465-486), A172 human glioblastoma (Olopade et al., 1992, Cancer Res. 52: 2523-2529), C6 rat glioma cells (Benda et al., 1968, Science 161: 370-371), Neuro-2a mouse neuroblastoma (Proc. Natl. Acad. Sci. USA, 1970, 65: 129-136), NB41A3 mouse neuroblastoma (Proc. Natl. Acad. Sci. USA, 1962, 48: 1184-1190), SCP sheep choroid plexus (Bolin et al., 1994, J. Virol. Methods 48: 211-221), G355-5, PG-4 Cat normal astrocyte (Haapala et al., 1985, J. Virol. 53: 827-833), Mpf ferret brain (Trowbridge et al., 1982, In Vitro 18: 952-960), and normal cell lines such as, for example, CTX TNA2 rat normal cortex brain (Radany et al., 1992, Proc. Natl. Acad. Sci. USA 89: 6467-6471) such as, for example, CRL7030 and Hs578Bst. Furthermore, different vector/host expression systems can effect processing reactions to different extents.

For long-term, high-yield production of recombinant proteins, stable expression is often preferred. For example, cell lines that stably express the modified heavy and light chains of the invention (e.g., antibody or fusion protein) can be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells are allowed to grow for 1-2 days in an enriched medium, and then are switched to a selective medium. The selectable marker in the recombinant plasmid confers resistance to the selection and allows cells to stably integrate the plasmid into their chromosomes and grow to form foci that in turn can be cloned and expanded into cell lines.

A number of selection systems can be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- or aprt-cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

Co-Expression of Heavy Chains and Light Chains

The immunoglobulin heavy chains and light chains of the heterodimer pairs described herein can be co-expressed in mammalian cells, as noted above. In one embodiment, one heavy chain is co-expressed with two different light chains in a LCCA design set as described above, where the heavy chain preferentially pairs with one of the two light chains. In another embodiment, two unique heavy chains are co-expressed with two unique light chains, where each heavy chain preferentially pairs with one of the light chains.

Testing of Heterodimer Pairs

As described above, at least one heterodimer of the heterodimer pairs described herein can comprise one or more amino acid modifications to their immunoglobulin heavy and/or immunoglobulin light chains such that when the two unique heavy chains and two unique light chains of the heterodimer pair are co-expressed in a mammalian cell, the heavy chain of the first heterodimer preferentially pairs with one of the light chains rather than the other. Likewise, the heavy chain of the second heterodimer preferentially pairs with the second light chain rather than the first. The degree of preferential pairing can be assessed, for example, by using the methods described below. The affinity of each heterodimer of the heterodimer pair for its respective antigen can be tested as described below. The thermal stability of each heterodimer of the heterodimer pair can also be tested as described below.

Methods to Measure Preferential Pairing

LCCA

In one embodiment, preferential pairing between immunoglobulin heavy and light chains is determined by performing a Light Chain Competition Assay (LCCA). Co-owned patent application PCT/US2013/063306, filed Oct. 3, 2013, describes various embodiments of LCCA and is herein incorporated by reference in its entirety for all purposes. The method allows quantitative analysis of the pairing of heavy chains with specific light chains within the mixture of co-expressed proteins and can be used to determine if one particular immunoglobulin heavy chain selectively associates with either one of two immunoglobulin light chains when the heavy chain and light chains are co-expressed. The method is briefly described as follows: At least one heavy chain and two different light chains are co-expressed in a cell, in ratios such that the heavy chain is the limiting pairing reactant; optionally separating the secreted proteins from the cell; separating the immunoglobulin light chain polypeptides bound to heavy chain from the rest of the secreted proteins to produce an isolated heavy chain paired fraction; detecting the amount of each different light chain in the isolated heavy chain fraction; and analyzing the relative amount of each different light chain in the isolated heavy chain fraction to determine the ability of the at least one heavy chain to selectively pair with one of the light chains.

The method provides reasonable throughput and is robust (i.e. insensitive to minor changes in operation, such as user or flow rate) and accurate. The method provides a sensitive assay that can measure the effects of small variations in the protein sequences. Promiscuous protein-protein; domain-domain; chain-chain interactions over large surface areas usually require multiple mutations (swaps) in order to introduce selectivity. The protein products do not need to be isolated and purified which enables more efficient screening. Further details regarding an embodiment of this method are described in the Examples.

Alternative Methods to Determine Preferential Pairing

Alternative methods for detecting preferential pairing include using LC-MS (Liquid chromatography-Mass spectrometry) to quantify the relative heterodimer populations including each light chain using differences in their molecular weight to identify each distinct species. An antigen activity assay could also be used to quantify relative heterodimer populations containing each light chain whereby the degree of binding measured (relative to controls) would be used to estimate each respective heterodimer population.

Additional methods such as SMCA are described in the Examples, Figures, and Tables.

Thermal Stability

The thermal stability of the heterodimers can be determined according to methods known in the art. The melting temperature of each heterodimer is indicative of its thermal stability. The melting point of the heterodimer can be measured using techniques such as differential scanning calorimetry (Chen et al (2003) Pharm Res 20:1952-60; Ghirlando et al (1999) Immunol Lett 68:47-52). Alternatively, the thermal stability of the heterodimer can be measured using circular dichroism (Murray et al. (2002) J. Chromatogr Sci 40:343-9).

Affinity for Antigen

The binding affinity of the heterodimers for their respective antigens and the off-rate of the interaction can be determined by competitive binding assays according to methods well known in the art. One example of a competitive binding assay is a radioimmunoassay comprising the incubation of labeled antigen (e.g., 3H or 125I with a molecule of interest (e.g., heterodimers of the present invention) in the presence of increasing amounts of unlabeled antigen, and the detection of the molecule bound to the labeled ligand. The affinity of the heterodimer of the present invention for the antigen and the binding off-rates can be determined from the saturation data by Scatchard analysis.

The kinetic parameters of a heterodimer described herein can also be determined using surface plasmon resonance (SPR) based assays known in the art (e.g., BIAcore kinetic analysis). For a review of SPR-based technology see Mullet et al., 2000, Methods 22: 77-91; Dong et al., 2002, Review in Mol. Biotech., 82: 303-23; Fivash et al., 1998, Current Opinion in Biotechnology 9: 97-101; Rich et al., 2000, Current Opinion in Biotechnology 11: 54-61. Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of the invention. FACS can also be used to measured affinity, as is known in the art.

Generation of Bispecific Antibodies Given Mab1 and Mab2 Using a Library of Bispecific Antibody Mutation Design Sets.

In one embodiment, described here is a bispecific antibody mutation design set aimed at selectively forming bispecific antibodies starting from two canonical antibodies Mab1 and Mab2 comprising of the antigen binding fragments Fab1 and Fab2 respectively. The design set consists of cognate mutations corresponding to Fab1, Fab2 and Fc respectively. In one embodiment, design set libraries are represented by design sets included in Table 5, Table 12, or any one of Tables 15 to 17. Mutations are introduced at the interface of light and heavy chain of Fab1 to achieve selective pairing between the two obligate chains in the presence of competing light and heavy chain of Fab2. Selective pairing is achieved by introducing favorable complementary mutations in the two obligate light and heavy chains on the basis of steric, hydrophobic or electrostatic complementarity between certain hotspot framework residues at the interface while involving these mutated residues in unfavorable interface interaction for the non-obligate chain pairs. In each design set selective pairing mutations can also be introduced at the interface of light and heavy chain of Fab2 to achieve selective pairing between these two obligate chains in the presence of competing light and heavy chain of Fab1. The mutations are aimed at reducing the mis-pairing of light chain from Fab1 with heavy chain of Fab2 and vice-versa. Mutations are introduced at the Fc interface in order to achieve selective pairing of heavy chains to form asymmetric antibody molecules comprising two different heavy chains.

Figure 12:
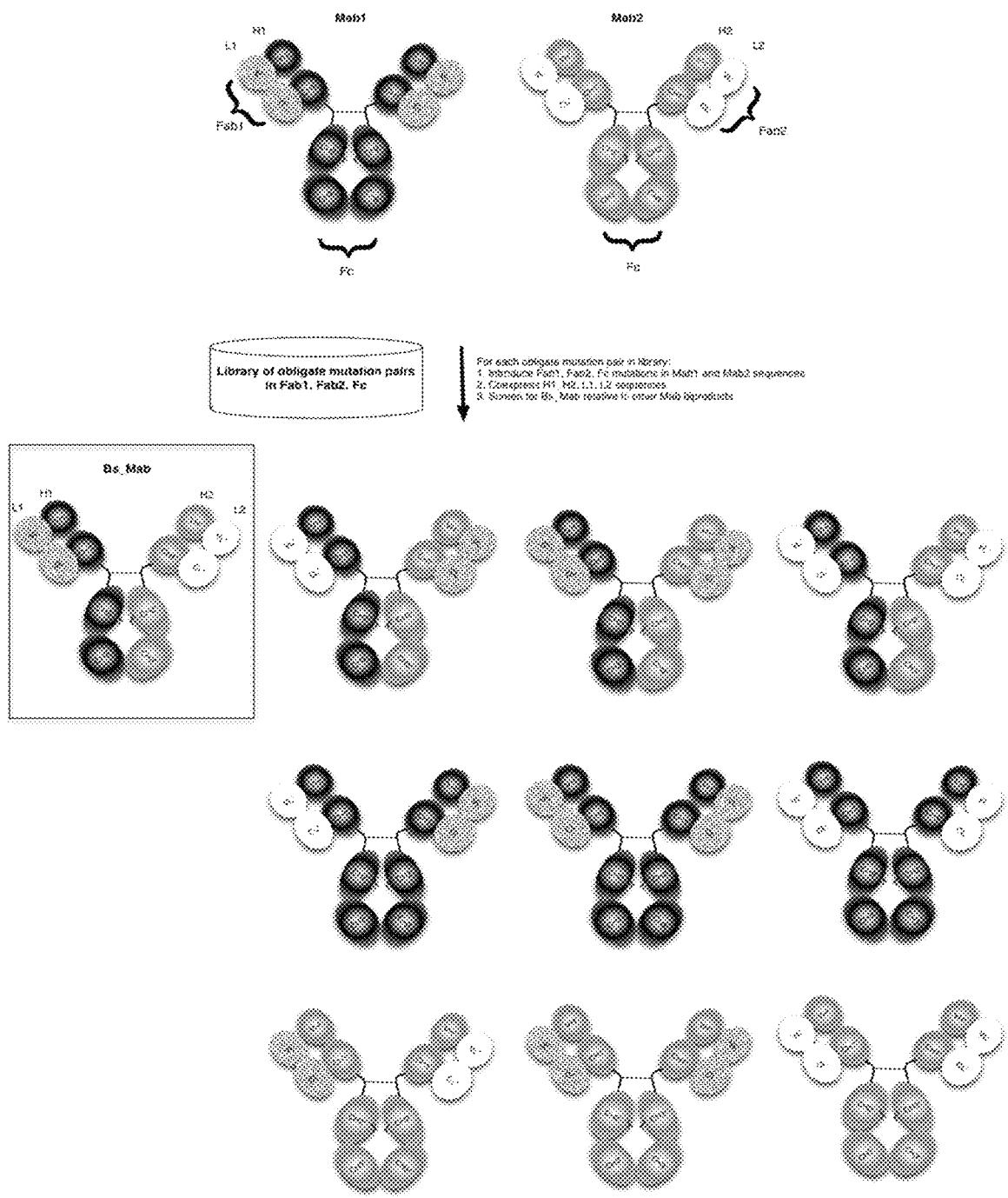
FIG. 12 depicts a method of preparing a bi-specific antibody using the library of obligate mutation pairs provided herein.

Engineering at certain interface residue positions of light and heavy chains of an antibody can often lead to detrimental effects such as loss in antigen binding affinity, stability, solubility, aggregation propensity etc of that antibody. A number of related properties can be affected such as kon and koff rates, melting temperature (Tm), stability to stress conditions like acid, base, oxidation, freeze/thaw, agitation, pressure etc. This is often impacted by the complementarity determining regions (CDRs) of the antibody of interest. Given that the CDRs of different antibodies are generally not identical, the impact of the mutation design set on the properties described above may not be the same across all antibodies. Presented here is a method to create a bispecific antibody with noted purity relative to other contaminants containing incorrectly paired antibody-like structures, given any two available antibodies Mab1 and Mab2. The light and heavy chains of Mab1 and Mab2 are co-expressed after introducing the cognate mutations of each of the mutation design sets and the expressed antibody product is analytically screened to estimate the purity of the preferred bispecific antibody relative to other Mab like species expressed in the protein product. In some embodiments the analytical screening procedure may be based on an LC-MS technique. In some embodiments the analytical screening procedure may be based on charge based separation such as a capillary isoelectric focusing (cIEF) technique or a chromatographic technique. An example of the screening technique is presented in Example 9 based on the SMCA procedure. In some embodiments the noted purity of the bispecific antibody is defined as being greater than 70% of all the obtained Mab like species in the expressed protein product. In some embodiments the noted purity of the bispecific antibody is defined as being greater than 90% of all the obtained Mab like species in the expressed protein product. The procedure for preparation and selection of bispecific Mab design set given Mab1 and Mab2 is shown schematically in FIG. 12.

Pharmaceutical Compositions

The present invention also provides pharmaceutical compositions comprising the heterodimers or heterodimer pairs described herein. Such compositions comprise a therapeutically effective amount of the heterodimer or heterodimer pair, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In certain embodiments, the composition comprising the heterodimer or heterodimer pair is formulated in accordance with routine procedures as a pharmaceutical composition adapted for intravenous administration to human beings.

Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

In certain embodiments, the compositions described herein are formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxide isopropylamine, triethylamine, 2-ethylamino ethanol, histidine, procaine, etc.

The amount of the composition described herein which will be effective in the treatment, inhibition and prevention of a disease or disorder associated with aberrant expression and/or activity of a therapeutic protein can be determined by standard clinical techniques. In addition, in vitro assays can optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

Uses of Heterodimer Pairs

As described above, the heterodimer pairs described herein can comprise a first heterodimer and a second heterodimer, where the immunoglobulin heavy chain and/or the immunoglobulin light chain of each heterodimer comprise one or more modifications from a known therapeutic antibody or from a known antibody that binds a molecule. Thus, it is contemplated that heterodimers comprising the modifications to these antibodies could be used for the treatment or prevention of the same disease, disorder, or infection that the known therapeutic antibody or known antibody can be used for.

In another embodiment, the heterodimer pairs described herein can also be advantageously utilized in combination with other therapeutic agents known in the art for the treatment or prevention of a cancer, autoimmune disease, inflammatory disorders or infectious diseases. In a specific embodiment, the heterodimer pairs described herein can be used in combination with monoclonal or chimeric antibodies, lymphokines, or hematopoietic growth factors (such as, e.g., IL-2, IL-3 and IL-7), which, for example, serve to increase the number or activity of effector cells which interact with the molecules and, increase immune response. The heterodimer pairs described herein can also be advantageously utilized in combination with one or more drugs used to treat a disease, disorder, or infection such as, for example anti-cancer agents, anti-inflammatory agents or anti-viral agents.

Kits

The present invention additionally provides for kits comprising one or more heterodimer pairs. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale. The kit can optionally contain instructions or directions outlining the method of use or administration regimen for the heterodimer pairs.

When one or more components of the kit are provided as solutions, for example an aqueous solution, or a sterile aqueous solution, the container means can itself be an inhalant, syringe, pipette, eye dropper, or other such like apparatus, from which the solution can be administered to a subject or applied to and mixed with the other components of the kit.

The components of the kit can also be provided in dried or lyophilized form and the kit can additionally contain a suitable solvent for reconstitution of the lyophilized components. Irrespective of the number or type of containers, the kits of the invention also can comprise an instrument for assisting with the administration of the composition to a patient. Such an instrument can be an inhalant, nasal spray device, syringe, pipette, forceps, measured spoon, eye dropper or similar medically approved delivery vehicle.

Computer Implementation

In one embodiment, a computer comprises at least one processor coupled to a chipset. Also coupled to the chipset are a memory, a storage device, a keyboard, a graphics adapter, a pointing device, and a network adapter. A display is coupled to the graphics adapter. In one embodiment, the functionality of the chipset is provided by a memory controller hub and an I/O controller hub. In another embodiment, the memory is coupled directly to the processor instead of the chipset.

The storage device is any device capable of holding data, like a hard drive, compact disk read-only memory (CD-ROM), DVD, or a solid-state memory device. The memory holds instructions and data used by the processor. The pointing device can be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W. H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pennsylvania: Mack Publishing Company, 1990); Carey and Sundberg Advanced Organic Chemistry 3rd Ed. (Plenum Press) Vols A and B (1992).

Example 1: Molecular Modeling and Computer Guided Engineering of Fab Interface

A structure and computational molecular modeling guided approach was used to produce a library of heavy and light chain mutation designs that can be screened in the context of other antibodies (Abs) or fragments thereof to identify mutations that exhibit the desired specificity in the antibodies of interest. The design strategy for engineering preferential heavy chain (H)-light chain (L) pairing included first identifying a representative Fab (i.e. D3H44).

As indicated in Table 1, key criteria for this Fab were that it was human/humanized, has the commonly used VH and VL subgroups and contained minimal framework region mutations. In addition, structural considerations were that the VH:VL interdomain angle should be close to the average observed for antibodies. After selection of the Fab D3H44, an in silico analysis of the Fab interface was carried out to identify and understand residues important for interaction between heavy and light chains, using a two-pronged approach.

The first approach involved a global analysis of the sequence conservation across the Fab variable and constant interfaces was carried out via sequence and structure alignments of known antibodies. An alignment of constant and variable domain sequences from various antibody subgroups is shown in FIGS. 1A-E. FIG. 1A depicts an alignment of representative human VH germline subgroups. FIG. 1B depicts an alignment of representative human kappa VL germline subgroups. FIG. 1C depicts an alignment of representative human lambda VL germline subgroups. FIG. 1D depicts an alignment of human CH1 allele sequences. FIG. 1E depicts an alignment of human kappa and lambda allele sequences. The second approach involved the analysis of the D3H44 crystal structure interface using a number of molecular modeling tools as shown in FIG. 2 (e.g. ResidueContacts™). These analyses resulted in the identification of a list of hotspot positions for engineering preferential H-L pairing. The hotspot positions determined from this analysis are listed in Table 2. These positions and amino acids are mainly framework residues (except for a few located in the CDR3 loops) and are also mostly conserved in the lambda L chains. The amino acids in the parent D3H44 sequences with Kabat numbering are provided in Tables 3a-3b.

Next, potential mutations at the hotspot positions as well as positions neighboring the hotspots of interest in the 3D crystal structure were simulated and identified via in silico mutagenesis and packing/modeling with Zymepack™. Zymepack™ is a software suite that, given an input structure and a set of mutations, will alter the residue types in the input structure according to the supplied mutations, and generate a new structure that is an approximation to the physical structure of the mutant protein. Additionally, Zymepack evaluates the properties of the mutant protein by computing a variety of quantitative metrics. These metrics include measures of steric and electrostatic complementarity, which may correlate with the stability, binding affinity, or heterodimeric specificity of the mutant protein.

FIG. 3 presents a subset of hotspot positions at the heavy and light chain interface in the variable domains and demonstrates how mutations can be introduced at these interface positions to facilitate selective pairing of the obligate chains while disfavoring the formation of incorrect chain pairs. Using computational methods including Zymepack™, steric complementarity was modeled and also computed on the basis of energy factors such as van der Waals packing, cavitation effects and close contact of hydrophobic groups. Similarly, electrostatic interaction energies were modeled and evaluated on the basis of coulomb interactions between charges, hydrogen bonds, and desolvation effects. Both the preferred heavy and light chain pair models such as H1:L1 (or H2:L2) and the incorrect pair models such as H1:L2 (and H2:L1) obtained by introducing the mutations of interest were simulated to compute the relative steric and electrostatic scores. This allowed the determination of whether a particular mutation set led to favorable energies i.e. greater steric and/or electrostatic complementarity for the preferred (obligate) heavy-light chain pairs relative to the incorrect (non-obligate) pairs. The computed steric and electrostatic energies are components of the free energy associated with the light and heavy chain pairing. Hence greater steric and electrostatic complementarity is indicative of a larger free energy change associated with the pairing of the obligate pair relative to the pairing of the non-obligate pair. The greater steric or electrostatic complementarity results in preferential (selective) pairing of the obligate heavy and light chains relative to the non-obligate pair.

Example 2: Selection and Description of Designs

The approach described in Example 1 was used to design heavy chain-light chain heterodimer pairs (i.e. H1-L1 and H2-L2) that exhibit selective or preferential pairing. The heterodimers were designed in pairs, referred to as a "design" or "design set," and include a set of substitutions on H1, L1, H2, and L2 chains that promote preferential pairing (Table 5). The design sets were initially tested as "LCCA designs" (Table 4) where one heavy chain was co-expressed with two light chains in order to assess relative pairing. The amino acid substitutions are identified with reference to Tables 3a, 3b, using the Kabat numbering system.

The design library described in Table 30 from International Patent application number PCT/CA2013/050914 was used as a starting point to identify some of the LCCA designs shown in Table 4 and the design sets shown in Table 5. Some of the designs in Table 4 and Table 5 are new independent designs. Core designs are shown in Table 6, along with the associated unique identifiers. Most of the designs span the constant region only, with a few of the designs also incorporating modifications in the variable region. These designs were proposed to further drive pairing specificity while also favoring transferability to other antibody systems.

For the derived designs, the library of designs described in Table 30 from International Patent application number PCT/CA2013/050914 was used as a starting point, with the designs clustered by structural similarity and ranked based on strength of pairing specificity, effect on antigen binding, and stability as measured by Differential Scanning Calorimetry (DSC). Designs were then combined (see example in Table 7) and/or optimized (see examples in Table 8 and Table 9) to yield the derived designs. For the combinations, at least one of the designs exhibited high pairing specificity with the other design(s) exhibiting a range of favorable pairing specificities. All of the designs chosen for combination and/or optimization exhibited no/minimal effects on antigen binding and no/minimal effects on melting temperature (Tm).

Independent designs were tested alone (classified as independent, under design type column, Table 5), and in combination with the derived designs as well (classified as independent/combination, under design type column, Table 5; see also example in Table 10).

The designs were packed onto a molecular model of D3H44 and metrics were calculated (as described in Example 1). The top designs were then selected based on risk (possible effects on stability as well as immunogenicity) and impact (which takes into account the proposed strength of the drive pairing specificity). These top designs are shown in Table 5.

Example 3: Preparation of Fab Constructs Encoding D3H44 IgG Heavy Chains and D3H44 IgG Light Chains The wild-type Fab heavy and light chains of the anti-tissue factor antibody D3H44 were prepared as follows. D3H44 Fab light (AJ308087.1) and heavy (AJ308086.1) chain sequences were taken from GENBANK® (Table 3c), gene synthesized and codon optimized for mammalian expression. Light chain vector inserts, consisting of a 5'-EcoRI cutsite—HLA-A signal peptide—HA or FLAG™ tag—Light chain Ig clone—'TGA stop'—BamH1 cutsite-3', were ligated into a pTT5 vector (Durocher Y et al., Nucl. Acids Res. 2002; 30, No.2 e9). The resulting vector+insert were sequenced to confirm correct reading frame and sequence of the coding DNA. Likewise, heavy chain vector inserts, consisting of a 5'-EcoR1cutsite—HLA-A signal peptide—heavy chain clone (terminating at T238; see Table 3a)—ABD$_2$-His$_6$tag—TGA stop—BamH1 cutsite-3', were ligated into a pTT5 vector (ABD; albumin binding domain). The resulting vector+insert were also sequenced to confirm correct reading frame and sequence of the coding DNA. The various Fab D3H44 constructs containing amino acid substitutions for the design sets were generated either by gene synthesis or by site-directed mutagenesis (Braman J, Papworth C & Greener A., Methods Mol. Biol. (1996) 57:31-44).

Heavy and light chains were tagged at the C- and N-termini respectively, in order to facilitate the assessment of preferential pairing via a competition assay-SPR screen. The ABD$_2$-His$_6$ heavy chain tag specifically allowed H-L complexes to be captured on an anti-his tag SPR chip surface, whilst FLAG and HA light chain tags allowed the relative L1 and L2 populations to be quantified.

Example 4: Assessment of Preferential Pairing of Fab Heterodimers Comprising Either Constant Domain Modifications or a Combination of Constant and Variable Domain Modifications in D3H44 IgG Light and/or Heavy Chains Constructs encoding the D3H44 IgG heavy and light chains in Fab format comprising amino acid modifications according to the LCCA design sets in Table 12 were prepared as described in Example 3. The ability of the constructs to preferentially pair to form the desired H1-L1 heterodimer in the context of an LCCA design set (H1, L1, L2) was determined using a Light Chain Competition Assay (LCCA).

Figure 4:
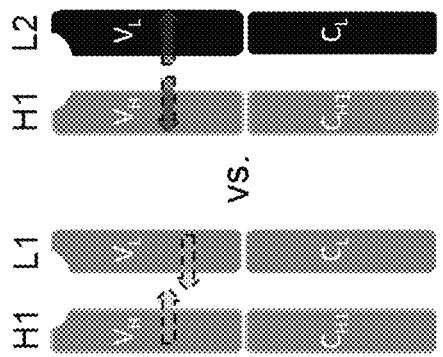
FIG. 4 illustrates a high level schematic overview of the engineering requirements for forming a bispecific Mab (monoclonal antibody), and the assay requirements needed to quantify heavy chain light chain pairs. The design goal of engineering a bispecific Mab with high purity (i.e., little or no mispaired H-L associations) can be achieved by rationally engineering (via the introduction of specific amino acid mutations) the preferential pairing of two unique heavy chains for their unique cognate light chains. This process is shown schematically; here H1 has been engineered to preferentially pair with L1 and not L2. Likewise, H2 has been engineered to preferentially pair with L2 and not L1. The experimental screening of bispecific Mab designs requires an assay capable of simultaneously quantifying H1-L1:H1-L2 and H2-L2:H2-L1. These assay requirements can be simplified by assuming that each bispecific Fab arm can be independently engineered. In this case, the assay would only need to quantify H1-L1:H1-L2 or H2-L2:H2-L1, and not both simultaneously.
Figure 5:
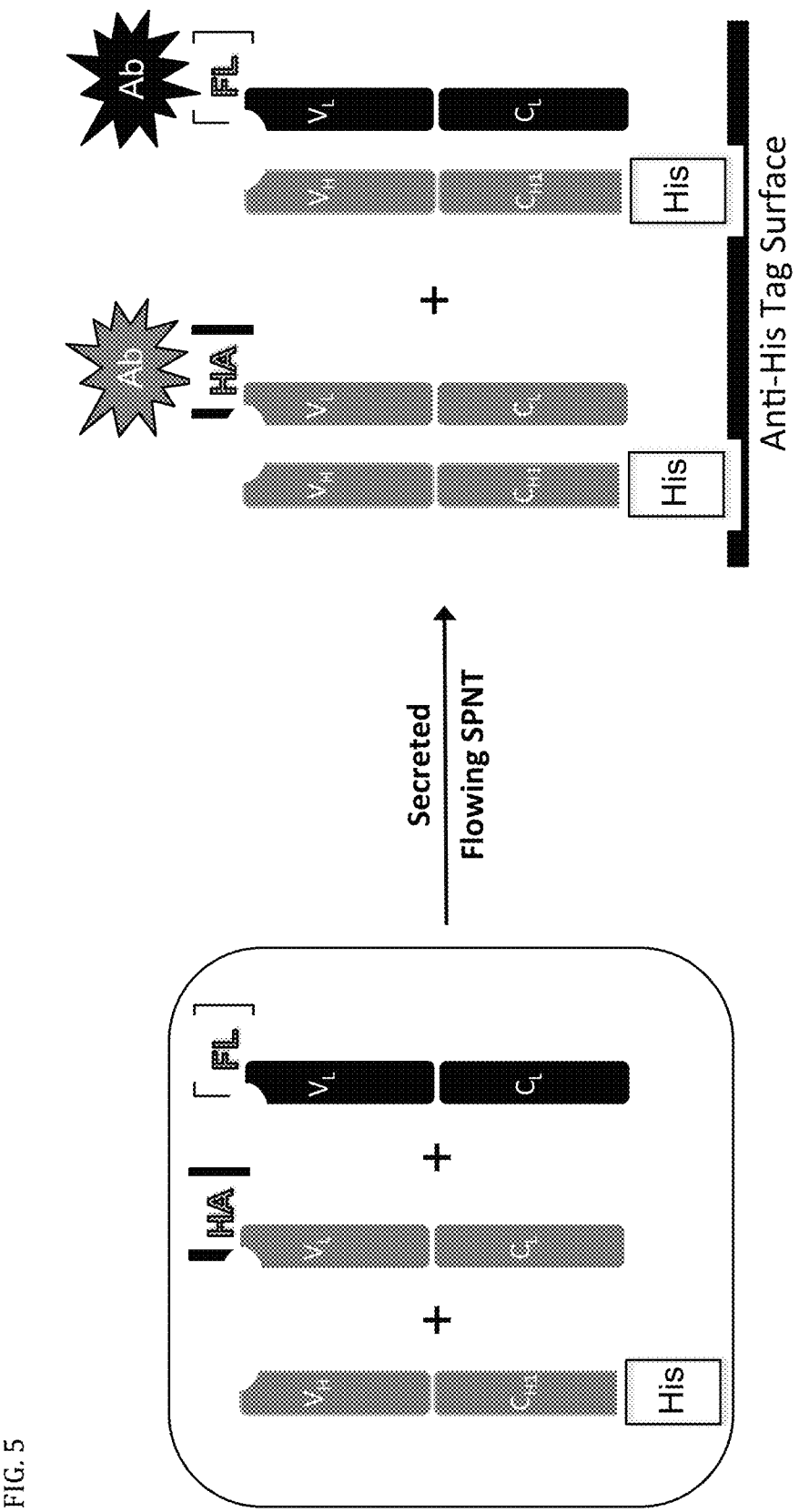
FIG. 5 provides a schematic depicting how heavy chains and light chains are tagged and preferential pairing is determined. In this schematic, the circle represents a cell in which 3 constructs are transfected. The expression products are secreted from the cell and the supernatant (SPNT) is flowed over a detection device, in this case an SPR chip. Based on the detection level of the two different tags fused to the two light chains competing for heavy chain pairing, a quantitative estimate of the preferential pairing of the heavy chain to the two light chains can be estimated.

The LCCA quantifies the relative pairing of one heavy chain for at least two unique light chains and can be summarized as follows. One D3H44 heavy chain Fab construct was co-expressed with two unique D3H44 light chain Fab constructs and the relative light chain pairing specificity (e.g. H1-L1:H1-L2) was determined from a competition assay-SPR screen, conducted in duplicate. The LCCA screen ratio was skewed to identify strong drivers, by reducing the amount of L1 (designed to preferentially pair with the H chain) compared to L2, (e.g. L1:L2=1:3, by weight), while keeping the heavy chain in limiting quantities (i.e. H1:L1+L2 of 1:3). The amount of each heterodimer formed (i.e. H1-L1 and H1-L2) was determined by binding heavy chains to the SPR chip via a his-tag pull-down, followed by detection of the amount of each light chain tag (HA or FLAG) using antibodies specific for these tags. Subsequently, selected heterodimer hits were verified via a light chain competition assay verification whereby the L1:L2 DNA ratios were varied by 1:3 and 1:9 during transfection, while keeping the heavy chain in limiting quantities. Also note that the light chain tags (HA or FLAG) do not affect LCCA pairing in the D3H44 system (see example 10 from International Patent application number PCT/CA2013/050914). A schematic representing the design of the assay is shown in FIG. 4. FIG. 5 depicts how the heavy chains and light chains are tagged and how preferential pairing is assessed. The experimental details of the LCCA are provided below.

Transfection Method

LCCA designs comprising one heavy chain and two light chain constructs, prepared as described in Example 3, were transfected into CHO-3E7 cells as follows. CHO-3E7 cells, at a density of 1.7-2×10$^6$cells/ml, were cultured at 37° C. in FreeStyle™ F17 medium (INVITROGEN™ cat #A-1383501) supplemented with 4 mM glutamine and 0.1% KOLLIPHOR© P188 (Sigma #K4894). A total volume of 2 ml was transfected with a total of 2 µg DNA using PEI-pro© (POLYPLUS TRANSFECTION© #115-375) at a DNA:PEI ratio of 1:2.5. Twenty-four hours after the addition of the DNA-PEI mixture, the cells were transferred to 32° C. Supernatants were tested for expression on day 7 by non-reducing SDS-PAGE analysis followed by COMASSIE® blue staining to visualize the bands. H:L ratios are as indicated in Table 11.

Competition Assay SPR Method

The degree of preferential D3H44 light chain pairing to D3H44 heavy chain in LCCA designs was assessed using an SPR-based readout of unique epitope tags located at the N-terminus of each light chain.

Surface Plasmon resonance (SPR) supplies. GLC sensor-chips, the Biorad PROTEON™ amine coupling kit (1-ethyl-3-(3-dimethylaminopropyl) carbodiimide hydrochloride (EDC), N-hydroxysulfosuccinimide (sNHS) and ethanolamine), and 10 mM sodium acetate buffers were purchased from BIO-RAD® Laboratories (Canada) Ltd. (Mississauga, ON). 4-(2-hydroxyethyl)-1-piperazineethanesulfonic acid (HEPES) buffer, ethylenediaminetetraacetic acid (EDTA), and NaCl were purchased from from SIGMA-ALDRICH® (Oakville, ON). 10% TWEEN® 20 solution was purchased from TEKNOVA® (Hollister, CA).

SPR biosensor assays. All surface plasmon resonance assays were carried out using a BIO-RAD® PROTEON™ XPR36 instrument (BIO-RAD® Laboratories (Canada) Ltd. (Mississauga, ON)) with PBST running buffer (PBS TEKNOVA® Inc with 0.05% TWEEN® 20) at a temperature of 25° C. The anti-penta His capture surface was generated using a GLM sensorchip activated by a 1:5 dilution of the standard BioRad sNHS/EDC solutions injected for 140 s at 100 µL/min in the analyte (horizontal) direction. Immediately after the activation, a 25 µg/mL solution of anti-penta His antibody (Qiagen Inc.) in 10 mM NaOAc pH 4.5 was injected in the analyte (vertical) direction at a flow rate of 25 µL/min until approximately 3000 resonance units (RUs) are immobilized. Remaining active groups were quenched by a 140 s injection of 1M ethanolamine at 100 µL/min in the analyte direction, and this also ensures mock-activated interspots were created for blank referencing.

The screening of the heterodimers for binding to the anti-FLAG (Sigma Inc.) and anti-HA (Roche Inc.) monoclonal antibodies occurred in two steps: an indirect capture of the heterodimers onto the anti-penta His surface in the ligand direction followed by an anti-FLAG and anti-HA injection in the analyte direction. First, one injection of PBST for 30 s at 100 µL/min in the ligand direction was used to stabilize the baseline. For each heterodimer capture, unpurified heterodimers in cell-culture media were diluted to 4% in PBST. One to five heterodimers or controls (i.e. controls containing either 100% HA-light chain or 100% FLAG-light chain) were simultaneously injected in individual ligand channels for 240 s at flow 25 µL/min, resulting in a saturating heterodimer capture of approximately 300 to 400 RUs onto the anti-penta His surface. The first ligand channel was left empty to use as a blank control if required. This heterodimer capture step was immediately followed by two buffer injections in the analyte direction to stabilize the baseline, and then 5 nM anti-FLAG and 5 nM anti-HA were each injected in duplicate at 50 µL/min for 120 s with a 180 s dissociation phase, resulting in a set of binding sensorgrams with a buffer reference for each of the captured heterodimer. The tissue factor (TF) antigen to which the heterodimer binds was also injected over the last remaining analyte channel as an activity control. The heterodimers were regenerated by an 18 s pulse of 0.85% phosphoric acid for 18 s at 100 µL/min to prepare the anti-penta His surface for the next injection cycle. Sensorgrams were aligned and double-referenced using the buffer blank injection and interspots, and the resulting sensorgrams were analyzed using PROTEON™ Manager software v3.0.

Results

The LCCA results are shown in Tables 12, 13a and 14a. Note that in Tables 13 and 14, the "Unique identifier" may not exactly correspond with Table 5, as the unique identifiers for the two constituent LCCAs may be in either of orientation ((Set #H1L1L2-Set #H2L2L1) or (Set #H2L2L1-Set #H1L1L2)). The assessment of preferential pairing for each LCCA design is shown in the last 3 columns of Table 12. The same data is also included in the context of design pairs in Tables 13a and 14a, in columns 5, 6, and 8, or 10, 11 and 13.

Each unique set of H1, L1 and L2 mutations (LCCA design) was assigned a unique number, or 'Set #' (e.g. 9567 or 9087). When data is presented in H1 L1 H2 L2 format (Fab pair format or design set), such a design set is consequently denoted with a 'unique identifier' comprised of set numbers for the two constituent LCCAs (e.g. 9567-9087). Note that the majority of LCCA experiments were performed on constructs containing the inter-chain Fab disulfide bond(s) located in the constant domain (H/C233-L/C214, Kabat numbering). Within Tables 13(a and b) and 14(a and b), for the purposes of highlighting a particular design's success with respect to preferential pairing, two complementary LCCA sets (H1, L1, L2 and H2, L2, L1) are represented in a Fab pair format. Presence of tags (L chain: HA and FLAG and H chain: $ABD_2$-$His_6$) did not affect the expected neutral pairing of ~50%: 50% for D3H44 WT.

In the tables, the LCCA data reported are the median values in ratio format (H1-L1:H1-L2 and H2-L2:H2-L1) normalized to L1:L2 DNA ratios of 1:1. Furthermore, the LCCA data were normalized to 100%, as it was observed for some variants that the total amount of L1 and L2 significantly differed from 100%. This discrepancy in total light chain percentage is believed to be due in part to the occurrence of variable non-specific binding during initial heterodimer capture on the SPR chip. As the LCCA experiments were conducted at 2 different L1:L2 DNA ratios (L1:L2 of 1:3 and 1:9, respectively), both of the LCCA normalized ratios are listed in the tables. Note that LCCA data were not reported for some LCCA experiments, as the experimental data obtained did not meet the inclusion criteria (e.g. Fab capture on SPR chip was less than 100, or the LCCA total amounts of L1 and L2 fell outside the 60 to 140 range).

Table 12 lists all of the LCCA designs (530) for which data were obtained. Out of the 530 LCCA designs, 490 (92.5%) of these LCCA designs had at least 60% correct pairing (at the normalized L1:L2 DNA ratio of 1:1), considering both of the L1:L2 DNA ratios of 1:3 and 1:9. The remaining LCCA designs included LCCA designs that were primarily neutral (32/530 or 6.0%) as well as a small proportion that yielded inconsistent (8/530 or 1.5%) results. The designs shown in Table 12 were primarily electrostatic (based on specificity drivers that utilize hydrogen bonding or charge-charge interactions) with some designs also including steric complementarity and/or inter-chain covalent disulfide bonds. Some designs also comprised mutations for the formation of new disulfide bonds in the absence of the natural inter-chain disulfide bond (formed by H/C233-L/C214).

Tables 13(a and b) and 14(a and b) list the 447 designs for which LCCA data was present for both heterodimers of a design set. Tables 13a and 14a demonstrate that the in silico design approach described in Example 1 led to achievement of preferential pairing of H1-L1 over H1-L2 and that of H2-L2 over H2-L1 across a diverse set of designs and their variations.

Tables 13(a and b) list those designs that have an average LCCA performance (average of the median normalized values to L1:L2 ratio of 1:1 for H1-L1:H1-L2 and H2-L2:H2-L1) of paired:mispaired Fab heterodimers of at least 86:14 whereas Tables 14 (a and b) list those designs that have an average LCCA performance of paired:mispaired Fab heterodimers below 86:14. The performance of each LCCA was normalized to 100% as well as to an L1:L2 DNA ratio of 1:1 (as described in this example above), and is described by both the scalar value ($\ln(r1/f1)$ or $\ln(r2/f2)$) where r1 and r2 correspond to the median values of H1L1:

H1L2 and H2L2:H2L1 at the experimental ratios, respectively, and f1 and f2 correspond to the respective experimental ratios) as well as by the ratio of paired to mispaired Fab heterodimers. Each design also has an associated average LCCA performance scalar value (0.5(ln(r1/f1)+ln(r2/f2))) that is also normalized to 100% as well as to an L1:L2 DNA ratio of 1:1 (as described in this example above). Furthermore, the scalar range for each LCCA of a design (LCCA1 and LCCA2, corresponding to H1L1:H1L2 and H2L2:H2L1 experiments, respectively) is shown. Out of 447 Mab designs, 354 (79.2%) exhibit at least an average LCCA performance of 86:14 (Table 13 a and b). The designs within Tables 13 (a and b) were further characterized into 13 clusters based on the similarity of designs. Designs within each cluster were arranged from highest to lowest average LCCA performance scalar value.

Figure 7:
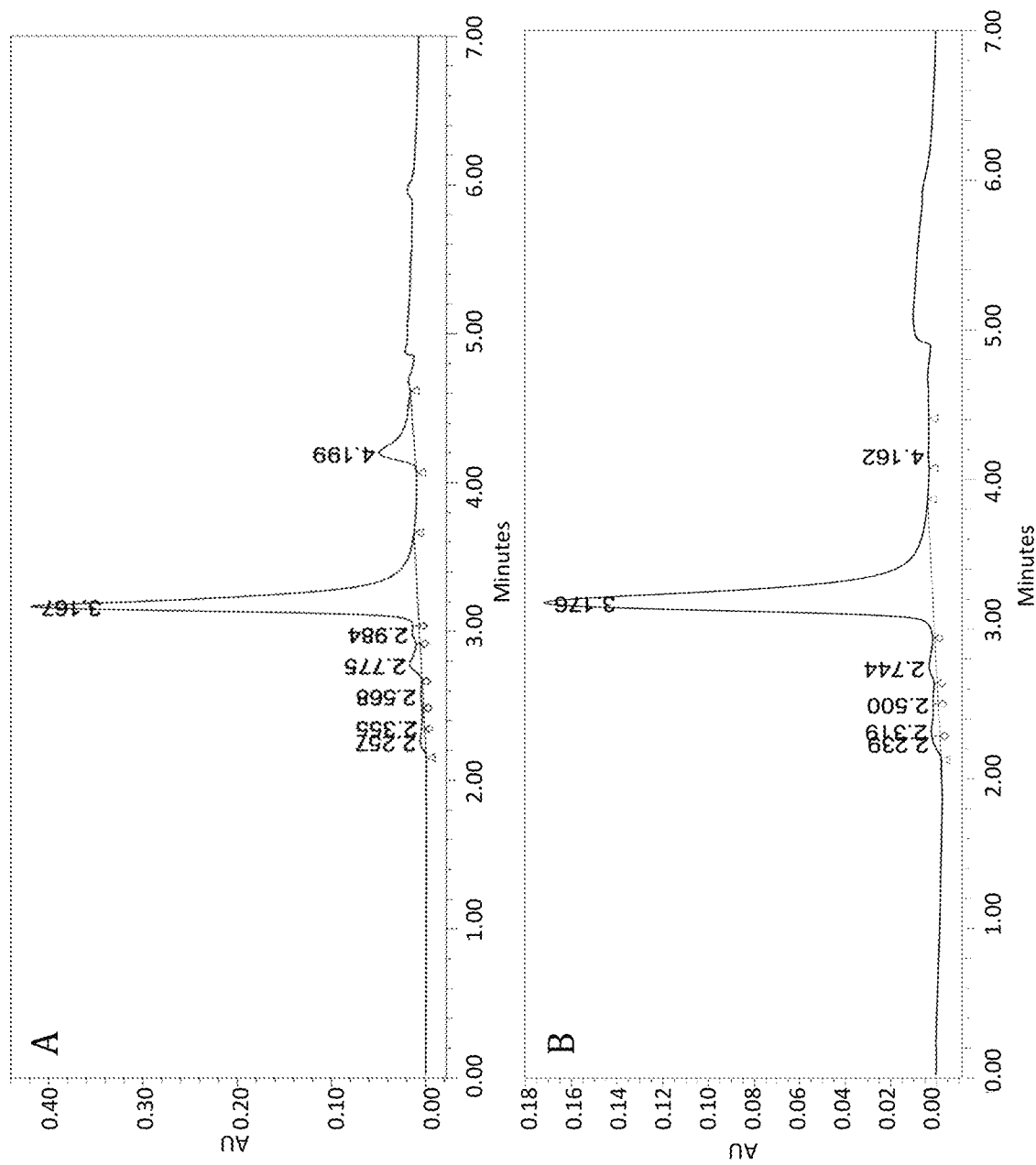
FIG. 7 shows representative UPLC-SEC profiles for A) WT Fab heterodimer as well as B) a representative designed Fab heterodimer (the H1L1 Fab component of LCCA designs 9735, 9737, and 9740).

In addition, the LCCA data within Table 13a was also graphically represented in FIG. 7. FIG. 7 depicts box plots that show the average LCCA performance values of paired: mispaired Fab heterodimers of at least 86:14 for each cluster. The bottom of each box indicates the first quartile (Q1), which is the middle average LCCA performance value between the smallest value and the median value, such that values below the $1^{st}$ quartile indicate the lowest 25% of data. The horizontal bar inside the box indicates the second quartile, which is the median average LCCA performance value for the cluster. The top of each box indicates the third quartile (Q3), which is the middle average LCCA performance value between the largest value and the median value, such that values above the $3^{rd}$ quartile indicate the highest 25% of data. The interquartile region is the difference between Q3 and Q1. The whiskers extending vertically in both directions indicate the data range for those values that are within Q1−(1.5*IQR) or Q3+(1.5*IQR). The horizontal bars that cap the whiskers indicate the largest and smallest values within the range. Data that exist outside the box plots and whiskers are identified as outliers, with mild outliers indicated by a dot (differs from Q1 or Q3 by 1.5*IQR to 3*IQR), and extreme outliers indicated by a plus sign (differs from Q1 or Q3 by greater than 3*IQR).

Example 5: Scale Up for Biophysical Characterization

Correctly paired heterodimers, as indicated in the unique identifier sets (Table 5), were scaled up (typically to 20 ml) and purified as follows in order to test for thermal stability and antigen binding. The heavy and light chains of each heterodimer were expressed in 20 ml cultures of CHO-3E7 cells. CHO-3E7 cells, at a density of 1.7-2×10⁶cells/ml, were cultured at 37° C. in FreeStyle™ F17 medium (INVITROGEN™ cat #A-1383501) supplemented with 4 mM glutamine and 0.1% KOLLIPHOR® P188 (Sigma #K4894). A total volume of 20 ml were transfected with a total of 20 μg DNA using PEI-pro® (Polyplus cat #115-375) at a DNA:PEI ratio of 1:2.5. Twenty-four hours after the addition of the DNA-PEI mixture, the cells were transferred to 32° C.

Cells were centrifuged 7 days after transfection, and heterodimers were purified from supernatant by high throughput nickel affinity chromatography purification, as follows. Supernatants were diluted to 20-25% cell culture supernatant in equilibration buffer (Dulbecco's phosphate buffered salines (DPBS) without Calcium, Magnesium, and phenol red (HYCLONE™#SH30028.02)) and then incubated with mixing for 12 hours with HisPur® Ni-NTA resin (Thermo Scientific #PI-88222), also previously equilibrated with the equilibration buffer. The resin was then collected by centrifugation, transferred to a 96 well-fritted plate, washed with equilibration buffer three times and eluted using HIS-Select® elution buffer (SIGMA-ALDRICH® #H5413).

Following purification, heterodimer expression was assessed by non-reducing High Throughput Protein Express assay using CALIPER LABCHIP® GXII (PERKIN ELMER® #760499). Procedures were carried out according to HT Protein Express LABCHIP® User Guide version2 LABCHIP® GXII User Manual, with the following modifications. Heterodimer samples, at either 2 μl or 5 μl (concentration range 5-2000 ng/μl), were added to separate wells in 96 well plates (BioRad #HSP9601) along with 7 μl of HT Protein Express Sample Buffer (PERKIN ELMER® #760328). The heterodimer samples were then denatured at 70° C. for 15 mins. The LABCHIP® instrument was operated using the HT Protein Express Chip (PERKIN ELMER® #760499) and the Ab-200 assay setting. After use, the chip was cleaned with MILLI-Q® water and stored at 4° C.

Example 6: Thermal Stability Measurements of Fab Heterodimers by DSF

To assess thermal stability, Differential Scanning Fluorescence (DSF) was used as a high throughput method to screen all correctly paired heterodimers in comparison to that of wild type, unmodified heavy chain-light chain pair. Heterodimers were prepared as described in Example 5.
Measurement of Thermal Stability The thermal stability of all heterodimer pairs was measured using DSF as follows. Each heterodimer was purified as described in Example 5 and diluted to 0.5 mg/mL in DPBS (HYCLONE™ Cat #SH30028.02). For the majority of samples, a working stock of SYPRO™ Orange gel stain (LIFE TECHNOLOGIES™ Cat #5-6650) was prepared by diluting 4 μL of SYPRO™ Orange gel stain to 2 ml DPBS. The DSF samples were prepared by adding 14 μL of 0.5 mg/mL protein to 60 μL of the diluted SYPRO™ Orange gel stain working stock. However, for proteins that had less than 0.5 mg/mL, each DSF sample were prepared by adding 14 μL of the undiluted protein to 60 μL of a working stock of SYPRO™ Orange dye (that was diluted to 1:1500 in DPBS). DSF analysis was then conducted, in duplicate, on 20 μl aliquots using the ROTO-GENE© 6000 qPCR instrument (QiaGen Inc). Each sample was scanned from 30° C. to 94° C. using 1° C. intervals with a 10 second equilibrium between each step and a 30 second wait time at the start. An excitation filter of 470 nM and emission filter of 610 nM with a gain of 9 was used. Data was analyzed with the ROTO-GENE® 6000 software using the maxima value from the first derivative of the denaturation curve as the Tm. The remaining DSF samples were prepared and analyzed similarly, with the following protocol modifications that do not alter the measured Tm values: 1) the working stock was prepared by diluting 1 μL of SYPRO™ Orange gel stain to 2 ml DPBS, 2) 30 μl aliquots were analyzed and 3) a gain of 10 was used.

DSF results are shown in Tables 12, 13b and 14b. The thermal stability of the H1:L1 Fab in the context of an LCCA design (DSF value and change in DSF value compared to wild-type) is shown in columns 3 and 4 of Table 12. The same DSF values are also included in the context of design pairs in Tables 13b and 14b, in columns 7 and 8. For each Fab heterodimer where repeats were conducted, the reported Tm value is the median value. Comparisons of the Fab heterodimer Tm values with respect to the Tm value of the wild-type Fab heterodimer (wild type Fab construct containing a HA tag, with a median Tm of 81.0° C.) are reported in the H1L1_dTm_dsf column. Note that for the few Fab heterodimers lacking the natural inter-chain disulfide (between H chain C233 and L chain C214), the H1L1_dTm_dsf values were not determined as the corresponding wild-type Fab lacking the natural inter-chain disulfide was not assessed. Also note that some Fab heterodimers do not have reported Tm values (17/230 or 7.4% of Fab heterodimers), due to the quality of the respective experiments (e.g. low yields, low intensities, partially occluded peaks, and variability between repeats of Fab heterodimers of greater than 1° C.). For some of these Fab heterodimers, estimated Tm values are reported instead, corresponding to the Tm values from similar Fab heterodimers that differ only in the presence/absence or identity of the attached L chain tag (HA or FLAG). For the estimated Tm values, the corresponding wild-type Tm value (81.2° C.) is the median value obtained from all wild-type Fab heterodimer constructs (i.e. Fab constructs containing HA tag or FLAG™ tag). The HA or FLAG™ tag does not significantly affect the Tm values of the wild-type Fab heterodimers. Overall, the Fab heterodimers exhibited similar Tm values compared to WT. Of the Fab heterodimers containing the natural inter-chain disulfide and also for which DSF data are available, 93% (195/209) of the Fab heterodimers exhibited a loss of 3° C. or less with respect to WT. Furthermore, the most affected Fab heterodimer exhibited a loss of 6.5° C. with respect to WT. Table 12 lists the LCCA designs in decreasing Tm rank order.

Furthermore, thirteen amino acid substitutions were identified that generally improved the stability of Fab heterodimers (see Table 34). The stabilizing mutations were identified following comparisons of Fab heterodimers that include the stabilizing mutation versus similar Fab heterodimers that differ in the absence of the stabilizing mutation. Heavy chain stabilizing mutations include A125R, H172R, L143F, Q179D, Q179E, Q39R, S188L, and V190F. Light chain stabilizing mutations include Q124E, Q124R, Q160F, S176L, and T180E. Overall, the stabilizing mutations increased stability by 0.4° C. to 2.1° C. The heavy chain stabilizing mutations A125R, H172R, L143F, Q179D, Q179E, Q39R, S188L, and V190F increased stability by 0.4° C. to 0.6° C., 0.4° C. to 2.1° C., 0.4° C., 0.5° C. to 0.6° C., 0.5° C. to 0.8° C., 1.1° C. to 1.6° C., 0.4° C. to 1.2° C., and 1° C., respectively. The light chain stabilizing mutations Q124E, Q124R, Q160F, S176L, and T180E increased stability by 0.4° C. to 0.5° C., 0.8° C. to 0.9° C., 0.6° C., 0.4° C. to 1.0° C., and 0.5° C., respectively.

Example 7: Antigen Affinity Measurements of Fab Heterodimers

The ability of the Fab heterodimers to bind to tissue factor was assessed in order to determine whether the amino acid substitutions had any effect on the ability of the heterodimer to bind to antigen. The affinity of each Fab heterodimer for tissue factor was determined by SPR as follows.

SPR supplies. GLC sensorchips, the Biorad PROTEON™ amine coupling kit (EDC, sNHS and ethanolamine), and 10 mM sodium acetate buffers were purchased from BIO-RAD® Laboratories (Canada) Ltd. (Mississauga, ON). PBS running buffer with 0.05% TWEEN® 20 (PBST) was purchased from Teknoca Inc. (Hollister, CA).

Fab heterodimer batches. The purified Fab heterodimers were tested in 3 batches, A, B, and C. Batches A and B were stored at 4° C. for approximately 1 month prior to conducting the SPR assays, whereas the purified Fab heterodimers from batch C were stored at 4° C. for approximately 2 months, prior to conducting the SPR assays. The Fab heterodimers from batch C are indicated by a "+" next to the corresponding KD values in Table 12.

All surface plasmon resonance assays were carried out using a BioRad PROTEON™ XPR36 instrument (BIO-RAD® Laboratories (Canada) Ltd. (Mississauga, ON)) with PBST running buffer at a temperature of 25° C. The anti-penta His capture surface was generated using a GLC sensorchip activated by a 1:5 dilution of the standard Bio-Rad sNHS/EDC solutions injected for 140 s at 100 µL/min in the analyte (horizontal) direction. Immediately after the activation, a 25 µg/mL solution of anti-penta His antibody (Qiagen Inc.) in 10 mM NaOAc pH 4.5 was injected in the analyte (vertical) direction at a flow rate of 25 µL/min until approximately 3000 resonance units (RUs) was immobilized. Remaining active groups were quenched by a 140 s injection of 1M ethanolamine at 100 µL/min in the analyte direction, and this also ensured mock-activated interspots were created for blank referencing.

The screening of the Fab heterodimers for binding to TF antigen occurred in two steps: an indirect capture of the Fab heterodimers onto the anti-penta His antibody surface in the ligand direction followed by the simultaneous injection of 5 concentrations of purified antigen and one buffer blank for double referencing in the analyte direction. First, the baseline was stabilized with one buffer injection for 30 s at 100 uL/min in the ligand direction. One to five variants or controls, at a concentration of 3.4 µg/ml in PBST, were simultaneously injected in individual ligand channels for 240 s at a flow 25 µL/min. This resulted in an average capture of approximately 1000 RUs onto the anti-penta His surface for batches A and B, and an average capture of approximately 600 RUs onto the anti-penta His surface for batch C. The first ligand channel was left empty to use as a blank control if required. This capture step was immediately followed by two buffer injections, at 100 µL/min for 30 s each, in the analyte direction to stabilize the baseline, and then 60 nM, 20 nM, 6.7 nM, 2.2 nM and 0.74 nM antigen (TF) along with a buffer blank was simultaneously injected at 50 µL/min for 120 s with a 600 s dissociation phase. The captured antibody surfaces were regenerated by two 18 s pulses of 0.85% phosphoric acid for 18 s at 100 µL/min to prepare for the next injection cycle. Sensorgrams were aligned and double-referenced using the buffer blank injection and interspots, and the resulting sensorgrams were analyzed using PROTEON™ Manager software v3.1. The double-referenced sensorgrams were fit to the 1:1 binding model. Rmax values for each antigen were normalized to antibody capture levels for each variant and compared to 100% controls.

Antigen affinity (KD) values for Fab heterodimer samples are reported in Tables 12, 13b and 14b. The KD values of the H1:L1 Fab in the context of an LCCA design (KD, range of KD values, and change in median KD values compared to wild-type) are shown in columns 5, 6, and 7, respectively, of Table 12. The same KD values are also included in the context of design pairs in Tables 13b and 14b, in columns 3 (KD of H1-L1 Fab heterodimer), 4 (change in KD of H1-L1 Fab heterodimer compared to wild-type), 5 (KD of H2-L2 Fab heterodimer), and 6 (change in KD of H2-L2 Fab heterodimer compared to wild-type). KD values were determined only for Fab heterodimer samples that exhibited a Fab heterodimer capture of at least 100 RU. The reference wild-type KD (0.157 nM) reflects the median value of the wild-type Fab heterodimer where the light chain contains a FLAG™ tag. The wild-type Fab heterodimers (containing either the FLAG or HA tag) exhibited similar KD values, such that a 2.6 fold difference was observed between the maximum and minimum values. In Tables 12, 13b and 14b, the difference in KD with respect to wild type antigen binding affinity is shown using the calculation –(log(KD) design–log(KD)wt), such that positive values indicate lower KD values whereas negative values indicate increased KD values of the Fab heterodimer compared with wild type binding affinity for antigen. Note that some Fab heterodimers lack measured KD values. In some of these cases, the Fab heterodimers were assessed but the SPR experiments exhibited low Fab heterodimer capture (i.e. less than 100 RU), and therefore accurate determinations of KD values were not possible. For those Fab heterodimers that exhibit similarity to other Fab heterodimers (i.e. differ only in the presence/absence or identity of the attached L chain tag (HA or FLAG)), estimated KD values are provided instead (as noted in Table 12, 13b and 14b), corresponding to the KD values from the similar Fab heterodimers. The corresponding estimated wild-type KD value (0.15 nM) was the median value obtained from all wild-type Fab heterodimers constructs (i.e. Fab constructs containing HA tag or FLAG™ tag). Overall, the results indicate that the correctly paired heterodimers (from a design perspective) exhibit wild-type like binding affinity for antigen (within approximately 2.3 times of the reference wild-type affinity).

Example 8. UltraPerformance Liquid Chromatography Size Exclusion Chromatography (UPLC-SEC) Profiles of Wild-Type Tagged D3H44 Heterodimers and Preferentially Paired Heterodimers Wild-type D3H44 heterodimers (one heavy chain and one light chain) with a C-terminus ABD2-His$_6$ tag on the heavy chain and an N-terminus tag (FLAG in one construct and HA in another construct) on the light chain were expressed and purified according to methods known in the art and similar to those described in Example 5. Preferentially or correctly paired heterodimers were individually scaled up and purified via His tag affinity purification as described in Example 5.

UPLC-SEC was performed using a WATERS® BEH200 SEC column (2.5 mL, 4.6×150 mm, stainless steel, 1.7 µm particles) set to 30° C. and mounted on a WATERS® Acquity UPLC™ system with a PDA detector. Run times consisted of 7 min and a total volume per injection of 2.8 mL with a running buffer of Hyclone DPBS/Modified -Calcium -Magnesium (part no. SH30028.02) at 0.4 ml/min. Elution was monitored by UV absorbance in the range 200-400 nm, and chromatograms were extracted at 280 nm. Peak integration was performed using Empower 3 software.

Figure 6:
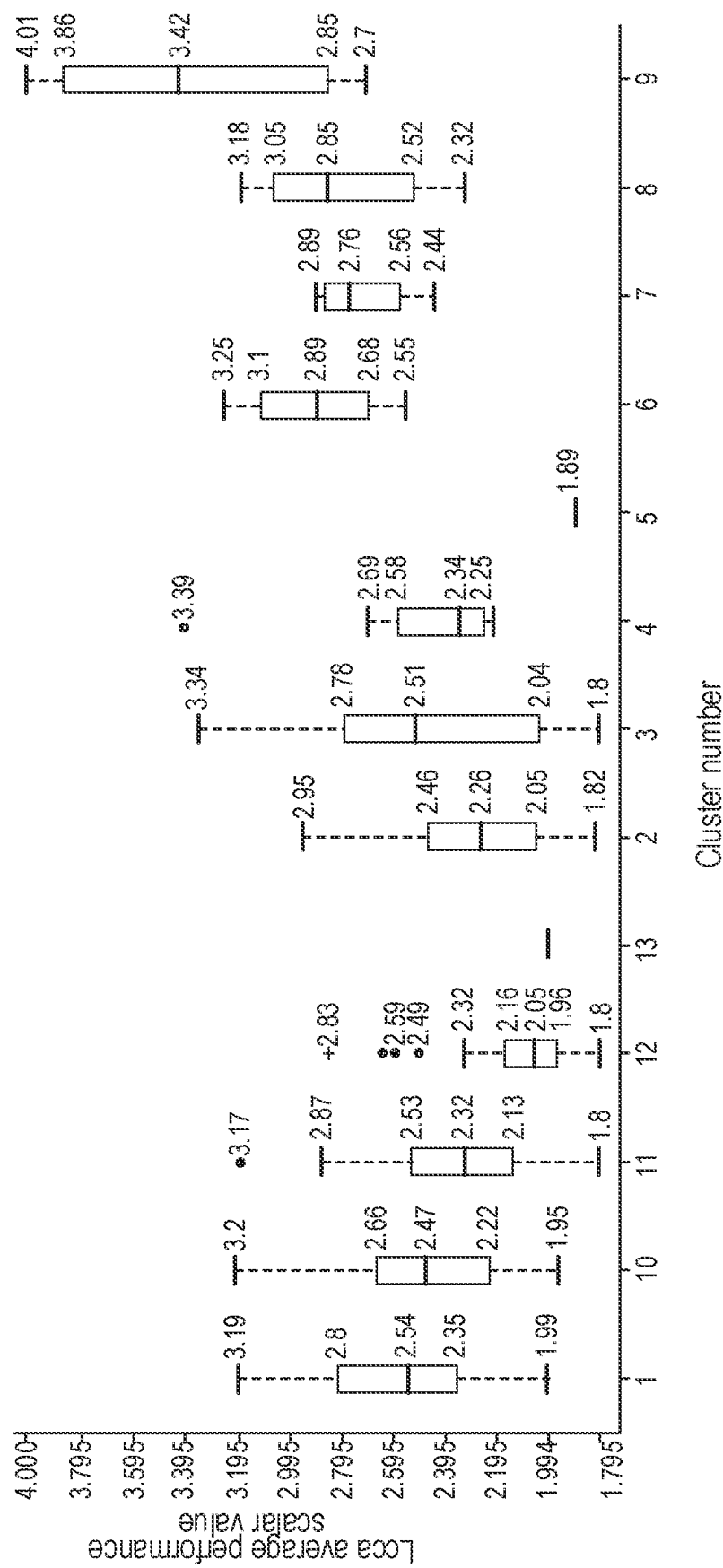
FIG. 6 depicts box plots that show the average LCCA performance values of paired:mispaired Fab heterodimers of at least 86:14 for each cluster.

FIG. 6 shows UPLC-SEC profiles for a representative WT Fab heterodimer pair (containing the FLAG™ tag on the L chain) as well as a representative (the H1L1 Fab component of LCCA designs 9735, 9737, and 9740) for the designed Fab heterodimer pairs. In general, the designed Fab heterodimer pairs exhibited similar UPLC-SEC profiles compared with WT.

Example 9: Assessment of Preferential Pairing of Heterodimers in Co-Expression Sets Comprising Either Constant Domain or Constant and Variable Domain Modifications in a Bi-Specific Antibody Format The heterodimer designs were assessed to determine if they also allowed for preferential pairing in bi-specific antibody format. In this example, to promote heterodimerization of the unique heavy chains, the Fc region of the full-length heavy chain of each heterodimer was asymmetrically modified such that one heavy chain comprised the mutations T350V, L351Y, F405A and Y407V and the other heavy chain comprised the mutations T350V, T366L, K392L and T394W (EU numbering). Preparation of constructs:

The heterodimer designs were tested in the context of the following bi-specific antibodies: a) D3H44/trastuzumab, b) D3H44/cetuximab, and c) trastuzumab/cetuximab. Note that D3H44 is a human antibody, trastuzumab is a humanized antibody and cetuximab is a chimeric antibody comprised of human IgG1 and mouse Fv regions. Constructs encoding the D3H44, trastuzumab and cetuximab IgG heavy and light chains comprising amino acid modifications according to the designs were prepared as follows. The base DNA sequences for the heavy and light chains of D3H44, trastuzumab and cetuximab are shown in Table 3C. The D3H44, trastuzumab and cetuximab light chain sequences were prepared as described in Example 3, except that some sequences lack a tag whereas other sequences contain a FLAG or HA tag. D3H44, trastuzumab and cetuximab heavy chain sequences were prepared as described in Example 3, except that full-length heavy chains were created by appending the IgG1*01 DNA sequence encoding the hinge-CH2-CH3 domains and modified to promote heterodimerization, onto the C-terminus of the CH1 domain of the Fab heavy chains. Of note, the canonical C-terminal heavy chain lysine residue was removed in order to prevent LC-MS signal heterogeneity due to C-terminal lysine clipping (Lawrence W. Dick Jr. et al., Biotechnol. Bioeng. (2008) 100:1132-43).

Assay Format (SMCA)

Figure 8:
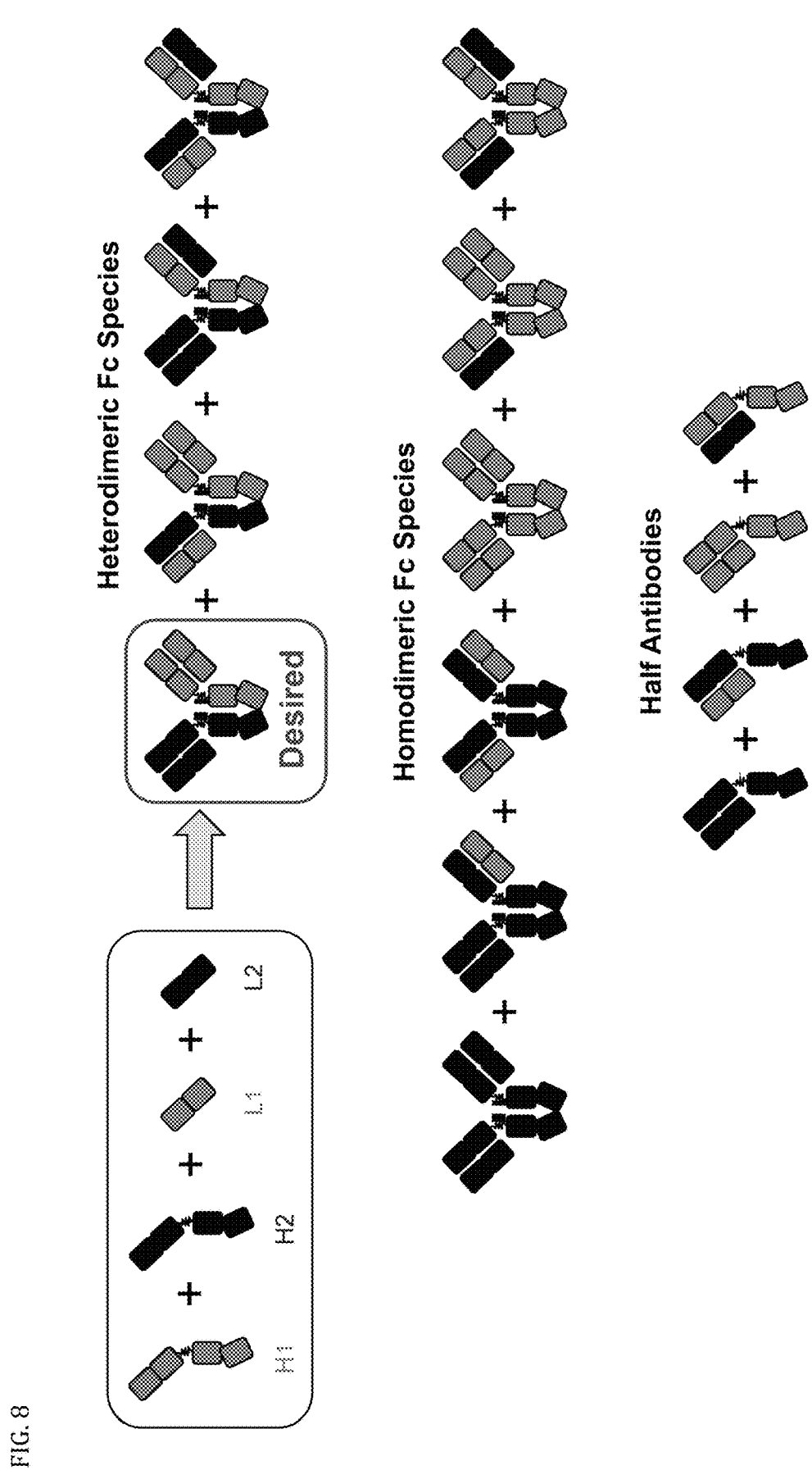
FIG. 8 depicts the potential heavy chain associated products that can be expected when two different light chains are co-expressed with two different heavy chains in a cell. Preferential pairing is assessed using an SMCA (monoclonal antibody competition assay).

The ability of the heterodimer co-expression set designs to preferentially pair to form a bi-specific antibody was assessed as described below. The assay is based on co-expressing the four chains (H1 and L1 chains from one antibody with the H2 and L2 chains from the other antibody) and detecting the presence of correctly formed bispecific antibody using mass spectrometry (LC-MS). FIG. 8 provides a schematic depicting the four starting polypeptide chains and the potential products resulting from co-expression of these starting polypeptide chains in the absence of preferential pairing between heavy and light chains of the heterodimer pairs. Two full-length heavy chain constructs were co-expressed with two unique light chain constructs, yielding ten possible antibody species: H1-L1:H1-L1, H1-L2:H1-L2, H1-L1:H1-L2, H2-L1:H2-L1, H2-L2:H2-L2, H2-L1:H2-L2, H1-L1:H2-L1, H1-L2:H2-L2, H1-L2:H2-L1 and H1-L1:H2-L2. The H1-L1:H2-L2 species is the correctly paired bispecific antibody (see FIG. 8). The relative pairing specificity in terms of amount of preferred species H1-L1:H2-L2 vs. others was determined using LC-MS after pA purification and deglycosylation. When possible, chains were left untagged, provided all Mab and half-Ab species differed from each other by at least 50 Da. When mass differences precluded this possibility, N-terminal tags (HA or FLAG) were added to the light chains in order to provide sufficient mass differentiation between species.

This assay, involving the expression and screening steps of a bispecific antibody, is referred to as SMCA.

Mass Spectrometry Method

The degree of preferential D3H44 light chain pairing to D3H44 heavy chain in co-expression sets was assessed using mass spectrometry after protein A purification and non-denaturating deglycosylation. As the D3H44/ trastuzumab heterodimers contained Fc N-linked glycans only, this system was treated with only one enzyme, N-glycosidase F (PNGase-F). The purified samples were de-glycosylated with PNGaseF as follows: 0.2U PNGaseF/µg of antibody in 50 mM Tris-HCl pH 7.0, overnight incubation at 37° C., final protein concentration of 0.5 mg/mL. For the D3H44/cetuximab and the trastuzumab/cetuximab systems, due to the additional N-linked glycan in the Fab region of cetuximab, the systems were treated with N-glycosidase F plus a number of exoglycosidases. Typically, a four enzyme mixture was used for this purpose: N-glycosidase F, β-galactosidase (Prozyme), β-N-acetylglucosaminidase (New England Biolabs) and neuraminidase. N-glycosidase F removes the Fc N-linked glycans while the exoglycosidases trim the Fab N-linked glycans to a uniform core structure, M3F ($GlcNAc_2Man_3Fuc_1$). The purified samples were de-glycosylated with the four enzyme mixture as follows: 0.2U PNGaseF/µg of antibody, 0.002U α-Neuraminidase/µg of antibody, 0.0001U β-Galactosidase/µg of antibody and 0.2U β-N-Acetylglucosaminidase/µg of antibody in 50 mM Tris-HCl pH 7.0, overnight incubation at 37° C., final protein concentration of 0.5 mg/mL. However, in some cases, a three enzyme treatment (N-glycosidase F, β-galactosidase and neuraminidase) was preferable in order to avoid mass overlaps of sample components in the LC-MS analysis. In these instances the Fab glycans were reduced to a slightly larger structure G0F ($Man_3GlcNAc_2Fuc_1GlcNAc_2$). The purified samples were de-glycosylated with the three enzyme mixture using the same concentrations and conditions as described for the four enzyme mixture. After deglycosylation, the samples were stored at 4° C. prior to LC-MS analysis.

The deglycosylated protein samples were analyzed by intact LC-MS using an AGILENT® 1100 HPLC system coupled to an LTQ®-Orbitrap XL™ mass spectrometer (THERMOFISHER SCIENTIFIC®) via an Ion Max electrospray ion source (THERMOFISHER®). The samples (5 µg) were injected onto a 2.1×30 mm POROS™ R2 reverse phase column (APPLIED BIOSYSTEMS™) and resolved using the following gradient conditions: 0-3 min: 20% solvent B; 3-6 min: 20-90% solvent B; 6-7 min: 90-20% Solvent B; 7-9 min: 20% solvent B. Solvent A was degassed 0.1% formic acid aq. and solvent B was degassed acetonitrile. The flow rate was 3 m/min. The flow was split post-column to direct 100 µL into the electrospray interface. The column was heated to 82.5° C. and solvents were heated pre-column to 80° C. to improve protein peak shape. The LTQ®-Orbitrap XL™ was calibrated using THERMOFISHER SCIENTIFIC®'s LTQ® Positive Ion ESI calibration solution (caffeine, MRFA and ULTRAMARK® 1621), and tuned using a 10 mg/mL solutions of CsI. The cone voltage (source fragmentation setting) was 40 V, the FT resolution was 7,500 and the scan range was m/z 400-4,000. The LTQ®-Orbitrap XL™ was tuned for optimal detection of larger proteins (>50 kDa).

The ranges containing the multiply charged ions from from the full-sized antibodies (m/z 2000-3800) and the half-antibodies (m/z 1400-2000) were separately deconvoluted into molecular weight profiles using MaxEnt 1 module of MASSLYNX™, the instrument control and data analysis software (WATERS®). Briefly, the raw protein LC-MS data were first opened in QualBrower, the spectrum viewing module of XCALIBUR™ (THERMO SCIENTIFIC™) and converted to be compatible with MASSLYNX™ using Databridge, a file conversion program provided by WATERS®. The converted protein spectra were viewed in the Spectrum module of MASSLYNX™ and deconvoluted using MaxEnt 1. The abundances of the different antibody species in each sample were determined directly from the resulting molecular weight profiles.

Representative Designs for the SMCA Assay

A total of 25 representative designs with high average LCCA performance values were selected from clusters 1 through 12 for testing in SMCA format. Representative designs were chosen based on the corresponding designs sets occupying similar space, using similar drivers while also sharing similar mutations. At least one representative design was chosen from each cluster. Some clusters were represented by one representative design (i.e. clusters 1, 5, 7, 8, 10). The remaining clusters had more than one representative design as the clusters were either large (i.e. cluster 2) or were comprised of minor clusters (i.e. clusters 3, 4, 6, 9, 11 and 12). Although the designs within each cluster shared sequence similarities, minor clusters within a cluster differed in at least one set of driver mutations. For the clusters that were comprised of minor clusters, additional representative designs were chosen from each of the minor clusters.

The amino acid substitutions for each of the clusters are listed in Tables 15 through 27 and the corresponding representatives for each cluster/minor cluster are indicated. For cluster 1, only one design (9134-9521) was chosen to represent the cluster as these designs utilized similar electrostatic drivers occupying similar space (see Table 15). For all members of this cluster, H1 was designed to allow negatively charged substitutions (L124E and Q179E) to form salt bridges with L1 positively charged substitutions (S176R and either S131K or S131R). H2 was designed to allow for positively charged substitutions (L124R and either Q179K or S186K) to form salt bridges with L2 negatively charged substitutions (S176D and either T178D or T178E and/or T180E). Mismatched pairing of H1L2 and H2L1 would be disfavored primarily due to electrostatic repulsion.

For cluster 2, two representative designs (9279-9518 and 9286-9402) were chosen to represent the large cluster (see Table 16). The designs within this cluster utilized similar electrostatic drivers occupying similar space. For all members of this cluster, H1 was designed to allow negatively charged substitutions (L124E and L143E or L143D) to form salt bridges with L1 positively charged substitutions (S176R and a combination of either (Q124K and/or T178K) or (Q124K and Q160K)). H2 was designed to allow for positively charged substitutions (L124R and Q179K or S186K or S186R) to form salt bridges with L2 negatively charged substitutions (S176D and T178D or T178E and/or T180E). Mismatched pairing of H1L2 and H2L1 would be disfavored primarily due to electrostatic repulsion.

For cluster 3, five representative designs (9338-9748, 9815-9825, 6054-9327, 9066-9335 and 9121-9373) were chosen to represent each of the five minor clusters (see Table 17). All members of this cluster utilized similar electrostatic drivers on H1 (L124E), L1 (S176R), H2 (L124R), and L2 (S176D), which would allow for the formation of salt bridges in the preferentially paired heterodimers while the mismatched pairs would be disfavored primarily due to electrostatic repulsion. To represent those designs that utilized primarily those constant region drivers, the 6054-9327 design was chosen to represent this minor cluster. In addition to these electrostatic interactions, one minor cluster also comprised a variable region steric driver (H1 L45P and L1 P44F) and therefore a representative including this variable region driver was chosen to represent this minor cluster (9338-9748). Another minor cluster also comprised variable region electrostatic drivers in both Fab heterodimers (H1

Q39E, L1 Q38R, H2 Q39R, L2 Q38E) and therefore a representative including this variable region driver was chosen to represent this minor cluster (9815-9825). Furthermore, one minor cluster comprised of one member and hence one representative design (9066-9335) includes an engineered disulfide between H1 F122C and L1 Q124C. The remaining minor cluster, represented by 9121-9373, utilized primarily the constant region drivers with additional substitutions H172T in H1 and S174R in L1 to slightly modify the interaction of the H1L1 constant region drivers, while also probing the effect of H172R in HC2.

For cluster 4, two representative designs (9168-9342 and 9118-6098) were chosen to represent each of the two minor clusters (see Table 18). All members of this cluster utilized similar electrostatic drivers on H1 (L124E), L1 (S176R or S176K), H2 (L124R), and L2 (S176D), which would allow for the formation of salt bridges in the preferentially paired heterodimers while the mismatched pairs would be disfavored primarily due to electrostatic repulsion. One minor cluster, represented by 9118-6098, primarily utilized the shared electrostatic drivers for preferential pairing whereas the other minor cluster represented by 9168-9342, further utilized substitutions from H1 (K228D) and L1 (S121K) that would allow for the formation of an additional salt bridge.

Cluster 5, represented by unique identifier 9116-9349, is comprised of only 1 member (see Table 19). This design utilized both electrostatic drivers on H1 (L124E), L1 (S176R), H2 (L124R) and L2 (S176D) as well as steric drivers on H1 (A139W), L1 (F116A_V133G_L135V), H2 (A139G_V190A) and L2 (V133G_L135W). As a result, for the preferentially paired heterodimers, the charged substitutions would allow for the formation of salt bridges. As for the mispaired Fab heterodimers, the formation would be disfavoured due to electrostatic repulsion as well as additional steric effects.

For cluster 6, two representative designs were chosen to represent each of the two minor clusters (see Table 20). All members of this cluster utilized similar electrostatic drivers in the constant region (Q179E on H1, S131K on L1, S186R on H2, and Q124E, Q160E, and T180E on L2) which would allow for the formation of salt bridges in the preferentially paired heterodimers while the mismatched pairs would be disfavored primarily due to electrostatic repulsion. In addition, the minor clusters also were comprised of different variable region drivers. One minor cluster, represented by unique identifier 9814-9828, utilized the electrostatic drivers in the variable regions (Q39E on H1, Q38R on L1, Q39R on H2, and Q38E on L2). The other minor cluster utilized a variable region steric driver comprised of L45P in H1 and P44F in L1. As a result, for this minor cluster, the mismatched pairs would be further disfavored due to the introduced steric effects. Note that this minor cluster is represented by a design derived from unique identifier 9745-9075, which differs only in the absence of Q38E on L2.

For cluster 7, only one design (9060-9756) was chosen to represent the cluster as these designs utilized similar electrostatic and steric drivers (see Table 21). Shared electrostatic drivers comprised L143E and Q179E on H1, Q124R on L1, Q179K on H2, and Q124E, Q160E, and T180E on L2. Shared steric drivers comprised A139W on H1, F116A_L135V on L1, and L135W on L2. As a result, for the preferentially paired heterodimers, the charged substitutions in the Fab regions would allow for the formation of salt bridges. As for the mispaired heterodimers, the formation would be disfavoured due to electrostatic repulsion as well as additional steric effects.

For cluster 8, only one design (9820-9823) was chosen to represent the cluster as these designs utilized similar electrostatic drivers (see Table 22). In the variable region, Q39E on H1, Q38R on L1, Q39R on H2, and Q38E on L2 were utilized. In the constant region, L143E on H1, Q124R, Q160K and T178R on L1, Q179K on H2, and Q124E, Q160E and T180E on L2 were utilized. For the preferentially paired heterodimers, the charged substitutions in the Fab regions would allow for the formation of salt bridges whereas for the mispaired heterodimers, the formation would be disfavoured primarily due to electrostatic repulsion.

For cluster 9, two representative designs were chosen to represent each of the two minor clusters (see Table 23). All members of this cluster utilized similar electrostatic drivers in the constant region (L143E on H1, Q124R on L1, Q179K on H2, and Q124E, Q160E, and T180E on L2) which would allow for the formation of salt bridges in the preferentially paired heterodimers while the mismatched pairs would be disfavored primarily due to electrostatic repulsion. In addition, the minor clusters differ in the presence/absence of a variable region driver (L45P on H1, and P44F on L1). As a result, for the minor cluster comprising the variable region driver, the mismatched pairs would be further disfavored due to the introduced steric effects. The representative design for this minor cluster comprising the variable region driver was derived from the unique identifier 9751-9065, which differs only in the absence of Q38E on L2. The representative design for the minor cluster lacking the variable region substitutions is 9611-9077.

For cluster 10, only one design (9561-9095) was chosen to represent the cluster as these designs utilized similar electrostatic and steric drivers occupying similar space (see Table 24). The shared electrostatic drivers comprised L143E and Q179E on H1, similarly located Q124R, Q124K or S131K on L1, Q179K on H2, and Q124E and T180E on L2. The shared steric drivers comprised L124W on H1, V133A on L1, and V133W on L2. As a result, for the preferentially paired heterodimers, the charged substitutions in the Fab regions would allow for the formation of salt bridges. As for the mispaired heterodimers, the formation would be disfavoured due to electrostatic repulsion as well as additional steric effects.

For cluster 11, three designs (9049-9759, 9682-9740 and 9667-9830) were chosen to represent each of the three minor clusters (see Table 25). All members of this cluster utilized electrostatic substitutions to drive preferential pairing of heterodimers. As a result, for the preferentially paired heterodimers, the charged substitutions in the Fab regions would allow for the formation of salt bridges. As for the mispaired heterodimers, the formation would be disfavoured primarily due to electrostatic repulsion. For the minor cluster represented by unique identifier 9667-9830, the shared substitutions comprised negatively charged substitutions (L143E or L143D and Q179E or Q179D) on H1, positively charged substitutions on (T178R or T178K) L1, positively charged substitutions (S186K or S186R or Q179K or Q179R) on H2 and negatively charged substitutions (Q124E) on L2. Another minor cluster, represented by the sole member of this minor cluster (unique identifier 9049-9759), additionally contained substitutions for the formation of an engineered disulfide bond. The remaining cluster, represented by unique identifier 9682-9740, utilized similar drivers for H1 and L1 as the other two minor clusters; however, different constant region H2 and L2 drivers were utilized. H2 utilized L143R or L143K and L2, in addition to the Q124E substitution (shared with the other two minor clusters), utilized V133E or V133D.

For cluster 12, four designs (9696-9848, 9986-9978, 9692-9846 and 9587-9735) were chosen to represent each of the four minor clusters (see Table 26). All members of this cluster utilized electrostatic substitutions to drive preferential pairing of heterodimers. Some members additionally utilized steric drivers. The minor cluster represented by the unique identifier 9696-9848, utilized both electrostatic and steric drivers. The shared electrostatic substitutions within this minor cluster comprised of L143E on H1, Q124R and T178R on L1, similarly located S186K or S186R or Q179K or Q179R on H2, and Q124E and T180E on L2. The shared steric substitutions within this minor cluster comprised of S188L on H1, and either S176L or V133Y or V133W on L2; for designs that utilized V133Y or V133W on L2, either L143A or L124A was also present on H2 to accommodate the bulky mutations. For the minor cluster represented by the unique identifier 9692-9846, similar electrostatic drivers were utilized compared with the minor cluster represented by the unique identifier 9696-9848; for some members, a similar located substitution, T178E, was utilized instead of T180E on L2. Furthermore, a subset from this minor cluster also utilized similar steric drivers, with a similarly located substitution of T178Y or T178F instead of S176L on L2. The minor cluster represented by the unique identifier 9986-9978 utilized only electrostatic drivers to drive preferential pairing. Similar shared substitutions were utilized for H1, L1 and H2; however, a different L2 substitution (S131E) was utilized. The remaining minor cluster, represented by the unique identifier 9587-9735, utilized similar electrostatic drivers on H1 and L1 (except that T178R on L1 was not utilized in all members within this minor cluster); however, different electrostatic drivers were utilized for H2 (L143R or L143K) and L2 (Q124E and V133E or Q124E and V133D). A couple of members within this minor cluster also utilized similar steric drivers comprised of S188L on H1 and S176L on L2. Overall, for the preferentially paired heterodimers, the charged substitutions in the Fab regions would allow for the formation of salt bridges. As for the mispaired heterodimers, the formation would be disfavoured due to electrostatic repulsion. Furthermore, for the designs that also utilized steric drivers, the formation would be additionally disfavoured due to steric effects. Cluster 13 is comprised of one member, 9122-9371 (see Table 27). This design utilized an engineered disulfide between H1 F122C and L1 Q124C as a covalent driver for preferential pairing of heterodimers. In addition, since the design also lacked the natural interchain disulfide, the formation of the disulfide bond was confirmed by non-reducing and reducing SDS-PAGE gel. This design was not tested in SMCA format; however, the engineered disulfide was tested in the presence of the natural interchain disulfide and in combination with additional constant region drivers (cluster 3, representative design 9066-9335).

Transfection Method

Co-expression sets comprising two heavy chains and two light chain constructs were transfected into CHO-3E7 cells as follows. CHO-3E7 cells, at a density of 1.7-2×10$^6$ cells/ml, were cultured at 37° C. in FreeStyle™ F17 medium (INVITROGEN™ cat #A-1383501) supplemented with 4 mM glutamine and 0.1% PLURONIC® F-68 (INVITROGEN™ cat #24040-032). A total volume of 50 ml were transfected with a total of 50 ug DNA using PEI-pro® (Polyplus cat #115-010) at a DNA:PEI ratio of 1:2.5. Twenty-four hours after the addition of the DNA-PEI mixture, the cells were transferred to 32° C. and incubated for 7 days prior to harvesting. Culture media was harvested by centrifugation and vacuum filtered using a STERIFLIP® 0.2 µM filter. The filtered culture media was then purified using protein A MABSELECT™ SURE™ resin (GE Healthcare #17-5438-02) as follows. The filtered culture media was applied to a column (Hyclone DPBS/modified, No Calcium, No Magnesium, #SH-300028.02) that was previously equilibrated with PBS. The heterodimeric antibody species was then washed with PBS and eluted with 100 mM citrate pH 3.6 in an AMICON® ultra 15 centrifuge filter Ultracel 10K (MILLIPORE® #SCGP00525). The buffer was then exchanged with PBS and the samples were assessed by caliper prior to deglycosylation and LC-MS.

Figure 9A:
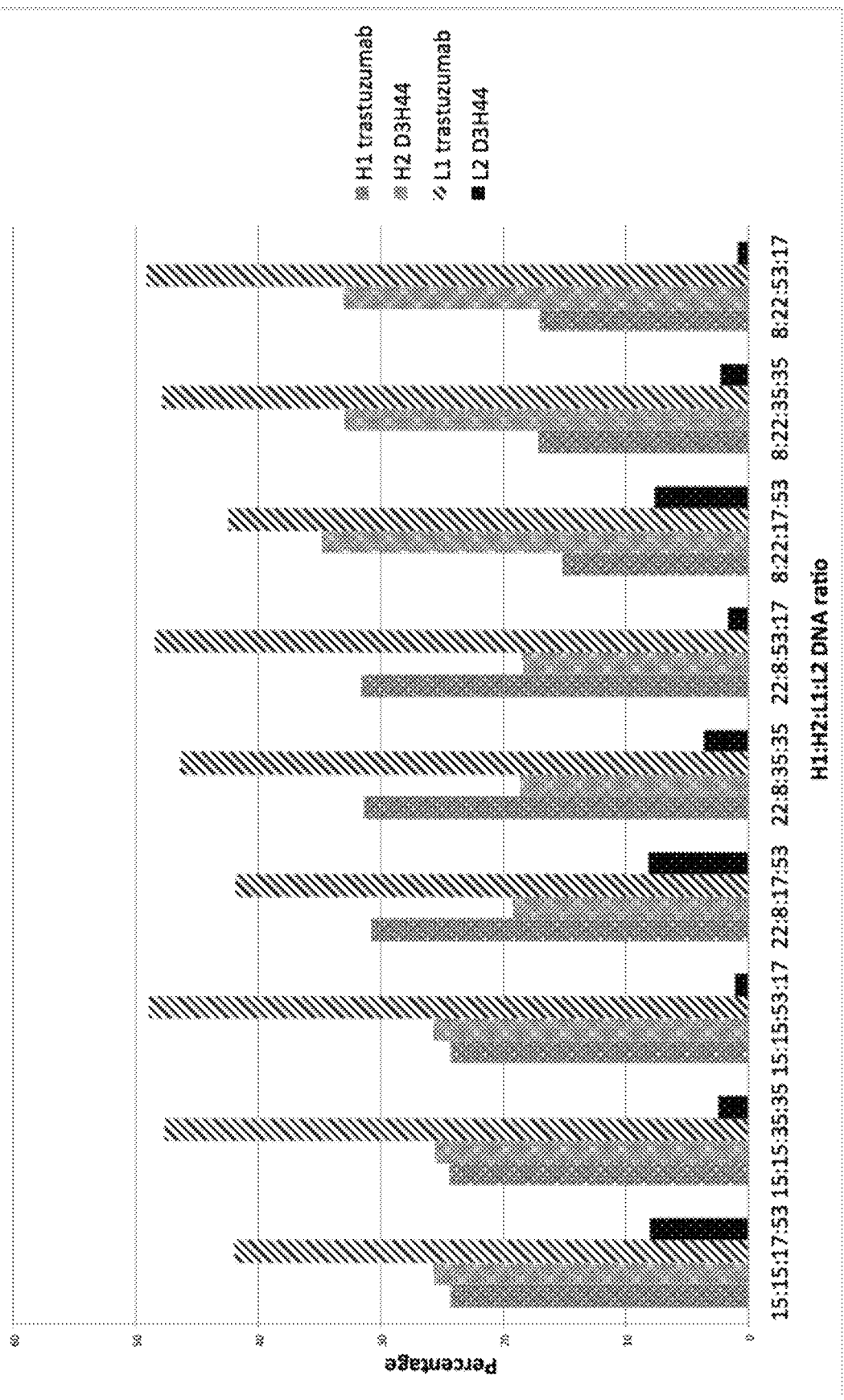
FIGS. 9a-9c depict the bias/chain utilization preferences within a) D3H44/trastuzumab, b) D3H44/cetuximab, and c) trastuzumab/cetuximab bispecific systems. The chain utilization was assessed in the different species observed by LC-MS. The x-axis presents the H1:H2:L1:L2 DNA ratio and the Y axis shows the corresponding percentage of each chain within the different transfection experiments. In a balanced system, all H and L chains would exhibit 25%. Bias towards utilization of one light chain is observed across all bispecific systems.
Figure 9B:
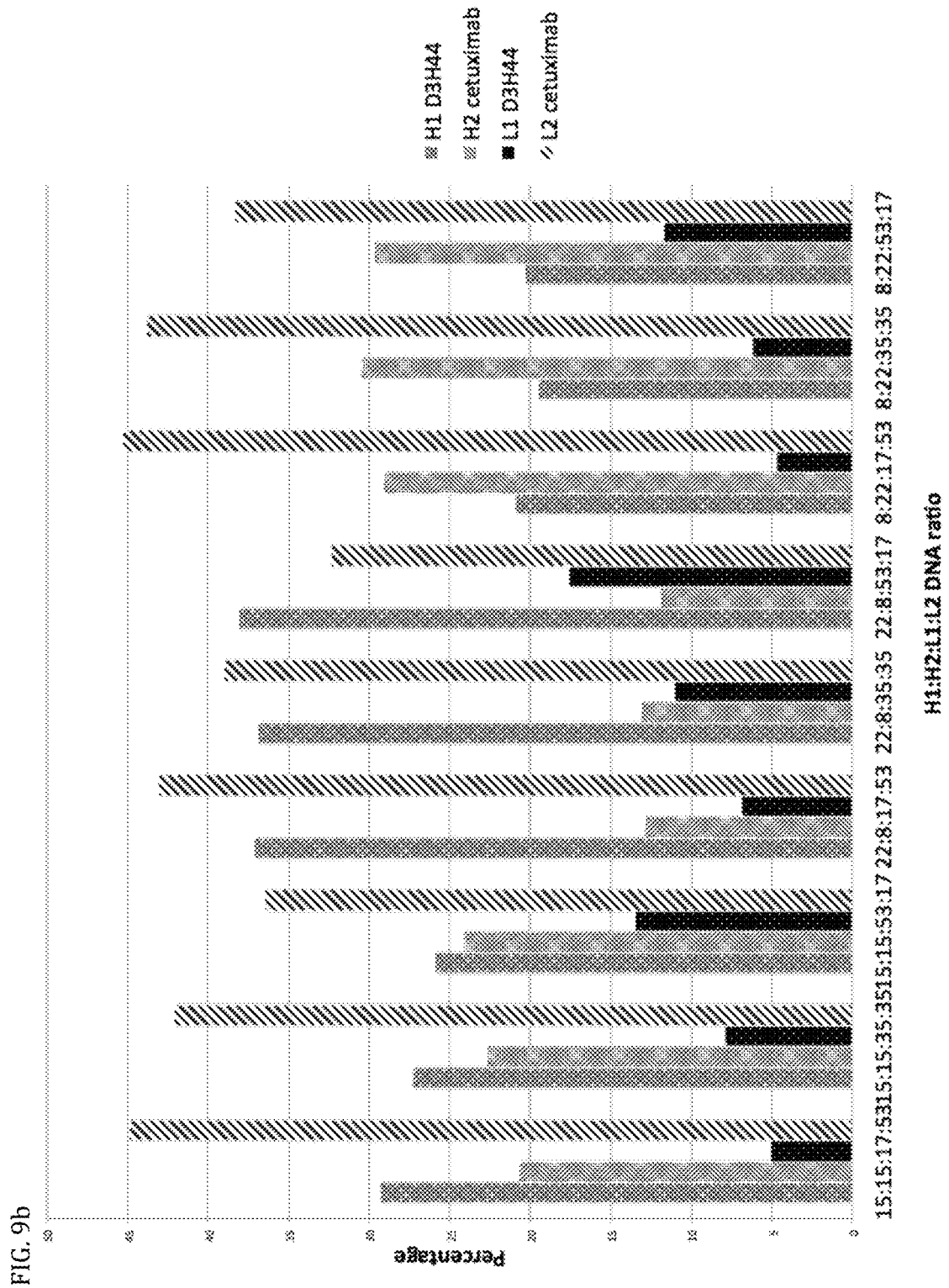
Figure 9C:
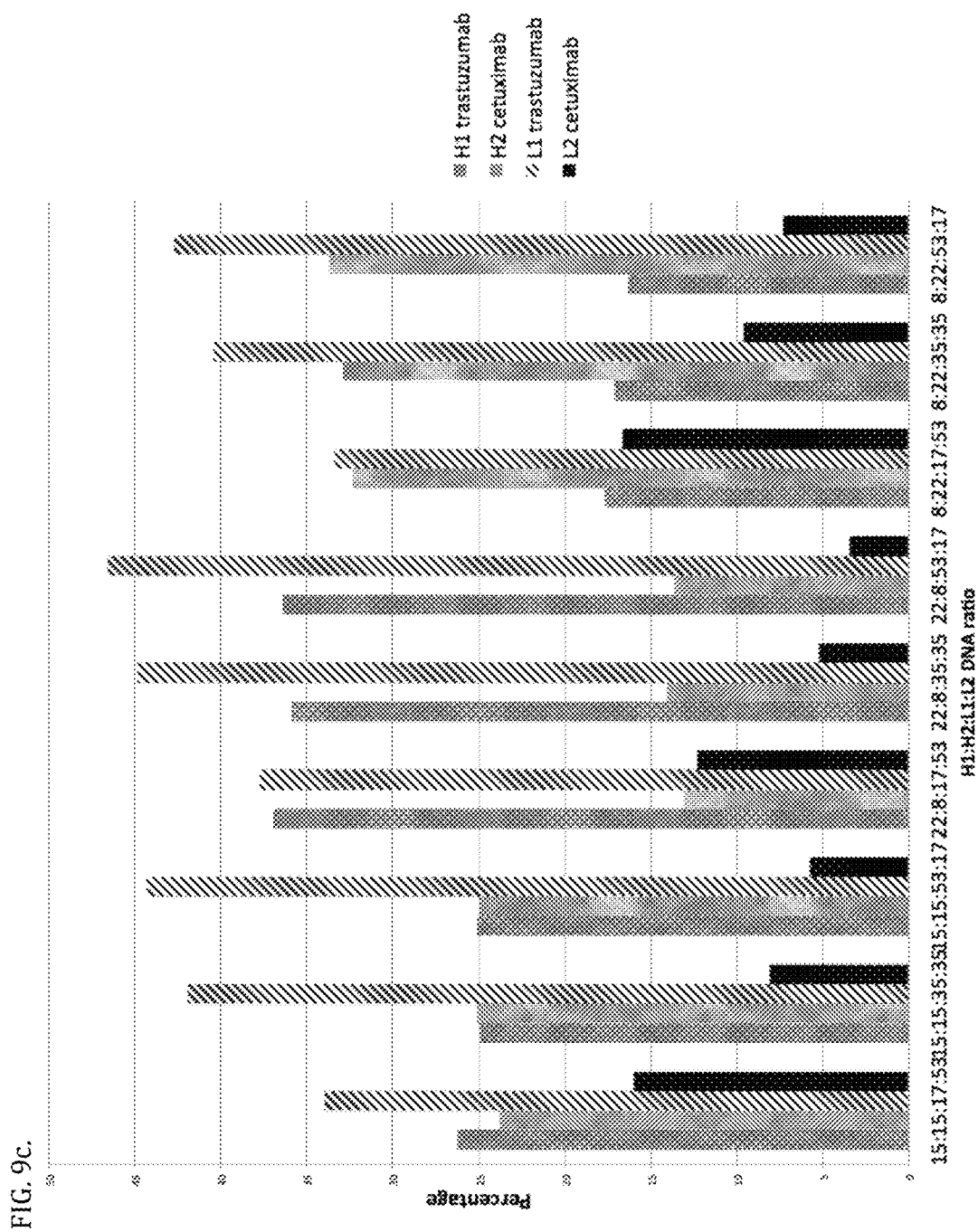
Figure 10C:
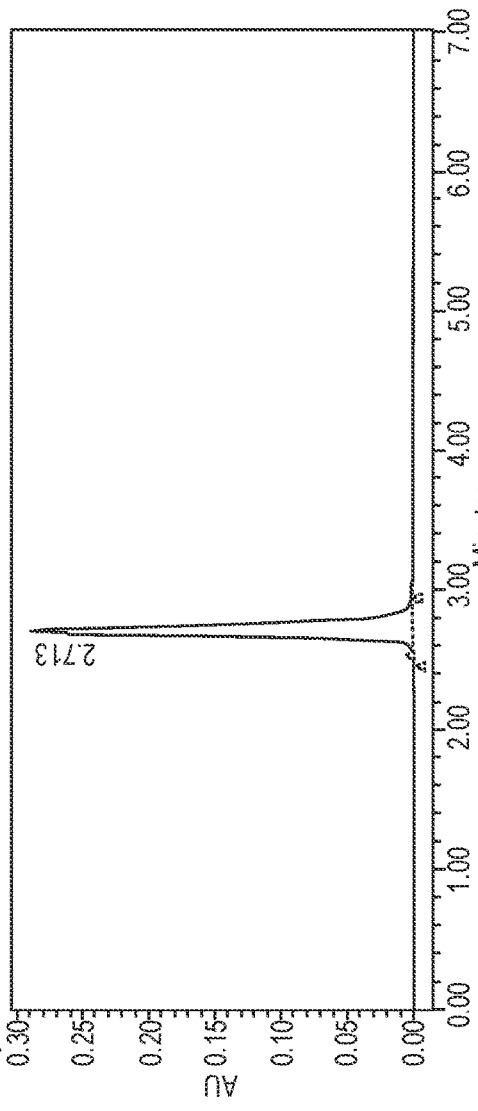
Figure 10D:
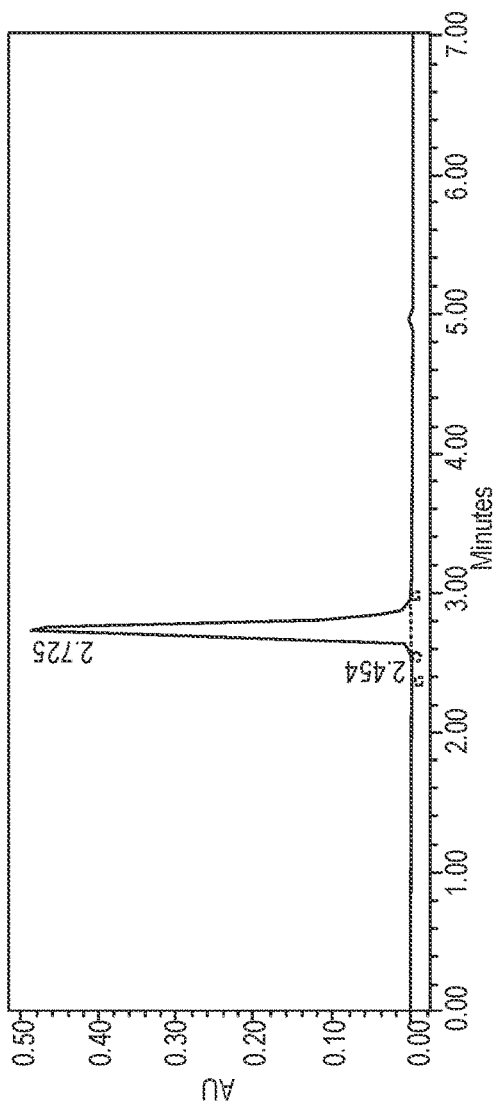

To assess bispecific system biases inherent in the wild-type bispecific Ab systems, where the light chain of one system preferentially binds the heavy chains of both Ab systems, a set of H1:H2:L1:L2 DNA ratios was then tested in CHO expressions. These ratios attempt to compensate for natural differences in expression levels and/or intrinsic pairing biases between heavy and light chains of the two different antibodies. For all of the bispecific Ab systems, biases were observed across all of the ratios tested (FIG. 9). For the D3H44/trastuzumab system, a bias is observed towards trastuzumab i.e. the D3H44 heavy chain preferentially pairs with the Trastuzumab light chain (see FIG. 9a). For the D3H44/cetuximab, a bias is observed towards Cetuximab i.e. the D31-144 heavy chain preferentially pairs with the cetuximab light chain (see FIG. 9b). For the trastuzumab/cetuximab system, a bias is observed towards trastuzumab i.e. the cetuximab heavy chain preferentially pairs with the trastuzumab light chain (see FIG. 9c).

For testing each of the 25 representative designs within each bispecific Ab system, the H1:H2:L1:L2 DNA ratios used were the ratios from the corresponding wild-type bispecific systems that yielded the most amount of bispecific Ab species while having a low amount of half Ab (see Tables 32a, b and c). For the D3H44/trastuzumab system, the ratio used was 15 (H1), 15 (H2), 53 (L1), 17 (L1), where H1 and L1 refer to D31144 and 12 and L2 refer to trastuzumab. For the trastuzumab/cetuximab system the ratio used was 15 (H1), 15 (H2), 17 (L1), 53 (L2) where H1 and L1 refer to trastuzumab and H2 and L2 refer to cetuximab. For the D3H44/cetuximab system, the ratio used was 15 (H1), 15 (H2), 53 (L1), 17 (L2), where H1 and L1 refer to D3H44 and H2 and L2 refer to cetuximab.

Furthermore, the designs were tested in both orientations for the D3H44/cetuximab and trastuzumab/cetuximab bispecific systems, such that in one orientation, substitutions present on H1L1 and H2L2 were tested on antibody 1 (Ab1) and antibody 2 (Ab2), of the bispecific Ab system, respectively, and in the other "flipped" orientation, substitutions present on H1L1 and H2L2 were tested on Ab2 and Ab1, respectively (see Table 28 a and b). An "_1" appended to the unique identifier indicates those designs where the heavy chain and associated light chain substitutions that gave the stronger LCCA preferential pairing result (see Table 13a) were placed on the antibody where the heavy chain competed weakly for its associated light chain compared with the light chain from the other antibody. An "_2" appended to the unique identifier indicates the opposite "flipped" orientation where the heavy chain and associated light chain substitutions that gave the stronger LCCA preferential pairing result (see Table 13a) were placed on the antibody where the heavy chain competed more strongly for its associated light chain compared with the light chain from the other antibody. For the D3H44/trastuzumab system, designs were tested only in the "_1" orientation (see Table 28c).

SMCA Results

The D3H44/trastuzumab system was treated with only one enzyme (PNGase-F) and was fully deglycosylated. For the multi-enzyme treatment, the attached sugars in the Fab region were generally truncated to either a core M3F (using the four enzyme treatment) or G0F (using the 3 enzyme treatment). Overall, in most cases, the deglycosylation treatments resulted in the ability to identify all of the possible different species identified by LC-MS. In many cases, each species was represented by a single LC-MS peak. Exceptions include side peaks that likely also correspond to the desired bispecific species (possibly adducts or heterogeneity in the cleavage of leader peptides); however, due to the ambiguity of the side peaks, these side peaks were not considered in the contributions to the bispecific species. In addition, some designs within the D3H44/cetuximab (3519_1, 3522_1) and the trastuzumab/cetuximab (9748-9338_1) systems required multiple peaks to account for a species due to the variability of the attached high mannose. All of these designs introduced a glycosylation site in the cetuximab light chain. Note that in some cases, it was not possible to distinguish between some minor species (comprise less than 5% of all species) due to low mass separation between the species (i.e. less than 50 Da difference). Furthermore, the desired bispecific species, H1-L1_H2-L2, cannot generally be distinguished experimentally on the basis of LC/MS from the mispaired type: H1-L2_H2-L1. As such, when bispecific content is reported in the tables, it cannot be completely excluded that it does not contain this type of mispaired species. However, the very low content observed for species such as H1-L2_H1-L2 and H2-L1_H2-L1 as well as H1-L2 and H2-L1 half antibodies is indicative that only minor if any contamination of the bispecific species occurred.

The LC-MS data are presented in Tables 29a, 29b and 29c. For comparison, wild-type data is also presented in Tables 33a, 33b and 33c and is indicated by "NA" in the "SMCA unique identifier" column as well as in the "Cluster" column. All of the three bispecific wild-type systems exhibited skewed biases such that one light chain dominated binding to both heavy chains (see Tables 33 and FIG. 9). Furthermore, at least in the in the trastuzumab/cetuximab system, tag placement also seemed to have a significant influence on H1L1 and H2L2 pairing. Therefore, to assess the effects of the designs on transferability and the percentage of the desired bispecific species vs wild-type, comparisons to the corresponding wild type bispecific construct at the same H1:H2:L1:L2 DNA ratio were conducted and reported in the "Change in % H1L1 Pairing (over all H1 species) with respect to wild type", "Change in % H2L2 Pairing (over all H2 species) with respect to wild type" and "Change in % of H1:H2:L1:L2 with respect to wild type" (considering full sized antibody species only) columns (see Table 29). Note that for assessing either % H1L1 Pairing (over all H1 species) or % H2L2 Pairing (over all H2 species), all species are assessed for pairing in the Fab region. When the corresponding wild type bispecific construct was not assessed by SMCA, comparisons were made to a similar wild-type construct. The estimates are indicated by a "***" next to the values reported. The similar wild type construct chosen for comparison was selected, as follows. To assess transferability, each wild type construct was represented by the SMCA experiment (conducted at the different ratios) that exhibited the highest "% H1L1 and % H2L2 Pairing (over all species)". To assess effects of designs on the percentage of the desired bispecific species vs wild-type, each wild type construct was represented by the SMCA experiment (conducted at the different ratios) that exhibited the highest % of H1:H2:L1:L2 (considering full sized antibody species only). For both cases, out of all of the wild type constructs within the bispecific system, the median values were then chosen as the wild-type values for comparison.

For each design, transferability was assessed by noting increases in the overall H:L pairing across all species with respect to WT, specifically in the % H1L1/all H1 species and/or % H2L2/all H2 species. In addition, the effects on the percentage of the desired bispecific species were also assessed, with an emphasis on the full sized antibody species only comparison, as half antibodies, if present, may be removed/minimized by preparative SEC or through further H1:H2:L1:L2 DNA titrations. Tables 30 a, b and c show that preparative SEC can be effective in the removal/minimization of half Ab species. Tables 32 a, b and c show that the percentage of half Ab species can also be manipulated during transfection using various DNA titration ratios.

For the D3H44/cetuximab system (Table 29a), all except one design (9327-6054_2) transferred as assessed by H1L1 pairing across all species with respect to wild-type. The majority of the designs (except for 9327-6054_2 and 9134-9521_2) also exhibited increased percentage of the desired bispecific antibodies when considering full Ab species only. Furthermore, except for the one design that did not transfer (9327-6054_2), the designs decreased the primary mispaired antibody species (H1H2L2L2) observed for the wild-type. In addition, except for 9327-6054_2 and the corresponding design 9327-6054_1 in the other orientation, the designs transferred in both orientations, with the majority of the designs showing similar effective H:L pairing in both orientations.

For the D3H44/trastuzumab system (Table 29b), all designs transferred as assessed by H1L1 pairing across all species with respect to wild-type. In addition, all of the designs exhibited increased percentage of the desired bispecific antibodies (when considering full Ab species only). Furthermore, most of the designs significantly decreased the primary mispaired antibody species (H1H2L2L2) observed for the wild-type. Note however, that no data was reported for 9611-9077_1 (table 28c), due to lack of expression.

As for the trastuzumab/cetuximab system (Table 29c), at least 35 out of 49 designs showed transferability as assessed by H2L2 pairing across all H2 species (positive values in the "Change in % H2L2 Pairing (over all H2 species) with respect to wild type" column). The designs that did not seem to transfer include 9279-9518_2, 3522_2, 9815-9825_2, 9327-6054_2, 9118-6098_2, 9748-9338_2, 9692-9846_2, 9587-9735_2, 9814-9828_2, 3519_2, 9986-9978_2, 9168-9342_2 and 9066-9335_1 (negative values in the "Change in % H2L2 Pairing (over all H2 species) with respect to wild type" column); however, the designs in the other orientation did exhibit transferability (note that 9279-9518_1 was not tested due to lack of sample). All of the designs that exhibited transferability exhibited decreased percentage of the primary mispaired antibody species (H1H2L1L1) that was observed in the wild-type experiments. In addition, of the designs that transferred, only 2 designs (9134-9521_1 and 9279-9518_2) showed decreased percentages of the desired bispecific Ab when considering the full antibody species only, compared with wild-type.

In general, most of the designs that increased the H:L pairing of the weaker competing antibody resulted in the increased percentage of the desired bispecific antibodies (considering full sized antibodies only). As for orientation, most designs in the "_1" orientation exhibited either similar or better transferability comparing the H:L pairing compared with the "_2" orientations (with exceptions being primarily observed in the trastuzumab/cetuximab system). Furthermore, table 35a lists those designs that transferred in both orientations across all 3 tested bispecific systems (D3H44/cetuximab, D3H44/trastuzumab, and trastuzumab/cetuximab). Table 35b lists those designs that transferred in one orientation across all 3 bispecific systems (D3H44/cetuximab, D3H44/trastuzumab, and trastuzumab/cetuximab) and transferred in the other orientation for only one bispecific system. In addition, in a specified orientation, the same mutations are present on the heavy chain and the weaker competing cognate light chain in all 3 bispecific systems, and light chain utilization is at least greater than 10%.

Figure 11A:
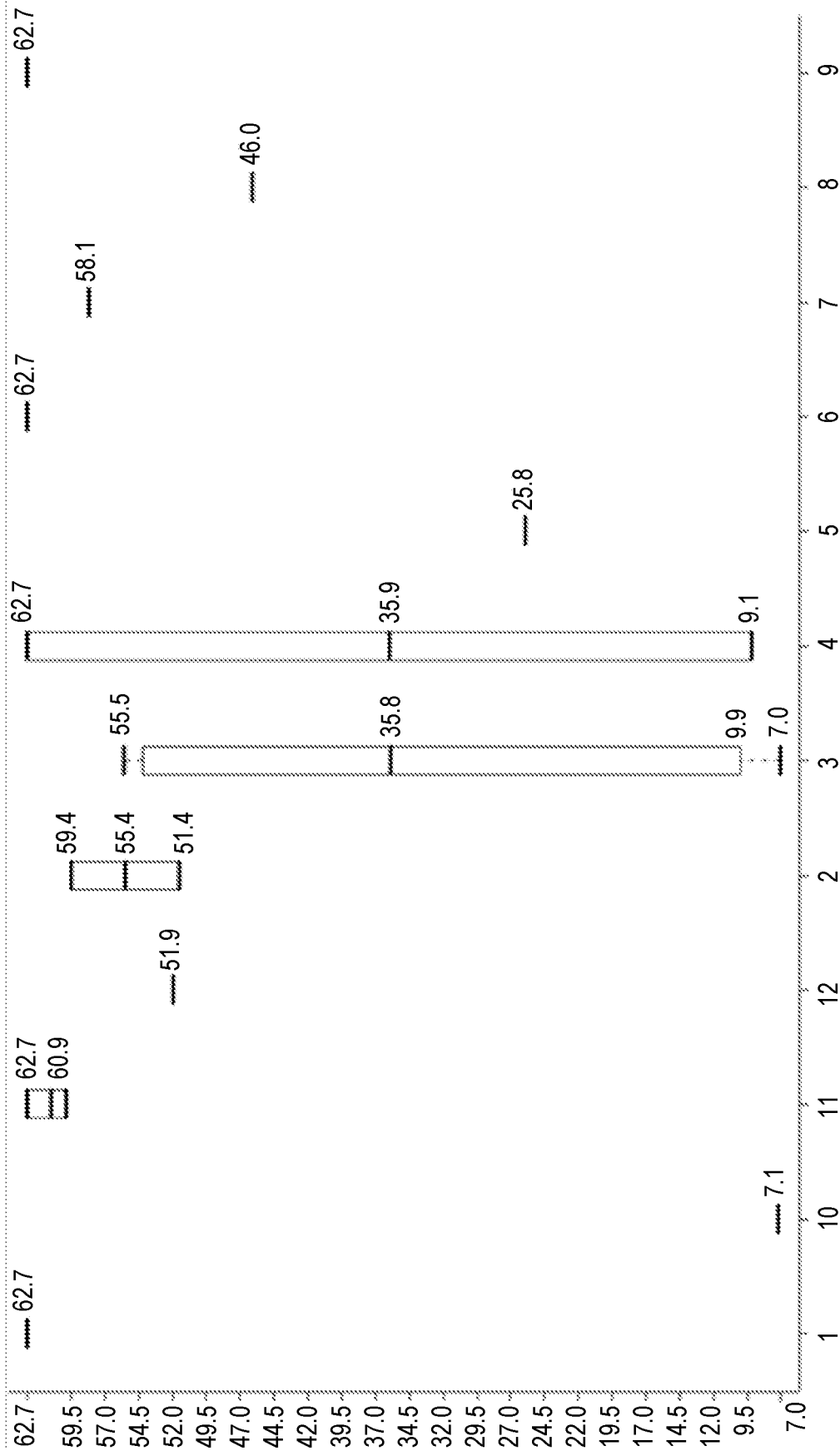
Figure 11B:
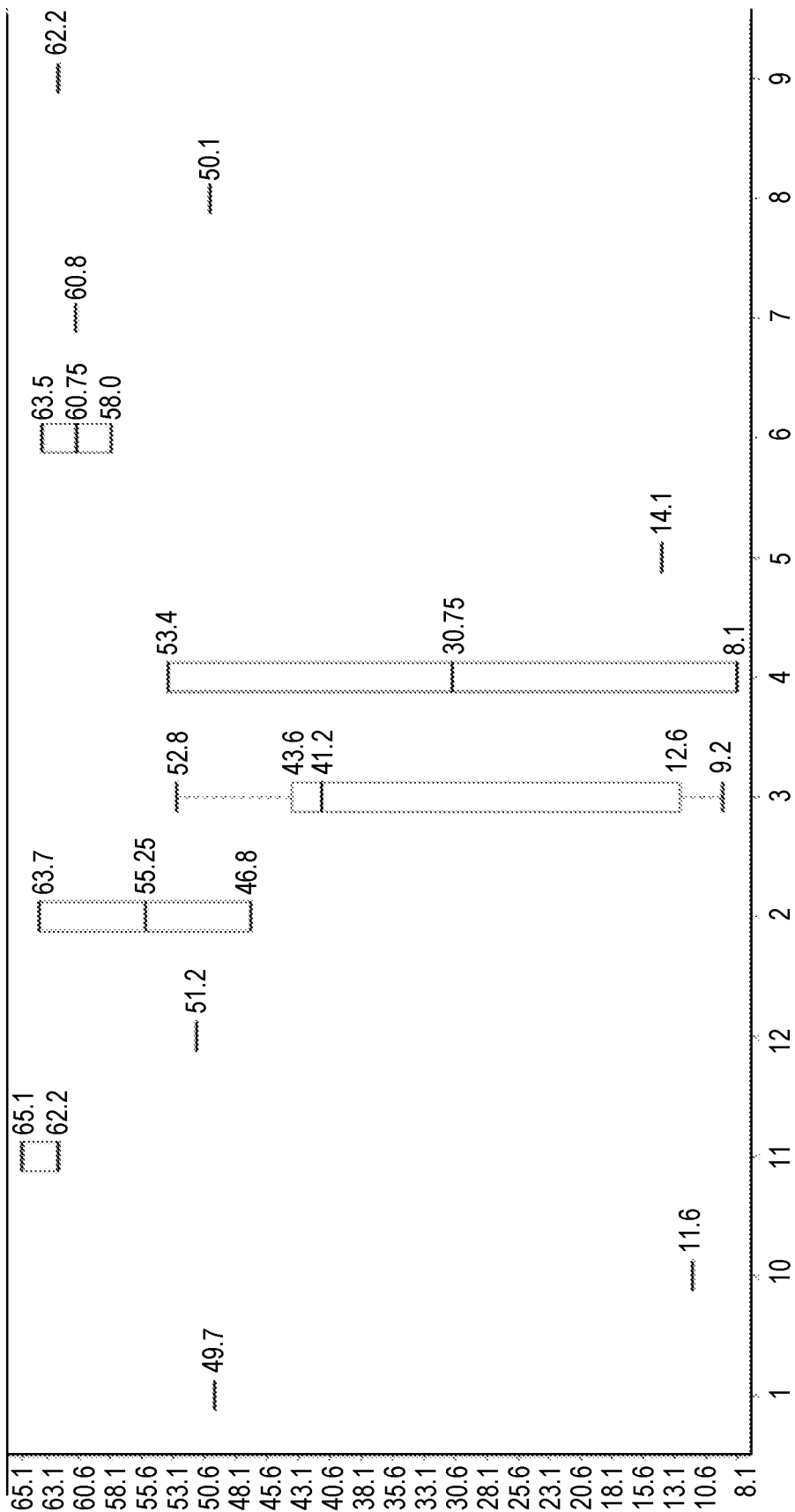
Figure 11D:
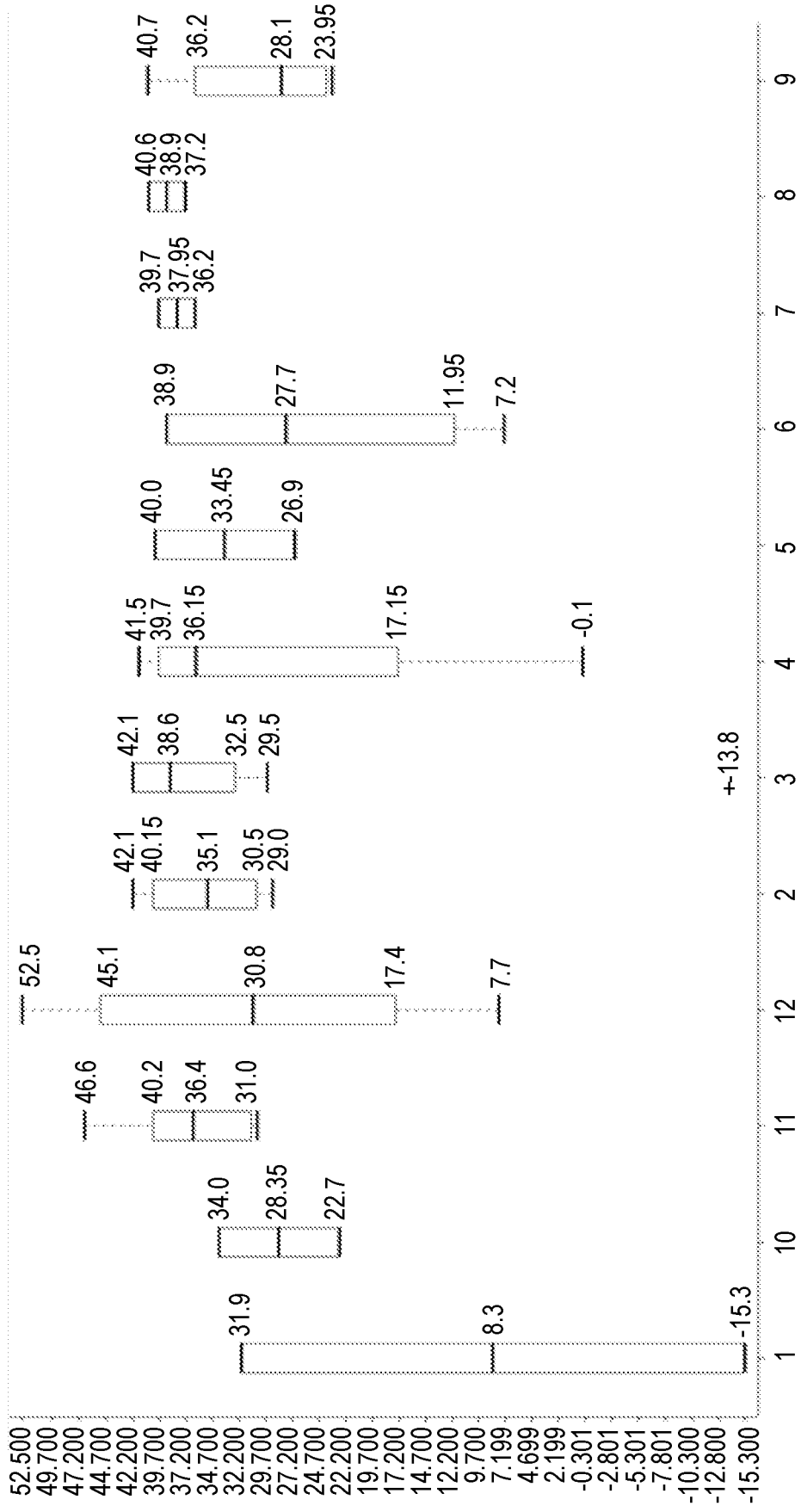
Figure 11E:
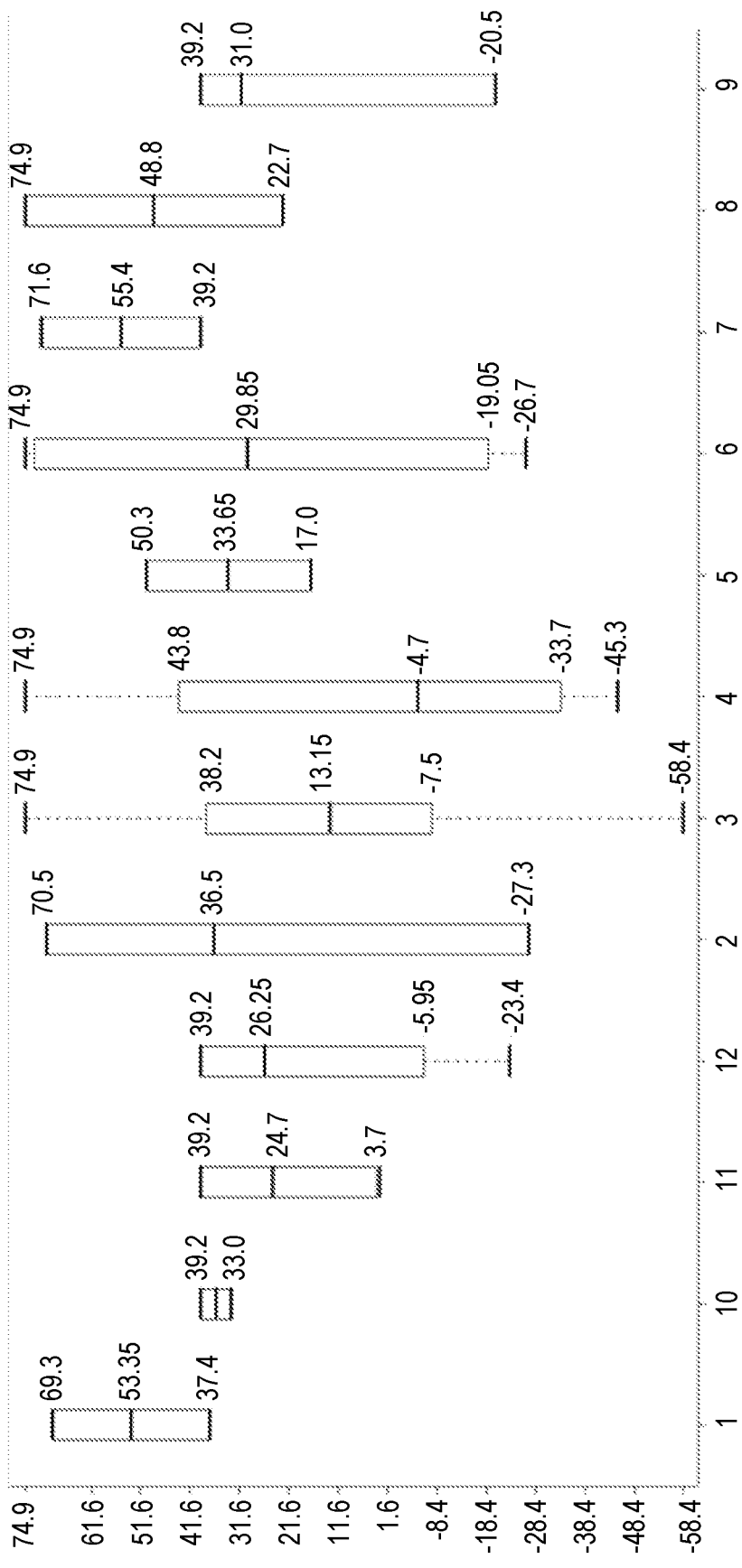
Figure 11F:
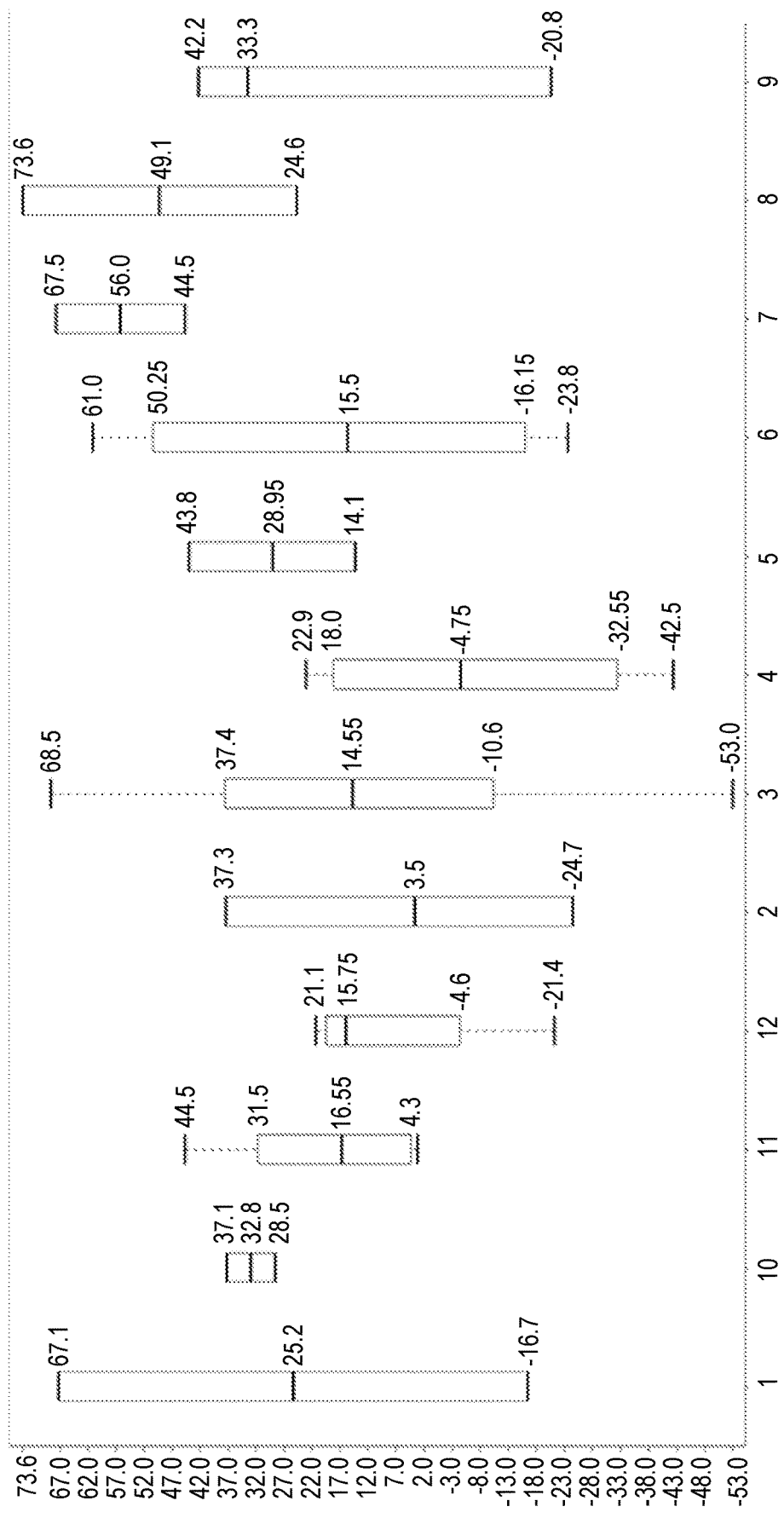

As for the transferability and performance of the clusters, for the D3H44/trastuzumab bispecific system, all of the members within all of the clusters exhibited transferability (see FIG. 11a) and increased the percentage of the desired bispecific antibody (considering full sized antibodies only) (see FIG. 11b). For the D3H44/cetuximab bispecific system, all clusters showed transferability, with only one member within cluster 3 that showed decreased H1L1 pairing over all H1 species, compared with wild-type (see FIG. 11c). Also, all clusters included members that exhibited increases in the percentage of the desired bispecific antibody with respect to wild type (considering full sized antibodies only); however 3 clusters (clusters 1, 3 and 4) also include members that showed decreases in the percentage of the desired bispecific antibody with respect to wild type (considering full sized antibodies only) (see FIG. 11d). As for the trastuzumab/cetuximab bispecific system, all clusters include variants that exhibit design transferability; however, only a few clusters (1, 5, 7, 8, 10, 11) include variants where all of the respective members exhibited transferability (see FIG. 11e). In addition, all clusters include members that exhibit increased percentage of the desired bispecific antibody with respect to wild type (considering full sized antibodies only) (see FIG. 11f). For those clusters where all members showed transferability, all of the members within clusters 5, 7, 8, 10 and 11 also showed increases in the percentage of the desired bispecific antibody with respect to wild type (considering full sized antibodies only).

Figure 11G:
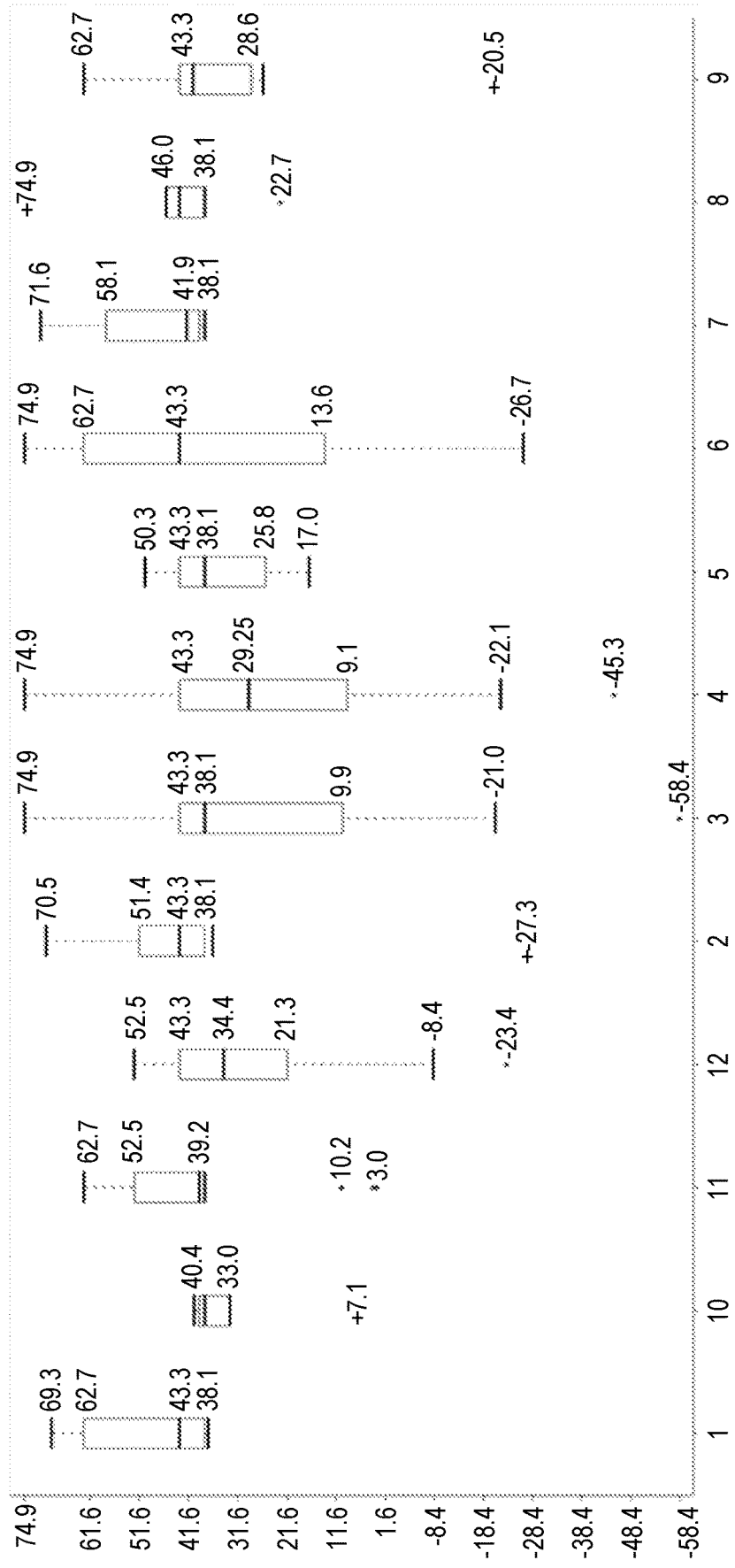
Figure 11H:
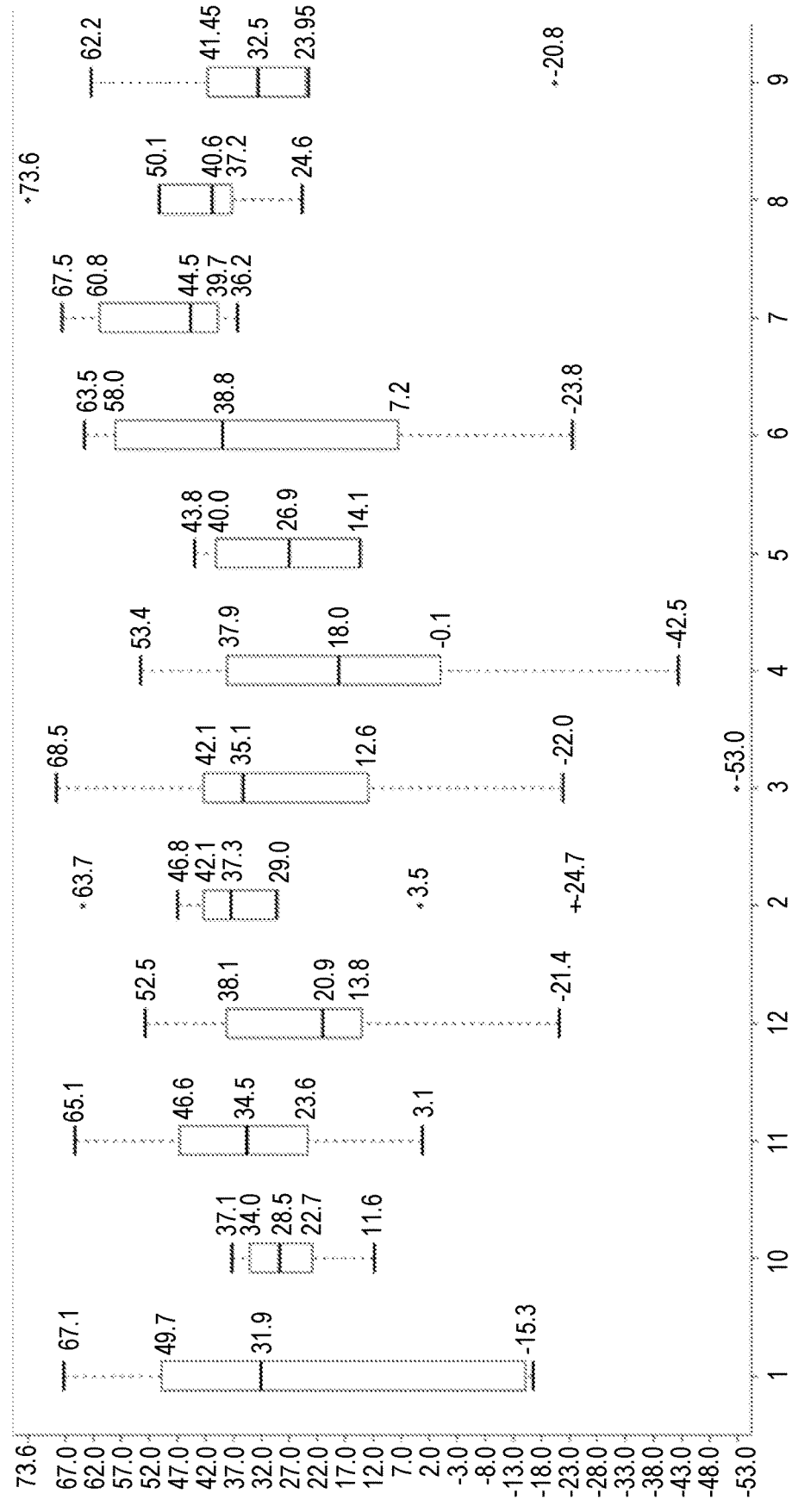

Overall, when considering all 3 bispecific systems altogether, all of the members within clusters 1, 5, 7, 8, 10, and 11 exhibited transferability (see FIG. 11g); clusters 5, 7, 8, 10, and 11 comprised members where all members exhibited increases in the percentage of the desired bispecific antibody with respect to wild type (considering full sized antibodies only) (see FIG. 11h).

Overall, most of the designs that increased the H:L pairing of the weaker competing antibody resulted in the increased percentage of the desired bispecific antibodies (considering full sized antibodies only). As for orientation, most designs in the "_1" orientation exhibited either similar or better transferability comparing the H:L pairing compared with the "_2" orientations (with exceptions being primarily observed in the trastuzumab/cetuximab system).

Example 10: Preparative Size Exclusion Chromatography (SEC) of Selected SMCA Bispecific Heterodimeric Antibodies and Parental Mabs for Biophysical Characterization A subset of the SMCA samples was selected for additional biophysical characterization. Most of these SMCA samples typically exhibited high pairing (greater than ~80% pairing in the H1L1+H2L2/all species column) and a low amount of half antibody species (less than ~30% considering all of the half antibody species). Preparative SEC was carried out as follows. Heterodimeric antibody samples were separated using a SUPERDEX® 200 10/300 GL (GE Healthcare) column mounted on a Pharmacia (GE Healthcare) ÄKTA™ Purifier system. Heterodimeric antibody samples (0.3-0.5 ml) in PBS (Hyclone DPBS/modified, No Calcium, No Magnesium, Cat no SH-300028.02) were manually loaded into a 0.5 ml loop filled with PBS. Samples were than automatically injected onto the column and resolved at 0.5 ml/min with a 1 CV elution volume. Protein elution was monitored at $OD_{280}$ and collected in 0.5 ml fractions. For each SMCA sample, those fractions that comprised the main peak were pooled and further biophysically characterized.

Example 11: Assessment of Preferential Pairing of Bi-Specific Heterodimers in Antibody Format Following Preparative Size Exclusion Chromatography Following preparative SEC, selected samples were analyzed for preferential pairing of bi-specific heterodimeric antibodies using the LC-MS method as described in Example 9. All of these samples show enrichment in the percentage of the desired bispecific antibody species as well as decreases in the percentage of half antibody species (Tables 29 and 30).

Example 12: Thermal Stability of SMCA Bispecific Heterodimeric Antibodies

Following preparative SEC, the thermal stability of selected SMCA bispecific heterodimeric antibodies was measured and compared with that of parental D3H44 and trastuzumab monoclonal antibodies as well as a cetuximab one armed antibody. In general, one-armed antibodies refer to constructs comprised of one full-length heavy chain, one truncated heavy chain lacking the Fab region (and incorporating a C233S substitution) and one light chain with heavy chain heterodimerization achieved as described in Example 9.

Measurement of Thermal Stability

The thermal stability of selected bispecific heterodimeric antibodies and wild-type controls was measured using differential scanning calorimetry (DSC) as follows. Following preparative SEC treatment, 400 µL samples primarily at concentrations of either 0.2 mg/ml or 0.4 mg/mL in PBS were used for DSC analysis with a VP-Capillary DSC (GE Healthcare). At the start of each DSC run, 5 buffer blank injections were performed to stabilize the baseline, and a buffer injection was placed before each sample injection for referencing. Each sample was scanned from 20 to 100° C. at a 60° C./hr rate, with low feedback, 8 sec filter, 5 min preTstat, and 70 psi nitrogen pressure. The resulting thermograms were referenced and analyzed using Origin 7 software.

The results are shown in Tables 31a, b and c. The Fab Tm values reported in the tables for the wild-type were obtained for the homodimeric antibodies for D3H44 (79° C.) and trastuzumab (81° C.) and for the one-armed antibody for cetuximab (72° C.). For the WT D3H44/cetuximab and trastuzumab/cetuximab heterodimeric antibodies, only 2 peaks corresponding to the Fab Tms are observed. Distinct peaks are not observed for CH2 (due to overlap with the cetuximab Fab) or CH3 (due to overlap with the Tm values of D3H44 and trastuzumab Fab). For the WT D3H44/trastuzumab heterodimeric antibody, as the Tm values of the two Fabs from D3H44 and trastuzumab are similar, the peak at 81° C. likely corresponds to both Fabs, while the peak at approximately 72° C. likely corresponds to CH2.

In Table 31a, b and c, only the Tm value(s) of the peak(s) corresponding to both Fabs were reported, unless otherwise indicated. Note also that for some heterodimeric samples, the protein concentration was low (below 0.4 mg/mL) leading to increased noise in the baseline. As a result, in the D3H44/trastuzumab system, some samples yielded DSC curves with low peak intensities, such that it was difficult to distinguish between the CH2 peak and a possibly destabilized Fab. In these cases, the Tm values at 70 to 72° C. are also reported (Table 31a). Overall, most of the heterodimeric antibodies exhibit thermal stabilities similar to the corresponding wild-type molecules (3° C. or less). Furthermore, most of the heterodimeric antibodies do not exhibit additional peaks to suggest significant destabilization of the CH2 or CH3 peaks. One exception includes the engineered heterodimeric antibody 9611-9077_2 from the trastuzumab/cetuximab system that exhibits an additional peak at 60° C., which may be due to CH2 destabilization.

Example 13: Antigen Affinity Measurements of Bispecific Heterodimeric Antibodies The ability of the bispecific antibodies to bind the associated antigens was assessed in order to determine whether the amino acid substitutions had any effects on antigen binding. The antigen binding affinity was determined by SPR as follows.

SPR Biosensor Assays

EDC: 1-ethyl-3-(3-dimethylaminopropyl) carbodiimide hydrochloride; NHS: N-Hydroxysuccinimide; SPR: surface plasmon resonance; EDTA: ethylenediaminetetraacetic acid; TF: tissue factor; EGFR ECD: epidermal growth factor receptor extracellular domain; Her2 ECD: human epithelial growth factor receptor 2 extracellular domain.

SPR supplies. Series S Sensor Chip CM5, BIACORE® amine coupling kit (NHS, EDC and 1 M ethanolamine), and 10 mM sodium acetate buffers were purchased from GE Healthcare Life Science (Mississauga, ON). Recombinant Her2 extracellular domain (ECD) protein was purchased from eBioscience (San Diego, CA). PBS running buffer with 1% TWEEN® 20 (PBST) was purchased from TEKNOVA® Inc. (Hollister, CA). Goat polyclonal anti-human Fc antibody was purchased from Jackson Immuno Research Laboratories Inc. (West Grove, PA). EDTA was purchased from Bioshop (Burlington, ON).

All surface plasmon resonance assays were carried out using a BIACORE® T200 Surface Plasmon Resonance instrument (GE Healthcare Life Science, (Mississauga, ON)) with PBST running buffer (with 0.5 M EDTA stock solution added to 3.4 mM final concentration) at a temperature of 25'C. The anti-human Fc capture surface was generated using a Series S Sensor Chip CM5 using the default parameters under the Immobilization Wizard in the BIACORE® T200 control software which was set to target 2000 resonance units (RUs). The screening of the antibody variants for binding to Her2 ECD, TF or EGFR ECD antigen targets occurred in two steps: an indirect capture of the antibody variants onto the anti-human Fc antibody flow cell surface followed by the injection of 5 concentrations of purified antigen for kinetic analysis using the single cycle kinetics methodology. Variants or controls for capture were injected at 1 µg/mL over individual flow cells for 60 s at a flow rate of 10 µL/min. In general, this resulted in a capture of approximately 50 to 100 RUs onto the anti-human Fc surface. The first flow cell was left empty to use as a blank control. This capture step was immediately followed by five concentrations of antigen (either 5 nM, 2.5 nM, 1.25 nM, 0.63 nM and 0.31 nM for TF or EGFR ECD antigens, or 40 nm, 20 nm, 10 nm, 5 nm, and 2.5 nm for Her2 ECD antigen) that were sequentially injected over all of the four flow cells at 100 µL/min for 180 s with a dissociation phase of 300 s for EGFR ECD, 1800 s for Her2 ECD, and 3600 s for TF. The captured antibody surfaces were regenerated by 10 mM Glycine pH 1.5 for 120 s at 30 µL/min to prepare for the next injection cycle. At least two mock-buffer injections were performed for each analyte injection to be used for referencing. The resulting single cycle kinetics sensorgrams were analyzed using BIACORE® T200 BiaEvaluation software and were fit to the 1:1 binding model.

Antigen affinities of the heterodimeric antibodies were assessed with reference to the respective wild-type controls: Mab for D3H44, trastuzumab OAA and cetuximab OAA. Antigen affinities were also obtained for the wild-type bispecific antibodies; however, SPR capture of the WT bispecifics can be heterogeneous (e.g. involving capture of mispaired heterodimers), thereby interfering with KD determination (see Table 31a and c). For the heterodimeric antibodies that had antigen binding measured in the D3H44/cetuximab system, antigen affinities were similar to the corresponding WT controls (see Table 31b). For most of the heterodimeric antibodies that had antigen binding measured in both the D3H44/trastuzumab and trastuzumab/cetuximab systems, antigen affinities were similar to the corresponding WT controls (see Tables 31a and c). Exceptions include eleven engineered antibodies that did not exhibit Her2 binding. In both of the D3H44/trastuzumab and trastuzumab/cetuximab systems, her2 binding was not observed for six engineered heterodimeric antibodies, 9049-9759_1 and 9682-9740_1 and 3522_1. Furthermore, for the trastuzumab/cetuximab system, five additional engineered antibodies, 9696-9848_1, 9561-9095_2, 9611-9077_2, 9286-9402_2 and 9060-9756_2 also lacked binding to Her2. Ten of these eleven engineered antibodies shared constant region mutations on the H chain (L143E_K145T) and L chain (Q124R_T178R). The other engineered antibody 9286-9402_2 shared the same constant region mutations on the H chain (L143E_K145T) and similar mutations on the L chain (Q124K and S176R).

Example 14: UltraPerformance Liquid Chromatography Size Exclusion Chromatography (UPLC-SEC) Profiles of Engineered Heterodimeric Antibodies as Well as Wild-Type Heterodimeric and Homodimeric Antibodies Following preparative SEC of the engineered heterodimeric antibodies as well as the control wild-type bispecific and homodimeric antibodies, UPLC-SEC was performed using a WATERS® BEH200 SEC column (2.5 mL, 4.6×150 mm, stainless steel, 1.7 µm particles) set to 30° C. and mounted on a WATERS® Acquity UPLC™ system with a PDA detector. Run times consisted of 7 min and a total volume per injection of 2.8 mL with a running buffer of either PBS and 0.02% polysorbate 20 or 20 mM NaPO4, 50 mM KCl, 0.02% polysorbate 20, 10% acetonitrile, pH 7 at 0.4 ml/min. Elution was monitored by UV absorbance in the range 210-400 nm, and chromatograms were extracted at 280 nm. Peak integration was performed using Empower 3 software.

FIGS. 10A-10F shows UPLC-SEC profiles for representatives of the engineered heterodimeric antibodies as well as representative WT heterodimeric antibodies. In most cases, the engineered heterodimeric antibodies exhibited UPLC-SEC profiles similar to the corresponding WT heterodimeric antibodies, with average percentage of the monomers of 99.18%, 98.70% and 98.77% for D3H44/trastuzumab, D3H44/cetuximab, and trastuzumab/cetuximab, respectively (see Tables 31a, 31b and 31c).

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents, patent publications, and sequence accession numbers disclosed herein are hereby incorporated by reference in their entirety, for all purposes.

TABLES

Key for Tables

Table 1. Key criteria for Fab model
Table 2. Hotspot amino acid positions at the interface of the heavy and light chains in D3H44 (a typical Fab containing a kappa light chain).
Table 3A. Kabat numbering of the heavy chain amino acid sequences of D3H44, Trastuzumab, and Cetuximab
Table 3B. Kabat numbering of the light chain amino acid sequences of D3H44, Trastuzumab, and Cetuximab
Table 3C. Amino acid and DNA sequences of D3H44, Trastuzumab and Cetuximab
Table 4: LCCA designs with modifications to one immunoglobulin heavy chain and/or two immunoglobulin light chains, where H1 preferentially pairs with L1
Table 5. Design library
Table 6. Core Designs
Table 7. Example of a combination design
Table 8. Example of a modified/optimized design
Table 9. Example of a combination design including an optimized design
Table 10. Example of a combination design including an independent design
Table 11. H1:L1:L2 DNA ratios used for the light chain competition assays and verifications
Table 12. LCCA performance, stability and antigen binding assessments of the LCCA designs, arranged by decreasing DSF values of H1L1 Fab heterodimers
Table 13a. LCCA performance of the designs that met the LCCA average performance criteria of correctly paired:mispaired Fab heterodimers of 86:14
Table 13b. Stability and antigen binding assessments of the designs that met the LCCA average performance criteria of correctly paired:mispaired Fab heterodimers of 86:14
Table 14a. LCCA performance of the designs that performed below the LCCA average performance criteria of correctly paired:mispaired Fab heterodimers of 86:14
Table 14b. Stability and antigen binding assessments of the designs that performed below the LCCA average performance criteria of correctly paired:mispaired Fab heterodimers of 86:14
Table 15. Cluster 1 designs including the representative design
Table 16. Cluster 2 designs including representative designs
Table 17. Cluster 3 designs including representative designs
Table 18. Cluster 4 designs including representative designs
Table 19. Cluster 5 designs including the representative design
Table 20. Cluster 6 designs including representative designs
Table 21. Cluster 7 designs including the representative design
Table 22. Cluster 8 designs including the representative design
Table 23. Cluster 9 designs including representative designs
Table 24. Cluster 10 designs including representative designs
Table 25. Cluster 11 designs including representative designs
Table 26. Cluster 12 designs including representative designs
Table 27. Cluster 13 designs including representative designs
Table 28a. SMCA unique identifiers for the trastuzumab/cetuximab bispecific system
Table 28b. SMCA unique identifiers for the D3H44/cetuximab bispecific system
Table 28c. SMCA unique identifiers for the D3H44/trastuzumab bispecific system

TABLES-continued

Key for Tables

Table 29a. LC-MS pairing data and post pA yields (mg/L) for the heterodimeric antibodies from the D3H44 (H1L1)/cetuximab (H2L2) bispecific system
Table 29b. LC-MS pairing data and post pA yields (mg/L) for the heterodimeric antibodies from the D3H44 (H1L1)/trastuzumab (H2L2) bispecific system
Table 29c. LC-MS pairing data and post pA yields (mg/L) for the heterodimeric antibodies from the trastuzumab (H1L1)/cetuximab (H2L2) bispecific system
Table 30a. LC-MS pairing of the heterodimeric antibodies from the D3H44 (H1L1)/cetuximab (H2L2) bispecific system following preparative SEC
Table 30b. LC-MS pairing of the heterodimeric antibodies from the D3H44 (H1L1)/trastuzumab (H2L2) bispecific system following preparative SEC
Table 30c. LC-MS pairing of the heterodimeric antibodies from the trastuzumab (H1L1)/cetuximab (H2L2) bispecific system following preparative SEC
Table 31a. Biophysical characterization (antigen binding, thermal stability, UPLC-SEC) of selected designs from the D3H44/trastuzumab system
Table 31b. Biophysical characterization (antigen binding, thermal stability, UPLC-SEC) of selected designs from the D3H44/cetuximab system
Table 31c. Biophysical characterization (antigen binding, thermal stability, UPLC-SEC) of selected designs from the trastuzumab/cetuximab system
Table 32a. Effect of DNA titration ratio on the percentage of antibody species, as assessed by LC-MS, of the wild-type D3H44/trastuzumab system. H1 and L1 refer to D3H44 heavy and light chains, respectively. H2 and L2 refer to trastuzumab heavy and light chains, respectively.
Table 32b. Effect of DNA titration ratio on the percentage of antibody species, as assessed by LC-MS, of the wild-type D3H44/cetuximab system. H1 and L1 refer to D3H44 heavy and light chains, respectively. H2 and L2 refer to cetuximab heavy and light chains, respectively.
Table 32c. Effect of DNA titration ratio on the percentage of antibody species, as assessed by LC-MS, of the wild-type trastuzumab/cetuximab system. H1 and L1 refer to trastuzumab heavy and light chains, respectively. H2 and L2 refer to cetuximab heavy and light chains, respectively.
Table 33a. LC-MS pairing for the wild type antibody constructs from the D3H44 (H1L1)/cetuximab (H2L2) bispecific system
Table 33b. LC-MS pairing for the wild type antibody constructs from the D3H44 (H1L1)/trastuzumab (H2L2) bispecific system
Table 33c. LC-MS pairing for the wild type antibody constructs from the trastuzumab (H1L1)/cetuximab (H2L2) bispecific system
Table 34. Stabilizing mutations in Fab heterodimers
Table 35a. Designs that exhibited transferability across all 3 bispecific systems (D3H44/cetuximab, D3H44/trastuzumab, and trastuzumab/cetuximab) in both orientations.
Table 35b. Designs that exhibited transferability across all 3 bispecific systems (D3H44/cetuximab, D3H44/trastuzumab, and trastuzumab/cetuximab) in one orientation, and transferred in the other orientation for only one bispecific system, while also meeting the light chain utilization criteria of at least 10%.

TABLE 1

Key criteria for Fab model

| Criteria | Importance |
| --- | --- |
| Human or humanized IgG1/κ<br>Has commonly used $V_H$ and $V_L$ subgroups<br>Framework close to germline<br>$V_H$:$V_L$ interdomain packing angle dose to observed average for Fabs | Similarity |

TABLE 1-continued

Key criteria for Fab model

| Criteria | Importance |
| --- | --- |
| Structure available for apo- and complexed Fab | Design |
| No major structural changes observed upon binding antigen | |
| Antigen binding can be readily assayed | Assay |

TABLE 2

Hotspot amino acid positions at the interface of the heavy and light chains in D3H44 (a typical Fab containing a kappa light chain).

| Heavy* | Light* |
| --- | --- |
| V37 | Y36 |
| Q39 | Q38 |
| L44 | P44 |
| W47 | L89 |
| F100 | F98 |
| W103 | F116 |
| L124 | F118 |
| A139 | V133 |
| F174 | L135 |

*Kabat numbering

TABLE 3A

Kabat numbering of the heavy chain amino acid sequences of D3H44, Trastuzumab and Cetuximab

| KABAT numbering | D3H44 | TRASTUZUMAB | CETUXIMAB |
| --- | --- | --- | --- |
| 1 | E | E | Q |
| 2 | V | V | V |
| 3 | Q | Q | Q |
| 4 | L | L | L |
| 5 | V | V | K |
| 6 | E | E | Q |
| 7 | S | S | S |
| 8 | G | G | G |
| 9 | G | G | P |
| 10 | G | G | G |
| 11 | L | L | L |
| 12 | V | V | V |
| 13 | Q | Q | Q |
| 14 | P | P | P |
| 15 | G | G | S |
| 16 | G | G | Q |
| 17 | S | S | S |
| 18 | L | L | L |
| 19 | R | R | S |
| 20 | L | L | I |
| 21 | S | S | T |
| 22 | C | C | C |
| 23 | A | A | T |
| 24 | A | A | V |
| 25 | S | S | S |
| 26 | G | G | G |
| 27 | F | F | F |
| 28 | N | N | S |
| 29 | I | I | L |
| 32 | K | K | T |
| 33 | E | D | N |
| 34 | Y | T | Y |
| 35 | Y | Y | G |
| 35A | M | I | V |
| 35B | H | H | H |
| 36 | W | w | W |
| 37 | V | V | V |
| 38 | R | R | R |
| 39 | Q | Q | Q |
| 40 | A | A | S |
| 41 | P | P | P |
| 42 | G | G | G |
| 43 | K | K | K |
| 44 | G | G | G |
| 45 | L | L | L |
| 46 | E | E | E |
| 47 | W | W | W |
| 48 | V | V | L |
| 49 | G | A | G |
| 50 | L | R | V |
| 51 | I | I | I |
| 52 | D | Y | W |
| 52A | P | P | — |
| 53 | E | T | S |
| 54 | Q | N | G |
| 55 | G | G | G |
| 56 | N | Y | N |
| 57 | T | T | T |
| 58 | I | R | D |
| 59 | Y | Y | Y |
| 60 | D | A | N |
| 61 | P | D | T |
| 62 | K | S | P |
| 63 | F | V | F |
| 64 | Q | K | T |
| 65 | D | G | S |
| 66 | R | R | R |
| 67 | A | F | L |
| 68 | T | T | S |
| 69 | I | I | I |
| 70 | S | S | N |
| 71 | A | A | K |
| 72 | D | D | D |
| 73 | N | T | N |
| 74 | S | S | S |
| 75 | K | K | K |
| 76 | N | N | S |
| 77 | T | T | Q |
| 78 | A | A | V |
| 79 | Y | Y | F |
| 80 | L | L | F |
| 81 | Q | Q | K |
| 82 | M | M | M |
| 82A | N | N | N |
| 82B | S | S | S |
| 82C | L | L | L |
| 83 | R | R | Q |
| 84 | A | A | S |
| 85 | E | E | N |
| 86 | D | D | D |
| 87 | T | T | T |
| 88 | A | A | A |
| 89 | V | V | I |
| 90 | Y | Y | Y |
| 91 | Y | Y | Y |
| 92 | C | C | C |
| 93 | A | S | A |
| 94 | R | R | R |
| 95 | D | W | A |
| 96 | T | G | L |
| 97 | A | G | T |
| 98 | A | D | Y |
| 99 | Y | G | Y |
| 100 | F | F | D |
| 100A | | Y | Y |
| 100B | | A | E |
| 100C | | M | F |
| 101 | D | D | A |
| 102 | Y | Y | Y |
| 103 | W | W | W |

TABLE 3A-continued

Kabat numbering of the heavy chain amino acid sequences of D3H44, Trastuzumab and Cetuximab

| KABAT numbering | D3H44 | TRASTUZUMAB | CETUXIMAB |
|---|---|---|---|
| 104 | G | G | G |
| 105 | Q | Q | Q |
| 106 | G | G | G |
| 107 | T | T | T |
| 108 | L | L | L |
| 109 | V | V | V |
| 110 | T | T | T |
| 111 | V | V | V |
| 112 | S | S | S |
| 113 | S | S | A |
| 114 | A | A | A |
| 115 | S | S | S |
| 116 | T | T | T |
| 117 | K | K | K |
| 118 | G | G | G |
| 119 | P | P | P |
| 120 | S | S | S |
| 121 | V | V | V |
| 122 | F | F | F |
| 123 | P | P | P |
| 124 | L | L | L |
| 125 | A | A | A |
| 126 | P | P | P |
| 127 | S | S | S |
| 128 | S | S | S |
| 129 | K | K | K |
| 130 | S | S | S |
| 133 | T | T | T |
| 134 | S | S | S |
| 135 | G | G | G |
| 136 | G | G | G |
| 137 | T | T | T |
| 138 | A | A | A |
| 139 | A | A | A |
| 140 | L | L | L |
| 141 | G | G | G |
| 142 | C | C | C |
| 143 | L | L | L |
| 144 | V | V | V |
| 145 | K | K | K |
| 146 | D | D | D |
| 147 | Y | Y | Y |
| 148 | F | F | F |
| 149 | P | P | P |
| 150 | E | E | E |
| 151 | P | P | P |
| 152 | V | V | V |
| 153 | T | T | T |
| 154 | V | V | V |
| 156 | S | S | S |
| 157 | W | W | W |
| 162 | N | N | N |
| 163 | S | S | S |
| 164 | G | G | G |
| 165 | A | A | A |
| 166 | L | L | L |
| 167 | T | T | T |
| 168 | S | S | S |
| 169 | G | G | G |
| 171 | V | V | V |
| 172 | H | H | H |
| 173 | T | T | T |
| 174 | F | F | F |
| 175 | P | P | P |
| 176 | A | A | A |
| 177 | V | V | V |
| 178 | L | L | L |
| 179 | Q | Q | Q |
| 180 | S | S | S |
| 182 | S | S | S |
| 183 | G | G | G |
| 184 | L | L | L |
| 185 | Y | Y | Y |
| 186 | S | S | S |
| 187 | L | L | L |
| 188 | S | S | S |
| 189 | S | S | S |
| 190 | V | V | V |
| 191 | V | V | V |
| 192 | T | T | T |
| 193 | V | V | V |
| 194 | P | P | P |
| 195 | S | S | S |
| 196 | S | S | S |
| 197 | S | S | S |
| 198 | L | L | L |
| 199 | G | G | G |
| 200 | T | T | T |
| 203 | Q | Q | Q |
| 205 | T | T | T |
| 206 | Y | Y | Y |
| 207 | I | I | I |
| 208 | C | C | C |
| 209 | N | N | N |
| 210 | V | V | V |
| 211 | N | N | N |
| 212 | H | H | H |
| 213 | K | K | K |
| 214 | P | P | P |
| 215 | S | S | S |
| 216 | N | N | N |
| 217 | T | T | T |
| 218 | K | K | K |
| 219 | V | V | V |
| 220 | D | D | D |
| 221 | K | K | K |
| 222 | K | K | K |
| 223 | V | V | V |
| 226 | E | E | E |
| 227 | P | P | P |
| 228 | K | K | K |
| 232 | S | S | S |
| 233 | C | C | C |
| 234 | D | D | D |
| 235 | K | K | K |
| 236 | T | T | T |
| 237 | H | H | H |
| 238 | T | T | T |
| 239 | C | C | C |
| 240 | P | P | P |
| 241 | P | P | P |
| 242 | C | C | C |
| 243 | P | P | P |
| 244 | A | A | A |
| 245 | P | P | P |
| 246 | E | E | E |
| 247 | L | L | L |
| 248 | L | L | L |
| 249 | G | G | G |
| 250 | G | G | G |
| 251 | P | P | P |
| 252 | S | S | S |
| 253 | V | V | V |
| 254 | F | F | F |
| 255 | L | L | L |
| 256 | F | F | F |
| 257 | P | P | P |
| 258 | P | P | P |
| 259 | K | K | K |
| 260 | P | P | P |
| 261 | K | K | K |
| 262 | D | D | D |
| 263 | T | T | T |
| 264 | L | L | L |

TABLE 3A-continued

Kabat numbering of the heavy chain amino acid sequences of D3H44, Trastuzumab and Cetuximab Table 3A
Heavy chain origin

| KABAT numbering | D3H44 | TRASTUZUMAB | CETUXIMAB |
|---|---|---|---|
| 265 | M | M | M |
| 266 | I | I | I |
| 267 | S | S | S |
| 268 | R | R | R |
| 269 | T | T | T |
| 270 | P | P | P |
| 271 | E | E | E |
| 272 | V | V | V |
| 273 | T | T | T |
| 274 | C | C | C |
| 275 | V | V | V |
| 276 | V | V | V |
| 277 | V | V | V |
| 278 | D | D | D |
| 279 | V | V | V |
| 280 | S | S | S |
| 281 | H | H | H |
| 282 | E | E | E |
| 283 | D | D | D |
| 284 | P | P | P |
| 285 | E | E | E |
| 286 | V | V | V |
| 287 | K | K | K |
| 288 | F | F | F |
| 289 | N | N | N |
| 290 | W | W | W |
| 291 | Y | Y | Y |
| 292 | V | V | V |
| 295 | D | D | D |
| 296 | G | G | G |
| 299 | V | V | V |
| 300 | E | E | E |
| 301 | V | V | V |
| 302 | H | H | H |
| 303 | N | N | N |
| 304 | A | A | A |
| 305 | K | K | K |
| 306 | T | T | T |
| 307 | K | K | K |
| 308 | P | P | P |
| 309 | R | R | R |
| 310 | E | E | E |
| 311 | E | E | E |
| 312 | Q | Q | Q |
| 313 | Y | Y | Y |
| 314 | N | N | N |
| 317 | S | S | S |
| 318 | T | T | T |
| 319 | Y | Y | Y |
| 320 | R | R | R |
| 321 | V | V | V |
| 322 | V | V | V |
| 323 | S | S | S |
| 324 | V | V | V |
| 325 | L | L | L |
| 326 | T | T | T |
| 327 | V | V | V |
| 328 | L | L | L |
| 329 | H | H | H |
| 330 | Q | Q | Q |
| 331 | D | D | D |
| 332 | W | W | W |
| 333 | L | L | L |
| 334 | N | N | N |
| 335 | G | G | G |
| 336 | K | K | K |
| 337 | E | E | E |
| 338 | Y | Y | Y |
| 339 | K | K | K |
| 340 | C | C | C |
| 341 | K | K | K |
| 342 | V | V | V |
| 343 | S | S | S |
| 344 | N | N | N |
| 345 | K | K | K |
| 346 | A | A | A |
| 347 | L | L | L |
| 348 | P | P | P |
| 349 | A | A | A |
| 350 | P | P | P |
| 351 | I | I | I |
| 352 | E | E | E |
| 353 | K | K | K |
| 354 | T | T | T |
| 355 | I | I | I |
| 357 | S | S | S |
| 358 | K | K | K |
| 359 | A | A | A |
| 360 | K | K | K |
| 361 | G | G | G |
| 363 | Q | Q | Q |
| 364 | P | P | P |
| 365 | R | R | R |
| 366 | E | E | E |
| 367 | P | P | P |
| 368 | Q | Q | Q |
| 369 | V | V | V |
| 370 | Y | Y | Y |
| 371 | T | T | T |
| 372 | L | L | L |
| 373 | P | P | P |
| 374 | P | P | P |
| 375 | S | S | S |
| 376 | R | R | R |
| 377 | D | D | D |
| 378 | E | E | E |
| 381 | L | L | L |
| 382 | T | T | T |
| 383 | K | K | K |
| 384 | N | N | N |
| 385 | Q | Q | Q |
| 386 | V | V | V |
| 387 | S | S | S |
| 388 | L | L | L |
| 389 | T | T | T |
| 390 | C | C | C |
| 391 | L | L | L |
| 392 | V | V | V |
| 393 | K | K | K |
| 394 | G | G | G |
| 395 | F | F | F |
| 396 | Y | Y | Y |
| 397 | P | P | P |
| 398 | S | S | S |
| 399 | D | D | D |
| 400 | I | I | I |
| 401 | A | A | A |
| 402 | V | V | V |
| 405 | E | E | E |
| 406 | W | W | W |
| 407 | E | E | E |
| 408 | S | S | S |
| 410 | N | N | N |
| 411 | G | G | G |
| 414 | Q | Q | Q |
| 415 | P | P | P |
| 416 | E | E | E |
| 417 | N | N | N |
| 418 | N | N | N |
| 419 | Y | Y | Y |
| 420 | K | K | K |
| 421 | T | T | T |
| 422 | T | T | T |
| 423 | P | P | P |

TABLE 3A-continued

Kabat numbering of the heavy chain amino acid sequences of D3H44, Trastuzumab and Cetuximab

| KABAT numbering | D3H44 | TRASTUZUMAB | CETUXIMAB |
|---|---|---|---|
| 424 | P | P | P |
| 425 | V | V | V |
| 426 | L | L | L |
| 427 | D | D | D |
| 428 | S | S | S |
| 430 | D | D | D |
| 433 | G | G | G |
| 434 | S | S | S |
| 435 | F | F | F |
| 436 | F | F | F |
| 437 | L | L | L |
| 438 | Y | Y | Y |
| 439 | S | S | S |
| 440 | K | K | K |
| 441 | L | L | L |
| 442 | T | T | T |
| 443 | V | V | V |
| 444 | D | D | D |
| 445 | K | K | K |
| 446 | S | S | S |
| 447 | R | R | R |
| 448 | W | W | W |
| 449 | Q | Q | Q |
| 450 | Q | Q | Q |
| 451 | G | G | G |
| 452 | N | N | N |
| 453 | V | V | V |
| 454 | F | F | F |
| 455 | S | S | S |
| 456 | C | C | C |
| 457 | S | S | S |
| 458 | V | V | V |
| 459 | M | M | M |
| 460 | H | H | H |
| 461 | E | E | E |
| 462 | A | A | A |
| 463 | L | L | L |
| 464 | H | H | H |
| 465 | N | N | N |
| 466 | H | H | H |
| 467 | Y | Y | Y |
| 468 | T | T | T |
| 469 | Q | Q | Q |
| 470 | K | K | K |
| 471 | S | S | S |
| 472 | L | L | L |
| 473 | S | S | S |
| 474 | L | L | L |
| 475 | S | S | S |
| 476 | P | P | P |
| 477 | G | G | G |

Variable regions: HFR1; 1-30, CDR-H1; 31-35, HFR2; 36-49, CDR-H2; 50-65, HFR3; 66-94, CDR-H3; 95-102, HFR4; 103-113 (Reference: Molecular Immunology. Volume 45, Issue 14, August 2008, Pages 3832-3839).

TABLE 3B

Table 3B. Kabat numbering of the light chain amino acid sequences of D3H44, Trastuzumab and Cetuximab

| KABAT numbering | D3H44 | TRASTUZUMAB | CETUXIMAB |
|---|---|---|---|
| 1 | D | D | D |
| 2 | I | I | I |
| 3 | Q | Q | L |
| 4 | M | M | L |
| 5 | T | T | T |
| 6 | Q | Q | Q |
| 7 | S | S | S |
| 8 | P | P | P |
| 9 | S | S | V |
| 10 | S | S | I |
| 11 | L | L | L |
| 12 | S | S | S |
| 13 | A | A | V |
| 14 | S | S | S |
| 15 | V | V | P |
| 16 | G | G | G |
| 17 | D | D | E |
| 18 | R | R | R |
| 19 | V | V | V |
| 20 | T | T | S |
| 21 | I | I | F |
| 22 | T | T | S |
| 23 | C | C | C |
| 24 | R | R | R |
| 25 | A | A | A |
| 26 | S | S | S |
| 27 | R | Q | Q |
| 28 | D | D | S |
| 29 | I | V | I |
| 30 | K | N | G |
| 31 | S | T | T |
| 32 | Y | A | N |
| 33 | L | V | I |
| 34 | N | A | H |
| 35 | W | W | W |
| 36 | Y | Y | Y |
| 37 | Q | Q | Q |
| 38 | Q | Q | Q |
| 39 | K | K | R |
| 40 | P | P | T |
| 41 | G | G | N |
| 42 | K | K | G |
| 43 | A | A | S |
| 44 | P | P | P |
| 45 | K | K | R |
| 46 | V | L | L |
| 47 | L | L | L |
| 48 | I | I | I |
| 49 | Y | Y | K |
| 50 | Y | S | Y |
| 51 | A | A | A |
| 52 | T | S | S |
| 53 | S | F | E |
| 54 | L | L | S |
| 55 | A | Y | I |
| 56 | E | S | S |
| 57 | G | G | G |
| 58 | V | V | I |
| 59 | P | P | P |
| 60 | S | S | S |
| 61 | R | R | R |
| 62 | F | F | F |
| 63 | S | S | S |
| 64 | G | G | G |
| 65 | S | S | S |
| 66 | G | R | G |
| 67 | S | S | S |
| 68 | G | G | G |
| 69 | T | T | T |
| 70 | D | D | D |
| 71 | Y | F | F |
| 72 | T | T | T |
| 73 | L | L | L |
| 74 | T | T | S |
| 75 | I | I | I |
| 76 | S | S | N |
| 77 | S | S | S |
| 78 | L | L | V |
| 79 | Q | Q | E |

TABLE 3B-continued

Table 3B. Kabat numbering of the light chain amino acid sequences of D3H44, Trastuzumab and Cetuximab

| KABAT numbering | D3H44 | TRASTUZUMAB | CETUXIMAB |
|---|---|---|---|
| 80 | P | P | S |
| 81 | E | E | E |
| 82 | D | D | D |
| 83 | F | F | I |
| 84 | A | A | A |
| 85 | T | T | D |
| 86 | Y | Y | Y |
| 87 | Y | Y | Y |
| 88 | C | C | C |
| 89 | L | Q | Q |
| 90 | Q | Q | Q |
| 91 | H | H | N |
| 92 | G | Y | N |
| 93 | E | T | N |
| 94 | S | T | W |
| 95 | P | P | P |
| 96 | W | P | T |
| 97 | T | T | T |
| 98 | F | F | F |
| 99 | G | G | G |
| 100 | Q | Q | A |
| 101 | G | G | G |
| 102 | T | T | T |
| 103 | K | K | K |
| 104 | V | V | L |
| 105 | E | E | E |
| 106 | I | I | L |
| 107 | K | K | K |
| 108 | R | R | R |
| 109 | T | T | T |
| 110 | V | V | V |
| 111 | A | A | A |
| 112 | A | A | A |
| 113 | P | P | P |
| 114 | S | S | S |
| 115 | V | V | V |
| 116 | F | F | F |
| 117 | I | I | I |
| 118 | F | F | F |
| 119 | P | P | P |
| 120 | P | P | P |
| 121 | S | S | S |
| 122 | D | D | D |
| 123 | E | E | E |
| 124 | Q | Q | Q |
| 125 | L | L | L |
| 126 | K | K | K |
| 127 | S | S | S |
| 128 | G | G | G |
| 129 | T | T | T |
| 130 | A | A | A |
| 131 | S | S | S |
| 132 | V | V | V |
| 133 | V | V | V |
| 134 | C | C | C |
| 135 | L | L | L |
| 136 | L | L | L |
| 137 | N | N | N |
| 138 | N | N | N |
| 139 | F | F | F |
| 140 | Y | Y | Y |
| 141 | P | P | P |
| 142 | R | R | R |
| 143 | E | E | E |
| 144 | A | A | A |
| 145 | K | K | K |
| 146 | V | V | V |
| 147 | Q | Q | Q |
| 148 | W | W | W |
| 149 | K | K | K |
| 150 | V | V | V |
| 151 | D | D | D |
| 152 | N | N | N |
| 153 | A | A | A |
| 154 | L | L | L |
| 155 | Q | Q | Q |
| 156 | S | S | S |
| 157 | G | G | G |
| 158 | N | N | N |
| 159 | S | S | S |
| 160 | Q | Q | Q |
| 161 | E | E | E |
| 162 | S | S | S |
| 163 | V | V | V |
| 164 | T | T | T |
| 165 | E | E | E |
| 166 | Q | Q | Q |
| 167 | D | D | D |
| 168 | S | S | S |
| 169 | K | K | K |
| 170 | D | D | D |
| 171 | S | S | S |
| 172 | T | T | T |
| 173 | Y | Y | Y |
| 174 | S | S | S |
| 175 | L | L | L |
| 176 | S | S | S |
| 177 | S | S | S |
| 178 | T | T | T |
| 179 | L | L | L |
| 180 | T | T | T |
| 181 | L | L | L |
| 182 | S | S | S |
| 183 | K | K | K |
| 184 | A | A | A |
| 185 | D | D | D |
| 186 | Y | V | Y |
| 187 | E | E | E |
| 188 | K | K | K |
| 189 | H | H | H |
| 190 | K | K | K |
| 191 | V | V | V |
| 192 | Y | Y | Y |
| 193 | A | A | A |
| 194 | C | C | C |
| 195 | E | E | E |
| 196 | V | V | V |
| 197 | T | T | T |
| 198 | H | H | H |
| 199 | Q | Q | Q |
| 200 | G | G | G |
| 201 | L | L | L |
| 202 | S | S | S |
| 203 | S | S | S |
| 204 | P | P | P |
| 205 | V | V | V |
| 206 | T | T | T |
| 207 | K | K | K |
| 208 | S | S | S |
| 209 | F | F | F |
| 210 | N | N | N |
| 211 | R | R | R |
| 212 | G | G | G |
| 213 | E | E | E |
| 214 | C | C | C |

Variable regions: LFR1; 1-23. CDR-L1; 24-34, LFR2; 35-49, CDR-L2; 50- 56, LFR3; 57-88; CDR-L3; 89-97, LER4; 98-110 (Reference: Molecular Immunology. Volume 45, Issue 14, August 2008, Pages 3832-3839).

TABLE 3C

AMINO ACID AND DNA SEQUENCES OF D3H44, TRASTUZUMAB, AND CETUXIMAB

| SEQ ID NO | DESCRIPTION | SEQUENCE |
|---|---|---|
| 1 | D3H44 light chain (Domain boundaries: VL; D1-K107, CL; R108-C214) | DIQMTQSPSSLSASVGDRVTITCRASRDIKSYLNWYQQKPGKAPKVLIYYATSLAEGVPSRFSGSGSGTDYT LTISSLQPEDFATYYCLQHGESPWTFGQGTKVEIKRTVAAPSVFIFPPSDEQLKSGTASVVCLLNNFYPREA KVQWKVDNALQSGNSQESVTEQDSKDSTYSLSSTLTLSKADYEKHKVYACEVTHQGLSSPVTKSFNRGEC |
| 2 | Trastuzumab light chain (Domain boundaries: VL; D1-K107, CL; R108-C214) | DIQMTQSPSSLSASVGDRVTITCRASQDVNTAVAWYQQKPGKAPKLLIYSASFLYSGVPSRFSGSRSGTDFTL TISSLQPEDFATYYCQQHYTTPPTFGQGTKVEIKRTVAAPSVFIFPPSDEQLKSGTASVVCLLNNFYPREAKV QWKVDNALQSGNSQESVTEQDSKDSTYSLSSTLTLSKADYEKHKVYACEVTHQGLSSPVTKSFNRGEC |
| 3 | Cetuximab light chain (Domain boundaries: VL; D1-K107, CL; R108-C214) | DILLTQSPVILSVSPGERVSFSCRASQSIGTNIHWYQQRTNGSPRLLIKYASESISGIPSRFSGSGSGTDFTL SINSVESEDIADYYCQQNNNWPTTFGAGTKLELKRTVAAPSVFIFPPSDEQLKSGTASVVCLLNNFYPREAKV QWKVDNALQSGNSQESVTEQDSKDSTYSLSSTLTLSKADYEKHKVYACEVTHQGLSSPVTKSFNRGEC |
| 4 | D3H44 heavy chain (Domain boundaries: VH; E1-S117, CH1; A118-V215, Hinge; E216-P230, CH2; A231-K340, CH3; G341-G446) | EVQLVESGGGLVQPGGSLRLSCAASGFNIKEYYMHWVRQAPGKGLEWVGLIDPEQGNTIYDPKFQDRATISAD NSKNTAYLQMNSLRAEDTAVYYCARDTAAYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQTYICNVNHKPSNTKVDKKVEPKS CDKTHTCPPCPAPELLGGPSVFLFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKGQPREPQVYTLPPSRDELTKNQVSL TCLVKGFYPSDIAVEWESNGQPENNYKTTPPVLDSDGSFFLYSKLTVDKSRWQQGNVFSCSVMHEALHNHYTQ KSLSLSPG |
| 5 | Trastuzumab heavy chain (Domain boundaries: VH; E1-S120, CH1; A121-V218, Hinge; E219-P233, CH2; A234-K343, CH3; G344-G449) | EVQLVESGGGLVQPGGSLRLSCAASGFNIKDTYIHWVRQAPGKGLEWVARIYPTNGYTRYADSVKGRFTISAD TSKNTAYLQMNSLRAEDTAVYYCSRWGGDGFYAMDYWGQGTLVTVSSASTKGPSVFPLAPSSKSTSGGTAALG CLVKDYFPEPVTVSWNSGALTSGVHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTVDKSRWQQGNVFSCSVMHEALHNH YTQKSLSLSPG |
| 6 | Cetuximab heavy chain (Domain boundaries: VH;Q1-A119, CH1; A120-V217, Hinge; E218-P232, CH2; A233-K342, CH3; G343-G448) | QVQLKQSGPGLVQPSQSLSITCTVSGFSLTNYGVHWVRQSPGKGLEWLGVIWSGGNTDYNTPFTSRLSINKDN SKSQVFFKMNSLQSNDTAIYYCARALTYYDYEFAYWGQGTLVTVSAASTKGPSVFPLAPSSKSTSGGTAALGC LVKDYFPEPVTVSWNSGALTSGVHTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRDELTKNQV SLTCLVKGFYPSDIAVEWESNGQPENNYKTTPPVLDSDGSFFLYSKLTVDKSRWQQGNVFSCSVMHEALHNHY TQKSLSLSPG |
| 7 | Trastuzumab_Heavy Chain | GAGGTGCAGCTGGTGGAAAGCGGAGGAGGACTGGTGCAGCCAGGAGGATCTCTGCGACTGAGTTGCGCCGCTT CAGGATTCAACATCAAGGACACCTACATTCACTGGGTGCGACAGGCTCCAGGAAAAGGACTGGAGTGGGTGGCT CGAATCTATCCCACTAATGGATACACCCGGTATGCCGACTCCGTGAAGGGGAGGTTTACTATTAGCGCCGATACA TCCAAAAACACTGCTTACCTGCAGATGAACAGCCTGCGAGCCGAAGATACCGCTGTGTACTATTGCAGTCGATGG GGAGGAGACGGATTCTACGCTATGGATTATTGGGGACAGGGGACCCTGGTGACAGTGAGCTCCGCCTCTACCAA GGGCCCCAGTGTGTTTCCCCTGGCTCCTTCTAGTAAATCCACCTCTGGAGGGACAGCCGCTCTGGGATGTCTGGT GAAGGACTATTTCCCCGAGCCTGTGACCGTGAGTTGGAACTCAGGCGCCCTGACAAGCGGAGTGCACACTTTTCC TGCTGTGCTGCAGTCAAGCGGGCTGTACTCCCTGTCCTCTGTGGTGACAGTGCCAAGTTCAAGCCTGGGCACACA GACTTATATCTGCAACGTGAATCATAAGCCCTCAAATACAAAAGTGGACAAGAAAGTGGAGCCCAAGAGCTGTG ATAAGACCCACACCTGCCCTCCCTGTCCAGCTCCAGAACTGCTGGGAGGACCTAGCGTGTTCCTGTTTCCCCCTA AGCCAAAAGACACTCTGATGATTTCCAGGACTCCCGAGGTGACCTGCGTGGTGGTGGACGTGTCTCACGAGGACC CCGAAGTGAAGTTCAACTGGTACGTGGATGGCGTGGAAGTGCATAATGCTAAGACAAAACCAAGAGAGGAACA GTACAACTCCACTTATCGCGTCGTGAGCGTGCTGACCGTGCTGCACCAGGACTGGCTGAACGGGAAGGAGTATA AGTGCAAAGTCAGTAATAAGGCCCTGCCTGCTCCAATCGAAAAAACCATCTCTAAGGCCAAAGGCCAGCCAAGG GAGCCCCAGGTGTACACACTGCCACCCAGCAGAGACGAACTGACCAAGAACCAGGTGTCCCTGACATGTCTGGT GAAAGGCTTCTATCCTAGTGATATTGCTGTGGAGTGGGAATCAAATGGACAGCCAGAGAACAATTACAAGACCA CACCTCCAGTGCTGGACAGCGATGGCAGCTTCTTCCTGTATTCCAAGCTGACAGTGGATAAATCTCGATGGCAGC AGGGGAACGTGTTTAGTTGTTCAGTGATGCATGAAGCCCTGCACAATCATTACACTCAGAAGAGCCTGTCCCTGT CTCCCGGC |
| 8 | Trastuzumab_Light Chain | GACATCCAGATGACCCAGTCTCCATCCTCCCTGTCTGCATCTGTAGGAGACAGAGTCACCATCACTTGCCGGGCA AGTCAGGACGTTAACACCGCTGTAGCTTGGTATCAGCAGAAACCAGGGAAAGCCCCTAAGCTCCTGATCTATTCT GCATCCTTTTTGTACAGTGGGGTCCCATCAAGGTTCAGTGGCAGTAGATCTGGGACAGATTTCACTCTCACCATC AGCAGTCTGCAACCTGAAGATTTTGCAACTTACTACTGTCAACAGCATTACACTACCCCACCCACTTTCGGCCAA GGGACCAAAGTGGATATCAAACGAACTGTGGCTGCACCATCTGTCTTCATCTTCCCGCCATCTGATGAGCAGTT GAAATCTGGAACTGCCTCTGTTGTGTGCCTGCTGAATAACTTCTATCCCAGAGAGGCCAAAGTACAGTGGAAGG TGGATAACGCCCTCCAATCGGGTAACTCCCAGGAGAGTGTCACAGAGCAGGACAGCAAGGACAGCACCTACAGC CTCAGCAGCACCCTGACGCTGAGCAAAGCAGACTACGAGAAACACAAAGTCTACGCCTGCGAAGTCACCCATCA GGGCCTGAGCTCGCCCGTCACAAAGAGCTTCAACAGGGGAGAGTGT |
| 9 | Cetuximab_Heavy Chain | CAGGTGCAGCTGAAACAGAGCGGCCCGGGCCTGGTGCAGCCGAGCCAGAGCCTGAGCATTACCTGCACCGTGA GCGGCTTTAGCCTGACCAACTATGGCGTGCATTGGGTGCGCCAGAGCCCGGGCAAAGGCCTGGAATGGCTGGG CGTGATTTGGAGCGGCGGCAACACCGATTATAACACCCCGTTTACCAGCCGCCTGAGCATTAACAAAGATAACAG CAAAAGCCAGGTGTTTTTTAAAATGAACAGCCTGCAGAGCAACGATACCGCGATTTATTATTGCGCGCGCGCTCT GACCTATTATGATTATGAATTTGCGTATTGGGGCCAGGGCACCCTGGTGACCGTGAGCGCGGCGAGCACCAAAG GCCCGAGCGTGTTTCCGCTGGCGCCGAGCAGCAAAAGCACCAGCGGCGGCACCGCGGCGCTGGGCTGCCTGGT |

TABLE 3C-continued

AMINO ACID AND DNA SEQUENCES OF D3H44, TRASTUZUMAB, AND CETUXIMAB

| SEQ ID NO | DESCRIPTION | SEQUENCE |
|---|---|---|
| | | GAAAGATTATTTTCCGGAACCGGTGACCGTGAGCTGGAACAGCGGCGCGCTGACCAGCGGCGTGCATACCTTTC<br>CGGCGGTGCTGCAGAGCAGCGGCCTGTATAGCCTGAGCAGCGTGGTGACCGTGCCGAGCAGCAGCCTGGGCAC<br>CCAGACCTATATTTGCAACGTGAACCATAAACCGAGCAACACCAAAGTGGATAAAAAAGTGGAACCGAAAAGCT<br>GCGATAAAACCCATACCTGCCCGCCGTGCCCGGCGCCGGAACTGCTGGGCGGCCCGAGCGTGTTTCTGTTTCCGC<br>CGAAACCGAAAGATACCCTGATGATTAGCCGCACCCCGGAAGTGACCTGCGTGGTGGTGGATGTGAGCCATGAA<br>GATCCGGAAGTGAAATTTAACTGGTATGTGGATGGCGTGGAAGTGCATAACGCGAAAACCAAACCGCGCGAAG<br>AACAGTATAACAGCACCTATCGCGTGGTGAGCGTGCTGACCGTGCTGCATCAGGATTGGCTGAACGGCAAAGAA<br>TATAAATGCAAAGTGAGCAACAAAGCGCTGCCGGCGCCGATTGAAAAAACCATTAGCAAAGCGAAAGGCCAGC<br>CGCGCGAACCGCAGGTGTATACCCTGCCGCCGAGCCGCGATGAACTGACCAAAAACCAGGTGAGCCTGACCTGC<br>CTGGTGAAAGGCTTTTATCCGAGCGATATTGCGGTGGAATGGGAAAGCAACGGCCAGCCGGAAAACAACTATAA<br>AACCACCCCGCCGGTGCTGGATAGCGATGGCAGCTTTTTTCTGTATAGCAAACTGACCGTGGATAAAAGCCGCTG<br>GCAGCAGGGCAACGTGTTTAGCTGCAGCGTGATGCATGAAGCGCTGCATAACCATTATACCCAGAAAAGCCTGA<br>GCCTGAGCCCGGGC |
| 10 | Cetuximab_Light Chain | GACATCCTGCTGACTCAGAGCCCAGTGATCCTGTCAGTCAGCCCAGGAGAGCGGGTGTCCTTCTCTTGCAGAGCA<br>AGTCAGTCAATCGGAACAAATATTCACTGGTACCAGCAGAGGACTAACGGCTCCCCTCGCCTGCTGATTAAGTAT<br>GCTAGCGAATCCATCTCTGGCATTCCATCTCGGTTCAGTGGCTCAGGGAGCGGAACAGACTTTACTCTGTCCATC<br>AATTCTGTGGAGAGTGAAGACATTGCCGATTACTATTGCCAGCAGAACAATAACTGGCCCACCACATTCGGCGCT<br>GGGACCAAGCTGGAGCTGAAACGAACAGTGGCCGCTCCTTCTGTCTTCATCTTTCCCCCTAGTGACGAACAGCTG<br>AAAAGCGGCACAGCCTCCGTGGTCTGTCTGCTGAATAACTTTTACCCAAGAGAGGCAAAGGTGCAGTGGAAAGT<br>CGATAATGCCCTGCAGTCAGGGAACAGCCAGGAGTCCGTGACTGAACAGGACTCTAAGGATAGTACCTATTCAC<br>TGAGCTCCACTCTGACCCTGTCCAAAGCTGATTACGAGAAGCACAAAGTGTATGCATGCGAAGTCACCCATCAGG<br>GGCTGTCTAGTCCCGTGACAAAGAGCTTTAACCGGGGAGAGTGT |
| 11 | D3H44_Heavy Chain | GAGGTGCAGCTGGTCGAATCTGGAGGAGGACTGGTGCAGCCAGGAGGGTCACTGAGACTGAGCTGCGCCGCTT<br>CCGGCTTCAACATCAAGGAGTACTATATGCACTGGGTGAGGCAGGCACCTGGCAAAGGACTGGAGTGGGTGGG<br>ACTGATCGACCCAGAACAGGGGAACACCATCTACGACCCTAAGTTTCAGGATAGGGCAACCATTTCTGCCGACAA<br>CAGTAAAAATACAGCTTATCTGCAGATGAACAGCCTGAGGGCTGAAGATACTGCAGTGTACTATTGCGCACGCG<br>ACACCGCAGCCTACTTCGATTATTGGGGACAGGGCACCCTGGTCACAGTGAGCTCCGCATCAACTAAGGGACCC<br>AGCGTGTTTCCACTGGCCCCCTCTAGTAAATCCACTTCTGGAGGCACCGCTGCACTGGGCTGTCTGGTGAAGGAT<br>TACTTCCCAGAGCCCGTCACAGTGAGCTGGAACTCCGGGGCCCTGACCAGCGGAGTCCATACATTTCCTGCTGTG<br>CTGCAGTCAAGCGGGCTGTACTCCCTGTCCTCTGTGGTCACCGTGCCAAGTTCAAGCCTGGGAACTCAGACCTAT<br>ATCTGCAACGTGAATCACAAGCCTTCAAATACAAAAGTCGACAAGAAAGTGGAACCAAAGAGCTGTGATAAAAC<br>ACATACTTGCCCACCTTGTCCTGCACCAGAGCTGCTGGGAGGACCAAGCGTGTTCCTGTTTCCACCCAAGCCCAA<br>AGACACCCTGATGATTTCCCGCACACCAGAAGTCACTTGCGTGGTCGTGGACGTGTCTCACGAGGACCCCGAAGT<br>CAAGTTCAACTGGTACGTGGATGGCGTCGAGGTGCATAATGCCAAGACAAAACCCCGGGAGGAACAGTACAACT<br>CCACATATAGAGTCGTGTCTGTCCTGACTGTGCTGCACCAGGACTGGCTGAACGGGAAGGAGTATAAGTGCAAA<br>GTGAGTAATAAGGCCCTGCCCGCTCCTATCGAGAAAACAATTAGCAAGGCCAAAGGCCAGCCTCGAGAACCACA<br>GGTGTACACTCTGCCTCCATCTCGGGACGAGCTGACTAAGAACCAGGTCAGTCTGACCTGTCTGGTGAAAGGATT<br>CTATCCCAGCGATATCGCTGTGGAGTGGGAATCCAATGGCCAGCCTGAGAACAATTACAAGACCACACCCCCTGT<br>GCTGGACTCTGATGGCAGTTTCTTTCTGTATAGTAAGCTGACCGTCGATAAATCACGATGGCAGCAGGGGAACGT<br>GTTCAGCTGTTCAGTGATGCACGAAGCCCTGCACAACCATTACACCCAGAAGAGCCTGAGCCTGTCTCCCGGC |
| 12 | D3H44_Light Chain | GACATCCAGATGACACAGTCCCCTAGCTCCCTGAGTGCCTCAGTGGGGGACAGAGTCACTATCACCTGCCGGGCT<br>TCCAGAGATATTAAGTCTTACCTGAACTGGTATCAGCAGAAGCCAGGCAAAGCACCCAAGGTGCTGATCTACTAT<br>GCCACCAGTCTGGCTGAAGGAGTGCCTTCACGGTTCAGCGGCTCCGGGTCTGGAACTGACTACACACTGACTATT<br>TCTAGTCTGCAGCCTGAGGATTTCGCTACCTACTATTGCCTGCAGCACGGCGAATCCCCATGGACTTTTGGCCAG<br>GGGACCAAAGTGGAGATCAAGAGGACAGTGGCCGCTCCATCCGTCTTCATTTTTCCCCCTTCTGACGAACAGCTG<br>AAATCAGGAACTGCCAGCGTGGTCTGTCTGCTGAACAATTTCTACCCCCGCGAGGCAAAAGTGCAGTGGAAGGT<br>CGATAACGCCCTGCAGAGTGGCAATTCACAGGAGAGCGTGACAGAACAGGACTCCAAAGATTCTACTTATAGTC<br>TGTCAAGCACCCTGACACTGTCTAAGGCTGATTACGAGAAGCACAAAGTGTATGCATGCGAAGTCACCCATCAG<br>GGGCTGTCCTCTCCCGTGACAAAGAGCTTTAATCGGGGAGAGTGT |

TABLE 4

LCCA designs with modifications to one immunoglobulin heavy chain and/or
two immunoglobulin light chains, where H1 preferentially pairs with L1

| Set #** | H1 mutation* | L1 mutation* | L2 mutation* |
|---|---|---|---|
| 9567 | L124W_L143F | V133A | V133W_S1761_R178L |
| 9087 | L124A_L143F | V133W_S176T_T178L | V133A |
| 9570 | L124W_L143F | V133G | V133W_S176T_T178L |
| 9089 | L124A_L143F | V133W_S176T_T178L | V133G |
| 9569 | L124W_L143F | V133A_S176T_T178L | V133W_S176T_T178L |
| 9088 | L124A_L143F | V133W_S176T_T178L | V133A_S176T_T178L |
| 9566 | L124W_L143F | V133A | V133W |
| 9085 | L124A_L143F | V133W | V133A |
| 9568 | L124W_L143F | V133A_S176T_T178L | V133W |
| 9086 | L124A_L143F | V133W | V133A_S176T_T178L |
| 9572 | L124W_L143F_K145T_Q179E | S131K_V133A_S176T_T178L | Q124E_V133W_S176T_T178L_T180E |
| 9096 | L124A_L143F_Q179K | Q124E_V133W_S176T_T178L_T180E | S131K_V133A_S176T_T178L |

TABLE 4-continued

LCCA designs with modifications to one immunoglobulin heavy chain and/or
two immunoglobulin light chains, where H1 preferentially pairs with L1

| Set #** | H1 mutation* | L1 mutation* | L2 mutation* |
|---|---|---|---|
| 9571 | L124W_L143F_K145T_Q179E | S131K_V133A_S176T_T178L | Q124E_V133W_S176T_T178E_T180E |
| 9092 | L124A_L143F_Q179K | Q124E_V133W_S176T_T178E_T180E | S131K_V133A_S176T_T178L |
| 9564 | L124W_L143E_K145T_Q179E | S131K_V133A_S176T_T178L | Q124E_V133W_S176T_T178L_T180E |
| 9562 | L124W_L143E_K145T_Q179E | S131K_V133A_S176T_T178L | Q124E_V133W_S176T_T178E_T180E |
| 9561 | L124W_L143E_K145T_Q179E | Q124R_V133A_S176T_T178R | Q124E_V133W_S176T_T178L_T180E |
| 9095 | L124A_L143F_Q179K | Q124E_V133W_S176T_T178L_T180E | Q124R_V133A_S176T_T178R |
| 9560 | L124W_L143E_K145T_Q179E | Q124E_V133A_S176T_T178R | Q124E_V133W_S176T_T178E_T180E |
| 9091 | L124A_L143F_Q179K | Q124E_V133W_S176T_T178E_T180E | Q124E_V133A_S176T_T178R |
| 9559 | L124W_L143E_K145T_Q179E | Q124K_V133A_S176T_T178R | Q124E_V133W_S176T_T178L_T180E |
| 9094 | L124A_L143F_Q179K | Q124E_V133W_S176T_T178L_T180E | Q124K_V133A_S176T_T178R |
| 9558 | L124W_L143E_K145T_Q179E | Q124E_V133A_S176T_T178R | Q124E_V133W_S176T_T178E_T180E |
| 9090 | L124A_L143F_Q179K | Q124E_V133W_S176T_T178E_T180E | Q124K_V133A_S176T_T178R |
| 9099 | L124A_Q179K | Q124E_V133W_S176T_T178L_T180E | S131K_V133A_S176T_T178L |
| 9098 | L124A_Q179K | Q124E_V133W_S176T_T178E_T180E | S131K_V133A_S176T_T178L |
| 9110 | L124E | V133G_S176R | V133G_S176D_T178Y |
| 9341 | L124R | V133G_S176D_T178Y | V133G_S176R |
| 9104 | L124E | S131T_V133G_S176R_T178Y | V133G_S176D |
| 9336 | L124R | V133G_S176D | S131T_V133G_S176R_T178Y |
| 9105 | L124E | S131T_V133G_S176R_T178Y | V133G_S176D_T178Y |
| 9340 | L124R | V133G_S176D_T178Y | S131T_V133G_S176R_T178Y |
| 9106 | L124E | V133G_S176K | V133G_S176D |
| 9337 | L124R | V133G_S176D | V133G_S176K |
| 9107 | L124E | V133G_S176K | V133G_S176D_T178D |
| 9339 | L124R | V133G_S176D_T178D | V133G_S176K |
| 9109 | L124E | V133G_S176R | S131E_V133G_S176D |
| 9332 | L124R | S131E_V133G_S176D | V133G_S176R |
| 9108 | L124E | V133G_S176K | S131E_V133G_S176D |
| 9330 | L124R | S131E_V133G_S176D | V133G_S176K |
| 9326 | L124E_L143F | V133G_S176R | V133G_S176D |
| 6048 | L124R | V133G_S176D | V133G_S176R |
| 9327 | L124E_L143F | V133G_S176R | V133G_S176D_T178D |
| 6054 | L124R | V133G_S176D_T178D | V133G_S176R |
| 9328 | L124E_L143F | V133G_S176R | S131E_V133G_S176D |
| 9113 | L124E_A125S_K228D | S121K_V133G_S176R | V133G_S176D |
| 9342 | L124R_A125R | V133G_S176D | S121K_V133G_S176R |
| 9114 | L124E_A125S_K228D | S121K_V133G_S176R | V133F_S176D_T178D |
| 9344 | L124R_A125R | V133G_S176D_T178D | S121K_V133G_S176R |
| 9168 | L124E_K228D | S121K_V133G_S176R | V133G_S176D |
| 9169 | L124E_K228D | S121K_V133G_S176R | V133G_S176D_T178D |
| 9119 | L124E_H172R | V133G_S176R | V133G_N137K_S174R_S176D |
| 9375 | L124R_H172T | V133G_N137K_S174R_S176D | V133G_S176R |
| 9118 | L124E_H172R | V133G_S176R | V133G_S174R_S176D |
| 6098 | L124R_H172T | V133G_S174R_S176D | V133G_S176R |
| 9117 | L124E_H172R | V133G_S176K | V133G_N137K_S174R_S176D |
| 9374 | L124R_H172T | V133G_N137K_S174R_S176D | V133G_S176K |
| 9120 | L124R_H172T | V133G_N137K_S174R_S176R | V133G_S176D |
| 9370 | L124R_H172R | V133G_S176D | V133G_N137K_S174R_S176R |
| 9122 | L124E_H172R | V133G_S174R_S176R | V133G_S176D |
| 9371 | L124R_H172R | V133G_S176D | V133G_S174R_S176R |
| 9121 | L124E_H172T | V133G_N137K_S174R_S176R | V133G_S176D_T178D |
| 9373 | L124R_H172R | V133G_S176D_T178D | V133G_N137K_S174R_S176R |
| 9111 | L124E_A125S_H172R_K228D | S121K_V133G_S176R | V133G_N137K_S174R_S176R |
| 9347 | L124R_A125R_H172T | V133G_N137K_S174R_S176D | S121K_V133G_S176R |
| 9112 | L124E_A125S_H172T_K228D | S121K_V133G_N137K_S174R_S176R | V133G_S176D |
| 9346 | L124R_A125R_H172R | V133G_S176D | S121K_V133G_N137K_S174R_S176R |
| 9115 | L124E_A139W | F116A_V133G_L135A_S176R | V133G_L135W_S176D |
| 9348 | L124R_A139G_V190A | V133G_L135W_S176D | F116A_V133G_L135A_S176R |
| 9116 | L124E_A139W | F116A_V133G_L135V_S176R | V133G_L135W_S176D |
| 9349 | L124R_A139G_V190A | V133G_L35W_S176D | F116A_V133G_L135V_S176R |
| 9140 | L124E_K145T_Q179E | S131K_V133G_S176R | V133G_S176D_T178D_T180E |
| 9481 | L124R_S186K | V133G_S176D_T178D_T180E | S131K_V133G_S176R |
| 9146 | L124E_K145T_Q179E | S131K_V133G_S176R | V133G_S176D_T180E |
| 9498 | L124R_S186K | V133G_S176D_T180E | S131K_V133G_S176R |
| 9134 | L124E_K145T_Q179E | S131K_V133G_S176R | V133G_S176D_T178D |
| 9466 | L124R_S186K | V133G_S176D_T178D | S131K_V133G_S176R |
| 9136 | L124E_K145T_Q179E | S131K_V133G_S176R | Q124E_V133G_S176D_T178D_T180E |
| 9459 | L124R_S186K | Q124E_V133G_S176D_T178D_T180E | S131K_V133G_S176R |
| 9158 | L124E_K145T_Q179E | S131R_V133G_S176R | V133G_S176D_T178D_T180E |
| 9483 | L124R_S186K | V133G_S176D_T178D_T180E | S131R_V133G_S176R |
| 9164 | L124E_K145T_Q179E | S131R_V133G_S176R | V133G_S176D_T180E |
| 9500 | L124R_S186K | V133G_S176D_T180E | S131R_V133G_S176R |
| 9150 | L124E_K145T_Q179E | S131R_V133G_S176R | V133G_S176D_T178D |
| 9468 | L124R_S186K | V133G_S176D_T178D | S131R_V133G_S176R |
| 9152 | L124E_K145T_Q179E | S131R_V133G_S176R | Q124E_V133G_S176D_T178D_T180E |

TABLE 4-continued

LCCA designs with modifications to one immunoglobulin heavy chain and/or two immunoglobulin light chains, where H1 preferentially pairs with L1

| Set #** | H1 mutation* | L1 mutation* | L2 mutation* |
|---|---|---|---|
| 9460 | L124R_S186K | Q124E_V133G_S176D_T178D_T180E | S131R_V133G_S176R |
| 9536 | L124R_S186R | V133G_S176D_T178D_T180E | S131K_V133G_S176R |
| 9553 | L124R_S186R | V133G_S176D_T180E | S131K_V133G_S176R |
| 9521 | L124R_S186R | V133G_S176D_T178D | S131K_V133G_S176R |
| 9513 | L124R_S186R | Q124E_V133G_S176D_T178D_T180E | S131K_V133G_S176R |
| 9538 | L124R_S186R | V133G_S176D_T178D_T180E | S131R_V133G_S176R |
| 9555 | L124R_S186R | V133G_S176D_T180E | S131R_V133G_S176R |
| 9523 | L124R_S186R | V133G_S176D_T178D | S131R_V133G_S176R |
| 9515 | L124R_S186R | Q124E_V133G_S176D_T178D_T180E | S131R_V133G_S176R |
| 9127 | L124E_K145M_Q179E | S131K_V133G_S176R | V133G_S176D_T178D_T180E |
| 9131 | L124E_K145M_Q179E | S131K_V133G_S176R | V133G_S176D_T180E |
| 9123 | L124E_K145M_Q179E | S131K_V133G_S176R | V133G_S176D_T178D |
| 9125 | L124E_K145M_Q179E | S131K_V133G_S176R | Q124E_V133G_S176D_T178D_T180E |
| 9296 | L124E_L142E_K145T | Q124K_V133G_S176R_T178K | Q124E_V133G_S176D_T178D_T180E |
| 9505 | L124R_S186R | Q124E_V133G_S176D_T178D_T180E | Q124K_V133G_S176R_T178K |
| 9308 | L124E_L143E_K145T | Q124K_V133G_S176R_T178K | V133G_S176D_T180E |
| 9547 | L124R_S186R | V133G_S176D_T180E | Q124K_V133G_S176R_T178K |
| 9300 | L124E_L143E_K145T | Q124K_V133G_S176R_T178K | V133G_S176D_T178D_T180E |
| 9528 | L124R_S186R | V133G_S176D_T178D_T180E | Q124K_V133G_S176R_T178K |
| 9294 | L124E_L143E_K145T | Q124K_V133G_S176R_T178K | V133G_S176D_T178D |
| 9519 | L124R_S186R | V133G_S176D_T178D | Q124K_V133G_S176R_T178K |
| 9304 | L124E_L143E_K145T | Q124K_V133G_S176R_T178K | V133G_S176D_T178E_T180E |
| 9542 | L124R_S186R | V133G_S176D_T178E_T180E | Q124K_V133G_S176R_T178K |
| 9314 | L124E_L143E_K145T | Q124K_V133G_S176R_T178R | Q124E_V133G_S176D_T178D_T180E |
| 9509 | L124R_S186R | Q124E_V133G_S176D_T178D_T180E | Q124K_V133G_S176R_T178R |
| 9323 | L124E_L143E_K145T | Q124K_V133G_S176R_T178R | V133G_S176D_T180E |
| 9550 | L124R_S186R | V133G_S176D_T180E | Q124K_V133G_S176R_T178R |
| 9317 | L124E_L143E_K145T | Q124K_V133G_S176R_T178R | V133G_S176D_T178D_T180E |
| 9532 | L124R_S186R | V133G_S176D_T178D_T180E | Q124K_V133G_S176R_T178R |
| 9312 | L124E_L143E_K145T | Q124K_V133G_S176R_T178R | V133G_S176D_T178R |
| 9520 | L124R_S186R | V133G_S176D_T178D | Q124K_V133G_S176R_T178R |
| 9320 | L124E_L142E_K145T | Q124K_V133G_S176R_T178R | V133G_S176D_T178E_T180E |
| 9543 | L124R_S186R | V133G_S176D_T178E_T180E | Q124K_V133G_S176R_T178R |
| 9281 | L124E_L143E_K145T | Q124K_V133G_S176R | Q124E_V133G_S176D_T178D_T180E |
| 9503 | L124R_S186R | Q124E_V133G_S176D_T178D_T180E | Q124K_V133G_S176R |
| 9290 | L124E_L143E_K145T | Q124K_V133G_S176R | V133G_S176D_T180E |
| 9546 | L124R_S186R | V133G_S176D_T180E | Q124K_V133G_S176R |
| 9284 | L124E_L143E_K145T | Q124K_V133G_S176R | V133G_S176D_T178D_T180E |
| 9526 | L124R_S186R | V133G_S176D_T178D_T180E | Q124K_V133G_S176R |
| 9279 | L124E_L143E_K145T | Q124K_V133G_S176R | V133G_S176D_T178D |
| 9518 | L124R_S186R | V133G_S176D_T178D | Q124K_V133G_S176R |
| 9287 | L124E_L143E_K145T | Q124K_V133G_S176R | V133G_S176D_T178E_T180E |
| 9541 | L124R_S186R | V133G_S176D_T178E_T180E | Q124K_V133G_S176R |
| 9451 | L124R_S186K | Q124E_V133G_S176D_T178D_T180E | Q124K_V133G_S176R_T178K |
| 9492 | L124R_S186K | V133G_S176D_T180E | Q124K_V133G_S176R_T178K |
| 9473 | L124R_S186K | V133G_S176D_T178D_T180E | Q124K_V133G_S176R_T178K |
| 9464 | L124R_S186K | V133G_S176D_T178D | Q124K_V133G_S176R_T178K |
| 9487 | L124R_S186K | V133G_S176D_T178E_T180E | Q124K_V133G_S176R_T178K |
| 9455 | L124R_S186K | Q124E_V133G_S176D_T178D_T180E | Q124K_V133G_S176R_T178R |
| 9495 | L124R_S186K | V133G_S176D_T180E | Q124K_V133G_S176R_T178R |
| 9477 | L124R_S186K | V133G_S176D_T178D_T180E | Q124K_V133G_S176R_T178R |
| 9465 | L124R_S186K | V133G_S176D_T178D | Q124K_V133G_S176R_T178R |
| 9488 | L124R_S186K | V133G_S176D_T178E_T180E | Q124K_V133G_S176R_T178R |
| 9449 | L124R_S186K | Q124E_V133G_S176D_T178D_T180E | Q124K_V133G_S176R |
| 9491 | L124R_S186K | V133G_S176D_T180E | Q124K_V133G_S176R |
| 9471 | L124R_S186K | V133G_S176D_T178D_T180E | Q124K_V133G_S176R |
| 9463 | L124R_S186K | V133G_S176D_T178D | Q124K_V133G_S176R |
| 9486 | L124R_S186K | V133G_S176D_T178E_T180E | Q124K_V133G_S176R |
| 9264 | L124E_L143E_K145M | Q124K_V133G_S176R_T178R | Q124E_V133G_S176D_T178D_T180E |
| 9267 | L124E_L143E_K145M | Q124K_V133G_S176R_T178R | V133G_S176D_T178D_T180E |
| 9250 | L124E_L143E_K145M | Q124K_V133G_S176R | Q124E_V133G_S176D_T178D_T180E |
| 9253 | L124E_L143E_K145M | Q124K_V133G_S176R | V133G_S176D_T178D_T180E |
| 9257 | L124E_L143E_K145M | Q124K_V133G_S176R_T178K | Q124E_V133G_S176D_T178D_T180E |
| 9260 | L124E_L143E_K145M | Q124K_V133G_S176R_T178K | V133G_S176D_T178D_T180E |
| 9214 | L124E_L143D_K145T | Q124K_V133G_S176R_T178K | Q124E_V133G_S176D_T178D_T180E |
| 9223 | L124E_L143D_K145T | Q124K_V133G_S176R_T178R | Q124E_V133G_S176D_T178D_T180E |
| 9217 | L124E_L143D_K145T | Q124K_V133G_S176R_T178K | V133G_S176D_T178D_T180E |
| 9226 | L124E_L143D_K145T | Q124K_V133G_S176R_T178R | V133G_S176D_T178D_T180E |
| 9220 | L124E_L143D_K145T | Q124K_V133G_S176R_T178K | V133G_S176D_T180E |
| 9229 | L124E_L143D_K145T | Q124K_V133G_S176R_T178R | V133G_S176D_T180E |
| 9234 | L124E_L143D_K145T | V133G_S176R_T178K | Q124E_V133G_S176D_T178D_T180E |
| 9516 | L124R_S186R | Q124E_V133G_S176D_T178D_T180E | V133G_S176R_T178K |
| 9243 | L124E_L143D_K145T | V133G_S176R_T178K | V133G_S176D_T180E |
| 9556 | L124R_S186R | V133G_S176D_T180E | V133G_S176R_T178K |

TABLE 4-continued

LCCA designs with modifications to one immunoglobulin heavy chain and/or
two immunoglobulin light chains, where H1 preferentially pairs with L1

| Set #** | H1 mutation* | L1 mutation* | L2 mutation* |
|---|---|---|---|
| 9237 | L124E_L143D_K145T | V133G_S176R_T178K | V133G_S176D_T178D_T180E |
| 9539 | L124R_S186R | V133G_S176D_T178D_T180E | V133G_S176R_T178K |
| 9232 | L124E_L143D_K145T | V133G_S176R_T178K | V133G_S176R_T178D |
| 9524 | L124R_S186R | V133G_S176D_T178D | V133G_S176R_T178K |
| 9240 | L124E_L143D_K145T | V133G_S176R_T178K | V133G_S176D_T178E_T180E |
| 9544 | L124R_S186R | V133G_S176D_T178E_T180E | V133G_S176R_T178K |
| 9461 | L124R_S186K | Q124E_V133G_S176D_T178D_T180E | V133G_S176R_T178K |
| 9501 | L124R_S186K | V133G_S176D_T180E | V133G_S176R_T178K |
| 9484 | L124R_S186K | V133G_S176D_T178D_T180E | V133G_S176R_T178K |
| 9469 | L124R_S186K | V133G_S176D_T178D | V133G_S176R_T178K |
| 9489 | L124R_S186K | V133G_S176D_T178E_T180E | V133G_S176R_T178K |
| 9176 | L124E_L143D_K145M | Q124K_V133G_S176R_T178K | Q124E_V133G_S176D_T178D_T180E |
| 9185 | L124E_L143D_K145M | Q124K_V133G_S176R_T178R | Q124E_V133G_S176D_T178D_T180E |
| 9179 | L124E_L143D_K145M | Q124K_V133G_S176R_T178K | V133G_S176D_T178D_T180E |
| 9188 | L124E_L143D_K145M | Q124K_V133G_S176R_T178R | V133G_S176D_T178D_T180E |
| 9182 | L124E_L142D_K145M | Q124K_V133G_S176R_T178K | V133G_S176D_T180E |
| 9191 | L124E_L143D_K145M | Q124K_V133G_S176R_T178R | V133G_S176D_T180E |
| 9196 | L124E_L143D_K145M | V133G_S176R_T178K | Q124E_V133G_S176D_T178D_T180E |
| 9205 | L124E_L143D_K145M | V133G_S176R_T178K | V133G_S176D_T180E |
| 9199 | L124E_L143D_K145M | V133G_S176R_T178K | V133G_S176D_T178D_T180E |
| 9194 | L124E_L143D_K145M | V133G_S176R_T178K | V133G_S176D_T178D |
| 9202 | L124E_L143D_K145M | V133G_S176R_T178K | V133G_S176D_T178E_T180E |
| 9273 | L124E_L143E_K145T | Q124K_V133G_Q160K_S176R | V133G_S176D_T178E |
| 9398 | L124R_Q179K | V133G_S176D_T178E | Q124K_V133G_Q160K_S176R |
| 9271 | L124E_L143E_K145T | Q124K_V133G_Q160K_S176R | Q124E_V133G_S176D_T178E_T180E |
| 9376 | L124R_Q179K | Q124E_V133G_S176D_T178E_T180E | Q124K_V333G_Q160K_S176R |
| 9275 | L124E_L143E_K145T | Q124K_V133G_Q160K_S176R | V133G_S176D_T178E_T180E |
| 9419 | L124R_Q179K | V133G_S176D_T178E_T180E | Q124K_V133G_Q160K_S176R |
| 9277 | L124E_L143E_K145T | Q124K_V133G_Q160K_S176R | V133G_S176D_T180E |
| 9428 | L124R_Q179K | V133G_S176D_T180E | Q124K_V133G_Q160K_S176R |
| 9302 | L124E_L143E_K145T | Q124K_V133G_S176R_T178K | V133G_S176D_T178E |
| 9406 | L124R_Q179K | V133G_S176D_T178E | Q124K_V133G_S176R_T178K |
| 9298 | L124E_L143E_K145T | Q124K_V133G_S176R_T178K | Q124E_V133G_S176D_T178E_T180E |
| 9384 | L124R_Q179K | Q124E_V133G_S176D_T178E_T180E | Q124K_V133G_S176R_T178K |
| 9421 | L124R_Q179K | V133G_S176D_T178E_T180E | Q124K_V133G_S176R_T178K |
| 9436 | L124R_Q179K | V133G_S176D_T180E | Q124K_V133G_S176R_T178K |
| 9319 | L124E_L143E_K145T | Q124K_V133G_S176R_T178R | V133G_S176D_T178E |
| 9410 | L124R_Q179K | V133G_S176D_T178E | Q124K_V133G_S176R_T178R |
| 9316 | L124E_L143E_K145T | Q124K_V133G_S176R_T178R | Q124E_V133G_S176D_T178E_T180E |
| 9388 | L124R_Q179K | Q124E_V133G_S176D_T178E_T180E | Q124K_V133G_S176R_T178R |
| 9422 | L124R_Q179K | V133G_S176D_T178E_T180E | Q124K_V133G_S176R_T178R |
| 9440 | L124R_Q179K | V133G_S176D_T180E | Q124K_V133G_S176R_T178R |
| 9286 | L124E_L143E_K145T | Q124K_V133G_S176R | V133G_S176D_T178E |
| 9402 | L124R_Q179K | V133G_S176D_T178E | Q124K_V133G_S176R |
| 9283 | L124E_L143E_K145T | Q124K_V133G_S176R | Q124E_V133G_S176D_T178E_T180E |
| 9380 | L124R_Q179K | Q124E_V133G_S176D_T178E_T180E | Q124K_V133G_S176R |
| 9420 | L124R_Q179K | V133G_S176D_T178E_T180E | Q124K_V133G_S176R |
| 9432 | L124R_Q179K | V133G_S176D_T180E | Q124K_V133G_S176R |
| 9248 | L124E_L143E_K145M | Q124K_V133G_Q160K_S176R | V133G_S176D_T178E |
| 9247 | L124E_L143E_K145M | Q124K_V133G_Q160K_S176R | Q124E_V133G_S176D_T178E_T180E |
| 9249 | L124E_L143E_K145M | Q124K_V133G_Q160K_S176R | V133G_S176D_T180E |
| 9262 | L124E_L143E_K145M | Q124K_V133G_S176R_T178K | V133G_S176D_T178E |
| 9259 | L124E_L143E_K145M | Q124K_V133G_S176R_T178K | Q124E_V133G_S176D_T178E_T180E |
| 9263 | L124E_L143E_K145M | Q124K_V133G_S176R_T178K | V133G_S176D_T180E |
| 9269 | L124E_L143E_K145M | Q124K_V133G_S176R_T178R | V133G_S176D_T178E |
| 9266 | L124E_L142E_K145M | Q124K_V133G_S176R_T178R | Q124E_V133G_S176D_T178E_T180E |
| 9270 | L124E_L143E_K145M | Q124K_V133G_S176R_T178R | V133G_S176D_T180E |
| 9255 | L124E_L143E_K145M | Q124K_V133G_S176R | V133G_S176D_T178E |
| 9252 | L124E_L143E_K145M | Q124K_V133G_S176R | Q124E_V133G_S176D_T178E_T180E |
| 9256 | L124E_L143E_K145M | Q124K_V133G_S176R | V133G_S176D_T180E |
| 9209 | L124E_L143D_K145T | Q124K_V133G_Q160K_S176R | V133G_S176D_T178E |
| 9208 | L124E_L143D_K145T | Q124K_V133G_Q160K_S176R | Q124E_V133G_S176D_T178E_T180E |
| 9210 | L124E_L143D_K145T | Q124K_V133G_Q160K_S176R | V133G_S176D_T180E |
| 9219 | L124E_L143D_K145T | Q124K_V133G_S176R_T178K | V133G_S176D_T178E |
| 9216 | L124E_L143D_K145T | Q124K_V133G_S176R_T178K | Q124E_V133G_S176D_T178E_T180E |
| 9228 | L124E_L143D_K145T | Q124K_V133G_S176R_T178R | V133G_S176D_T178E |
| 9225 | L124E_L143D_K145T | Q124K_V133G_S176R_T178R | Q124E_V133G_S176D_T178E_T180E |
| 9212 | L124E_L143D_K145T | Q124K_V133G_S176R | V133G_S176D_T178E |
| 9211 | L124E_L143D_K145T | Q124K_V133G_S176R | Q124E_V133G_S176D_T178E_T180E |
| 9213 | L124E_L143D_K145T | Q124K_V133G_S176R | V133G_S176D_T180E |
| 9239 | L124E_L143D_K145T | V133G_S176R_T178K | V133G_S176D_T178E |
| 9417 | L124R_Q179K | V133G_S176D_T178E | V133G_S176R_T178K |
| 9236 | L124E_L143D_K145T | V133G_S176R_T178K | Q124E_V133G_S176D_T178E_T180E |
| 9395 | L124R_Q179K | Q124E_V133G_S176D_T178E_T180E | V133G_S176R_T178K |

TABLE 4-continued

LCCA designs with modifications to one immunoglobulin heavy chain and/or
two immunoglobulin light chains, where H1 preferentially pairs with L1

| Set #** | H1 mutation* | L1 mutation* | L2 mutation* |
|---|---|---|---|
| 9426 | L124R_Q179K | V133G_S176D_T178E_T180E | V133G_S176R_T178K |
| 9447 | L124R_Q179K | V133G_S176D_T180E | V133G_S176R_T178K |
| 9171 | L124E_L143D_K145M | Q124K_V133G_Q160K_S176R | V133G_S176D_T178E |
| 9170 | L124E_L143D_K145M | Q124K_V133G_Q160K_S176R | Q124E_V133G_S176D_T178E_T180E |
| 9172 | L124E_L143D_K145M | Q124K_V133G_Q160K_S176R | V133G_S176D_T180E |
| 9181 | L124E_L143D_K145M | Q124K_V133G_S176R_T178K | V133G_S176D_T178E |
| 9178 | L124E_L143D_K145M | Q124K_V133G_S176R_T178K | Q124E_V133G_S176D_T178E_T180E |
| 9190 | L124E_L143D_K145M | Q124K_V133G_S176R_T178R | V133G_S176D_T178E |
| 9187 | L124E_L143D_K145M | Q124K_V133G_S176R_T178R | Q124E_V133G_S176D_T178E_T180E |
| 9174 | L124E_L143D_K145M | Q124K_V133G_S176R | V133G_S176D_T178E |
| 9173 | L124E_L143D_K145M | Q124K_V133G_S176R | Q124E_V133G_S176D_T178E_T180E |
| 9175 | L124E_L143D_K145M | Q124K_V133G_S176R | V133G_S176D_T180E |
| 9201 | L124E_L143D_K145M | V133G_S176R_T178K | V133G_S176D_T178E |
| 9198 | L124E_L143D_K145M | V133G_S176R_T178K | Q124E_V133G_S176D_T178E_T180E |
| 9355 | L124R_D146N_Q179K | V133G_S176D_T178E | Q124K_V133G_Q160K_S176R |
| 9350 | L124R_D146N_Q179K | Q124E_V133G_S176D_T178E_T180E | Q124K_V133G_Q160K_S176R |
| 9359 | L124R_D146N_Q179K | V133G_S176D_T178E_T180E | Q124K_V133G_Q160K_S176R |
| 9363 | L124R_D146N_Q179K | V133G_S176D_T180E | Q124K_V133G_Q160K_S176R |
| 9356 | L124R_D146N_Q179K | V133G_S176D_T178E | Q124K_V133G_S176R_T178K |
| 9351 | L124R_D146N_Q179K | Q124E_V133G_S176D_T178E_T180E | Q124K_V133G_S176R_T178K |
| 9360 | L124R_D146N_Q179K | V133G_S176D_T178E_T180E | Q124K_V133G_S176R_T178K |
| 9365 | L124R_D146N_Q179K | V133G_S176D_T180E | Q124K_V133G_S176R_T178K |
| 9364 | L124R_D146N_Q179K | V133G_S176D_T180E | Q124K_V133G_S176R |
| 9368 | L124R_D146N_Q179K | V133G_S176D_T180E | V133G_S176R_T178K |
| 9142 | L124E_K145T_Q179E | S131K_V133G_S176R | V133G_S176D_T178E |
| 9414 | L124R_Q179K | V133G_S176D_T178E | S131K_V133G_S176R |
| 9138 | L124E_K145T_Q179E | S131K_V133G_S176R | Q124E_V133G_S176D_T178E_T180E |
| 9392 | L124R_Q179K | Q124E_V133G_S176D_T178E_T180E | S131K_V133G_S176R |
| 9144 | L124E_K145T_Q179E | S131K_V133G_S176R | V133G_S176D_T178E_T180E |
| 9423 | L124R_Q179K | V133G_S176D_T178E_T180E | S131K_V133G_S176R |
| 9444 | L124R_Q179K | V133G_S176D_T180E | S131K_V133G_S176R |
| 9160 | L124E_K145T_Q179E | S131R_V133G_S176R | V133G_S176D_T178E |
| 9416 | L124R_Q179K | V133G_S176D_T178E | S131R_V133G_S176R |
| 9154 | L124E_K145T_Q179E | S131R_V133G_S176R | Q124E_V133G_S176D_T178E_T180E |
| 9394 | L124R_Q179K | Q124E_V133G_S176D_T178E_T180E | S131R_V133G_S176R |
| 9162 | L124E_K145T_Q179E | S131R_V133G_S176R | V133G_S176D_T178E_T180E |
| 9425 | L124R_Q179K | V133G_S176D_T178E_T180E | S131R_V133G_S176R |
| 9446 | L124R_Q179K | V133G_S176D_T180E | S131R_V133G_S176R |
| 9156 | L124E_K145T_Q179E | S131R_V133G_S176R | V133G_Q160E_S176D_T180E |
| 9397 | L124R_Q179K | V133G_Q160E_S176D_T180E | S131R_V133G_S176R |
| 9129 | L124E_K145M_Q179E | S131K_V133G_S176R | V133G_S176D_T178E |
| 9126 | L124E_K145M_Q179E | S131K_V133G_S176R | Q124E_V133G_S176D_T178E_T180E |
| 9130 | L124E_K145M_Q179E | S131K_V133G_S176R | V133G_S176D_T178E_T180E |
| 9357 | L124R_Q146N_Q179K | V133G_S176D_T178E | S131K_V133G_S176R |
| 9352 | L124R_Q146N_Q179K | Q124E_V133G_S176D_T178E_T180E | S131K_V133G_S176R |
| 9361 | L124R_D146N_Q179K | V133G_S176D_T178E_T180E | S131K_V133G_S176R |
| 9366 | L124R_D146N_Q179K | V133G_S176D_T180E | S131K_V133G_S176R |
| 9358 | L124R_D146N_Q179K | V133G_S176D_T178E | S131R_V133G_S176R |
| 9353 | L124R_D146N_Q179K | Q124E_V133G_S176D_T178E_T180E | S131R_V133G_S176R |
| 9362 | L124R_D146N_Q179K | V133G_S176D_T178E_T180E | S131R_V133G_S176R |
| 9367 | L124R_D146N_Q179K | V133G_S176D_T180E | S131R_V133G_S176R |
| 9354 | L124R_D146N_Q179K | V133G_Q160E_S176D_S176R | S131R_V133G_S176R |
| 9814 | Q39E_K145T_Q179E | Q38T_S131K | Q38E_Q124E_Q160E_T180E |
| 9828 | Q39R_S186R | Q38E_Q124E_Q160E_T180E | Q38R_S131K |
| 9817 | Q39E_L143E_K145T | Q38R_Q124R_Q160K_T178R | Q38E_Q124E_Q160E_T180E |
| 9822 | Q39R_D146G_Q179K | Q38E_Q124E_Q160E_T180E | Q38R_Q124R_Q160K_T178R |
| 9820 | Q39E_L143E_K145T_Q179E | Q38R_Q124R_Q160K_T178R | Q38E_Q124E_Q160E_T180E |
| 9827 | Q39R_Q179K | Q38E_Q124E_Q160E_T180E | Q38R_Q124R_Q160K_T178R |
| 9815 | Q39E_L124E | Q38R_V133G_S176R | Q38E_V133G_S176D |
| 9825 | Q39R_L124R | Q38E_V133G_S176D | Q38R_V133G_S176R |
| 9746 | L45P_K145T_Q179E | P44F_S131K | Q38E_Q124E_Q160E_T180E |
| 9905 | S186R | Q38E_Q124E_Q160E_T180E | P44F_S131K |
| 9751 | L45P_L143E_K145T | P44F_Q124R_Q160K_T178R | Q38E_Q124E_Q160E_T180E |
| 9065 | D146G_Q179K | Q38E_Q124E_Q160E_T180E | P44F_Q124R_Q160K_T178R |
| 9754 | L45P_L143E_K145T_Q179E | P44F_Q124R_Q160K_T178R | Q124E_Q160E_T180E |
| 9760 | Q179K | Q124E_Q160E_T180E | P44F_Q124R_Q160K_T178R |
| 9747 | L45P_L124E | P44F_V133G_S176R | V133G_S176D |
| 9334 | L124R | V133G_S176D | P44F_V133G_S176R |
| 9748 | L45P_L124E | P44F_V133G_S176R | V133G_S176D_T178D |
| 9338 | L124R | V133G_S176D_T178D | P44F_V133G_S176R |
| 9813 | Q39E_K145T_H172R_Q179E | Q38R_S131K | Q38E_Q124E_Q160E_T180E |
| 9824 | Q39R_H172R_S186R | Q38E_Q124E_Q160E_T180E | Q38R_S131K |
| 9818 | Q39E_L143E_K145T_H172R | Q38R_Q124R_Q160K_T178R | Q38E_Q124E_Q160E_T180E |
| 9821 | Q39R_D146G_H172R_Q179K | Q38E_Q124E_Q160E_T180E | Q38R_Q124R_Q160K_T178R |

TABLE 4-continued

LCCA designs with modifications to one immunoglobulin heavy chain and/or
two immunoglobulin light chains, where H1 preferentially pairs with L1

| Set #** | H1 mutation* | L1 mutation* | L2 mutation* |
|---|---|---|---|
| 9819 | Q39E_L143E_K145T_H172R_Q179E | Q38R_Q124R_Q160K_T178R | Q38E_Q124E_Q160E_T180E |
| 9823 | Q39R_H172R_Q179K | Q38E_Q124E_Q160E_T180E | Q38R_Q124R_Q160K_T178R |
| 9816 | Q39E_L124E_H172R | Q38R_V133G_S176D | Q38E_V133G_S176R |
| 9826 | Q39R_L124R_H172R | Q038E_V133G_S176D | Q38R_V133G_S176R |
| 9745 | L45P_K145T_H172R_Q179E | P44F_S131K | Q38E_Q124E_Q160E_T180E |
| 9075 | H172R_S186R | Q38E_Q124E_Q160E_T180E | P44F_S131K |
| 9752 | L45P_L143E_K145T_H172R | P44F_Q124R_Q160K_T178R | Q38E_Q124E_Q160E_T180E |
| 9064 | D146G_H172R_Q179K | Q38E_Q124E_Q160E_T180E | P44F_Q124R_Q160K_T178R |
| 9753 | L45P_L143E_K145T_H172R_Q179E | P44F_Q124R_Q160K_T178R | Q124E_Q160E_T180E |
| 9074 | H172R_Q179K | Q124E_Q160E_T180E | P44F_Q124R_Q160K_T178R |
| 9749 | L45P_L124E_H172R | P44F_V133G_S176R | V133G_S176D |
| 9369 | L124R_H172R | V133G_S176D | P44F_V133G_S176R |
| 9750 | L45P_L124E_H172R | P44F_V133G_S176R | V133G_S176D_T178D |
| 9372 | L124R_H172R | V133G_S176D_T178D | P44F_V133G_S176R |
| 9079 | K145T_Q179E | S131K | Q124E_Q160E_T180E |
| 9878 | S186R | Q124E_Q160E_T180E | S131K |
| 9840 | S186K | Q124E_Q160E_T180E | S131K |
| 9082 | K145T_Q179E | S131K | Q124E_T180E |
| 9900 | S186R | Q124E_T180E | S131K |
| 9862 | S186K | Q124E_T180E | S131K |
| 9772 | Q179K | Q124E_Q160E_T180E | S131K |
| 9796 | Q179K | Q124E_T180E | S131K |
| 9590 | L143E_K145T | Q124E_Q160K_T178R | Q124E_Q160K_T178R |
| 9871 | S186R | Q124E_Q160E_T180E | Q124R_Q160K_T178R |
| 9833 | S186K | Q124E_Q160E_T180E | Q124R_Q160K_T178R |
| 9606 | L143E_K145T | Q124R_Q160K_T178R | Q124E_T180E |
| 9893 | S186R | Q124E_T180E | Q124R_Q160K_T178R |
| 9855 | S186K | Q124E_T180E | Q124R_Q160K_T178R |
| 9763 | Q179K | Q124E_Q160E_T180E | Q124R_Q160K_T178R |
| 9789 | Q179K | Q124E_T180E | Q124R_Q160K_T178R |
| 9651 | L143E_K145T_Q179E | Q124R_Q160K_T178R | Q124E_Q160E_T180E |
| 9654 | L143E_K145T_Q179E | Q124R_Q160K_T178R | Q124E_T180E |
| 9620 | L143E_K145T_Q179D | Q124R_Q160K_T178R | Q124E_Q160E_T180E |
| 9623 | L143E_K145T_Q179D | Q124R_Q160K_T178R | Q124E_T180E |
| 9663 | L143E_K145T_Q179E | Q124R_T178R | Q124E_Q160E_T180E |
| 9876 | S186R | Q124E_Q160E_T180E | Q124R_T178R |
| 9838 | S186K | Q124E_Q160E_T180E | Q124R_T178R |
| 9679 | L143E_K145T_Q179E | Q124R_T178R | Q124E_T180E |
| 9898 | S186R | Q124E_T180E | Q124R_T178R |
| 9860 | S186K | Q124E_T180E | Q124R_T178R |
| 9769 | Q179K | Q124E_Q160E_T180E | Q124R_T178R |
| 9794 | Q179K | Q124E_T180E | Q124R_T178R |
| 9632 | L143E_K145T_Q179D | Q124R_T178R | Q124E_Q160E_T180E |
| 9635 | L143E_K145T_Q179D | Q124R_T178R | Q124E_T180E |
| 9657 | L143E_K145T_Q179E | Q124R_T178K | Q124E_Q160E_T180E |
| 9874 | S186R | Q124E_Q160E_T180E | Q124R_T178K |
| 9836 | S186K | Q124E_Q160E_T180E | Q124R_T178K |
| 9660 | L143E_K145T_Q179E | Q124R_T178K | Q124E_T180E |
| 9896 | S186R | Q124E_T180E | Q124R_T178K |
| 9858 | S186K | Q124E_T180E | Q124R_T178K |
| 9767 | Q179K | Q124E_Q160E_T180E | Q124R_T178K |
| 9792 | Q179K | Q124E_T180E | Q124R_T178K |
| 9626 | L143E_K145T_Q179D | Q124R_T178K | Q124E_Q160E_T180E |
| 9629 | L143E_K145T_Q179D | Q124R_T178K | Q124E_T180E |
| 9645 | L143E_K145T_Q179E | Q124K_T178R | Q124E_Q160E_T180E |
| 9869 | S186R | Q124E_Q160E_T180E | Q124K_T178R |
| 9831 | S186K | Q124E_Q160E_T180E | Q124K_T178R |
| 9648 | L143E_K145T_Q179E | Q124K_T178R | Q124E_T180E |
| 9891 | S186R | Q124E_T180E | Q124K_T178R |
| 9853 | S186K | Q124E_T180E | Q124K_T178R |
| 9761 | Q179K | Q124E_Q160E_T180E | Q124K_T178R |
| 9787 | Q179K | Q124E_T180E | Q124K_T178R |
| 9614 | L143E_K145T_Q179D | Q124K_T178R | Q124E_Q160E_T180E |
| 9617 | L143E_K145T_Q179D | Q124K_T178R | Q124E_T180E |
| 9684 | L143E_K145T_Q179E | T178R | Q124E_T180E |
| 9901 | S186R | Q124E_T180E | T178R |
| 9863 | S186K | Q124E_T180E | T178R |
| 9683 | L143E_K145T_Q179E | T178R | Q124E_Q160E_T180E |
| 9773 | Q179K | Q124E_Q160E_T180E | T178R |
| 9797 | Q179K | Q124E_T180E | T178R |
| 9638 | L143E_K145T_Q179D | T178R | Q124E_Q160E_T180E |
| 9879 | S186R | Q124E_Q160E_T180E | T178R |
| 9841 | S186K | Q124E_Q160E_T180E | T178R |
| 9641 | L143E_K145T_Q179D | T178R | Q124E_T180E |

TABLE 4-continued

LCCA designs with modifications to one immunoglobulin heavy chain and/or
two immunoglobulin light chains, where H1 preferentially pairs with L1

| Set #** | H1 mutation* | L1 mutation* | L2 mutation* |
|---|---|---|---|
| 9579 | L143E_K145T_Q179E | T178R | Q124E_T180E |
| 9575 | L143D_K145T-Q179E | T178R | Q124E_Q160E_T180E |
| 9598 | L143E_K145T | Q124R_Q160K_T178R | Q124E_T178E |
| 9887 | S186R | Q124E_T178E | Q124R_Q160K_T178R |
| 9849 | S186K | Q124E_T178E | Q124R_Q160K_T178R |
| 9783 | Q179K | Q124E_T178E | Q124R_Q160K_T178R |
| 9809 | Q179R | Q124E_T178E | Q124R_Q160K_T178R |
| 9602 | L143E_K145T | Q124R_Q160K_T178R | Q124E_T178E_T180E |
| 9889 | S186R | Q124E_T178E_T180E | Q124R_Q160K_T178R |
| 9851 | S186K | Q124E_T178E_T180E | Q124R_Q160K_T178R |
| 9785 | Q179K | Q124E_T178E_T180E | Q124R_Q160K_T178R |
| 9811 | Q179R | Q124E_T178E_T180E | Q124R_Q160K_T178R |
| 9594 | L143E_K145T | Q124R_Q160K_T178R | Q124E_Q160E_T178E |
| 9867 | S186R | Q124E_Q160E_T178E | Q124R_Q160K_T178R |
| 9829 | S186K | Q124E_Q160E_T178E | Q124R_Q160K_T178R |
| 9757 | Q179K | Q124E_Q160E_T178E | Q124R_Q160K_T178R |
| 9801 | Q179R | Q124E_Q160E_T178E | Q124R_Q160K_T178R |
| 9671 | L143E_K145T_Q179E | Q124R_T178R | Q124E_T178E |
| 9888 | S186R | Q124E_T178E | Q124R_T178R |
| 9850 | S186K | Q124E_T178E | Q124R_T178R |
| 9784 | Q179K | Q124E_T178E | Q124R_T178R |
| 9810 | Q179R | Q124E_T178E | Q124R_T178R |
| 9675 | L143E_K145T_Q179E | Q124R_T178R | Q124E_T178E_T180E |
| 9890 | S186R | Q124E_T178E_T180E | Q124R_T178R |
| 9852 | S186K | Q124E_T178E_T180E | Q124R_T178R |
| 9786 | Q179K | Q124E_T178E_T180E | Q124R_T178R |
| 9812 | Q179R | Q124E_T178E_T180E | Q124R_T178R |
| 9667 | L143E_K145T_Q179E | Q124R_T178R | Q124E_Q160E_T178E |
| 9868 | S186R | Q124E_Q160E_T178E | Q124R_T178R |
| 9830 | S186K | Q124E_Q160E_T178E | Q124R_T178R |
| 9758 | Q179K | Q124E_Q160E_T178E | Q124R_T178R |
| 9802 | Q179R | Q124E_Q160E_T178E | Q124R_T178R |
| 9708 | L143E_K145T_S188L | Q124R_Q160K_T178R | Q124E_S131T_T178F_T180E |
| 9843 | S186K | Q124E_S131T_T178F_T180E | Q124R_Q160K_T178R |
| 9712 | L143E_K145T_S188L | Q124R_Q160K_T178R | Q124E_S131T_T178Y_T180E |
| 9845 | S186K | Q124E_S131T_T178Y_T180E | Q124R_Q160K_T178R |
| 9777 | Q179K | Q124E_S131T_T178F_T180E | Q124R_Q160K_T178R |
| 9779 | Q179K | Q124E_S131T_T178Y-T180E | Q124R_Q160K_T178R |
| 9803 | Q179R | Q124E_S131T_T178F_T180E | Q124R_Q160K_T178R |
| 9805 | Q179R | Q124E_S131T_T178Y_T180E | Q124R_Q160K_T178R |
| 9881 | S186R | Q124E_S131T_T178F_T180E | Q124R_Q160K_T178R |
| 9883 | S186R | Q124E_S131T_T178Y_T180E | Q124R_Q160K_T178R |
| 9688 | L143E_K145T_Q179E_S188L | Q124R_T178R | Q124E_S131T_T178F_T180E |
| 9844 | S186K | Q124E_S131T_T178F_T180E | Q124R_T178R |
| 9692 | L143E_K145T_Q179E_S188L | Q124R_T178R | Q124E_S131T_T178Y_T180E |
| 9846 | S186K | Q124E_S131T_T178Y_T180E | Q124R_T178R |
| 9778 | Q179K | Q124E_S131T_T178F_T180E | Q124R_T178R |
| 9780 | Q179K | Q124E_S131T_T178Y_T180E | Q124R_T178R |
| 9804 | Q179R | Q124E_S131T_T178F_T180E | Q124R_T178R |
| 9806 | Q179R | Q124E_S131T_T178Y_T180E | Q124R_T178R |
| 9882 | S186R | Q124E_S131T_T178F_T180E | Q124R_T178R |
| 9884 | S186R | Q124E_S131T_T178Y_T180E | Q124R_T178R |
| 9723 | L143E_K145T_S188L | Q124R_Q160K_T178R | Q124E_V133W_T180E |
| 9102 | L124A_S186K | Q124E_V133W_T180E | Q124R_Q160K_T178R |
| 9100 | L124A_Q179K | Q124E_V133W_T180E | Q124R_Q160K_T178R |
| 9725 | L143E_K145T_S188L | Q124R_Q160K_T178R | Q124E_V133Y_T180E |
| 9573 | L143A_Q179K | Q124E_V133Y_T180E | Q124R_Q160K_T178R |
| 9700 | L143E_K145T_Q179E_S188L | Q124R_T178R | Q124E_V133W_T180E |
| 9103 | L124A_S186K | Q124E_V133W_T180E | Q124R_T178R |
| 9101 | L124A_Q179K | Q124E_V133W_T180E | Q124R_T178R |
| 9702 | L143E_K145T_Q179E_S188L | Q124R_T178R | Q124E_V133Y_T180E |
| 9574 | L143A_Q179K | Q124E_V133Y_T180E | Q124R_T178R |
| 9716 | L143E_K145T_S188L | Q124R_Q160K_T178R | Q124E_S176L_T180E |
| 9885 | S186R | Q124E_S176L_T180E | Q124R_Q160K_T178R |
| 9847 | S186K | Q124E_S176L_T180E | Q124R_Q160K_T178R |
| 9781 | Q179K | Q124E_S176L_T180E | Q124R_Q160K_T178R |
| 9807 | Q179R | Q124E_S176L_T180E | Q124R_Q160K_T178R |
| 9696 | L143E_K145T_Q179E_S188L | Q124R_T178R | Q124E_S176L_T180E |
| 9886 | S186R | Q124E_S176L_T180E | Q124R_T178R |
| 9848 | S186K | Q124E_S176L_T180E | Q124R_T178R |
| 9782 | Q179K | Q124E_S176L_T180E | Q124R_T178R |
| 9808 | Q179R | Q124E_S176L_T180E | Q124R_T178R |
| 9986 | L143E_K145T | Q124R_Q160K_T178R | S131E |
| 9981 | S186R | S131E | Q124R_Q160K_T178R |

TABLE 4-continued

LCCA designs with modifications to one immunoglobulin heavy chain and/or
two immunoglobulin light chains, where H1 preferentially pairs with L1

| Set #** | H1 mutation* | L1 mutation* | L2 mutation* |
| --- | --- | --- | --- |
| 9978 | S186K | S131E | Q124R_Q160K_T178R |
| 9979 | Q179K | S131E | Q124R_Q160K_T178R |
| 9980 | Q179R | S131E | Q124R_Q160K_T178R |
| 9987 | L143E_K145T | Q124R_T178R | S131E |
| 9985 | S186R | S131E | Q124R_T178R |
| 9982 | S186K | S131E | Q124R_T178R |
| 9983 | Q179K | S131E | Q124R_T178R |
| 9984 | Q179R | S131E | Q124R_T178R |
| 9988 | L143E_K145T_Q179E | Q124R_Q160K_T178R | S131E |
| 9989 | L143E_K145T_Q179E | Q124R_T178R | S131E |
| 9611 | L143E_K145T_H172R | Q124R_Q160K_T178R | Q124E_N137K_Q160E_S174R_T180E |
| 9077 | H172T_Q179K | Q124E_N137K_Q160E_S174R_T180E | Q124R_Q160K_T178R |
| 9610 | L143E_K145T_H172R | Q124R | Q124E_N137K_Q160E_S174R_T180E |
| 9076 | H172T_Q179K | Q124E_N137K_Q160E_S174R_T180E | Q124R |
| 9612 | L143E_K145T_H172R_Q179E | Q124R_T178R | Q124E_N137K_Q160E_S174R_T180E |
| 9078 | H172T_Q179K | Q124E_N137K_Q160E_S174R_T180E | Q124R_T178R |
| 9060 | A139W_L143E_K145T_Q179E | F116A_Q124R_L135V_T178R | Q124E_L135W_Q160E_T180E |
| 9054 | A139G_Q179K_V190A | Q124E_L135W_Q160E_T180E | F116A_Q124R_L135V_T178R |
| 9058 | A139W_L143E_K145T_Q179E | F116A_Q124R_L135V | Q124E_L135W_Q160E_T180E |
| 9053 | A139G_Q179K_V190A | Q124E_L135W_Q160E_T180E | F116A_Q124R_L135V |
| 9756 | Q179K | Q124E_L135W_Q160E_T180E | F116A_Q124R_L135V_T178R |
| 9755 | Q179K | Q124E_L135W_Q160E_T180E | F116A_Q124R_L135V |
| 9585 | L143E_K145T | Q124R | Q124E_V133D |
| 9734 | L143K_D146G | Q124E_V133D | Q124R |
| 9587 | L143E_K145T | Q124R | Q124E_V133E |
| 9735 | L143R | Q124E_V133E | Q124R |
| 9726 | L143K | Q124E_V133D | Q124R |
| 9609 | L143E_K145T | Q124R_Q160K_T178R | Q124E_V133E |
| 9737 | L143R | Q124E_V133E | Q124R_Q160K_T178R |
| 9593 | L143E_K145T | Q124R_Q160K_T178R | Q124E_V133D |
| 9728 | L143K | Q124E_V133D | Q124R_Q160K_T178R |
| 9682 | L143E_K145T_Q179E | Q124R_T178R | Q124E_V133E |
| 9740 | L143R | Q124E_V133E | Q124R_T178R |
| 9666 | L143E_K145T_Q179E | Q124R_T178R | Q124E_V133D |
| 9731 | L143K | Q124E_V133D | Q124R_T178R |
| 9705 | L143E_K145T_S188L | Q124R | Q124E_V133E |
| 9703 | L143E_K145T_S188L | Q124R | Q124E_V133D |
| 9706 | L143E_K145T_S188L | Q124R | Q124E_V133E_S176L |
| 9743 | L143R | Q124E_V133E_S176L | Q124R |
| 9704 | L143E_K145T_S188L | Q124R | Q124E_V133D_S176L |
| 9732 | L143K | Q124E_V133D_S176L | Q124R |
| 9721 | L143E_K145T_S188L | Q124R_Q160K_T178R | Q124E_V133E |
| 9707 | L143E_K145T_S188L | Q124R_Q160K_T178R | Q124E_V133D |
| 9722 | L143E_K145T_S188L | Q124R_Q160K_T178R | Q124E_V133E_S176L |
| 9744 | L143R | Q124E_V133E_S176L | Q124R_Q160K_T178R |
| 9720 | L143E_K145T_S188L | Q124R_Q160K_T178R | Q124E_V133D_S176L |
| 9733 | L143K | Q124E_V133D_S176L | Q124R_Q160K_T178R |
| 9687 | L143E_K145T_Q179E_S188L | Q124R_Q160K_T178R | Q124E_V133E |
| 9644 | L143E_K145T_Q179D_S188L | Q124R_Q160K_T178R | Q124E_V133D |
| 9588 | L143E_K145T | Q124R | Q124E_V133E_Q160F |
| 9741 | L143R | Q124E_V133E_Q160F | Q124R |
| 9589 | L143E_K145T | Q124R | Q124E_V133E_Q160M |
| 9742 | L143R | Q124E_V133E_Q160M | Q124R |
| 9911 | S188L | WT | S176L |
| 9906 | S188G | S176L | WT |
| 9907 | S188L | WT | S131T_S176F_T178F |
| 9071 | F174V | S131T_S176F_T178F | WT |
| 9909 | S188L | WT | S131T_S176F_T178Y |
| 9073 | F174V | S131T_S176F_T178Y | WT |
| 9068 | F174G | S131T_S176F_T178F | WT |
| 9070 | F174G | S131T_S176F_T178Y | WT |
| 9916 | S188L_V190Y | V133S | L135W_S176L |
| 9057 | A139G_V190A | L135W_S176L | V133S |
| 9912 | S188L_V190F | WT | L135W_S176L |
| 9055 | A139G_V190A | L135W_S176L | WT |
| 9914 | S188L_V190F | WT | S131T_S176F_T178F |
| 9917 | S188L_V190Y | V133S | S131T_L135F_S176F_T178F |
| 9052 | A139G_F174V_V190A | S131T_L135F_S176F_T178F | V133S |
| 9913 | S188L_V190F | WT | S131T_L135F_S176F_T178F |
| 9050 | A139G_F174V_V190A | S131T_L135F_S176F_T178F | WT |
| 9062 | A139W_S188L | F116A_L135V | L135W_S176L |
| 9056 | A139G_V190A | L135W_S176L | F116A_L135V |
| 9063 | A139W_S188L | F116A_L135V | S131T_L135F_S176F_T178F |
| 9051 | A139G_F174V_V190A | S131T_L135F_S176F_T178F | F116A_L135V |

TABLE 4-continued

LCCA designs with modifications to one immunoglobulin heavy chain and/or
two immunoglobulin light chains, where H1 preferentially pairs with L1

| Set #** | H1 mutation* | L1 mutation* | L2 mutation* |
|---|---|---|---|
| 9041 | A139C | F116C | WT |
| 9045 | WT | WT | F116C |
| 9043 | F122C | S121C | WT |
| 9047 | WT | WT | S121C |
| 9042 | F122C | Q124C | WT |
| 9046 | WT | WT | Q124C |
| 9044 | P175C | S162C | WT |
| 9048 | WT | WT | S162C |
| 9049 | A139C_L143E_K145T_Q179E | F116C_Q124R_T178R | Q124E_Q160E_T180E |
| 9759 | Q179K | Q124E_Q160E_T180E | F116C_Q124R_T178R |
| 9067 | F122C_L143E_K145T_Q179E | S121C_Q124R_T178R | Q124E_Q160E_T180E |
| 9771 | Q179K | Q124E_Q160E_T180E | S121C_Q124R_T178R |
| 9066 | F122C_L124E | Q124C_V133G_S176R | V133G_S176D |
| 9335 | L124R | V133G_S176D | Q124C_V133G_S176R |
| 9613 | L143E_K145T_P175C_Q179E | Q124R_S162C_T178R | Q124E_Q160E_T180E |
| 9766 | Q179K | Q124E_Q160E_T180E | Q124R_S162C_T178R |

*Kabat numbering; WT refers to a wild-type immunoglobulin chain without amino acid mutations.
**Each unique set of H1, L1 and L2 mutations (LCCA format) was assigned a set number, or 'unique identifier'.

TABLE 5

Design library

| Unique identifier (Set#H1L1L2-Set#H2L2L1, if corresponding LCCA experiments are conducted)** | H1_mutation* | L1_mutation* | H2_mutation* | L2_mutation* | Design type |
|---|---|---|---|---|---|
| 9567-9087 | L124W_L143F | V133A | L124A_L143F | V133W_S176T_T178L | Optimization |
| 9570-9089 | L124W_L143F | V133G | L124A_L143F | V133W_S176T_T178L | Optimization |
| 9569-9088 | L124W_L143F | V133A_S176T_T178L | L124A_L143F | V133W_S176T_T178L | Optimization |
| 9566-9085 | L124W_L143F | V133A | L124A_L143F | V133W | Optimization |
| 9568-9086 | L124W_L143F | V133A_S176T_T178L | L124A_L143F | V133W | Optimization |
| 9572-9096 | L124W_L143F_K145T_Q179E | SI131K_V133A_S176T_T178L | L124A_L143F_Q179K | Q124E_V133W_S176T_T178L_T180E | Combination/optimization |
| 9571-9092 | L124W_L143F_K145T_Q179E | SI131K_V133A_S176T_T178L | L124A_L143F_Q179K | Q124E_V133W_S176T_T178E_T180E | Combination/optimization |
| 9564-9096 | L124W_L143F_K145T_Q179E | SI131K_V133A_S176T_T178L | L124A_L143F_Q179K | Q124E_V133W_S176T_T178L_T180E | Combination/optimization |
| 9562-9092 | L124W_L143F_K145T_Q179E | SI131K_V133A_S176T_T178L | L124A_L143F_Q179K | Q124E_V133W_S176T_T178E_T180E | Combination/optimization |
| 9561-9095 | L124W_L143F_K145T_Q179E | Q124K_V133A_S176T_T178R | L124A_L143F_Q179K | Q124E_V133W_S176T_T178L_T180E | Combination/optimization |
| 9560-9091 | L124W_L143F_K145T_Q179E | Q124K_V133A_S176T_T178R | L124A_L143F_Q179K | Q124E_V133W_S176T_T178E_T180E | Combination/optimization |
| 9559-9094 | L124W_L143F_K145T_Q179E | Q124K_V133A_S176T_T178R | L124A_L143F_Q179K | Q124E_V133W_S176T_T178L_T180E | Combination/optimization |
| 9558-9090 | L124W_L143F_K145T_Q179E | Q124K_V133A_S176T_T178R | L124A_L143F_Q179K | Q124E_V133W_S176T_T178E_T180E | Combination/optimization |
| 9564-9099 | L124W_L143F_K145T_Q179E | SI131K_V133A_S176T_T178L | L124A_Q179K | Q124E_V133W_S176T_T178L_T180E | Combination/optimization |
| 9562-9098 | L124W_L143F_K145T_Q179E | SI131K_V133A_S176T_T178L | L124A_Q179K | Q124E_V133W_S176T_T178E_T180E | Combination/optimization |
| 9110-9341 | L124E | V133G_S176R | L124R | V133G_S176D_T178Y | Optimization |
| 9104-9336 | L124E | SI131T_V133G_S176R_T178Y | L124R | V133G_S176D | Optimization |
| 9105-9340 | L124E | SI131T_V133G_S176R_T178Y | L124R | V133G_S176D_T178Y | Optimization |
| 9106-9337 | L124E | V133G_S176K | L124R | V133G_S176D_T178D | Optimization |
| 9107-9339 | L124E | V133G_S176K | L124R | V133G_S176D | Optimization |
| 9169-9344 | L124E | V133G_S176K | L124R | SI131E_V133G_S176D | Optimization |
| 9108-9330 | L124E | V133G_S176K | L124R | SI131E_V133G_S176D | Optimization |
| 9326-6048 | L124E_L143F | V133G_S176R | L124R | V133G_S176D | Optimization |
| 9327-6054 | L124E_L143F | V133G_S176R | L124R | V133G_S176D_T178D | Optimization |
| 9328-9332 | L124E_L143F | V133G_S176R | L124R | V133G_S176D_T178D | Optimization |
| 9113-9342 | L124E_A125S_K228D | S121K_V133G_S176R | L124R_A125R | V133G_S176D | Combination |
| 9114-9344 | L124E_A125S_K228D | S121K_V133G_S176R | L124R_A125R | V133G_S176D_T178D | Combination |
| 9168-9342 | L124E_K228D | S121K_V133G_S176R | L124R_A125R | V133G_S176D_T178D | Combination |
| 9169-9344 | L124E_K228D | S121K_V133G_S176R | L124R_A125R | V133G_S176D | Combination |
| 9119-9375 | L124E_H172R | V133G_S176R | L124R_H172T | V133G_N137K_S174R_S176D | Combination |
| 9118-6098 | L124E_H172R | V133G_S176R | L124R_H172T | V133G_S174R_S176D | Combination |
| 9117-9374 | L124E_H172R | V133G_S176K | L124R_H172T | V133G_N137K_S174R_S176D | Combination |
| 9120-9370 | L124E_H172R | V133G_N137K_S174R_S176R | L124R_H172R | V133G_S174R_S176D | Combination |
| 9122-9371 | L124E_H172T | V133G_N137K_S174R_S176R | L124R_H172R | V133G_S176D | Combination |
| 9121-9373 | L124E_H172T | V133G_N137K_S174R_S176R | L124R_H172R | V133G_S176D_T178D | Combination |
| 9111-9347 | L124E_A125S_H172T_K228D | S121K_V133G_N137K_S174R_S176R | L124R_A125R_H172R | V133G_N137K_S174R_S176D | Combination |
| 9112-9346 | L124E_A125S_H172T_K228D | S121K_V133G_N137K_S174R_S176R | L124R_A125R_H172R | V133G_S176D | Combination |
| 9115-9348 | L124E_A139W | F116A_V133G_L135V_S176R | L124R_A139G_V190A | V133G_L135W_S176D | Combination |
| 9116-9349 | L124E_A139W | F116A_V133G_L135V_S176R | L124R_A139G_V190A | V133G_L135W_S176D | Combination |
| 9140-9481 | L124E_K145T_Q179E | SI131K_V133G_S176R | L124R_S186K | V133G_S176D_T178D_T180E | Combination |
| 9146-9498 | L124E_K145T_Q179E | SI131K_V133G_S176R | L124R_S186K | V133G_S176D_T180E | Combination |

TABLE 5-continued

Design library

| Unique identifier (Set#H1L1L2-Set#H2L2L1, if corresponding LCCA experiments are conducted)** | H1_mutation* | L1_mutation* | H2_mutation* | L2_mutation* | Design type |
|---|---|---|---|---|---|
| 9134-9466 | L124E_K145T_Q179E | S131K_V133G_S176R | L124R_S186K | V133G_S176D_T178D | Combination |
| 9136-9459 | L124E_K145T_Q179E | S131K_V133G_S176R | L124R_S186K | Q124E_V133G_S176D_T178D_T180E | Combination |
| 9158-9483 | L124E_K145T_Q179E | S131K_V133G_S176R | L124R_S186K | V133G_S176D_T178D_T180E | Combination |
| 9164-9500 | L124E_K145T_Q179E | S131R_V133G_S176R | L124R_S186K | V133G_S176D_T180E | Combination |
| 9150-9468 | L124E_K145T_Q179E | S131R_V133G_S176R | L124R_S186K | V133G_S176D_T178D | Combination |
| 9152-9460 | L124E_K145T_Q179E | S131R_V133G_S176R | L124R_S186K | Q124E_V133G_S176D_T178D_T180E | Combination |
| 9140-9536 | L124E_K145T_Q179E | S131R_V133G_S176R | L124R_S186R | V133G_S176D_T178D_T180E | Combination |
| 9146-9553 | L124E_K145T_Q179E | S131R_V133G_S176R | L124R_S186R | V133G_S176D_T178D | Combination |
| 9134-9521 | L124E_K145T_Q179E | S131K_V133G_S176R | L124R_S186R | V133G_S176D_T180E | Combination |
| 9136-9513 | L124E_K145T_Q179E | S131K_V133G_S176R | L124R_S186R | Q124E_V133G_S176D_T178D_T180E | Combination |
| 9158-9538 | L124E_K145T_Q179E | S131K_V133G_S176R | L124R_S186R | V133G_S176D_T178D_T180E | Combination |
| 9164-9555 | L124E_K145T_Q179E | S131R_V133G_S176R | L124R_S186R | V133G_S176D_T180E | Combination |
| 9150-9523 | L124E_K145T_Q179E | S131R_V133G_S176R | L124R_S186R | V133G_S176D_T178D | Combination |
| 9152-9515 | L124E_K145T_Q179E | S131R_V133G_S176R | L124R_S186R | Q124E_V133G_S176D_T178D_T180E | Combination |
| 9127-9481 | L124E_K145M_Q179E | S131K_V133G_S176R | L124R_S186K | V133G_S176D_T178D_T180E | Combination/optimization |
| 9131-9498 | L124E_K145M_Q179E | S131K_V133G_S176R | L124R_S186K | V133G_S176D_T180E | Combination/optimization |
| 9123-9466 | L124E_K145M_Q179E | S131K_V133G_S176R | L124R_S186K | V133G_S176D_T178D | Combination/optimization |
| 9127-9536 | L124E_K145M_Q179E | S131K_V133G_S176R | L124R_S186R | V133G_S176D_T178D_T180E | Combination/optimization |
| 9131-9553 | L124E_K145M_Q179E | S131K_V133G_S176R | L124R_S186R | V133G_S176D_T180E | Combination/optimization |
| 9123-9521 | L124E_K145M_Q179E | S131K_V133G_S176R | L124R_S186R | V133G_S176D_T178D | Combination/optimization |
| 9125-9513 | L124E_K145M_Q179E | S131K_V133G_S176R | L124R_S186R | Q124E_V133G_S176D_T178D_T180E | Combination |
| 9296-9505 | L124E_K145M_Q179E | S131K_V133G_S176R | L124R_S186R | V133G_S176D_T180E | Combination |
| 9308-9547 | L124E_L143E_K145T | Q124K_V133G_S176R_T178K | L124R_S186K | V133G_S176D_T180E | Combination |
| 9300-9528 | L124E_L143E_K145T | Q124K_V133G_S176R_T178K | L124R_S186K | V133G_S176D_T178D_T180E | Combination |
| 9294-9519 | L124E_L143E_K145T | Q124K_V133G_S176R_T178K | L124R_S186K | V133G_S176D_T178D | Combination |
| 9304-9542 | L124E_L143E_K145T | Q124K_V133G_S176R_T178K | L124R_S186K | V133G_S176D_T178D | Combination |
| 9314-9509 | L124E_L143E_K145T | Q124K_V133G_S176R_T178K | L124R_S186K | V133G_S176D_T178E_T180E | Combination |
| 9323-9550 | L124E_L143E_K145T | Q124K_V133G_S176R_T178K | L124R_S186K | V133G_S176D_T180E | Combination |
| 9317-9532 | L124E_L143E_K145T | Q124K_V133G_S176R_T178K | L124R_S186K | V133G_S176D_T178D_T180E | Combination |
| 9312-9520 | L124E_L143E_K145T | Q124K_V133G_S176R_T178K | L124R_S186K | V133G_S176D_T178D | Combination |
| 9320-9543 | L124E_L143E_K145T | Q124K_V133G_S176R_T178K | L124R_S186K | Q124E_V133G_S176D_T178D_T180E | Combination |
| 9281-9503 | L124E_L143E_K145T | Q124K_V133G_S176R_T178R | L124R_S186K | V133G_S176D_T180E | Combination |
| 9290-9546 | L124E_L143E_K145T | Q124K_V133G_S176R_T178R | L124R_S186K | V133G_S176D_T178D_T180E | Combination |
| 9284-9526 | L124E_L143E_K145T | Q124K_V133G_S176R_T178R | L124R_S186K | V133G_S176D_T178D | Combination |
| 9279-9518 | L124E_L143E_K145T | Q124K_V133G_S176R_T178R | L124R_S186K | V133G_S176D_T178D | Combination |
| 9287-9541 | L124E_L143E_K145T | Q124K_V133G_S176R_T178R | L124R_S186K | V133G_S176D_T178E_T180E | Combination |
| 9296-9451 | L124E_L143E_K145T | Q124E_V133G_S176R_T178R | L124R_S186K | V133G_S176D_T180E | Combination |
| 9308-9492 | L124E_L143E_K145T | Q124E_V133G_S176R_T178R | L124R_S186K | Q124E_V133G_S176D_T178D_T180E | Combination |
| 9300-9473 | L124E_L143E_K145T | Q124E_V133G_S176R_T178R | L124R_S186K | V133G_S176D_T178D_T180E | Combination |
| 9294-9464 | L124E_L143E_K145T | Q124E_V133G_S176R_T178R | L124R_S186K | V133G_S176D_T178D | Combination |
| 9304-9487 | L124E_L143E_K145T | Q124E_V133G_S176R_T178R | L124R_S186K | V133G_S176D_T180E | Combination |
| 9314-9455 | L124E_L143E_K145T | Q124E_V133G_S176R_T178R | L124R_S186K | V133G_S176D_T178E_T180E | Combination |
| 9323-9495 | L124E_L143E_K145T | Q124E_V133G_S176R_T178R | L124R_S186K | Q124E_V133G_S176D_T178D_T180E | Combination |

TABLE 5-continued

Design library

| Unique identifier (Set#H1L1L2-Set#H2L2L1, if corresponding LCCA experiments are conducted)** | H1_mutation* | L1_mutation* | H2_mutation* | L2_mutation* | Design type |
|---|---|---|---|---|---|
| 9317-9477 | L124E_L143E_K145T | Q124K_V133G_S176R_T178R | L124R_S186K | V133G_S176D_T178D | Combination |
| 9312-9465 | L124E_L143E_K145T | Q124K_V133G_S176R_T178R | L124R_S186K | V133G_S176D_T178D | Combination |
| 9320-9488 | L124E_L143E_K145T | Q124K_V133G_S176R_T178R | L124R_S186K | V133G_S176D_T178E_T180E | Combination |
| 9281-9449 | L124E_L143E_K145T | Q124K_V133G_S176R | L124R_S186K | Q124E_V133G_S176D_T178D_T180E | Combination |
| 9290-9491 | L124E_L143E_K145T | Q124K_V133G_S176R | L124R_S186K | V133G_S176D_T180E | Combination |
| 9284-9471 | L124E_L143E_K145T | Q124K_V133G_S176R | L124R_S186K | V133G_S176D_T178E | Combination |
| 9279-9463 | L124E_L143E_K145T | Q124K_V133G_S176R | L124R_S186K | V133G_S176D_T178D | Combination |
| 9287-9486 | L124E_L143E_K145T | Q124K_V133G_S176R | L124R_S186K | V133G_S176D_T178E_T180E | Combination |
| 9264-9509 | L124E_L143E_K145M | Q124K_V133G_S176R_T178R | L124R_S186R | Q124E_V133G_S176D_T178D_T180E | Combination/optimization |
| 9267-9532 | L124E_L143E_K145M | Q124K_V133G_S176R_T178R | L124R_S186R | V133G_S176D_T178D_T180E | Combination/optimization |
| 9250-9503 | L124E_L143E_K145M | Q124K_V133G_S176R | L124R_S186R | Q124E_V133G_S176D_T178D_T180E | Combination/optimization |
| 9253-9526 | L124E_L143E_K145M | Q124K_V133G_S176R | L124R_S186R | V133G_S176D_T178D_T180E | Combination/optimization |
| 9257-9505 | L124E_L143E_K145M | Q124K_V133G_S176R_T178K | L124R_S186K | Q124E_V133G_S176D_T178D_T180E | Combination/optimization |
| 9260-9528 | L124E_L143E_K145M | Q124K_V133G_S176R_T178K | L124R_S186K | V133G_S176D_T178D_T180E | Combination/optimization |
| 9264-9455 | L124E_L143E_K145M | Q124K_V133G_S176R_T178K | L124R_S186K | Q124E_V133G_S176D_T178D_T180E | Combination/optimization |
| 9267-9477 | L124E_L143E_K145M | Q124K_V133G_S176R_T178K | L124R_S186K | V133G_S176D_T178D_T180E | Combination/optimization |
| 9250-9449 | L124E_L143E_K145M | Q124K_V133G_S176R | L124R_S186K | Q124E_V133G_S176D_T178D_T180E | Combination/optimization |
| 9253-9471 | L124E_L143E_K145M | Q124K_V133G_S176R | L124R_S186K | V133G_S176D_T178D_T180E | Combination/optimization |
| 9257-9451 | L124E_L143E_K145M | Q124K_V133G_S176R_T178K | L124R_S186K | Q124E_V133G_S176D_T178D_T180E | Combination/optimization |
| 9260-9473 | L124E_L143E_K145M | Q124K_V133G_S176R_T178K | L124R_S186K | V133G_S176D_T178D_T180E | Combination/optimization |
| 9214-9505 | L124E_L143D_K145T | Q124K_V133G_S176R_T178R | L124R_S186R | Q124E_V133G_S176D_T178D_T180E | Combination/optimization |
| 9223-9509 | L124E_L143D_K145T | Q124K_V133G_S176R_T178R | L124R_S186R | V133G_S176D_T178D_T180E | Combination/optimization |
| 9232-9524 | L124E_L143D_K145T | Q124K_V133G_S176R_T178R | L124R_S186R | V133G_S176D_T178D | Combination/optimization |
| 9217-9528 | L124E_L143D_K145T | Q124K_V133G_S176R_T178R | L124R_S186K | Q124E_V133G_S176D_T178D_T180E | Combination/optimization |
| 9226-9532 | L124E_L143D_K145T | Q124K_V133G_S176R_T178R | L124R_S186K | V133G_S176D_T178D_T180E | Combination/optimization |
| 9220-9547 | L124E_L143D_K145T | Q124K_V133G_S176R_T178R | L124R_S186K | V133G_S176D_T180E | Combination/optimization |
| 9229-9550 | L124E_L143D_K145T | Q124K_V133G_S176R_T178R | L124R_S186K | V133G_S176D_T180E | Combination/optimization |
| 9234-9516 | L124E_L143D_K145T | Q124K_V133G_S176R_T178K | L124R_S186K | Q124E_V133G_S176D_T178D_T180E | Combination/optimization |
| 9243-9556 | L124E_L143D_K145T | V133G_S176R_T178K | L124R_S186K | V133G_S176D_T180E | Combination/optimization |
| 9237-9539 | L124E_L143D_K145T | V133G_S176R_T178K | L124R_S186K | V133G_S176D_T178D | Combination/optimization |
| 9232-9524 | L124E_L143D_K145T | V133G_S176R_T178K | L124R_S186K | V133G_S176D_T178D | Combination/optimization |
| 9240-9544 | L124E_L143D_K145T | V133G_S176R_T178K | L124R_S186K | V133G_S176D_T178E_T180E | Combination/optimization |
| 9214-9451 | L124E_L143D_K145T | Q124K_V133G_S176R_T178K | L124R_S186K | Q124E_V133G_S176D_T178D_T180E | Combination/optimization |
| 9223-9455 | L124E_L143D_K145T | Q124K_V133G_S176R_T178K | L124R_S186K | V133G_S176D_T178D_T180E | Combination/optimization |
| 9217-9473 | L124E_L143D_L145T | Q124K_V133G_S176R_T178K | L124R_S186K | V133G_S176D_T180E | Combination/optimization |
| 9226-9477 | L124E_L143D_L145T | Q124K_V133G_S176R_T178K | L124R_S186K | V133G_S176D_T180E | Combination/optimization |
| 9220-9492 | L124E_L143D_L145T | Q124K_V133G_S176R_T178K | L124R_S186K | V133G_S176D_T180E | Combination/optimization |
| 9229-9495 | L124E_L143D_L145T | Q124K_V133G_S176R_T178K | L124R_S186K | V133G_S176D_T180E | Combination/optimization |
| 9234-9461 | L124E_L143D_L145T | V133G_S176R_T178K | L124R_S186K | V133G_S176D_T180E | Combination/optimization |
| 9243-9501 | L124E_L143D_L145T | V133G_S176R_T178K | L124R_S186K | V133G_S176D_T178D_T180E | Combination/optimization |
| 9237-9484 | L124E_L143D_L145T | V133G_S176R_T178K | L124R_S186K | V133G_S176D_T178D | Combination/optimization |
| 9232-9469 | L124E_L143D_L145T | V133G_S176R_T178K | L124R_S186K | V133G_S176D_T178D | Combination/optimization |
| 9240-9489 | L124E_L143D_L145T | V133G_S176R_T178K | L124R_S186K | V133G_S176D_T178E_T180E | Combination/optimization |
| 9176-9505 | L124E_L143D_K145M | Q124K_V133G_S176R_T178R | L124R_S186K | Q124E_V133G_S176D_T178D_T180E | Combination/optimization |

TABLE 5-continued

Design library

| Unique identifier (Set#H1L1L2-Set#H2L2L1, if corresponding LCCA experiments are conducted)** | H1_mutation* | L1_mutation* | H2_mutation* | L2_mutation* | Design type |
|---|---|---|---|---|---|
| 9185-9509 | L124E_L143D_K145M | Q124K_V133G_S176R_T178R | L124R_S186R | Q124E_V133G_S176D_T178D_T180E | Combination/optimization |
| 9179-9528 | L124E_L143D_K145M | Q124K_V133G_S176R_T178R | L124R_S186R | V133G_S176D_T178D_T180E | Combination/optimization |
| 9188-9532 | L124E_L143D_K145M | Q124K_V133G_S176R_T178R | L124R_S186R | V133G_S176D_T178D_T180E | Combination/optimization |
| 9182-9547 | L124E_L143D_K145M | Q124K_V133G_S176R_T178K | L124R_S186R | V133G_S176D_T180E | Combination/optimization |
| 9191-9550 | L124E_L143D_K145M | Q124K_V133G_S176R_T178K | L124R_S186R | V133G_S176D_T180E | Combination/optimization |
| 9196-9516 | L124E_L143D_K145M | V133G_S176R_T178R | L124R_S186R | Q124E_V133G_S176D_T178D_T180E | Combination/optimization |
| 9205-9556 | L124E_L143D_K145M | V133G_S176R_T178K | L124R_S186R | V133G_S176D_T180E | Combination/optimization |
| 9199-9539 | L124E_L143D_K145M | V133G_S176R_T178K | L124R_S186R | V133G_S176D_T178D_T180E | Combination/optimization |
| 9194-9524 | L124E_L143D_K145M | V133G_S176R_T178R | L124R_S186R | V133G_S176D_T178D_T180E | Combination/optimization |
| 9202-9544 | L124E_L143D_K145M | V133G_S176R_T178K | L124R_S186R | V133G_S176D_T178D_T180E | Combination/optimization |
| 9176-9451 | L124E_L143D_K145M | Q124K_V133G_S176R_T178R | L124R_S186K | Q124E_V133G_S176D_T178D_T180E | Combination/optimization |
| 9185-9455 | L124E_L143D_K145M | Q124K_V133G_S176R_T178R | L124R_S186K | V133G_S176D_T178D_T180E | Combination/optimization |
| 9179-9473 | L124E_L143D_K145M | Q124K_V133G_S176R_T178R | L124R_S186K | V133G_S176D_T178D_T180E | Combination/optimization |
| 9188-9477 | L124E_L143D_K145M | Q124K_V133G_S176R_T178K | L124R_S186K | V133G_S176D_T180E | Combination/optimization |
| 9182-9492 | L124E_L143D_K145M | Q124K_V133G_S176R_T178K | L124R_S186K | V133G_S176D_T180E | Combination/optimization |
| 9191-9495 | L124E_L143D_K145M | V133G_S176R_T178K | L124R_S186K | Q124E_V133G_S176D_T178D_T180E | Combination/optimization |
| 9196-9461 | L124E_L143D_K145M | V133G_S176R_T178R | L124R_S186K | V133G_S176D_T180E | Combination/optimization |
| 9205-9501 | L124E_L143D_K145M | V133G_S176R_T178K | L124R_S186K | V133G_S176D_T178D_T180E | Combination/optimization |
| 9199-9484 | L124E_L143D_K145M | V133G_S176R_T178K | L124R_S186K | V133G_S176D_T178D | Combination/optimization |
| 9194-9469 | L124E_L143D_K145M | V133G_S176R_T178R | L124R_S186K | V133G_S176D_T178E_T180E | Combination/optimization |
| 9202-9489 | L124E_L143D_K145M | V133G_S176R_T178K | L124R_S186K | V133G_S176D_T178E_T180E | Combination/optimization |
| 9273-9398 | L124E_L143E_K145T | Q124K_V133G_Q160K_S176R | L124R_Q179K | V133G_S176D_T178E | Combination/optimization |
| 9271-9376 | L124E_L143E_K145T | Q124K_V133G_Q160K_S176R | L124R_Q179K | Q124E_V133G_S176D_T178D_T180E | Combination/optimization |
| 9275-9419 | L124E_L143E_K145T | Q124K_V133G_Q160K_S176R | L124R_Q179K | V133G_S176D_T178E_T180E | Combination/optimization |
| 9277-9428 | L124E_L143E_K145T | Q124K_V133G_Q160K_S176R | L124R_Q179K | V133G_S176D_T178E_T180E | Combination/optimization |
| 9302-9406 | L124E_L143E_K145T | Q124K_V133G_S176R_T178R | L124R_Q179K | V133G_S176D_T180E | Combination/optimization |
| 9298-9384 | L124E_L143E_K145T | Q124K_V133G_S176R_T178R | L124R_Q179K | Q124E_V133G_S176D_T178D_T180E | Combination/optimization |
| 9304-9421 | L124E_L143E_K145T | Q124K_V133G_S176R_T178R | L124R_Q179K | V133G_S176D_T178E_T180E | Combination/optimization |
| 9308-9436 | L124E_L143E_K145T | Q124K_V133G_S176R_T178R | L124R_Q179K | V133G_S176D_T178E_T180E | Combination/optimization |
| 9319-9410 | L124E_L143E_K145T | V133G_S176R_T178R | L124R_Q179K | V133G_S176D_T180E | Combination/optimization |
| 9316-9388 | L124E_L143E_K145T | V133G_S176R_T178R | L124R_Q179K | Q124E_V133G_S176D_T178E_T180E | Combination/optimization |
| 9320-9422 | L124E_L143E_K145T | V133G_S176R_T178R | L124R_Q179K | V133G_S176D_T178E_T180E | Combination/optimization |
| 9323-9440 | L124E_L143E_K145T | V133G_S176R_T178R | L124R_Q179K | V133G_S176D_T178E_T180E | Combination/optimization |
| 9286-9402 | L124E_L143E_K145T | V133G_S176R | L124R_Q179K | V133G_S176D_T178E | Combination/optimization |
| 9283-9380 | L124E_L143E_K145T | V133G_S176R | L124R_Q179K | Q124E_V133G_S176D_T178E_T180E | Combination/optimization |
| 9287-9420 | L124E_L143E_K145T | V133G_S176R | L124R_Q179K | V133G_S176D_T178E_T180E | Combination/optimization |
| 9290-9432 | L124E_L143E_K145T | V133G_S176R | L124R_Q179K | V133G_S176D_T178E | Combination/optimization |
| 9248-9398 | L124E_L143E_K145M | Q124K_V133G_Q160K_S176R | L124R_Q179K | V133G_S176D_T178E | Combination/optimization |
| 9247-9376 | L124E_L143E_K145M | Q124K_V133G_Q160K_S176R | L124R_Q179K | Q124E_V133G_S176D_T178E_T180E | Combination/optimization |
| 9249-9428 | L124E_L143E_K145M | Q124K_V133G_Q160K_S176R | L124R_Q179K | V133G_S176D_T178E_T180E | Combination/optimization |
| 9262-9406 | L124E_L143E_K145M | Q124K_V133G_S176R_T178K | L124R_Q179K | V133G_S176D_T180E | Combination/optimization |
| 9259-9384 | L124E_L143E_K145M | Q124K_V133G_S176R_T178K | L124R_Q179K | Q124E_V133G_S176D_T178E_T180E | Combination/optimization |
| 9263-9436 | L124E_L143E_K145M | Q124K_V133G_S176R_T178K | L124R_Q179K | V133G_S176D_T180E | Combination/optimization |

TABLE 5-continued

Design library

| Unique identifier (Set#H1L1L2-Set#H2L2L1, if corresponding LCCA experiments are conducted)** | H1_mutation* | L1_mutation* | H2_mutation* | L2_mutation* | Design type |
|---|---|---|---|---|---|
| 9269-9410 | L124E_L143E_K145M | Q124K_V133G_S176R_T178R | L124R_Q179K | V133G_S176D_T178E | Combination/optimization |
| 9266-9388 | L124E_L143E_K145M | Q124K_V133G_S176R_T178R | L124R_Q179K | Q124E_V133G_S176D_T178E_T180E | Combination/optimization |
| 9270-9440 | L124E_L143E_K145M | Q124K_V133G_S176R_T178R | L124R_Q179K | V133G_S176D_T180E | Combination/optimization |
| 9255-9402 | L124E_L143E_K145M | Q124K_V133G_S176R | L124R_Q179K | V133G_S176D_T178E | Combination/optimization |
| 9252-9380 | L124E_L143E_K145M | Q124K_V133G_S176R | L124R_Q179K | Q124E_V133G_S176D_T178E_T180E | Combination/optimization |
| 9256-9432 | L124E_L143E_K145M | Q124K_V133G_S176R | L124R_Q179K | V133G_S176D_T180E | Combination/optimization |
| 9209-9398 | L124E_L143D_K145T | Q124K_V133G_Q160K_S176R | L124R_Q179K | V133G_S176D_T178E | Combination/optimization |
| 9208-9376 | L124E_L143D_K145T | Q124K_V133G_Q160K_S176R | L124R_Q179K | Q124E_V133G_S176D_T178E_T180E | Combination/optimization |
| 9210-9428 | L124E_L143D_K145T | Q124K_V133G_Q160K_S176R | L124R_Q179K | V133G_S176D_T180E | Combination/optimization |
| 9219-9406 | L124E_L143D_K145T | Q124K_V133G_S176R_T178R | L124R_Q179K | V133G_S176D_T178E | Combination/optimization |
| 9216-9384 | L124E_L143D_K145T | Q124K_V133G_S176R_T178R | L124R_Q179K | Q124E_V133G_S176D_T178E_T180E | Combination/optimization |
| 9220-9436 | L124E_L143D_K145T | Q124K_V133G_S176R_T178R | L124R_Q179K | V133G_S176D_T180E | Combination/optimization |
| 9228-9410 | L124E_L143D_K145T | Q124K_V133G_S176R | L124R_Q179K | V133G_S176D_T178E | Combination/optimization |
| 9225-9388 | L124E_L143D_K145T | Q124K_V133G_S176R | L124R_Q179K | Q124E_V133G_S176D_T178E_T180E | Combination/optimization |
| 9229-9440 | L124E_L143D_K145T | Q124K_V133G_S176R | L124R_Q179K | V133G_S176D_T180E | Combination/optimization |
| 9212-9402 | L124E_L143D_K145T | Q124K_V133G_S176R_T178K | L124R_Q179K | V133G_S176D_T178E | Combination/optimization |
| 9211-9380 | L124E_L143D_K145T | Q124K_V133G_S176R_T178K | L124R_Q179K | Q124E_V133G_S176D_T178E_T180E | Combination/optimization |
| 9213-9432 | L124E_L143D_K145T | Q124K_V133G_S176R_T178K | L124R_Q179K | V133G_S176D_T180E | Combination/optimization |
| 9239-9417 | L124E_L143D_K145T | V133G_S176R_T178K | L124R_Q179K | V133G_S176D_T178E | Combination/optimization |
| 9236-9395 | L124E_L143D_K145T | V133G_S176R_T178K | L124R_Q179K | Q124E_V133G_S176D_T178E_T180E | Combination/optimization |
| 9240-9426 | L124E_L143D_K145T | V133G_S176R_T178K | L124R_Q179K | V133G_S176D_T180E | Combination/optimization |
| 9243-9447 | L124E_L143D_K145T | V133G_S176R_T178K | L124R_Q179K | V133G_S176D_T178E_T180E | Combination/optimization |
| 9171-9398 | L124E_L143D_K145M | Q124K_V133G_Q160K_S176R | L124R_Q179K | V133G_S176D_T178E | Combination/optimization |
| 9170-9376 | L124E_L143D_K145M | Q124K_V133G_Q160K_S176R | L124R_Q179K | Q124E_V133G_S176D_T178E_T180E | Combination/optimization |
| 9172-9428 | L124E_L143D_K145M | Q124K_V133G_Q160K_S176R | L124R_Q179K | V133G_S176D_T180E | Combination/optimization |
| 9181-9406 | L124E_L143D_K145M | Q124K_V133G_S176R_T178R | L124R_Q179K | V133G_S176D_T178E | Combination/optimization |
| 9178-9384 | L124E_L143D_K145M | Q124K_V133G_S176R_T178R | L124R_Q179K | Q124E_V133G_S176D_T178E_T180E | Combination/optimization |
| 9182-9436 | L124E_L143D_K145M | Q124K_V133G_S176R_T178R | L124R_Q179K | V133G_S176D_T180E | Combination/optimization |
| 9190-9410 | L124E_L143D_K145M | Q124K_V133G_S176R | L124R_Q179K | V133G_S176D_T178E | Combination/optimization |
| 9187-9388 | L124E_L143D_K145M | Q124K_V133G_S176R | L124R_Q179K | Q124E_V133G_S176D_T178E_T180E | Combination/optimization |
| 9191-9440 | L124E_L143D_K145M | Q124K_V133G_S176R | L124R_Q179K | V133G_S176D_T180E | Combination/optimization |
| 9174-9402 | L124E_L143D_K145M | Q124K_V133G_S176R_T178K | L124R_Q179K | V133G_S176D_T178E | Combination/optimization |
| 9173-9380 | L124E_L143D_K145M | Q124K_V133G_S176R_T178K | L124R_Q179K | Q124E_V133G_S176D_T178E_T180E | Combination/optimization |
| 9175-9432 | L124E_L143D_K145M | Q124K_V133G_S176R_T178K | L124R_Q179K | V133G_S176D_T180E | Combination/optimization |
| 9201-9417 | L124E_L143E_K145T | V133G_S176R_T178K | L124R_Q179K | V133G_S176D_T178E | Combination/optimization |
| 9198-9395 | L124E_L143E_K145T | V133G_S176R_T178K | L124R_Q179K | Q124E_V133G_S176D_T178E_T180E | Combination/optimization |
| 9202-9426 | L124E_L143E_K145T | V133G_S176R_T178K | L124R_Q179K | V133G_S176D_T180E | Combination/optimization |
| 9205-9447 | L124E_L143E_K145T | V133G_S176R_T178K | L124R_Q179K | V133G_S176D_T178E_T180E | Combination/optimization |
| 9273-9355 | L124E_L143E_K145T | Q124K_V133G_Q160K_S176R | L124R_D146N_Q179K | V133G_S176D_T178E | Combination/optimization |
| 9271-9350 | L124E_L143E_K145T | Q124K_V133G_Q160K_S176R | L124R_D146N_Q179K | Q124E_V133G_S176D_T178E_T180E | Combination/optimization |
| 9275-9359 | L124E_L143E_K145T | Q124K_V133G_Q160K_S176R | L124R_D146N_Q179K | V133G_S176D_T178E_T180E | Combination/optimization |
| 9277-9963 | L124E_L143E_K145T | Q124K_V133G_S176R | L124R_D146N_Q179K | V133G_S176D_T180E | Combination/optimization |
| 9302-9956 | L124E_L143E_K145T | Q124K_V133G_S176R_T178K | L124R_D146N_Q179K | V133G_S176D_T178E | Combination/optimization |

TABLE 5-continued

Design library

| Unique identifier (Set#H1L1L2-Set#H2L2L1, if corresponding LCCA experiments are conducted)** | H1_mutation* | L1_mutation* | H2_mutation* | L2_mutation* | Design type |
|---|---|---|---|---|---|
| 9298-9351 | L124E_L143E_K145T | Q124K_V133G_S176R_T178K | L124R_D146N_Q179K | Q124E_V133G_S176D_T178E_T180E | Combination/optimization |
| 9304-9360 | L124E_L143E_K145T | Q124K_V133G_S176R_T178K | L124R_D146N_Q179K | V133G_S176D_T178E_T180E | Combination/optimization |
| 9308-9365 | L124E_L143E_K145T | Q124K_V133G_S176R_T178K | L124R_D146N_Q179K | V133G_S176D_T180E | Combination/optimization |
| 9290-9364 | L124E_L143E_K145T | Q124K_V133G_S176R | L124R_D146N_Q179K | V133G_S176D_T178E | Combination/optimization |
| 9243-9368 | L124E_L143D_L145T | V133G_S176R_T178K | L124R_D146N_Q179K | V133G_S176D_T178E | Combination/optimization |
| 9142-9414 | L124E_K145T_Q179E | S131K_V133G_S176R | L124R_Q179K | Q124E_V133G_S176D_T178E_T180E | Combination/optimization |
| 9138-9392 | L124E_K145T_Q179E | S131K_V133G_S176R | L124R_Q179K | V133G_S176D_T178E_T180E | Combination/optimization |
| 9144-9423 | L124E_K145T_Q179E | S131K_V133G_S176R | L124R_Q179K | V133G_S176D_T180E | Combination/optimization |
| 9146-9444 | L124E_K145T_Q179E | S131K_V133G_S176R | L124R_Q179K | V133G_S176D_T178E | Combination/optimization |
| 9160-9416 | L124E_K145T_Q179E | S131R_V133G_S176R | L124R_Q179K | V133G_S176D_T178E | Combination/optimization |
| 9154-9394 | L124E_K145T_Q179E | S131R_V133G_S176R | L124R_D146N_Q179K | Q124E_V133G_S176D_T178E_T180E | Combination/optimization |
| 9162-9425 | L124E_K145T_Q179E | S131R_V133G_S176R | L124R_D146N_Q179K | V133G_S176D_T178E_T180E | Combination/optimization |
| 9164-9446 | L124E_K145T_Q179E | S131R_V133G_S176R | L124R_D146N_Q179K | V133G_S176D_T180E | Combination/optimization |
| 9156-9397 | L124E_K145T_Q179E | S131R_V133G_S176R | L124R_Q179K | V133G_S176D_T178E | Combination/optimization |
| 9129-9414 | L124E_K145M_Q179E | S131K_V133G_S176R | L124R_Q179K | V133G_S176D_T178E | Combination/optimization |
| 9126-9392 | L124E_K145M_Q179E | S131K_V133G_S176R | L124R_Q179K | Q124E_V133G_S176D_T178E_T180E | Combination/optimization |
| 9130-9423 | L124E_K145M_Q179E | S131K_V133G_S176R | L124R_Q179K | V133G_S176D_T178E_T180E | Combination/optimization |
| 9131-9444 | L124E_K145M_Q179E | S131K_V133G_S176R | L124R_Q179K | V133G_S176D_T180E | Combination/optimization |
| 9142-9357 | L124E_K145T_Q179E | S131K_V133G_S176R | L124R_D146N_Q179K | V133G_S176D_T178E | Combination/optimization |
| 9138-9352 | L124E_K145T_Q179E | S131K_V133G_S176R | L124R_D146N_Q179K | Q124E_V133G_S176D_T178E_T180E | Combination/optimization |
| 9144-9361 | L124E_K145T_Q179E | S131K_V133G_S176R | L124R_D146N_Q179K | V133G_S176D_T178E_T180E | Combination/optimization |
| 9146-9366 | L124E_K145T_Q179E | S131K_V133G_S176R | L124R_D146N_Q179K | V133G_S176D_T180E | Combination/optimization |
| 9160-9358 | L124E_K145T_Q179E | S131R_V133G_S176R | L124R_D146N_Q179K | V133G_S176D_T178E | Combination/optimization |
| 9154-9353 | L124E_K145T_Q179E | S131R_V133G_S176R | L124R_D146N_Q179K | Q124E_V133G_S176D_T178E_T180E | Combination/optimization |
| 9162-9362 | L124E_K145T_Q179E | S131R_V133G_S176R | L124R_D146N_Q179K | V133G_S176D_T178E_T180E | Combination/optimization |
| 9164-9367 | L124E_K145T_Q179E | S131R_V133G_S176R | L124R_D146N_Q179K | V133G_S176D_T180E | Combination/optimization |
| 9156-9354 | L124E_K145T_Q179E | S131R_V133G_S176R | L124R_D146N_Q179K | V133G_Q160E_S176D_T180E | Combination/optimization |
| 9814-9828 | Q39E_K145T_Q179E | Q38R_S131K | Q39R_S186R | Q38E_Q124E_Q160E_T180E | Combination |
| 9817-9822 | Q39E_L143E_K145T | Q38R_Q124R_Q160K_T178R | Q39R_D146G_H172R_Q179K | Q38E_Q124E_Q160E_T180E | Combination |
| 9820-9827 | Q39E_L143E_K145T_Q179E | Q38R_Q124R_Q160K_T178R | Q39R_Q179K | Q38E_Q124E_Q160E_T180E | Combination |
| 9815-9825 | Q39E_L124E | Q38R_V133G_S176R | Q39R_L124R | Q38E_V133G_S176D | Combination |
| 9746-9905 | I45P_K145T_Q179E | P44F_S131K | S186R | Q38E_Q124E_Q160E_T180E | Combination |
| 9751-9065 | I45P_L143E_K145T | P44F_Q124R_Q160K_T178R | D146G_Q179K | Q38E_Q124E_Q160E_T180E | Combination |
| 9754-9760 | I45P_L143E_K145T_Q179E | P44F_Q124R_Q160K_T178R | Q179K | Q38E_Q124E_Q160E_T180E | Combination |
| 9747-9934 | I45P_L124E | P44F_V133G_S176R | L124R | Q124E_Q160E_T180E | Combination |
| 9748-9338 | I45P_L124E | P44F_V133G_S176R | L124R | V133G_S176D | Combination |
| 9813-9824 | Q39E_K145T_Q179E | Q38R_S131K | Q39R_H172R_S186R | V133G_S176D_T178D | Combination |
| 9818-9821 | Q39E_L143E_K145T_H172R | Q38R_Q124R_Q160K_T178R | Q39R_D146G_H172R_Q179K | Q38E_Q124E_Q160E_T180E | Combination |
| 9819-9823 | Q39E_L143E_K145T_H172R_Q179E | Q38R_Q124R_Q160K_T178R | Q39R_H172R_Q179K | Q38E_Q124E_Q160E_T180E | Combination |
| 9816-9826 | Q39E_L124E_H172R | Q38R_V133G_S176R | Q39R_L124R_H172R | Q38E_V133G_S176D | Combination |
| 9745-9075 | I45P_K145T_H172R_Q179E | P44F_S131K | H172R_S186R | Q38E_Q124E_Q160E_T180E | Combination |
| 9752-9064 | I45P_L143E_K145T_H172R | P44F_Q124R_Q160K_T178R | D146G_H172R_Q179K | Q38E_Q124E_Q160E_T180E | Combination |
| 9753-9074 | I45P_L143E_K145T_H172R_Q179E | P44F_Q124R_Q160K_T178R | H172R_Q179K | Q38E_Q124E_Q160E_T180E | Combination |

TABLE 5-continued

Design library

| Unique identifier (Set#H1L1L2-Set#H2L2L1, if corresponding LCCA experiments are conducted)** | H1_mutation* | L1_mutation* | H2_mutation* | L2_mutation* | Design type |
|---|---|---|---|---|---|
| 9749-9369 | L45P_L124E_H172R | P44F_V133G_S176R | L124R_H172R | V133G_S176D | Combination |
| 9750-9372 | L45P_L124E_H172R | P44F_V133G_S176R | L124R_H172R | V133G_S176D_T178D | Combination |
| 9079-9878 | K145T_Q179E | S131K | S186K | Q160E_Q160E_T180E | Optimization |
| 9079-9840 | K145T_Q179E | S131K | S186K | Q160E_Q160E_T180E | Optimization |
| 9082-9900 | K145T_Q179E | S131K | S186K | Q124E_T180E | Optimization |
| 9082-9862 | K145T_Q179E | S131K | S186K | Q124E_T180E | Optimization |
| 9079-9772 | K145T_Q179E | S131K | Q179K | Q124E_Q160E_T180E | Combination/optimization |
| 9082-9796 | K145T_Q179E | S131K | Q179K | Q124E_T180E | Combination/optimization |
| 9590-9871 | L143E_K145T | Q124R_Q160K_T178R | S186R | Q124E_Q160E_T180E | Combination/optimization |
| 9590-9833 | L143E_K145T | Q124R_Q160K_T178R | S186R | Q124E_T180E | Optimization |
| 9606-9893 | L143E_K145T | Q124R_Q160K_T178R | S186K | Q124E_T180E | Optimization |
| 9606-9855 | L143E_K145T | Q124R_Q160K_T178R | S186K | Q124E_Q160E_T180E | Combination/optimization |
| 9590-9763 | L143E_K145T | Q124R_Q160K_T178R | Q179K | Q124E_Q160E_T180E | Combination/optimization |
| 9606-9789 | L143E_K145T | Q124R_Q160K_T178R | Q179K | Q124E_T180E | Optimization |
| 9651-9971 | L143E_K145T_Q179E | Q124R_Q160K_T178R | S186R | Q124E_Q160E_T180E | Optimization |
| 9651-9833 | L143E_K145T_Q179E | Q124R_Q160K_T178R | S186R | Q124E_T180E | Optimization |
| 9654-9893 | L143E_K145T_Q179E | Q124R_Q160K_T178R | S186K | Q124E_Q160E_T180E | Combination/optimization |
| 9654-9855 | L143E_K145T_Q179E | Q124R_Q160K_T178R | S186K | Q124E_T180E | Optimization |
| 9651-9763 | L143E_K145T_Q179E | Q124R_Q160K_T178R | Q179K | Q124E_Q160E_T180E | Combination/optimization |
| 9654-9789 | L143E_K145T_Q179E | Q124R_Q160K_T178R | Q179K | Q124E_T180E | Optimization |
| 9620-9871 | L143E_K145T_Q179D | Q124R_Q160K_T178R | S186R | Q124E_Q160E_T180E | Combination/optimization |
| 9620-9833 | L143E_K145T_Q179D | Q124R_Q160K_T178R | S186R | Q124E_T180E | Optimization |
| 9623-9893 | L143E_K145T_Q179D | Q124R_Q160K_T178R | S186K | Q124E_Q160E_T180E | Combination/optimization |
| 9623-9855 | L143E_K145T_Q179D | Q124R_Q160K_T178R | S186K | Q124E_T180E | Optimization |
| 9620-9763 | L143E_K145T_Q179D | Q124R_Q160K_T178R | Q179K | Q124E_Q160E_T180E | Combination/optimization |
| 9623-9789 | L143E_K145T_Q179D | Q124R_Q160K_T178R | Q179K | Q124E_T180E | Optimization |
| 9663-9876 | L143E_K145T_Q179E | Q124R_T178R | S186R | Q124E_Q160E_T180E | Combination/optimization |
| 9663-9838 | L143E_K145T_Q179E | Q124R_T178R | S186R | Q124E_T180E | Optimization |
| 9679-9898 | L143E_K145T_Q179E | Q124R_T178R | S186K | Q124E_Q160E_T180E | Optimization |
| 9679-9860 | L143E_K145T_Q179E | Q124R_T178R | S186K | Q124E_T180E | Optimization |
| 9663-9769 | L143E_K145T_Q179E | Q124R_T178R | Q179K | Q124E_Q160E_T180E | Combination/optimization |
| 9679-9794 | L143E_K145T_Q179E | Q124R_T178R | Q179K | Q124E_T180E | Combination/optimization |
| 9632-9876 | L143E_K145T_Q179D | Q124R_T178R | S186R | Q124E_Q160E_T180E | Combination/optimization |
| 9632-9838 | L143E_K145T_Q179D | Q124R_T178R | S186R | Q124E_T180E | Optimization |
| 9635-9898 | L143E_K145T_Q179D | Q124R_T178R | S186K | Q124E_Q160E_T180E | Optimization |
| 9635-9860 | L143E_K145T_Q179D | Q124R_T178R | S186K | Q124E_T180E | Optimization |
| 9632-9769 | L143E_K145T_Q179D | Q124R_T178R | Q179K | Q124E_Q160E_T180E | Combination/optimization |
| 9635-9794 | L143E_K145T_Q179D | Q124R_T178R | Q179K | Q124E_T180E | Combination/optimization |
| 9657-9874 | L143E_K145T_Q179E | Q124E_T178K | S186R | Q124E_Q160E_T180E | Optimization |
| 9657-9836 | L143E_K145T_Q179E | Q124E_T178K | S186R | Q124E_T180E | Optimization |
| 9660-9896 | L143E_K145T_Q179E | Q124E_T178K | S186K | Q124E_Q160E_T180E | Optimization |
| 9660-9858 | L143E_K145T_Q179E | Q124E_T178K | S186K | Q124E_T180E | Optimization |
| 9657-9767 | L143E_K145T_Q179E | Q124E_T178K | Q179K | Q124E_Q160E_T180E | Combination/optimization |

TABLE 5-continued

Design library

| Unique identifier (Set#H1L1L2-Set#H2L2L1, if corresponding LCCA experiments are conducted)** | H1_mutation* | L1_mutation* | H2_mutation* | L2_mutation* | Design type |
|---|---|---|---|---|---|
| 9660-9792 | L143E_K145T_Q179E | Q124R_T178K | Q179K | Q124E_T180E | Combination/optimization |
| 9626-9874 | L143E_K145T_Q179D | Q124R_T178K | S186R | Q124E_Q160E_T180E | Optimization |
| 9626-9836 | L143E_K145T_Q179D | Q124R_T178K | S186K | Q124E_Q160E_T180E | Optimization |
| 9629-9896 | L143E_K145T_Q179D | Q124R_T178K | S186R | Q124E_T180E | Optimization |
| 9629-9858 | L143E_K145T_Q179D | Q124R_T178K | S186K | Q124E_T180E | Optimization |
| 9629-9767 | L143E_K145T_Q179D | Q124R_T178K | Q179K | Q124E_Q160E_T180E | Combination/optimization |
| 9629-9792 | L143E_K145T_Q179D | Q124R_T178K | Q179K | Q124E_T180E | Combination/optimization |
| 9645-9869 | L143E_K145T_Q179E | Q124R_T178R | S186R | Q124E_Q160E_T180E | Optimization |
| 9645-9831 | L143E_K145T_Q179E | Q124R_T178R | S186K | Q124E_Q160E_T180E | Optimization |
| 9648-9891 | L143E_K145T_Q179E | Q124R_T178R | S186R | Q124E_T180E | Optimization |
| 9648-9853 | L143E_K145T_Q179E | Q124R_T178R | S186K | Q124E_T180E | Optimization |
| 9645-9761 | L143E_K145T_Q179E | Q124R_T178R | Q179K | Q124E_Q160E_T180E | Combination/optimization |
| 9648-9787 | L143E_K145T_Q179E | Q124R_T178R | Q179K | Q124E_T180E | Combination/optimization |
| 9614-9869 | L143E_K145T_Q179D | Q124R_T178R | S186R | Q124E_Q160E_T180E | Optimization |
| 9614-9831 | L143E_K145T_Q179D | Q124R_T178R | S186K | Q124E_Q160E_T180E | Optimization |
| 9617-9891 | L143E_K145T_Q179D | Q124R_T178R | S186R | Q124E_T180E | Optimization |
| 9617-9853 | L143E_K145T_Q179D | Q124R_T178R | S186K | Q124E_T180E | Optimization |
| 9614-9761 | L143E_K145T_Q179D | Q124R_T178R | Q179K | Q124E_Q160E_T180E | Combination/optimization |
| 9617-9787 | L143E_K145T_Q179D | Q124R_T178R | Q179K | Q124E_T180E | Combination/optimization |
| 9684-9901 | L143E_K145T_Q179E | T178R | S186R | Q124E_Q160E_T180E | Optimization |
| 9684-9863 | L143E_K145T_Q179E | T178R | S186K | Q124E_Q160E_T180E | Optimization |
| 9683-9773 | L143E_K145T_Q179E | T178R | S186R | Q124E_T180E | Combination/optimization |
| 9684-9797 | L143E_K145T_Q179E | T178R | S186K | Q124E_T180E | Combination/optimization |
| 9638-9879 | L143E_K145T_Q179D | T178R | Q179K | Q124E_Q160E_T180E | Optimization |
| 9638-9841 | L143E_K145T_Q179D | T178R | S186R | Q124E_T180E | Optimization |
| 9641-9901 | L143E_K145T_Q179D | T178R | S186K | Q124E_T180E | Optimization |
| 9641-9863 | L143E_K145T_Q179D | T178R | S186K | Q124E_T180E | Optimization |
| 9638-9773 | L143E_K145T_Q179D | T178R | Q179K | Q124E_Q160E_T180E | Combination/optimization |
| 9641-9797 | L143E_K145T_Q179D | T178R | Q179K | Q124E_T180E | Combination/optimization |
| 9579-9901 | L143D_K145T_Q179E | T178R | S186R | Q124E_Q160E_T180E | Optimization |
| 9579-9863 | L143D_K145T_Q179E | T178R | S186K | Q124E_Q160E_T180E | Optimization |
| 9575-9879 | L143D_K145T_Q179E | T178R | S186R | Q124E_T180E | Optimization |
| 9575-9841 | L143D_K145T_Q179E | T178R | S186K | Q124E_T180E | Optimization |
| 9579-9863 | L143D_K145T_Q179E | T178R | Q179K | Q124E_Q160E_T180E | Combination/optimization |
| 9575-9773 | L143D_K145T_Q179E | T178R | Q179K | Q124E_T180E | Combination/optimization |
| 9579-9797 | L143D_K145T_Q179E | T178R | Q179R | Q124E_T180E | Combination/optimization |
| 9598-9887 | L143E_K145T | Q124R_Q160K_T178R | S186R | Q124E_T180E | Optimization |
| 9598-9849 | L143E_K145T | Q124R_Q160K_T178R | S186K | Q124E_T180E | Optimization |
| 9598-9783 | L143E_K145T | Q124R_Q160K_T178R | Q179K | Q124E_T180E | Combination/optimization |
| 9598-9809 | L143E_K145T | Q124R_Q160K_T178R | Q179R | Q124E_T180E | Combination/optimization |
| 9602-9889 | L143E_K145T | Q124E_Q160K_T178R | S186R | Q124E_T178E_T180E | Optimization |
| 9602-9851 | L143E_K145T | Q124E_Q160K_T178R | S186K | Q124E_T178E_T180E | Optimization |

TABLE 5-continued

Design library

| Unique identifier (Set#H1L1L2-Set#H2L2L1, if corresponding LCCA experiments are conducted)** | H1_mutation* | L1_mutation* | H2_mutation* | L2_mutation* | Design type |
|---|---|---|---|---|---|
| 9602-9785 | L143E_K145T | Q124R_Q160K_T178R | Q179K | Q124E_T178E_T180E | Combination/optimization |
| 9602-9811 | L143E_K145T | Q124R_Q160K_T178R | Q179R | Q124E_T178E_T180E | Combination/optimization |
| 9594-9867 | L143E_K145T | Q124R_Q160K_T178R | S186R | Q124E_Q160E_T178E | Optimization |
| 9594-9829 | L143E_K145T | Q124R_Q160K_T178R | S186K | Q124E_Q160E_T178E | Optimization |
| 9594-9757 | L143E_K145T | Q124R_Q160K_T178R | Q179K | Q124E_Q160E_T178E | Combination/optimization |
| 9594-9801 | L143E_K145T | Q124R_Q160K_T178R | Q179R | Q124E_Q160E_T178E | Combination/optimization |
| 9671-9888 | L143E_K145T_Q179E | Q124R_T178R | S186R | Q124E_T178E | Optimization |
| 9671-9850 | L143E_K145T_Q179E | Q124R_T178R | S186K | Q124E_T178E | Optimization |
| 9671-9784 | L143E_K145T_Q179E | Q124R_T178R | Q179K | Q124E_T178E | Combination/optimization |
| 9671-9810 | L143E_K145T_Q179E | Q124R_T178R | Q179R | Q124E_T178E | Combination/optimization |
| 9675-9890 | L143E_K145T_Q179E | Q124R_T178R | S186R | Q124E_T178E_T180E | Optimization |
| 9675-9852 | L143E_K145T_Q179E | Q124R_T178R | S186K | Q124E_T178E_T180E | Optimization |
| 9675-9786 | L143E_K145T_Q179E | Q124R_T178R | Q179K | Q124E_T178E_T180E | Combination |
| 9675-9812 | L143E_K145T_Q179E | Q124R_T178R | Q179R | Q124E_T178E_T180E | Combination |
| 9667-9868 | L143E_K145T_Q179E | Q124R_Q160K_T178R | S186R | Q124E_Q160E_T178E | Optimization |
| 9667-9830 | L143E_K145T_Q179E | Q124R_Q160K_T178R | S186K | Q124E_Q160E_T178E | Combination |
| 9667-9758 | L143E_K145T_Q179E | Q124R_Q160K_T178R | Q179K | Q124E_Q160E_T178E | Combination |
| 9667-9802 | L143E_K145T_Q179E | Q124R_Q160K_T178R | Q179R | Q124E_Q160E_T178E | Combination |
| 9708-9843 | L143E_K145T_S188L | Q124R_T178R | S186R | Q124E_S131T_T178F_T180E | Optimization |
| 9712-9845 | L143E_K145T_S188L | Q124R_T178R | S186K | Q124E_S131T_T178Y_T180E | Optimization |
| 9708-9777 | L143E_K145T_S188L | Q124R_T178R | Q179K | Q124E_S131T_T178F_T180E | Combination/optimization |
| 9712-9779 | L143E_K145T_S188L | Q124R_T178R | Q179K | Q124E_S131T_T178Y_T180E | Combination/optimization |
| 9708-9803 | L143E_K145T_S188L | Q124R_T178R | Q179R | Q124E_S131T_T178F_T180E | Combination/optimization |
| 9712-9805 | L143E_K145T_S188L | Q124R_T178R | Q179R | Q124E_S131T_T178Y_T180E | Combination/optimization |
| 9708-9881 | L143E_K145T_Q179E_S188L | Q124R_T178R | S186R | Q124E_S131T_T178F_T180E | Optimization |
| 9712-9883 | L143E_K145T_Q179E_S188L | Q124R_T178R | S186R | Q124E_S131T_T178Y_T180E | Optimization |
| 9688-9844 | L143E_K145T_Q179E_S188L | Q124R_Q160K_T178R | S186K | Q124E_S131T_T178F_T180E | Optimization |
| 9692-9846 | L143E_K145T_Q179E_S188L | Q124R_Q160K_T178R | S186K | Q124E_S131T_T178Y_T180E | Optimization |
| 9688-9778 | L143E_K145T_Q179E_S188L | Q124R_Q160K_T178R | Q179K | Q124E_S131T_T178F_T180E | Combination/optimization |
| 9692-9780 | L143E_K145T_Q179E_S188L | Q124R_Q160K_T178R | Q179K | Q124E_S131T_T178Y_T180E | Combination/optimization |
| 9688-9804 | L143E_K145T_Q179E_S188L | Q124R_Q160K_T178R | Q179R | Q124E_S131T_T178F_T180E | Combination/optimization |
| 9692-9806 | L143E_K145T_Q179E_S188L | Q124R_Q160K_T178R | Q179R | Q124E_S131T_T178Y_T180E | Combination/optimization |
| 9688-9882 | L143E_K145T_Q179E_S188L | Q124R_Q160K_T178R | S186R | Q124E_S131T_T178F_T180E | Optimization |
| 9692-9884 | L143E_K145T_Q179E_S188L | Q124R_Q160K_T178R | S186R | Q124E_S131T_T178Y_T180E | Optimization |
| 9723-9102 | L143E_K145T_S188L | Q124R_Q160K_T178R | L124A_S186K | Q124E_V133W_T180E | Combination/optimization |
| 9723-9100 | L143E_K145T_S188L | Q124R_Q160K_T178R | L124A_Q179K | Q124E_V133W_T180E | Combination/optimization |
| 9725-9573 | L143E_K145T_S188L | Q124R_Q160K_T178R | L143A_Q179K | Q124E_V133W_T180E | Combination/optimization |
| 9700-9103 | L143E_K145T_Q179E_S188L | Q124R_Q160K_T178R | L124A_S186K | Q124E_V133W_T180E | Combination/optimization |
| 9700-9101 | L143E_K145T_Q179E_S188L | Q124R_Q160K_T178R | L124A_Q179K | Q124E_V133W_T180E | Combination/optimization |
| 9702-9574 | L143E_K145T_Q179E_S188L | Q124R_Q160K_T178R | L143A_Q179K | Q124E_V133W_T180E | Combination/optimization |
| 9716-9885 | L143E_K145T_S188L | Q124R_Q160K_T178R | S186R | Q124E_V133W_T180E | Optimization |
| 9716-9847 | L143E_K145T_S188L | Q124R_Q160K_T178R | S186K | Q124E_V133W_T180E | Optimization |
| 9716-9781 | L143E_K145T_S188L | Q124R_Q160K_T178R | Q179K | Q124E_V133W_T180E | Combination/optimization |

TABLE 5-continued

Design library

| Unique identifier (Set#H1L1L2-Set#H2L2L1, if corresponding LCCA experiments are conducted)** | H1_mutation* | L1_mutation* | H2_mutation* | L2_mutation* | Design type |
|---|---|---|---|---|---|
| 9716-9807 | L143E_K145T_S188L | Q124R_Q160K_T178R | Q179R | Q124E_S176L_T180E | Combination/optimization |
| 9696-9886 | L143E_K145T_Q179E_S188L | Q124R_T178R | S186R | Q124E_S176L_T180E | Optimization |
| 9696-9848 | L143E_K145T_Q179E_S188L | Q124R_T178R | S186K | Q124E_S176L_T180E | Optimization |
| 9696-9782 | L143E_K145T_Q179E_S188L | Q124R_T178R | Q179K | Q124E_S176L_T180E | Combination/optimization |
| 9696-9808 | L143E_K145T_Q179E_S188L | Q124R_T178R | Q179R | Q124E_S176L_T180E | Combination/optimization |
| 9999-9981 | L143E_K145T | Q124R_Q160K_T178R | S186K | S131E | Optimization |
| 9986-9978 | L143E_K145T | Q124R_Q160K_T178R | Q179K | S131E | Optimization |
| 9986-9979 | L143E_K145T | Q124R_Q160K_T178R | Q179R | S131E | Optimization |
| 9986-9980 | L143E_K145T | Q124R_Q160K_T178R | S186R | S131E | Optimization |
| 9987-9985 | L143E_K145T | Q124R_T178R | S186K | S131E | Optimization |
| 9987-9982 | L143E_K145T | Q124R_T178R | Q179K | S131E | Optimization |
| 9987-9983 | L143E_K145T | Q124R_T178R | Q179R | S131E | Optimization |
| 9987-9984 | L143E_K145T | Q124R_T178R | S186R | S131E | Optimization |
| 9988-9981 | L143E_K145T_Q179E | Q124R_Q160K_T178R | S186K | S131E | Optimization |
| 9988-9978 | L143E_K145T_Q179E | Q124R_Q160K_T178R | Q179K | S131E | Optimization |
| 9988-9979 | L143E_K145T_Q179E | Q124R_Q160K_T178R | Q179R | S131E | Optimization |
| 9988-9980 | L143E_K145T_Q179E | Q124R_Q160K_T178R | S186R | S131E | Optimization |
| 9989-9985 | L143E_K145T_Q179E | Q124R_T178R | S186K | S131E | Optimization |
| 9989-9982 | L143E_K145T_Q179E | Q124R_T178R | Q179K | S131E | Optimization |
| 9989-9983 | L143E_K145T_Q179E | Q124R_T178R | Q179R | S131E | Optimization |
| 9989-9984 | L143E_K145T_Q179E | Q124R_T178R | S186R | S131E | Optimization |
| 9611-9077 | L143E_K145T_H172R | Q124R_Q160K_T178R | H172T_Q179K | Q124E_N137K_Q160E_S174R_T180E | Combination |
| 9610-9076 | L143E_K145T_H172R | Q124R_T178R | H172T_Q179K | Q124E_N137K_Q160E_S174R_T180E | Combination |
| 9612-9078 | L143E_K145T_H172R_Q179E | Q124R_T178R | H172T_Q179K | Q124E_N137K_Q160E_S174R_T180E | Combination |
| 9060-9054 | A139W_L143E_K145T_Q179E | F116A_Q124R_L135V_T178R | A139G_Q179K_V190A | Q124E_L135W_Q160E_T180E | Combination |
| 9058-9053 | A139W_L143E_K145T_Q179E | F116A_Q124R_L135V | A139G_Q179K_V190A | Q124E_L135W_Q160E_T180E | Combination |
| 9060-9756 | A139W_L143E_K145T_Q179E | F116A_Q124R_L135V_T178R | Q179R | Q124E_L135W_Q160E_T180E | Combination |
| 9058-9755 | A139W_L143E_K145T_Q179E | F116A_Q124R_L135V | Q179R | Q124E_L135W_Q160E_T180E | Combination |
| 9585-9734 | L143E_K145T | Q124R | L143K_D146G | Q124E_V133D | Optimization |
| 9587-9735 | L143E_K145T | Q124R | L143R | Q124E_V133D | Optimization |
| 9585-9726 | L143E_K145T | Q124R | L143K | Q124E_V133D | Optimization |
| 9609-9737 | L143E_K145T | Q124R_Q160K_T178R | L143R | Q124E_V133E | Optimization |
| 9593-9728 | L143E_K145T | Q124R_Q160K_T178R | L143K | Q124E_V133E | Optimization |
| 9682-9740 | L143E_K145T_Q179E | Q124R_T178R | L143R | Q124E_V133E | Combination/optimization |
| 9666-9731 | L143E_K145T_Q179E | Q124R_T178R | L143K | Q124E_V133E | Combination/optimization |
| 9705-9735 | L143E_K145T_S188L | Q124R | L143R | Q124E_V133D | |
| 9703-9726 | L143E_K145T_S188L | Q124R | L143K | Q124E_V133D | Optimization |
| 9706-9743 | L143E_K145T_S188L | Q124R | L143R | Q124E_V133E_S176L | Optimization |
| 9704-9732 | L143E_K145T_S188L | Q124R | L143K | Q124E_V133E_S176L | Optimization |
| 9721-9737 | L143E_K145T_S188L | Q124R_Q160K_T178R | L143R | Q124E_V133E | Optimization |
| 9707-9728 | L143E_K145T_S188L | Q124R_Q160K_T178R | L143K | Q124E_V133E | Optimization |
| 9722-9744 | L143E_K145T_S188L | Q124R_Q160K_T178R | L143R | Q124E_V133E_S176L | Optimization |
| 9720-9733 | L143E_K145T_S188L | Q124R_Q160K_T178R | L143K | Q124E_V133D_S176L | Optimization |

TABLE 5-continued

Design library

| Unique identifier (Set#H1L1L2-Set#H2L2L1, if corresponding LCCA experiments are conducted)** | H1_mutation* | L1_mutation* | H2_mutation* | L2_mutation* | Design type |
|---|---|---|---|---|---|
| 9687-9737 | L143E_K145T_Q179E_S188L | Q124R_Q160K_T178R | L143R | Q124E_V133E | Optimization |
| 9644-9728 | L143E_K145T_Q179D_S188L | Q124R_Q160K_T178R | L143K | Q124E_V133D | Optimization |
| 9588-9741 | L143E_K145T | Q124R | L143R | Q124E_V133E_Q160F | Optimization |
| 9589-9742 | L143E_K145T | Q124R | L143R | Q124E_V133E_Q160M | Optimization |
| 9911-9906 | S188L | WT | S188G | S176L | Optimization |
| 9907-9071 | S188L | WT | F174V | S131T_S176F_T178F | Optimization |
| 9909-9073 | S188L | WT | F174V | S131T_S176F_T178Y | Optimization |
| 9909-9068 | S188L | WT | F174G | S131T_S176F_T178F | Optimization |
| 9909-9070 | S188L | WT | F174G | S131T_S176F_T178Y | Optimization |
| 9916-9057 | S188L_V190Y | V133S | A139G_V190A | L135W_S176L | Combination/optimization |
| 9912-9055 | S188L_V190F | WT | A139G_V190A | L135W_S176L | Combination/optimization |
| 9914-9071 | S188L_V190F | WT | F174V | S131T_S176F_T178F | Optimization |
| 9914-9068 | S188L_V190F | WT | F174G | S131T_S176F_T178F | Optimization |
| 9917-9052 | S188L_V190Y | V133S | A139G_F174V_V190A | S131T_L135F_S176F_T178F | Combination/optimization |
| 9913-9050 | S188L_V190F | WT | A139G_F174V_V190A | S131T_L135F_S176F_T178F | Combination/optimization |
| 9062-9056 | A139W_S188L | F116A_L135V | A139G_F174V_V190A | L135W_S176L | Combination/optimization |
| 9063-9051 | A139W_S188L | F116A_L135V | A139G_F174V_V190A | S131T_L135F_S176F_T178F | Combination/optimization |
| 9041-9045 | A139C_C233S | F116C_C214S | WT | WT | independent |
| 9043-9047 | F122C_C233S | S121C_C214S | WT | WT | independent |
| 9042-9045 | F122C_C233S | Q124C_C214S | WT | WT | independent |
| 9044-9048 | P175C_C233S | S162C_C214S | WT | WT | independent |
| 9049-9759 | A139C_L143E_K145T_Q179E | F116C_Q124R_T178R | Q179K | Q124E_Q160E_T180E | Independent/combination |
| 9067-9771 | F122C_L143E_K145T_Q179E | S121C_Q124R_T178R | Q179K | Q124E_Q160E_T180E | Independent/combination |
| 9066-9335 | F122C_L124E | Q124C_V133G_S176R | L124R | V133G_S176D | Independent/combination |
| 9613-9766 | L143E_K145T_P175C_Q179E | Q124R_S162C_T178R | Q179K | Q124E_Q160E_T180E | Independent/combination |
| 6037-9566 | L124A | V133W | L124W_L143F | V133A | Optimization |
| 9064-9751 | D146G_H172R_Q179K | Q38E_Q124E_Q160E_T180E | L45P_L143E_K145T | P44F_Q124R_Q160K_T178R | Combination |
| 9065-9752 | D146G_Q179K | Q38E_Q124E_Q160E_T180E | L45P_L143E_K145T_H172R | P44F_Q124R_Q160K_T178R | Combination |
| 9074-9754 | H172R_Q179K | Q38E_Q160E_T180E | L45P_L143E_K145T_Q179E | P44F_Q124R_Q160K_T178R | Combination |
| 9075-9746 | H172R_S186R | Q38E_Q124E_Q160E_T180E | L45P_K145T_Q179E | P44F_S131K | Combination |
| 9098-9571 | L124A_Q179K | Q124E_V133W_S176T_T178E_T180E | L124W_L143F_K145T_Q179E | S131K_V133A_S176T_T178L | Combination/optimization |
| 9099-9572 | L124A_Q179K | Q124E_V133W_S176T_T178L_T180E | L124W_L143F_K145T_Q179E | S131K_V133A_S176T_T178L | Combination/optimization |
| 9125-9459 | L124E_K145M_Q179E | S131K_V133G_S176R | L124R_D146N_Q179K | Q124E_V133G_S176D_T178E_T180E | Combination/optimization |
| 9126-9352 | L124E_K145M_Q179E | S131K_V133G_S176R | L124R_D146N_Q179K | Q124E_V133G_S176D_T178E_T180E | Combination/optimization |
| 9129-9357 | L124E_K145M_Q179E | S131K_V133G_S176R | L124R_D146N_Q179K | V133G_S176D_T178E | Combination/optimization |
| 9130-9361 | L124E_K145M_Q179E | S131K_V133G_S176R | L124R_D146N_Q179K | V133G_S176D_T178E_T180E | Combination/optimization |
| 9131-9366 | L124E_K145M_Q179E | S131K_V133G_S176R | L124R_D146N_Q179K | V133G_S176D_T180E | Combination/optimization |
| 9170-9350 | Q124K_V133G_Q160K_S176R | Q124K_V133G_S176R | L124R_D146N_Q179K | Q124E_V133G_S176D_T178E_T180E | Combination/optimization |
| 9175-9364 | L143E_L143D_K145M | Q124K_V133G_S176R | L124R_D146N_Q179K | V133G_S176D_T180E | Combination/optimization |
| 9175-9491 | L143E_L143D_K145M | Q124K_V133G_S176R | L124R_S186K | V133G_S176D_T180E | Combination/optimization |
| 9175-9546 | L143E_L143D_K145M | Q124K_V133G_S176R | L124R_S186R | V133G_S176D_T180E | Combination/optimization |
| 9178-9351 | L124E_L143D_K145M | Q124K_V133G_S176R | L124R_D146N_Q179K | Q124E_V133G_S176D_T178E_T180E | Combination/optimization |
| 9205-9368 | L124E_L143D_K145M | V133G_S176R_T178K | L124R_D146N_Q179K | V133G_S176D_T180E | Combination/optimization |

TABLE 5-continued

Design library

| Unique identifier (Set#H1L1L2-Set#H2L2L1, if corresponding LCCA experiments are conducted)** | H1_mutation* | L1_mutation* | H2_mutation* | L2_mutation* | Design type |
|---|---|---|---|---|---|
| 9208-9350 | L124E_L143D_K145T | Q124K_V133G_Q160K_S176R | L124R_D146N_Q179K | Q124E_V133G_S176D_T178E_T180E | Combination/optimization |
| 9213-9364 | L124E_L143D_K145T | Q124K_V133G_S176R | L124R_D146N_Q179K | V133G_S176D_T180E | Combination/optimization |
| 9213-9491 | L124E_L143D_K145T | Q124K_V133G_S176R | L124R_S186K | V133G_S176D_T180E | Combination/optimization |
| 9213-9546 | L124E_L143D_K145T | Q124K_V133G_S176R | L124R_S186R | V133G_S176D_T180E | Combination/optimization |
| 9216-9351 | L124E_L143D_K145T | Q124K_V133G_S176R_T178E | L124R_D146N_Q179K | Q124E_V133G_S176D_T178E_T180E | Combination/optimization |
| 9247-9350 | L124E_L143E_K145M | Q124K_V133G_Q160K_S176R | L124R_D146N_Q179K | Q124E_V133G_S176D_T178E_T180E | Combination/optimization |
| 9256-9364 | L124E_L143E_K145M | Q124K_V133G_S176R | L124R_D146N_Q179K | V133G_S176D_T180E | Combination/optimization |
| 9256-9491 | L124E_L143E_K145M | Q124K_V133G_S176R | L124R_S186K | V133G_S176D_T180E | Combination/optimization |
| 9256-9546 | L124E_L143E_K145M | Q124K_V133G_S176R | L124R_S186R | V133G_S176D_T180E | Combination/optimization |
| 9259-9351 | L124E_L143E_K145M | Q124K_V133G_S176R_T178E | L124R_D146N_Q179K | Q124E_V133G_S176D_T178E_T180E | Combination/optimization |
| 9263-9492 | L124E_L143E_K145M | Q124K_V133G_S176R_T178E | L124R_S186K | V133G_S176D_T180E | Combination/optimization |
| 9263-9547 | L124E_L143E_K145M | Q124K_V133G_S176R_T178E | L124R_S186R | V133G_S176D_T180E | Combination/optimization |
| 9270-9495 | L124E_L143E_K145M | Q124K_V133G_S176R_T178K | L124R_S186K | V133G_S176D_T180E | Combination/optimization |
| 9270-9550 | L124E_L143E_K145M | Q124K_V133G_S176R_T178K | L124R_S186R | V133G_S176D_T180E | Combination/optimization |
| 9749-9334 | I45P_L124E_H172R | P44F_V133G_S176R | L124R | V133G_S176D | Combination |
| 9750-9338 | I45P_L124E_H172R | P44F_V133G_S176R | L124R | V133G_S176D_T178D | Combination |
| 9747-9969 | I45P_L124E | P44F_V133G_S176R | L124R_H172R | V133G_S176D | Combination |
| 9748-9372 | I45P_L124E | P44F_V133G_S176R | L124R_H172R | V133G_S176D_T178D | Combination |
| 9683-9841 | L143E_K145T_Q179E | T178R | S186K | Q124E_Q160E_T180E | Optimization |
| 9683-9879 | L143E_K145T_Q179E | T178R | S186K | Q124E_Q160E_T180E | Optimization |
| 9703-9734 | L143E_K145T_S188L | Q124R | L143K_D146G | Q124E_V133D | Optimization |
| 9745-9905 | L45P_K145T_H172R_Q179E | P44F_S131K | S186K | Q38E_Q124E_Q160E_T180E | Combination |
| 9753-9760 | L45P_L143E_K145T_H172R_Q179E | P44F_Q124R_Q160K_T178R | Q179K | Q124E_Q160E_T180E | Combination |
| 9813-9828 | Q39E_K145T_H172R_Q179E | Q38R_S131K | Q39R_S186R | Q38E_Q124E_Q160E_T180E | Combination |
| 9814-9824 | Q39E_K145T_Q179E | Q38R_S131K | Q39R_H172R_S186R | Q38E_Q124E_Q160E_T180E | Combination |
| 9815-9826 | Q39E_L124E | Q38R_V133G_S176R | Q39R_L124R_H172R | Q38E_V133G_S176D | Combination |
| 9816-9825 | Q39E_L124E_H172R | Q38R_V133G_S176R | Q39R_L124R | Q38E_V133G_S176D | Combination |
| 9817-9821 | Q39E_L124E_K145T | Q38R_Q124R_Q160K_T178R | Q39R_D146G_H172R_Q179K | Q38E_Q124E_Q160E_T180E | Combination |

TABLE 5-continued

Design library

| Unique identifier (Set#H1L1L2-Set#H2L2L1, if corresponding LCCA experiments are conducted)** | H1_mutation* | L1_mutation* | H2_mutation* | L2_mutation* | Design type |
|---|---|---|---|---|---|
| 9817-9823 | Q39E_L124E_K145T | Q38R_Q124R_Q160K_T178R | Q39R_H172R_Q179K | Q38E_Q124E_Q160E_T180E | Combination |
| 9817-9827 | Q39E_L124E_K145T | Q38R_Q124R_Q160K_T178R | Q39R_Q179K | Q38E_Q124E_Q160E_T180E | Combination |
| 9818-9822 | Q39E_L143E_K145T_H172R | Q38R_Q124R_Q160K_T178R | Q39R_D146G_Q179K | Q38E_Q124E_Q160E_T180E | Combination |
| 9818-9823 | Q39E_L143E_K145T_H172R | Q38R_Q124R_Q160K_T178R | Q39R_H172R_Q179K | Q38E_Q124E_Q160E_T180E | Combination |
| 9818-9827 | Q39E_L143E_K145T_H172R | Q38R_Q124R_Q160K_T178R | Q39R_Q179K | Q38E_Q124E_Q160E_T180E | Combination |
| 9819-9821 | Q39E_L143E_K145T_H172R_Q179E | Q38R_Q124R_Q160K_T178R | Q39R_D146G_H172R_Q179K | Q38E_Q124E_Q160E_T180E | Combination |
| 9819-9822 | Q39E_L143E_K145T_H172R_Q179E | Q38R_Q124R_Q160K_T178R | Q39R_D146G_Q179K | Q38E_Q124E_Q160E_T180E | Combination |
| 9819-9827 | Q39E_L143E_K145T_H172R_Q179E | Q38R_Q124R_Q160K_T178R | Q39R_Q179K | Q38E_Q124E_Q160E_T180E | Combination |
| 9820-9821 | Q39E_L143E_K145T_Q179E | Q38R_Q124R_Q160K_T178R | Q39R_D146G_H172R_Q179K | Q38E_Q124E_Q160E_T180E | Combination |
| 9820-9822 | Q39E_L143E_K145T_Q179E | Q38R_Q124R_Q160K_T178R | Q39R_D146G_Q179K | Q38E_Q124E_Q160E_T180E | Combination |
| 9820-9823 | Q39E_L143E_K145T_Q179E | Q38R_Q124R_Q160K_T178R | Q39R_H172R_Q179K | Q38E_Q124E_Q160E_T180E | Combination |
| 10549-10545 | L45P_K145T_Q179E | P44F_S131K | S186R | Q124E_Q160E_T180E_C214S | Combination |
| 10551-10545 | L45P_K145T_H172R_Q179E | P44F_S131K | S186R | Q124E_Q160E_T180E_C214S | Combination |
| 10546-10550 | D146G_Q179K | Q124E_Q160E_T180E_C214S | L45P_L143E_K145T | P44F_Q124R_Q160K_T178R | Combination |
| 10546-10552 | D146G_Q179K | Q124E_Q160E_T180E_C214S | L45P_L143E_K145T_H172R | P44F_Q124R_Q160K_T178R | Combination |
| 10547-10549 | H172R_S186R | Q124E_Q160E_T180E_C214S | L45P_K145T_Q179E | P44F_S131K | Combination |
| 10547-10551 | H172R_S186R | Q124E_Q160E_T180E_C214S | L45P_K145T_H172R_Q179E | P44F_S131K | Combination |
| 10548-10550 | D146G_H172R_Q179K | Q124E_Q160E_T180E_C214S | L45P_L143E_K145T | P44F_Q124R_Q160K_T178R | Combination |
| 10548-10552 | D146G_H172R_Q179K | Q124E_Q160E_T180E_C214S | L45P_L143E_K145T_H172R | P44F_Q124R_Q160K_T178R | Combination |
| 3522 | L45P_L143E_K145T | P44F_Q124R_Q160K_T178R | D146G_Q179K | Q124E_Q160E_T180E | Combination |
| 3519 | L45P_K145T_H172R_Q179E | P44F_S131K | H172R_S186R | Q124E_Q160E_T180E | Combination |

*Kabat numbering; WT refers to a wild-type immunoglobulin chain without amino acid mutations
**A 'unique identifier' is either comprised of the unique identifiers for the two constituent LCCAs or a single identifier for those designs tested only in SMCA format.

TABLE 6

Core Designs

| Unique identifier (Set#H1L1.2-Set#H2L2L1)** | H1_mutation* | L1_mutation* | H2_mutation* | L2_mutation* |
|---|---|---|---|---|
| 9567-9087 9570-9089 9569-9088 9566-9085 9568-9086 | L124W_L143F | V133[AG] | L124A_L143F | V133W |
| 9572-9096 9571-9092 9564-9096 9562-9092 9564-9099 9562-9098 | L124W_L143[FE]_K145T_Q179E | S131K_V133A_S176T_T178L | L124A_Q179K | Q124E_V133W_S176T_T178[LE]_T180E |
| 9561-9095 9560-9091 9559-9094 9558-9090 | L124W_L143E_K145T_Q179E | Q124[RK]_V133A_S176T_T178R | L124A_L143F_Q179K | Q124E_V133W_S176T_T178[LE]_T180E |
| 9110-9341 9104-9336 9105-9340 9106-9337 9107-9339 9109-9332 9108-9330 9326-6048 9327-6054 9328-9332 | L124E | V133G_S176[RK] | L124R | V133G_S176D |
| 9113-9342 9114-9344 9168-9342 9169-9344 | L124E_K228D | S121K_V133G_S176R | L124R_A125R | V133G_S176D |
| 9119-9375 9118-6098 9117-9374 | L124E_H172R L124E_H172R L124E_H172T | V133G_S176R V133G_S176K V133G_S174R_S176R | L124R_H172T L124R_H172T L124R_H172R | V133G_S174R_S176D V133G_N137K_S174R_S176R V133G_S176D |
| 9120-9370 9122-9371 9121-9373 9111-9347 9112-9346 | L124E_A125S_H172T_K228D L124E_A125S_H172T_K228D L124E_A139W L124E_K145T[TM]_Q179E | S121K_V133G_S176R S121K_V133G_N137K_S174R_S176R F116A_V133G_L135[AV]_S176R S131[KR]_V133G_S176R | L124R_A125R_H172T L124R_A125R_H172R L124R_A139G_V190A L124R_S186[KR] | V133G_N137K_S174R_S176D V133G_S176D V133G_L135W_S176D V133G_S176D_T180E |
| 9115-9348 9116-9349 9146-9498 9164-9500 9146-9553 9164-9555 9131-9498 9131-9553 | L124E_K145T[TM]_Q179E | S131[KR]_V133G_S176R | L124R_S186[KR] | V133G_S176D_T178D |
| 9134-9466 9150-9468 9134-9521 9150-9523 9123-9466 9123-9521 | L124E_K145T[TM]_Q179E | S131[KR]_V133G_S176R | L124R_S186[KR] | V133G_S176D_T178D_T180E |
| 9140-9481 9140-9536 9158-9483 9158-9538 9127-9481 9127-9536 | L124E_K145T[TM]_Q179E | S131[KR]_V133G_S176R | L124R_S186[KR] | Q124E_V133G_S176D_T178D_T180E |
| 9136-9459 9152-9460 9136-9513 9152-9515 9125-9513 | L124E_L143[ED]_K145T[TM] | Q124K_V133G_S176R | L124R_S186[KR] | |
| 9308-9547 9323-9550 9290-9546 9308-9492 9323-9495 9290-9491 9220-9547 9229-9550 9220-9492 9229-9495 9182-9547 9191-9550 9182-9492 9191-9495 | L124E_L143E_K145T | Q124K_V133G_S176R | L124R_S186[RK] | V133G_S176D_T178D |
| 9294-9519 9312-9520 9279-9518 9294-9464 9312-9465 9279-9463 9296-9505 9300-9528 9304-9542 9314-9509 | L124E_L143[ED]_K145T[TM] | Q124K_V133G_S176R | L124R_S186[RK] | V133G_S176D_T178[DE]_T180E |

TABLE 6-continued

Core Designs

| Unique identifier (Set#H1L1L2-Set#H2L2L1)** | H1_mutation* | L1_mutation* | H2_mutation* | L2_mutation* |
|---|---|---|---|---|
| 9317-9532 9320-9543 | | | | |
| 9281-9503 9284-9526 | | | | |
| 9287-9541 9296-9451 | | | | |
| 9300-9473 9304-9487 | | | | |
| 9314-9455 9317-9477 | | | | |
| 9320-9488 9281-9449 | | | | |
| 9284-9471 9287-9486 | | | | |
| 9264-9509 9267-9532 | | | | |
| 9250-9503 9253-9526 | | | | |
| 9257-9505 9260-9528 | | | | |
| 9264-9455 9267-9477 | | | | |
| 9250-9449 9253-9471 | | | | |
| 9257-9451 9260-9473 | | | | |
| 9214-9505 9223-9509 | | | | |
| 9217-9528 9226-9532 | | | | |
| 9214-9451 9223-9455 | | | | |
| 9217-9473 9226-9477 | | | | |
| 9176-9505 9185-9509 | | | | |
| 9179-9528 9188-9532 | | | | |
| 9176-9451 9185-9455 | | | | |
| 9179-9473 9188-9477 | | | | |
| 9273-9398 9271-9376 | L124E_L143[ED]_K145[TM] | Q124K_V133G_S176R | L124R_Q179K | V133G_S176D_T178E |
| 9275-9419 9302-9406 | | | | |
| 9298-9384 9304-9421 | | | | |
| 9319-9410 9316-9388 | | | | |
| 9320-9422 9286-9402 | | | | |
| 9283-9380 9287-9420 | | | | |
| 9248-9398 9247-9376 | | | | |
| 9262-9406 9259-9384 | | | | |
| 9269-9410 9266-9388 | | | | |
| 9255-9402 9252-9380 | | | | |
| 9209-9398 9208-9376 | | | | |
| 9219-9406 9216-9384 | | | | |
| 9228-9410 9225-9388 | | | | |
| 9212-9402 9211-9380 | | | | |
| 9171-9398 9170-9376 | | | | |
| 9181-9406 9178-9384 | | | | |
| 9190-9410 9187-9388 | | | | |
| 9174-9402 9173-9380 | | | | |
| 9273-9355 9271-9350 | | | | |
| 9275-9359 9302-9356 | | | | |
| 9298-9351 9308-9436 | | | | |
| 9277-9428 9308-9436 | L124E_L143[ED]_K145[TM] | Q124K_V133G_S176R | L124R_Q179K | V133G_S176D_T180E |
| 9323-9440 9290-9432 | | | | |
| 9249-9428 9263-9436 | | | | |
| 9270-9440 9256-9432 | | | | |
| 9210-9428 9220-9436 | | | | |
| 9229-9440 9213-9432 | | | | |

TABLE 6-continued

Core Designs

| Unique identifier (Set#H1L1L2-Set#H2L2L1)** | H1_mutation* | L1_mutation* | H2_mutation* | L2_mutation* |
|---|---|---|---|---|
| 9172-9428 9182-9436 | | | | |
| 9191-9440 9175-9432 | | | | |
| 9277-9363 9308-9365 | | | | |
| 9290-9364 | | | | |
| 9243-9556 9234-9516 | L124E_L143D_K145[MT] | V133G_S176R_T178K | L124R_S186[KR] | V133G_S176D_T180E |
| 9237-9539 9240-9544 | | | | |
| 9243-9501 9371-9484 | | | | |
| 9240-9489 9205-9556 | | | | |
| 9199-9539 9202-9544 | | | | |
| 9196-9461 9205-9501 | | | | |
| 9199-9484 9202-9489 | | | | |
| 9232-9524 9234-9461 | L124E_L143D_K145[MT] | V133G_S176R_T178K | L124R_S186[KR] | V133G_S176D_T178D |
| 9232-9469 9196-9516 | | | | |
| 9194-9524 9194-9469 | | | | |
| 9239-9417 9236-9395 | L124E_L143D_K145[TM] | V133G_S176R_T178K | L124R_Q179K | V133G_S176D_T178E |
| 9240-9426 9201-9417 | | | | |
| 9198-9395 9202-9426 | L124E_L143D_K145[TM] | V133G_S176R_T178K | L124R_Q179K | V133G_S176D_T180E |
| 9243-9447 9205-9447 | L124E_L143D_K145[TM] | V133G_S176R_T178R | L124R_Q179K | V133G_S176D_T180E |
| 9243-9368 | | | | |
| 9142-9414 9138-9392 | L124E_K145[TM]_Q179E | S131[KR]_V133G_S176R | L124R_Q179K | V133G_S176D_T178E |
| 9144-9423 9160-9416 | | | | |
| 9154-9394 9162-9425 | | | | |
| 9129-9414 9126-9392 | | | | |
| 9130-9423 9142-9357 | | | | |
| 9138-9352 9144-9361 | | | | |
| 9160-9358 9154-9353 | | | | |
| 9162-9362 | | | | |
| 9146-9444 9164-9446 | L124E_K145T[TM]_Q179E | S131[KR]_V133G_S176R | L124R_Q179K | V133G_S176D_T180E |
| 9156-9397 9131-9444 | | | | |
| 9146-9366 9164-9367 | | | | |
| 9156-9354 | | | | |
| 9814-9828 9813-9824 | Q39E_K145T_Q179E | Q38R_S131K | Q39R_S186R | Q38E_Q124E_Q160E_T180E |
| 9817-9822 9818-9821 | Q39E_L143E_K145T | Q38R_Q124E_Q160K_T178R | Q39R_D146G_Q179K | Q38E_Q124E_Q160E_T180E |
| 9820-9827 9819-9823 | Q39E_L143E_K145T_Q179E | Q38R_Q124E_Q160K_T178R | Q39R_Q179K | Q38E_Q124E_Q160E_T180E |
| 9815-9825 9816-9826 | Q39E_L123E | Q38R_V133G_S176R | Q39R_L124R | Q38E_V133G_S176D |
| 9746-9905 9745-9075 | L45P_K145T_Q179E | P44F_S131K | S186R | Q38E_Q124E_Q160E_T180E |
| 9751-9065 9752-9064 | L45P_L143E_K145T | P44F_Q124R_Q160K_T178R | D146G_Q179K | Q38E_Q124E_Q160E_T180E |
| 9754-9760 9753-9074 | L45P_L143E_K145T_Q179E | P44F_Q124R_Q160K_T178R | Q179K | Q124E_Q160E_T180E |
| 9747-9334 9748-9338 | L45P_124E | P44F_V133G_S176R | L124R | V133G_S176D |
| 9749-9369 9750-9372 | | | | |
| 9079-9878 9079-9840 | K145T_Q179E | S131K | S186[RK] | Q124E_T180E |
| 9082-9900 9082-9862 | | | | |
| 9079-9772 9082-9796 | K145T_Q179E | S131K | Q179K | Q124E_T180E |
| 9590-9871 9590-9833 | L143E_K145T | Q124R_Q160K_T178R | S186[RK] | Q124E_T180E |
| 9606-9893 9606-9855 | | | | |
| 9651-9871 9651-9833 | | | | |
| 9654-9893 9654-9855 | | | | |
| 9620-9871 9620-9833 | | | | |

TABLE 6-continued

Core Designs

| Unique identifier (Set#H1L1L2-Set#H2L2L1)** | H1_mutation* | L1_mutation* | H2_mutation* | L2_mutation* |
|---|---|---|---|---|
| 9623-9893 9623-9855 | | | | |
| 9602-9889 9602-9851 | | | | |
| 9708-9843 9712-9845 | | | | |
| 9708-9881 9712-9883 | | | | |
| 9716-9885 9716-9847 | | | | |
| 9598-9887 9598-9849 | L143E_K145T | Q124R_Q160K_T178R | S186[RK] | Q124E_T178E |
| 9594-9867 9594-9829 | | | | |
| 9663-9876 9663-9838 | L143[DE]_K145T_Q179[DE] | T178[KR] | S186[RK] | Q124E_T180E |
| 9679-9898 9679-9860 | | | | |
| 9632-9876 9632-9838 | | | | |
|

TABLE 6-continued

Core Designs

| Unique identifier (Set#H1L1L2-Set#H2L2L1)** | H1_mutation* | L1_mutation* | H2_mutation* | L2_mutation* |
|---|---|---|---|---|
| 9675-9786 9688-9778 9692-9780 9700-9101 9702-9574 9696-9782 9612-9078 | | | | |
| 9657-9767 9660-9792 9626-9767 9629-9792 | L143E_K145T_Q179[DE] | Q124R_T178K | Q179K | Q124E_T180E |
| 9598-9783 9598-9809 9594-9757 9594-9801 9602-9811 | L143E_K145T | Q124R_Q160K_T178R | Q179[RK] | Q124E_T178E |
| 9671-9784 9671-9810 9675-9812 9667-9758 | L143E_K145T_Q179E | Q124R_T178R | Q179[RK] | Q124E_T178E |
| 9667-9802 | L143E_K145T_Q179E_S188L | Q124R_T178R | Q179R | Q124E_S131T_T178F_T180E |
| 9688-9804 | L143E_K145T_Q179E_S188L | Q124R_T178R | Q179R | Q124E_S131T_T178Y_T180E |
| 9692-9806 | L143E_K145T_S188L | Q124R_Q160K_T178R | L124A_S186K | Q124E_V133W_T180E |
| 9723-9102 | L143E_K145T_Q179E_S188L | Q124R_T178R | L124A_S186K | Q124E_V133W_T180E |
| 9700-9103 | L143E_K145T_Q179E_S188L | Q124R_T178R | Q179R | Q124E_S176L_T180E |
| 9696-9808 | L143_K145T_S188L | Q124R_Q160K_T178R | Q179R | Q124E_S176L_T180E |
| 9716-9807 | L143E_K145T | Q124R_T178R | S186[RK] | S131E |
| 9986-9981 9986-9978 9987-9985 9987-9982 9988-9981 9988-9978 9989-9985 9989-9982 | L143E_K145T | Q124R_T178R | Q179[KR] | S131E |
| 9986-9979 9986-9980 9987-9983 9987-9984 9988-9979 9988-9980 9989-9983 9989-9984 | | | | |
| 9610-9076 | L143E_K145T_H172R | Q124R | H172T_Q179K | Q124E_Q160E_T180E_N137K_S174R |
| 9060-9054 9058-9053 9060-9756 9058-9755 | A139W_L143E_K145T_Q179E | Q124R_F116A_L135V | Q179K | Q124E_Q160E_T180E_L135W |
| 9587-9735 9609-9737 9682-9740 9705-9735 9706-9743 9721-9737 9722-9744 9687-9737 9588-9741 9589-9742 | L143E_K145T | Q124R | L143R | Q124E_V133E |

TABLE 6-continued

Core Designs

| Unique identifier (Set#H1L1L2-Set#H2L2L1)** | H1_mutation* | L1_mutation* | H2_mutation* | L2_mutation* |
|---|---|---|---|---|
| 9585-9734 9585-9726 9593-9728 9666-9731 9703-9726 9704-9732 9707-9728 9720-9733 9644-9728 | L143E_K145T | Q124R | L143K | Q124E_V133D |
| 9911-9906 | S188L | WT | S188G | S176L |
| 9907-9071 9909-9073 9917-9052 | S188L | WT | F174V | S131T_S176F_T178[FY] |
| 9907-9068 9909-9070 | S188L | WT | F174G | S131T_S176F_T178[FY] |
| 9916-9057 | S188L_V190Y | V133S | A139G_V190A | L135W_S176L |
| 9912-9055 | S188L_V190F | WT | A139G_V190A | L135W_S176L |
| 9914-9071 9914-9068 9913-9050 | S188L_V190F | WT | F174[GV] | S131T_S176F_T178F |
| 9062-9056 | A139W_S188L | F116A_L135V | A139G_V190A | L135W_S176L |
| 9063-9051 | A139W_S188L | F116A_L135V | A139G_F174V_V190A | S131T_L135F_S176F_T178F |
| 9041-9045 9049-9759 | A139C | F116C | WT | WT |
| 9043-9047 9067-9771 | F122C | S121C | WT | WT |
| 9042-9046 9066-9335 | F122C | Q124C | WT | WT |
| 9044-9048 9613-9766 | P175C | S162C | WT | WT |

*Kabat numbering; WT refers to a wild-type immunoglobulin chain without amino acid mutations
**A 'unique identifier set' is comprised of the unique identifiers for the two constituent LCCAs

TABLE 7

Example of a combination design

| Unique identifier (Set#H1L1L2-Set#H2L2L1) | H1_mutation* | L1_mutation* | H2_mutation* | L2_mutation* | Normalized Median H1 L1:H1 L2 | Normalized Median H2-L2:H2-L1 |
|---|---|---|---|---|---|---|
| 9818-9825 (from table 5 above) | Q39E_L124E | Q38R_V133G_S176R | Q39R_L124R | Q38E_V133G_S176D | | |
| 51-52 (from Table 14 in PCT/CA2013/050914) | Q39E | Q38R | Q39R | Q38E | 76:24 | 70:30 |
| 263-364 (from Table 15 in PCT/CA2013/050914) | L124E | V133G_S176R | L124R | V133G_S176D | 88:12 | 84:16 |

*Kabat numbering.

TABLE 8

Example of a modified/optimized design

| Unique identifier (Set#H1L1L2-Set#H2L2L1) | H1_mutation* | L1_mutation* | H2_mutation* | L2_mutation* | Normalized Median H1 L1:H1 L2 | Normalized Median H2-L2:H2-L1 |
|---|---|---|---|---|---|---|
| 9110-9341 (from table 5 above) | L124E | V133G_S176R | L124R | V133G_S176D_T178Y | | |
| 263-264 (from Table 15 in PCT/CA2013/050914) | L124E | V133G_S176R | L124R | V133G_S176D | 88:12 | 84:16 |

*Kabat numbering

TABLE 9

Example of a combination design including an optimized design

| Unique identifier (Set#H1L1L2-Set#H2L2L1) | H1_mutation* | L1_mutation* | H2_mutation* | L2_mutation* | Normalized Median H1 L1:H1 L2 | Normalized Median H2-L2:H2-L1 |
|---|---|---|---|---|---|---|
| 9314-9509 (combination including optimized design from Table 5 above) | L124E_L143E_K145T | Q124K_V133G_S176R_T178R | L124R_S186R | Q124E_V133G_S176D_T178D_T180E | | |
| 263-264 (from Table 15 in PCT/CA2013/050914) | L124E | V133G_S176R | L124R | V133G_S176D | 88:12 | 84:16 |
| 265-266 (from Table 15 in PCT/CA2013/050914) | L143E_K145T | Q124K_T178R | S186R | Q124E | 90:13 | 96:6 |

TABLE 10

Example of a combination design including an independent design

| Unique identifier (Set#H1L1L2-Set#H2L2L1) | H1_mutation* | L1_mutation* | H2_mutation* | L2_mutation* | Normalized Median H1 L1:H1 L2 | Normalized Median H2-L2:H2-L1 |
|---|---|---|---|---|---|---|
| 9066-9335 (combination including independent design from Table 5 above) | F122C_L124E | Q124C_V133G_S176R | L124R | V133G_S176D | | |
| 535-536 (independent design from Table 15 above) | F122C | Q124C | WT | WT | | |
| 263-364 (from Table 15 in PCT/CA2013/050914) | L124E | V133G_S176R | L124R | V133G-S176D | 88:12 | 84:16 |

*Kabat numbering.
WT refers to a wild-type immunoglobulin chain without amino acid mutations

TABLE 11

H1:L1:L2 DNA ratios used for the light chain competition assays and verifications

| H1:L1:L2 ratio | Experiment | DNA quantity used for transfection (ng) | | | ^Additional DNA | |
|---|---|---|---|---|---|---|
| | | H1 | L1 | L2 | AKTdd pTT22 | ssDNA |
| 1:0.75:2.25 | Competition assay screen | 333 | 250 | 749 | 300 | 368 |
| 1:0.75:2.25 | Competition assay verification | 333 | 250 | 749 | 300 | 368 |
| 1:0.3:2.7 | Competition assay verification | 333 | 100 | 899 | 300 | 368 |

^Additional DNA: AKTdd pTT22 refers to a vector containing a constitutively active protein kinase B mutant (dominant positive AKT mutant); ssDNA refers to salmon sperm DNA.

TABLE 12

LCCA performance, stability and antigen binding assessments of the LCCA designs, arranged by decreasing DSF values of H1L1 Fab heterodimers

| Row # | Set # | DSF values of h1\|1 Fab heterodimer (° C.) | Change in DSF values of h1\|1 Fab heterodimer compared to wild-type | KD of h1\|1 Fab heterodimer (nM) | Range of KD values for h1\|1 Fab heterodimer (nM) | Change in median values of KD of h1\|1 Fab heterodimer compared to wild type (−(log(KD_design) − log(KD_wt))) | Median LCCA performance normalized to a L1:L2 DNA ratio of 1:1 (Ratio)** | LCCA performance range (Max-Min) at L1:L2 DNA ratio of 1:1** | Median LCCA performance normalized to a L1:L2 DNA ratio of 1:1 (Ratio)*** |
|---|---|---|---|---|---|---|---|---|---|
| 1 | 6113 | 83.1 | 2.1 | 0.12 | 0 | 0.11 | 64:36 | 1.4 | ND |
| 2 | 9780 | 83 | 2 | 0.16+ | 0.00+ | −0.01+ | 93:7 | 1 | ND |
| 3 | 9779 | 83 | 2 | 0.16+ | 0.00+ | −0.01+ | 95:5 | 2.1 | ND |
| 4 | 9845 | 82.7 | 1.7 | 0.13+ | 0.00+ | 0.09+ | 94:6 | 12.8 | 89:11 |
| 5 | 9846 | 82.7 | 1.7 | 0.13+ | 0.00+ | 0.09+ | 95:5 | 2 | 89:11 |
| 6 | 9805 | 82.6 | 1.6 | 0.13+ | 0.00+ | 0.07+ | 95:5 | 2.3 | ND |
| 7 | 9806 | 82.6 | 1.6 | 0.13+ | 0.00+ | 0.07+ | 94:6 | 0.9 | 91:9 |
| 8 | 6163 | 82.5 | 1.5 | 0.15 | 0 | 0.02 | 75:25 | 7.4 | ND |
| 9 | 6024 | 82.50* | 1.30* | 0.15+ | 0.00* | 0.02* | 50:50 | 0.9 | ND |
| 10 | 9906 | 82.5 | 1.5 | 0.11+ | 0.00+ | 0.14+ | 22:78 | 6.3 | ND |
| 11 | 9068 | 82.5 | 1.5 | 0.13 | 0 | 0.07 | 63:37 | 9.5 | 61:39 |
| 12 | 9070 | 82.5 | 1.5 | 0.16 | 0 | 0 | 67:33 | 3.3 | ND |
| 13 | 9074 | 82.5 | 1.5 | 0.16 | 0 | −0.01 | 97:3 | 1.4 | 99:1 |
| 14 | 9570 | 82.4 | 1.4 | 0.23 | 0 | −0.17 | 64:36 | 3.2 | ND |
| 15 | 9883 | 82.3 | 1.3 | ND, low Fab capture | ND, low Fab capture | ND, low Feb capture | 88:12 | 2.5 | ND |
| 16 | 9884 | 82.3 | 1.3 | ND, low Fab capture | ND, low Fab capture | ND, low Fab capture | 33:12 | 6.3 | ND |
| 17 | 9844 | 82.3 | 1.3 | 0.17+ | 0.00+ | −0.03+ | 96:4 | 1.1 | ND |
| 18 | 9343 | 82.3 | 1.3 | 0.17+ | 0.00+ | −0.03+ | 96:4 | 1.5 | ND |
| 19 | 9073 | 82.3 | 1.3 | 0.14 | 0 | 0.04 | 63:37 | 1.9 | ND |
| 20 | 9803 | 82.2 | 1.2 | 0.11+ | 0.00+ | 0.14+ | 96:4 | 0.6 | ND |
| 21 | 9804 | 82.2 | 1.2 | 0.11+ | 0.00+ | 0.14+ | 96:4 | 0.5 | ND |
| 22 | 9782 | 82.2 | 1.2 | 0.08+ | 0.00+ | 0.28+ | 96:4 | 5.6 | ND |
| 23 | 9781 | 82.2 | 1.2 | 0.08+ | 0.00+ | 0.28+ | 97:3 | 5.2 | ND |
| 24 | 9610 | 82.1 | 1.1 | ND, low Fab capture | ND, low Fab capture | ND, low Fab capture | 99:1 | 1.8 | 98:2 |
| 25 | 6042 | 82.1 | 1.1 | 0.11 | 0 | 0.14 | 66:34 | 5.3 | ND |
| 26 | 9914 | 82 | 1 | 0.15+ | 0.00+ | 0.01+ | 61:39 | 13.2 | 72:28 |
| 27 | 9569 | 82 | 1 | 0.3 | 0 | −0.28 | 70:30 | 0 | ND |
| 28 | 9568 | 82 | 1 | 0.3 | 0 | −0.28 | 61:39 | 1.4 | ND |
| 29 | 9807 | 81.3 | 0.8 | 0.17+ | 0.00+ | −0.02+ | 98:2 | 5.6 | ND |
| 30 | 9808 | 81.3 | 0.8 | 0.17+ | 0.00+ | −0.02+ | 93:7 | 12.7 | 85:15 |
| 31 | 9794 | 81.8 | 0.8 | 0.11+ | 0.00+ | 0.16+ | 96:4 | 0.9 | ND |
| 32 | 9796 | 81.8 | 0.8 | 0.11+ | 0.00+ | 0.16+ | 98:2 | 10.8 | 33:12 |
| 33 | 9797 | 81.8 | 0.8 | 0.11+ | 0.00+ | 0.16+ | 96:4 | 2.9 | ND |
| 34 | 9792 | 81.3 | 0.8 | 0.11+ | 0.00+ | 0.16+ | 96:4 | 1 | ND |
| 35 | 9567 | 81.3 | 0.8 | 0.25 | 0 | −0.21 | 58:42 | 1.9 | ND |
| 36 | 9881 | 81.8 | 0.8 | 0.11+ | 0.00+ | 0.15+ | 90:10 | 0.9 | ND |
| 37 | 9882 | 81.8 | 0.8 | 0.11+ | 0.00+ | 0.15+ | 90:10 | 3.2 | ND |
| 38 | 9611 | 81.8 | 0.8 | 0.12+ | 0.00+ | 0.12+ | 99:1 | 4.6 | 99:1 |

TABLE 12-continued

LCCA performance, stability and antigen binding assessments of the LCCA designs, arranged by decreasing DSF values of H1L1 Fab heterodimers

| Row # | Set # | DSF values of h1\|1 Fab heterodimer (° C.) | Change in DSF values of h1\|1 Fab heterodimer compared to wild-type | KD of h1\|1 Fab heterodimer (nM) | Range of KD values for h1\|1 Fab heterodimer (nM) | Change in median values of KD of h1\|1 Fab heterodimer compared to wild type (−(log(KD_design) − log(KD_wt))) | Median LCCA performance normalized to a L1:L2 DNA ratio of 1:1 (Ratio)** | LCCA performance range (Max-Min) at L1:L2 DNA ratio of 1:1** | Median LCCA performance normalized to a L1:L2 DNA ratio of 1:1 (Ratio)*** |
|---|---|---|---|---|---|---|---|---|---|
| 39 | 9789 | 81.3 | 0.8 | 0.11+ | 0.00+ | 0.16+ | 96:4 | 1.1 | ND |
| 40 | 9737 | 81.3 | 0.8 | 0.11+ | 0.00+ | 0.16+ | 96:4 | 1.4 | 87:13 |
| 41 | 9566 | 81.8 | 0.8 | 0.25 | 0 | −0.21 | 56:44 | 3.6 | ND |
| 42 | 9692 | 81.6 | 0.6 | 0.34 | 0 | −0.34 | 83:17 | 5.2 | 79:21 |
| 43 | 9696 | 81.6 | 0.6 | 0.34 | 0 | −0.34 | 37:13 | 18.1 | 90:10 |
| 44 | 6017 | 81.6 | 0.6 | 0.14 | 0 | 0.06 | 47:53 | 7.1 | ND |
| 45 | 9705 | 81.6 | 0.6 | 0.21 | 0 | −0.12 | 69:31 | 0 | ND |
| 46 | 9688 | 81.6 | 0.6 | 0.34 | 0 | −0.34 | 77:23 | 0.6 | ND |
| 47 | 9706 | 81.6 | 0.6 | 0.21 | 0 | −0.12 | 69:31 | 0.2 | ND |
| 48 | 9704 | 81.6 | 0.6 | 0.21 | 0 | −0.12 | 74:26 | 0.1 | ND |
| 49 | 9703 | 81.60* | 0.40* | 0.21* | 0.00* | −0.12* | 84:16 | 14.8 | 79:21 |
| 50 | 9702 | 81.6 | 0.6 | 0.34 | 0 | −0.34 | 71:29 | 5 | ND |
| 51 | 9700 | 81.6 | 0.6 | 0.34 | 0 | −0.34 | 75:25 | 3.1 | ND |
| 52 | 9346 | 81.6 | 0.6 | 0.2 | 0 | −0.11 | 95:5 | 1.9 | ND |
| 53 | 9612 | 81.5 | 0.5 | ND, low Fab capture | ND, low Fab capture | ND, low Fab capture | 99:1 | 2.7 | 99:1 |
| 54 | 9057 | 81.5 | 0.5 | 0.16 | 0 | −0.02 | 43:57 | 22.8 | ND |
| 55 | 9056 | 81.5 | 0.5 | 0.16 | 0 | −0.02 | 32:68 | 6.8 | 72:28 |
| 56 | 9055 | 81.5 | 0.5 | 0.16 | 0 | −0.02 | 40:60 | 15 | ND |
| 57 | 9731 | 81.5 | 0.5 | 0.28 | 0 | −0.26 | 92:8 | 3.9 | 92:8 |
| 58 | 9071 | 81.5 | 0.5 | 0.21 | 0 | −0.12 | 56:44 | 14 | 85:15 |
| 59 | 9104 | 81.40* | 0.30 | 0.16* | 0.00* | −0.01 | 90:10 | 1.8 | ND |
| 60 | 9885 | 81.4 | 0.4 | 0.18+ | 0.00+ | −0.06+ | 95:5 | 2.3 | ND |
| 61 | 9886 | 81.4 | 0.4 | 0.18+ | 0.00+ | −0.06+ | 93:7 | 4.3 | ND |
| 62 | 10551 | 81.4 | 0.4 | ND, low Fab capture | ND, low Fab capture | ND, low Fab capture | 94:6 | 1.1 | 92:8 |
| 63 | 5998 | 81.4 | 0.4 | 0.14 | 0 | 0.06 | 71:29 | 5 | ND |
| 64 | 6036 | 81.4 | 0.4 | 0.17 | 0 | −0.03 | 59:41 | 0.1 | ND |
| 65 | 9745 | 81.4 | 0.4 | ND, low Fab capture | ND, low Fab capture | ND, low Fab capture | 95:5 | 0.1 | ND |
| 66 | 9769 | 81.3 | 0.3 | 0.32 | 0 | −0.31 | 88:12 | 10.6 | 90:10 |
| 67 | 9767 | 81.3 | 0.3 | 0.32 | 0 | −0.31 | 89:11 | 14.7 | 93:7 |
| 68 | 9763 | 81.3 | 0.3 | 0.32 | 0 | −0.31 | 87:13 | 2.4 | 88:12 |
| 69 | 9759 | 81.3 | 0.3 | 0.32 | 0 | −0.31 | 94:6 | 0 | ND |
| 70 | 9813 | 81.3 | 0.3 | 0.18+ | 0.00+ | −0.05+ | 93:7 | 3.6 | 89:11 |
| 71 | 9099 | 81.3 | 0.3 | 0.19 | 0 | −0.09 | 97:3 | 11.1 | 92:8 |
| 72 | 9052 | 81.3 | 0.3 | 0.14 | 0 | 0.06 | 74:26 | 36.9 | 89:11 |
| 73 | 9051 | 81.3 | 0.3 | 0.14 | 0 | 0.06 | 51:49 | 3.9 | 60:40 |
| 74 | 9050 | 81.3 | 0.3 | 0.14 | 0 | 0.06 | 53:47 | 6 | ND |
| 75 | 9761 | 81.3 | 0.3 | 0.32 | 0 | −0.31 | 92:8 | 5.9 | 90:10 |
| 76 | 9760 | 81.3 | 0.3 | 0.32 | 0 | −0.31 | 97:3 | 2.8 | 95:5 |
| 77 | 9062 | 81.3 | 0.3 | 0.17 | 0 | −0.02 | 66:34 | 7 | 75:25 |
| 78 | 9063 | 81.3 | 0.3 | 0.17 | 0 | −0.02 | 59:41 | 6.1 | 55:45 |
| 79 | 9687 | 81.3 | 0.3 | ND, low Fab capture | ND, low Fab capture | ND, low tab capture | 89:11 | 5.4 | 87:13 |
| 80 | 9732 | 81.3 | 0.3 | 0.28 | 0 | −0.25 | 90:10 | 5.7 | ND |
| 81 | 9733 | 81.3 | 0.3 | 0.28 | 0 | −0.25 | 94:6 | 8.2 | 91:9 |
| 82 | 9848 | 81.3 | 0.3 | 0.15+ | 0.00+ | 0.03+ | 96:4 | 11.8 | 91:9 |
| 83 | 9847 | 81.3 | 0.3 | 0.15+ | 0.00+ | 0.03+ | 97:3 | 3.3 | ND |
| 84 | 9773 | 81.3 | 0.3 | 0.32 | 0 | −0.31 | 78:22 | 5 | ND |
| 85 | 9066 | 81.2 | 0.2 | 0.17 | 0 | −0.04 | 93:7 | 2.7 | 96:4 |
| 86 | 9118 | 81.20* | 0.00 | 0.01 | 0 | −0.28 | 95:5 | 1.9 | ND |
| 87 | 9119 | 81.2 | 0.2 | 0.17 | 0 | −0.03 | 97:3 | 1.7 | 97:3 |
| 88 | 9741 | 81.1 | 0.1 | 0.07+ | 0.00+ | 0.34+ | 83:17 | 0.1 | ND |
| 89 | 9101 | 81 | 0 | 0.12 | 0 | 0.1 | 95:5 | 0.2 | ND |
| 90 | 9100 | 81 | 0 | 0.12 | 0 | 0.1 | 93:7 | 1.2 | ND |
| 91 | 9635 | 81.00* | −0.20* | 0.14* | 0.00* | 0.04* | 76:24 | 28.6 | ND |
| 92 | 9632 | 81 | 0 | 0.14+ | 0.00+ | 0.04+ | 87:13 | 14.8 | 82:18 |
| 93 | 9045 | 81 | 0 | 0.14+ | 0.11+ | 0.00+ | 65:35 | 4.8 | 52:48 |
| 94 | 9046 | 81 | 0 | 0.14+ | 0.11+ | 0.00+ | 55:45 | 11.4 | 55:45 |
| 95 | 9047 | 81 | 0 | 0.14+ | 0.11+ | 0.00+ | 38:62 | 5.2 | ND |
| 96 | 9048 | 81 | 0 | 0.14+ | 0.11+ | 0.00+ | 63:37 | 9.3 | 79:21 |

TABLE 12-continued

LCCA performance, stability and antigen binding assessments of the LCCA designs, arranged by decreasing DSF values of H1L1 Fab heterodimers

| Row # | Set # | DSF values of h1\|1 Fab heterodimer (° C.) | Change in DSF values of h1\|1 Fab heterodimer compared to wild-type | KD of h1\|1 Fab heterodimer (nM) | Range of KD values for h1\|1 Fab heterodimer (nM) | Change in median values of KD of h1\|1 Fab heterodimer compared to wild type (−(log(KD_design) − log(KD_wt))) | Median LCCA performance normalized to a L1:L2 DNA ratio of 1:1 (Ratio)** | LCCA performance range (Max-Min) at L1:L2 DNA ratio of 1:1** | Median LCCA performance normalized to a L1:L2 DNA ratio of 1:1 (Ratio)*** |
|---|---|---|---|---|---|---|---|---|---|
| 97 | 9786 | 81 | 0 | 0.13 | 0.05 | 0.1 | 92:3 | 6.7 | 91:9 |
| 98 | 9785 | 81 | 0 | 0.13 | 0.05 | 0.1 | 94:6 | 0.1 | ND |
| 99 | 9911 | 81 | 0 | 0.09+ | 0.00+ | 0.27+ | 93:7 | 1.5 | ND |
| 100 | 9571 | 81 | 0 | 0.26 | 0 | −0.21 | 70:30 | 10.7 | ND |
| 101 | 9572 | 81 | 0 | 0.26 | 0 | −0.21 | 69:31 | 8.7 | ND |
| 102 | 9371 | 81 | 0 | 0.22 | 0 | −0.14 | 93:7 | 2 | ND |
| 103 | 9370 | 81 | 0 | 0.22 | 0 | −0.14 | 92:8 | 0.5 | ND |
| 104 | 9909 | 81 | 0 | 0.09+ | 0.00+ | 0.27+ | 61:39 | 0 | ND |
| 105 | 9907 | 81 | 0 | 0.09+ | 0.00+ | 0.27+ | 63:37 | 0 | ND |
| 106 | 9060 | 81 | 0 | 0.14 | 0 | 0.04 | 98:2 | 2.7 | 97:3 |
| 107 | 9369 | 81 | 0 | 0.22 | 0 | −0.14 | 84:16 | 56.1 | ND |
| 108 | 5957 | 81 | 0 | 0.14+ | 0.11+ | 0.00+ | 71:29 | 4.4 | ND |
| 109 | 9082 | 80.9 | −0.1 | 0.16 | 0.02 | −0.01 | 42:58 | 22.9 | 75:25 |
| 110 | 6136 | 80.9 | −0.1 | 0.16 | 0.02 | −0.01 | 52:48 | 2.2 | ND |
| 111 | 6138 | 80.9 | −0.1 | 0.16 | 0.02 | −0.01 | 56:44 | 5.7 | ND |
| 112 | 6666 | 80.9 | −0.1 | 0.16 | 0.02 | −0.01 | 60:40 | 2.6 | ND |
| 113 | 9079 | 80.90* | −0.30* | 0.16* | 0.02* | −0.01* | 73:27 | 3.7 | ND |
| 114 | 9078 | 80.9 | −0.1 | 0.15 | 0 | 0.01 | 92:8 | 3.7 | 85:15 |
| 115 | 9077 | 80.9 | −0.1 | 0.15 | 0 | 0.01 | 91:9 | 2.1 | 80:20 |
| 116 | 9076 | 80.9 | −0.1 | 0.15 | 0 | 0.01 | 77:23 | 5.2 | 82:18 |
| 117 | 9858 | 80.8 | −0.2 | 0.06+ | 0.00+ | 0.46+ | 97:3 | 0.8 | ND |
| 118 | 9853 | 80.8 | −0.2 | 0.06+ | 0.00+ | 0.46+ | 98:2 | 2.6 | 95:5 |
| 119 | 2951 | 80.8 | −0.2 | 0.13 | 0 | 0.08 | 66:34 | 8.7 | ND |
| 120 | 6164 | 80.8 | −0.2 | 0.17 | 0 | −0.04 | 43:57 | 18.5 | ND |
| 121 | 9721 | 80.8 | −0.2 | 0.24 | 0 | −0.19 | 51:49 | 7.5 | ND |
| 122 | 9720 | 80.8 | −0.2 | 0.24 | 0 | −0.19 | 77:23 | 6.9 | 76:24 |
| 123 | 9723 | 80.8 | −0.2 | 0.24 | 0 | −0.19 | 60:40 | 10.2 | ND |
| 124 | 9722 | 80.8 | −0.2 | 0.24 | 0 | −0.19 | 74:26 | 6.4 | 86:14 |
| 125 | 9725 | 80.8 | −0.2 | 0.24 | 0 | −0.19 | 56:44 | 7.5 | ND |
| 126 | 9855 | 80.8 | −0.2 | 0.06+ | 0.00+ | 0.46+ | 97:3 | 0.7 | ND |
| 127 | 9812 | 80.8 | −0.2 | 0.16+ | 0.00+ | −0.01+ | 94:6 | 5.3 | 90:10 |
| 128 | 9811 | 80.8 | −0.2 | 0.16+ | 0.00+ | −0.01+ | 93:7 | 6.3 | 92:8 |
| 129 | 9862 | 80.8 | −0.2 | 0.06+ | 0.00+ | 0.46+ | 98:2 | 8.1 | 93:7 |
| 130 | 9863 | 80.8 | −0.2 | 0.06+ | 0.00+ | 0.46+ | 96:4 | 3.9 | ND |
| 131 | 9860 | 80.8 | −0.2 | 0.06+ | 0.00+ | 0.46+ | 94:6 | 10.8 | 89:11 |
| 132 | 9589 | 80.8 | −0.2 | 0.28 | 0 | −0.25 | 85:15 | 1.9 | ND |
| 133 | 9716 | 80.8 | −0.2 | 0.24 | 0 | −0.19 | 57:43 | 0 | ND |
| 134 | 9712 | 80.8 | −0.2 | 0.24 | 0 | −0.19 | 74:26 | 13.9 | 84:16 |
| 135 | 9574 | 80.8 | −0.2 | 0.27 | 0 | −0.23 | 96:4 | 1.2 | ND |
| 136 | 9573 | 80.8 | −0.2 | 0.27 | 0 | −0.23 | 96:4 | 0.8 | ND |
| 137 | 9587 | 80.8 | −0.2 | 0.28 | 0 | −0.25 | 91:9 | 6.3 | 88:12 |
| 138 | 5933 | 80.8 | −0.2 | 0.15 | 0 | 0.03 | 62:38 | 2.1 | ND |
| 139 | 9898 | 80.8 | −0.2 | 0.07+ | 0.00+ | 0.36+ | 96:4 | 0.3 | ND |
| 140 | 9708 | 80.8 | −0.2 | 0.24 | 0 | −0.19 | 59:41 | 11.3 | ND |
| 141 | 9893 | 80.8 | −0.2 | 0.07+ | 0.00+ | 0.36+ | 98:2 | 2.3 | ND |
| 142 | 9891 | 80.8 | −0.2 | 0.07+ | 0.00+ | 0.36+ | 97:3 | 0.5 | ND |
| 143 | 9896 | 80.8 | −0.2 | 0.07+ | 0.00+ | 0.36+ | 97:3 | 1.6 | ND |
| 144 | 9058 | 80.8 | −0.2 | 0.12 | 0 | 0.12 | 97:3 | 2 | 95:5 |
| 145 | 9588 | 80.8 | −0.2 | 0.28 | 0 | −0.25 | 85:15 | 0 | ND |
| 146 | 9585 | 80.80* | −0.40* | 0.28* | 0.00 | −0.25* | 67:33 | 2 | ND |
| 147 | 9336 | 80.8 | −0.2 | 0.2 | 0 | −0.1 | 86:14 | 1.9 | ND |
| 148 | 9337 | 80.8 | −0.2 | 0.2 | 0 | −0.1 | 83:17 | 2.5 | ND |
| 149 | 9334 | 80.8 | −0.2 | 0.2 | 0 | −0.1 | 97:3 | 2.4 | 95:5 |
| 150 | 9335 | 80.8 | −0.2 | 0.2 | 0 | −0.1 | 92:8 | 2.8 | 95:5 |
| 151 | 6048 | 80.8 | −0.2 | 0.2 | 0 | −0.1 | 88:12 | 4 | ND |
| 152 | 9901 | 80.8 | −0.2 | 0.07+ | 0.00+ | 0.36+ | 96:4 | 1 | ND |
| 153 | 9900 | 80.8 | −0.2 | 0.07+ | 0.00+ | 0.36+ | 96:4 | 2.7 | ND |
| 154 | 9707 | 80.80* | −0.40 | 0.24* | 0.00* | −0.19* | 90:10 | 0 | ND |
| 155 | 9117 | 80.8 | −0.2 | 0.17 | 0 | −0.03 | 97:3 | 1.2 | ND |
| 156 | 9742 | 80.8 | −0.2 | 0.25 | 0 | −0.21 | 88:12 | 2.4 | ND |
| 157 | 9644 | 80.8 | −0.2 | 0.13+ | 0.00+ | 0.09+ | 85:15 | 9.7 | ND |
| 158 | 9809 | 80.7 | −0.3 | 0.14+ | 0.00+ | 0.04+ | 97:3 | 0.3 | ND |
| 159 | 9810 | 80.7 | −0.3 | 0.14+ | 0.00+ | 0.04+ | 97:3 | 4.9 | 85:15 |
| 160 | 9054 | 80.7 | −0.3 | 0.14 | 0 | 0.05 | 87:13 | 5 | 86:14 |
| 161 | 9053 | 80.7 | −0.3 | 0.14 | 0 | 0.05 | 85:15 | 7.6 | 91:9 |
| 162 | 9559 | 80.6 | −0.4 | 0.27 | 0 | −0.24 | 96:4 | 1.4 | ND |

TABLE 12-continued

LCCA performance, stability and antigen binding assessments of the LCCA designs, arranged by decreasing DSF values of H1L1 Fab heterodimers

| Row # | Set # | DSF values of h1\|1 Fab heterodimer (° C.) | Change in DSF values of h1\|1 Fab heterodimer compared to wild-type | KD of h1\|1 Fab heterodimer (nM) | Range of KD values for h1\|1 Fab heterodimer (nM) | Change in median values of KD of h1\|1 Fab heterodimer compared to wild type ($-(\log(KD\_design) - \log(KD\_wt))$) | Median LCCA performance normalized to a L1:L2 DNA ratio of 1:1 (Ratio)** | LCCA performance range (Max-Min) at L1:L2 DNA ratio of 1:1** | Median LCCA performance normalized to a L1:L2 DNA ratio of 1:1 (Ratio)*** |
|---|---|---|---|---|---|---|---|---|---|
| 163 | 9098 | 80.6 | −0.4 | 0.17 | 0 | −0.03 | 97:3 | 2.3 | ND |
| 164 | 9626 | 80.6 | −0.4 | 0.12+ | 0.00+ | 0.12+ | 89:11 | 5.8 | 78:22 |
| 165 | 9629 | 80.60* | −0.60* | 0.12* | 0.00* | 0.12* | 84:16 | 2.6 | ND |
| 166 | 9111 | 80.6 | −0.4 | 0.13 | 0 | 0.09 | 91:9 | 4.3 | 98:2 |
| 167 | 9558 | 80.6 | −0.4 | 0.27 | 0 | −0.24 | 39:11 | 2.4 | 92:3 |
| 168 | 6112 | 80.50* | −0.70* | 0.13* | 0.00* | 0.10* | 13:87 | 9.2 | ND |
| 169 | 2950 | 80.5 | −0.5 | 0.13 | 0 | 0.1 | 62:38 | 4.4 | ND |
| 170 | 9831 | 80.5 | −0.5 | 0.13+ | 0.00+ | 0.09+ | 83:17 | 0 | ND |
| 171 | 9833 | 80.5 | −0.5 | 0.13+ | 0.00+ | 0.09+ | 81:19 | 0 | ND |
| 172 | 9841 | 80.5 | −0.5 | 0.13+ | 0.00+ | 0.09+ | 91:9 | 2 | 87:13 |
| 173 | 10549 | 80.5 | −0.5 | 0.35 | 0 | −0.35 | 96:4 | 2.9 | 93:7 |
| 174 | 9784 | 80.5 | −0.5 | 0.14+ | 0.00+ | 0.05+ | 96:4 | 9.4 | 89:11 |
| 175 | 9783 | 80.5 | −0.5 | 0.14+ | 0.00+ | 0.05+ | 96:4 | 1.4 | ND |
| 176 | 9657 | 80.50* | −0.70* | 0.19* | 0.00* | −0.08* | 83:17 | 33.4 | ND |
| 177 | 9753 | 80.5 | −0.5 | ND, low Fab capture | ND, low Fab capture | ND, low Fab capture | 89:11 | 4.9 | 77:23 |
| 178 | 9660 | 80.5 | −0.5 | 0.19+ | 0.00+ | −0.08+ | 34:16 | 4.8 | ND |
| 179 | 9836 | 80.5 | −0.5 | 0.13+ | 0.00+ | 0.09+ | 92:8 | 5 | 89:11 |
| 180 | 9338 | 80.5 | −0.5 | 0.13+ | 0.00+ | 0.09+ | 94:6 | 3.5 | 94:6 |
| 181 | 9987 | 80.5 | −0.5 | 0.11+ | 0.00+ | 0.15+ | 46:54 | 0 | ND |
| 182 | 9740 | 80.5 | −0.5 | 0.2 | 0 | −0.09 | 95:5 | 3.3 | 89:11 |
| 183 | 9746 | 80.5 | −0.5 | 0.35 | 0 | −0.35 | 94:6 | 0.1 | ND |
| 184 | 9342 | 80.5 | −0.5 | 0.34 | 0 | −0.34 | 97:3 | 3.1 | 96:4 |
| 185 | 9737 | 80.5 | −0.5 | 0.2 | 0 | −0.09 | 96:4 | 10 | 93:7 |
| 186 | 9735 | 80.5 | −0.5 | 0.2 | 0 | −0.09 | 96:4 | 21.1 | 74:26 |
| 187 | 7046 | 80.50* | −0.70* | 0.17* | 0.00* | −0.04 | 91:9 | 4.3 | ND |
| 188 | 9801 | 80.4 | −0.6 | 0.11+ | 0.00+ | 0.16+ | 97:3 | 1.4 | ND |
| 189 | 9802 | 80.4 | −0.6 | 0.11+ | 0.00+ | 0.16+ | 95:5 | 10.8 | 86:14 |
| 190 | 9667 | 80.4 | −0.6 | 0.27 | 0 | −0.23 | 91:9 | 3.6 | 90:10 |
| 191 | 9869 | 80.4 | −0.6 | 0.05 | 0 | 0.51 | 82:18 | 7.5 | ND |
| 192 | 9654 | 80.4 | −0.6 | 0.15+ | 0.00+ | 0.02+ | 73:27 | 38.5 | ND |
| 193 | 9651 | 80.40* | −0.80* | 0.15* | 0.00* | 0.02* | 34:16 | 24.7 | ND |
| 194 | 9755 | 80.4 | −0.6 | 0.28 | 0 | −0.26 | 77:23 | 3.2 | 80:20 |
| 195 | 9756 | 80.4 | −0.6 | 0.28 | 0 | −0.26 | 88:12 | 0.9 | 87:13 |
| 196 | 9620 | 80.4 | −0.6 | 0.06+ | 0.00+ | 0.39+ | 84:16 | 10.3 | 88:12 |
| 197 | 9623 | 80.40* | −0.80* | 0.06* | 0.00* | 0.39* | 69:31 | 30.5 | ND |
| 198 | 9871 | 80.4 | −0.6 | 0.05 | 0 | 0.51 | 80:20 | 0 | ND |
| 199 | 9874 | 80.4 | −0.6 | 0.05 | 0 | 0.51 | 83:17 | 6.3 | 89:11 |
| 200 | 9876 | 80.4 | −0.6 | 0.05 | 0 | 0.51 | 81:19 | 17.1 | 86:14 |
| 201 | 9879 | 80.4 | −0.6 | 0.05 | 0 | 0.51 | 72:28 | 5.7 | ND |
| 202 | 9663 | 80.40* | −0.80* | 0.27* | 0.00* | −0.23* | 91:9 | 13.6 | 78:22 |
| 203 | 9666 | 80.40* | −0.80* | 0.27* | 0.00* | −0.23* | 92:8 | 5.1 | 88:12 |
| 204 | 9682 | 80.4 | −0.6 | 0.27 | 0 | −0.23 | 93:7 | 1.3 | 92:8 |
| 205 | 9679 | 80.4 | −0.6 | 0.27 | 0 | −0.23 | 85:15 | 5.6 | 83:17 |
| 206 | 9671 | 80.4 | −0.6 | 0.27 | 0 | −0.23 | 86:14 | 2.5 | 85:15 |
| 207 | 9675 | 80.4 | −0.6 | 0.27 | 0 | −0.23 | 92:8 | 15.4 | 92:8 |
| 208 | 9140 | 80.30* | −0.90* | 0.16* | 0.00* | 0.00* | 95:5 | 3.4 | ND |
| 209 | 10552 | 80.3 | −0.7 | 0.29 | 0 | −0.27 | 99:1 | 0.1 | 99:1 |
| 210 | 9547 | 80.3 | −0.7 | 0.24 | 0 | −0.18 | 92:8 | 0 | ND |
| 211 | 9546 | 80.3 | −0.7 | 0.24 | 0 | −0.18 | 87:13 | 14.2 | 85:15 |
| 212 | 9144 | 80.30* | −0.90* | 0.16* | 0.00* | 0.00* | 95:5 | 2.6 | ND |
| 213 | 9146 | 80.30* | −0.90* | 0.16* | 0.00* | 0.00* | 96:4 | 3.1 | 96:4 |
| 214 | 9142 | 80.30* | −0.90* | 0.16* | 0.00* | 0.00* | 97:3 | 3.4 | 97:3 |
| 215 | 9758 | 80.3 | −0.7 | 0.29 | 0 | −0.27 | 95:5 | 17.8 | 84:16 |
| 216 | 9614 | 80.3 | −0.7 | ND, low Fab capture | ND, low Fab capture | ND, low Fab capture | 86:14 | 6.2 | 86:14 |
| 217 | 9757 | 80.3 | −0.7 | 0.29 | 0 | −0.27 | 98:2 | 3.9 | ND |
| 218 | 9134 | 80.3 | −0.7 | 0.16 | 0 | 0 | 94:6 | 6.7 | ND |
| 219 | 9136 | 80.30* | −0.90* | 0.16* | 0.00* | 0.00* | 96:4 | 2.2 | ND |
| 220 | 9374 | 80.3 | −0.7 | 0.23 | 0 | −0.16 | 77:23 | 34.8 | ND |
| 221 | 9375 | 80.3 | −0.7 | 0.23 | 0 | −0.16 | 76:24 | 23.2 | 75:25 |
| 222 | 6135 | 80.3 | −0.7 | 0.13 | 0 | 0.07 | 87:13 | 0.3 | ND |
| 223 | 9752 | 80.3 | −0.7 | 0.29 | 0 | −0.27 | 95:5 | 3 | ND |
| 224 | 9138 | 80.30* | −0.90* | 0.16* | 0.00* | 0.00* | 95:5 | 4.6 | ND |

TABLE 12-continued

LCCA performance, stability and antigen binding assessments of the LCCA designs, arranged by decreasing DSF values of H1L1 Fab heterodimers

| Row # | Set # | DSF values of h1\|1 Fab heterodimer (° C.) | Change in DSF values of h1\|1 Fab heterodimer compared to wild-type | KD of h1\|1 Fab heterodimer (nM) | Range of KD values for h1\|1 Fab heterodimer (nM) | Change in median values of KD of h1\|1 Fab heterodimer compared to wild type ($-(\log(KD\_design) - \log(KD\_wt))$) | Median LCCA performance normalized to a L1:L2 DNA ratio of 1:1 (Ratio)** | LCCA performance range (Max-Min) at L1:L2 DNA ratio of 1:1** | Median LCCA performance normalized to a L1:L2 DNA ratio of 1:1 (Ratio)*** |
|---|---|---|---|---|---|---|---|---|---|
| 225 | 9347 | 80.3 | −0.7 | 0.23 | 0 | −0.16 | 89:11 | 1.8 | 94:6 |
| 226 | 9617 | 80.30* | −0.90* | ND | ND | ND | 35:15 | 3.3 | 89:11 |
| 227 | 9556 | 80.3 | −0.7 | 0.24 | 0 | −0.18 | 93:7 | 0 | ND |
| 228 | 9555 | 80.3 | −0.7 | 0.24 | 0 | −0.18 | 92:8 | 13.4 | 92:8 |
| 229 | 9553 | 80.3 | −0.7 | 0.24 | 0 | −0.18 | 93:7 | 2.7 | 88:12 |
| 230 | 9550 | 80.3 | −0.7 | 0.24 | 0 | −0.18 | 89:11 | 19.8 | ND |
| 231 | 9917 | 80.2 | −0.8 | 0.10+ | 0.00+ | 0.20+ | 58:42 | 21.2 | 62:38 |
| 232 | 5995 | 80.2 | −0.8 | 0.14 | 0 | 0.04 | 49:51 | 11.6 | ND |
| 233 | 9561 | 80.2 | −0.3 | 0.21 | 0 | −0.13 | 97:3 | 0.3 | ND |
| 234 | 9560 | 80.2 | −0.8 | 0.21 | 0 | −0.13 | 91:9 | 1.3 | 89:11 |
| 235 | 6098 | 80.2 | −0.8 | 0 | 0 | 0.34 | 87:13 | 3.1 | ND |
| 236 | 9641 | 80.10* | −1.10* | 0.11* | 0.00* | 0.17* | 65:35 | 3.3 | ND |
| 237 | 9432 | 80.1 | −0.9 | 0.28 | 0 | −0.26 | 91:9 | 2.8 | 82:18 |
| 238 | 9436 | 80.1 | −0.9 | 0.28 | 0 | −0.26 | 96:4 | 0 | ND |
| 239 | 6043 | 80.1 | −0.9 | 0.13 | 0 | 0.07 | 39:61 | 6.8 | ND |
| 240 | 6037 | 80.1 | −0.9 | 0.13 | 0 | 0.07 | 41:59 | 0.8 | ND |
| 241 | 9440 | 80.1 | −0.9 | 0.28 | 0 | −0.26 | 95:5 | 0 | ND |
| 242 | 9444 | 80.1 | −0.9 | 0.28 | 0 | −0.26 | 67:33 | 66.2 | ND |
| 243 | 9446 | 80.1 | −0.9 | 0.28 | 0 | −0.26 | 83:17 | 24.8 | ND |
| 244 | 9447 | 80.1 | −0.9 | 0.28 | 0 | −0.26 | 85:15 | 23.3 | ND |
| 245 | 9638 | 80.1 | −0.9 | 0.11+ | 0.00+ | 0.17+ | 76:24 | 16.7 | ND |
| 246 | 9102 | 80 | −1 | 0.15 | 0 | 0.02 | 93:7 | 1.5 | ND |
| 247 | 9978 | 80 | −1 | 0.14+ | 0.00+ | 0.05+ | 99:1 | 0.6 | ND |
| 248 | 9579 | 80.00* | −1.20* | 0.28* | 0.00* | −0.25* | 79:21 | 14.5 | ND |
| 249 | 9575 | 80 | −1 | 0.28 | 0 | −0.25 | 89:11 | 1.4 | 89:11 |
| 250 | 9982 | 80 | −1 | 0.14+ | 0.00+ | 0.05+ | 98:2 | 0.3 | ND |
| 251 | 6137 | 80 | −1 | 0.16 | 0 | 0 | 92:8 | 6.5 | ND |
| 252 | 9122 | 80 | −1 | 0.13 | 0 | 0.1 | 81:19 | 8 | ND |
| 253 | 6665 | 80 | −1 | 0.17 | 0 | −0.04 | 86:14 | 4 | ND |
| 254 | 5997 | 80 | −1 | 0.08 | 0 | 0.29 | 47:53 | 9.1 | ND |
| 255 | 9743 | 80 | −1 | 0.28 | 0 | −0.25 | 86:14 | 1.4 | ND |
| 256 | 9744 | 80 | −1 | 0.28 | 0 | −0.25 | 94:6 | 15.2 | 79:21 |
| 257 | 9103 | 80 | −1 | 0.15 | 0 | 0.02 | 95:5 | 0.7 | ND |
| 258 | 9486 | 80 | −1 | 0.23 | 0 | −0.17 | 92:8 | 0 | ND |
| 259 | 9437 | 80 | −1 | 0.23 | 0 | −0.17 | 93:7 | 2.9 | ND |
| 260 | 9488 | 80 | −1 | 0.23 | 0 | −0.17 | 91:9 | 1.3 | ND |
| 261 | 9489 | 80 | −1 | 0.23 | 0 | −0.17 | 88:12 | 10.8 | ND |
| 262 | 9109 | 79.9 | −1.1 | 0.16 | 0 | −0.01 | 85:15 | 0.6 | ND |
| 263 | 9645 | 79.90* | −1.30* | 0.14* | 0.00 | 0.05* | 88:12 | 4 | 88:12 |
| 264 | 9643 | 79.9 | −1.1 | 0.14+ | 0.00+ | 0.05+ | 70:30 | 34.2 | ND |
| 265 | 9888 | 79.9 | −1.1 | 0.14+ | 0.00+ | 0.06+ | 96:4 | 4.3 | 82:18 |
| 266 | 9887 | 79.9 | −1.1 | 0.14+ | 0.00+ | 0.06+ | 96:4 | 1.1 | ND |
| 267 | 6054 | 79.9 | −1.1 | 0.24 | 0 | −0.18 | 67:33 | 1.8 | ND |
| 268 | 9092 | 79.9 | −1.1 | 0.16 | 0 | −0.02 | 97:3 | 2 | ND |
| 269 | 9091 | 79.9 | −1.1 | 0.16 | 0 | −0.02 | 94:6 | 3.6 | 96:4 |
| 270 | 9090 | 79.9 | −1.1 | 0.16 | 0 | −0.02 | 95:5 | 9.9 | 94:6 |
| 271 | 9338 | 79.9 | −1.1 | 0.24 | 0 | −0.18 | 39:11 | 3.4 | ND |
| 272 | 9339 | 79.9 | −1.1 | 0.24 | 0 | −0.18 | 53:42 | 5.5 | 72:23 |
| 273 | 9116 | 79.9 | −1.1 | 0.16 | 0 | −0.02 | 87:13 | 0 | ND |
| 274 | 9609 | 79.30* | −1.40* | ND | ND | ND | 79:21 | 9.1 | 87:13 |
| 275 | 9606 | 79.80* | −1.40* | ND | ND | ND | 59:41 | 14.3 | ND |
| 276 | 9602 | 79.80* | −1.40* | ND | ND | ND | 32:18 | 10.2 | 81:19 |
| 277 | 9107 | 79.8 | −1.2 | 0.16 | 0 | −0.01 | 99:1 | 6.7 | 98:2 |
| 278 | 9106 | 79.8 | −1.2 | 0.16 | 0 | −0.01 | 90:10 | 0.5 | ND |
| 279 | 9108 | 79.30* | −1.40* | 0.16* | 0.00* | −0.01* | 93:7 | 1.3 | ND |
| 280 | 9850 | 79.8 | −1.2 | 0.15+ | 0.00+ | 0.01+ | 96:4 | 10.5 | 96:4 |
| 281 | 9981 | 79.8 | −1.2 | 0.12+ | 0.00+ | 0.10+ | 96:4 | 1.7 | ND |
| 282 | 9495 | 79.8 | −1.2 | 0.24 | 0 | −0.19 | 93:7 | 0.1 | ND |
| 283 | 9492 | 79.8 | −1.2 | 0.24 | 0 | −0.19 | 76:24 | 62.6 | ND |
| 284 | 9491 | 79.8 | −1.2 | 0.24 | 0 | −0.19 | 70:30 | 58.7 | ND |
| 285 | 9498 | 79.8 | −1.2 | 0.24 | 0 | −0.19 | 79:21 | 52.3 | ND |
| 286 | 9889 | 79.8 | −1.2 | 0.05+ | 0.00+ | 0.49+ | 94:6 | 8.4 | 87:13 |
| 287 | 9593 | 79.3 | −1.2 | ND, low Fab capture | ND, low Fab capture | ND, low Fab capture | 73:27 | 4.7 | ND |

TABLE 12-continued

LCCA performance, stability and antigen binding assessments of the LCCA designs, arranged by decreasing DSF values of H1L1 Fab heterodimers

| Row # | Set # | DSF values of h1\|1 Fab heterodimer (° C.) | Change in DSF values of h1\|1 Fab heterodimer compared to wild-type | KD of h1\|1 Fab heterodimer (nM) | Range of KD values for h1\|1 Fab heterodimer (nM) | Change in median values of KD of h1\|1 Fab heterodimer compared to wild type (−(log(KD_design) − log(KD_wt))) | Median LCCA performance normalized to a L1:L2 DNA ratio of 1:1 (Ratio)** | LCCA performance range (Max-Min) at L1:L2 DNA ratio of 1:1** | Median LCCA performance normalized to a L1:L2 DNA ratio of 1:1 (Ratio)*** |
|---|---|---|---|---|---|---|---|---|---|
| 288 | 9590 | 79.8 | −1.2 | ND, low Fab capture | ND, low Fab capture | ND, low Fab capture | 72:28 | 6.7 | ND |
| 289 | 9594 | 79.80* | −1.40* | ND | ND | ND | 59:41 | 22.4 | ND |
| 290 | 9598 | 79.80* | −1.40* | ND | ND | ND | 59:41 | 26 | ND |
| 291 | 9867 | 79.8 | −1.2 | 0.14+ | 0.00+ | 0.06+ | 95:5 | 2.1 | ND |
| 292 | 9368 | 79.3 | −1.2 | 0.14+ | 0.00+ | 0.06+ | 94:6 | 10.4 | 87:13 |
| 293 | 9501 | 79.8 | −1.2 | 0.24 | 0 | −0.19 | 92:8 | 0 | ND |
| 294 | 9500 | 79.8 | −1.2 | 0.24 | 0 | −0.19 | 89:11 | 10.2 | ND |
| 295 | 9849 | 79.8 | −1.2 | 0.15+ | 0.00+ | 0.01+ | 98:2 | 2.8 | ND |
| 296 | 9392 | 79.8 | −1.2 | 0.22 | 0 | −0.15 | 93:7 | 2.9 | ND |
| 297 | 9394 | 79.3 | −1.2 | 0.22 | 0 | −0.15 | 92:8 | 13.9 | 91:9 |
| 298 | 9395 | 79.3 | −1.2 | 0.22 | 0 | −0.15 | 93:7 | 1.3 | ND |
| 299 | 9096 | 79.8 | −1.2 | 0.17 | 0 | −0.04 | 96:4 | 4.5 | 94:6 |
| 300 | 9095 | 79.8 | −1.2 | 0.17 | 0 | −0.04 | 94:6 | 1.2 | 96:4 |
| 301 | 9094 | 79.8 | −1.2 | 0.17 | 0 | −0.04 | 94:6 | 10 | 93:7 |
| 302 | 9986 | 79.30* | −1.40* | ND | ND | ND | 47:53 | 0 | ND |
| 303 | 9376 | 79.3 | −1.2 | 0.22 | 0 | −0.15 | 92:8 | 0.3 | ND |
| 304 | 9471 | 79.8 | −1.2 | 0.18 | 0 | −0.07 | 90:10 | 0 | ND |
| 305 | 9473 | 79.8 | −1.2 | 0.18 | 0 | −0.07 | 93:7 | 0 | ND |
| 306 | 9890 | 79.8 | −1.2 | 0.05+ | 0.00+ | 0.49+ | 93:7 | 14.2 | 82:18 |
| 307 | 9754 | 79.8 | −1.2 | 0.3 | 0 | −0.28 | 86:14 | 13.3 | 82:18 |
| 308 | 9330 | 79.3 | −1.2 | 0.22 | 0 | −0.15 | 92:8 | 0.7 | 84:16 |
| 309 | 9384 | 79.8 | −1.2 | 0.22 | 0 | −0.15 | 92:8 | 0 | ND |
| 310 | 9980 | 79.8 | −1.2 | 0.16+ | 0.00+ | 0.00+ | 97:3 | 0.1 | ND |
| 311 | 9985 | 79.8 | −1.2 | 0.12+ | 0.00+ | 0.10+ | 95:5 | 2.3 | ND |
| 312 | 9984 | 79.8 | −1.2 | 0.16+ | 0.00+ | 0.00+ | 97:3 | 0.5 | ND |
| 313 | 9327 | 79.3 | −1.2 | 0.24 | 0 | −0.19 | 99:1 | 0.5 | ND |
| 314 | 9326 | 79.8 | −1.2 | 0.24 | 0 | −0.19 | 94:6 | 0 | ND |
| 315 | 9328 | 79.80* | −1.40* | 0.24* | 0.00* | −0.19 | 93:7 | 0 | ND |
| 316 | 9484 | 79.8 | −1.2 | 0.18 | 0 | −0.07 | 92:8 | 0 | ND |
| 317 | 9481 | 79.8 | −1.2 | 0.18 | 0 | −0.07 | 91:9 | 4.5 | ND |
| 318 | 9433 | 79.3 | 2 | 0.18 | 0 | −0.07 | 90:10 | 7.4 | ND |
| 319 | 9388 | 79.8 | −1.2 | 0.22 | 0 | −0.15 | 92:8 | 0 | ND |
| 320 | 9451 | 79.7 | −1.3 | 0.26 | 0 | −0.23 | 93:7 | 0 | ND |
| 321 | 9459 | 79.7 | −1.3 | 0.26 | 0 | −0.23 | 92:8 | 1.2 | ND |
| 322 | 9541 | 79.7 | −1.3 | 0.22 | 0 | −0.15 | 91:9 | 0 | ND |
| 323 | 9463 | 79.7 | −1.3 | 0.18 | 0 | −0.07 | 82:18 | 50.6 | ND |
| 324 | 9469 | 79.7 | −1.3 | 0.18 | 0 | −0.07 | 82:18 | 46.8 | ND |
| 325 | 9544 | 79.7 | −1.3 | 0.22 | 0 | −0.15 | 92:8 | 0 | ND |
| 326 | 9463 | 79.7 | −1.3 | 0.18 | 0 | −0.07 | 31:19 | 47.9 | ND |
| 327 | 9460 | 79.7 | −1.3 | 0.26 | 0 | −0.23 | 91:9 | 3.1 | ND |
| 328 | 9461 | 79.7 | −1.3 | 0.26 | 0 | −0.23 | 89:11 | 0 | ND |
| 329 | 9466 | 79.7 | −1.3 | 0.18 | 0 | −0.07 | 85:15 | 50 | ND |
| 330 | 9464 | 79.7 | −1.3 | 0.18 | 0 | −0.07 | 93:7 | 4.4 | ND |
| 331 | 9465 | 79.7 | −1.3 | 0.18 | 0 | −0.07 | 93:7 | 2.9 | ND |
| 332 | 9824 | 79.7 | −1.3 | 0.15+ | 0.00+ | 0.03+ | 94:6 | 11.6 | 93:7 |
| 333 | 9364 | 79.7 | −1.3 | 0.15 | 0 | 0.01 | 73:27 | 0 | ND |
| 334 | 9367 | 79.7 | −1.3 | 0.15 | 0 | 0.01 | 78:22 | 0 | ND |
| 335 | 9366 | 79.7 | −1.3 | 0.15 | 0 | 0.01 | 30:20 | 0 | ND |
| 336 | 9368 | 79.7 | −1.3 | 0.15 | 0 | 0.01 | 91:9 | 0 | ND |
| 337 | 9449 | 79.7 | −1.3 | 0.26 | 0 | −0.23 | 82:18 | 0 | ND |
| 338 | 9778 | 79.7 | −1.3 | 0.12+ | 0.00+ | 0.13+ | 94:6 | 0.5 | ND |
| 339 | 9542 | 79.7 | −1.3 | 0.22 | 0 | −0.15 | 94:6 | 0 | ND |
| 340 | 9777 | 79.7 | −1.3 | 0.12+ | 0.00+ | 0.13+ | 97:3 | 0.1 | ND |
| 341 | 9852 | 79.6 | −1.4 | 0.15+ | 0.00+ | 0.02+ | 95:5 | 9.7 | 89:11 |
| 342 | 9851 | 79.6 | −1.4 | 0.15+ | 0.00+ | 0.02+ | 91:9 | 14.4 | 90:10 |
| 343 | 9130 | 79.60* | −1.60* | 0.15* | 0.00* | 0.02* | 92:8 | 5.1 | ND |
| 344 | 9131 | 79.60* | −1.60* | 0.15* | 0.00* | 0.02* | 94:6 | 3.7 | ND |
| 345 | 9152 | 79.60* | −1.60* | 0.16* | 0.00* | −0.01* | 96:4 | 2.3 | ND |
| 346 | 9126 | 79.60* | −1.60* | 0.15* | 0.00* | 0.02* | 94:6 | 2.2 | ND |
| 347 | 9125 | 79.60* | −1.60* | 0.15* | 0.00* | 0.02* | 92:8 | 2.2 | ND |
| 348 | 9123 | 79.6 | −1.4 | 0.15 | 0 | 0.02 | 94:6 | 3.2 | ND |
| 349 | 9684 | 79.6 | −1.4 | 0.3 | 0 | −0.28 | 60:40 | 3.1 | ND |
| 350 | 9683 | 79.60* | −1.60* | 0.30* | 0.00 | −0.28* | 89:11 | 6.5 | 75:25 |
| 351 | 9129 | 79.60* | −1.60* | 0.15* | 0.00* | 0.02* | 94:6 | 6.4 | ND |

TABLE 12-continued

LCCA performance, stability and antigen binding assessments of the LCCA designs, arranged by decreasing DSF values of H1L1 Fab heterodimers

| Row # | Set # | DSF values of h1\|1 Fab heterodimer (° C.) | Change in DSF values of h1\|1 Fab heterodimer compared to wild-type | KD of h1\|1 Fab heterodimer (nM) | Range of KD values for h1\|1 Fab heterodimer (nM) | Change in median values of KD of h1\|1 Fab heterodimer compared to wild type (−(log(KD_design) − log(KD_wt))) | Median LCCA performance normalized to a L1:L2 DNA ratio of 1:1 (Ratio)** | LCCA performance range (Max-Min) at L1:L2 DNA ratio of 1:1** | Median LCCA performance normalized to a L1:L2 DNA ratio of 1:1 (Ratio)*** |
|---|---|---|---|---|---|---|---|---|---|
| 352 | 9127 | 79.60* | −1.60* | 0.15* | 0.00* | 0.02* | 94:6 | 4.3 | ND |
| 353 | 9162 | 79.60* | −1.60* | 0.16* | 0.00* | −0.01* | 97:3 | 1.2 | ND |
| 354 | 9160 | 79.60* | −1.60* | 0.16* | 0.00* | −0.01* | 96:4 | 3.1 | ND |
| 355 | 9164 | 79.60* | −1.60* | 0.16* | 0.00 | −0.01* | 97:3 | 2.6 | 99:1 |
| 356 | 9150 | 79.6 | −1.4 | 0.16 | 0 | −0.01 | 97:3 | 1.3 | 37:63 |
| 357 | 9156 | 79.60* | −1.60* | 0.16* | 0.00* | −0.01* | 96:4 | 3.5 | 95:5 |
| 358 | 9154 | 79.60* | −1.60* | 0.16* | 0.00* | −0.01* | 97:3 | 2.8 | 97:3 |
| 359 | 9158 | 79.60* | −1.60* | 0.16* | 0.00* | −0.01* | 96:4 | 2.2 | ND |
| 360 | 9426 | 79.5 | −1.5 | 0.23 | 0 | −0.16 | 88:12 | 0 | ND |
| 361 | 9425 | 79.5 | −1.5 | 0.23 | 0 | −0.16 | 92:8 | 0 | ND |
| 362 | 9423 | 79.5 | −1.5 | 0.23 | 0 | −0.16 | 93:7 | 6.3 | ND |
| 363 | 9420 | 79.5 | −1.5 | 0.23 | 0 | −0.16 | 90:10 | 0 | ND |
| 364 | 9979 | 79.5 | −1.5 | 0.14+ | 0.00+ | 0.05+ | 98:2 | 0.4 | ND |
| 365 | 9419 | 79.5 | −1.5 | 0.23 | 0 | −0.16 | 90:10 | 0.3 | ND |
| 366 | 9393 | 79.5 | −1.5 | 0.2 | 0 | −0.12 | 92:8 | 1.3 | ND |
| 367 | 9397 | 79.5 | −1.5 | 0.19 | 0 | −0.08 | 91:9 | 3.1 | 94:6 |
| 368 | 9121 | 79.5 | −1.5 | 0.13 | 0 | 0.03 | 93:2 | 3.3 | 93:2 |
| 369 | 9983 | 79.5 | −1.5 | 0.14+ | 0.00+ | 0.05+ | 97:3 | 0.2 | ND |
| 370 | 9750 | 79.5 | −1.5 | 0.23 | 0 | −0.16 | 97:3 | 0 | ND |
| 371 | 9406 | 79.5 | −1.5 | 0.2 | 0 | −0.12 | 96:4 | 0 | ND |
| 372 | 9402 | 79.5 | −1.5 | 0.2 | 0 | −0.12 | 90:10 | 19.1 | 84:16 |
| 373 | 9830 | 79.5 | −1.5 | 0.06+ | 0.00+ | 0.41+ | 93:2 | 2.9 | 90:10 |
| 374 | 9829 | 79.5 | −1.5 | 0.06+ | 0.00+ | 0.41+ | 99:1 | 0.5 | ND |
| 375 | 9120 | 79.5 | −1.5 | 0.13 | 0 | 0.08 | 53:47 | 17.4 | ND |
| 376 | 9749 | 79.5 | −1.5 | 0.23 | 0 | −0.16 | 87:13 | 7.1 | ND |
| 377 | 9417 | 79.5 | −1.5 | 0.2 | 0 | −0.12 | 73:27 | 49.1 | ND |
| 378 | 9416 | 79.5 | −1.5 | 0.2 | 0 | −0.12 | 91:9 | 0 | ND |
| 379 | 9414 | 79.5 | −1.5 | 0.2 | 0 | −0.12 | 89:11 | 6.2 | 94:6 |
| 380 | 9410 | 79.5 | −1.5 | 0.2 | 0 | −0.12 | 93:7 | 3.4 | ND |
| 381 | 9341 | 79.4 | −1.6 | 0.26 | 0 | −0.22 | 75:25 | 4.1 | ND |
| 382 | 9340 | 79.4 | −1.6 | 0.26 | 0 | −0.22 | 66:34 | 1.9 | ND |
| 383 | 9819 | 79.3 | −1.7 | 0.15+ | 0.00+ | 0.03+ | 97:3 | 0.4 | 95:5 |
| 384 | 9564 | 79.3 | −1.7 | ND, low Fab capture | ND, low Fab capture | ND, low Fab capture | 89:11 | 3.3 | ND |
| 385 | 9562 | 79.3 | −1.7 | ND, low Fab capture | ND, low Fab capture | ND, low Fab capture | 78:22 | 4.8 | ND |
| 386 | 9814 | 79.2 | −1.8 | 0.16+ | 0.00+ | −0.01+ | 93:7 | 4.5 | 90:10 |
| 387 | 9332 | 79.2 | −1.8 | 0.25 | 0 | −0.2 | 86:14 | 1.4 | ND |
| 388 | 9330 | 79.2 | −1.8 | 0.25 | 0 | −0.2 | 79:21 | 5.2 | ND |
| 389 | 9114 | 79.1 | −1.9 | 0.14 | 0 | 0.04 | 90:10 | 0 | ND |
| 390 | 9113 | 79.1 | −1.9 | 0.14 | 0 | 0.04 | 74:26 | 0 | ND |
| 391 | 9748 | 79.1 | −1.9 | 0.36 | 0 | −0.36 | 99:1 | 1.6 | ND |
| 392 | 9747 | 79.1 | −1.9 | 0.36 | 0 | −0.36 | 89:11 | 5.3 | 78:22 |
| 393 | 10550 | 79 | −2 | ND, low Fab capture | ND, low Fab capture | ND, low Fab capture | 99:1 | 1.3 | 99:1 |
| 394 | 9290 | 79 | −2 | 0.2 | 0 | −0.11 | 95:5 | 4.3 | 95:5 |
| 395 | 9049 | 79 | −2 | 0.16 | 0 | −0.01 | 39:11 | 0.7 | ND |
| 396 | 9827 | 79 | −2 | 0.17+ | 0.00+ | −0.03 | 92:8 | 6.5 | ND |
| 397 | 9751 | 79 | −2 | ND, low Fab capture | ND, low Fab capture | ND, low Fab capture | 97:3 | 0.3 | ND |
| 398 | 9067 | 79 | −2 | 0.18 | 0 | −0.06 | 96:4 | 2.3 | ND |
| 399 | 9279 | 79.00* | −2.20* | 0.20* | 0.00* | −0.11* | 95:5 | 3.2 | ND |
| 400 | 9283 | 79 | −2 | 0.2 | 0 | −0.11 | 95:5 | 6.4 | 98:2 |
| 401 | 9281 | 79 | −2 | 0.2 | 0 | −0.11 | 96:4 | 2.4 | ND |
| 402 | 9286 | 79 | −2 | 0.2 | 0 | −0.11 | 97:3 | 1.9 | 97:3 |

TABLE 12-continued

LCCA performance, stability and antigen binding assessments of the LCCA
designs, arranged by decreasing DSF values of H1L1 Fab heterodimers

| Row # | Set # | DSF values of h1\|1 Fab heterodimer (° C.) | Change in DSF values of h1\|1 Fab heterodimer compared to wild-type | KD of h1\|1 Fab heterodimer (nM) | Range of KD values for h1\|1 Fab heterodimer (nM) | Change in median values of KD of h1\|1 Fab heterodimer compared to wild type (−(log(KD_design) − log(KD_wt))) | Median LCCA performance normalized to a L1:L2 DNA ratio of 1:1 (Ratio)** | LCCA performance range (Max-Min) at L1:L2 DNA ratio of 1:1** | Median LCCA performance normalized to a L1:L2 DNA ratio of 1:1 (Ratio)*** |
|---|---|---|---|---|---|---|---|---|---|
| 403 | 9287 | 79 | −2 | 0.2 | 0 | −0.11 | 95:5 | 3 | ND |
| 404 | 9284 | 79 | −2 | 0.2 | 0 | −0.11 | 96:4 | 2.7 | ND |
| 405 | 9169 | 78.8 | −2.2 | ND, low Fab capture | ND, low Fab capture | ND, low Fab capture | 94:6 | 7.7 | ND |
| 406 | 9168 | 78.8 | −2.2 | ND, low Fab capture | ND, low Fab capture | ND, low Fab capture | 95:5 | 26.9 | ND |
| 407 | 9818 | 78.7 | −2.3 | 0.18+ | 0.00+ | −0.07+ | 90:10 | 10.5 | 94:6 |
| 408 | 9277 | 78.6 | −2.4 | 0.2 | 0 | −0.12 | 96:4 | 2.2 | ND |
| 409 | 9275 | 78.6 | −2.4 | 0.2 | 0 | −0.12 | 94:6 | 2.6 | ND |
| 410 | 9273 | 78.6 | −2.4 | 0.2 | 0 | −0.12 | 95:5 | 1.6 | ND |
| 411 | 9271 | 78.6 | −2.4 | 0.2 | 0 | −0.12 | 95:5 | 1.3 | ND |
| 412 | 9211 | 78.5 | −2.5 | 0.2 | 0 | −0.11 | 92:8 | 3.2 | ND |
| 413 | 9213 | 78.5 | −2.5 | 0.2 | 0 | −0.11 | 93:7 | 0.7 | ND |
| 414 | 9212 | 78.5 | −2.5 | 0.2 | 0 | −0.11 | 94:6 | 1 | ND |
| 415 | 9173 | 78.5 | −2.5 | 0.25 | 0 | −0.21 | 91:9 | 0 | ND |
| 416 | 9174 | 78.5 | −2.5 | 0.25 | 0 | −0.21 | 93:7 | 0 | ND |
| 417 | 9175 | 78.5 | −2.5 | 0.25 | 0 | −0.21 | 92:8 | 2.4 | ND |
| 418 | 9823 | 78.4 | −2.6 | 0.24+ | 0.00+ | −0.18+ | 94:6 | 3.4 | 97:3 |
| 419 | 9210 | 78.3 | −2.7 | ND, low Fab capture | ND, low Fab capture | ND, low Feb capture | 92:8 | 1.4 | ND |
| 420 | 9042 | 78.3 | ND | 0.18 | 0 | ND | 98:2 | 2.2 | 98:2 |
| 421 | 9816 | 78.3 | −2.7 | 0.19+ | 0.00+ | −0.09+ | 96:4 | 2 | ND |
| 422 | 9256 | 73.3 | −2.7 | 0.26 | 0 | −0.21 | 95:5 | 1.6 | ND |
| 423 | 9821 | 78.3 | −2.7 | 0.07+ | 0.00+ | 0.38+ | 92:8 | 4.3 | ND |
| 424 | 9826 | 78.3 | −2.7 | 0.06+ | 0.00+ | 0.43+ | 86:14 | 3.5 | ND |
| 425 | 9208 | 78.3 | −2.7 | ND, low Fab capture | ND, low Fab capture | ND, low Fab capture | 92:8 | 2.9 | ND |
| 426 | 9209 | 78.3 | −2.7 | ND, low Fab capture | ND, low Fab capture | ND, low Fab capture | 94:6 | 0.5 | ND |
| 427 | 9250 | 78.3 | −2.7 | 0.26 | 0 | −0.21 | 95:5 | 0.6 | ND |
| 428 | 9253 | 73.3 | −2.7 | 0.26 | 0 | −0.21 | 95:5 | 0.4 | ND |
| 429 | 9252 | 78.3 | −2.7 | 0.26 | 0 | −0.21 | 95:5 | 2 | ND |
| 430 | 9255 | 78.3 | −2.7 | 0.26 | 0 | −0.21 | 95:5 | 0.6 | ND |
| 431 | 9316 | 78.20* | −3.00* | 0.18* | 0.00* | −0.07* | 88:12 | 3.5 | ND |
| 432 | 9319 | 78.20* | −3.00* | 0.18* | 0.00 | −0.07* | 90:10 | 0.7 | ND |
| 433 | 9298 | 73.20* | −3.00* | 0.21* | 0.00 | −0.12* | 88:12 | 0.3 | ND |
| 434 | 9302 | 78.20* | −3.00* | 0.21* | 0.00* | −0.12* | 89:11 | 1.3 | ND |
| 435 | 9300 | 78.20* | −3.00* | 0.21* | 0.00* | −0.12* | 62:38 | 0 | ND |
| 436 | 9304 | 78.20* | −3.00* | 0.21* | 0.00* | −0.12 | 37:13 | 8.4 | ND |
| 437 | 9308 | 78.20* | −3.00* | 0.21* | 0.00* | −0.12* | 89:11 | 3 | ND |
| 438 | 9820 | 78.2 | −2.8 | 0.20+ | 0.00+ | −0.10+ | 97:3 | 4.2 | ND |
| 439 | 9320 | 78.20* | −3.00* | 0.18* | 0.00* | −0.07* | 86:14 | 7 | ND |
| 440 | 9323 | 78.20* | −3.00* | 0.18* | 0.00* | −0.07* | 91:9 | 0.9 | ND |
| 441 | 9247 | 78.1 | −2.9 | 0.28 | 0 | −0.26 | 92:8 | 2 | ND |
| 442 | 9248 | 78.1 | −2.9 | 0.28 | 0 | −0.26 | 94:6 | 1.9 | ND |
| 443 | 9249 | 78.1 | −2.9 | 0.28 | 0 | −0.26 | 94:6 | 0.8 | ND |
| 444 | 9075 | 78.1 | −2.9 | 0.17 | 0 | −0.03 | 97:3 | 1.9 | ND |
| 445 | 9828 | 78 | −3 | 0.14+ | 0.00+ | 0.07+ | 96:4 | 0.6 | 96:4 |
| 446 | 9041 | 77.8 | ND | 0.14 | 0 | ND | 80:20 | 3.2 | 80:20 |
| 447 | 9815 | 77.8 | −3.2 | 0.16+ | 0.00+ | −0.01+ | 97:3 | 9.4 | 98:2 |
| 448 | 9613 | 77.8 | −3.2 | 0.12+ | 0.00+ | 0.12+ | 96:4 | 0.4 | ND |
| 449 | 9170 | 77.8 | −3.2 | 0.27 | 0 | −0.24 | 92:8 | 0 | ND |
| 450 | 9171 | 77.8 | −3.2 | 0.27 | 0 | −0.24 | 91:9 | 0 | ND |
| 451 | 9172 | 77.8 | −3.2 | 0.27 | 0 | −0.24 | 93:7 | 0 | ND |
| 452 | 9825 | 77.7 | −3.3 | 0.15+ | 0.00+ | 0.01+ | 87:13 | 26.1 | 91:9 |
| 453 | 9822 | 77.7 | −3.3 | 0.11+ | 0.00+ | 0.17+ | 93:7 | 4.1 | ND |
| 454 | 9734 | 77.7 | −3.3 | 0.26 | 0 | −0.22 | 91:9 | 4.7 | 88:12 |
| 455 | 9817 | 77.5 | −3.5 | 0.18+ | 0.00+ | −0.05+ | 94:6 | 3.3 | ND |
| 456 | 9064 | 77.2 | −3.8 | 0.17 | 0 | −0.05 | 98:2 | 0.6 | ND |
| 457 | 9905 | 76.8 | −4.2 | 0.10+ | 0.00+ | 0.20+ | 96:4 | 0.4 | ND |
| 458 | 9198 | 76.4 | −4.6 | 0.28 | 0 | −0.25 | 90:10 | 4.6 | ND |

TABLE 12-continued

LCCA performance, stability and antigen binding assessments of the LCCA designs, arranged by decreasing DSF values of H1L1 Fab heterodimers

| Row # | Set # | DSF values of h1\|1 Fab heterodimer (° C.) | Change in DSF values of h1\|1 Fab heterodimer compared to wild-type | KD of h1\|1 Fab heterodimer (nM) | Range of KD values for h1\|1 Fab heterodimer (nM) | Change in median values of KD of h1\|1 Fab heterodimer compared to wild type (−(log(KD_design) − log(KD_wt))) | Median LCCA performance normalized to a L1:L2 DNA ratio of 1:1 (Ratio)** | LCCA performance range (Max-Min) at L1:L2 DNA ratio of 1:1** | Median LCCA performance normalized to a L1:L2 DNA ratio of 1:1 (Ratio)*** |
|---|---|---|---|---|---|---|---|---|---|
| 459 | 9199 | 76.4 | −4.6 | 0.28 | 0 | −0.25 | 87:13 | 2.4 | ND |
| 460 | 9196 | 76.4 | −4.6 | 0.28 | 0 | −0.25 | 88:12 | 0.9 | ND |
| 461 | 9202 | 76.4 | −4.6 | 0.28 | 0 | −0.25 | 34:16 | 2.6 | ND |
| 462 | 9201 | 76.4 | −4.6 | 0.28 | 0 | −0.25 | 85:15 | 1.8 | ND |
| 463 | 9205 | 76.4 | −4.6 | 0.28 | 0 | −0.25 | 86:14 | 5.5 | ND |
| 464 | 9065 | 76.3 | −4.7 | 0.18 | 0 | −0.05 | 98:2 | 0.2 | ND |
| 465 | 9044 | 75.8 | ND | 0.18 | 0 | ND | 86:14 | 6 | 78:22 |
| 466 | 9112 | 74.8 | −6.2 | ND, low Fab capture | ND, low Fab capture | ND, low Fab capture | 27:73 | 0 | ND |
| 467 | 9372 | 74.5 | −6.5 | 0.27 | 0 | −0.24 | 81:19 | 33 | ND |
| 468 | 9373 | 74.5 | −6.5 | 0.27 | 0 | −0.24 | 86:14 | 3.8 | 94:6 |
| 469 | 9043 | 74.1 | ND | 0.16 | 0 | ND | 96:4 | 0.1 | ND |
| 470 | 9518 | ND | ND | 0.2 | 0 | −0.1 | 95:5 | 3.1 | 94:6 |
| 471 | 9513 | ND | ND | 0.26 | 0 | −0.21 | 92:8 | 3.4 | ND |
| 472 | 9516 | ND | ND | 0.26 | 0 | −0.21 | 94:6 | 0 | ND |
| 473 | 9515 | ND | ND | 0.26 | 0 | −0.21 | 95:5 | 0 | ND |
| 474 | 9214 | ND | ND | 0.19 | 0 | −0.08 | 85:15 | 5 | ND |
| 475 | 9217 | ND | ND | 0.19 | 0 | −0.08 | 82:18 | 0.1 | ND |
| 476 | 9216 | ND | ND | 0.19 | 0 | −0.08 | 79:21 | 0 | ND |
| 477 | 9219 | ND | ND | 0.19 | 0 | −0.08 | 84:16 | 2.4 | ND |
| 478 | 9358 | ND | ND | 0.18 | 0 | −0.07 | 79:21 | 0 | ND |
| 479 | 9359 | ND | ND | 0.16 | 0 | −0.01 | 74:26 | 0 | ND |
| 480 | 9357 | ND | ND | 0.18 | 0 | −0.07 | 80:20 | 0 | ND |
| 481 | 9351 | ND | ND | 0.2 | 0 | −0.1 | 84:16 | 0 | ND |
| 432 | 9352 | ND | ND | 0.2 | 0 | −0.1 | 90:10 | 1.9 | ND |
| 483 | 9353 | ND | ND | 0.2 | 0 | −0.1 | 89:11 | 1.8 | ND |
| 484 | 9354 | ND | ND | 0.17 | 0 | −0.04 | 81:19 | 0 | ND |
| 485 | 9350 | ND | ND | 0.2 | 0 | −0.1 | 82:18 | 0 | ND |
| 486 | 9269 | ND | ND | 0.31 | 0 | −0.29 | 87:13 | 1.2 | ND |
| 437 | 9266 | ND | ND | 0.31 | 0 | −0.29 | 84:16 | 1.9 | ND |
| 488 | 9267 | ND | ND | 0.31 | 0 | −0.29 | 62:38 | 0 | ND |
| 489 | 9260 | ND | ND | 0.24 | 0 | −0.19 | 63:37 | 0 | ND |
| 490 | 9262 | ND | ND | 0.24 | 0 | −0.19 | 85:15 | 1.1 | ND |
| 491 | 9263 | ND | ND | 0.24 | 0 | −0.19 | 88:12 | 3.3 | ND |
| 492 | 9220 | ND | ND | 0.19 | 0 | −0.08 | 81:19 | 7.6 | ND |
| 493 | 9225 | ND | ND | 0.16 | 0 | −0.02 | 83:17 | 0.1 | ND |
| 494 | 9228 | ND | ND | 0.16 | 0 | −0.02 | 76:24 | 0 | ND |
| 495 | 9229 | ND | ND | 0.16 | 0 | −0.02 | 87:13 | 3.3 | ND |
| 496 | 9185 | ND | ND | 0.13 | 0 | 0.09 | 69:31 | 0 | ND |
| 497 | 9349 | ND | ND | 0.15 | 0 | 0.03 | 36:14 | 3 | ND |
| 498 | 9348 | ND | ND | 0.15 | 0 | 0.03 | 82:18 | 1.3 | ND |
| 499 | 9505 | ND | ND | 0.26 | 0 | −0.21 | 94:6 | 0 | ND |
| 500 | 9503 | ND | ND | 0.26 | 0 | −0.21 | 88:12 | 16.2 | ND |
| 501 | 10548 | ND | ND | ND | ND | ND | 96:4 | 3.2 | 97:3 |
| 502 | 10546 | ND | ND | ND | ND | ND | 95:5 | 2.4 | ND |
| 503 | 10547 | ND | ND | ND | ND | ND | 93:7 | 1.4 | 93:7 |
| 504 | 10545 | ND | ND | ND | ND | ND | 91:9 | 2.6 | 88:12 |
| 505 | 9521 | ND | ND | 0.2 | 0 | −0.1 | 97:3 | 2.7 | ND |
| 506 | 9520 | ND | ND | 0.2 | 0 | −0.1 | 95:5 | 0 | ND |
| 507 | 9176 | ND | ND | 0.22 | 0 | −0.15 | 83:17 | 0 | ND |
| 508 | 9178 | ND | ND | 0.22 | 0 | −0.15 | 83:17 | 0 | ND |
| 509 | 9179 | ND | ND | 0.22 | 0 | −0.15 | 78:22 | 0 | ND |
| 510 | 9362 | ND | ND | 0.16 | 0 | −0.01 | 80:20 | 0 | ND |
| 511 | 9270 | ND | ND | 0.31 | 0 | −0.29 | 88:12 | 1.2 | ND |
| 512 | 9237 | ND | ND | 0.22 | 0 | −0.15 | 89:11 | 5.5 | ND |
| 513 | 9236 | ND | ND | 0.22 | 0 | −0.15 | 89:11 | 1.9 | ND |
| 514 | 9234 | ND | ND | 0.22 | 0 | −0.15 | 86:14 | 1.9 | ND |
| 515 | 9239 | ND | ND | 0.22 | 0 | −0.15 | 89:11 | 2.4 | ND |
| 516 | 9243 | ND | ND | 0.22 | 0 | −0.15 | 87:13 | 1.2 | ND |
| 517 | 9240 | ND | ND | 0.22 | 0 | −0.15 | 87:13 | 2.4 | ND |
| 518 | 9538 | ND | ND | 0.17 | 0 | −0.04 | 85:15 | 0 | ND |
| 519 | 9344 | ND | ND | 0.27 | 0 | −0.23 | 94:6 | 5.4 | ND |
| 520 | 9361 | ND | ND | 0.16 | 0 | −0.01 | 83:17 | 0 | ND |
| 521 | 9188 | ND | ND | 0.13 | 0 | 0.09 | 63:37 | 0 | ND |
| 522 | 9226 | ND | ND | 0.16 | 0 | −0.02 | 67:33 | 0 | ND |

TABLE 12-continued

LCCA performance, stability and antigen binding assessments of the LCCA designs, arranged by decreasing DSF values of H1L1 Fab heterodimers

| Row # | Set # | DSF values of h1\|1 Fab heterodimer (° C.) | Change in DSF values of h1\|1 Fab heterodimer compared to wild-type | KD of h1\|1 Fab heterodimer (nM) | Range of KD values for h1\|1 Fab heterodimer (nM) | Change in median values of KD of h1\|1 Fab heterodimer compared to wild type ($-(\log(KD\_design) - \log(KD\_wt))$) | Median LCCA performance normalized to a L1:L2 DNA ratio of 1:1 (Ratio)** | LCCA performance range (Max-Min) at L1:L2 DNA ratio of 1:1** | Median LCCA performance normalized to a L1:L2 DNA ratio of 1:1 (Ratio)*** |
|---|---|---|---|---|---|---|---|---|---|
| 523 | 9181 | ND | ND | 0.22 | 0 | −0.15 | 85:15 | 0 | ND |
| 524 | 9536 | ND | ND | 0.17 | 0 | −0.04 | 88:12 | 0 | ND |
| 525 | 9523 | ND | ND | 0.2 | 0 | −0.1 | 93:7 | 9.8 | 91:9 |
| 526 | 9526 | ND | ND | 0.17 | 0 | −0.04 | 80:20 | 0 | ND |
| 527 | 9257 | ND | ND | 0.24 | 0 | −0.19 | 84:16 | 10 | ND |
| 528 | 9524 | ND | ND | 0.2 | 0 | −0.1 | 95:5 | 4 | ND |
| 529 | 9259 | ND | ND | 0.24 | 0 | −0.19 | 84:16 | 2.5 | ND |

*Indicates estimated values that were derived from other Fab heterodimers that differ only in the presence/absence of the attached L chain tag (HA or FLAG)).
**Values derived from the 333 (H1), 250 (L1), 749 (L2) LCCA experiments.
***Values derived from the 333 (H1), 100 (L1), 899 (L2) LCCA experiments.
ND indicates that no data are available.

TABLE 13a

LCCA performance of the designs that met the LCCA average performance criteria of correctly paired:mispaired Fab heterodimers of 86:14

| Cluster | Unique identifier*** | lcca average performance (i.e. 0.5 (ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L2 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 1 | 9134-9521 | 3.19 | 2.8 | 94:6 | 6.7 | NA | NA | 3.57 | 97:3 | 2.7 | NA | NA |
| 1 | 9123-9521 | 3.12 | 2.67 | 94:6 | 3.2 | NA | NA | 3.57 | 97:3 | 2.7 | NA | NA |
| 1 | 9150-9523 | 3.08 | 3.52 | 97:3 | 1.3 | −0.52 | 37:63 | 2.64 | 93:7 | 9.8 | 2.36 | 91:9 |
| 1 | 9152-9515 | 3.065 | 3.28 | 96:4 | 2.3 | NA | NA | 2.36 | 95:5 | 0 | NA | NA |
| 1 | 9154-9394 | 3.03 | 3.61 | 97:3 | 2.8 | 3.39 | 97:3 | 2.45 | 92:8 | 13.9 | 2.32 | 91:9 |
| 1 | 9164-9555 | 3.025 | 3.64 | 97:3 | 2.6 | 4.37 | 99:1 | 2.41 | 92:8 | 13.4 | 2.45 | 92:8 |
| 1 | 9146-9553 | 2.915 | 3.26 | 96:4 | 3.1 | 3.3 | 96:4 | 2.57 | 93:7 | 2.7 | 2 | 88:12 |
| 1 | 9162-9425 | 2.875 | 3.34 | 97:3 | 1.2 | NA | NA | 2.41 | 92:8 | 0 | NA | NA |
| 1 | 9164-9500 | 2.875 | 3.64 | 97:3 | 2.6 | NA | NA | 2.11 | 89:11 | 10.2 | NA | NA |
| 1 | 9154-9353 | 2.85 | 3.61 | 97:3 | 2.8 | NA | NA | 2.09 | 89:11 | 1.8 | NA | NA |
| 1 | 9152-9460 | 2.815 | 3.28 | 96:4 | 2.3 | NA | NA | 2.36 | 91:9 | 3.1 | NA | NA |
| 1 | 9160-9416 | 2.805 | 3.26 | 96:4 | 3.1 | NA | NA | 2.34 | 91:9 | 0 | NA | NA |
| 1 | 9136-9513 | 2.8 | 3.1 | 96:4 | 2.2 | NA | NA | 2.5 | 92:8 | 3.4 | NA | NA |
| 1 | 9136-9459 | 2.755 | 3.1 | 96:4 | 2.2 | NA | NA | 2.42 | 92:8 | 1.2 | NA | NA |
| 1 | 9144-9423 | 2.735 | 2.9 | 95:5 | 2.6 | NA | NA | 2.57 | 93:7 | 6.3 | NA | NA |
| 1 | 9158-9483 | 2.73 | 3.27 | 96:4 | 2.2 | NA | NA | 2.2 | 90:10 | 7.4 | NA | NA |
| 1 | 9142-9414 | 2.73 | 3.39 | 97:3 | 3.4 | 3.32 | 97:3 | 2.07 | 89:11 | 6.2 | 2.83 | 94:6 |
| 1 | 9138-9392 | 2.73 | 2.95 | 95:5 | 4.6 | NA | NA | 2.53 | 93:7 | 2.9 | NA | NA |
| 1 | 9156-9397 | 2.705 | 3.11 | 96:4 | 3.5 | 3 | 95:5 | 2.3 | 91:9 | 3.1 | 2.73 | 94:6 |
| 1 | 9140-9481 | 2.655 | 2.98 | 95:5 | 3.4 | NA | NA | 2.33 | 91:9 | 4.5 | NA | NA |
| 1 | 9131-9553 | 2.63 | 2.7 | 94:6 | 3.7 | NA | NA | 2.57 | 93:7 | 2.7 | NA | NA |

TABLE 13a-continued

LCCA performance of the designs that met the LCCA average performance criteria of correctly paired:mispaired Fab heterodimers of 86:14

| Cluster | Unique identifier*** | lcca average performance (i.e. 0.5 (ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L2 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 1 | 9164-9446 | 2.6 | 3.64 | 97:3 | 2.6 | NA | NA | 1.56 | 83:17 | 24.8 | NA | NA |
| 1 | 9126-9392 | 2.59 | 2.67 | 94:6 | 2.2 | NA | NA | 2.53 | 93:7 | 2.9 | NA | NA |
| 1 | 9133-9352 | 2.58 | 2.95 | 95:5 | 4.6 | NA | NA | 2.22 | 90:10 | 1.9 | NA | NA |
| 1 | 9127-9431 | 2.54 | 2.75 | 94:6 | 4.3 | NA | NA | 2.33 | 91:9 | 4.5 | NA | NA |
| 1 | 9130-9423 | 2.52 | 2.47 | 92:8 | 5.1 | NA | NA | 2.57 | 93:7 | 6.3 | NA | NA |
| 1 | 9158-9538 | 2.515 | 3.27 | 96:4 | 2.2 | NA | NA | 1.76 | 85:15 | 0 | NA | NA |
| 1 | 9150-9468 | 2.51 | 3.52 | 97:3 | 1.3 | NA | NA | 1.5 | 82:18 | 50.6 | NA | NA |
| 1 | 9125-9513 | 2.48 | 2.46 | 92:8 | 2.2 | NA | NA | 2.5 | 92:8 | 3.4 | NA | NA |
| 1 | 9140-9536 | 2.465 | 2.98 | 95:5 | 3.4 | NA | NA | 1.95 | 88:12 | 0 | NA | NA |
| 1 | 9126-9352 | 2.44 | 2.67 | 94:6 | 2.2 | NA | NA | 2.22 | 90:10 | 1.9 | NA | NA |
| 1 | 9164-9367 | 2.44 | 3.64 | 97:3 | 2.6 | NA | NA | 1.24 | 78:22 | 0 | NA | NA |
| 1 | 9125-9459 | 2.435 | 2.46 | 92:8 | 2.2 | NA | NA | 2.42 | 92:8 | 1.2 | NA | NA |
| 1 | 9142-9357 | 2.4 | 3.39 | 97:3 | 3.4 | NA | NA | 1.41 | 80:20 | 0 | NA | NA |
| 1 | 9129-9414 | 2.395 | 2.72 | 94:6 | 6.4 | NA | NA | 2.07 | 89:11 | 6.2 | NA | NA |
| 1 | 9162-9362 | 2.37 | 3.34 | 97:3 | 1.2 | NA | NA | 1.4 | 80:20 | 0 | NA | NA |
| 1 | 9127-9536 | 2.35 | 2.75 | 94:6 | 4.3 | NA | NA | 1.95 | 88:12 | 0 | NA | NA |
| 1 | 9146-9366 | 2.325 | 3.26 | 96:4 | 3.1 | NA | NA | 1.39 | 80:20 | 0 | NA | NA |
| 1 | 9160-9358 | 2.31 | 3.26 | 96:4 | 3.1 | NA | NA | 1.35 | 79:21 | 0 | NA | NA |
| 1 | 9146-9498 | 2.3 | 3.26 | 96:4 | 3.5 | NA | NA | 1.33 | 79:21 | 52.3 | NA | NA |
| 1 | 9156-9354 | 2.265 | 3.11 | 96:4 | 3.1 | NA | NA | 1.42 | 81:19 | 0 | NA | NA |
| 1 | 9134-9466 | 2.255 | 2.8 | 94:6 | 6.7 | NA | NA | 1.7 | 85:15 | 50 | NA | NA |
| 1 | 9144-9361 | 2.25 | 2.9 | 95:5 | 2.6 | NA | NA | 1.6 | 83:17 | 0 | NA | NA |

TABLE 13a-continued

LCCA performance of the designs that met the LCCA average performance criteria of correctly paired:mispaired Fab heterodimers of 86:14

| Cluster | Unique identifier *** | lcca average performance (i.e. 0.5 (ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L1 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 1 | 9123-9466 | 2.185 | 2.67 | 94:6 | 3.2 | NA | NA | 1.7 | 85:15 | 50 | NA | NA |
| 1 | 9129-9357 | 2.065 | 2.72 | 94:6 | 6.4 | NA | NA | 1.41 | 80:20 | 0 | NA | NA |
| 1 | 9131-9366 | 2.04 | 2.7 | 94:6 | 3.7 | NA | NA | 1.39 | 80:20 | 0 | NA | NA |
| 1 | 9130-9361 | 2.035 | 2.47 | 92:8 | 5.1 | NA | NA | 1.6 | 83:17 | 0 | NA | NA |
| 1 | 9131-9498 | 2.015 | 2.7 | 94:6 | 3.7 | NA | NA | 1.33 | 79:21 | 52.3 | NA | NA |
| 1 | 9146-9444 | 1.99 | 3.26 | 96:4 | 3.1 | NA | NA | 0.72 | 67:33 | 66.2 | NA | NA |
| 2 | 9279-9518 | 2.945 | 3.03 | 95:5 | 3.2 | NA | NA | 2.86 | 95:5 | 3.1 | NA | NA |
| 2 | 9286-9402 | 2.84 | 3.47 | 97:3 | 1.9 | 3.39 | 97:3 | 2.21 | 90:10 | 19.1 | 1.64 | 84:16 |
| 2 | 9287-9486 | 2.735 | 3.03 | 95:5 | 3 | NA | NA | 2.44 | 92:8 | 0 | NA | NA |
| 2 | 9283-9380 | 2.7 | 2.93 | 95:5 | 6.4 | 3.99 | 98:2 | 2.47 | 92:8 | 0.7 | 1.66 | 84:16 |
| 2 | 9273-9398 | 2.7 | 3 | 95:5 | 1.6 | NA | NA | 2.4 | 92:8 | 1.8 | NA | NA |
| 2 | 9252-9380 | 2.67 | 2.87 | 95:5 | 2 | NA | NA | 2.47 | 92:8 | 0.7 | NA | NA |
| 2 | 9323-9440 | 2.67 | 2.34 | 91:9 | 0.9 | NA | NA | 2.99 | 95:5 | 0 | NA | NA |
| 2 | 9287-9541 | 2.665 | 3.03 | 95:5 | 3 | NA | NA | 2.3 | 91:9 | 0 | NA | NA |
| 2 | 9271-9376 | 2.66 | 2.92 | 95:5 | 1.8 | NA | NA | 2.4 | 92:8 | 0.3 | NA | NA |
| 2 | 9284-9471 | 2.655 | 3.09 | 96:4 | 2.7 | NA | NA | 2.22 | 90:10 | 0 | NA | NA |
| 2 | 9290-9432 | 2.65 | 3.04 | 95:5 | 4.3 | 3.02 | 95:5 | 2.26 | 91:9 | 2.8 | 1.49 | 82:18 |
| 2 | 9256-9432 | 2.645 | 3.03 | 95:5 | 1.6 | NA | NA | 2.26 | 91:9 | 2.8 | NA | NA |
| 2 | 9253-9471 | 2.63 | 3.04 | 95:5 | 0.4 | NA | NA | 2.22 | 90:10 | 0 | NA | NA |
| 2 | 9302-9405 | 2.61 | 2.12 | 89:11 | 1.3 | NA | NA | 3.1 | 96:4 | 0 | NA | NA |
| 2 | 9287-9420 | 2.605 | 3.03 | 95:5 | 3 | NA | NA | 2.18 | 90:10 | 0 | NA | NA |
| 2 | 9308-9436 | 2.58 | 2.08 | 89:11 | 3 | NA | NA | 3.08 | 96:4 | 0 | NA | NA |

TABLE 13a-continued

LCCA performance of the designs that met the LCCA average performance criteria of correctly paired:mispaired Fab heterodimers of 86:14

| Cluster | Unique identifier *** | lcca average performance (i.e. 0.5 (ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L1 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 2 | 9255-9402 | 2.575 | 2.94 | 95:5 | 0.6 | NA | NA | 2.21 | 90:10 | 19.1 | NA | NA |
| 2 | 9248-9398 | 2.56 | 2.72 | 94:6 | 1.9 | NA | NA | 2.4 | 92:8 | 1.8 | NA | NA |
| 2 | 9209-9398 | 2.545 | 2.69 | 94:6 | 0.5 | NA | NA | 2.4 | 92:8 | 1.8 | NA | NA |
| 2 | 9281-9503 | 2.525 | 1.1 | 96:4 | 2.4 | NA | NA | 1.95 | 88:12 | 16.2 | NA | NA |
| 2 | 9253-9435 | 2.51 | 1.95 | 88:12 | 3.3 | NA | NA | 3.08 | 96:4 | 0 | NA | NA |
| 2 | 9275-9419 | 2.505 | 2.81 | 94:6 | 2.6 | NA | NA | 2.2 | 90:10 | 0.3 | NA | NA |
| 2 | 9212-9402 | 2.495 | 2.78 | 94:6 | 1 | NA | NA | 2.21 | 90:10 | 19.1 | NA | NA |
| 2 | 9211-9380 | 2.49 | 2.51 | 92:8 | 3.2 | NA | NA | 2.47 | 92:8 | 0.7 | NA | NA |
| 2 | 9270-9440 | 2.47 | 1.95 | 88:12 | 1.2 | NA | NA | 2.99 | 95:5 | 0 | NA | NA |
| 2 | 9229-9440 | 2.465 | 1.94 | 87:13 | 3.3 | NA | NA | 2.99 | 95:5 | 0 | NA | NA |
| 2 | 9250-9503 | 2.465 | 2.98 | 95:5 | 0.6 | NA | NA | 1.95 | 88:12 | 16.2 | NA | NA |
| 2 | 9290-9546 | 2.46 | 3.04 | 95:5 | 4.3 | 3.02 | 95:5 | 1.88 | 87:13 | 14.2 | 1.75 | 85:15 |
| 2 | 9247-9376 | 2.455 | 2.51 | 92:8 | 2 | NA | NA | 2.4 | 92:8 | 0.3 | NA | NA |
| 2 | 9256-9546 | 2.455 | 3.03 | 95:5 | 1.6 | NA | NA | 1.88 | 87:13 | 14.2 | NA | NA |
| 2 | 9323-9495 | 2.455 | 2.34 | 91:9 | 0.9 | NA | NA | 2.56 | 93:7 | 0.1 | NA | NA |
| 2 | 9213-9432 | 2.45 | 2.65 | 93:7 | 0.7 | NA | NA | 2.26 | 91:9 | 2.8 | NA | NA |
| 2 | 9262-9406 | 2.44 | 1.77 | 85:15 | 1.1 | NA | NA | 3.1 | 96:4 | 0 | NA | NA |
| 2 | 9181-9406 | 2.43 | 1.76 | 85:15 | 0 | NA | NA | 3.1 | 96:4 | 0 | NA | NA |
| 2 | 9208-9376 | 2.415 | 2.44 | 92:8 | 2.9 | NA | NA | 2.4 | 92:8 | 0.3 | NA | NA |
| 2 | 9173-9380 | 2.4 | 2.33 | 91:9 | 0 | NA | NA | 2.47 | 92:8 | 0.7 | NA | NA |
| 2 | 9170-9376 | 2.39 | 2.38 | 92:8 | 0 | NA | NA | 2.4 | 92:8 | 0.3 | NA | NA |
| 2 | 9196-9516 | 2.39 | 2.02 | 88:12 | 0.9 | NA | NA | 2.76 | 94:6 | 0 | NA | NA |

TABLE 13a-continued

LCCA performance of the designs that met the LCCA average performance criteria of correctly paired:mispaired Fab heterodimers of 86:14

| Cluster | Unique identifier *** | lcca average performance (i.e. 0.5 (ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L2 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 2 | 9319-9410 | 2.385 | 2.15 | 90:10 | 0.7 | NA | NA | 2.63 | 93:7 | 3.4 | NA | NA |
| 2 | 9171-9398 | 2.38 | 2.36 | 91:9 | 0 | NA | NA | 2.4 | 92:8 | 1.8 | NA | NA |
| 2 | 9219-9406 | 2.375 | 1.66 | 84:16 | 2.4 | NA | NA | 3.1 | 96:4 | 0 | NA | NA |
| 2 | 9174-9402 | 2.37 | 2.53 | 93:7 | 0 | NA | NA | 2.21 | 90:10 | 19.1 | NA | NA |
| 2 | 9198-9395 | 2.365 | 2.17 | 90:10 | 4.6 | NA | NA | 2.57 | 93:7 | 1.3 | NA | NA |
| 2 | 9175-9432 | 2.345 | 2.44 | 92:8 | 2.4 | NA | NA | 2.26 | 91:9 | 2.8 | NA | NA |
| 2 | 9236-9395 | 2.33 | 2.08 | 89:11 | 1.9 | NA | NA | 2.57 | 93:7 | 1.3 | NA | NA |
| 2 | 9281-9449 | 2.325 | 3.1 | 96:4 | 2.4 | NA | NA | 1.55 | 82:13 | 0 | NA | NA |
| 2 | 9234-9516 | 2.3 | 1.84 | 86:14 | 1.9 | NA | NA | 2.76 | 94:6 | 0 | NA | NA |
| 2 | 9308-9547 | 2.29 | 2.08 | 89:11 | 3 | NA | NA | 2.5 | 92:8 | 0 | NA | NA |
| 2 | 9304-9542 | 2.29 | 1.89 | 87:13 | 8.4 | NA | NA | 2.7 | 94:6 | 0 | NA | NA |
| 2 | 9243-9556 | 2.27 | 1.93 | 87:13 | 1.2 | NA | NA | 2.61 | 93:7 | 0 | NA | NA |
| 2 | 9250-9449 | 2.265 | 2.98 | 95:5 | 0.6 | NA | NA | 1.55 | 82:18 | 0 | NA | NA |
| 2 | 9213-9546 | 2.26 | 2.65 | 93:7 | 0.7 | NA | NA | 1.88 | 87:13 | 14.2 | NA | NA |
| 2 | 9269-9410 | 2.26 | 1.9 | 87:13 | 1.2 | NA | NA | 2.63 | 93:7 | 3.4 | NA | NA |
| 2 | 9237-9484 | 2.255 | 2.12 | 89:11 | 5.5 | NA | NA | 2.39 | 92:8 | 0 | NA | NA |
| 2 | 9270-9495 | 2.255 | 1.95 | 88:12 | 1.2 | NA | NA | 2.56 | 93:7 | 0.1 | NA | NA |
| 2 | 9220-9436 | 2.255 | 1.44 | 81:19 | 7.6 | NA | NA | 3.08 | 96:4 | 0 | NA | NA |
| 2 | 9229-9495 | 2.25 | 1.94 | 87:13 | 3.3 | NA | NA | 2.56 | 93:7 | 0.1 | NA | NA |
| 2 | 9234-9495 | 2.25 | 3.09 | 96:4 | 2.7 | NA | NA | 1.41 | 80:20 | 0 | NA | NA |
| 2 | 9279-9463 | 2.235 | 3.03 | 95:5 | 3.2 | NA | NA | 1.45 | 81:19 | 47.9 | NA | NA |
| 2 | 9304-9487 | 2.235 | 1.89 | 87:13 | 8.4 | NA | NA | 2.59 | 93:7 | 2.9 | NA | NA |

TABLE 13a-continued

LCCA performance of the designs that met the LCCA average performance criteria of correctly paired:mispaired Fab heterodimers of 86:14

| Cluster | Unique identifier*** | lcca average performance (i.e. 0.5 (ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L2 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 2 | 9323-9550 | 2.225 | 2.34 | 91:9 | 0.9 | NA | NA | 2.1 | 89:11 | 19.8 | NA | NA |
| 2 | 9214-9505 | 2.225 | 1.71 | 85:15 | 5 | NA | NA | 2.74 | 94:6 | 0 | NA | NA |
| 2 | 9253-9526 | 2.225 | 3.04 | 95:5 | 0.4 | NA | NA | 1.41 | 80:20 | 0 | NA | NA |
| 2 | 9263-9547 | 2.22 | 1.95 | 88:12 | 3.3 | NA | NA | 2.5 | 92:8 | 0 | NA | NA |
| 2 | 9271-9350 | 2.22 | 2.92 | 95:5 | 1.3 | NA | NA | 1.52 | 82:18 | 0 | NA | NA |
| 2 | 9316-9388 | 2.215 | 2 | 88:12 | 3.5 | NA | NA | 2.42 | 92:8 | 0 | NA | NA |
| 2 | 9298-9384 | 2.215 | 2.01 | 88:12 | 0.3 | NA | NA | 2.41 | 92:8 | 0 | NA | NA |
| 2 | 9243-9501 | 2.2 | 1.93 | 87:13 | 1.2 | NA | NA | 2.47 | 92:8 | 0 | NA | NA |
| 2 | 9257-9505 | 2.195 | 1.65 | 84:16 | 10 | NA | NA | 2.74 | 94:6 | 0 | NA | NA |
| 2 | 9205-9556 | 2.195 | 1.78 | 86:14 | 5.5 | NA | NA | 2.61 | 93:7 | 0 | NA | NA |
| 2 | 9176-9505 | 2.18 | 1.62 | 83:17 | 0 | NA | NA | 2.74 | 94:6 | 0 | NA | NA |
| 2 | 9175-9546 | 2.155 | 2.44 | 92:8 | 2.4 | NA | NA | 1.88 | 87:13 | 14.2 | NA | NA |
| 2 | 9214-9451 | 2.15 | 1.71 | 85:15 | 5 | NA | NA | 2.59 | 93:7 | 0 | NA | NA |
| 2 | 9199-9484 | 2.145 | 1.9 | 87:13 | 2.4 | NA | NA | 2.39 | 92:8 | 0 | NA | NA |
| 2 | 9240-9544 | 2.135 | 1.87 | 87:13 | 24 | NA | NA | 2.4 | 92:8 | 0 | NA | NA |
| 2 | 9205-9501 | 2.125 | 1.78 | 86:14 | 5.5 | NA | NA | 2.47 | 92:8 | 0 | NA | NA |
| 2 | 9257-9451 | 2.12 | 1.65 | 84:16 | 10 | NA | NA | 2.59 | 93:7 | 0 | NA | NA |
| 2 | 9243-9368 | 2.11 | 1.93 | 87:13 | 1.2 | NA | NA | 2.29 | 91:9 | 0 | NA | NA |
| 2 | 9176-9451 | 2.105 | 1.62 | 83:17 | 0 | NA | NA | 2.59 | 93:7 | 0 | NA | NA |
| 2 | 9196-9461 | 2.06 | 2.02 | 88:12 | 0.9 | NA | NA | 2.1 | 89:11 | 0 | NA | NA |
| 2 | 9217-9473 | 2.055 | 1.52 | 82:18 | 0.1 | NA | NA | 2.59 | 93:7 | 0 | NA | NA |
| 2 | 9320-9488 | 2.05 | 1.82 | 86:14 | 7 | NA | NA | 2.28 | 91:9 | 1.3 | NA | NA |

TABLE 13a-continued

LCCA performance of the designs that met the LCCA average performance criteria of correctly paired:mispaired Fab heterodimers of 86:14

| Cluster | Unique identifier*** | lcca average performance (i.e. 0.5 (ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L2 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 2 | 9266-9388 | 2.045 | 1.67 | 84:16 | 1.9 | NA | NA | 2.42 | 92:8 | 0 | NA | NA |
| 2 | 9202-9544 | 2.04 | 1.68 | 84:16 | 2.6 | NA | NA | 2.4 | 92:8 | 0 | NA | NA |
| 2 | 9205-9368 | 2.035 | 1.78 | 86:14 | 5.5 | NA | NA | 2.29 | 91:9 | 0 | NA | NA |
| 2 | 9259-9384 | 2.035 | 1.67 | 84:16 | 2.5 | NA | NA | 2.41 | 92:8 | 0 | NA | NA |
| 2 | 9290-9,364 | 2.03 | 3.04 | 95:5 | 4.3 | NA | NA | 1.02 | 73:27 | 0 | NA | NA |
| 2 | 9256-9364 | 2.025 | 3.03 | 95:5 | 1.6 | NA | NA | 1.02 | 73:27 | 0 | NA | NA |
| 2 | 9270-9550 | 2.025 | 1.95 | 88:12 | 1.2 | NA | NA | 2.1 | 89:11 | 19.8 | NA | NA |
| 2 | 9229-9550 | 2.02 | 1.94 | 87:13 | 3.3 | NA | NA | 2.1 | 89:11 | 19.8 | NA | NA |
| 2 | 9247-9350 | 2.015 | 2.51 | 92:8 | 2 | NA | NA | 1.52 | 82:18 | 0 | NA | NA |
| 2 | 9178-9384 | 2 | 1.59 | 83:17 | 0 | NA | NA | 2.41 | 92:8 | 0 | NA | NA |
| 2 | 9225-9388 | 1.99 | 1.56 | 83:17 | 0.1 | NA | NA | 2.42 | 92:8 | 0 | NA | NA |
| 2 | 9208-9350 | 1.975 | 2.44 | 92:8 | 2.9 | NA | NA | 1.52 | 82:18 | 0 | NA | NA |
| 2 | 9234-9461 | 1.97 | 1.84 | 86:14 | 1.9 | NA | NA | 2.1 | 89:11 | 0 | NA | NA |
| 2 | 9220-9547 | 1.965 | 1.44 | 81:19 | 7.6 | NA | NA | 2.5 | 92:8 | 0 | NA | NA |
| 2 | 9290-9491 | 1.95 | 3.04 | 95:5 | 4.3 | NA | NA | 0.86 | 70:30 | 58.7 | NA | NA |
| 2 | 9170-9350 | 1.95 | 2.3.8 | 92:8 | 0 | NA | NA | 1.52 | 82:18 | 0 | NA | NA |
| 2 | 9256-9491 | 1.945 | 3.03 | 95:5 | 1.6 | NA | NA | 0.86 | 70:30 | 58.7 | NA | NA |
| 2 | 9275-9359 | 1.94 | 2.81 | 94:6 | 2.6 | NA | NA | 1.07 | 74:26 | 0 | NA | NA |
| 2 | 9179-9473 | 1.915 | 1.24 | 78:22 | 0 | NA | NA | 2.59 | 93:7 | 0 | NA | NA |
| 2 | 9240-9489 | 1.915 | 1.87 | 87:13 | 2.4 | NA | NA | 1.96 | 88:12 | 10.8 | NA | NA |
| 2 | 9240-9426 | 1.91 | 1.87 | 87:13 | 2.4 | NA | NA | 1.95 | 88:12 | 0 | NA | NA |
| 2 | 9228-9410 | 1.89 | 1.16 | 76:24 | 0 | NA | NA | 2.63 | 93:7 | 3.4 | NA | NA |

TABLE 13a-continued

LCCA performance of the designs that met the LCCA average performance criteria of correctly paired:mispaired Fab heterodimers of 86:14

| Cluster | Unique identifier *** | lcca average performance (i.e. 0.5 (ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L2 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 2 | 9216-9384 | 1.86 | 1.31 | 79:21 | 0 | NA | NA | 2.41 | 92:8 | 0 | NA | NA |
| 2 | 9298-9351 | 1.83 | 2.01 | 88:12 | 0.3 | NA | NA | 1.64 | 84:16 | 0 | NA | NA |
| 2 | 9213-9364 | 1.83 | 2.65 | 93:7 | 0.7 | NA | NA | 1.02 | 73:27 | 0 | NA | NA |
| 2 | 9202-9489 | 1.82 | 1.68 | 84:16 | 2.6 | NA | NA | 1.96 | 88:12 | 10.8 | NA | NA |
| 2 | 9243-9447 | 1.815 | 1.93 | 87:13 | 1.2 | NA | NA | 1.7 | 85:15 | 23.8 | NA | NA |
| 2 | 9202-9426 | 1.815 | 1.63 | 84:16 | 2.6 | NA | NA | 1.95 | 88:12 | 0 | NA | NA |
| 3 | 9338-9748 | 3.335 | 4.42 | 99:1 | 1.6 | NA | NA | 2.12 | 89:11 | 3.4 | NA | NA |
| 3 | 9372-9748 | 2.995 | 4.42 | 99:1 | 1.6 | NA | NA | 1.44 | 81:19 | 33 | NA | NA |
| 3 | 6054-9327 | 2.865 | 4.81 | 99:1 | 0.5 | NA | NA | 0.72 | 67:33 | 1.8 | NA | NA |
| 3 | 9338-9750 | 2.86 | 3.6 | 97:3 | 0 | NA | NA | 2.12 | 89:11 | 3.4 | NA | NA |
| 3 | 9334-9747 | 2.795 | 2.08 | 89:11 | 5.3 | 1.25 | 78:22 | 3.51 | 97:3 | 2.4 | 2.93 | 95:5 |
| 3 | 9121-9373 | 2.78 | 3.72 | 98:2 | 3.3 | 3.99 | 98:2 | 1.34 | 86:14 | 3.8 | 2.69 | 94:6 |
| 3 | 9334-9749 | 2.685 | 1.86 | 87:13 | 7.1 | NA | NA | 3.51 | 97:3 | 2.4 | NA | NA |
| 3 | 9815-9825 | 2.66 | 3.43 | 97:3 | 9.4 | 3.69 | 93:2 | 1.89 | 87:13 | 26.1 | 2.3 | 91:9 |
| 3 | 9815-9826 | 2.625 | 3.43 | 97:3 | 9.4 | NA | NA | 1.82 | 86:14 | 3.5 | NA | NA |
| 3 | 9816-9825 | 2.535 | 3.18 | 96:4 | 2 | NA | NA | 1.89 | 87:13 | 26.1 | NA | NA |
| 3 | 9372-9750 | 2.52 | 3.6 | 97:3 | 0 | NA | NA | 1.44 | 81:19 | 33 | NA | NA |
| 3 | 9816-9826 | 2.5 | 3.18 | 96:4 | 2 | NA | NA | 1.32 | 86:14 | 3.5 | NA | NA |
| 3 | 9107-9339 | 2.475 | 4.62 | 99:1 | 6.7 | 3.87 | 98:2 | 0.33 | 58:42 | 5.5 | 0.93 | 72:28 |
| 3 | 9066-9335 | 2.475 | 2.52 | 93:7 | 2.7 | 3.06 | 96:4 | 2.43 | 92:8 | 2.8 | 2.89 | 95:5 |
| 3 | 6048-9326 | 2.415 | 2.79 | 94:6 | 0 | NA | NA | 2.04 | 88:12 | 4 | NA | NA |
| 3 | 9328-9332 | 2.175 | 2.53 | 93:7 | 0 | NA | NA | 1.82 | 86:14 | 1.4 | NA | NA |

TABLE 13a-continued

LCCA performance of the designs that met the LCCA average performance criteria of correctly paired:mispaired Fab heterodimers of 86:14

| Cluster | Unique identifier*** | lcca average performance (i.e. 0.5 (ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L2 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 3 | 9122-9371 | 2.035 | 1.44 | 81:19 | 8 | NA | NA | 2.63 | 93:7 | 2 | NA | NA |
| 3 | 9104-9336 | 2.02 | 2.23 | 90:10 | 1.8 | NA | NA | 1.3 | 86:14 | 1.9 | NA | NA |
| 3 | 9108-9330 | 1.945 | 2.54 | 93:7 | 1.3 | NA | NA | 1.35 | 79:21 | 5.2 | NA | NA |
| 3 | 9106-9337 | 1.885 | 2.16 | 90:10 | 0.5 | NA | NA | 1.6 | 83:17 | 2.5 | NA | NA |
| 3 | 9369-9747 | 1.86 | 2.08 | 89:11 | 5.3 | NA | NA | 1.64 | 84:16 | 56.1 | NA | NA |
| 3 | 9109-9332 | 1.8 | 1.77 | 85:15 | 0.6 | NA | NA | 1.82 | 86:14 | 1.4 | NA | NA |
| 4 | 9168-9342 | 3.39 | 2.99 | 95:5 | 26.9 | NA | NA | 3.51 | 97:3 | 3.1 | NA | NA |
| 4 | 9169-9344 | 2.69 | 2.67 | 94:6 | 7.7 | NA | NA | 2.71 | 94:6 | 5.4 | NA | NA |
| 4 | 9114-9344 | 2.47 | 2.23 | 90:10 | 0 | NA | NA | 2.71 | 94:6 | 5.4 | NA | NA |
| 4 | 6098-9118 | 2.4 | 2.88 | 95:5 | 1.9 | NA | NA | 1.93 | 87:13 | 3.1 | NA | NA |
| 4 | 9113-9342 | 2.28 | 1.05 | 74:26 | 0 | NA | NA | 3.51 | 97:3 | 3.1 | NA | NA |
| 4 | 9117-9374 | 2.265 | 3.34 | 97:3 | 1.2 | NA | NA | 1.19 | 77:23 | 34.8 | NA | NA |
| 4 | 9119-9375 | 2.23 | 3.33 | 97:3 | 1.7 | 3.32 | 97:3 | 1.13 | 76:24 | 23.2 | 1.12 | 75:25 |
| 4 | 9111-9347 | 2.215 | 2.3 | 91:9 | 4.3 | 3.67 | 98:2 | 2.13 | 89:11 | 1.8 | 2.69 | 94:6 |
| 5 | 9116-9349 | 1.89 | 1.93 | 87:13 | 0 | NA | NA | 1.85 | 86:14 | 3 | NA | NA |
| 6 | 9075-9745 | 3.245 | 3.43 | 97:3 | 1.9 | NA | NA | 3.05 | 95:5 | 0.1 | NA | NA |
| 6 | 9745-9905 | 3.185 | 3.05 | 95:5 | 0.1 | NA | NA | 3.31 | 96:4 | 0.4 | NA | NA |
| 6 | 9075-9746 | 3.13 | 3.43 | 97:3 | 1.9 | NA | NA | 2.83 | 94:6 | 0.1 | NA | NA |
| 6 | 9746-9905 | 3.07 | 2.83 | 94:6 | 0.1 | NA | NA | 3.31 | 96:4 | 0.4 | NA | NA |
| 6 | 9814-9828 | 2.96 | 2.66 | 93:7 | 4.5 | 2.16 | 90:10 | 3.26 | 96:4 | 0.6 | 3.26 | 96:4 |
| 6 | 9813-9828 | 2.895 | 2.53 | 93:7 | 3.6 | 2.09 | 89:11 | 3.26 | 96:4 | 0.6 | 3.26 | 96:4 |
| 6 | 10547-10549 | 2.88 | 2.57 | 93:7 | 1.4 | 2.54 | 93:7 | 3.19 | 96:4 | 2.9 | 2.54 | 93:7 |

TABLE 13a-continued

LCCA performance of the designs that met the LCCA average performance criteria of correctly paired:mispaired Fab heterodimers of 86:14

| Cluster | Unique identifier *** | lcca average performance (i.e. 0.5 (ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L1 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 6 | 10545-10549 | 2.755 | 3.19 | 96:4 | 2.9 | 2.54 | 93:7 | 2.32 | 91:9 | 2.6 | 2 | 88:12 |
| 6 | 9814-9824 | 2.695 | 265 | 93:7 | 4.5 | 2.16 | 90:10 | 2.73 | 94:6 | 11.6 | 2.52 | 93:7 |
| 6 | 10547-10551 | 2.675 | 2.57 | 93:7 | 1.4 | 2.54 | 93:7 | 2.78 | 94:6 | 1.1 | 2.42 | 92:8 |
| 6 | 9813-9824 | 2.63 | 2.53 | 93:7 | 3.6 | 2.09 | 89:11 | 2.73 | 94:6 | 11.6 | 2.52 | 93:7 |
| 6 | 10545-10551 | 2.55 | 2.78 | 94:6 | 1.1 | 2.42 | 92:8 | 2.32 | 91:9 | 2.6 | 2 | 88:12 |
| 7 | 9060-9756 | 2.89 | 3.79 | 98:2 | 2.7 | 3.38 | 97:3 | 1.99 | 88:12 | 0.9 | 1.92 | 87:13 |
| 7 | 9054-9060 | 2.835 | 1.88 | 87:13 | 5 | 1.85 | 86:14 | 3.79 | 98:2 | 2.7 | 3.38 | 97:3 |
| 7 | 9053-9058 | 2.685 | 1.71 | 85:15 | 7.6 | 2.31 | 91:9 | 3.66 | 97:3 | 2 | 2.96 | 95:5 |
| 7 | 9058-9755 | 2.44 | 3.66 | 97:3 | 2 | 2.96 | 95:5 | 1.22 | 77:23 | 3.2 | 1.39 | 80:20 |
| 8 | 9820-9823 | 3.175 | 3.58 | 97:3 | 4.2 | NA | NA | 2.77 | 94:6 | 3.4 | NA | NA |
| 8 | 9819-9823 | 3.135 | 15 | 97:3 | 0.4 | 2.96 | 95:5 | 2.77 | 94:6 | 3.4 | 3.55 | 97:3 |
| 8 | 9820-9822 | 3.11 | 3.58 | 97:3 | 4.2 | NA | NA | 2.64 | 93:7 | 4.1 | NA | NA |
| 8 | 9819-9822 | 3.07 | 3.5 | 97:3 | 0.4 | NA | NA | 2.64 | 93:7 | 4.1 | NA | NA |
| 8 | 9820-9821 | 3.03 | 1.58 | 97:3 | 4.2 | NA | NA | 2.48 | 92:8 | 4.3 | NA | NA |
| 8 | 9820-9827 | 3.005 | 3.58 | 97:3 | 4.2 | NA | NA | 2.43 | 92:8 | 6.5 | NA | NA |
| 8 | 9819-9821 | 2.99 | 3.5 | 97:3 | 0.4 | NA | NA | 2.48 | 92:8 | 4.3 | NA | NA |
| 8 | 9819-9827 | 2.965 | 3.5 | 97:3 | 0.4 | NA | NA | 2.43 | 92:8 | 6.5 | NA | NA |
| 8 | 9817-9823 | 2.725 | 2.68 | 94:6 | 3.3 | NA | NA | 2.77 | 94:6 | 3.4 | NA | NA |
| 8 | 9817-9822 | 2.66 | 2.68 | 94:6 | 3.3 | NA | NA | 2.64 | 93:7 | 4.1 | NA | NA |
| 8 | 9817-9821 | 2.58 | 2.68 | 94:6 | 3.3 | NA | NA | 2.48 | 92:8 | 4.3 | NA | NA |
| 8 | 9817-9827 | 2.555 | 2.68 | 94:6 | 3.3 | NA | NA | 2.43 | 92:8 | 6.5 | NA | NA |
| 8 | 9818-9823 | 2.485 | 2.2 | 90:10 | 10.5 | 2.71 | 94:6 | 2.77 | 94:6 | 3.4 | 3.55 | 97:3 |

TABLE 13a-continued

LCCA performance of the designs that met the LCCA average performance criteria of correctly paired:mispaired Fab heterodimers of 86:14

| Cluster | Unique identifier *** | lcca average performance (i.e. 0.5 (ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L1 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 8 | 9818-9822 | 2.42 | 2.2 | 90:10 | 10.5 | NA | NA | 2.64 | 93:7 | 4.1 | NA | NA |
| 8 | 9818-9821 | 2.34 | 2.2 | 90:10 | 10.5 | NA | NA | 2.48 | 92:8 | 4.3 | NA | NA |
| 8 | 9818-9827 | 2.315 | 2.2 | 90:10 | 10.5 | NA | NA | 2.43 | 92:8 | 6.5 | NA | NA |
| 9 | 10548-10550 | 4.01 | 3.13 | 96:4 | 3.2 | 3.51 | 97:3 | 4.89 | 99:1 | 1.8 | 4.59 | 99:1 |
| 9 | 10548-10552 | 3.94 | 3.13 | 96:4 | 3.2 | 3.51 | 97:3 | 4.75 | 99:1 | 0.1 | 5 | 99:1 |
| 9 | 10548-10550 | 3.93 | 2.97 | 95:5 | 2.4 | NA | NA | 4.89 | 99:1 | 1.8 | NA | NA |
| 9 | 10546-10550 | 3.86 | 2.97 | 95:5 | 2.4 | NA | NA | 4.75 | 99:1 | 0.1 | NA | NA |
| 9 | 10546-10552 | 3.73 | 2.33 | 91:9 | 2.1 | 1.38 | 80:20 | 5 | 99:1 | 4.6 | 5 | 99:1 |
| 9 | 9077-9611 | 3.61 | 3.88 | 98:2 | 0.2 | NA | NA | 3.33 | 97:3 | 0.3 | NA | NA |
| 9 | 9065-9751 | 3.5 | 3.67 | 98:2 | 0.6 | NA | NA | 3.33 | 97:3 | 0.3 | NA | NA |
| 9 | 9064-9751 | 3.415 | 3.88 | 98:2 | 0.2 | NA | NA | 2.95 | 95:5 | 3 | NA | NA |
| 9 | 9065-9752 | 3.41 | 2.49 | 92:8 | 3.7 | 1.74 | 85:15 | 4.33 | 99:1 | 2.7 | 4.33 | 99:1 |
| 9 | 9078-9612 | 3.375 | 1.21 | 77:23 | 5.2 | 1.5 | 82:18 | 5 | 99:1 | 1.8 | 3.75 | 98:2 |
| 9 | 9076-9610 | 3.305 | 3.67 | 98:2 | 0.6 | NA | NA | 2.95 | 95:5 | 3 | NA | NA |
| 9 | 9064-9752 | 2.845 | 3.62 | 97:3 | 1.4 | 4.29 | 99:1 | 2.07 | 89:11 | 4.9 | 1.2 | 77:23 |
| 9 | 9074-9753 | 2.83 | 2.07 | 89:11 | 4.9 | 1.2 | 77:23 | 3.59 | 97:3 | 2.8 | 2.86 | 95:5 |
| 9 | 9753-9760 | 2.715 | 1.62 | 86:14 | 13.3 | 4.29 | 99:1 | 1.81 | 86:14 | 13.3 | 1.54 | 82:18 |
| 9 | 9074-9754 | 2.7 | 1.81 | 97:3 | 1.2 | 1.54 | 82:18 | 3.59 | 97:3 | 2.8 | 2.86 | 95:5 |
| 9 | 9754-9760 | 3.2 | 2.81 | 94:6 | 10 | NA | NA | 3.59 | 97:3 | 0.3 | NA | NA |
| 10 | 9095-9561 | 2.995 | 2.82 | 94:6 | 11.1 | NA | NA | 3.17 | 96:4 | 1.4 | NA | NA |
| 10 | 9094-9559 | 2.735 | 3.38 | 97:3 | 11.1 | NA | NA | 2.09 | 89:11 | 3.3 | NA | NA |
| 10 | 9099-9564 | 2.585 | 3.08 | 96:4 | 4.5 | NA | NA | 2.09 | 89:11 | 3.3 | NA | NA |
| 10 | 9096-9564 | | | | | | | | | | | |

TABLE 13a-continued

LCCA performance of the designs that met the LCCA average performance criteria of correctly paired:mispaired Fab heterodimers of 86:14

| Cluster | Unique identifier*** | lcca average performance (i.e. 0.5 (ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L2 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 10 | 9091-9560 | 2.54 | 2.8 | 94:6 | 3.6 | 3.13 | 96:4 | 2.28 | 91:9 | 1.3 | 2.06 | 89:11 |
| 10 | 9090-9558 | 2.495 | 2.88 | 95:5 | 9.9 | 2.69 | 94:6 | 2.11 | 89:11 | 2.4 | 2.45 | 92:8 |
| 10 | 9092-9562 | 2.435 | 3.61 | 97:3 | 2 | NA | NA | 1.26 | 78:22 | 4.8 | NA | NA |
| 10 | 9098-9562 | 2.425 | 3.59 | 97:3 | 2.3 | NA | NA | 1.26 | 78:22 | 4.8 | NA | NA |
| 10 | 9092-9571 | 2.225 | 3.61 | 97:3 | 2 | NA | NA | 0.84 | 70:30 | 10.7 | NA | NA |
| 10 | 9098-9571 | 2.215 | 3.59 | 97:3 | 2.3 | NA | NA | 0.84 | 70:30 | 10.7 | NA | NA |
| 10 | 9099-9572 | 2.1 | 3.38 | 97:3 | 11.1 | NA | NA | 0.82 | 69:31 | 8.7 | NA | NA |
| 10 | 9096-9572 | 1.95 | 3.08 | 96:4 | 4.5 | NA | NA | 0.82 | 69:31 | 8.7 | NA | NA |
| 11 | 9667-9830 | 3.17 | 2.29 | 91:9 | 8.6 | 2.18 | 90:10 | 4.05 | 98:2 | 2.9 | 2.17 | 90:10 |
| 11 | 9617-9853 | 2.865 | 1.74 | 85:15 | 3.3 | 2.05 | 89:11 | 3.99 | 98:2 | 2.6 | 2.89 | 95:5 |
| 11 | 9682-9740 | 2.77 | 2.62 | 93:7 | 1.3 | 2.45 | 92:8 | 2.92 | 95:5 | 3.3 | 2.1 | 89:11 |
| 11 | 9675-9852 | 2.73 | 2.46 | 92:8 | 15.4 | 2.45 | 92:8 | 3 | 95:5 | 9.7 | 2.13 | 89:11 |
| 11 | 9671-9810 | 2.71 | 1.83 | 86:14 | 2.5 | 1.77 | 85:15 | 3.59 | 97:3 | 4.9 | 1.77 | 85:15 |
| 11 | 9617-9891 | 2.7 | 1.74 | 85:15 | 3.3 | NA | NA | 3.65 | 97:3 | 0.5 | NA | NA |
| 11 | 9667-9802 | 2.665 | 2.29 | 91:9 | 8.6 | 2.18 | 90:10 | 3.04 | 95:5 | 10.8 | 1.84 | 86:14 |
| 11 | 9660-9858 | 2.665 | 1.69 | 84:16 | 4.8 | NA | NA | 3.63 | 97:3 | 0.8 | NA | NA |
| 11 | 9660-9896 | 2.64 | 1.69 | 84:16 | 4.8 | NA | NA | 3.59 | 97:3 | 1.6 | NA | NA |
| 11 | 9629-9858 | 2.635 | 1.63 | 84:16 | 2.6 | NA | NA | 3.63 | 97:3 | 0.8 | NA | NA |
| 11 | 9667-9758 | 2.62 | 2.29 | 91:9 | 8.6 | 2.18 | 90:10 | 2.95 | 95:5 | 17.8 | 1.66 | 84:16 |
| 11 | 9629-9896 | 2.61 | 1.63 | 84:16 | 2.6 | NA | NA | 3.59 | 97:3 | 1.6 | NA | NA |
| 11 | 9675-9812 | 2.61 | 2.46 | 92:8 | 15.4 | 2.45 | 92:8 | 2.76 | 94:6 | 5.3 | 2.22 | 90:10 |
| 11 | 9671-9784 | 2.545 | 1.83 | 86:14 | 2.5 | 1.77 | 85:15 | 3.26 | 96:4 | 9.4 | 2.14 | 89:11 |

TABLE 13a-continued

LCCA performance of the designs that met the LCCA average performance criteria of correctly paired:mispaired Fab heterodimers of 86:14

| Cluster | Unique identifier *** | lcca average performance (i.e. 0.5 (ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L2 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 11 | 9679-9898 | 2.53 | 1.75 | 85:15 | 5.6 | NA | NA | 3.3 | 96:4 | 0.3 | NA | NA |
| 11 | 9667-9868 | 2.525 | 2.29 | 91:9 | 8.6 | 2.18 | 90:10 | 2.76 | 94:6 | 10.4 | 1.9 | 87:13 |
| 11 | 9663-9838 | 2.52 | 2.27 | 91:9 | 13.6 | 1.29 | 78:22 | 2.77 | 94:6 | 3.5 | 2.83 | 94:6 |
| 11 | 9675-9890 | 2.51 | 2.46 | 92:8 | 15.4 | 2.45 | 92:8 | 2.56 | 93:7 | 14.2 | 1.52 | 82:18 |
| 11 | 9671-9888 | 2.5 | 1.83 | 86:14 | 2.5 | 1.77 | 85:15 | 3.17 | 96:4 | 4.3 | 1.55 | 82:18 |
| 11 | 9617-9787 | 2.5 | 1.74 | 85:15 | 3.3 | 2.05 | 89:11 | 3.26 | 96:4 | 1.4 | 1.86 | 87:13 |
| 11 | 9679-9794 | 2.48 | 1.75 | 85:15 | 5.6 | NA | NA | 3.21 | 96:4 | 0.9 | NA | NA |
| 11 | 9654-9893 | 2.455 | 1 | 73:27 | 38.5 | NA | NA | 3.9 | 98:2 | 2.3 | NA | NA |
| 11 | 9671-9850 | 2.445 | 1.83 | 86:14 | 2.5 | 1.77 | 85:15 | 3.06 | 96:4 | 10.5 | 3.08 | 96:4 |
| 11 | 9675-9786 | 2.44 | 2.46 | 92:8 | 15.4 | 2.45 | 92:8 | 2.42 | 93:7 | 6.7 | 2.29 | 91:9 |
| 11 | 9660-9792 | 2.425 | 1.69 | 84:16 | 4.8 | NA | NA | 3.17 | 96:4 | 1 | NA | NA |
| 11 | 9648-9853 | 2.415 | 0.84 | 70:30 | 34.2 | NA | NA | 3.99 | 98:2 | 2.6 | NA | NA |
| 11 | 9666-9731 | 2.405 | 2.41 | 92:8 | 5.1 | 1.96 | 88:12 | 2.4 | 92:8 | 3.9 | 2.49 | 92:8 |
| 11 | 9049-9759 | 2.395 | 2.08 | 89:11 | 0.7 | NA | NA | 2.72 | 94:6 | 0 | NA | NA |
| 11 | 9629-9792 | 2.395 | 1.63 | 84:16 | 2.6 | NA | NA | 3.17 | 96:4 | 1 | NA | NA |
| 11 | 9623-9893 | 2.345 | 0.79 | 69:31 | 30.5 | NA | NA | 3.9 | 98:2 | 2.3 | NA | NA |
| 11 | 9632-9838 | 2.335 | 1.9 | 87:13 | 14.8 | 1.55 | 82:18 | 2.77 | 94:6 | 3.5 | 2.83 | 94:6 |
| 11 | 9654-9855 | 2.295 | 1 | 73:27 | 38.5 | NA | NA | 3.59 | 97:3 | 0.7 | NA | NA |
| 11 | 9679-9860 | 2.26 | 1.75 | 85:15 | 5.6 | 1.59 | 83:17 | 2.77 | 94:6 | 10.8 | 2.11 | 89:11 |
| 11 | 9645-9761 | 2.255 | 2 | 88:12 | 4 | 2.02 | 88:12 | 2.51 | 92:8 | 5.9 | 2.15 | 90:10 |
| 11 | 9648-9891 | 2.25 | 0.84 | 70:30 | 34.2 | NA | NA | 3.65 | 97:3 | 0.5 | NA | NA |
| 11 | 9626-9836 | 2.25 | 2.08 | 89:11 | 5.3 | 1.28 | 78:22 | 2.42 | 92:8 | 5 | 2.1 | 89:11 |

TABLE 13a-continued

LCCA performance of the designs that met the LCCA average performance criteria of correctly paired:mispaired Fab heterodimers of 86:14

| Cluster | Unique identifier*** | lcca average performance (i.e. 0.5 (ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L2 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 11 | 9579-9797 | 2.25 | 1.31 | 79:21 | 14.5 | NA | NA | 3.17 | 96:4 | 2.9 | NA | NA |
| 11 | 9579-9901 | 2.24 | 1.31 | 79:21 | 14.5 | NA | NA | 3.16 | 96:4 | 1 | NA | NA |
| 11 | 9635-9898 | 2.22 | 1.14 | 76:24 | 28.6 | NA | NA | 3.3 | 96:4 | 0.3 | NA | NA |
| 11 | 9579-9863 | 2.21 | 1.31 | 79:71 | 14.5 | NA | NA | 3.1 | 96:4 | 3.9 | NA | NA |
| 11 | 9683-9841 | 2.205 | 2.14 | 89:11 | 6.5 | 1.1 | 75:25 | 2.27 | 91:9 | 2 | 1.9 | 87:13 |
| 11 | 9623-9855 | 2.185 | 0.79 | 69:31 | 30.5 | NA | NA | 3.59 | 97:3 | 0.7 | NA | NA |
| 11 | 9575-9841 | 2.185 | 2.1 | 89:11 | 1.4 | 2.09 | 89:11 | 2.27 | 91:9 | 2 | 1.9 | 87:13 |
| 11 | 9635-9794 | 2.17 | 1.14 | 76:24 | 28.6 | NA | NA | 3.21 | 96:4 | 0.9 | NA | NA |
| 11 | 9606-9893 | 2.145 | 0.33 | 59:41 | 14.3 | NA | NA | 3.9 | 98:2 | 2.3 | NA | NA |
| 11 | 9614-9761 | 2.145 | 1.78 | 86:14 | 6.2 | 1.84 | 86:14 | 2.51 | 92:8 | 5.9 | 2.15 | 90:10 |
| 11 | 9663-9769 | 7.13 | 2.27 | 91:9 | 13.6 | 1.29 | 78:22 | 1.99 | 88:12 | 10.6 | 2.16 | 90:10 |
| 11 | 9654-9789 | 2.09 | 1. | 73:27 | 38.5 | NA | NA | 3.17 | 96:4 | 1.1 | NA | NA |
| 11 | 9626-9767 | 2.075 | 2.08 | 89:11 | 5.3 | 1.28 | 78:22 | 2.07 | 89:11 | 14.7 | 2.54 | 93:7 |
| 11 | 9648-9737 | 2.05 | 0.84 | 70:30 | 34.2 | NA | NA | 3.26 | 96:4 | 1.4 | NA | NA |
| 11 | 9657-9836 | 2.02 | 1.62 | 83:17 | 33.4 | NA | NA | 2.42 | 92:8 | 5 | NA | NA |
| 11 | 9606-9855 | 1.985 | 0.38 | 59:41 | 14.3 | NA | NA | 3.59 | 97:3 | 0.7 | NA | NA |
| 11 | 9623-9789 | 1.98 | 0.79 | 69:31 | 30.5 | NA | NA | 3.17 | 96:4 | 1.1 | NA | NA |
| 11 | 9635-9860 | 1.95 | 1.14 | 76:24 | 28.6 | NA | NA | 2.77 | 94:6 | 10.3 | NA | NA |
| 11 | 9632-9769 | 1.945 | 1.9 | 87:13 | 14.8 | 1.55 | 82:18 | 1.99 | 88:12 | 10.6 | 2.16 | 90:10 |
| 11 | 9641-9797 | 1.91 | 0.64 | 65:35 | 3.3 | NA | NA | 3.17 | 96:4 | 2.9 | NA | NA |
| 11 | 9641-9901 | 1.9 | 0.64 | 65:35 | 3.3 | NA | NA | 3.16 | 96:4 | 1 | NA | NA |
| 11 | 9663-9876 | 1.875 | 2.27 | 91:9 | 13.6 | 1.29 | 78:22 | 1.43 | 81:19 | 17.1 | 1.85 | 86:14 |

TABLE 13a-continued

LCCA performance of the designs that met the LCCA average performance criteria of correctly paired:mispaired Fab heterodimers of 86:14

| Cluster | Unique identifier *** | lcca average performance (i.e. 0.5 (ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L2 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 11 | 9641-9863 | 1.87 | 0.64 | 65:35 | 3.3 | NA | NA | 3.1 | 96:4 | 3.9 | NA | NA |
| 11 | 9626-9874 | 1.85 | 2.03 | 89:11 | 5.8 | 1.28 | 78:22 | 1.62 | 83:17 | 6.3 | 2.14 | 89:11 |
| 11 | 9657-9767 | 1.845 | 1.62 | 33:17 | 33.4 | NA | NA | 2.07 | 89:11 | 14.7 | NA | NA |
| 11 | 9684-9797 | 1.795 | 0.41 | 60:40 | 3.1 | NA | NA | 3.17 | 96:4 | 2.9 | NA | NA |
| 12 | 9537-9735 | 2.83 | 2.37 | 91:9 | 6.3 | 1.95 | 88:12 | 3.29 | 96:4 | 21.1 | 1.07 | 74:26 |
| 12 | 9637-9737 | 2.63 | 2.06 | 89:11 | 5.4 | 1.86 | 87:13 | 3.2 | 96:4 | 10 | 2.63 | 93:7 |
| 12 | 9696-9732 | 2.585 | 1.9 | 87:13 | 18.1 | NA | NA | 3.27 | 96:4 | 5.6 | NA | NA |
| 12 | 9696-9848 | 2.49 | 1.9 | 87:13 | 18.1 | 2.25 | 90:10 | 3.08 | 96:4 | 11.8 | 2.28 | 91:9 |
| 12 | 9594-9829 | 2.315 | 0.37 | 59:41 | 22.4 | NA | NA | 4.26 | 99:1 | 0.5 | NA | NA |
| 12 | 9692-9846 | 2.305 | 1.62 | 83:17 | 5.2 | 1.33 | 79:21 | 2.99 | 95:5 | 2 | 2.05 | 89:11 |
| 12 | 9696-9886 | 2.28 | 1.9 | 87:13 | 18.1 | NA | NA | 2.66 | 93:7 | 4.3 | NA | NA |
| 12 | 9696-9808 | 2.28 | 1.9 | 87:13 | 18.1 | 2.25 | 90:10 | 2.66 | 93:7 | 12.7 | 1.7 | 85:15 |
| 12 | 9609-9737 | 2.275 | 1.35 | 79:21 | 9.1 | 92 | 37:13 | 3.2 | 96:4 | 10 | 2.63 | 93:7 |
| 12 | 9978-9986 | 2.27 | -0.14 | 47:53 | 0 | NA | NA | 4.67 | 99:1 | 0.6 | NA | NA |
| 12 | 9692-9806 | 2.16 | 1.62 | 83:17 | 5.2 | 1.33 | 79:21 | 2.7 | 94:6 | 0.9 | 2.28 | 91:9 |
| 12 | 9688-9844 | 2.135 | 1.19 | 77:23 | 0.6 | NA | NA | 3.03 | 96:4 | 1.1 | NA | NA |
| 12 | 9688-9804 | 2.125 | 1.19 | 77:23 | 0.6 | NA | NA | 3.06 | 96:4 | 0.5 | NA | NA |
| 12 | 9602-9889 | 2.105 | 1.52 | 82:18 | 10.2 | 1.44 | 81:19 | 2.69 | 94:6 | 8.4 | 1.87 | 87:13 |
| 12 | 9602-9785 | 2.1 | 1.52 | 82:18 | 10.2 | NA | NA | 2.68 | 94:6 | 0.1 | NA | NA |
| 12 | 9574-9702 | 2.1 | 1 | 96:4 | 1.2 | NA | NA | 0.89 | 71:29 | 5 | NA | NA |
| 12 | 9602-9811 | 2.09 | 1.52 | 82:18 | 10.2 | 1.44 | 81:19 | 2.66 | 93:7 | 6.3 | 2.44 | 92:8 |
| 12 | 9692-9780 | 2.075 | 1.62 | 83:17 | 5.2 | NA | NA | 2.53 | 93:7 | 1 | NA | NA |

TABLE 13a-continued

LCCA performance of the designs that met the LCCA average performance criteria of correctly paired:mispaired Fab heterodimers of 86:14

| Cluster | Unique identifier*** | lcca average performance (i.e. 0.5 (ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L2 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 12 | 9594-9757 | 2.065 | 0.37 | 59:41 | 22.4 | NA | NA | 3.76 | 98:2 | 3.9 | NA | NA |
| 12 | 9705-9735 | 2.05 | 0.81 | 69:31 | 0 | NA | NA | 3.29 | 96:4 | 21.1 | NA | NA |
| 12 | 9103-9700 | 2.045 | 2.98 | 95:5 | 0.7 | NA | NA | 1.1 | 75:25 | 3.1 | NA | NA |
| 12 | 9598-9849 | 2.03 | 0.36 | 59:41 | 26 | NA | NA | 3.7 | 98:2 | 2.8 | NA | NA |
| 12 | 9720-9733 | 2.025 | 1.22 | 77:23 | 6.9 | 4 | 76:24 | 2.83 | 94:6 | 8.2 | 2.31 | 91:9 |
| 12 | 9688-9778 | 2.01 | 1.19 | 77:23 | 0.6 | NA | NA | 2.83 | 94:6 | 0.5 | NA | NA |
| 12 | 9598-9809 | 2.005 | 0.36 | 59:41 | 26 | NA | NA | 3.65 | 97:3 | 0.3 | NA | NA |
| 12 | 9982-9987 | 1.995 | −0.16 | 46:54 | 0 | NA | NA | 4.15 | 98:2 | 0.3 | NA | NA |
| 12 | 9101-9700 | 1.995 | 2.9 | 95:5 | 0.2 | NA | NA | 1.1 | 75:25 | 3.1 | NA | NA |
| 12 | 9716-9807 | 1.99 | 0.28 | 57:43 | 0 | NA | NA | 3.69 | 98:2 | 5.6 | NA | NA |
| 12 | 9703-9734 | 1.985 | 1.63 | 84:16 | 14.8 | 1.32 | 79:21 | 2.34 | 91:9 | 4.7 | 2 | 88:12 |
| 12 | 9712-9779 | 1.97 | 1.03 | 74:26 | 13.9 | NA | NA | 2.91 | 95:5 | 2.1 | NA | NA |
| 12 | 9594-9801 | 1.96 | 0.37 | 59:41 | 22.4 | NA | NA | 3.54 | 97:3 | 1.4 | NA | NA |
| 12 | 9712-9805 | 1.95 | 1.03 | 74:26 | 13.9 | NA | NA | 2.87 | 95:5 | 2.3 | NA | NA |
| 12 | 9602-9851 | 1.945 | 1.77 | 82:18 | 10.2 | 1.44 | 81:19 | 2.37 | 91:9 | 14.4 | 2.23 | 90:10 |

TABLE 13a-continued

LCCA performance of the designs that met the LCCA average performance criteria of correctly paired:mispaired Fab heterodimers of 86:14

| Cluster | Unique identifier *** | lcca average performance (i.e. 0.5 (ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L2 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 12 | 9716-9847 | 1.94 | 0.28 | 57:43 | 0 | NA | NA | 3.6 | 97:3 | 3.3 | NA | NA |
| 12 | 9979-9986 | 1.885 | −0.14 | 47:53 | 0 | NA | NA | 3.9 | 98:2 | 0.4 | NA | NA |
| 12 | 9708-9777 | 1.885 | 0.37 | 59:41 | 11.3 | NA | NA | 3.4 | 97:3 | 0.1 | NA | NA |
| 12 | 9722-9744 | 1.88 | 1.04 | 74:26 | 6.4 | 1.79 | 86:14 | 2.72 | 94:6 | 15.2 | 1.33 | 79:21 |
| 12 | 9712-9845 | 1.88 | 1.03 | 74:26 | 13.9 | 1.65 | 84:16 | 2.73 | 94:6 | 12.8 | 2.1 | 89:11 |
| 12 | 9589-9742 | 1.87 | 1.77 | 85:15 | 1.9 | NA | NA | 1.96 | 88:12 | 2.4 | NA | NA |
| 12 | 9716-9781 | 1.85 | 0.23 | 57:43 | 0 | NA | NA | 3.42 | 97:3 | 5.2 | NA | NA |
| 12 | 9692-9884 | 1.795 | 1.62 | 83:17 | 5.2 | NA | NA | 1.97 | 88:12 | 6.3 | NA | NA |
| 13 | 9042-9046 | 1.99 | 3.78 | 98:2 | 2.2 | 4.18 | 98:2 | 0.2 | 55:45 | 11.4 | 0.2 | 55:45 |

*values were obtained from LCCA experiments conducted with L1:L2 DNA ratio of 1:3 and normalized to L1:L2 DNA ratio of 1:1
**values were obtained from LCCA experiments conducted with L1:L2 DNA ratio of 1:9 and normalized to L1:L2 DNA ratio of 1:1
*** the "Unique identifier" consists of the unique identifiers for the two constituent LCCAs in either (Set#H1L1L2-Set#H2L2L1) or (Set#H2L2L1-Set#H1L1L2) orientation TABLE 13b Stability and antigen binding assessments of the designs that met the LCCA average performance criteria of correctly paired:mispaired Fab heterodimers of 86:14

| Cluster | Unique identifier** | KD of h1\|1 Fab heterodimer (nM) | Change in KD of h1\|1 Fab heterodimer with respect to wild type (−(log(KD_design) − log(KD_wt))) | KD of h2\|2 Fab heterodimer (nM) | Change in KD of h2\|2 Fab heterodimer with respect to wild type (−(log(KD_design) − log(KD_wt))) | DSF values of h1\|1 Fab heterodimer (° C.) | DSF values of h2\|2 Fab heterodimer (° C.) |
|---|---|---|---|---|---|---|---|
| 1 | 9134-9521 | 0.16 | 0 | 0.2 | −0.1 | 80.3 | ND |
| 1 | 9123-9521 | 0.15 | 0.02 | 0.2 | −0.1 | 79.6 | ND |
| 1 | 9150-9523 | 0.16 | −0.01 | 0.2 | −0.1 | 79.6 | ND |
| 1 | 9152-9515 | 0.16* | −0.01* | 0.26 | −0.21 | 79.60* | ND |
| 1 | 9154-9394 | 0.16* | −0.01* | 0.22 | −0.15 | 79.60* | 79.8 |
| 1 | 9164-9555 | 0.16* | −0.01* | 0.24 | −0.18 | 79.60* | 80.3 |
| 1 | 9146-9553 | 0.16* | 0.00* | 0.24 | −0.18 | 80.30* | 80.3 |
| 1 | 9162-9425 | 0.16* | −0.01* | 0.23 | −0.16 | 79.60* | 79.5 |
| 1 | 9164-9500 | 0.16* | −0.01* | 0.24 | −0.19 | 79.60* | 79.8 |
| 1 | 9154-9353 | 0.16* | −0.01* | 0.2 | −0.1 | 79.60* | ND |
| 1 | 9152-9460 | 0.16* | −0.01* | 0.26 | −0.23 | 79.60* | 79.7 |
| 1 | 9160-9416 | 0.16* | −0.01* | 0.2 | −0.12 | 79.60* | 79.5 |
| 1 | 9136-9513 | 0.16* | 0.00* | 0.26 | −0.21 | 80.30* | ND |
| 1 | 9136-9459 | 0.16* | 0.00* | 0.26 | −0.23 | 80.30* | 79.7 |
| 1 | 9144-9423 | 0.16* | 0.00* | 0.23 | −0.16 | 80.30* | 79.5 |
| 1 | 9158-9483 | 0.16* | −0.01* | 0.18 | −0.07 | 79.60* | 79.8 |
| 1 | 9142-9414 | 0.16* | 0.00* | 0.2 | −0.12 | 80.30* | 79.5 |
| 1 | 9138-9392 | 0.16* | 0.00* | 0.22 | −0.15 | 80.30* | 79.8 |
| 1 | 9156-9397 | 0.16* | −0.01* | 0.19 | −0.08 | 79.60* | 79.5 |
| 1 | 9140-9481 | 0.16* | 0.00* | 0.18 | −0.07 | 80.30* | 79.8 |
| 1 | 9131-9553 | 0.15* | 0.02* | 0.24 | −0.18 | 79.60* | 80.3 |
| 1 | 9164-9446 | 0.16* | −0.01* | 0.28 | −0.26 | 79.60* | 80.1 |
| 1 | 9126-9392 | 0.15* | 0.02* | 0.22 | −0.15 | 79.60* | 79.8 |
| 1 | 9138-9352 | 0.16* | 0.00* | 0.2 | −0.1 | 80.30* | ND |
| 1 | 9127-9481 | 0.15* | 0.02* | 0.18 | −0.07 | 79.60* | 79.8 |
| 1 | 9130-9423 | 0.15* | 0.02* | 0.23 | −0.16 | 79.60* | 79.5 |
| 1 | 9158-9538 | 0.16* | −0.01* | 0.17 | −0.04 | 79.60* | ND |
| 1 | 9150-9468 | 0.16 | −0.01 | 0.18 | −0.07 | 79.6 | 79.7 |
| 1 | 9125-9513 | 0.15* | 0.02* | 0.26 | −0.21 | 79.60* | ND |
| 1 | 9140-9536 | 0.16* | 0.00* | 0.17 | −0.04 | 80.30* | ND |
| 1 | 9126-9352 | 0.15* | 0.02* | 0.2 | −0.1 | 79.60* | ND |
| 1 | 9164-9367 | 0.16* | −0.01* | 0.15 | 0.01 | 79.60* | 79.7 |
| 1 | 9125-9459 | 0.15* | 0.02* | 0.26 | −0.23 | 79.60* | 79.7 |
| 1 | 9142-9357 | 0.16* | 0.00* | 0.18 | −0.07 | 80.30* | ND |
| 1 | 9129-9414 | 0.15* | 0.02* | 0.2 | −0.12 | 79.60* | 79.5 |
| 1 | 9162-9362 | 0.16* | −0.01* | 0.16 | −0.01 | 79.60* | ND |
| 1 | 9127-9536 | 0.15* | 0.02* | 0.17 | −0.04 | 79.60* | ND |
| 1 | 9146-9366 | 0.16* | 0.00* | 0.15 | 0.01 | 80.30* | 79.7 |
| 1 | 9160-9358 | 0.16* | −0.01* | 0.18 | −0.07 | 79.60* | ND |
| 1 | 9146-9498 | 0.16* | 0.00* | 0.24 | −0.19 | 80.30* | 79.8 |
| 1 | 9156-9354 | 0.16* | −0.01* | 0.17 | −0.04 | 79.60* | ND |
| 1 | 9134-9466 | 0.16 | 0 | 0.18 | −0.07 | 80.3 | 79.7 |
| 1 | 9144-9361 | 0.16* | 0.00* | 0.16 | −0.01 | 80.30* | ND |
| 1 | 9123-9466 | 0.15 | 0.02 | 0.18 | −0.07 | 79.6 | 79.7 |
| 1 | 9129-9357 | 0.15* | 0.02* | 0.18 | −0.07 | 79.60* | ND |
| 1 | 9131-9366 | 0.15* | 0.02* | 0.15 | 0.01 | 79.60* | 79.7 |
| 1 | 9130-9361 | 0.15* | 0.02* | 0.16 | −0.01 | 79.60* | ND |
| 1 | 9131-9498 | 0.15* | 0.02* | 0.24 | −0.19 | 79.60* | 79.8 |
| 1 | 9146-9444 | 0.16* | 0.00* | 0.28 | −0.26 | 80.30* | 80.1 |
| 2 | 9279-9518 | 0.20* | −0.11* | 0.2 | −0.1 | 79.00* | ND |
| 2 | 9286-9402 | 0.2 | −0.11 | 0.2 | −0.12 | 79 | 79.5 |
| 2 | 9287-9486 | 0.2 | −0.11 | 0.23 | −0.17 | 79 | 80 |
| 2 | 9283-9380 | 0.2 | −0.11 | 0.22 | −0.15 | 79 | 79.8 |
| 2 | 9273-9398 | 0.2 | −0.12 | 0.2 | −0.12 | 78.6 | 79.5 |
| 2 | 9252-9380 | 0.26 | −0.21 | 0.22 | −0.15 | 78.3 | 79.8 |
| 2 | 9323-9440 | 0.18* | −0.07* | 0.28 | −0.26 | 78.20* | 80.1 |
| 2 | 9287-9541 | 0.2 | −0.11 | 0.22 | −0.15 | 79 | 79.7 |
| 2 | 9271-9376 | 0.2 | −0.12 | 0.22 | −0.15 | 78.6 | 79.8 |
| 2 | 9284-9471 | 0.2 | −0.11 | 0.18 | −0.07 | 79 | 79.8 |
| 2 | 9290-9432 | 0.2 | −0.11 | 0.28 | −0.26 | 79 | 80.1 |
| 2 | 9256-9432 | 0.26 | −0.21 | 0.28 | −0.26 | 78.3 | 80.1 |
| 2 | 9253-9471 | 0.26 | −0.21 | 0.18 | −0.07 | 78.3 | 79.8 |
| 2 | 9302-9406 | 0.21* | −0.12* | 0.2 | −0.12 | 78.20* | 79.5 |
| 2 | 9287-9420 | 0.2 | −0.11 | 0.23 | −0.16 | 79 | 79.5 |
| 2 | 9308-9436 | 0.21* | −0.12* | 0.28 | −0.26 | 78.20* | 80.1 |
| 2 | 9255-9402 | 0.26 | −0.21 | 0.2 | −0.12 | 78.3 | 79.5 |
| 2 | 9248-9398 | 0.28 | −0.26 | 0.2 | −0.12 | 78.1 | 79.5 |
| 2 | 9209-9398 | ND | ND | 0.2 | −0.12 | 78.3 | 79.5 |
| 2 | 9281-9503 | 0.2 | −0.11 | 0.26 | −0.21 | 79 | ND |

TABLE 13b-continued

Stability and antigen binding assessments of the designs that met the LCCA average performance criteria of correctly paired:mispaired Fab heterodimers of 86:14

| Cluster | Unique identifier** | KD of h1\|1 Fab heterodimer (nM) | Change in KD of h1\|1 Fab heterodimer with respect to wild type (−(log(KD_design) − log(KD_wt))) | KD of h2\|2 Fab heterodimer (nM) | Change in KD of h2\|2 Fab heterodimer with respect to wild type (−(log(KD_design) − log(KD_wt))) | DSF values of h1\|1 Fab heterodimer (° C.) | DSF values of h2\|2 Fab heterodimer (° C.) |
|---|---|---|---|---|---|---|---|
| 2 | 9263-9436 | 0.24 | −0.19 | 0.28 | −0.26 | ND | 80.1 |
| 2 | 9275-9419 | 0.2 | −0.12 | 0.23 | −0.16 | 78.6 | 79.5 |
| 2 | 9212-9402 | 0.2 | −0.11 | 0.2 | −0.12 | 78.5 | 79.5 |
| 2 | 9211-9380 | 0.2 | −0.11 | 0.22 | −0.15 | 78.5 | 79.8 |
| 2 | 9270-9440 | 0.31 | −0.29 | 0.28 | −0.26 | ND | 80.1 |
| 2 | 9229-9440 | 0.16 | −0.02 | 0.28 | −0.26 | ND | 80.1 |
| 2 | 9250-9503 | 0.26 | −0.21 | 0.26 | −0.21 | 78.3 | ND |
| 2 | 9290-9546 | 0.2 | −0.11 | 0.24 | −0.18 | 79 | 80.3 |
| 2 | 9247-9376 | 0.28 | −0.26 | 0.22 | −0.15 | 78.1 | 79.8 |
| 2 | 9256-9546 | 0.26 | −0.21 | 0.24 | −0.18 | 78.3 | 80.3 |
| 2 | 9323-9495 | 0.18* | −0.07* | 0.24 | −0.19 | 78.20* | 79.8 |
| 2 | 9213-9432 | 0.2 | −0.11 | 0.28 | −0.26 | 78.5 | 80.1 |
| 2 | 9262-9406 | 0.24 | −0.19 | 0.2 | −0.12 | ND | 79.5 |
| 2 | 9181-9406 | 0.22 | −0.15 | 0.2 | −0.12 | ND | 79.5 |
| 2 | 9208-9376 | ND | ND | 0.22 | −0.15 | 78.3 | 79.8 |
| 2 | 9173-9380 | 0.25 | −0.21 | 0.22 | −0.15 | 78.5 | 79.8 |
| 2 | 9170-9376 | 0.27 | −0.24 | 0.22 | −0.15 | 77.8 | 79.8 |
| 2 | 9196-9516 | 0.28 | −0.25 | 0.26 | −0.21 | 76.4 | ND |
| 2 | 9319-9410 | 0.18* | −0.07* | 0.2 | −0.12 | 78.20* | 79.5 |
| 2 | 9171-9398 | 0.27 | −0.24 | 0.2 | −0.12 | 77.8 | 79.5 |
| 2 | 9219-9406 | 0.19 | −0.08 | 0.2 | −0.12 | ND | 79.5 |
| 2 | 9174-9402 | 0.25 | −0.21 | 0.2 | −0.12 | 78.5 | 79.5 |
| 2 | 9198-9395 | 0.28 | −0.25 | 0.22 | −0.15 | 76.4 | 79.8 |
| 2 | 9175-9432 | 0.25 | −0.21 | 0.28 | −0.26 | 78.5 | 80.1 |
| 2 | 9236-9395 | 0.22 | −0.15 | 0.22 | −0.15 | ND | 79.8 |
| 2 | 9281-9449 | 0.2 | −0.11 | 0.26 | −0.23 | 79 | 79.7 |
| 2 | 9234-9516 | 0.22 | −0.15 | 0.26 | −0.21 | ND | ND |
| 2 | 9308-9547 | 0.21* | −0.12* | 0.24 | −0.18 | 78.20* | 80.3 |
| 2 | 9304-9542 | 0.21* | −0.12* | 0.22 | −0.15 | 78.20* | 79.7 |
| 2 | 9243-9556 | 0.22 | −0.15 | 0.24 | −0.18 | ND | 80.3 |
| 2 | 9250-9449 | 0.26 | −0.21 | 0.26 | −0.23 | 78.3 | 79.7 |
| 2 | 9213-9546 | 0.2 | −0.11 | 0.24 | −0.18 | 78.5 | 80.3 |
| 2 | 9269-9410 | 0.31 | −0.29 | 0.2 | −0.12 | ND | 79.5 |
| 2 | 9237-9484 | 0.22 | −0.15 | 0.18 | −0.07 | ND | 79.8 |
| 2 | 9270-9495 | 0.31 | −0.29 | 0.24 | −0.19 | ND | 79.8 |
| 2 | 9220-9436 | 0.19 | −0.08 | 0.28 | −0.26 | ND | 80.1 |
| 2 | 9229-9495 | 0.15 | −0.02 | 0.24 | −0.19 | ND | 79.8 |
| 2 | 9284-9526 | 0.2 | −0.11 | 0.17 | −0.04 | 79 | ND |
| 2 | 9279-9463 | 0.20* | −0.11* | 0.18 | −0.07 | 79.00* | 79.7 |
| 2 | 9304-9487 | 0.21* | −0.12* | 0.23 | −0.17 | 78.20* | 80 |
| 2 | 9323-9550 | 0.18* | −0.07* | 0.24 | −0.18 | 78.20* | 80.3 |
| 2 | 9214-9505 | 0.19 | −0.08 | 0.26 | −0.21 | ND | ND |
| 2 | 9253-9526 | 0.26 | −0.21 | 0.17 | −0.04 | 78.3 | ND |
| 2 | 9263-9547 | 0.24 | −0.19 | 0.24 | −0.18 | ND | 80.3 |
| 2 | 9271-9350 | 0.2 | −0.12 | 0.2 | −0.1 | 78.6 | ND |
| 2 | 9316-9388 | 0.18* | −0.07* | 0.22 | −0.15 | 78.20* | 79.8 |
| 2 | 9298-9384 | 0.21* | −0.12* | 0.22 | −0.15 | 78.20* | 79.8 |
| 2 | 9243-9501 | 0.22 | −0.15 | 0.24 | −0.19 | ND | 79.8 |
| 2 | 9257-9505 | 0.24 | −0.19 | 0.26 | −0.21 | ND | ND |
| 2 | 9205-9556 | 0.28 | −0.25 | 0.24 | −0.18 | 76.4 | 80.3 |
| 2 | 9176-9505 | 0.22 | −0.15 | 0.26 | −0.21 | ND | ND |
| 2 | 9175-9546 | 0.25 | −0.21 | 0.24 | −0.18 | 78.5 | 80.3 |
| 2 | 9214-9451 | 0.19 | −0.08 | 0.26 | −0.23 | ND | 79.7 |
| 2 | 9199-9484 | 0.28 | −0.25 | 0.18 | −0.07 | 76.4 | 79.8 |
| 2 | 9240-9544 | 0.22 | −0.15 | 0.22 | −0.15 | ND | 79.7 |
| 2 | 9205-9501 | 0.28 | −0.25 | 0.24 | −0.19 | 76.4 | 79.8 |
| 2 | 9257-9451 | 0.24 | −0.19 | 0.26 | −0.23 | ND | 79.7 |
| 2 | 9243-9368 | 0.22 | −0.15 | 0.15 | 0.01 | ND | 79.7 |
| 2 | 9176-9451 | 0.22 | −0.15 | 0.26 | −0.23 | ND | 79.7 |
| 2 | 9196-9461 | 0.28 | −0.25 | 0.26 | −0.23 | 76.4 | 79.7 |
| 2 | 9217-9473 | 0.19 | −0.08 | 0.18 | −0.07 | ND | 79.8 |
| 2 | 9320-9488 | 0.18* | −0.07* | 0.23 | −0.17 | 78.20* | 80 |
| 2 | 9266-9388 | 0.31 | −0.29 | 0.22 | −0.15 | ND | 79.8 |
| 2 | 9202-9544 | 0.28 | −0.25 | 0.22 | −0.15 | 76.4 | 79.7 |
| 2 | 9205-9368 | 0.28 | −0.25 | 0.15 | 0.01 | 76.4 | 79.7 |
| 2 | 9259-9384 | 0.24 | −0.19 | 0.22 | −0.15 | ND | 79.8 |
| 2 | 9290-9364 | 0.2 | −0.11 | 0.15 | 0.01 | 79 | 79.7 |
| 2 | 9256-9364 | 0.26 | −0.21 | 0.15 | 0.01 | 78.3 | 79.7 |
| 2 | 9270-9550 | 0.31 | −0.29 | 0.24 | −0.18 | ND | 80.3 |

TABLE 13b-continued

Stability and antigen binding assessments of the designs that met the LCCA average performance criteria of correctly paired:mispaired Fab heterodimers of 86:14

| Cluster | Unique identifier** | KD of h1\|1 Fab heterodimer (nM) | Change in KD of h1\|1 Fab heterodimer with respect to wild type (−(log(KD_design) − log(KD_wt))) | KD of h2\|2 Fab heterodimer (nM) | Change in KD of h2\|2 Fab heterodimer with respect to wild type (−(log(KD_design) − log(KD_wt))) | DSF values of h1\|1 Fab heterodimer (° C.) | DSF values of h2\|2 Fab heterodimer (° C.) |
|---|---|---|---|---|---|---|---|
| 2 | 9229-9550 | 0.16 | −0.02 | 0.24 | −0.18 | ND | 80.3 |
| 2 | 9247-9350 | 0.28 | −0.26 | 0.2 | −0.1 | 78.1 | ND |
| 2 | 9178-9384 | 0.22 | −0.15 | 0.22 | −0.15 | ND | 79.8 |
| 2 | 9225-9388 | 0.16 | −0.02 | 0.22 | −0.15 | ND | 79.8 |
| 2 | 9208-9350 | ND | ND | 0.2 | −0.1 | 78.3 | ND |
| 2 | 9234-9461 | 0.22 | −0.15 | 0.26 | −0.23 | ND | 79.7 |
| 2 | 9220-9547 | 0.19 | −0.08 | 0.24 | −0.18 | ND | 80.3 |
| 2 | 9290-9491 | 0.2 | −0.11 | 0.24 | −0.19 | 79 | 79.8 |
| 2 | 9170-9350 | 0.27 | −0.24 | 0.2 | −0.1 | 77.8 | ND |
| 2 | 9256-9491 | 0.26 | −0.21 | 0.24 | −0.19 | 78.3 | 79.8 |
| 2 | 9275-9359 | 0.2 | −0.12 | 0.16 | −0.01 | 78.6 | ND |
| 2 | 9179-9473 | 0.22 | −0.15 | 0.18 | −0.07 | ND | 79.8 |
| 2 | 9240-9489 | 0.22 | −0.15 | 0.23 | −0.17 | ND | 80 |
| 2 | 9240-9426 | 0.22 | −0.15 | 0.23 | −0.16 | ND | 79.5 |
| 2 | 9228-9410 | 0.16 | −0.02 | 0.2 | −0.12 | ND | 79.5 |
| 2 | 9216-9384 | 0.19 | −0.08 | 0.22 | −0.15 | ND | 79.8 |
| 2 | 9298-9351 | 0.21* | −0.12* | 0.2 | −0.1 | 78.20* | ND |
| 2 | 9213-9364 | 0.2 | −0.11 | 0.15 | 0.01 | 78.5 | 79.7 |
| 2 | 9202-9489 | 0.28 | −0.25 | 0.23 | −0.17 | 76.4 | 80 |
| 2 | 9243-9447 | 0.22 | −0.15 | 0.28 | −0.26 | ND | 80.1 |
| 2 | 9202-9426 | 0.28 | −0.25 | 0.23 | −0.16 | 76.4 | 79.5 |
| 3 | 9338-9748 | 0.36 | −0.36 | 0.24 | −0.18 | 79.1 | 79.9 |
| 3 | 9372-9748 | 0.36 | −0.36 | 0.27 | −0.24 | 79.1 | 74.5 |
| 3 | 6054-9327 | 0.24 | −0.19 | 0.24 | −0.18 | 79.8 | 79.9 |
| 3 | 9338-9750 | 0.23 | −0.16 | 0.24 | −0.18 | 79.5 | 79.9 |
| 3 | 9334-9747 | 0.36 | −0.36 | 0.2 | −0.1 | 79.1 | 80.8 |
| 3 | 9121-9373 | 0.13 | 0.08 | 0.27 | −0.24 | 79.5 | 74.5 |
| 3 | 9334-9749 | 0.23 | −0.16 | 0.2 | −0.1 | 79.5 | 80.8 |
| 3 | 9815-9825 | 0.16 | −0.01 | 0.15 | 0.01 | 77.8 | 77.7 |
| 3 | 9815-9826 | 0.16 | −0.01 | 0.06 | 0.43 | 77.8 | 78.3 |
| 3 | 9816-9825 | 0.19 | −0.09 | 0.15 | 0.01 | 78.3 | 77.7 |
| 3 | 9372-9750 | 0.23 | −0.16 | 0.27 | −0.24 | 79.5 | 74.5 |
| 3 | 9816-9826 | 0.19 | −0.09 | 0.06 | 0.43 | 78.3 | 78.3 |
| 3 | 9107-9339 | 0.16 | −0.01 | 0.24 | −0.18 | 79.8 | 79.9 |
| 3 | 9066-9335 | 0.17 | −0.04 | 0.2 | −0.1 | 81.2 | 80.8 |
| 3 | 6048-9326 | 0.24 | −0.19 | 0.2 | −0.1 | 79.8 | 80.8 |
| 3 | 9328-9332 | 0.24* | −0.19* | 0.25 | −0.2 | 79.80* | 79.2 |
| 3 | 9122-9371 | 0.13 | 0.1 | 0.22 | −0.14 | 80 | 81 |
| 3 | 9104-9336 | 0.16* | −0.01* | 0.2 | −0.1 | 81.40* | 80.8 |
| 3 | 9108-9330 | 0.16* | −0.01* | 0.25 | −0.2 | 79.80* | 79.2 |
| 3 | 9106-9337 | 0.16 | −0.01 | 0.2 | −0.1 | 79.8 | 80.8 |
| 3 | 9369-9747 | 0.36 | −0.36 | 0.22 | −0.14 | 79.1 | 81 |
| 3 | 9109-9332 | 0.16 | −0.01 | 0.25 | −0.2 | 79.9 | 79.2 |
| 4 | 9168-9342 | ND | ND | 0.34 | −0.34 | 78.8 | 80.5 |
| 4 | 9169-9344 | ND | ND | 0.27 | −0.23 | 78.8 | ND |
| 4 | 9114-9344 | 0.14 | 0.04 | 0.27 | −0.23 | 79.1 | ND |
| 4 | 6098-9118 | 0.01 | −0.28 | 0 | 0.34 | 81.20* | 80.2 |
| 4 | 9113-9342 | 0.14 | 0.04 | 0.34 | −0.34 | 79.1 | 80.5 |
| 4 | 9117-9374 | 0.17 | −0.03 | 0.23 | −0.16 | 80.8 | 80.3 |
| 4 | 9119-9375 | 0.17 | −0.03 | 0.23 | −0.16 | 81.2 | 80.3 |
| 4 | 9111-9347 | 0.13 | 0.09 | 0.23 | −0.16 | 80.6 | 80.3 |
| 5 | 9116-9349 | 0.16 | −0.02 | 0.15 | 0.03 | 79.9 | ND |
| 6 | 9075-9745 | 0.17 | −0.03 | ND | ND | 78.1 | 81.4 |
| 6 | 9745-9905 | ND | ND | 0.1 | 0.2 | 81.4 | 76.8 |
| 6 | 9075-9746 | 0.17 | −0.03 | 0.35 | −0.35 | 78.1 | 80.5 |
| 6 | 9746-9905 | 0.35 | −0.35 | 0.1 | 0.2 | 80.5 | 76.8 |
| 6 | 9814-9828 | 0.16 | −0.01 | 0.14 | 0.07 | 79.2 | 78 |
| 6 | 9813-9828 | 0.18 | −0.05 | 0.14 | 0.07 | 81.3 | 78 |
| 6 | 10547-10549 | ND | ND | 0.35 | −0.35 | ND | 80.5 |
| 6 | 10545-10549 | 0.35 | −0.35 | ND | ND | 80.5 | ND |
| 6 | 9814-9824 | 0.16 | −0.01 | 0.15 | 0.03 | 79.2 | 79.7 |
| 6 | 10547-10551 | ND | ND | ND | ND | ND | 81.4 |
| 6 | 9813-9824 | 0.18 | −0.05 | 0.15 | 0.03 | 81.3 | 79.7 |
| 6 | 10545-10551 | ND | ND | ND | ND | 81.4 | ND |
| 7 | 9060-9756 | 0.14 | 0.04 | 0.28 | −0.25 | 81 | 80.4 |
| 7 | 9054-9060 | 0.14 | 0.05 | 0.14 | 0.04 | 80.7 | 81 |
| 7 | 9053-9058 | 0.14 | 0.05 | 0.12 | 0.12 | 80.7 | 80.8 |
| 7 | 9058-9755 | 0.12 | 0.12 | 0.28 | −0.26 | 80.8 | 80.4 |
| 8 | 9820-9823 | 0.2 | −0.1 | 0.24 | −0.18 | 78.2 | 78.4 |

TABLE 13b-continued

Stability and antigen binding assessments of the designs that met the LCCA average performance criteria of correctly paired:mispaired Fab heterodimers of 86:14

| Cluster | Unique identifier** | KD of h1\|1 Fab heterodimer (nM) | Change in KD of h1\|1 Fab heterodimer with respect to wild type (−(log(KD_design) − log(KD_wt))) | KD of h2\|2 Fab heterodimer (nM) | Change in KD of h2\|2 Fab heterodimer with respect to wild type (−(log(KD_design) − log(KD_wt))) | DSF values of h1\|1 Fab heterodimer (° C.) | DSF values of h2\|2 Fab heterodimer (° C.) |
|---|---|---|---|---|---|---|---|
| 8 | 9819-9823 | 0.15 | 0.03 | 0.24 | −0.18 | 79.3 | 78.4 |
| 8 | 9820-9822 | 0.2 | −0.1 | 0.11 | 0.17 | 78.2 | 77.7 |
| 8 | 9819-9822 | 0.15 | 0.03 | 0.11 | 0.17 | 79.3 | 77.7 |
| 8 | 9820-9821 | 0.2 | −0.1 | 0.07 | 0.38 | 78.2 | 78.3 |
| 8 | 9820-9827 | 0.2 | −0.1 | 0.17 | −0.03 | 78.2 | 79 |
| 8 | 9819-9821 | 0.15 | 0.03 | 0.07 | 0.38 | 79.3 | 78.3 |
| 8 | 9819-9827 | 0.15 | 0.03 | 0.17 | −0.03 | 79.3 | 79 |
| 8 | 9817-9823 | 0.18 | −0.05 | 0.24 | −0.18 | 77.5 | 78.4 |
| 8 | 9817-9822 | 0.18 | −0.05 | 0.11 | 0.17 | 77.5 | 77.7 |
| 8 | 9817-9821 | 0.18 | −0.05 | 0.07 | 0.38 | 77.5 | 78.3 |
| 8 | 9817-9827 | 0.18 | −0.05 | 0.17 | −0.03 | 77.5 | 79 |
| 8 | 9818-9823 | 0.18 | −0.07 | 0.24 | −0.18 | 78.7 | 78.4 |
| 8 | 9818-9822 | 0.18 | −0.07 | 0.11 | 0.17 | 78.7 | 77.7 |
| 8 | 9818-9821 | 0.18 | −0.07 | 0.07 | 0.38 | 78.7 | 78.3 |
| 8 | 9818-9827 | 0.18 | −0.07 | 0.17 | −0.03 | 78.7 | 79 |
| 9 | 10548-10550 | ND | ND | ND | ND | ND | 79 |
| 9 | 10548-10552 | ND | ND | 0.29 | −0.27 | ND | 80.3 |
| 9 | 10546-10550 | ND | ND | ND | ND | ND | 79 |
| 9 | 10546-10552 | ND | ND | 0.29 | −0.27 | ND | 80.3 |
| 9 | 9077-9611 | 0.15 | 0.01 | 0.12 | 0.12 | 80.9 | 81.8 |
| 9 | 9065-9751 | 0.18 | −0.05 | ND | ND | 76.3 | 79 |
| 9 | 9064-9751 | 0.17 | −0.05 | ND | ND | 77.2 | 79 |
| 9 | 9065-9752 | 0.18 | −0.05 | 0.29 | −0.27 | 76.3 | 80.3 |
| 9 | 9078-9612 | 0.15 | 0.01 | ND | ND | 80.9 | 81.5 |
| 9 | 9076-9610 | 0.15 | 0.01 | ND | ND | 80.9 | 82.1 |
| 9 | 9064-9752 | 0.17 | −0.05 | 0.29 | −0.27 | 77.2 | 80.3 |
| 9 | 9074-9753 | 0.16 | −0.01 | ND | ND | 82.5 | 80.5 |
| 9 | 9753-9760 | ND | ND | 0.32 | −0.31 | 80.5 | 81.3 |
| 9 | 9074-9754 | 0.16 | −0.01 | 0.3 | −0.28 | 82.5 | 79.8 |
| 9 | 9754-9760 | 0.3 | −0.28 | 0.32 | −0.31 | 79.8 | 81.3 |
| 10 | 9095-9561 | 0.17 | −0.04 | 0.21 | −0.13 | 79.8 | 80.2 |
| 10 | 9094-9559 | 0.17 | −0.04 | 0.27 | −0.24 | 79.8 | 80.6 |
| 10 | 9099-9564 | 0.19 | −0.09 | ND | ND | 81.3 | 79.3 |
| 10 | 9096-9564 | 0.17 | −0.04 | ND | ND | 79.8 | 79.3 |
| 10 | 9091-9560 | 0.16 | −0.02 | 0.21 | −0.13 | 79.9 | 80.2 |
| 10 | 9090-9558 | 0.16 | −0.02 | 0.27 | −0.24 | 79.9 | 80.6 |
| 10 | 9092-9562 | 0.16 | −0.02 | ND | ND | 79.9 | 79.3 |
| 10 | 9098-9562 | 0.17 | −0.03 | ND | ND | 80.6 | 79.3 |
| 10 | 9092-9571 | 0.16 | −0.02 | 0.26 | −0.21 | 79.9 | 81 |
| 10 | 9098-9571 | 0.17 | −0.03 | 0.26 | −0.21 | 80.6 | 81 |
| 10 | 9099-9572 | 0.19 | −0.09 | 0.26 | −0.21 | 81.3 | 81 |
| 10 | 9096-9572 | 0.17 | −0.04 | 0.26 | −0.21 | 79.8 | 81 |
| 11 | 9667-9830 | 0.27 | −0.23 | 0.06 | 0.41 | 80.4 | 79.5 |
| 11 | 9617-9853 | ND | ND | 0.06 | 0.46 | 80.30* | 80.8 |
| 11 | 9682-9740 | 0.27 | −0.23 | 0.2 | −0.09 | 80.4 | 80.5 |
| 11 | 9675-9852 | 0.27 | −0.23 | 0.15 | 0.02 | 80.4 | 79.6 |
| 11 | 9671-9810 | 0.27 | −0.23 | 0.14 | 0.04 | 80.4 | 80.7 |
| 11 | 9617-9891 | ND | ND | 0.07 | 0.36 | 80.30* | 80.8 |
| 11 | 9667-9802 | 0.27 | −0.23 | 0.11 | 0.16 | 80.4 | 80.4 |
| 11 | 9660-9858 | 0.19 | −0.08 | 0.06 | 0.46 | 80.5 | 80.8 |
| 11 | 9660-9896 | 0.19 | −0.08 | 0.07 | 0.36 | 80.5 | 80.8 |
| 11 | 9629-9858 | 0.12* | 0.12* | 0.06 | 0.46 | 80.60* | 80.8 |
| 11 | 9667-9758 | 0.27 | −0.23 | 0.29 | −0.27 | 80.4 | 80.3 |
| 11 | 9629-9896 | 0.12* | 0.12* | 0.07 | 0.36 | 80.60* | 80.8 |
| 11 | 9675-9812 | 0.27 | −0.23 | 0.16 | −0.01 | 80.4 | 80.8 |
| 11 | 9671-9784 | 0.27 | −0.23 | 0.14 | 0.05 | 80.4 | 80.5 |
| 11 | 9679-9898 | 0.27 | −0.23 | 0.07 | 0.36 | 80.4 | 80.8 |
| 11 | 9667-9868 | 0.27 | −0.23 | 0.14 | 0.06 | 80.4 | 79.8 |
| 11 | 9663-9838 | 0.27* | −0.23* | 0.13 | 0.09 | 80.40* | 80.5 |
| 11 | 9675-9890 | 0.27 | −0.23 | 0.05 | 0.49 | 80.4 | 79.8 |
| 11 | 9671-9888 | 0.27 | −0.23 | 0.14 | 0.06 | 80.4 | 79.9 |
| 11 | 9617-9787 | ND | ND | 0.11 | 0.16 | 80.30* | 81.8 |
| 11 | 9679-9794 | 0.27 | −0.23 | 0.11 | 0.16 | 80.4 | 81.8 |
| 11 | 9654-9893 | 0.15 | 0.02 | 0.07 | 0.36 | 80.4 | 80.8 |
| 11 | 9671-9850 | 0.27 | −0.23 | 0.15 | 0.01 | 80.4 | 79.8 |
| 11 | 9675-9786 | 0.27 | −0.23 | 0.13 | 0.1 | 80.4 | 81 |
| 11 | 9660-9792 | 0.19 | −0.08 | 0.11 | 0.16 | 80.5 | 81.8 |
| 11 | 9648-9853 | 0.14 | 0.05 | 0.06 | 0.46 | 79.9 | 80.8 |
| 11 | 9666-9731 | 0.27* | −0.23* | 0.28 | −0.26 | 80.40* | 81.5 |

TABLE 13b-continued

Stability and antigen binding assessments of the designs that met the LCCA average performance criteria of correctly paired:mispaired Fab heterodimers of 86:14

| Cluster | Unique identifier** | KD of h1\|1 Fab heterodimer (nM) | Change in KD of h1\|1 Fab heterodimer with respect to wild type (−(log(KD_design) − log(KD_wt))) | KD of h2\|2 Fab heterodimer (nM) | Change in KD of h2\|2 Fab heterodimer with respect to wild type (−(log(KD_design) − log(KD_wt))) | DSF values of h1\|1 Fab heterodimer (° C.) | DSF values of h2\|2 Fab heterodimer (° C.) |
|---|---|---|---|---|---|---|---|
| 11 | 9049-9759 | 0.16 | −0.01 | 0.32 | −0.31 | 79 | 81.3 |
| 11 | 9629-9792 | 0.12* | 0.12* | 0.11 | 0.16 | 80.60* | 81.8 |
| 11 | 9623-9893 | 0.06* | 0.39* | 0.07 | 0.36 | 80.40* | 80.8 |
| 11 | 9632-9838 | 0.14 | 0.04 | 0.13 | 0.09 | 81 | 80.5 |
| 11 | 9654-9855 | 0.15 | 0.02 | 0.06 | 0.46 | 80.4 | 80.8 |
| 11 | 9679-9860 | 0.27 | −0.23 | 0.06 | 0.46 | 80.4 | 80.8 |
| 11 | 9645-9761 | 0.14* | 0.05* | 0.32 | −0.31 | 79.90* | 81.3 |
| 11 | 9648-9891 | 0.14 | 0.05 | 0.07 | 0.36 | 79.9 | 80.8 |
| 11 | 9626-9836 | 0.12 | 0.12 | 0.13 | 0.09 | 80.6 | 80.5 |
| 11 | 9579-9797 | 0.28* | −0.25* | 0.11 | 0.16 | 80.00* | 81.8 |
| 11 | 9579-9901 | 0.28* | −0.25* | 0.07 | 0.36 | 80.00* | 80.8 |
| 11 | 9635-9898 | 0.14* | 0.04* | 0.07 | 0.36 | 81.00* | 80.8 |
| 11 | 9579-9863 | 0.28* | −0.25* | 0.06 | 0.46 | 80.00* | 80.8 |
| 11 | 9683-9841 | 0.30* | −0.28* | 0.13 | 0.09 | 79.60* | 80.5 |
| 11 | 9623-9855 | 0.06* | 0.39* | 0.06 | 0.46 | 80.40* | 80.8 |
| 11 | 9575-9841 | 0.28 | −0.25 | 0.13 | 0.09 | 80 | 80.5 |
| 11 | 9635-9794 | 0.14* | 0.04* | 0.11 | 0.16 | 81.00* | 81.8 |
| 11 | 9606-9893 | ND | ND | 0.07 | 0.36 | 79.80* | 80.8 |
| 11 | 9614-9761 | ND | ND | 0.32 | −0.31 | 80.3 | 81.3 |
| 11 | 9663-9769 | 0.27* | −0.23* | 0.32 | −0.31 | 80.40* | 81.3 |
| 11 | 9654-9789 | 0.15 | 0.02 | 0.11 | 0.16 | 80.4 | 81.8 |
| 11 | 9626-9767 | 0.12 | 0.12 | 0.32 | −0.31 | 80.6 | 81.3 |
| 11 | 9648-9787 | 0.14 | 0.05 | 0.11 | 0.16 | 79.9 | 81.8 |
| 11 | 9657-9836 | 0.19* | −0.08* | 0.13 | 0.09 | 80.50* | 80.5 |
| 11 | 9606-9855 | ND | ND | 0.06 | 0.46 | 79.80* | 80.8 |
| 11 | 9623-9789 | 0.06* | 0.39* | 0.11 | 0.16 | 80.40* | 81.8 |
| 11 | 9635-9860 | 0.14* | 0.04* | 0.06 | 0.46 | 81.00* | 80.8 |
| 11 | 9632-9769 | 0.14 | 0.04 | 0.32 | −0.31 | 81 | 81.3 |
| 11 | 9641-9797 | 0.11* | 0.17* | 0.11 | 0.16 | 80.10* | 81.8 |
| 11 | 9641-9901 | 0.11* | 0.17* | 0.07 | 0.36 | 80.10* | 80.8 |
| 11 | 9663-9876 | 0.27* | −0.23* | 0.05 | 0.51 | 80.40* | 80.4 |
| 11 | 9641-9863 | 0.11* | 0.17* | 0.06 | 0.46 | 80.10* | 80.8 |
| 11 | 9626-9874 | 0.12 | 0.12 | 0.05 | 0.51 | 80.6 | 80.4 |
| 11 | 9657-9767 | 0.19* | −0.08* | 0.32 | −0.31 | 80.50* | 81.3 |
| 11 | 9684-9797 | 0.3 | −0.28 | 0.11 | 0.16 | 79.6 | 81.8 |
| 12 | 9587-9735 | 0.28 | −0.25 | 0.2 | −0.09 | 80.8 | 80.5 |
| 12 | 9687-9737 | ND | ND | 0.2 | −0.09 | 81.3 | 80.5 |
| 12 | 9696-9782 | 0.34 | −0.34 | 0.08 | 0.28 | 81.6 | 82.2 |
| 12 | 9696-9848 | 0.34 | −0.34 | 0.15 | 0.03 | 81.6 | 81.3 |
| 12 | 9594-9829 | ND | ND | 0.06 | 0.41 | 79.80* | 79.5 |
| 12 | 9692-9846 | 0.34 | −0.34 | 0.13 | 0.09 | 81.6 | 82.7 |
| 12 | 9696-9886 | 0.34 | −0.34 | 0.18 | −0.06 | 81.6 | 81.4 |
| 12 | 9696-9808 | 0.34 | −0.34 | 0.17 | −0.02 | 81.6 | 81.8 |
| 12 | 9609-9737 | ND | ND | 0.2 | −0.09 | 79.80* | 80.5 |
| 12 | 9978-9986 | ND | ND | 0.14 | 0.05 | 79.80* | 80 |
| 12 | 9692-9806 | 0.34 | −0.34 | 0.13 | 0.07 | 81.6 | 82.6 |
| 12 | 9688-9844 | 0.34 | −0.34 | 0.17 | −0.03 | 81.6 | 82.3 |
| 12 | 9688-9804 | 0.34 | −0.34 | 0.11 | 0.14 | 81.6 | 82.2 |
| 12 | 9602-9889 | ND | ND | 0.05 | 0.49 | 79.80* | 79.8 |
| 12 | 9602-9785 | ND | ND | 0.13 | 0.1 | 79.80* | 81 |
| 12 | 9574-9702 | 0.27 | −0.23 | 0.34 | −0.34 | 80.8 | 81.6 |
| 12 | 9602-9811 | ND | ND | 0.16 | −0.01 | 79.80* | 80.8 |
| 12 | 9692-9780 | 0.34 | −0.34 | 0.16 | −0.01 | 81.6 | 83 |
| 12 | 9594-9757 | ND | ND | 0.29 | −0.27 | 79.80* | 80.3 |
| 12 | 9705-9735 | 0.21 | −0.12 | 0.2 | −0.09 | 81.6 | 80.5 |
| 12 | 9103-9700 | 0.15 | 0.02 | 0.34 | −0.34 | 80 | 81.6 |
| 12 | 9598-9849 | ND | ND | 0.15 | 0.01 | 79.80* | 79.8 |
| 12 | 9720-9733 | 0.24 | −0.19 | 0.28 | −0.25 | 80.8 | 81.3 |
| 12 | 9688-9778 | 0.34 | −0.34 | 0.12 | 0.13 | 81.6 | 79.7 |
| 12 | 9598-9809 | ND | ND | 0.14 | 0.04 | 79.80* | 80.7 |
| 12 | 9982-9987 | 0.11 | 0.15 | 0.14 | 0.05 | 80.5 | 80 |
| 12 | 9101-9700 | 0.12 | 0.1 | 0.34 | −0.34 | 81 | 81.6 |
| 12 | 9716-9807 | 0.24 | −0.19 | 0.17 | −0.02 | 80.8 | 81.8 |
| 12 | 9703-9734 | 0.21* | −0.12* | 0.25 | −0.22 | 81.60* | 77.7 |
| 12 | 9712-9779 | 0.24 | −0.19 | 0.16 | −0.01 | 80.8 | 83 |
| 12 | 9594-9801 | ND | ND | 0.11 | 0.16 | 79.80* | 80.4 |
| 12 | 9712-9805 | 0.24 | −0.19 | 0.13 | 0.07 | 80.8 | 82.6 |
| 12 | 9602-9851 | ND | ND | 0.15 | 0.02 | 79.80* | 79.6 |
| 12 | 9716-9847 | 0.24 | −0.19 | 0.15 | 0.03 | 80.8 | 81.3 |

TABLE 13b-continued

Stability and antigen binding assessments of the designs that met the LCCA average performance criteria of correctly paired:mispaired Fab heterodimers of 86:14

| Cluster | Unique identifier** | KD of h1\|1 Fab heterodimer (nM) | Change in KD of h1\|1 Fab heterodimer with respect to wild type (−(log(KD_design) − log(KD_wt))) | KD of h2\|2 Fab heterodimer (nM) | Change in KD of h2\|2 Fab heterodimer with respect to wild type (−(log(KD_design) − log(KD_wt))) | DSF values of h1\|1 Fab heterodimer (° C.) | DSF values of h2\|2 Fab heterodimer (° C.) |
|---|---|---|---|---|---|---|---|
| 12 | 9979-9986 | ND | ND | 0.14 | 0.05 | 79.80* | 79.5 |
| 12 | 9708-9777 | 0.24 | −0.19 | 0.12 | 0.13 | 80.8 | 79.7 |
| 12 | 9722-9744 | 0.24 | −0.19 | 0.28 | −0.25 | 80.8 | 80 |
| 12 | 9712-9845 | 0.24 | −0.19 | 0.13 | 0.09 | 80.8 | 82.7 |
| 12 | 9589-9742 | 0.28 | −0.25 | 0.25 | −0.21 | 80.8 | 80.8 |
| 12 | 9716-9781 | 0.24 | −0.19 | 0.08 | 0.28 | 80.8 | 82.2 |
| 12 | 9692-9884 | 0.34 | −0.34 | ND | ND | 81.6 | 82.3 |
| 13 | 9042-9046 | 0.18 | ND | 0.14 | 0 | 78.3 | 81 |

*Indicates estimated values that were derived from other Fab heterodimers that differ only in the presence/absence of the attached L chain tag (HA or FLAG)).
**the "Unique identifier" consists of the unique identifiers for the two constituent LCCAs in either (Set#H1L1L2-Set#H2L2L1) or (Set#H2L2L1-Set#H1L1L2) orientation TABLE 14a LCCA performance of the designs that performed below the LCCA average performance criteria of correctly paired:mispaired Fab heterodimers of 86:14

| Related Clusters | Unique identifier*** | lcca average performance (i.e. 0.5(ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1) | H1L1:H1L2 normalized median ratio | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2) | H2L2:H2L1 normalized median ratio |
|---|---|---|---|---|---|---|---|---|---|---|---|---|
| 1 | 9131-9444 | 1.705 | 2.7 | 94:6 | 3.7 | NA | NA | 0.72 | 67:33 | 66.2 | NA | NA |
| 11 | 9645-9831 | 1.785 | 2 | 88:12 | 4 | NA | NA | 1.57 | 83:17 | 0 | NA | NA |
| 11 | 9684-9901 | 1.785 | 0.41 | 60:40 | 3.1 | NA | NA | 3.16 | 96:4 | 1 | NA | NA |
| 11 | 9651-9763 | 1.77 | 1.65 | 84:16 | 24.7 | NA | NA | 1.9 | 87:13 | 2.4 | NA | NA |
| 11 | 9684-9863 | 1.755 | 0.41 | 60:40 | 3.1 | NA | NA | 3.1 | 96:4 | 3.9 | NA | NA |
| 11 | 9645-9869 | 1.755 | 2 | 88:17 | 4 | NA | NA | 1.51 | 82:18 | 7.5 | NA | NA |
| 11 | 9688-9982 | 1.715 | 1.19 | 77:23 | 0.6 | NA | NA | 2.24 | 90:10 | 3.2 | NA | NA |
| 11 | 9683-9773 | 1.715 | 2.14 | 89:11 | 6.5 | NA | NA | 1.29 | 78:22 | 5 | NA | NA |
| 11 | 9575-9773 | 1.695 | 2.1 | 89:11 | 1.4 | NA | NA | 1.29 | 78:22 | 5 | NA | NA |
| 11 | 9638-9841 | 1.695 | 1.13 | 76:24 | 16.7 | NA | NA | 2.27 | 91:9 | 2 | NA | NA |
| 11 | 9632-9876 | 1.69 | 1.9 | 87:13 | 14.8 | NA | NA | 1.48 | 81:19 | 17.1 | 1.85 | 86:14 |
| 11 | 9614-9831 | 1.675 | 1.78 | 86:14 | 6.2 | NA | NA | 1.57 | 83:17 | 0 | NA | NA |
| 11 | 9588-9741 | 1.665 | 1.75 | 85:15 | 0 | NA | NA | 1.58 | 83:17 | 0.1 | NA | NA |
| 11 | 9594-9867 | 1.655 | 0.37 | 59:41 | 22.4 | NA | NA | 2.94 | 95:5 | 2.1 | NA | NA |
| 11 | 9614-9869 | 1.645 | 1.78 | 86:14 | 6.2 | NA | NA | 1.51 | 82:18 | 7.5 | NA | NA |
| 11 | 9657-9874 | 1.62 | 1.62 | 83:17 | 33.4 | NA | NA | 1.62 | 83:17 | 6.3 | NA | NA |
| 11 | 9620-9833 | 1.58 | 1.68 | 84:16 | 10.3 | NA | NA | 1.48 | 81:19 | 0 | NA | NA |
| 11 | 9651-9833 | 1.56 | 1.65 | 84:16 | 24.7 | NA | NA | 1.48 | 81:19 | 0 | NA | NA |
| 11 | 9620-9871 | 1.545 | 1.68 | 84:16 | 10.3 | NA | NA | 1.41 | 80:20 | 5.7 | NA | NA |
| 11 | 9683-9879 | 1.535 | 2.14 | 89:11 | 6.5 | NA | NA | 0.93 | 72:28 | 0 | NA | NA |
| 11 | 9651-9871 | 1.525 | 1.65 | 84:16 | 24.7 | NA | NA | 0.93 | 80:20 | 5.7 | NA | NA |
| 11 | 9575-9879 | 1.515 | 2.1 | 89:11 | 1.4 | NA | NA | 0.93 | 72:28 | 0 | NA | NA |
| 11 | 9590-9833 | 1.22 | 0.95 | 72:28 | 6.7 | NA | NA | 1.48 | 81:19 | 5.7 | NA | NA |
| 11 | 9638-9773 | 1.205 | 1.13 | 76:24 | 16.7 | NA | NA | 1.29 | 78:22 | 5 | NA | NA |
| 11 | 9590-9871 | 1.185 | 0.96 | 72:28 | 6.7 | NA | NA | 1.41 | 80:20 | 0 | NA | NA |
| 11 | 9638-9879 | 1.025 | 1.13 | 76:24 | 16.7 | NA | NA | 0.93 | 72:28 | 5.7 | NA | NA |
| 11 | 9708-9803 | 1.75 | 0.37 | 59:41 | 11.3 | NA | NA | 3.13 | 96:4 | 0.6 | NA | NA |
| 11 | 9598-9987 | 1.745 | 0.36 | 59:41 | 26 | NA | NA | 3.13 | 96:4 | 1.1 | NA | NA |
| 11 | 9708-9843 | 1.725 | 0.37 | 59:41 | 11.3 | NA | NA | 3.08 | 96:4 | 1.5 | NA | NA |
| 11 | 9716-9885 | 1.575 | 0.28 | 57:43 | 0 | NA | NA | 2.87 | 95:5 | 2.3 | NA | NA |
| 11 | 9712-9883 | 1.535 | 1.03 | 74:26 | 13.9 | NA | NA | 2.04 | 88:12 | 2.5 | NA | NA |
| 11 | 9708-9981 | 1.305 | 0.37 | 59:41 | 11.3 | NA | NA | 2.24 | 90:10 | 0.9 | NA | NA |
| 11, 12, 13 | 9980-9986 | 1.74 | -0.14 | 47:53 | 0 | NA | NA | 3.63 | 97:3 | 0.1 | NA | NA |
| 11, 12, 13 | 9984-9987 | 1.73 | -0.16 | 46:54 | 0 | NA | NA | 3.62 | 97:3 | 0.5 | NA | NA |
| 11, 12, 13 | 9983-9987 | 1.675 | -0.16 | 46:54 | 0 | NA | NA | 3.51 | 97:3 | 0.2 | NA | NA |
| 11, 12, 13 | 9981-9986 | 1.58 | -0.14 | 47:53 | 0 | NA | NA | 3.3 | 96:4 | 1.7 | NA | NA |
| 11, 12, 13 | 9585-9734 | 1.52 | 0.71 | 67:33 | 2 | NA | NA | 2.34 | 91:9 | 4.7 | NA | NA |
| 11, 12, 13 | 9985-9987 | 1.35 | -0.16 | 46:54 | 0 | NA | NA | 2.86 | 95:5 | 2.3 | NA | NA |
| 12 | 9573-9725 | 1.68 | 3.13 | 96:4 | 0.8 | NA | NA | 0.23 | 56:44 | 7.5 | NA | NA |
| 12 | 9721-9737 | 1.615 | 0.03 | 51:49 | 7.5 | NA | NA | 3.2 | 96:4 | 10 | NA | NA |
| 12 | 9704-9732 | 1.61 | 1.06 | 74:26 | 0.1 | NA | NA | 2.17 | 90:10 | 5.7 | NA | NA |
| 12 | 9102-9723 | 1.48 | 2.54 | 93:7 | 1.5 | NA | NA | 0.42 | 60:40 | 10.2 | NA | NA |
| 12 | 9100-9723 | 1.47 | 2.52 | 93:7 | 1.2 | NA | NA | 0.42 | 60:40 | 10.2 | NA | NA |
| 12 | 9706-9743 | 1.33 | 0.82 | 69:31 | 0.2 | NA | NA | 1.84 | 86:14 | 1.4 | NA | NA |

TABLE 14a-continued

LCCA performance of the designs that performed below the LCCA average performance criteria of correctly paired:mispaired Fab heterodimers of 86:14

| Related Clusters | Unique identifier *** | lcca average performance (i.e. 0.5(ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L2 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 13 | 9043-9047 | 1.305 | 3.12 | 96:4 | 0.1 | NA | NA | −0.51 | 38:62 | 5.2 | NA | NA |
| 13 | 9044-9048 | 1.19 | 1.84 | 86:14 | 6 | 1.24 | 78:22 | 0.54 | 63:37 | 9.3 | 1.33 | 79:21 |
| 13 | 6665-6666 | 1.12 | 0.4 | 60:40 | 2.6 | NA | NA | 1.85 | 86:14 | 4 | NA | NA |
| 13 | 9041-9045 | 1.005 | 1.37 | 80:20 | 3.2 | 1.39 | 80:20 | 0.64 | 65:35 | 4.8 | 0.07 | 52:48 |
| 13 | 5933-5957 | 0.685 | 0.48 | 62:38 | 2.1 | NA | NA | 0.88 | 71:29 | 4.4 | NA | NA |
| 13 | 9052-9917 | 0.685 | 1.03 | 74:26 | 36.9 | 2.05 | 89:11 | 0.34 | 58:42 | 21.2 | 0.5 | 62:38 |
| 13 | 9906-9911 | 0.66 | −1.25 | 22:78 | 6.3 | NA | NA | 2.55 | 93:7 | 1.5 | NA | NA |
| 13 | 9070-9909 | 0.58 | 0.72 | 67:33 | 3.3 | NA | NA | 0.44 | 61:39 | 0 | NA | NA |
| 13 | 9068-9907 | 0.53 | 0.54 | 63:37 | 9.5 | NA | NA | 0.52 | 63:37 | 0 | NA | NA |
| 13 | 9068-9914 | 0.49 | 0.54 | 63:37 | 9.5 | 0.45 | 61:39 | 0.44 | 61:39 | 13.2 | 0.94 | 72:28 |
| 13 | 9073-9909 | 0.49 | 0.54 | 63:37 | 1.9 | NA | NA | 0.44 | 61:39 | 0 | NA | NA |
| 13 | 5995-5998 | 0.415 | 0.88 | 71:29 | 5 | NA | NA | −0.05 | 49:51 | 11.6 | NA | NA |
| 13 | 6163-6164 | 0.395 | 1.09 | 75:25 | 7.4 | NA | NA | −0.3 | 43:57 | 18.5 | NA | NA |
| 13 | 9071-9907 | 0.385 | 0.25 | 56:44 | 14 | NA | NA | 0.52 | 63:37 | 0 | NA | NA |
| 13 | 5997-5998 | 0.375 | 0.88 | 71:29 | 5 | NA | NA | −0.13 | 47:53 | 9.1 | NA | NA |
| 13 | 9071-9914 | 0.345 | 0.25 | 56:44 | 14 | 1.73 | 85:15 | 0.44 | 61:39 | 13.2 | 0.94 | 72:28 |
| 13 | 6042-6043 | 0.105 | −0.44 | 39:61 | 6.8 | NA | NA | 0.66 | 66:34 | 5.3 | NA | NA |
| 13 | 6036-6037 | −0.005 | −0.38 | 41:59 | 0.8 | NA | NA | 0.37 | 59:41 | 0.1 | NA | NA |
| 13 | 6037-9566 | −0.065 | −0.38 | 41:59 | 0.8 | NA | NA | 0.24 | 56:44 | 3.6 | NA | NA |
| 13 | 6017-6024 | −0.065 | −0.01 | 50:50 | 0.9 | NA | NA | −0.14 | 47:53 | 7.1 | NA | NA |
| 2 | 9213-9491 | 1.75 | 2.65 | 93:7 | 0.7 | NA | NA | 0.86 | 70:30 | 58.7 | NA | NA |
| 2 | 9205-9447 | 1.74 | 1.78 | 86:14 | 5.5 | NA | NA | 1.7 | 85:15 | 23.8 | NA | NA |
| 2 | 9175-9364 | 1.725 | 2.44 | 92:8 | 2.4 | NA | NA | 1.02 | 73:27 | 0 | NA | NA |
| 2 | 9259-9351 | 1.65 | 1.67 | 84:16 | 2.5 | NA | NA | 1.64 | 84:16 | 0 | NA | NA |
| 2 | 9175-9491 | 1.645 | 2.44 | 92:8 | 2.4 | NA | NA | 0.86 | 70:30 | 58.7 | NA | NA |
| 2 | 9308-9492 | 1.62 | 2.08 | 89:11 | 3 | NA | NA | 1.16 | 76:24 | 62.6 | NA | NA |
| 2 | 9178-9351 | 1.615 | 1.59 | 83:17 | 0 | NA | NA | 1.64 | 84:16 | 0 | NA | NA |

TABLE 14a-continued

LCCA performance of the designs that performed below the LCCA average performance criteria of correctly paired:mispaired Fab heterodimers of 86:14

| Related Clusters | Unique identifier *** | lcca average performance (i.e. 0.5(ln(r1/f1) + ln(r2/f2)) | H1L1:H1L2 normalized median scalar value ln(r1/f1)* | H1L1:H1L2 normalized median ratio* | H1L1:H1L2 range of normalized ratios* | H1L1:H1L2 normalized median scalar value ln(r1/f1)** | H1L1:H1L2 normalized median ratio** | H2L2:H2L1 normalized median scalar value ln(r2/f2)* | H2L2:H2L1 normalized median ratio* | H2L2:H2L1 range of normalized ratios* | H2L2:H2L1 normalized median scalar value ln(r2/f2)** | H2L2:H2L1 normalized median ratio** |
|---|---|---|---|---|---|---|---|---|---|---|---|---|
| 2 | 9260-9473 | 1.57 | 0.55 | 63:37 | 0 | NA | NA | 2.59 | 93:7 | 0 | NA | NA |
| 2 | 9239-9417 | 1.555 | 2.11 | 89:11 | 2.4 | NA | NA | 1 | 73:27 | 49.1 | NA | NA |
| 2 | 9263-9492 | 1.55 | 1.95 | 88:12 | 3.3 | NA | NA | 1.16 | 76:24 | 62.6 | NA | NA |
| 2 | 9300-9473 | 1.54 | 0.43 | 62:38 | 0 | NA | NA | 2.59 | 93:7 | 0 | NA | NA |
| 2 | 9216-9351 | 1.475 | 1.31 | 79:21 | 0 | NA | NA | 1.64 | 84:16 | 0 | NA | NA |
| 2 | 9201-9417 | 1.365 | 1.73 | 85:15 | 1.8 | NA | NA | 1 | 73:27 | 49.1 | NA | NA |
| 2 | 9220-9492 | 1.295 | 1.44 | 81:19 | 7.6 | NA | NA | 1.16 | 76:24 | 62.6 | NA | NA |
| 3 | 9369-9749 | 1.75 | 1.86 | 87:13 | 7.1 | NA | NA | 1.64 | 84:16 | 56.1 | NA | NA |
| 3 | 9120-9370 | 1.305 | 0.12 | 53:47 | 17.4 | NA | NA | 2.49 | 92:8 | 0.5 | NA | NA |
| 4 | 9112-9346 | 1.015 | -0.97 | 27:73 | 0 | NA | NA | 3 | 95:5 | 1.9 | NA | NA |
| 5 | 2950-2951 | 0.57 | 0.47 | 62:38 | 4.4 | NA | NA | 0.68 | 66:34 | 8.7 | NA | NA |
| 5 | 9051-9063 | 0.2 | 0.03 | 51:49 | 3.9 | 60:40 | NA | 0.37 | 59:41 | 6.1 | 55:45 | NA |
| 5 | 9056-9062 | -0.06 | -0.77 | 32:68 | 6.8 | 72:28 | NA | 0.65 | 66:34 | 7 | 75:25 | NA |
| 5 | 6112-6113 | -0.67 | -1.92 | 13:87 | 9.2 | NA | NA | 0.58 | 64:36 | 1.4 | NA | NA |
| 6 | 9082-9862 | 1.78 | -0.34 | 42:58 | 22.9 | 75:25 | NA | 3.9 | 98:2 | 8.1 | 93:7 | NA |
| 6 | 9082-9900 | 1.43 | -0.34 | 42:58 | 22.9 | NA | NA | 3.2 | 96:4 | 2.7 | NA | NA |
| 6 | 6137-6138 | 1.32 | 0.23 | 56:44 | 5.7 | NA | NA | 2.4 | 92:8 | 6.5 | NA | NA |
| 6 | 6135-6136 | 0.965 | 0.07 | 52:48 | 2.2 | NA | NA | 1.87 | 87:13 | 0.3 | NA | NA |
| 6, 11, 13 | 9082-9796 | 1.685 | -0.34 | 42:58 | 22.9 | 75:25 | NA | 3.71 | 98:2 | 10.8 | 88:12 | NA |
| 9 | 9590-9763 | 1.43 | 0.96 | 72:28 | 6.7 | NA | NA | 1.9 | 87:13 | 2.4 | NA | NA |
| 9, 11 | 9620-9763 | 1.79 | 1.68 | 84:16 | 10.3 | 88:12 | NA | 1.9 | 87:13 | 2.4 | NA | NA |
| 9, 11 | 9606-9789 | 1.78 | 0.38 | 59:41 | 14.3 | NA | NA | 3.17 | 96:4 | 1.1 | 88:12 | NA |
| 9, 11, 12 | 9538-9783 | 1.715 | 0.36 | 59:41 | 26 | NA | NA | 3.07 | 96:4 | 1.4 | NA | NA |

*values were obtained from LCCA experiments conducted with L1:L2 DNA ratio of 1:3 and normalized to L1:L2 DNA ratio of 1:1
**values were obtained from LCCA experiments conducted with L1:L2 DNA ratio of 1:9 and normalized to L1:L2 DNA ratio of 1:1
*** the "Unique identifier" consists of the unique identifiers for the two constituent LCCAs in either (Set#H1L1L2-Set#H2L2L1) or (Set#H2L2L1-Set#H1L1L2) orientation TABLE 14b Stability and antigen binding assessments of the designs that performed below the LCCA average performance criteria of correctly paired:mispaired Fab heterodimers of 86:14

| Related Clusters | Unique identifier ** | KD of h1\|1 Fab heterodimer (nM) | Change in KD of h1\|1 Fab heterodimer with respect to wild type (−(log(KD_design) − log(KD_wt))) | KD of h2\|2 Fab heterodimer (nM) | Change in KD of h2\|2 Fab heterodimer with respect to wild type (−(log(KD_design) − log(KD_wt))) | DSF values of h1\|1 Fab heterodimer (° C.) | DSF values of h2\|2 Fab heterodimer (° C.) |
|---|---|---|---|---|---|---|---|
| 1 | 9131-9444 | 0.15* | 0.02* | 0.28 | −0.26 | 79.60* | 80.1 |
| 11 | 9645-9831 | 0.14* | 0.05* | 0.13 | 0.09 | 79.90* | 80.5 |
| 11 | 9684-9901 | 0.3 | −0.28 | 0.07 | 0.36 | 79.6 | 80.8 |
| 11 | 9651-9763 | 0.15* | 0.02* | 0.32 | −0.31 | 80.40* | 81.3 |
| 11 | 9684-9863 | 0.3 | −0.28 | 0.06 | 0.46 | 79.6 | 80.8 |
| 11 | 9645-9869 | 0.14* | 0.05* | 0.05 | 0.51 | 79.90* | 80.4 |
| 11 | 9688-9882 | 0.34 | −0.34 | 0.11 | 0.15 | 81.6 | 81.8 |
| 11 | 9683-9773 | 0.30* | −0.28* | 0.32 | −0.31 | 79.60* | 81.3 |
| 11 | 9575-9773 | 0.28 | −0.25 | 0.32 | −0.31 | 80 | 81.3 |
| 11 | 9638-9841 | 0.11 | 0.17 | 0.13 | 0.09 | 80.1 | 80.5 |
| 11 | 9632-9876 | 0.14 | 0.04 | 0.05 | 0.51 | 81 | 80.4 |
| 11 | 9614-9831 | ND | ND | 0.13 | 0.09 | 80.3 | 80.5 |
| 11 | 9588-9741 | 0.28 | −0.25 | 0.07 | 0.34 | 80.8 | 81.1 |
| 11 | 9594-9867 | ND | ND | 0.14 | 0.06 | 79.80* | 79.8 |
| 11 | 9614-9869 | ND | ND | 0.05 | 0.51 | 80.3 | 80.4 |
| 11 | 9657-9874 | 0.19* | −0.08* | 0.05 | 0.51 | 80.50* | 80.4 |
| 11 | 9620-9833 | 0.06 | 0.39 | 0.13 | 0.09 | 80.4 | 80.5 |
| 11 | 9651-9833 | 0.15* | 0.02* | 0.13 | 0.09 | 80.40* | 80.5 |
| 11 | 9620-9871 | 0.06 | 0.39 | 0.05 | 0.51 | 80.4 | 80.4 |
| 11 | 9683-9879 | 0.30* | −0.28* | 0.05 | 0.51 | 79.60* | 80.4 |
| 11 | 9651-9871 | 0.15* | 0.02* | 0.05 | 0.51 | 80.40* | 80.4 |
| 11 | 9575-9879 | 0.28 | −0.25 | 0.05 | 0.51 | 80 | 80.4 |
| 11 | 9590-9833 | ND | ND | 0.13 | 0.09 | 79.8 | 80.5 |
| 11 | 9638-9773 | 0.11 | 0.17 | 0.32 | −0.31 | 80.1 | 81.3 |
| 11 | 9590-9871 | ND | ND | 0.05 | 0.51 | 79.8 | 80.4 |
| 11 | 9638-9879 | 0.11 | 0.17 | 0.05 | 0.51 | 80.1 | 80.4 |
| 11, 12 | 9708-9803 | 0.24 | −0.19 | 0.11 | 0.14 | 80.8 | 82.2 |
| 11, 12 | 9598-9887 | ND | ND | 0.14 | 0.06 | 79.80* | 79.9 |
| 11, 12 | 9708-9843 | 0.24 | −0.19 | 0.17 | −0.03 | 80.8 | 82.3 |
| 11, 12 | 9716-9885 | 0.24 | −0.19 | 0.18 | −0.06 | 80.8 | 81.4 |
| 11, 12 | 9712-9883 | 0.24 | −0.19 | ND | ND | 80.8 | 82.3 |
| 11, 12 | 9708-9881 | 0.24 | −0.19 | 0.11 | 0.15 | 80.8 | 81.8 |
| 11, 12, 13 | 9980-9986 | ND | ND | 0.16 | 0 | 79.80* | 79.8 |
| 11, 12, 13 | 9984-9987 | 0.11 | 0.15 | 0.16 | 0 | 80.5 | 79.8 |
| 11, 12, 13 | 9983-9987 | 0.11 | 0.15 | 0.14 | 0.05 | 80.5 | 79.5 |
| 11, 12, 13 | 9981-9986 | ND | ND | 0.12 | 0.1 | 79.80* | 79.8 |
| 11, 12, 13 | 9585-9734 | 0.28* | −0.25* | 0.26 | −0.22 | 80.80* | 77.7 |
| 11, 12, 13 | 9985-9987 | 0.11 | 0.15 | 0.12 | 0.1 | 80.5 | 79.8 |
| 12 | 9573-9725 | 0.27 | −0.23 | 0.24 | −0.19 | 80.8 | 80.8 |
| 12 | 9721-9737 | 0.24 | −0.19 | 0.2 | −0.09 | 80.8 | 80.5 |
| 12 | 9704-9732 | 0.21 | −0.12 | 0.28 | −0.25 | 81.6 | 81.3 |
| 12 | 9102-9723 | 0.15 | 0.02 | 0.24 | −0.19 | 80 | 80.8 |
| 12 | 9100-9723 | 0.12 | 0.1 | 0.24 | −0.19 | 81 | 80.8 |
| 12 | 9706-9743 | 0.21 | −0.12 | 0.28 | −0.25 | 81.6 | 80 |
| 13 | 9043-9047 | 0.16 | ND | 0.14 | 0 | 74.1 | 81 |
| 13 | 9044-9048 | 0.18 | ND | 0.14 | 0 | 75.8 | 81 |
| 13 | 6665-6666 | 0.16 | −0.01 | 0.17 | −0.04 | 80.9 | 80 |
| 13 | 9041-9045 | 0.14 | ND | 0.14 | 0 | 77.8 | 81 |
| 13 | 5933-5957 | 0.15 | 0.03 | 0.14 | 0 | 80.8 | 81 |
| 13 | 9052-9917 | 0.14 | 0.06 | 0.1 | 0.2 | 81.3 | 80.2 |
| 13 | 9906-9911 | 0.11 | 0.14 | 0.09 | 0.27 | 82.5 | 81 |
| 13 | 9070-9909 | 0.16 | 0 | 0.09 | 0.27 | 82.5 | 81 |
| 13 | 9068-9907 | 0.13 | 0.07 | 0.09 | 0.27 | 82.5 | 81 |
| 13 | 9068-9914 | 0.13 | 0.07 | 0.15 | 0.01 | 82.5 | 82 |
| 13 | 9073-9909 | 0.14 | 0.04 | 0.09 | 0.27 | 82.3 | 81 |
| 13 | 5995-5998 | 0.14 | 0.06 | 0.14 | 0.04 | 81.4 | 80.2 |
| 13 | 6163-6164 | 0.15 | 0.02 | 0.17 | −0.04 | 82.5 | 80.8 |
| 13 | 9071-9907 | 0.21 | −0.12 | 0.09 | 0.27 | 81.5 | 81 |
| 13 | 5997-5998 | 0.14 | 0.06 | 0.08 | 0.29 | 81.4 | 80 |
| 13 | 9071-9914 | 0.21 | −0.12 | 0.15 | 0.01 | 81.5 | 82 |
| 13 | 6042-6043 | 0.13 | 0.07 | 0.11 | 0.14 | 80.1 | 82.1 |
| 13 | 6036-6037 | 0.13 | 0.07 | 0.17 | −0.03 | 80.1 | 81.4 |
| 13 | 6037-9566 | 0.13 | 0.07 | 0.25 | −0.21 | 80.1 | 81.8 |
| 13 | 6017-6024 | 0.15* | 0.02* | 0.14 | 0.06 | 82.50* | 81.6 |
| 2 | 9213-9491 | 0.2 | −0.11 | 0.24 | −0.19 | 78.5 | 79.8 |
| 2 | 9205-9447 | 0.28 | −0.25 | 0.28 | −0.26 | 76.4 | 80.1 |
| 2 | 9175-9364 | 0.25 | −0.21 | 0.15 | 0.01 | 78.5 | 79.7 |
| 2 | 9259-9351 | 0.24 | −0.19 | 0.2 | −0.1 | ND | ND |
| 2 | 9175-9491 | 0.25 | −0.21 | 0.24 | −0.19 | 78.5 | 79.8 |

TABLE 14b-continued

Stability and antigen binding assessments of the designs that performed below the LCCA average performance criteria of correctly paired:mispaired Fab heterodimers of 86:14

| Related Clusters | Unique identifier ** | KD of h1\|1 Fab heterodimer (nM) | Change in KD of h1\|1 Fab heterodimer with respect to wild type (−(log(KD_design) − log(KD_wt))) | KD of h2\|2 Fab heterodimer (nM) | Change in KD of h2\|2 Fab heterodimer with respect to wild type (−(log(KD_design) − log(KD_wt))) | DSF values of h1\|1 Fab heterodimer (° C.) | DSF values of h2\|2 Fab heterodimer (° C.) |
|---|---|---|---|---|---|---|---|
| 2 | 9308-9492 | 0.21* | −0.12* | 0.24 | −0.19 | 78.20* | 79.8 |
| 2 | 9178-9351 | 0.22 | −0.15 | 0.2 | −0.1 | ND | ND |
| 2 | 9260-9473 | 0.24 | −0.19 | 0.18 | −0.07 | ND | 79.8 |
| 2 | 9239-9417 | 0.22 | −0.15 | 0.2 | −0.12 | ND | 79.5 |
| 2 | 9263-9492 | 0.24 | −0.19 | 0.24 | −0.19 | ND | 79.8 |
| 2 | 9300-9473 | 0.21* | −0.12* | 0.18 | −0.07 | 78.20* | 79.8 |
| 2 | 9216-9351 | 0.19 | −0.08 | 0.2 | −0.1 | ND | ND |
| 2 | 9201-9417 | 0.28 | −0.25 | 0.2 | −0.12 | 76.4 | 79.5 |
| 2 | 9220-9492 | 0.19 | −0.08 | 0.24 | −0.19 | ND | 79.8 |
| 3 | 9369-9749 | 0.23 | −0.16 | 0.22 | −0.14 | 79.5 | 81 |
| 3 | 9120-9370 | 0.13 | 0.08 | 0.22 | −0.14 | 79.5 | 81 |
| 4 | 9112-9346 | ND | ND | 0.2 | −0.11 | 74.8 | 81.6 |
| 5 | 2950-2951 | 0.13 | 0.1 | 0.13 | 0.08 | 80.5 | 80.8 |
| 5 | 9051-9063 | 0.14 | 0.06 | 0.17 | −0.02 | 81.3 | 81.3 |
| 5 | 9056-9062 | 0.16 | −0.02 | 0.17 | −0.02 | 81.5 | 81.3 |
| 5 | 6112-6113 | 0.13* | 0.10* | 0.12 | 0.11 | 80.50* | 83.1 |
| 6 | 9082-9862 | 0.16 | −0.01 | 0.06 | 0.46 | 80.9 | 80.8 |
| 6 | 9082-9900 | 0.16 | −0.01 | 0.07 | 0.36 | 80.9 | 80.8 |
| 6 | 6137-6138 | 0.16 | −0.01 | 0.16 | 0 | 80.9 | 80 |
| 6 | 6135-6136 | 0.16 | −0.01 | 0.13 | 0.07 | 80.9 | 80.3 |
| 6, 11, 13 | 9082-9796 | 0.16 | −0.01 | 0.11 | 0.16 | 80.9 | 81.8 |
| 9 | 9590-9763 | ND | ND | 0.32 | −0.31 | 79.8 | 81.3 |
| 9, 11 | 9620-9763 | 0.06 | 0.39 | 0.32 | −0.31 | 80.4 | 81.3 |
| 9, 11 | 9606-9789 | ND | ND | 0.11 | 0.16 | 79.80* | 81.8 |
| 9, 11, 12 | 9598-9783 | ND | ND | 0.14 | 0.05 | 79.80* | 80.5 |

*Indicates estimated values that were derived from other Fab heterodimers that differ only in the presence/absence of the attached L chain tag (HA or FLAG)).
** the "Unique identifier" consists of the unique identifiers for the two constituent LCCAs in either (Set#H1L1L2-Set#H2L2L1) or (Set#H2L2L1-Set#H1L1L2) orientation

TABLE 15

Cluster 1 designs including the representative design

| Unique Identifier | H1_mutation* | L1_mutation* | H2_mutation* | L2_mutation* |
|---|---|---|---|---|
| 9134-9521** | L124E_K145T_Q179E | S131K_V133G_S176R | L124R_S186R | V133G_S176D_T178D |
| 9125-9459 | L124E_K145M_Q179E | S131K_V133G_S176R | L124R_S186K | Q124E_V133G_S176D_T178D_T180E |
| 9126-9352 | L124E_K145M_Q179E | S131K_V133G_S176R | L124R_D146N_Q179K | Q124E_V133G_S176D_T178E_T180E |
| 9129-9357 | L124E_K145M_Q179E | S131K_V133G_S176R | L124R_D146N_Q179K | V133G_S176D_T178D |
| 9130-9361 | L124E_K145M_Q179E | S131K_V133G_S176R | L124R_D146N_Q179K | V133G_S176D_T178E_T180E |
| 9131-9366 | L124E_K145M_Q179E | S131K_V133G_S176R | L124R_D146N_Q179K | V133G_S176D_T180E |
| 9140-9481 | L124E_K145T_Q179E | S131K_V133G_S176R | L124R_S186K | V133G_S176D_T178D_T180E |
| 9146-9498 | L124E_K145T_Q179E | S131K_V133G_S176R | L124R_S186K | V133G_S176D_T180E |
| 9134-9466 | L124E_K145T_Q179E | S131K_V133G_S176R | L124R_S186K | V133G_S176D_T178D |
| 9136-9459 | L124E_K145T_Q179E | S131K_V133G_S176R | L124R_S186K | Q124E_V133G_S176D_T178D_T180E |
| 9158-9483 | L124E_K145T_Q179E | S131K_V133G_S176R | L124R_S186K | V133G_S176D_T178D_T180E |
| 9164-9500 | L124E_K145T_Q179E | S131K_V133G_S176R | L124R_S186K | V133G_S176D_T180E |
| 9150-9468 | L124E_K145T_Q179E | S131K_V133G_S176R | L124R_S186K | V133G_S176D_T178D |
| 9152-9460 | L124E_K145T_Q179E | S131R_V133G_S176R | L124R_S186K | Q124E_V133G_S176D_T178D_T180E |
| 9140-9536 | L124E_K145T_Q179E | S131K_V133G_S176R | L124R_S186R | V133G_S176D_T178D_T180E |
| 9146-9553 | L124E_K145T_Q179E | S131K_V133G_S176R | L124R_S186R | V133G_S176D_T180E |
| 9136-9513 | L124E_K145T_Q179E | S131K_V133G_S176R | L124R_S186R | Q124E_V133G_S176D_T178D_T180E |
| 9158-9538 | L124E_K145T_Q179E | S131K_V133G_S176R | L124R_S186R | V133G_S176D_T178D_T180E |
| 9164-9555 | L124E_K145T_Q179E | S131K_V133G_S176R | L124R_S186R | V133G_S176D_T180E |
| 9150-9523 | L124E_K145T_Q179E | S131K_V133G_S176R | L124R_S186R | V133G_S176D_T178D |
| 9152-9515 | L124E_K145T_Q179E | S131K_V133G_S176R | L124R_S186R | Q124E_V133G_S176D_T178D_T180E |
| 9127-9481 | L124E_K145M_Q179E | S131K_V133G_S176R | L124R_S186K | V133G_S176D_T178D_T180E |
| 9131-9498 | L124E_K145M_Q179E | S131K_V133G_S176R | L124R_S186K | V133G_S176D_T180E |
| 9123-9466 | L124E_K145M_Q179E | S131K_V133G_S176R | L124R_S186K | V133G_S176D_T178D |
| 9127-9536 | L124E_K145M_Q179E | S131K_V133G_S176R | L124R_S186R | V133G_S176D_T178D_T180E |
| 9131-9553 | L124E_K145M_Q179E | S131K_V133G_S176R | L124R_S186R | V133G_S176D_T180E |
| 9123-9521 | L124E_K145M_Q179E | S131K_V133G_S176R | L124R_S186R | V133G_S176D_T178D |
| 9125-9513 | L124E_K145M_Q179E | S131K_V133G_S176R | L124R_S186R | Q124E_V133G_S176D_T178D_T180E |
| 9142-9414 | L124E_K145T_Q179E | S131K_V133G_S176R | L124R_Q179K | V133G_S176D_T178E |
| 9138-9392 | L124E_K145T_Q179E | S131K_V133G_S176R | L124R_Q179K | Q124E_V133G_S176D_T178E_T180E |
| 9144-9423 | L124E_K145T_Q179E | S131K_V133G_S176R | L124R_Q179K | V133G_S176D_T178E_T180E |
| 9146-9444 | L124E_K145T_Q179E | S131K_V133G_S176R | L124R_Q179K | V133G_S176D_T180E |

TABLE 15-continued

| Cluster 1 designs including the representative design | | | | |
|---|---|---|---|---|
| Unique Identifier | H1_mutation* | L1_mutation* | H2_mutation* | L2_mutation* |
| 9160-9416 | L124E_K145T_Q179E | S131R_V133G_S176R | L124R_Q179K | V133G_S176D_T178E |
| 9154-9394 | L124E_K145T_Q179E | S131R_V133G_S176R | L124R_Q179K | Q124E_V133G_S176D_T178E_T180E |
| 9162-9425 | L124E_K145T_Q179E | S131R_V133G_S176R | L124R_Q179K | V133G_S176D_T178E_T180E |
| 9164-9446 | L124E_K145T_Q179E | S131R_V133G_S176R | L124R_Q179K | V133G_S176D_T180E |
| 9156-9397 | L124E_K145T_Q179E | S131R_V133G_S176R | L124R_Q179K | V133G_Q160E_S176D_T180E |
| 9129-9414 | L124E_K145M_Q179E | S131K_V133G_S176R | L124R_Q179K | V133G_S176D_T178E |
| 9126-9392 | L124E_K145M_Q179E | S131K_V133G_S176R | L124R_Q179K | Q124E_V133G_S176D_T178E_T180E |
| 9130-9423 | L124E_K145M_Q179E | S131K_V133G_S176R | L124R_Q179K | V133G_S176D_T178E_T180E |
| 9142-9357 | L124E_K145T_Q179E | S131K_V133G_S176R | L124R_D146N_Q179K | V133G_S176D_T178E |
| 9138-9352 | L124E_K145T_Q179E | S131K_V133G_S176R | L124R_D146N_Q179K | Q124E_V133G_S176D_T178E_T180E |
| 9144-9361 | L124E_K145T_Q179E | S131K_V133G_S176R | L124R_D146N_Q179K | V133G_S176D_T178E_T180E |
| 9146-9366 | L124E_K145T_Q179E | S131K_V133G_S176R | L124R_D146N_Q179K | V133G_S176D_T180E |
| 9160-9358 | L124E_K145T_Q179E | S131R_V133G_S176R | L124R_D146N_Q179K | V133G_S176D_T178E |
| 9154-9353 | L124E_K145T_Q179E | S131R_V133G_S176R | L124R_D146N_Q179K | Q124E_V133G_S176D_T178E_T180E |
| 9162-9362 | L124E_K145T_Q179E | S131R_V133G_S176R | L124R_D146N_Q179K | V133G_S176D_T178E_T180E |
| 9164-9367 | L124E_K145T_Q179E | S131R_V133G_S176R | L124R_D146N_Q179K | V133G_S176D_T180E |
| 9156-9354 | L124E_K145T_Q179E | S131R_V133G_S176R | L124R_D146N_Q179K | V133G_Q160E_S176D_T180E |

*Kabat numbering
**Representative design

TABLE 16

| Cluster 2 designs including representative designs. | | | | |
|---|---|---|---|---|
| Unique Identifier | H1_mutation* | L1_mutation* | H2_mutation* | L2_mutation* |
| 9286-9402** | L124E_L143E_K145T | Q124K_V133G_S176R | L124R_Q179K | V133G_S176D_T178E |
| 9170-9350 | L124E_L143D_K145M | Q124K_V133G_Q160K_S176R | L124R_D146N_Q179K | Q124E_V133G_S176D_T178E_T180E |
| 9170-9376 | L124E_L143D_K145M | Q124K_V133G_Q160K_S176R | L124R_Q179K | Q124E_V133G_S176D_T178E_T180E |
| 9171-9398 | L124E_L143D_K145M | Q124K_V133G_Q160K_S176R | L124R_Q179K | V133G_S176D_T178E |
| 9173-9380 | L124E_L143D_K145M | Q124K_V133G_S176R | L124R_Q179K | Q124E_V133G_S176D_T178E_T180E |
| 9174-9402 | L124E_L143D_K145M | Q124K_V133G_S176R | L124R_Q179K | V133G_S176D_T178E |
| 9175-9432 | L124E_L143D_K145M | Q124K_V133G_S176R | L124R_Q179K | V133G_S176D_T180E |
| 9178-9384 | L124E_L143D_K145M | Q124K_V133G_S176R_T178K | L124R_Q179K | Q124E_V133G_S176D_T178E_T180E |
| 9181-9406 | L124E_L143D_K145M | Q124K_V133G_S176R_T178K | L124R_Q179K | V133G_S176D_T178E |
| 9205-9368 | L124E_L143D_K145M | V133G_S176R_T178K | L124R_D146N_Q179K | V133G_S176D_T180E |
| 9198-9395 | L124E_L143D_K145M | V133G_S176R_T178K | L124R_Q179K | Q124E_V133G_S176D_T178E_T180E |
| 9202-9426 | L124E_L143D_K145M | V133G_S176R_T178K | L124R_Q179K | V133G_S176D_T178E_T180E |
| 9208-9350 | L124E_L143D_K145T | Q124K_V133G_Q160K_S176R | L124R_D146N_Q179K | Q124E_V133G_S176D_T178E_T180E |
| 9208-9376 | L124E_L143D_K145T | Q124K_V133G_Q160K_S176R | L124R_Q179K | Q124E_V133G_S176D_T178E_T180E |
| 9209-9398 | L124E_L143D_K145T | Q124K_V133G_Q160K_S176R | L124R_Q179K | V133G_S176D_T178E |
| 9211-9380 | L124E_L143D_K145T | Q124K_V133G_S176R | L124R_Q179K | Q124E_V133G_S176D_T178E_T180E |
| 9212-9402 | L124E_L143D_K145T | Q124K_V133G_S176R | L124R_Q179K | V133G_S176D_T178E |
| 9213-9432 | L124E_L143D_K145T | Q124K_V133G_S176R | L124R_Q179K | V133G_S176D_T180E |
| 9216-9384 | L124E_L143D_K145T | Q124K_V133G_S176R_T178K | L124R_Q179K | Q124E_V133G_S176D_T178E_T180E |
| 9219-9406 | L124E_L143D_K145T | Q124K_V133G_S176R_T178K | L124R_Q179K | V133G_S176D_T178E |
| 9220-9436 | L124E_L143D_K145T | Q124K_V133G_S176R_T178K | L124R_Q179K | V133G_S176D_T180E |
| 9225-9388 | L124E_L143D_K145T | Q124K_V133G_S176R_T178R | L124R_Q179K | Q124E_V133G_S176D_T178E_T180E |
| 9228-9410 | L124E_L143D_K145T | Q124K_V133G_S176R_T178R | L124R_Q179K | V133G_S176D_T178E |
| 9229-9440 | L124E_L143D_K145T | Q124K_V133G_S176R_T178R | L124R_Q179K | V133G_S176D_T180E |
| 9243-9368 | L124E_L143D_K145T | V133G_S176R_T178K | L124R_D146N_Q179K | V133G_S176D_T180E |
| 9236-9395 | L124E_L143D_K145T | V133G_S176R_T178K | L124R_Q179K | Q124E_V133G_S176D_T178E_T180E |
| 9240-9426 | L124E_L143D_K145T | V133G_S176R_T178K | L124R_Q179K | V133G_S176D_T178E_T180E |
| 9243-9447 | L124E_L143D_K145T | V133G_S176R_T178K | L124R_Q179K | V133G_S176D_T180E |
| 9247-9350 | L124E_L143E_K145M | Q124K_V133G_Q160K_S176R | L124R_D146N_Q179K | Q124E_V133G_S176D_T178E_T180E |
| 9247-9376 | L124E_L143E_K145M | Q124K_V133G_Q160K_S176R | L124R_Q179K | Q124E_V133G_S176D_T178E_T180E |
| 9248-9398 | L124E_L143E_K145M | Q124K_V133G_Q160K_S176R | L124R_Q179K | V133G_S176D_T178E |
| 9252-9380 | L124E_L143E_K145M | Q124K_V133G_S176R | L124R_Q179K | Q124E_V133G_S176D_T178E_T180E |
| 9255-9402 | L124E_L143E_K145M | Q124K_V133G_S176R | L124R_Q179K | V133G_S176D_T178E |
| 9256-9432 | L124E_L143E_K145M | Q124K_V133G_S176R | L124R_Q179K | V133G_S176D_T180E |
| 9259-9384 | L124E_L143E_K145M | Q124K_V133G_S176R_T178K | L124R_Q179K | Q124E_V133G_S176D_T178E_T180E |
| 9262-9406 | L124E_L143E_K145M | Q124K_V133G_S176R_T178K | L124R_Q179K | V133G_S176D_T178E |
| 9263-9436 | L124E_L143E_K145M | Q124K_V133G_S176R_T178K | L124R_Q179K | V133G_S176D_T180E |
| 9266-9388 | L124E_L143E_K145M | Q124K_V133G_S176R_T178R | L124R_Q179K | Q124E_V133G_S176D_T178E_T180E |
| 9269-9410 | L124E_L143E_K145M | Q124K_V133G_S176R_T178R | L124R_Q179K | V133G_S176D_T178E |
| 9270-9440 | L124E_L143E_K145M | Q124K_V133G_S176R_T178K | L124R_Q179K | V133G_S176D_T180E |
| 9271-9350 | L124E_L143E_K145T | Q124K_V133G_Q160K_S176R | L124R_D146N_Q179K | Q124E_V133G_S176D_T178E_T180E |
| 9275-9359 | L124E_L143E_K145T | Q124K_V133G_Q160K_S176R | L124R_D146N_Q179K | V133G_S176D_T178E_T180E |
| 9271-9376 | L124E_L143E_K145T | Q124K_V133G_Q160K_S176R | L124R_Q179K | Q124E_V133G_S176D_T178E_T180E |
| 9273-9398 | L124E_L143E_K145T | Q124K_V133G_Q160K_S176R | L124R_Q179K | V133G_S176D_T178E |
| 9275-9419 | L124E_L143E_K145T | Q124K_V133G_Q160K_S176R | L124R_Q179K | V133G_S176D_T178E_T180E |
| 9290-9364 | L124E_L143E_K145T | Q124K_V133G_S176R | L124R_D146N_Q179K | V133G_S176D_T180E |
| 9283-9380 | L124E_L143E_K145T | Q124K_V133G_S176R | L124R_Q179K | Q124E_V133G_S176D_T178E_T180E |

TABLE 16-continued

Cluster 2 designs including representative designs.

| Unique Identifier | H1_mutation* | L1_mutation* | H2_mutation* | L2_mutation* |
|---|---|---|---|---|
| 9287-9420 | L124E_L143E_K145T | Q124K_V133G_S176R | L124R_Q179K | V133G_S176D_T178E_T180E |
| 9290-9432 | L124E_L143E_K145T | Q124K_V133G_S176R | L124R_Q179K | V133G_S176D_T180E |
| 9298-9351 | L124E_L143E_K145T | Q124K_V133G_S176R_T178K | L124R_D146N_Q179K | Q124E_V133G_S176D_T178E_T180E |
| 9298-9384 | L124E_L143E_K145T | Q124K_V133G_S176R_T178K | L124R_Q179K | Q124E_V133G_S176D_T178E_T180E |
| 9302-9406 | L124E_L143E_K145T | Q124K_V133G_S176R_T178K | L124R_Q179K | V133G_S176D_T178E |
| 9308-9436 | L124E_L143E_K145T | Q124K_V133G_S176R_T178K | L124R_Q179K | V133G_S176D_T180E |
| 9316-9388 | L124E_L143E_K145T | Q124K_V133G_S176R_T178R | L124R_Q179K | Q124E_V133G_S176D_T178E_T180E |
| 9319-9410 | L124E_L143E_K145T | Q124K_V133G_S176R_T178R | L124R_Q179K | V133G_S176D_T178E |
| 9323-9440 | L124E_L143E_K145T | Q124K_V133G_S176R_T178R | L124R_Q179K | V133G_S176D_T180E |
| 9213-9364 | L124E_L143D_K145T | Q124K_V133G_S176R | L124R_D146N_Q179K | V133G_S176D_T180E |
| 9256-9364 | L124E_L143E_K145M | Q124K_V133G_S176R | L124R_D146N_Q179K | V133G_S176D_T180E |
| 9279-9518** | L124E_L143E_K145T | Q124K_V133G_S176R | L124R_S186R | V133G_S176D_T178D |
| 9175-9546 | L124E_L143D_K145M | Q124K_V133G_S176R | L124R_S186R | V133G_S176D_T180E |
| 9176-9451 | L124E_L143D_K145M | Q124K_V133G_S176R_T178K | L124R_S186K | Q124E_V133G_S176D_T178D_T180E |
| 9179-9473 | L124E_L143D_K145M | Q124K_V133G_S176R_T178K | L124R_S186K | V133G_S176D_T178D_T180E |
| 9176-9505 | L124E_L143D_K145M | Q124K_V133G_S176R_T178K | L124R_S186R | Q124E_V133G_S176D_T178D_T180E |
| 9196-9461 | L124E_L143D_K145M | V133G_S176R_T178K | L124R_S186K | Q124E_V133G_S176D_T178D_T180E |
| 9199-9484 | L124E_L143D_K145M | V133G_S176R_T178K | L124R_S186K | V133G_S176D_T178D_T180E |
| 9202-9489 | L124E_L143D_K145M | V133G_S176R_T178K | L124R_S186K | V133G_S176D_T178E_T180E |
| 9205-9501 | L124E_L143D_K145M | V133G_S176R_T178K | L124R_S186K | V133G_S176D_T180E |
| 9196-9516 | L124E_L143D_K145M | V133G_S176R_T178K | L124R_S186R | Q124E_V133G_S176D_T178D_T180E |
| 9202-9544 | L124E_L143D_K145M | V133G_S176R_T178K | L124R_S186R | V133G_S176D_T178E_T180E |
| 9205-9556 | L124E_L143D_K145M | V133G_S176R_T178K | L124R_S186R | V133G_S176D_T180E |
| 9213-9546 | L124E_L143D_K145T | Q124K_V133G_S176R | L124R_S186R | V133G_S176D_T180E |
| 9214-9451 | L124E_L143D_K145T | Q124K_V133G_S176R_T178K | L124R_S186K | Q124E_V133G_S176D_T178D_T180E |
| 9217-9473 | L124E_L143D_K145T | Q124K_V133G_S176R_T178K | L124R_S186K | V133G_S176D_T178D_T180E |
| 9214-9505 | L124E_L143D_K145T | Q124K_V133G_S176R_T178K | L124R_S186R | Q124E_V133G_S176D_T178D_T180E |
| 9220-9547 | L124E_L143D_K145T | Q124K_V133G_S176R_T178K | L124R_S186R | V133G_S176D_T180E |
| 9229-9495 | L124E_L143D_K145T | Q124K_V133G_S176R_T178R | L124R_S186K | V133G_S176D_T180E |
| 9229-9550 | L124E_L143D_K145T | Q124K_V133G_S176R_T178R | L124R_S186R | V133G_S176D_T180E |
| 9234-9461 | L124E_L143D_K145T | V133G_S176R_T178K | L124R_S186K | Q124E_V133G_S176D_T178D_T180E |
| 9237-9484 | L124E_L143D_K145T | V133G_S176R_T178K | L124R_S186K | V133G_S176D_T178D_T180E |
| 9240-9489 | L124E_L143D_K145T | V133G_S176R_T178K | L124R_S186K | V133G_S176D_T178E_T180E |
| 9243-9501 | L124E_L143D_K145T | V133G_S176R_T178K | L124R_S186K | V133G_S176D_T180E |
| 9234-9516 | L124E_L143D_K145T | V133G_S176R_T178K | L124R_S186R | Q124E_V133G_S176D_T178D_T180E |
| 9240-9544 | L124E_L143D_K145T | V133G_S176R_T178K | L124R_S186R | V133G_S176D_T178E_T180E |
| 9243-9556 | L124E_L143D_K145T | V133G_S176R_T178K | L124R_S186R | V133G_S176D_T180E |
| 9250-9449 | L124E_L143E_K145M | Q124K_V133G_S176R | L124R_S186K | Q124E_V133G_S176D_T178D_T180E |
| 9253-9471 | L124E_L143E_K145M | Q124K_V133G_S176R | L124R_S186K | V133G_S176D_T178D_T180E |
| 9250-9503 | L124E_L143E_K145M | Q124K_V133G_S176R | L124R_S186R | Q124E_V133G_S176D_T178D_T180E |
| 9253-9526 | L124E_L143E_K145M | Q124K_V133G_S176R | L124R_S186R | V133G_S176D_T178D_T180E |
| 9256-9546 | L124E_L143E_K145M | Q124K_V133G_S176R | L124R_S186R | V133G_S176D_T180E |
| 9257-9451 | L124E_L143E_K145M | Q124K_V133G_S176R_T178K | L124R_S186K | Q124E_V133G_S176D_T178D_T180E |
| 9257-9505 | L124E_L143E_K145M | Q124K_V133G_S176R_T178K | L124R_S186R | Q124E_V133G_S176D_T178D_T180E |
| 9263-9547 | L124E_L143E_K145M | Q124K_V133G_S176R_T178K | L124R_S186R | V133G_S176D_T180E |
| 9270-9495 | L124E_L143E_K145M | Q124K_V133G_S176R_T178R | L124R_S186K | V133G_S176D_T180E |
| 9281-9449 | L124E_L143E_K145T | Q124K_V133G_S176R | L124R_S186K | Q124E_V133G_S176D_T178D_T180E |
| 9279-9463 | L124E_L143E_K145T | Q124K_V133G_S176R | L124R_S186K | V133G_S176D_T178D |
| 9284-9471 | L124E_L143E_K145T | Q124K_V133G_S176R | L124R_S186K | V133G_S176D_T178D_T180E |
| 9287-9486 | L124E_L143E_K145T | Q124K_V133G_S176R | L124R_S186K | V133G_S176D_T178E_T180E |
| 9290-9491 | L124E_L143E_K145T | Q124K_V133G_S176R | L124R_S186K | V133G_S176D_T180E |
| 9281-9503 | L124E_L143E_K145T | Q124K_V133G_S176R | L124R_S186R | Q124E_V133G_S176D_T178D_T180E |
| 9284-9526 | L124E_L143E_K145T | Q124K_V133G_S176R | L124R_S186R | V133G_S176D_T178D_T180E |
| 9287-9541 | L124E_L143E_K145T | Q124K_V133G_S176R | L124R_S186R | V133G_S176D_T178E_T180E |
| 9290-9546 | L124E_L143E_K145T | Q124K_V133G_S176R | L124R_S186R | V133G_S176D_T180E |
| 9304-9487 | L124E_L143E_K145T | Q124K_V133G_S176R_T178K | L124R_S186K | V133G_S176D_T178E_T180E |
| 9304-9542 | L124E_L143E_K145T | Q124K_V133G_S176R_T178K | L124R_S186R | V133G_S176D_T178E_T180E |
| 9308-9547 | L124E_L143E_K145T | Q124K_V133G_S176R_T178K | L124R_S186R | V133G_S176D_T180E |
| 9320-9488 | L124E_L143E_K145T | Q124K_V133G_S176R_T178R | L124R_S186K | V133G_S176D_T178E_T180E |
| 9323-9495 | L124E_L143E_K145T | Q124K_V133G_S176R_T178R | L124R_S186K | V133G_S176D_T180E |
| 9323-9550 | L124E_L143E_K145T | Q124K_V133G_S176R_T178R | L124R_S186R | V133G_S176D_T180E |
| 9256-9491 | L124E_L143E_K145M | Q124K_V133G_S176R | L124R_S186K | V133G_S176D_T180E |
| 9270-9550 | L124E_L143E_K145M | Q124K_V133G_S176R_T178R | L124R_S186R | V133G_S176D_T180E |

*Kabat numbering
**Representative designs

TABLE 17

Cluster 3 designs including representative designs

| Unique Identifier | H1_mutation* | L1_mutation* | H2_mutation* | L2_mutation* |
|---|---|---|---|---|
| 9815-9825** | Q39E_L124E | Q38R_V133G_S176R | Q39R_L124R | Q38E_V133G_S176D |
| 9815-9826 | Q39E_L124E | Q38R_V133G_S176R | Q39R_L124R_H172R | Q38E_V133G_S176D |
| 9816-9825 | Q39E_L124E_H172R | Q38R_V133G_S176R | Q39R_L124R | Q38E_V133G_S176D |
| 9816-9826 | Q39E_L124E_H172R | Q38R_V133G_S176R | Q39R_L124R_H172R | Q38E_V133G_S176D |
| 9747-9334 | L45P_L124E | P44F_V133G_S176R | L124R | V133G_S176D |
| 9334-9749 | L45P_L124E_H172R | P44F_V133G_S176R | L124R | V133G_S176D |
| 9369-9747 | L45P_L124E | P44F_V133G_S176R | L124R_H172R | V133G_S176D |
| 9748-9338** | L45P_L124E | P44F_V133G_S176R | L124R | V133G_S176D_T178D |
| 9372-9748 | L45P_L124E | P44F_V133G_S176R | L124R_H172R | V133G_S176D_T178D |
| 9338-9750 | L45P_L124E_H172R | P44F_V133G_S176R | L124R | V133G_S176D_T178D |
| 9750-9372 | L45P_L124E_H172R | P44F_V133G_S176R | L124R_H172R | V133G_S176D_T178D |
| 9327-6054** | L124E_L143F | V133G_S176R | L124R | V133G_S176D_T178D |
| 9107-9339 | L124E | V133G_S176K | L124R | V133G_S176D_T178D |
| 9326-6048 | L124E_L143F | V133G_S176R | L124R | V133G_S176D |
| 9328-9332 | L124E_L143F | V133G_S176R | L124R | S131E_V133G_S176D |
| 9104-9336 | L124E | S131T_V133G_S176R_T178Y | L124R | V133G_S176D |
| 9108-9330 | L124E | V133G_S176K | L124R | S131E_V133G_S176D |
| 9106-9337 | L124E | V133G_S176K | L124R | V133G_S176D |
| 9109-9332 | L124E | V133G_S176R | L124R | S131E_V133G_S176D |
| 9066-9335** | F122C_L124E | Q124C_V133G_S176R | L124R | V133G_S176D |
| 9121-9373** | L124E_H172T | V133G_N137K_S174R_S176R | L124R_H172R | V133G_S176D_T178D |
| 9122-9371 | L124E_H172T | V133G_S174R_S176R | L124R_H172R | V133G_S176D |

*Kabat numbering
**Representative designs

TABLE 18

Cluster 4 designs including representative designs

| Unique Identifier | H1_mutation* | L1_mutation* | H2_mutation* | L2_mutation* |
|---|---|---|---|---|
| 9168-9342** | L124E_K228D | S121K_V133G_S176R | L124R_A125R | V133G_S176D |
| 9169-9344 | L124E_K228D | S121K_V133G_S176R | L124R_A125R | V133G_S176D_T178D |
| 9114-9344 | L124E_A125S_K228D | S121K_V133G_S176R | L124R_A125R | V133G_S176D_T178D |
| 9113-9342 | L124E_A125S_K228D | S121K_V133G_S176R | L124R_A125R | V133G_S176D |
| 9111-9347 | L124E_A125S_H172R_K228D | S121K_V133G_S176R | L124R_A125R_H172T | V133G_N137K_S174R_S176D |
| 9118-6098** | L124E_H172R | V133G_S176R | L124R_H172T | V133G_S174R_S176D |
| 9117-9374 | L124E_H172R | V133G_S176K | L124R_H172T | V133G_N137K_S174R_S176D |
| 9119-9375 | L124E_H172R | V133G_S176R | L124R_H172T | V133G_N137K_S174R_S176D |

*Kabat numbering
**Representative designs

TABLE 19

Cluster 5 designs including the representative design

| Unique Identifier | H1_mutation* | L1_mutation* | H2_mutation* | L2_mutation* |
|---|---|---|---|---|
| 9116-9349** | L124E_A139W | F116A_V133G_L135V_S176R | L124R_A139G_V190A | V133G_L135W_S176D |

*Kabat numbering
**Representative design

TABLE 20

Cluster 6 designs including representative designs

| Unique Identifier | H1_mutation* | L1_mutation* | H2_mutation* | L2_mutation* |
|---|---|---|---|---|
| 9814-9828** | Q39E_K145T_Q179E | Q38R_S131K | Q39R_S186R | Q38E_Q124E_Q160E_T180E |
| 9813-9828 | Q39E_K145T_H172R_Q179E | Q38R_S131K | Q39R_S186R | Q38E_Q124E_Q160E_T180E |
| 9814-9824 | Q39E_K145T_Q179E | Q38R_S131K | Q39R_H172R_S186R | Q38E_Q124E_Q160E_T180E |
| 9813-9824 | Q39E_K145T_H172R_Q179E | Q38R_S131K | Q39R_H172R_S186R | Q38E_Q124E_Q160E_T180E |
| 9745-9075*** | L45P_K145T_H172R_Q179E | P44F_S131K | H172R_S186R | Q38E_Q124E_Q160E_T180E |
| 9075-9746 | L45P_K145T_Q179E | P44F_S131K | H172R_S186R | Q38E_Q124E_Q160E_T180E |
| 10547-10549 | L45P_K145T_Q179E | P44F_S131K | H172R_S186R | Q124E_Q160E_T180E_C214S |
| 10547-10551 | L45P_K145T_H172R_Q179E | P44F_S131K | H172R_S186R | Q124E_Q160E_T180E_C214S |
| 9745-9905 | L45P_K145T_H172R_Q179E | P44F_S131K | S186R | Q38E_Q124E_Q160E_T180E |
| 9746-9905 | L45P_K145T_Q179E | P44F_S131K | S186R | Q38E_Q124E_Q160E_T180E |
| 10545-10551 | L45P_K145T_H172R_Q179E | P44F_S131K | S186R | Q124E_Q160E_T180E_C214S |
| 10545-10549 | L45P_K145T_Q179E | P44F_S131K | S186R | Q124E_Q160E_T180E_C214S |

*Kabat numbering
**Representative designs
***The representative design is similar to 9745-9075 except that L2 lacks the Q38E substitution.

TABLE 21

Cluster 7 designs including the representative design

| Unique Identifier | H1_mutation* | L1_mutation* | H2_mutation* | L2_mutation* |
|---|---|---|---|---|
| 9060-9756** | A139W_L143E_K145T_Q179E | Q124R_T178R_F116A_L135V | Q179K | Q124E_Q160E_T180E_L135W |
| 9060-9054 | A139W_L143E_K145T_Q179E | Q124R_T178R_F116A_L135V | A139G_Q179K_V190A | Q124E_Q160E_T180E_L135W |
| 9058-9053 | A139W_L143E_K145T_Q179E | Q124R_F116A_L135V | A139G_Q179K_V190A | Q124E_Q160E_T180E_L135W |
| 9058-9755 | A139W_L143E_K145T_Q179E | Q124R_F116A_L135V | Q179K | Q124E_Q160E_T180E_L135W |

*Kabat numbering
**Representative design

TABLE 22

Cluster 8 designs including the representative design

| Unique Identifier | H1_mutation* | L1_mutation* |
|---|---|---|
| 9820-9823** | Q39E_L143E_K145T_Q179E | Q38R_Q124R_Q160K_T178R |
| 9819-9823 | Q39E_L143E_K145T_H172R_Q179E | Q38R_Q124R_Q160K_T178R |
| 9820-9822 | Q39E_L143E_K145T_Q179E | Q38R_Q124R_Q160K_T178R |
| 9819-9822 | Q39E_L143E_K145T_H172R_Q179E | Q38R_Q124R_Q160K_T178R |
| 9820-9821 | Q39E_L143E_K145T_Q179E | Q38R_Q124R_Q160K_T178R |
| 9820-9827 | Q39E_L143E_K145T_Q179E | Q38R_Q124R_Q160K_T178R |
| 9819-9821 | Q39E_L143E_K145T_H172R_Q179E | Q38R_Q124R_Q160K_T178R |
| 9819-9827 | Q39E_L143E_K145T_H172R_Q179E | Q38R_Q124R_Q160K_T178R |
| 9817-9823 | Q39E_L143E_K145T | Q38R_Q124R_Q160K_T178R |
| 9817-9822 | Q39E_L143E_K145T | Q38R_Q124R_Q160K_T178R |
| 9817-9821 | Q39E_L143E_K145T | Q38R_Q124R_Q160K_T178R |
| 9817-9827 | Q39E_L143E_K145T | Q38R_Q124R_Q160K_T178R |
| 9818-9823 | Q39E_L143E_K145T_H172R | Q38R_Q124R_Q160K_T178R |
| 9818-9822 | Q39E_L143E_K145T_H172R | Q38R_Q124R_Q160K_T178R |
| 9818-9821 | Q39E_L143E_K145T_H172R | Q38R_Q124R_Q160K_T178R |
| 9818-9827 | Q39E_L143E_K145T_H172R | Q38R_Q124R_Q160K_T178R |

| Unique Identifier | H2_mutation* | L2_mutation* |
|---|---|---|
| 9820-9823** | Q39R_H172R_Q179K | Q38E_Q124E_Q160E_T180E |
| 9819-9823 | Q39R_H172R_Q179K | Q38E_Q124E_Q160E_T180E |
| 9820-9822 | Q39R_D146G_Q179K | Q38E_Q124E_Q160E_T180E |
| 9819-9822 | Q39R_D146G_Q179K | Q38E_Q124E_Q160E_T180E |
| 9820-9821 | Q39R_D146G_H172R_Q179K | Q38E_Q124E_Q160E_T180E |
| 9820-9827 | Q39R_Q179K | Q38E_Q124E_Q160E_T180E |
| 9819-9821 | Q39R_D146G_H172R_Q179K | Q38E_Q124E_Q160E_T180E |
| 9819-9827 | Q39R_Q179K | Q38E_Q124E_Q160E_T180E |
| 9817-9823 | Q39R_H172R_Q179K | Q38E_Q124E_Q160E_T180E |

TABLE 22-continued

Cluster 8 designs including the representative design

| | | |
|---|---|---|
| 9817-9822 | Q39R_D146G_Q179K | Q38E_Q124E_Q160E_T180E |
| 9817-9821 | Q39R_D146G_H172R_Q179K | Q38E_Q124E_Q160E_T180E |
| 9817-9827 | Q39R_Q179K | Q38E_Q124E_Q160E_T180E |
| 9818-9823 | Q39R_H172R_Q179K | Q38E_Q124E_Q160E_T180E |
| 9818-9822 | Q39R_D146G_Q179K | Q38E_Q124E_Q160E_T180E |
| 9818-9821 | Q39R_D146G_H172R_Q179K | Q38E_Q124E_Q160E_T180E |
| 9818-9827 | Q39R_Q179K | Q38E_Q124E_Q160E_T180E |

*Kabat numbering
**Representative design

TABLE 23

Cluster 9 designs including representative designs

| Unique Identifier | H1_mutation* | L1_mutation* |
|---|---|---|
| 9751-9065*** | L45P_L143E_K145T | P44F_Q124R_Q160K_T178R |
| 9752-9064 | L45P_L143E_K145T_H172R | P44F_Q124R_Q160K_T178R |
| 9064-9751 | L45P_L143E_K145T | P44F_Q124R_Q160K_T178R |
| 9065-9752 | L45P_L143E_K145T_H172R | P44F_Q124R_Q160K_T178R |
| 9753-9074 | L45P_L143E_K145T_H172R_Q179E | P44F_Q124R_Q160K_T178R |
| 9753-9760 | L45P_L143E_K145T_H172R_Q179E | P44F_Q124R_Q160K_T178R |
| 9754-9760 | L45P_L143E_K145T_Q179E | P44F_Q124R_Q160K_T178R |
| 9074-9754 | L45P_L143E_K145T_Q179E | P44F_Q124R_Q160K_T178R |
| 10548-10550 | L45P_L143E_K145T | P44F_Q124R_Q160K_T178R |
| 10548-10552 | L45P_L143E_K145T_H172R | P44F_Q124R_Q160K_T178R |
| 10546-10550 | L45P_L143E_K145T | P44F_Q124R_Q160K_T178R |
| 10546-10552 | L45P_L143E_K145T_H172R | P44F_Q124R_Q160K_T178R |
| 9611-9077** | L143E_K145T_H172R | Q124R_Q160K_T178R |
| 9612-9078 | L143E_K145T_H172R_Q179E | Q124R_T178R |
| 9610-9076 | L143E_K145T_H172R | Q124R |

| Unique Identifier | H2_mutation* | L2_mutation* |
|---|---|---|
| 9751-9065*** | D146G_Q179K | Q38E_Q124E_Q160E_T180E |
| 9752-9064 | D146G_H172R_Q179K | Q38E_Q124E_Q160E_T180E |
| 9064-9751 | D146G_H172R_Q179K | Q38E_Q124E_Q160E_T180E |
| 9065-9752 | D146G_Q179K | Q38E_Q124E_Q160E_T180E |
| 9753-9074 | H172R_Q179K | Q124E_Q160E_T180E |
| 9753-9760 | Q179K | Q124E_Q160E_T180E |
| 9754-9760 | Q179K | Q124E_Q160E_T180E |
| 9074-9754 | H172R_Q179K | Q124E_Q160E_T180E |
| 10548-10550 | D146G_H172R_Q179K | Q124E_Q160E_T180E_C214S |
| 10548-10552 | D146G_H172R_Q179K | Q124E_Q160E_T180E_C214S |
| 10546-10550 | D146G_Q179K | Q124E_Q160E_T180E_C214S |
| 10546-10552 | D146G_Q179K | Q124E_Q160E_T180E_C214S |
| 9611-9077** | H172T_Q179K | Q124E_Q160E_T180E_N137K_S174R |
| 9612-9078 | H172T_Q179K | Q124E_Q160E_T180E_N137K_S174R |
| 9610-9076 | H172T_Q179K | Q124E_Q160E_T180E_N137K_S174R |

*Kabat numbering
**Representative designs
***The representative design is similar to 9751-9065 except that L2 lacks the Q38E substitution.

TABLE 24

Cluster 10 designs including representative designs

| Unique Identifier | H1_mutation* | L1_mutation* |
|---|---|---|
| 9561-9095** | L124W_L143E_K145T_Q179E | Q124R_V133A_S176T_T178R |
| 9559-9094 | L124W_L143E_K145T_Q179E | Q124K_V133A_S176T_T178R |
| 9564-9099 | L124W_L143E_K145T_Q179E | S131K_V133A_S176T_T178L |
| 9564-9096 | L124W_L143E_K145T_Q179E | S131K_V133A_S176T_T178L |
| 9560-9091 | L124W_L143E_K145T_Q179E | Q124R_V133A_S176T_T178R |
| 9558-9090 | L124W_L143E_K145T_Q179E | Q124K_V133A_S176T_T178R |
| 9562-9092 | L124W_L143E_K145T_Q179E | S131K_V133A_S176T_T178L |

TABLE 24-continued

Cluster 10 designs including representative designs

| | | |
|---|---|---|
| 9562-9098 | L124W_L143E_K145T_Q179E | S131K_V133A_S176T_T178L |
| 9571-9092 | L124W_L143F_K145T_Q179E | S131K_V133A_S176T_T178L |
| 9572-9096 | L124W_L143F_K145T_Q179E | S131K_V133A_S176T_T178L |
| 9098-9571 | L124W_L143F_K145T_Q179E | S131K_V133A_S176T_T178L |
| 9099-9572 | L124W_L143F_K145T_Q179E | S131K_V133A_S176T_T178L |

| Unique Identifier | H2_mutation* | L2_mutation* |
|---|---|---|
| 9561-9095** | L124A_L143F_Q179K | Q124E_V133W_S176T_T178L_T180E |
| 9559-9094 | L124A_L143F_Q179K | Q124E_V133W_S176T_T178L_T180E |
| 9564-9099 | L124A_Q179K | Q124E_V133W_S176T_T178L_T180E |
| 9564-9096 | L124A_L143F_Q179K | Q124E_V133W_S176T_T178L_T180E |
| 9560-9091 | L124A_L143F_Q179K | Q124E_V133W_S176T_T178E_T180E |
| 9558-9090 | L124A_L143F_Q179K | Q124E_V133W_S176T_T178E_T180E |
| 9562-9092 | L124A_L143F_Q179K | Q124E_V133W_S176T_T178E_T180E |
| 9562-9098 | L124A_Q179K | Q124E_V133W_S176T_T178E_T180E |
| 9571-9092 | L124A_L143F_Q179K | Q124E_V133W_S176T_T178E_T180E |
| 9572-9096 | L124A_L143F_Q179K | Q124E_V133W_S176T_T178L_T180E |
| 9098-9571 | L124A_Q179K | Q124E_V133W_S176T_T178E_T180E |
| 9099-9572 | L124A_Q179K | Q124E_V133W_S176T_T178L_T180E |

*Kabat numbering
**Representative design

TABLE 25

Cluster 11 designs including representative designs

| Unique Identifier | H1_mutation* | L1_mutation* | H2_mutation* | L2_mutation* |
|---|---|---|---|---|
| 9049-9759** | A139C_L143E_K145T_Q179E | F116C_Q124R_T178R | Q179K | Q124E_Q160E_T180E |
| 9667-9830** | L143E_K145T_Q179E | Q124R_T178R | S186K | Q124E_T178E_Q160E |
| 9667-9758 | L143E_K145T_Q179E | Q124R_T178R | Q179K | Q124E_T178E_Q160E |
| 9667-9802 | L143E_K145T_Q179E | Q124R_T178R | Q179R | Q124E_T178E_Q160E |
| 9667-9868 | L143E_K145T_Q179E | Q124R_T178R | S186R | Q124E_T178E_Q160E |
| 9671-9784 | L143E_K145T_Q179E | Q124R_T178R | Q179K | Q124E_T178E |
| 9671-9810 | L143E_K145T_Q179E | Q124R_T178R | Q179R | Q124E_T178E |
| 9671-9850 | L143E_K145T_Q179E | Q124R_T178R | S186K | Q124E_T178E |
| 9671-9888 | L143E_K145T_Q179E | Q124R_T178R | S186R | Q124E_T178E |
| 9675-9786 | L143E_K145T_Q179E | Q124R_T178R | Q179K | Q124E_T178E_T180E |
| 9675-9812 | L143E_K145T_Q179E | Q124R_T178R | Q179R | Q124E_T178E_T180E |
| 9675-9852 | L143E_K145T_Q179E | Q124R_T178R | S186K | Q124E_T178E_T180E |
| 9675-9890 | L143E_K145T_Q179E | Q124R_T178R | S186R | Q124E_T178E_T180E |
| 9579-9797 | L143D_K145T_Q179E | T178R | Q179K | Q124E_T180E |
| 9614-9761 | L143E_K145T_Q179D | Q124K_T178R | Q179K | Q124E_T180E |
| 9617-9787 | L143E_K145T_Q179D | Q124K_T178R | Q179K | Q124E_T180E |
| 9623-9789 | L143E_K145T_Q179D | Q124R_Q160K_T178R | Q179K | Q124E_T180E |
| 9626-9767 | L143E_K145T_Q179D | Q124R_T178K | Q179K | Q124E_Q160E_T180E |
| 9629-9792 | L143E_K145T_Q179D | Q124R_T178R | Q179K | Q124E_T180E |
| 9632-9769 | L143E_K145T_Q179D | Q124R_T178R | Q179K | Q124E_Q160E_T180E |
| 9635-9794 | L143E_K145T_Q179D | Q124R_T178R | Q179K | Q124E_T180E |
| 9641-9797 | L143E_K145T_Q179D | T178R | Q179K | Q124E_T180E |
| 9645-9761 | L143E_K145T_Q179E | Q124K_T178R | Q179K | Q124E_Q160E_T180E |
| 9648-9787 | L143E_K145T_Q179E | Q124K_T178R | Q179K | Q124E_T180E |
| 9654-9789 | L143E_K145T_Q179E | Q124R_Q160K_T178R | Q179K | Q124E_T180E |
| 9657-9767 | L143E_K145T_Q179E | Q124R_T178K | Q179K | Q124E_Q160E_T180E |
| 9660-9792 | L143E_K145T_Q179E | Q124R_T178R | Q179K | Q124E_T180E |
| 9663-9769 | L143E_K145T_Q179E | Q124R_T178R | Q179K | Q124E_Q160E_T180E |
| 9679-9794 | L143E_K145T_Q179E | Q124R_T178R | Q179K | Q124E_T180E |
| 9684-9797 | L143E_K145T_Q179E | T178R | Q179K | Q124E_T180E |
| 9575-9841 | L143D_K145T_Q179E | T178R | S186K | Q124E_Q160E_T180E |
| 9579-9863 | L143D_K145T_Q179E | T178R | S186K | Q124E_T180E |
| 9579-9901 | L143D_K145T_Q179E | T178R | S186R | Q124E_T180E |
| 9617-9853 | L143E_K145T_Q179D | Q124K_T178R | S186K | Q124E_T180E |
| 9617-9891 | L143E_K145T_Q179D | Q124K_T178R | S186R | Q124E_T180E |
| 9623-9855 | L143E_K145T_Q179D | Q124R_Q160K_T178R | S186K | Q124E_T180E |
| 9623-9893 | L143E_K145T_Q179D | Q124R_Q160K_T178R | S186R | Q124E_T180E |
| 9626-9836 | L143E_K145T_Q179D | Q124R_T178K | S186K | Q124E_Q160E_T180E |
| 9626-9874 | L143E_K145T_Q179D | Q124R_T178K | S186R | Q124E_Q160E_T180E |
| 9629-9858 | L143E_K145T_Q179D | Q124R_T178K | S186K | Q124E_T180E |
| 9629-9896 | L143E_K145T_Q179D | Q124R_T178K | S186R | Q124E_T180E |
| 9632-9838 | L143E_K145T_Q179D | Q124R_T178R | S186K | Q124E_Q160E_T180E |
| 9635-9860 | L143E_K145T_Q179D | Q124R_T178R | S186K | Q124E_T180E |
| 9635-9898 | L143E_K145T_Q179D | Q124R_T178R | S186R | Q124E_T180E |

TABLE 25-continued

| Cluster 11 designs including representative designs | | | | |
|---|---|---|---|---|
| Unique Identifier | H1_mutation* | L1_mutation* | H2_mutation* | L2_mutation* |
| 9641-9863 | L143E_K145T_Q179D | T178R | S186K | Q124E_T180E |
| 9641-9901 | L143E_K145T_Q179D | T178R | S186R | Q124E_T180E |
| 9648-9853 | L143E_K145T_Q179E | Q124K_T178R | S186K | Q124E_T180E |
| 9648-9891 | L143E_K145T_Q179E | Q124K_T178R | S186R | Q124E_T180E |
| 9654-9855 | L143E_K145T_Q179E | Q124R_Q160K_T178R | S186K | Q124E_T180E |
| 9654-9893 | L143E_K145T_Q179E | Q124R_Q160K_T178R | S186R | Q124E_T180E |
| 9657-9836 | L143E_K145T_Q179E | Q124R_T178K | S186K | Q124E_Q160E_T180E |
| 9660-9858 | L143E_K145T_Q179E | Q124R_T178K | S186K | Q124E_T180E |
| 9660-9896 | L143E_K145T_Q179E | Q124R_T178K | S186R | Q124E_T180E |
| 9663-9838 | L143E_K145T_Q179E | Q124R_T178R | S186K | Q124E_Q160E_T180E |
| 9663-9876 | L143E_K145T_Q179E | Q124R_T178R | S186R | Q124E_Q160E_T180E |
| 9679-9860 | L143E_K145T_Q179E | Q124R_T178R | S186K | Q124E_T180E |
| 9679-9898 | L143E_K145T_Q179E | Q124R_T178R | S186R | Q124E_T180E |
| 9683-9841 | L143E_K145T_Q179E | T178R | S186K | Q124E_Q160E_T180E |
| 9606-9855 | L143E_K145T | Q124R_Q160K_T178R | S186K | Q124E_T180E |
| 9606-9893 | L143E_K145T | Q124R_Q160K_T178R | S186R | Q124E_T180E |
| 9682-9740** | L143E_K145T_Q179E | Q124R_T178R | L143R | Q124E_V133E |
| 9666-9731 | L143E_K145T_Q179E | Q124R_T178R | L143K | Q124E_V133D |

*Kabat numbering
**Representative designs

TABLE 26

| Cluster 12 designs including representative designs | | | | |
|---|---|---|---|---|
| Unique Identifier | H1_mutation* | L1_mutation* | H2_mutation* | L2_mutation* |
| 9696-9848** | L143E_K145T_Q179E_S188L | Q124R_T178R | S186K | Q124E_S176L_T180E |
| 9696-9782 | L143E_K145T_Q179E_S188L | Q124R_T178R | Q179K | Q124E_S176L_T180E |
| 9696-9886 | L143E_K145T_Q179E_S188L | Q124R_T178R | S186R | Q124E_S176L_T180E |
| 9696-9808 | L143E_K145T_Q179E_S188L | Q124R_T178R | Q179R | Q124E_S176L_T180E |
| 9702-9574 | L143E_K145T_Q179E_S188L | Q124R_T178R | L143A_Q179K | Q124E_V133Y_T180E |
| 9700-9103 | L143E_K145T_Q179E_S188L | Q124R_T178R | L124A_S186K | Q124E_V133W_T180E |
| 9700-9101 | L143E_K145T_Q179E_S188L | Q124R_T178R | L124A_Q179K | Q124E_V133W_T180E |
| 9716-9807 | L143E_K145T_S188L | Q124R_Q160K_T178R | Q179R | Q124E_S176L_T180E |
| 9716-9847 | L143E_K145T_S188L | Q124R_Q160K_T178R | S186K | Q124E_S176L_T180E |
| 9716-9781 | L143E_K145T_S188L | Q124R_Q160K_T178R | Q179K | Q124E_S176L_T180E |
| 9692-9846** | L143E_K145T_Q179E_S188L | Q124R_T178R | S186K | Q124E_S131T_T178Y_T180E |
| 9692-9806 | L143E_K145T_Q179E_S188L | Q124R_T178R | Q179R | Q124E_S131T_T178Y_T180E |
| 9688-9844 | L143E_K145T_Q179E_S188L | Q124R_T178R | S186K | Q124E_S131T_T178F_T180E |
| 9688-9804 | L143E_K145T_Q179E_S188L | Q124R_T178R | Q179R | Q124E_S131T_T178F_T180E |
| 9692-9780 | L143E_K145T_Q179E_S188L | Q124R_T178R | Q179K | Q124E_S131T_T178Y_T180E |
| 9688-9778 | L143E_K145T_Q179E_S188L | Q124R_T178R | Q179K | Q124E_S131T_T178F_T180E |
| 9712-9779 | L143E_K145T_S188L | Q124R_Q160K_T178R | Q179K | Q124E_S131T_T178Y_T180E |
| 9712-9805 | L143E_K145T_S188L | Q124R_Q160K_T178R | Q179R | Q124E_S131T_T178Y_T180E |
| 9708-9777 | L143E_K145T_S188L | Q124R_Q160K_T178R | Q179K | Q124E_S131T_T178F_T180E |
| 9712-9845 | L143E_K145T_S188L | Q124R_Q160K_T178R | S186K | Q124E_S131T_T178Y_T180E |
| 9692-9884 | L143E_K145T_Q179E_S188L | Q124R_T178R | S186R | Q124E_S131T_T178Y_T180E |
| 9594-9829 | L143E_K145T | Q124R_Q160K_T178R | S186K | Q124_Q160E_T178E |
| 9602-9889 | L143E_K145T | Q124R_Q160K_T178R | S186R | Q124E_T178E_T180E |
| 9602-9785 | L143E_K145T | Q124R_Q160K_T178R | Q179K | Q124E_T178E_T180E |
| 9602-9811 | L143E_K145T | Q124R_Q160K_T178R | Q179R | Q124E_T178E_T180E |
| 9594-9757 | L143E_K145T | Q124R_Q160K_T178R | Q179K | Q124_Q160E_T178E |
| 9598-9849 | L143E_K145T | Q124R_Q160K_T178R | S186K | Q124E_T178E |
| 9598-9809 | L143E_K145T | Q124R_Q160K_T178R | Q179R | Q124E_T178E |
| 9594-9801 | L143E_K145T | Q124R_Q160K_T178R | Q179R | Q124_Q160E_T178E |
| 9602-9851 | L143E_K145T | Q124R_Q160K_T178R | S186K | Q124E_T178E_T180E |
| 9986-9978** | L143E_K145T | Q124R_Q160K_T178R | S186K | S131E |
| 9987-9982 | L143E_K145T | Q124R_T178R | S186K | S131E |
| 9986-9979 | L143E_K145T | Q124R_Q160K_T178R | Q179K | S131E |
| 9587-9735** | L143E_K145T | Q124R | L143R | Q124E_V133E |
| 9609-9737 | L143E_K145T | Q124R_Q160K_T178R | L143R | Q124E_V133E |
| 9589-9742 | L143E_K145T | Q124R | L143R | Q124E_V133E_Q160M |
| 9687-9737 | L143E_K145T_Q179E_S188L | Q124R_Q160K_T178R | L143R | Q124E_V133E |
| 9705-9735 | L143E_K145T_S188L | Q124R | L143R | Q124E_V133E |

TABLE 26-continued

Cluster 12 designs including representative designs

| Unique Identifier | H1_mutation* | L1_mutation* | H2_mutation* | L2_mutation* |
|---|---|---|---|---|
| 9720-9733 | L143E_K145T_S188L | Q124R_Q160K_T178R | L143K | Q124E_V133D_S176L |
| 9703-9734 | L143E_K145T_S188L | Q124R | L143K_D146G | Q124E_V133D |
| 9722-9744 | L143E_K145T_S188L | Q124R_Q160K_T178R | L143R | Q124E_V133E_S176L |

*Kabat numbering
**Representative designs

TABLE 27

Cluster 13 designs including representative designs

| Unique Identifier | H1_mutation* | L1_mutation* | H2_mutation* | L2_mutation* |
|---|---|---|---|---|
| 9042-9046 | F122C_C233S | Q124C_C214S | WT | WT |

TABLE 28a

SMCA unique identifiers for the trastuzumab/cetuximab bispecific system

| SMCA unique identifiers | H1L1 Ab | H2L2 Ab | H1* | L1* |
|---|---|---|---|---|
| 3519_1 | Trastuzumab | Cetuximab | L45P_K145T_H172R_Q179E | P44F_S131K |
| 3519_2 | Cetuximab | Trastuzumab | L45P_K145T_H172R_Q179E | P44F_S131K |
| 3522_1 | Trastuzumab | Cetuximab | L45P_L143E_K145T | P44F_Q124R_Q160K_T178R |
| 3522_2 | Cetuximab | Trastuzumab | L45P_L143E_K145T | P44F_Q124R_Q160K_T178R |
| 9049-9759_1 | Trastuzumab | Cetuximab | A139C_L143E_K145T_Q179E | F116C_Q124R_T178R |
| 9049-9759_2 | Cetuximab | Trastuzumab | A139C_L143E_K145T_Q179E | F116C_Q124R_T178R |
| 9060-9756_1 | Cetuximab | Trastuzumab | A139W_L143E_K145T_Q179E | F116A_Q124R_L135V_T178R |
| 9060-9756_2 | Trastuzumab | Cetuximab | A139W_L143E_K145T_Q179E | F116A_Q124R_L135V_T178R |
| 9066-9335_1 | Cetuximab | Trastuzumab | F122C_L124E | Q124C_V133G_S176R |
| 9066-9335_2 | Trastuzumab | Cetuximab | F122C_L124E | Q124C_V133G_S176R |
| 9116-9349_1 | Cetuximab | Trastuzumab | L124E_A139W | F116A_V133G_L135V_S176R |
| 9116-9349_2 | Trastuzumab | Cetuximab | L124E_A139W | F116A_V133G_L135V_S176R |
| 9118-6098_1 | Cetuximab | Trastuzumab | L124E_H172R | V133G_S176R |
| 9118-6098_2 | Trastuzumab | Cetuximab | L124E_H172R | V133G_S176R |
| 9121-9373_1 | Cetuximab | Trastuzumab | L124E_H172T | V133G_N137K_S174R_S176R |
| 9121-9373_2 | Trastuzumab | Cetuximab | L124E_H172T | V133G_N137K_S174R_S176R |
| 9134-9521_1 | Trastuzumab | Cetuximab | L124E_K145T_Q179E | S131K_V133G_S176R |
| 9134-9521_2 | Cetuximab | Trastuzumab | L124E_K145T_Q179E | S131K_V133G_S176R |
| 9168-9342_1 | Trastuzumab | Cetuximab | L124E_K228D | S121K_V133G_S176R |
| 9168-9342_2 | Cetuximab | Trastuzumab | L124E_K228D | S121K_V133G_S176R |
| 9279-9518_1 | Cetuximab | Trastuzumab | L124E_L143E_K145T | Q124K_V133G_S176R |
| 9279-9518_2 | Trastuzumab | Cetuximab | L124E_L143E_K145T | Q124K_V133G_S176R |
| 9286-9402_1 | Cetuximab | Trastuzumab | L124E_L143E_K145T | Q124K_V133G_S176R |
| 9286-9402_2 | Trastuzumab | Cetuximab | L124E_L143E_K145T | Q124K_V133G_S176R |
| 9327-6054_1 | Cetuximab | Trastuzumab | L124E_L143F | V133G_S176R |
| 9327-6054_2 | Trastuzumab | Cetuximab | L124E_L143F | V133G_S176R |
| 9561-9095_1 | Cetuximab | Trastuzumab | L124W_L143E_K145T_Q179E | Q124R_V133A_S176T_T178R |
| 9561-9095_2 | Trastuzumab | Cetuximab | L124W_L143E_K145T_Q179E | Q124R_V133A_S176T_T178R |
| 9587-9735_1 | Trastuzumab | Cetuximab | L143E_K145T | Q124R |
| 9587-9735_2 | Cetuximab | Trastuzumab | L143E_K145T | Q124R |
| 9611-9077_1 | Cetuximab | Trastuzumab | L143E_K145T_H172R | Q124R_Q160K_T178R |
| 9611-9077_2 | Trastuzumab | Cetuximab | L143E_K145T_H172R | Q124R_Q160K_T178R |
| 9667-9830_1 | Trastuzumab | Cetuximab | L143E_K145T_Q179E | Q124R_T178R |
| 9667-9830_2 | Cetuximab | Trastuzumab | L143E_K145T_Q179E | Q124R_T178R |
| 9682-9740_1 | Trastuzumab | Cetuximab | L143E_K145T_Q179E | Q124R_T178R |
| 9682-9740_2 | Cetuximab | Trastuzumab | L143E_K145T_Q179E | Q124R_T178R |
| 9692-9846_1 | Trastuzumab | Cetuximab | L143E_K145T_Q179E_S188L | Q124R_T178R |
| 9692-9846_2 | Cetuximab | Trastuzumab | L143E_K145T_Q179E_S188L | Q124R_T178R |
| 9696-9848_1 | Trastuzumab | Cetuximab | L143E_K145T_Q179E_S188L | Q124R_T178R |
| 9696-9848_2 | Cetuximab | Trastuzumab | L143E_K145T_Q179E_S188L | Q124R_T178R |
| 9748-9338_1 | Cetuximab | Trastuzumab | L45P_L124E | P44F_V133G_S176R |
| 9748-9338_2 | Trastuzumab | Cetuximab | L45P_L124E | P44F_V133G_S176R |
| 9814-9828_1 | Trastuzumab | Cetuximab | Q39E_K145T_Q179E | Q38R_S131K |
| 9814-9828_2 | Cetuximab | Trastuzumab | Q39E_K145T_Q179E | Q38R_S131K |
| 9815-9825_1 | Cetuximab | Trastuzumab | Q39E_L124E | Q38R_V133G_S176R |

TABLE 28a-continued

SMCA unique identifiers for the trastuzumab/cetuximab bispecific system

| | | | | |
|---|---|---|---|---|
| 9815-9825_2 | Trastuzumab | Cetuximab | Q39E_L124E | Q38R_V133G_S176R |
| 9820-9823_1 | Cetuximab | Trastuzumab | Q39E_L143E_K145T_Q179E | Q38R_Q124R_Q160K_T178R |
| 9820-9823_2 | Trastuzumab | Cetuximab | Q39E_L143E_K145T_Q179E | Q38R_Q124R_Q160K_T178R |
| 9986-9978_1 | Trastuzumab | Cetuximab | L143E_K145T | Q124R_Q160K_T178R |
| 9986-9978_2 | Cetuximab | Trastuzumab | L143E_K145T | Q124R_Q160K_T178R |

| SMCA unique identifiers | H2* | L2* |
|---|---|---|
| 3519_1 | H172R_S186R | Q124E_Q160E_T180E |
| 3519_2 | H172R_S186R | Q124E_Q160E_T180E |
| 3522_1 | D146G_Q179K | Q124E_Q160E_T180E |
| 3522_2 | D146G_Q179K | Q124E_Q160E_T180E |
| 9049-9759_1 | Q179K | Q124E_Q160E_T180E |
| 9049-9759_2 | Q179K | Q124E_Q160E_T180E |
| 9060-9756_1 | Q179K | Q124E_L135W_Q160E_T180E |
| 9060-9756_2 | Q179K | Q124E_L135W_Q160E_T180E |
| 9066-9335_1 | L124R | V133G_S176D |
| 9066-9335_2 | L124R | V133G_S176D |
| 9116-9349_1 | L124R_A139G_V190A | V133G_L135W_S176D |
| 9116-9349_2 | L124R_A139G_V190A | V133G_L135W_S176D |
| 9118-6098_1 | L124R_H172T | V133G_S174R_S176D |
| 9118-6098_2 | L124R_H172T | V133G_S174R_S176D |
| 9121-9373_1 | L124R_H172R | V133G_S176D_T178D |
| 9121-9373_2 | L124R_H172R | V133G_S176D_T178D |
| 9134-9521_1 | L124R_S186R | V133G_S176D_T178D |
| 9134-9521_2 | L124R_S186R | V133G_S176D_T178D |
| 9168-9342_1 | L124R_A125R | V133G_S176D |
| 9168-9342_2 | L124R_A125R | V133G_S176D |
| 9279-9518_1 | L124R_S186R | V133G_S176D_T178D |
| 9279-9518_2 | L124R_S186R | V133G_S176D_T178D |
| 9286-9402_1 | L124R_Q179K | V133G_S176D_T178E |
| 9286-9402_2 | L124R_Q179K | V133G_S176D_T178E |
| 9327-6054_1 | L124R | V133G_S176D_T178D |
| 9327-6054_2 | L124R | V133G_S176D_T178D |
| 9561-9095_1 | L124A_L143F_Q179K | Q124E_V133W_S176T_T178L_T180E |
| 9561-9095_2 | L124A_L143F_Q179K | Q124E_V133W_S176T_T178LT180E |
| 9587-9735_1 | L143R | Q124E_V133E |
| 9587-9735_2 | L143R | Q124E_V133E |
| 9611-9077_1 | H172T_Q179K | Q124E_N137K_Q160E_S174R_T180E |
| 9611-9077_2 | H172T_Q179K | Q124E_N137K_Q160E_S174R_T180E |
| 9667-9830_1 | S186K | Q124E_Q160E_T178E |
| 9667-9830_2 | S186K | Q124E_Q160E_T178E |
| 9682-9740_1 | L143R | Q124E_V133E |
| 9682-9740_2 | L143R | Q124E_V133E |
| 9692-9846_1 | S186K | Q124E_S131T_T178Y_T180E |
| 9692-9846_2 | S186K | Q124E_S131T_T178Y_T180E |
| 9696-9848_1 | S186K | Q124E_S176L_T180E |
| 9696-9848_2 | S186K | Q124E_S176L_T180E |
| 9748-9338_1 | L124R | V133G_S176D_T178D |
| 9748-9338_2 | L124R | V133G_S176D_T178D |
| 9814-9828_1 | Q39R_S186R | Q38E_Q124E_Q160E_T180E |
| 9814-9828_2 | Q39R_S186R | Q38E_Q124E_Q160E_T180E |
| 9815-9825_1 | Q39R_L124R | Q38E_V133G_S176D |
| 9815-9825_2 | Q39R_L124R | Q38E_V133G_S176D |
| 9820-9823_1 | Q39R_H172R_Q179K | Q38E_Q124E_Q160E_T180E |
| 9820-9823_2 | Q39R_H172R_Q179K | Q38E_Q124E_Q160E_T180E |
| 9986-9978_1 | S186K | S131E |
| 9986-9978_2 | S186K | S131E |

*Kabat numbering. Note that the WT residues refer to the D3H44 system.

TABLE 28b

SMCA unique identifiers for the D3H44/cetuximab bispecific system

| SMCA unique identifiers | H1L1 Ab | H2L2 Ab | H1* | L1* |
|---|---|---|---|---|
| 3519_1 | Cetuximab | D3H44 | L45P_K145T_H127R_Q179E | P44F_S131K |
| 3519_2 | D3H44 | Cetuximab | L45P_K145T_H127R_Q179E | P44F_S131K |
| 3522_1 | Cetuximab | D3H44 | L459_L143E_K145T | P44F_Q124R_Q160K_T178R |
| 3522_2 | D3H44 | Cetuximab | L459_L143E_K145T | P44F_Q124R_Q160K_T178R |
| 9049-9759_1 | Cetuximab | D3H44 | A139C_L143E_K145T_Q179E | F116C_Q124R_T178R |
| 9049-9759_2 | D3H44 | Cetuximab | A139C_L143E_K145T_Q179E | F116C_Q124R_T178R |

TABLE 28b-continued

SMCA unique identifiers for the D3H44/cetuximab bispecific system

| | | | | |
|---|---|---|---|---|
| 9060-9756_1 | D3H44 | Cetuximab | A139W_L143E_K145T_Q179E | F116A_Q124R_L135V_T178R |
| 9060-9756_2 | Cetuximab | D3H44 | A139W_L143E_K145T_Q179E | F116A_Q124R_L135V_T178R |
| 9066-9335_1 | D3H44 | Cetuximab | F122C_L124E | Q124C_V133G_S176R |
| 9066-9335_2 | Cetuximab | D3H44 | F122C_L124E | Q124C_V133G_S176R |
| 9116-9349_1 | D3H44 | Cetuximab | L124E_A139W | F116A_V113G_L135V_S176R |
| 9116-9349_2 | Cetuximab | D3H44 | L124E_A139W | F116A_V113G_L135V_S176R |
| 9118-6098_1 | D3H44 | Cetuximab | L124E_H172R | V133G_S176R |
| 9118-6098_2 | Cetuximab | D3H44 | L124E_H172R | V133G_S176R |
| 9121-9373_1 | D3H44 | Cetuximab | L124E_H172T | V133G_N137K_S174R_S176R |
| 9121-9373_2 | Cetuximab | D3H44 | L124E_H172T | V133G_N137K_S174R_S176R |
| 9134-9521_1 | D3H44 | Cetuximab | L124E_K145T_Q179E | S131K_V133G_S176R |
| 9134-9521_2 | Cetuximab | D3H44 | L124E_K145T_Q179E | S131K_V133G_S176R |
| 9168-9342_1 | D3H44 | Cetuximab | L124E_K228D | S121K_V133G_S176R |
| 9168-9342_2 | Cetuximab | D3H44 | L124E_K228D | S121K_V133G_S176R |
| 9279-9518_1 | D3H44 | Cetuximab | L124E_L124E_K145T | Q124K_V133G_S176R |
| 9279-9518_2 | Cetuximab | D3H44 | L124E_L124E_K145T | Q124K_V133G_S176R |
| 9286-9402_1 | D3H44 | Cetuximab | L124E_L124E_K145T | Q124K_V133G_S176R |
| 9286-9402_2 | Cetuximab | D3H44 | L124E_L124E_K145T | Q124K_V133G_S176R |
| 9327-6054_1 | D3H44 | Cetuximab | L124E_L124F | V133G_S176R |
| 9327-6054_2 | Cetuximab | D3H44 | L124E_L124F | V133G_S176R |
| 9561-9095_1 | D3H44 | Cetuximab | L124W_L142E_K145T_Q179E | Q124R_V133A_S176T_T178R |
| 9561-9095_2 | Cetuximab | D3H44 | L124W_L142E_K145T_Q179E | Q124R_V133A_S176T_T178R |
| 9587-9735_1 | Cetuximab | D3H44 | L124E_K145T | Q124R |
| 9587-9735_2 | D3H44 | Cetuximab | L124E_K145T | Q124R |
| 9611-9077_1 | Cetuximab | D3H44 | L124E_K145T_H172R | Q124R_Q160K_T178R |
| 9611-9077_2 | D3H44 | Cetuximab | L124E_K145T_H172R | Q124R_Q160K_T178R |
| 9667-9830_1 | Cetuximab | D3H44 | L124E_K145T_Q179E | Q124R_T178R |
| 9667-9830_2 | D3H44 | Cetuximab | L124E_K145T_Q179E | Q124R_T178R |
| 9682-9740_1 | Cetuximab | D3H44 | L124E_K145T_Q179E | Q124R_T178R |
| 9682-9740_2 | Cetuximab | D3H44 | L124E_K145T_Q179E | Q124R_T178R |
| 9692-9846_1 | Cetuximab | D3H44 | L124E_K145T_Q179E_S188L | Q124R_T178R |
| 9692-9846_2 | D3H44 | Cetuximab | L124E_K145T_Q179E_S188L | Q124R_T178R |
| 9696-9848_1 | D3H44 | Cetuximab | L124E_K145T_Q179E_S188L | Q124R_T178R |
| 9696-9848_2 | Cetuximab | D3H44 | L124E_K145T_Q179E_S188L | Q124R_T178R |
| 9748-9338_1 | D3H44 | Cetuximab | L45P_L124E | P44F_V133G_S176R |
| 9748-9338_2 | Cetuximab | D3H44 | L45P_L124E | P44F_V133G_S176R |
| 9814-9828_1 | Cetuximab | D3H44 | Q39E_K145T | Q38R_S131K |
| 9814-9828_2 | Cetuximab | D3H44 | Q39E_K145T | Q38R_S131K |
| 9815-9825_1 | D3H44 | Cetuximab | Q39E_K145T | Q38R_V133G_S176R |
| 9815-9825_2 | D3H44 | Cetuximab | Q39E_K145T | Q38R_V133G_S176R |
| 9820-9823_1 | D3H44 | Cetuximab | Q39E_L143E_K145T_Q179E | Q38R_Q124R_Q160K_T178R |
| 9820-9823_2 | Cetuximab | D3H44 | Q39E_L143E_K145T_Q179E | Q38R_Q124R_Q160K_T178R |
| 9986-9978_1 | Cetuximab | D3H44 | L143E_K145T | Q124R_Q160K_T178R |
| 9986-9978_2 | D3H44 | Cetuximab | L143E_K145T | Q124R_Q160K_T178R |

| SMCA unique identifiers | H2* | L2* |
|---|---|---|
| 3519_1 | H172R_S186R | Q124E_Q160E_T180E |
| 3519_2 | H172R_S186R | Q124E_Q160E_T180E |
| 3522_1 | D146G_Q179K | Q124E_Q160E_T180E |
| 3522_2 | D146G_Q179K | Q124E_Q160E_T180E |
| 9049-9759_1 | Q179K | Q124E_Q160E_T180E |
| 9049-9759_2 | Q179K | Q124E_Q160E_T180E |
| 9060-9756_1 | Q179K | Q124E_L135W_Q160E_T180E |
| 9060-9756_2 | Q179K | Q124E_L135W_Q160E_T180E |
| 9066-9335_1 | L124R | V133G_S176D |
| 9066-9335_2 | L124R | V133G_S176D |
| 9116-9349_1 | L124R_A139G_V190A | V133G_L135W_S176D |
| 9116-9349_2 | L124R_A139G_V190A | V133G_L135W_S176D |
| 9118-6098_1 | L124R_H172T | V133G_S174R_S176D |
| 9118-6098_2 | L124R_H172T | V133G_S174R_S176D |
| 9121-9373_1 | L124R_H172R | V133G_S176D_T178D |
| 9121-9373_2 | L124R_H172R | V133G_S176D_T178D |
| 9134-9521_1 | L124R_S186R | V133G_S176D_T178D |
| 9134-9521_2 | L124R_S186R | V133G_S176D_T178D |
| 9168-9342_1 | L124R_A12SR | V133G_S176D |
| 9168-9342_2 | L124R_A125R | V133G_S176D |
| 9279-9518_1 | L124R_S186R | V133G_S176D_T178D |
| 9279-9518_2 | L124R_S186R | V133G_S176D_T178D |
| 9286-9402_1 | L124R_Q179K | V133G_S176D_T178E |
| 9286-9402_2 | L124R_Q179K | V133G_S176D_T178E |
| 9327-6054_1 | L124R | V133G_S176D_T178D |
| 9327-6054_2 | L124R | V133G_S176D_T178D |
| 9561-9095_1 | L124A_L143F_Q179K | Q124E_V133W_S176T_T178L_T180E |
| 9561-9095_2 | L124A_L143F_Q179K | Q124E_V133W_S176T_T178L_T180E |
| 9587-9735_1 | L143R | Q124E_V133E |
| 9587-9735_2 | L143R | Q124E_V133E |

TABLE 28b-continued

SMCA unique identifiers for the D3H44/cetuximab bispecific system

| | | |
|---|---|---|
| 9611-9077_1 | H172T_Q179K | Q124E_N137K_Q160E_S174R_T180E |
| 9611-9077_2 | H172T_Q179K | Q124E_N137K_Q160E_S174R_T180E |
| 9667-9830_1 | S186K | Q124E_Q160E_T178E |
| 9667-9830_2 | S186K | Q124E_Q160E_T178E |
| 9682-9740_1 | L143R | Q124E_V133E |
| 9682-9740_2 | L143R | Q124E_V133E |
| 9692-9846_1 | S186K | Q124E_S131T_T178Y_T180E |
| 9692-9846_2 | S186K | Q124E_S131T_T178Y_T180E |
| 9696-9848_1 | S186K | Q124E_S176L_T180E |
| 9696-9848_2 | S186K | Q124E_S176L_T180E |
| 9748-9338_1 | L124R | V133G_S176D_T178D |
| 9748-9338_2 | L124R | V133G_S176D_T178D |
| 9814-9828_1 | Q39R_S186R | Q38E_Q124E_Q160E_T180E |
| 9814-9828_2 | Q39R_S186R | Q38E_Q124E_Q160E_T180E |
| 9815-9825_1 | Q39R_L124R | Q38E_V133G_S176D |
| 9815-9825_2 | Q39R_L124R | Q38E_V133G_S176D |
| 9820-9823_1 | Q39R_H172R_Q179K | Q38E_Q124E_Q160E_T180E |
| 9820-9823_2 | Q39R_H172R_Q179K | Q38E_Q124E_Q160E_T180E |
| 9986-9978_1 | S186K | S131E |
| 9986-9978_2 | S186K | S131E |

*Kabat numbering.
Note that the WT residues refer to the D3H44 system.

TABLE 28c

SMCA unique identifiers for the D3H44/trastuzumab bispecific system

| SMCA unique identifiers | H1L1 Ab | H2L2 Ab | H1* | H2* |
|---|---|---|---|---|
| 3519_1 | Trastuzumab | D3H44 | L45P_K145T_H172R_Q179E | P44F_S131K |
| 3522_1 | Trastuzumab | D3H44 | L45P_L143E_K145T | P44F_Q124R_Q160K_T178R |
| 9049-9759_1 | Trastuzumab | D3H44 | A139C_L143E_K145T_Q179E | F116C_Q124R_T178R |
| 9060-9756_1 | D3H44 | Trastuzumab | A139W_L143E_K145T_Q179E | F116A_Q124R_L135W_T178R |
| 9066-9335_1 | D3H44 | Trastuzumab | F122C_L124E | Q124C_V133G_S176R |
| 9116-9349_1 | D3H44 | Trastuzumab | L124E_A139W | F116A_V133G_L135V_S176R |
| 9118-6098_1 | D3H44 | Trastuzumab | L124E_H172R | V133G_S176R |
| 9121-9373_1 | D3H44 | Trastuzumab | L124E_H172T | V133G_N137K_S174R_S176R |
| 9134-9521_1 | Trastuzumab | D3H44 | L124E_K145T_Q179E | S131K_V133G_S176R |
| 9168-9342_1 | Trastuzumab | D3H44 | L124E_K228D | S121K_V133G_S176R |
| 9279-9518_1 | D3H44 | Trastuzumab | L124E_L143E_K145 | Q124K_V133G_S176R |
| 9286-9402_1 | D3H44 | Trastuzumab | L124E_L143E_K145T | Q124K_V133G_S176R |
| 9327-6054_1 | D3H44 | Trastuzumab | L124E_L143F | V133G_S176R |
| 9561-9095_1 | D3H44 | Trastuzumab | L124W_L143E_K145T_Q179E | Q124R_V133A_S176T_T178R |
| 9587-9735_1 | Trastuzumab | D3H44 | L143E_K145T | Q124R |
| 9611-9077_1 | D3H44 | Trastuzumab | L143E_K145T_M172R | Q124R_Q160K_T178R |
| 9667-9830_1 | Trastuzumab | D3H44 | L143E_K145T_Q179E | Q124R_T178R |
| 9682-9740_1 | Trastuzumab | D3H44 | L143E_K145T_Q179E | Q124R_T178R |
| 9692-9846_1 | Trastuzumab | D3H44 | L143E_K145T_Q179E_S188L | Q124R_T178R |
| 9696-9848_1 | Trastuzumab | D3H44 | L143E_K145T_Q179E_S188L | Q124R_T178R |
| 9748-9338_1 | D3H44 | Trastuzumab | L45P_L124E | P44F_V133G_S176R |
| 9814-9828_1 | D3H44 | Trastuzumab | Q39E_K145T_Q179E | Q38R_S131K |
| 9815-9825_1 | D3H44 | Trastuzumab | Q39E_L124E | Q38R_V133G_S176R |
| 9820-9823_1 | D3H44 | Trastuzumab | Q39E_L143E_K145T_Q179E | Q38R_Q124R_Q160K_T178R |
| 9986-9978_1 | Trastuzumab | D3H44 | L143E_K145T | Q124R_Q160K_T178R |

| SMCA unique identifiers | H2* | L2* |
|---|---|---|
| 3519_1 | H172R_S186R | Q124E_Q160E_T180E |
| 3522_1 | D146G_Q179K | Q124E_Q160E_T180E |
| 9049-9759_1 | Q179K | Q124E_Q160E_T180E |
| 9060-9756_1 | Q179K | Q124E_L135W_Q160E_T180E |
| 9066-9335_1 | L124R | V133G_S176D |
| 9116-9349_1 | L124R_A139G_V190A | V133G_L135W_S176D |
| 9118-6098_1 | L124R_H172T | V133G_S174R_S176D |
| 9121-9373_1 | L124R_H172R | V133G_S176D_T178D |
| 9134-9521_1 | L124R_S186R | V133G_S176D_T178D |
| 9168-9342_1 | L124R_A125R | V133G_S176D |
| 9279-9518_1 | L124R_S186R | V133G_S176D_T178D |
| 9286-9402_1 | L124R_Q179K | V133G_S176D_T178E |
| 9327-6054_1 | L124R | V133G_S176D_T178D |
| 9561-9095_1 | L124A_L143F_Q179K | Q124E_V133W_S176T_T178L_T180E |
| 9587-9735_1 | L143R | Q124E_V133E |
| 9611-9077_1 | H172T_Q179K | Q124E_N137K_Q160E_S174R_T180E |

TABLE 28c-continued

SMCA unique identifiers for the D3H44/trastuzumab bispecific system

| | | |
|---|---|---|
| 9667-9830_1 | S186K | Q124E_Q160E_T178E |
| 9682-9740_1 | L143R | Q124E_V133E |
| 9692-9846_1 | S186K | Q124E_S131T_T178Y_T180E |
| 9696-9848_1 | S186K | Q124E_S176L_T180E |
| 9748-9338_1 | L124R | V133G_S176D_T178D |
| 9814-9828_1 | Q39R_S186R | Q38E_Q124E_Q160E_T180E |
| 9815-9825_1 | Q39R_L124R | Q38E_V133G_S176D |
| 9820-9823_1 | Q39R_H172R_Q179K | Q38E_Q124E_Q160E_T180E |
| 9986-9978_1 | S186K | S131E |

*Kabat numbering.
Note that the WT residues refer to the D3H44 system.

TABLE 29a

LC-MS pairing data and post pA yields (mg/L) for the heterodimeric antibodies from the D3H44 (H1L1)/cetuximab (H2L2) bispecific system

| SMCA unique identifier | Cluster | Post pA yield (mg/L A280) | % H1L1 Pairing (over all H1 species) | % H2L2 Pairing (over all H2 species) | % H1L1 and % H2L2 Pairing (over all species) | H1 + H2 + L1 + L2* | Change in % of H1:H2:L1:L respect to wild type* | H1 + H2 + L1 + L2** | H1 + H1 + L1 + L1** | H1 + H1 + L1 + L2** | H1 + H1 + L2 + L2** |
|---|---|---|---|---|---|---|---|---|---|---|---|
| 9327-6054_2 | 3 | 7 | 33.1 | 100 | 68.2 | 32.4 | −13.8 | 27.9 | 0 | 0 | 0 |
| 3519_2 | 6 | 21 | 75.5 | 100 | 82.8 | 67.2 | 7.2 | 42.1 | 4 | 2.2 | 0 |
| 9168-9342_2 | 4 | 17 | 80.5 | 100 | 83.4 | 59.9 | −0.1 | 25.7 | 7.5 | 2.3 | 0 |
| 9986-9978_2 | 12 | 21 | 83.2 | 100 | 85.8 | 67.7 | 7.7 | 35.7 | 8.3 | 2.7 | 0 |
| 9692-9846_2 | 12 | 25 | 89.7 | 100 | 89.5 | 83.6 | 23.5 | 43 | 7.2 | 1.2 | 0 |
| 9587-9735_2 | 12 | 25 | 91.5 | 100 | 92 | 73.9 | 13.9 | 39.2 | 10.7 | 1 | 0 |
| 3522_2 | 9 | 13 | 88.1 | 100 | 95.8 | 84.6 | 24.5 | 58.2 | 0 | 0 | 0 |
| 9696-9848_2 | 12 | 21 | 94.3 | 100 | 95.9 | 80.9 | 20.9 | 47.9 | 7.3 | 0 | 0 |
| 9667-9830_1 | 11 | 35 | 100 | 95.1 | 96.8 | 98.1 | 40.2*** | 85.4 | 0 | 0 | 0 |
| 9986-9978_1 | 12 | 49 | 100 | 95.1 | 97.5 | 96 | 38.1*** | 85.4 | 0 | 0 | 0 |
| 9811-6098_2 | 4 | 13 | 96.6 | 100 | 97.8 | 92.3 | 34.4*** | 52.6 | 2 | 0 | 0 |
| 9748-9338_2 | 3 | 5 | 97.8 | 100 | 97.8 | 97.2 | 39.3*** | 50.9 | 1.5 | 0 | 0 |
| 9682-9740_1 | 11 | 34 | 100 | 97 | 98.5 | 96.2 | 38.3*** | 73.6 | 0 | 0 | 0 |
| 9692-9846_1 | 12 | 46 | 100 | 97.6 | 98.8 | 97.5 | 51.3 | 91.2 | 0 | 0 | 0 |
| 9286-9402_1 | 2 | 16 | 100 | 98.4 | 99.1 | 98.2 | 38.2 | 89.3 | 0 | 0 | 0 |
| 9066-9335_1 | 3 | 12 | 100 | 98 | 99.1 | 97.9 | 37.9 | 83.8 | 0 | 0 | 0 |
| 9561-9095_1 | 10 | 41 | 98.5 | 100 | 99.2 | 79.4 | 22.7 | 34.6 | 7.4 | 0 | 0 |
| 9168-9342_1 | 4 | 18 | 100 | 98.5 | 99.2 | 95.8 | 37.9*** | 66.8 | 0 | 0 | 0 |
| 3519_1 | 6 | 45 | 100 | 98.3 | 99.2 | 96.6 | 38.7*** | 80.4 | 1.2 | 0 | 0 |
| 9118-6098_1 | 4 | 26 | 98.5 | 100 | 99.3 | 98.2 | 41.5 | 85.5 | 0 | 0 | 0 |
| 9049-9759_2 | 11 | 16 | 100 | 98 | 99.3 | 94.6 | 34.5 | 71.1 | 2.6 | 0 | 0 |
| 9696-9848_1 | 12 | 43 | 100 | 98.8 | 99.4 | 98.7 | 52.5 | 90.4 | 0 | 0 | 0 |
| 9820-9823_1 | 8 | 27 | 100 | 98.6 | 99.4 | 97.2 | 37.2 | 81.8 | 1.1 | 0 | 0 |
| 9561-9095_2 | 10 | 28 | 100 | 100 | 99.9 | 94 | 34 | 70.6 | 4.5 | 0 | 0 |
| 9116-9349_2 | 5 | 1 | 100 | 100 | 99.9 | 100 | 40 | 64.7 | 0 | 0 | 0 |
| 9134-9521_1 | 1 | 17 | 100 | 100 | 99.9 | 89.8 | 31.9*** | 36.3 | 0 | 0 | 0 |
| 9279-9518_2 | 2 | 6 | 100 | 100 | 99.9 | 100 | 42.1*** | 77.8 | 0 | 0 | 0 |

TABLE 29a-continued

LC-MS pairing data and post pA yields (mg/L) for the heterodimeric antibodies from the D3H44 (H1L1)/cetuximab (H2L2) bispecific system

| | | | | | | | | | | |
|---|---|---|---|---|---|---|---|---|---|---|
| 9611-9077_2 | 9 | 19 | 100 | 100 | 99.9 | 81.3 | 23.4*** | 41.2 | 9.5 | 0 | 0 |
| 9060-9756_1 | 7 | 57 | 100 | 100 | 99.9 | 96.4 | 39.7 | 70.2 | 2.6 | 0 | 0 |
| 9587-9735_1 | 12 | 35 | 100 | 100 | 99.9 | 96.8 | 38.9*** | 71.2 | 0 | 0 | 0 |
| 9327-6054_1 | 3 | 13 | 100 | 100 | 100 | 92.5 | 32.5 | 44.2 | 3.6 | 0 | 0 |
| 9121-9373_1 | 3 | 17 | 100 | 100 | 100 | 89.5 | 29.5 | 37 | 4.3 | 0 | 0 |
| 9121-9373_2 | 3 | 9 | 100 | 100 | 100 | 100 | 42.1*** | 82.7 | 0 | 0 | 0 |
| 9116-9349_1 | 5 | 10 | 100 | 100 | 100 | 84.8 | 26.9*** | 22.2 | 4 | 0 | 0 |
| 9134-9521_2 | 1 | 15 | 100 | 100 | 100 | 44.8 | −15.3 | 15.7 | 19.3 | 0 | 0 |
| 9279-9518_1 | 2 | 11 | 100 | 100 | 100 | 89 | 29 | 33.1 | 4.1 | 0 | 0 |
| 9286-9402_2 | 2 | 12 | 100 | 100 | 100 | 89.9 | 32.0*** | 40.1 | 4.5 | 0 | 0 |
| 9814-9828_2 | 6 | 19 | 100 | 100 | 100 | 76.7 | 16.7 | 39.3 | 11.9 | 0 | 0 |
| 9814-9828_1 | 6 | 37 | 100 | 100 | 100 | 96.8 | 38.9*** | 66.3 | 0 | 0 | 0 |
| 9815-9825_1 | 3 | 14 | 100 | 100 | 100 | 100 | 40 | 89.4 | 0 | 0 | 0 |
| 9815-9825_2 | 3 | 7 | 100 | 100 | 100 | 100 | 42.1*** | 86 | 0 | 0 | 0 |
| 9748-9338_1 | 3 | 12 | 100 | 100 | 100 | 93.7 | 33.7 | 41.1 | 2.7 | 0 | 0 |
| 9667-9830_2 | 11 | 15 | 100 | 100 | 100 | 91.1 | 31 | 58.2 | 5.7 | 0 | 0 |
| 9611-9077_1 | 9 | 32 | 100 | 100 | 100 | 97.4 | 40.7 | 69.5 | 0 | 0 | 0 |
| 9060-9756_2 | 7 | 29 | 100 | 100 | 100 | 96.2 | 36.2 | 77.6 | 3.1 | 0 | 0 |
| 9682-9740_2 | 11 | 17 | 100 | 100 | 100 | 90.4 | 30.4 | 61 | 6.5 | 0 | 0 |
| 9049-9759_1 | 11 | 51 | 100 | 100 | 100 | 92.8 | 46.6 | 60.6 | 4.7 | 0 | 0 |
| 9066-9335_2 | 3 | 6 | 100 | 100 | 100 | 100 | 42.1*** | 69.9 | 0 | 0 | 0 |
| 3522_1 | 9 | 38 | 100 | 100 | 100 | 89.6 | 31.7*** | 53.4 | 6.2 | 0 | 0 |
| 9820-9823_2 | 8 | 24 | 100 | 100 | 100 | 98.5 | 40.6*** | 77.2 | 1.2 | 0 | 0 |

| SMCA unique identifier | H2 + H2 + L1 + L1** | H2 + H2 + L1 + L2** | H2 + H2 + L2 + L2** | H1 + H2 + L1 + L1** | H1 + H2 + L2 + L2** | H1 + L1** | H1 + L2** | H2 + L1** | H2 + L2** |
|---|---|---|---|---|---|---|---|---|---|
| 9327-6054_2 | 0 | 0 | 0 | 0 | 58.2 | 2.2 | 2.7 | 0 | 9 |
| 3519_2 | 0 | 0 | 0 | 0 | 14.4 | 26.4 | 9 | 0 | 2 |
| 9168-9342_2 | 0 | 0 | 0 | 0 | 7.4 | 45.4 | 11.7 | 0 | 0 |
| 9986-9978_2 | 0 | 0 | 0 | 0 | 6.1 | 37.4 | 9.9 | 0 | 0 |
| 9692-9846_2 | 0 | 0 | 0 | 0 | 0 | 37.5 | 9.8 | 0 | 1.2 |
| 9587-9735_2 | 0 | 0 | 0 | 0 | 2.1 | 40.5 | 6.4 | 0 | 0 |
| 3522_2 | 0 | 0 | 2.5 | 0 | 8.1 | 1.8 | 0 | 0 | 29.3 |
| 9696-9848_2 | 0 | 0 | 0 | 0 | 4 | 37.5 | 2.1 | 0 | 1.2 |
| 9667-9830_1 | 1.7 | 0 | 0 | 0 | 0 | 2.5 | 0 | 1.5 | 8.9 |
| 9986-9978_1 | 1.4 | 0 | 0 | 2.1 | 0 | 1.6 | 0 | 0 | 9.5 |
| 9811-6098_2 | 0 | 0 | 0 | 0 | 2.4 | 40.9 | 1 | 0 | 1.1 |
| 9748-9338_2 | 0 | 0 | 0 | 0 | 0 | 45.4 | 2.2 | 0 | 0 |
| 9682-9740_1 | 1.5 | 0 | 1.4 | 0 | 0 | 1.7 | 0 | 0 | 21.8 |

TABLE 29a-continued

LC-MS pairing data and post pA yields (mg/L) for the heterodimeric
antibodies from the D3H44 (H1L1)/cetuximab (H2L2) bispecific system

| | | | | | | | | | |
|---|---|---|---|---|---|---|---|---|---|
| 9692-9846_1 | 0 | 0 | 0 | 2.3 | 0 | 3.2 | 0 | 0 | 3.3 |
| 9286-9402_1 | 0 | 0 | 0 | 1.6 | 0 | 1.9 | 0 | 0 | 7.1 |
| 9066-9335_1 | 0 | 0 | 0 | 1.8 | 0 | 12.1 | 0 | 0 | 2.3 |
| 9561-9095_1 | 0 | 0 | 0 | 0 | 1.6 | 56.4 | 0 | 0 | 0 |
| 9168-9342_1 | 0 | 0 | 1.4 | 1.5 | 0 | 3.1 | 0 | 0 | 27.2 |
| 3519_1 | 0 | 1.6 | 0 | 0 | 0 | 8.4 | 0 | 0 | 8.4 |
| 9118-6098_1 | 0 | 0 | 0 | 1.5 | 0 | 3.1 | 0 | 0 | 2.7 |
| 9049-9759_2 | 0 | 0 | 0 | 1.5 | 0 | 22.5 | 0 | 0 | 2.4 |
| 9696-9848_1 | 0 | 0 | 0 | 1.2 | 0 | 3.8 | 0 | 0 | 4.6 |
| 9820-9823_1 | 0 | 0 | 0 | 1.2 | 0 | 14.2 | 0 | 0 | 1.7 |
| 9561-9095_2 | 0 | 0 | 0 | 0 | 0 | 23.1 | 0 | 0 | 1.7 |
| 9116-9349_2 | 0 | 0 | 0 | 0 | 0 | 28.4 | 0 | 0 | 6.8 |
| 9134-9521_1 | 0 | 0 | 4.1 | 0 | 0 | 0 | 0 | 0 | 59.5 |
| 9279-9518_2 | 0 | 0 | 0 | 0 | 0 | 2.9 | 0 | 0 | 19.2 |
| 9611-9077_2 | 0 | 0 | 0 | 0 | 0 | 49.2 | 0 | 0 | 0 |
| 9060-9756_1 | 0 | 0 | 0 | 0 | 0 | 27.1 | 0 | 0 | 0 |
| 9587-9735_1 | 0 | 0 | 2.3 | 0 | 0 | 0 | 0 | 0 | 26.4 |
| 9327-6054_1 | 0 | 0 | 0 | 0 | 0 | 52.3 | 0 | 0 | 0 |
| 9121-9373_1 | 0 | 0 | 0 | 0 | 0 | 58.7 | 0 | 0 | 0 |
| 9121-9373_2 | 0 | 0 | 0 | 0 | 0 | 11.2 | 0 | 0 | 6.1 |
| 9116-9349_1 | 0 | 0 | 0 | 0 | 0 | 73.8 | 0 | 0 | 0 |
| 9134-9521_2 | 0 | 0 | 0 | 0 | 0 | 65.1 | 0 | 0 | 0 |
| 9279-9518_1 | 0 | 0 | 0 | 0 | 0 | 62.8 | 0 | 0 | 0 |
| 9286-9402_2 | 0 | 0 | 0 | 0 | 0 | 55.4 | 0 | 0 | 0 |
| 9814-9828_2 | 0 | 0 | 0 | 0 | 0 | 48.8 | 0 | 0 | 0 |
| 9814-9828_1 | 0 | 0 | 2.2 | 0 | 0 | 0 | 0 | 0 | 31.5 |
| 9815-9825_1 | 0 | 0 | 0 | 0 | 0 | 7.6 | 0 | 0 | 3 |
| 9815-9825_2 | 0 | 0 | 0 | 0 | 0 | 7.4 | 0 | 0 | 6.6 |
| 9748-9338_1 | 0 | 0 | 0 | 0 | 0 | 56.2 | 0 | 0 | 0 |
| 9667-9830_2 | 0 | 0 | 0 | 0 | 0 | 33.3 | 0 | 0 | 2.8 |
| 9611-9077_1 | 0 | 0 | 1.9 | 0 | 0 | 1.4 | 0 | 0 | 27.2 |
| 9060-9756_2 | 0 | 0 | 0 | 0 | 0 | 17.2 | 0 | 0 | 2.2 |
| 9682-9740_2 | 0 | 0 | 0 | 0 | 0 | 29.9 | 0 | 0 | 2.7 |
| 9049-9759_1 | 0 | 0 | 0 | 0 | 0 | 34.7 | 0 | 0 | 0 |
| 9066-9335_2 | 0 | 0 | 0 | 0 | 0 | 27.3 | 0 | 0 | 2.8 |
| 3522_1 | 0 | 0 | 0 | 0 | 0 | 40.4 | 0 | 0 | 0 |
| 9820-9823_2 | 0 | 0 | 0 | 0 | 0 | 19 | 0 | 0 | 2.7 |

*% considering full Ab species only
**% considering all species
***estimated change in % of H1:H2:L1:L2 with respect to wild type TABLE 29b LC-MS pairing data and post pA yields (mg/L) for the heterodimeric antibodies from the D3H44 (H1L1)/trastuzumab (H2L2) bispecific system

| SMCA unique identifier | Cluster | Post pA yield (mg/L A280) | % H1L1 Pairing (over all H1 species) | % H2L2 Pairing (over all H2 species) | % H1L1 and % H2L2 Pairing (overall species) | H1 + H2 + L1 + L2* | Change in % of H1:H2:L1:L2 with respect to wild type* | H1 + H2 + L1 + L2 | H1 + H1 + L1 + L1 | H1 + H1 + L1 + L2 | H1 + H1 + L2 + L2 |
|---|---|---|---|---|---|---|---|---|---|---|---|
| 9279-9518_1 | 2 | 4 | 100 | 100 | 100 | 100 | 63.7 | 87.9 | 0 | 0 | 0 |
| 9134-9521_1 | 1 | 26 | 100 | 100 | 100 | 79.1 | 49.7 | 25.3 | 0 | 0 | 0 |
| 9060-9756_1 | 7 | 49 | 98.7 | 98.6 | 98.5 | 97.1 | 60.8 | 93.1 | 0 | 0 | 0 |
| 9286-9402_1 | 2 | 16 | 92 | 100 | 98.3 | 83.1 | 46.8 | 37.9 | 0 | 0 | 0 |
| 9049-9759_1 | 11 | 44 | 100 | 96.1 | 98 | 94.5 | 65.1 | 92.7 | 0 | 0 | 0 |
| 3522_1 | 9 | 61 | 100 | 94.8 | 98 | 91.6 | 62.2 | 74 | 2.8 | 0 | 0 |
| 3519_1 | 6 | 53 | 100 | 96.3 | 97.2 | 92.9 | 63.5 | 65.1 | 0 | 0 | 0 |
| 9814-9828_1 | 6 | 49 | 100 | 94.3 | 95.7 | 87.4 | 58 | 54.3 | 0 | 0 | 0 |
| 9748-9338_1 | 3 | 11 | 94.7 | 95.1 | 95.2 | 89.1 | 52.8 | 79.2 | 0 | 0 | 0 |
| 9682-9740_1 | 11 | 46 | 97.1 | 95.7 | 95.1 | 91.6 | 62.2 | 67.7 | 0 | 0 | 0 |
| 9667-9830_1 | 11 | 48 | 98.2 | 93.1 | 94.2 | 91.6 | 62.2 | 71 | 0 | 0 | 0 |
| 9820-9823_1 | 8 | 54 | 86.6 | 100 | 93.6 | 86.4 | 50.1 | 81.3 | 0 | 0 | 0 |
| 9327-6054_1 | 3 | 7 | 96.1 | 84.1 | 90.1 | 79.9 | 43.6 | 79 | 0 | 0 | 0 |
| 9587-9735_1 | 12 | 58 | 89.2 | 88.7 | 87.3 | 80.6 | 51.2 | 59.6 | 0 | 0 | 0 |
| 9168-9342_1 | 4 | 33 | 100 | 84.5 | 87.2 | 82.8 | 53.4 | 43.4 | 0 | 0 | 0 |
| 9815-9825_1 | 3 | 23 | 76.4 | 100 | 85.3 | 77.5 | 41.2 | 61.8 | 0 | 0 | 0 |
| 9118-6098_1 | 4 | 42 | 49.7 | 94.6 | 77 | 44.4 | 8.1 | 36.4 | 0 | 0 | 0 |
| 9066-9335_1 | 3 | 11 | 47.6 | 100 | 75.4 | 45.5 | 9.2 | 42.3 | 0 | 0 | 0 |
| 9561-9095_1 | 10 | 41 | 47.7 | 100 | 73.6 | 47.9 | 11.6 | 44.4 | 0 | 0 | 0 |
| 9121-9373_1 | 3 | 10 | 50.5 | 100 | 72.4 | 48.9 | 12.6 | 41.9 | 0 | 0 | 0 |
| 9116-9349_1 | 5 | 6 | 46.8 | 100 | 68.9 | 44.9 | 14.1*** | 34.4 | 0 | 0 | 0 |
| 9696-9848_1 | 12 | 50 | 100 | 88 | 92.8 | 86.5 | 57.1 | 75.6 | 0.0 | 0.0 | 0.0 |
| 9692-9846_1 | 12 | 51 | 100 | 85 | 91.4 | 85.0 | 55.6 | 74.9 | 0.0 | 0.0 | 0.0 |
| 9986-9978_1 | 12 | 49 | 100 | 91 | 95.6 | 90.7 | 61.3 | 86.0 | 0.0 | 0.0 | 0.0 |

| SMCA unique identifier | H2 + H2 + L1 + L1** | H2 + H2 + L1 + L2** | H2 + H2 + L2 + L2** | H1 + H2 + L1 + L1** | H1 + H2 + L2 + L2** | H1 + L1** | H1 + L2** | H2 + L1** | H2 + L2** |
|---|---|---|---|---|---|---|---|---|---|
| 9279-9518_1 | 0 | 0 | 0 | 0 | 0 | 11 | 0 | 0 | 1.1 |
| 9134-9521_1 | 0 | 0 | 6.7 | 0 | 0 | 0 | 0 | 0 | 68 |
| 9060-9756_1 | 0 | 0 | 0 | 1.4 | 1.3 | 1.9 | 0 | 0 | 2.2 |
| 9286-9402_1 | 0 | 0 | 4.4 | 0 | 3.3 | 0 | 0 | 0 | 54.4 |
| 9049-9759_1 | 0 | 0 | 1.4 | 4 | 0 | 0 | 0 | 0 | 1.9 |
| 3522_1 | 0 | 1.1 | 0 | 3 | 0 | 19.2 | 0 | 0 | 0 |
| 3519_1 | 0 | 0 | 3.3 | 1.7 | 0 | 2.1 | 0 | 2 | 25.8 |
| 9814-9828_1 | 0 | 0 | 4.4 | 3.4 | 0 | 0 | 0 | 2.6 | 35.3 |

TABLE 29b-continued

LC-MS pairing data and post pA yields (mg/L) for the
heterodimeric antibodies from the D3H44 (H1L1)/trastuzumab (H2L2) bispecific system

| | | | | | | | | | |
|---|---|---|---|---|---|---|---|---|---|
| 9748-9338_1 | 0 | 1.4 | 0 | 3.2 | 5.1 | 8.2 | 0 | 0 | 2.9 |
| 9682-9740_1 | 0 | 1.3 | 3.1 | 1.8 | 0 | 1.8 | 2.1 | 1.2 | 21 |
| 9667-9830_1 | 0 | 0 | 1.8 | 4.8 | 0 | 2.1 | 1.4 | 2 | 16.9 |
| 9820-9823_1 | 0 | 0 | 0 | 0 | 12.8 | 1.7 | 0 | 0 | 4.2 |
| 9327-6054_1 | 0 | 1.6 | 0 | 14.4 | 3.8 | 1.2 | 0 | 0 | 0 |
| 9587-9735_1 | 0 | 0 | 1.5 | 6.4 | 6.5 | 2.4 | 1.8 | 4.6 | 17.3 |
| 9168-9342_1 | 0 | 0 | 2.8 | 6.2 | 0 | 0 | 0 | 9.7 | 37.9 |
| 9815-9825_1 | 0 | 0 | 0 | 0 | 17.9 | 14.6 | 5.7 | 0 | 0 |
| 9118-6098_1 | 0 | 3.1 | 1.9 | 1.4 | 39.2 | 1 | 0 | 1.1 | 15.9 |
| 9066-9335_1 | 0 | 0 | 1.4 | 0 | 49.3 | 2.5 | 0 | 0 | 4.6 |
| 9561-9095_1 | 0 | 0 | 0 | 0 | 48.3 | 1.8 | 2.3 | 0 | 3.3 |
| 9121-9373_1 | 0 | 0 | 0 | 0 | 48.3 | 8.6 | 5.7 | 0 | 0 |
| 9116-9349_1 | 0 | 0 | 0 | 0 | 42.2 | 11.6 | 10 | 0 | 1.8 |
| 9696-9848_1 | 0.0 | 3.3 | 1.3 | 7.2 | 0.0 | 1.9 | 0.0 | 1.8 | 8.8 |
| 9692-9846_1 | 0.0 | 3.0 | 1.2 | 9.0 | 0.0 | 1.9 | 0.0 | 2.5 | 7.4 |
| 9986-9978_1 | 0.0 | 0.0 | 0.0 | 8.8 | 0.0 | 1.5 | 0.0 | 0.0 | 3.7 |

*% considering full Ab species only
**% considering all species
***estimated change in % of H1:H2:L1:L2 with respect to wild type TABLE 29c LC-MS pairing data and post pA yields (mg/L) for the heterodimeric
antibodies from the trastuzumab (H1L1)/cetuximab (H2L2) bispecific system

| SMCA unique identifier | Cluster | Post pA yield (mg/L A280) | % H1L1 Pairing (over all H1 species) | Change in % H1L1 Pairing (over all H1 species) with respect to wild type | % H2L2 Pairing (over all H2 species) | Change in % H2L2 Pairing (over all H2 species) with respect to wild type | % H1L1 and % H2L2 Pairing (over all species) | H2 + L1 L2* | Change in % of H1:H2:L1:L2 with respect to wild type* | H1 + H2 + L1 + L2** | H1 + H1 + L1** | H1 + H1 + L1 + L2** |
|---|---|---|---|---|---|---|---|---|---|---|---|---|
| 9561-9095_2 | 10 | 16 | 100 | 6.8 | 100 | 39.2 | 100 | 92.6 | 37.1 | 53.6 | 4.3 | 0 |
| 9561-9095_1 | 10 | 52 | 100 | 2.7*** | 58.1 | 33.0*** | 85.3 | 54.9 | 28.5*** | 40.8 | 4 | 0 |
| 9327-6054_1 | 3 | 2 | 98.3 | 1 | 91.3 | 68.5 | 95.4 | 89.1 | 68.5 | 74.8 | 0 | 0 |
| 9327-6054_2 | 3 | 8 | 100 | 6.8 | 2.4 | −58.4 | 55.1 | 2.5 | −53 | 2.1 | 0 | 0 |
| 9168-9342_1 | 4 | 36 | 98.5 | 1.2*** | 100 | 74.9*** | 98.3 | 49.3 | 22.9*** | 13.4 | 13.8 | 0 |
| 9168-9342_2 | 4 | 7 | 100 | 6 | 7.5 | −22.1 | 30 | 3.8 | −22.6 | 1.8 | 0 | 0 |
| 9118-6098_1 | 4 | 15 | 100 | 6 | 42.2 | 12.7 | 87 | 39.5 | 13.1 | 19 | 3.1 | 0 |
| 9118-6098_2 | 4 | 12 | 100 | 6.8 | 15.5 | −45.3 | 50.2 | 13 | −42.5 | 9.9 | 0 | 0 |
| 9121-9373_2 | 3 | 8 | 100 | 2.7*** | 100 | 74.9*** | 100 | 76.5 | 50.1*** | 21.7 | 6.7 | 0 |
| 9121-9373_1 | 3 | 2 | 100 | 6 | 44 | 14.4 | 76.2 | 42.1 | 15.7 | 34.6 | 0 | 0 |
| 9116-9349_2 | 5 | 2 | 100 | 6 | 79.8 | 50.3 | 98 | 70.2 | 43.8 | 14.6 | 2.5 | 0 |
| 9116-9349_1 | 5 | 1 | 100 | 2.7*** | 42.1 | 17.0*** | 89.4 | 40.5 | 14.1*** | 15.2 | 1.5 | 0 |

TABLE 29c-continued

LC-MS pairing data and post pA yields (mg/L) for the heterodimeric
antibodies from the trastuzumab (H1L1)/cetuximab (H2L2) bispecific system

| | | | | | | | | | | | | |
|---|---|---|---|---|---|---|---|---|---|---|---|---|
| 9134-9521_2 | 1 | 2 | 100 | 6 | 98.8 | 69.3 | 99.4 | 93.5 | 67.1 | 44.3 | 0 | 0 |
| 9134-9521_1 | 1 | 35 | 100 | 2.7*** | 62.5 | 37.4*** | 99.3 | 9.7 | −16.7*** | 2 | 17.8 | 0 |
| 9279-9518_2 | 2 | 5 | 100 | 6.8 | 33.5 | −27.3 | 87.1 | 30.8 | −24.7 | 13 | 3.3 | 0 |
| 9286-9402_1 | 2 | 11 | 100 | 6 | 100 | 70.5 | 100 | 29.9 | 3.5 | 3.3 | 7.7 | 0 |
| 9286-9402_2 | 2 | 8 | 100 | 6.8 | 97.3 | 36.5 | 98.7 | 92.8 | 37.3 | 61.8 | 0 | 0 |
| 9828-9828_1 | 6 | 12 | 96.4 | −0.9*** | 100 | 74.9*** | 96 | 65.9 | 39.5*** | 22.2 | 11.5 | 0 |
| 9814-9828_2 | 6 | 16 | 100 | 6 | 18.2 | −11.4 | 35.5 | 17.9 | −8.5 | 8 | 0 | 0 |
| 9815-9825_1 | 3 | 4 | 100 | 6 | 41.5 | 11.9 | 68.2 | 39.8 | 13.4 | 34.4 | 0 | 0 |
| 9815-9825_2 | 3 | 5 | 100 | 2.7*** | 17.6 | −7.5*** | 64.3 | 15.8 | −10.6*** | 12.7 | 0 | 0 |
| 9748-9338_1 | 3 | 1 | 98.7 | 4.7 | 67.7 | 38.2 | 93.4 | 61.5 | 35.1 | 23.6 | 1.7 | 0 |
| 9748-9338_2 | 3 | 7 | 100 | 2.7*** | 4.1 | −21.0*** | 54.8 | 4.4 | −22.0*** | 3.7 | 0 | 0 |
| 9667-9830_1 | 11 | 20 | 98.5 | 5.3 | 100 | 39.2 | 99.1 | 87 | 31.5 | 41.9 | 4.6 | 0 |
| 9667-9830_2 | 11 | 14 | 100 | 6 | 33.3 | 3.7 | 55.2 | 30.7 | 4.3 | 19.5 | 0 | 0 |
| 9692-9846_1 | 12 | 40 | 82.3 | −10.9 | 100 | 39.2 | 84.9 | 73.4 | 17.9 | 37.1 | 5.4 | 2.3 |
| 9692-9846_2 | 12 | 25 | 100 | 2.7 | 19.3 | −3.5 | 45 | 19.1 | −1.5 | 12.5 | 0 | 0 |
| 9696-9848_1 | 12 | 40 | 88.3 | −4.9 | 100 | 39.2 | 91.8 | 76.4 | 20.9 | 42.8 | 4.6 | 1.9 |
| 9696-9848_2 | 12 | 24 | 100 | 2.7 | 40.9 | 18.1 | 59.1 | 41.7 | 21.1 | 26.3 | 0 | 0 |
| 9986-9978_1 | 12 | 37 | 85.9 | −7.3 | 100 | 39.2 | 89 | 73.2 | 17.7 | 39 | 5.9 | 2 |
| 9986-9978_2 | 12 | 24 | 100 | 6 | 6.2 | −23.4 | 34.1 | 5 | −21.4 | 3.1 | 0 | 0 |
| 9611-9077_1 | 9 | 28 | 100 | 6 | NaN | NaN | 100 | 0 | −26.4 | 0 | 17.3 | 0 |
| 9611-9077_2 | 9 | 17 | 100 | 6.8 | 91.8 | 31 | 94 | 88.8 | 33.3 | 54.8 | 0 | 0 |
| 9060-9756_2 | 7 | 15 | 100 | 6.8 | 100 | 39.2 | 99.9 | 100 | 44.5 | 84.7 | 0 | 0 |
| 9060-9756_1 | 7 | 41 | 100 | 2.7*** | 96.7 | 71.6*** | 98.6 | 93.9 | 67.5*** | 77.2 | 2.4 | 0 |
| 9587-9735_1 | 12 | 38 | 93.9 | 0.7 | 95.2 | 34.4 | 94.7 | 69.3 | 13.8 | 34.2 | 8.6 | 1.5 |
| 9587-9735_2 | 12 | 17 | 100 | 6 | 21.1 | −8.4 | 40.8 | 18.7 | −7.7 | 9.9 | 0 | 0 |
| 9682-9740_1 | 11 | 31 | 100 | 6.8 | 100 | 39.2 | 100 | 79.1 | 23.6 | 36.5 | 9.7 | 0 |
| 9682-9740_2 | 11 | 15 | 100 | 6 | 39.7 | 10.2 | 56 | 35.9 | 9.5 | 19.3 | 0 | 0 |
| 9049-9759_1 | 11 | 24 | 100 | 6.8 | 100 | 39.2 | 100 | 100 | 44.5 | 84.2 | 0 | 0 |
| 9049-9759_2 | 11 | 23 | 100 | 2.7 | 25.8 | 3 | 79 | 23.7 | 3.1 | 14.6 | 5 | 0 |
| 9066-9335_2 | 3 | 4 | 100 | 6.8 | 97 | 36.2 | 98.5 | 92.9 | 37.4 | 62.6 | 0 | 0 |
| 9066-9335_1 | 3 | 2 | 100 | 6 | 29.5 | −0.1 | 84.8 | 28.5 | 2.1 | 12.7 | 1.6 | 0 |
| 3522_1 | 9 | 37 | 100 | 6.8 | 100 | 39.2 | 100 | 97.7 | 42.2 | 79.7 | 1.9 | 0 |
| 3522_2 | 9 | 14 | 98.8 | 4.8 | 9.1 | −20.5 | 76.8 | 5.6 | −20.8 | 3.1 | 7.6 | 0 |
| 3519_1 | 6 | 25 | 99 | 1.7*** | 96.2 | 71.1*** | 98.3 | 87.4 | 61.0*** | 57.2 | 4.9 | 0 |

TABLE 29c-continued

LC-MS pairing data and post pA yields (mg/L) for the heterodimeric
antibodies from the trastuzumab (H1L1)/cetuximab (H2L2) bispecific system

| | | | | | | | | | | | |
|---|---|---|---|---|---|---|---|---|---|---|---|
| 3519_2 | 6 | 14 | 100 | 6 | 2.9 | −26.7 | 35.1 | 2.6 | −23.8 | 1.8 | 0 | 0 |
| 9820-9823_2 | 8 | 12 | 100 | 2.7*** | 100 | 74.9*** | 100 | 100 | 73.6*** | 84.5 | 0 | 0 |
| 9820-9823_1 | 8 | 31 | 100 | 6 | 52.3 | 22.7 | 83.1 | 51 | 24.6 | 37.1 | 1.9 | 0 |

| SMCA unique identifier | H1 + H1 + L2 + L2** | H2 + H2 + L1 + L1** | H2 + H2 + L1 + L2** | H2 + H2 + L2 + L2** | H1 + H2 + L1 + L1** | H1 + H2 + L2 + L2** | H1 + L1** | H1 + L2** | H1 + L1** | H2 + L2** |
|---|---|---|---|---|---|---|---|---|---|---|
| 9561-9095_2 | 0 | 0 | 0 | 0 | 0 | 0 | 40.7 | 0 | 0 | 1.5 |
| 9561-9095_1 | 0 | 0 | 0 | 0 | 29.4 | 0 | 25.8 | 0 | 0 | 0 |
| 9327-6054_1 | 0 | 0 | 0 | 0 | 7.6 | 1.6 | 12.7 | 0 | 0 | 3.3 |
| 9327-6054_2 | 0 | 0 | 0 | 0 | 80.1 | 0 | 13 | 0 | 4.8 | 0 |
| 9168-9342_1 | 0 | 0 | 0 | 0 | 0 | 0 | 71.1 | 1.7 | 0 | 0 |
| 9168-9342_2 | 0 | 2 | 0 | 0 | 44.8 | 0 | 0 | 0 | 45.6 | 5.8 |
| 9118-6098_1 | 0 | 0 | 0 | 0 | 26 | 0 | 51.9 | 0 | 0 | 0 |
| 9118-6098_2 | 0 | 0 | 0 | 0 | 66.2 | 0 | 1.9 | 0 | 16.7 | 5.3 |
| 9121-9373_2 | 0 | 0 | 0 | 0 | 0 | 0 | 71.6 | 0 | 0 | 0 |
| 9121-9373_1 | 0 | 0 | 0 | 0 | 47.6 | 0 | 15 | 0 | 0 | 2.8 |
| 9116-9349_2 | 0 | 0 | 0 | 0 | 3.7 | 0 | 79.1 | 0 | 0 | 0 |
| 9116-9349_1 | 0 | 0 | 0 | 0 | 20.9 | 0 | 62.3 | 0 | 0 | 0 |
| 9134-9521_2 | 0 | 0 | 0 | 1.9 | 1.2 | 0 | 2 | 0 | 0 | 50.6 |
| 9134-9521_1 | 0 | 0 | 0 | 0 | 1.2 | 0 | 78.9 | 0 | 0 | 0 |
| 9279-9518_2 | 0 | 0 | 0 | 0 | 25.8 | 0 | 57.9 | 0 | 0 | 0 |
| 9286-9402_1 | 0 | 0 | 0 | 0 | 0 | 0 | 89 | 0 | 0 | 0 |
| 9286-9402_2 | 0 | 0 | 0 | 2.1 | 2.7 | 0 | 2.7 | 0 | 0 | 30.7 |
| 9814-9828_1 | 0 | 0 | 0 | 0 | 0 | 0 | 62.3 | 4 | 0 | 0 |
| 9814-9828_2 | 0 | 3.2 | 0 | 0 | 33.3 | 0 | 0 | 0 | 44.7 | 10.8 |
| 9815-9825_1 | 0 | 0 | 0 | 0 | 52 | 0 | 1.2 | 0 | 5.8 | 6.6 |
| 9815-9825_2 | 0 | 0 | 0 | 0 | 67.9 | 0 | 15.4 | 0 | 1.9 | 2.2 |
| 9748-9338_1 | 0 | 0 | 0 | 0 | 11.9 | 1.3 | 61.5 | 0 | 0 | 0 |
| 9748-9338_2 | 0 | 0 | 0 | 0 | 81.4 | 0 | 10.4 | 0 | 4.4 | 0 |
| 9667-9830_1 | 0 | 0 | 0 | 0 | 0 | 1.6 | 51.8 | 0 | 0 | 0 |
| 9667-9830_2 | 0 | 1.1 | 0 | 0 | 42.9 | 0 | 0 | 0 | 22.3 | 14.2 |
| 9692-9846_1 | 0 | 0 | 0 | 0 | 0 | 5.8 | 38.4 | 11 | 0 | 0 |
| 9692-9846_2 | 0 | 2.3 | 0 | 0 | 50.5 | 0 | 0 | 0 | 27.5 | 7.3 |
| 9696-9848_1 | 0 | 0 | 0 | 0 | 0 | 6.7 | 40.1 | 3.8 | 0 | 0 |
| 9696-9848_2 | 0 | 1.1 | 0 | 0 | 35.6 | 0 | 0 | 0 | 22 | 15 |
| 9986-9978_1 | 0 | 0 | 0 | 0 | 0 | 6.4 | 39.9 | 6.8 | 0 | 0 |
| 9986-9978_2 | 0 | 4.4 | 0 | 0 | 55.3 | 0 | 0 | 0 | 33.7 | 3.4 |
| 9611-9077_1 | 0 | 0 | 0 | 0 | 0 | 0 | 82.7 | 0 | 0 | 0 |

TABLE 29c-continued

LC-MS pairing data and post pA yields (mg/L) for the heterodimeric antibodies from the trastuzumab (H1L1)/cetuximab (H2L2) bispecific system

| | | | | | | | | | | |
|---|---|---|---|---|---|---|---|---|---|---|
| 9611-9077_2 | 0 | 0 | 0 | 2.2 | 4.7 | 0 | 1.2 | 0 | 3.6 | 33.5 |
| 9060-9756_2 | 0 | 0 | 0 | 0 | 0 | 0 | 10.6 | 0 | 0 | 4.6 |
| 9060-9756_1 | 0 | 0 | 0 | 0 | 2.6 | 0 | 17.7 | 0 | 0 | 0 |
| 9587-9735_1 | 0 | 0 | 0 | 0 | 1.9 | 3.2 | 48.6 | 2 | 0 | 0 |
| 9587-9735_2 | 0 | 3.5 | 1.1 | 0 | 38.4 | 0 | 0 | 0 | 36 | 11.1 |
| 9682-9740_1 | 0 | 0 | 0 | 0 | 0 | 0 | 53.8 | 0 | 0 | 0 |
| 9682-9740_2 | 0 | 1.6 | 1.5 | 0 | 31.4 | 0 | 0 | 0 | 26.1 | 20.2 |
| 9049-9759_1 | 0 | 0 | 0 | 0 | 0 | 0 | 13.5 | 0 | 0 | 2.3 |
| 9049-9759_2 | 0 | 0 | 0 | 0 | 42 | 0 | 38.4 | 0 | 0 | 0 |
| 9066-9335_2 | 0 | 0 | 3.1 | 1.7 | 0 | 0 | 2.3 | 0 | 0 | 30.4 |
| 9066-9335_1 | 0 | 0 | 0 | 0 | 30.3 | 0 | 55.4 | 0 | 0 | 0 |
| 3522_1 | 0 | 0 | 0 | 0 | 0 | 0 | 16.1 | 0 | 0 | 2.4 |
| 3522_2 | 0 | 0 | 0 | 0 | 43 | 1.3 | 43.9 | 0 | 1.1 | 0 |
| 3519_1 | 0 | 0 | 0 | 0 | 2.4 | 1 | 31.9 | 0 | 0 | 2.6 |
| 3519_2 | 0 | 1.9 | 0 | 0 | 64.3 | 0 | 0 | 0 | 30.8 | 1.2 |
| 9820-9823_2 | 0 | 0 | 0 | 0 | 0 | 0 | 9.9 | 0 | 0 | 5.6 |
| 9820-9823_1 | 0 | 0 | 0 | 0 | 33.8 | 0 | 27.2 | 0 | 0 | 0 |

*% considering full Ab species only
**% considering all species
***estimated change with respect to wild type

TABLE 30a

LC-MS pairing of the heterodimeric antibodies from the D3H44 (H1L1)/cetuximab (H2L2) bispecific system following preparative SEC

| SMCA unique identifier | Cluster | Post pA yield (mg/L A280) | % H1L1 Pairing (over all H1 species) | % H2L2 Pairing (over all H2 species) | % H1L1 and % H2L2 Pairing (over all species) | H1 + H2 + L1 + L2* | Change in % of H1:H2:L1:L2 with respect to wild type* | H1 + H2 + L1 + L2** | H1 + H1 + L1 + L1** | H1 + H1 + L1 + L2** | H1 + H1 + L2 + L2** |
|---|---|---|---|---|---|---|---|---|---|---|---|
| 9611-9077_1 | 9 | 32 | 100 | 100 | 100 | 100 | 43.3 | 80.4 | 0 | 0 | 0 |
| 9168-9342_1 | 4 | 18 | 100 | 100 | 100 | 100 | 42.1*** | 78.5 | 0 | 0 | 0 |
| 3519_1 | 6 | 45 | 100 | 100 | 100 | 100 | 42.1*** | 90 | 0 | 0 | 0 |
| 3522_1 | 9 | 38 | 100 | 100 | 100 | 96.7 | 38.8*** | 94.2 | 3.3 | 0 | 0 |

| SMCA unique identifier | H2 + H2 + L1 + L1** | H2 + H2 + L1 + L2** | H2 + H2 + L2 + L2** | H1 + H2 + L1 + L1** | H1 + H2 + L2 + L2** | H1 + L1** | H1 + L2** | H2 + L1** | H2 + L2** |
|---|---|---|---|---|---|---|---|---|---|
| 9611-9077_1 | 0 | 0 | 0 | 0 | 0 | 0 | 0 | 0 | 19.6 |
| 9168-9342_1 | 0 | 0 | 0 | 0 | 0 | 2.9 | 0 | 0 | 18.6 |
| 3519_1 | 0 | 0 | 0 | 0 | 0 | 5 | 0 | 0 | 5.1 |
| 3522_1 | 0 | 0 | 0 | 0 | 0 | 2.5 | 0 | 0 | 0 |

*% considering full Ab species only
**% considering all species
***estimated change in % of H1:H2:L1:L2 with respect to wild type TABLE 30b LC-MS pairing of the heterodimeric antibodies from the
D3H44 (H1L1)/trastuzumab (H2L2) bispecific system following preparative SEC

| SMCA unique identifier | Cluster | Post pA yield (mg/L A280) | % H1L1 Pairing (over all H1 species) | % H2L2 Pairing (over all H2 species) | % H1L1 and % H2L2 Pairing (over all species) | H1 + H2 + L1 + L2* | Change in % of H1:H2:L1:L2 with respect to wild type* | H1 + H2 + L1 + L2** | H1 + H1 + L1 + L1** | H1 + H1 + L1 + L2** | H1 + H1 + L2 + L2** |
|---|---|---|---|---|---|---|---|---|---|---|---|
| 3522_1 | 9 | 61 | 100 | 97 | 98.7 | 94.9 | 65.5 | 83.1 | 1.9 | 0 | 0 |
| 3519_1 | 6 | 53 | 100 | 97.5 | 98.3 | 95.7 | 66.3 | 79.8 | 0 | 0 | 0 |
| 9748-9338_1 | 3 | 10 | 95.6 | 96.1 | 96 | 91.3 | 55 | 85.3 | 0 | 0 | 0 |

| SMCA unique identifier | H2 + H2 + L1 + L1** | H2 + H2 + L1 + L2** | H2 + H2 + L2 + L2** | H1 + H2 + L1 + L1** | H1 + H2 + L2 + L2** | H1 + L1** | H1 + L2** | H2 + L1** | H2 + L2** |
|---|---|---|---|---|---|---|---|---|---|
| 3522_1 | 0 | 0 | 0 | 2.6 | 0 | 12.4 | 0 | 0 | 0 |
| 3519_1 | 0 | 0 | 2.2 | 1.4 | 0 | 1.3 | 0 | 1.1 | 14.3 |
| 9748-9338_1 | 0 | 1.1 | 0 | 2.7 | 4.3 | 4.8 | 0 | 0 | 1.9 |

*% considering full Ab species only
**% considering all species
***estimated change in % of H1:H2:L1:L2 with respect to wild type TABLE 30c LC-MS pairing of the heterodimeric antibodies from the
trastuzumab (H1L1)/cetuximab (H2L2) bispecific system following preparative SEC

| SMCA unique identifier | Cluster | Post pA yield (mg/L A280) | % H1L1 Pairing (over all H1 species) | Change in % H1L1 Pairing (over all H1 species) with respect to wild type | % H2L2 Pairing (over all H2 species) | Change in % H2L2 Pairing (over all H2 species) with respect to wild type | % H1L1 and % H2L2 Pairing (over all species) | H1 + H2 + L1 + L2* | Change in % of H1:H2:L1:L2 with respect to wild type* | H1 + H2 + L1 + L2** | H1 + H1 + L1 + L1** | H1 + H1 + L1 + L2** |
|---|---|---|---|---|---|---|---|---|---|---|---|---|
| 3522_1 | 9 | 37 | 100 | 6.8 | 100 | 39.2 | 100 | 100 | 44.5 | 95.7 | 0 | 0 |
| 3519_1 | 6 | 25 | 100 | 2.7*** | 96.1 | 71.0*** | 98.3 | 93.7 | 67.3*** | 87.1 | 2.2 | 0 |

| SMCA unique identifier | H1 + H1 + L2 + L2** | H2 + H2 + L1 + L1** | H2 + H2 + L1 + L2** | H2 + H2 + L2 + L2** | H1 + H2 + L1 + L1** | H1 + H2 + L2 + L2** | H1 + L1** | H1 + L2** | H2 + L1** | H2 + L2** |
|---|---|---|---|---|---|---|---|---|---|---|
| 3522_1 | 0 | 0 | 0 | 0 | 0 | 0 | 2.5 | 0 | 0 | 1.9 |
| 3519_1 | 0 | 0 | 0 | 0 | 3.7 | 0 | 2.9 | 0 | 0 | 4.2 |

*% considering full Ab species only
**% considering all species
***estimated change with respect to wild type TABLE 31a Biophysical characterization (antigen binding, thermal stability,
UPLC-SEC) of selected designs from the D3H44/trastuzumab system

| SMCA unique identifier | Cluster | KD (TF) (M)* KD from mAb construct = 1.02E−11 | KD (HER2) (M)* KD from WT one armed antibody = 1.12E−09 | DSC (° C.) with Fab Tms reported. D3H44 Fab Tm from homodimeric antibody = 79° C. Trastuzumab Fab Tm from homodimeric antibody = 81° C. | UPLC-SEC (% heterodimer) |
|---|---|---|---|---|---|
| NA | WT | Low Response/no binding | Low Response/no binding | 81, 81 | 99.69 |
| NA | WT | Low Response/no binding | 8.88E−10 | 79, 81 | 99.91 |
| NA | WT | Low Response/no binding | Low Response/no binding | 79, 81 | 100 |
| 9279-9518_1 | 2 | 2.20E−11 | 1.54E−09 | 70, 76 | 99.95 |
| 9815-9825_1 | 3 | 3.97E−11 | 6.98E−10 | 70, 76 | 93.1 |
| 9748-9338_1 | 3 | 2.78E−11 | 4.80E−10 | 71, 77 | 100 |
| 9060-9756_1 | 7 | 1.72E−11 (1.73-1.73E−11) | 9.39E−10 (1.04-0.83E−09) | 72, 79 | 99.6 |
| 9682-9740_1 | 11 | 8.50E−12 | Low Response/no binding | 72, 79 | 99.4 |
| 9049-9759_1 | 11 | 7.22E−12 | Low Response/no binding | 72, 79 | 100 |
| 3522_1 | 9 | 8.42E−12 | Low Response/no binding | 79 | 99.88 |
| 3519_1 | 6 | 1.61E−11 | 1.66E−09 | 72, 81 | 98.98 |
| 9820-9823_1 | 8 | 4.65E−11 (5.25-4.07E−11) | 7.16E−10 (7.58-6.74E−10) | 71, 76 | 99.68 |

*KD values reported are either a single measurement or the average of 2 measurements. The range is indicated in parentheses.

TABLE 31b

Biophysical characterization (antigen binding, thermal stability, UPLC-SEC) of selected designs from the D3H44/cetuximab system

| SMCA unique identifier | Cluster | KD (TF) (M)* KD from WT mAb construct = 1.02E−11 | KD (EGFR) (M)* KD from WT one armed antibody = 4.94E−10 | DSC(° C.). D3H44 Fab Tm from homodimeric antibody = 79° C. Cetuximab Fab Tm from one armed antibody = 72° C. | UPLC-SEC (% heterodimer) |
|---|---|---|---|---|---|
| NA | WT | 3.62E−11 | 3.94E−10 | 72, 79 | 100 |
| NA | WT | 7.93E−12 | 5.39E−10 | 71, 80 | 100 |
| NA | WT | 1.40E−11 | 3.96E−10 | 71, 79 | 100 |
| NA | WT | 6.33E−12 | 4.00E−10 | 71, 79 | 100 |
| 9561-9095_2 | 10 | 1.07E−11 | 4.57E−10 | 71, 77 | 99.86 |
| 9168-9342_1 | 4 | 1.27E−11 | 2.05E−10 | 70, 78 | 93.7 |
| 9118-6098_1 | 4 | 1.76E−11 | 4.90E−10 | 70, 78 | 100 |
| 9121-9373_1 | 3 | 1.14E−11 | 4.35E−10 | 71, 78 | 99.6 |
| 9121-9373_2 | 3 | 9.09E−12 | 3.18E−10 | 69, 78 | 100 |
| 9279-9518_2 | 2 | 1.06E−11 | 3.14E−10 | 70, 78 | 96 |
| 9286-9402_1 | 2 | 8.26E−12 (7.9-8.63E−12) | 4.18E−10 (4.28-4.09E−10) | 71, 78 | 100 |
| 9815-9825_1 | 3 | 1.84E−11 | 5.09E−10 | 69, 78 | 100 |
| 9815-9825_2 | 3 | 1.01E−11 | 3.70E−10 | 68, 75 | 100 |
| 9667-9830_1 | 11 | 1.31E−11 (1.75-0.8E−11) | 2.55e−10 (3.24-1.88E−10) | 70, 78 | 99.86 |
| 9667-9830_2 | 11 | 1.35E−11 | 4.55E−10 | 71, 78 | 99.54 |
| 9611-9077_1 | 9 | 1.71E−11 | 4.55E−10 | 71, 78 | 87.16 |
| 9060-9756_2 | 7 | 1.17E−11 | 6.43E−10 | 72, 78 | 100 |
| 9682-9740_1 | 11 | 1.22E−11 | 2.16E−10 | 70, 78 | 92 |
| 9682-9740_2 | 11 | 9.99E−12 | 6.23E−10 | 72, 78 | 99.9 |
| 9049-9759_1 | 11 | 9.33E−12 | 6.23E−10 | 70, 79 | 100 |
| 9066-9335_1 | 3 | 4.04E−12 | 4.46E−10 | 72, 79 | 100 |
| 9066-9335_2 | 3 | 8.41E−12 | 3.10E−10 | 70, 78 | 100 |
| 3522_1 | 9 | 7.75E−12 | 2.69E−10 | 70, 78 | 99.1 |
| 3519_1 | 6 | 1.15E−11 | 2.63E−10 | 71, 78 | 99.76 |
| 9820-9823_2 | 8 | 1.40E−11 | 2.49E−10 | 69, 76 | 100 |
| 9820-9823_1 | 8 | 1.33E−11 (1.34-1.33E−11) | 2.65E−10 (2.47-2.84E−10) | 70, 78 | 99.77 |

*KD values reported are either a single measurement or the average of 2 measurements. The range is indicated in parentheses.

TABLE 31c

Biophysical characterization (antigen binding, thermal stability, UPLC-SEC) of selected designs from the trastuzumab/cetuximab system

| SMCA unique identifier | Cluster | KD (HER2) (M)* KD from WT one armed antibody = 1.12E−09 | KD (EGFR) (M)* KD from one armed antibody = 4.94E−10 | DSC (° C.). Tm values refer to Fab transitions unless otherwise indicated. Tm values qualified with a (?) indicate a new peak not observed in WT. Cetuximab Fab Tm from one armed antibody = 72° C. Trastuzumab Fab Tm from homodimeric antibody = 81° C. | UPLC-SEC (% heterodimer) |
|---|---|---|---|---|---|
| NA | WT | Low Response/no binding | 4.79E−10 | 71, 81 | 100 |
| NA | WT | 2.36E−10 | 1.87E−10 | 71, 81 | 100 |
| NA | WT | 2.04E−10 | 2.03E−10 | 71, 81 | 100 |
| 9286-9402_2 | 2 | Low Response/no binding | 5.93E−10 | 71, 80 | 92.8 |
| 9327-6054_1 | 3 | 8.18E−10 (8.18E−10-ND) | 5.4E−10 (5.24-5.59E−10) | ND** | 100 |
| 3519_1 | 6 | 9.78E−10 | 4.07E−10 | 71, 78 | 99.1 |
| 9060-9756_2 | 7 | Low Response/no binding | 6.25E−10 | 71, 81 | 100 |
| 9820-9823_2 | 8 | 7.52E−10 | 5.09E−10 | 70, 78 | 100 |
| 9611-9077_2 | 9 | Low Response/no binding | 4.71E−10 | 60(?), 71, 81 | 97.07 |
| 3522_1 | 9 | Low Response/no binding | 3.95E−10 | 71, 78 | 98.97 |
| 9561-9095_2 | 10 | Low Response/no binding | 4.17E−10 | 71, 81 | 99.39 |
| 9682-9740_1 | 11 | Low Response/no binding | 4.72E−10 | 72, 81 | 96.2 |
| 9049-9759_1 | 11 | Low Response/no binding | 4.77E−10 | 72, 79 | 100 |
| 9696-9848_1 | 12 | Low Response/no binding | 4.49E−10 | 71, 81 | 99.3 |

*KD values reported are either a single measurement or the average of 2 measurements. The range is indicated in parentheses.
**ND—Not Determined TABLE 32a Effect of DNA titration ratio on the percentage of antibody species, as assessed by LC-MS, of the wild-type D3H44/trastuzumab system. H1 and L1 refer to D3H44 heavy and light chains, respectively. H2 and L2 refer to trastuzurnab heavy and light chains, respectively.

| H1:H2:L1:L2 DNA ratio | H1 + H2 + L1 + L2 (%) | H1 + L1 (%) | H1 + L1 + L2 (%) | H1 + L2 (%) | H2 + L1 (%) | H2 + L2 (%) | H2 + L1 + L2 (%) | H1 + H2 + L1 (%) | H1 + H2 + L2 (%) | H1 + L1 (%) | H1 + L2 (%) | H2 + L1 (%) | H2 + L2 (%) | Half Ab (sum %) |
|---|---|---|---|---|---|---|---|---|---|---|---|---|---|---|
| 15:15:53:17 | 22.8 | 0.0 | 0.0 | 0.0 | 0.0 | 0.0 | 0.0 | 1.6 | 59.5 | 1.9 | 8.8 | 1.7 | 3.8 | 16.2 |
| 8:22:53:17 | 16.4 | 0.0 | 0.0 | 0.0 | 0.0 | 0.0 | 2.9 | 0.0 | 45.7 | 0.0 | 1.3 | 10.4 | 23.3 | 35.0 |
| 22:8:53:17 | 13.3 | 0.0 | 0.0 | 3.2 | 0.0 | 0.0 | 0.0 | 1.5 | 28.4 | 5.9 | 46.5 | 0.0 | 1.2 | 53.6 |
| 15:15:35:35 | 8.9 | 0.0 | 0.0 | 0.0 | 0.0 | 0.0 | 1.5 | 0.0 | 74.0 | 0.0 | 11.6 | 0.0 | 4.0 | 15.6 |
| 8:22:35:35 | 6.1 | 0.0 | 0.0 | 0.0 | 0.0 | 0.0 | 3.1 | 0.0 | 51.4 | 0.0 | 2.2 | 5.5 | 31.8 | 39.5 |
| 22:8:35:35 | 5.6 | 0.0 | 0.0 | 4.8 | 0.0 | 0.0 | 0.0 | 0.0 | 48.9 | 1.3 | 39.4 | 0.0 | 0.0 | 40.7 |
| 15:15:17:53 | 4.1 | 0.0 | 0.0 | 0.0 | 0.0 | 0.0 | 0.0 | 0.0 | 82.8 | 0.0 | 9.2 | 0.0 | 3.9 | 13.1 |
| 8:22:17:53 | 2.8 | 0.0 | 0.0 | 0.0 | 0.0 | 0.0 | 4.6 | 0.0 | 54.3 | 0.0 | 2.4 | 2.4 | 33.5 | 38.3 |
| 22:8:17:53 | 2.7 | 0.0 | 0.0 | 4.2 | 0.0 | 0.0 | 0.0 | 0.0 | 51.0 | 0.0 | 42.2 | 0.0 | 0.0 | 42.2 |

| H1:H2:L1:L2 DNA ratio | H1 + H2 + L1 + L2 (%) | H1 + L1 (%) | H1 + L1 + L2 (%) | H1 + L2 (%) | H2 + L1 (%) | H2 + L2 (%) | H2 + L1 + L2 (%) | H1 + H2 + L1 (%) | H1 + H2 + L2 (%) | H1 + L1 (%) | H1 + L2 (%) | H2 + L1 (%) | H2 + L2 (%) | Half Ab (sum %) |
|---|---|---|---|---|---|---|---|---|---|---|---|---|---|---|
| 15:15:53:17 | 22.8 | 0.0 | 0.0 | 0.0 | 0.0 | 0.0 | 0.0 | 1.6 | 59.5 | 1.9 | 8.8 | 1.7 | 3.8 | 16.2 |
| 8:22:53:17 | 16.4 | 0.0 | 0.0 | 0.0 | 0.0 | 0.0 | 2.9 | 0.0 | 45.7 | 0.0 | 1.3 | 10.4 | 23.3 | 35.0 |
| 22:8:53:17 | 13.3 | 0.0 | 0.0 | 3.2 | 0.0 | 0.0 | 0.0 | 1.5 | 28.4 | 5.9 | 46.5 | 0.0 | 1.2 | 53.6 |
| 15:15:35:35 | 8.9 | 0.0 | 0.0 | 0.0 | 0.0 | 0.0 | 1.5 | 0.0 | 74.0 | 0.0 | 11.6 | 0.0 | 4.0 | 15.6 |
| 8:22:35:35 | 6.1 | 0.0 | 0.0 | 0.0 | 0.0 | 0.0 | 3.1 | 0.0 | 51.4 | 0.0 | 2.2 | 5.5 | 31.8 | 39.5 |
| 22:8:35:35 | 5.6 | 0.0 | 0.0 | 4.8 | 0.0 | 0.0 | 0.0 | 0.0 | 48.9 | 1.3 | 39.4 | 0.0 | 0.0 | 40.7 |
| 15:15:17:53 | 4.1 | 0.0 | 0.0 | 0.0 | 0.0 | 0.0 | 0.0 | 0.0 | 82.8 | 0.0 | 9.2 | 0.0 | 3.9 | 13.1 |
| 8:22:17:53 | 2.8 | 0.0 | 0.0 | 0.0 | 0.0 | 0.0 | 4.6 | 0.0 | 54.3 | 0.0 | 2.4 | 2.4 | 33.5 | 38.3 |
| 22:8:17:53 | 2.7 | 0.0 | 0.0 | 4.2 | 0.0 | 0.0 | 0.0 | 0.0 | 51.0 | 0.0 | 42.2 | 0.0 | 0.0 | 42.2 |

TABLE 32b

Effect of DNA titration ratio on the percentage of antibody species, as assessed by LC-MS, of the wild-type D3H44/cetuximab system. H1 and L1 refer to D3H44 heavy and light chains, respectively. H2 and L2 refer to cetuximab heavy and light chains, respectively.

| H1:H2:L1:L2 DNA ratio | H1+H2+L1+L2 (%) | H1+L1 (%) | H1+L1+L2 (%) | H1+L1+L2+L2 (%) | H2+L1 (%) | H2+L1+L2 (%) | H2+L2 (%) | H1+H2+L1 (%) | H1+H2+L2 (%) | H1+L1 (%) | H1+L2 (%) | H2+L1 (%) | H2+L2 (%) | Half Ab (sum %) |
|---|---|---|---|---|---|---|---|---|---|---|---|---|---|---|
| 15:15:53:17 | 45.6 | 0.0 | 0.0 | 0.0 | 0.0 | 0.0 | 0.0 | 0.0 | 39.2 | 4.5 | 6.7 | 0.0 | 4.1 | 15.3 |
| 8:22:53:17 | 37.9 | 0.0 | 0.0 | 0.0 | 0.0 | 0.0 | 0.0 | 0.0 | 30.6 | 0.0 | 0.0 | 1.6 | 29.9 | 31.5 |
| 15:15:35:35 | 23.5 | 0.0 | 0.0 | 0.0 | 0.0 | 0.0 | 0.0 | 0.0 | 54.1 | 4.5 | 14.9 | 0.0 | 2.9 | 22.3 |
| 8:22:35:35 | 19.9 | 0.0 | 0.0 | 0.0 | 0.0 | 0.0 | 0.0 | 0.0 | 43.9 | 0.0 | 0.0 | 0.0 | 36.2 | 36.2 |
| 8:22:17:53 | 15.6 | 0.0 | 0.0 | 0.0 | 0.0 | 0.0 | 0.0 | 0.0 | 54.0 | 0.0 | 1.4 | 0.0 | 29.0 | 30.4 |
| 22:8:53:17 | 15.5 | 3.6 | 5.2 | 3.2 | 0.0 | 0.0 | 0.0 | 0.0 | 19.5 | 23.7 | 29.3 | 0.0 | 0.0 | 53.0 |
| 22:8:35:35 | 13.4 | 1.3 | 4.3 | 5.3 | 0.0 | 0.0 | 0.0 | 0.0 | 31.4 | 1.7 | 42.6 | 0.0 | 0.0 | 44.3 |
| 15:15:17:53 | 10.2 | 0.0 | 0.0 | 2.1 | 0.0 | 0.0 | 0.0 | 0.0 | 39.5 | 5.1 | 30.1 | 0.0 | 13.0 | 48.2 |
| 22:8:17:53 | 7.2 | 0.0 | 2.3 | 5.4 | 0.0 | 0.0 | 0.0 | 0.0 | 30.4 | 10.3 | 44.5 | 0.0 | 0.0 | 54.8 |

TABLE 32c

Effect of DNA titration ratio on the percentage of antibody species, as assessed by LC-MS, of the wild-type trastuzumab/cetuximab system. H1 and L1 refer to trastuzumab heavy and light chains, respectively. H2 and L2 refer to cetuximab heavy and light chains, respectively.

| H1:H2:L1:L2 DNA ratio | H1+H2+L1+L2 (%) | H1+L1 (%) | H1+L1+L2 (%) | H1+L1+L2+L2 (%) | H2+L1 (%) | H2+L1+L2 (%) | H2+L2 (%) | H1+H2+L1 (%) | H1+H2+L2 (%) | H1+L1 (%) | H1+L2 (%) | H2+L1 (%) | H2+L2 (%) | Half Ab (sum %) |
|---|---|---|---|---|---|---|---|---|---|---|---|---|---|---|
| 15:15:17:53 | 42.1 | 0.0 | 0.0 | 0.0 | 0.0 | 0.0 | 0.0 | 35.2 | 3.9 | 9.8 | 1.3 | 4.3 | 3.4 | 18.8 |
| 15:15:35:35 | 28.2 | 0.0 | 0.0 | 0.0 | 0.0 | 0.0 | 0.0 | 58.1 | 0.0 | 6.6 | 0.0 | 5.2 | 1.9 | 13.7 |
| 8:22:17:53 | 24.7 | 0.0 | 0.0 | 0.0 | 0.0 | 0.0 | 0.0 | 28.2 | 1.9 | 0.0 | 0.0 | 22.3 | 23.0 | 45.3 |
| 22:8:17:53 | 20.5 | 5.3 | 0.0 | 0.0 | 0.0 | 0.0 | 0.0 | 13.7 | 3.2 | 49.1 | 8.2 | 0.0 | 0.0 | 57.3 |
| 15:15:53:17 | 19.7 | 0.0 | 0.0 | 0.0 | 0.0 | 0.0 | 0.0 | 63.8 | 0.0 | 8.7 | 0.0 | 6.5 | 1.4 | 16.6 |
| 8:22:35:35 | 15.2 | 0.0 | 0.0 | 0.0 | 1.5 | 0.0 | 0.0 | 37.7 | 0.0 | 0.0 | 0.0 | 31.1 | 14.5 | 45.6 |
| 22:8:35:35 | 14.4 | 8.3 | 0.0 | 0.0 | 0.0 | 0.0 | 0.0 | 28.1 | 0.0 | 47.7 | 1.4 | 0.0 | 0.0 | 49.1 |
| 22:8:53:17 | 10.3 | 9.7 | 0.0 | 0.0 | 0.0 | 0.0 | 0.0 | 30.7 | 0.0 | 49.3 | 0.0 | 0.0 | 0.0 | 49.3 |
| 8:22:53:17 | 10.3 | 0.0 | 0.0 | 0.0 | 2.2 | 0.0 | 0.0 | 39.1 | 0.0 | 0.0 | 0.0 | 36.6 | 11.8 | 48.4 |

TABLE 33a

LC-MS pairing for the wild type antibody constructs from the D3H44 (H1L1)/cetuximab (H2L2) bispecific system

| Tag | Post pA yield (mg/L A280) | % H1L1 Pairing (over all H1 species) | % H2L2 Pairing (over all H2 species) | % H1L1 and % H2L2 Pairing (over all species) | H1+H2+L1+L2* | Change in % of H1:H2:L1:L2 with respect to median wild type* | H1+H2+L1+L2** | H1+H2+L1+L1** | H1+H2+L1+L2** | H1+H2+L2+L2** |
|---|---|---|---|---|---|---|---|---|---|---|
| HA on D3H44 LC | 20 | 65.5 | 98.4 | 80.4 | 63.6 | 4.5 | 51.2 | 0 | 0 | 0 |
| HA on D3H44 LC | 18 | 65 | 98.6 | 80.1 | 63.7 | 4.6 | 51.1 | 0 | 0 | 0 |
| HA on D3H44 LC | 20 | 58.5 | 100 | 76.4 | 58.6 | −0.5 | 45.9 | 0 | 0 | 0 |

TABLE 33a-continued

LC-MS pairing for the wild type antibody constructs from the D3H44 (H1L1)/cetuximab (H2L2) bispecific system

| | | | | | | | | | | |
|---|---|---|---|---|---|---|---|---|---|---|
| None | 24 | 56.4 | 98 | 75.3 | 54.7 | −5.3 | 43 | 0 | 0 | 0 |
| FLAG on D3H44 LC | 22 | 53.4 | 98.9 | 74.7 | 52.4 | −4.4 | 44 | 0 | 0 | 0 |
| None | 27 | 55.7 | 98 | 74.4 | 54.1 | −5.9 | 43.3 | 0 | 0 | 0 |
| FLAG on D3H44 LC | 26 | 51.2 | 100 | 74.2 | 50.6 | −6.1 | 41.7 | 0 | 0 | 0 |
| FLAG on D3H44 LC | 24 | 52.1 | 98.6 | 73.8 | 50.5 | −6.3 | 41.9 | 0 | 0 | 0 |
| None | 24 | 53.2 | 98 | 73.4 | 51.5 | −8.5 | 41.1 | 0 | 0 | 0 |
| HA on cetuximab LC | 24 | 45.6 | 100 | 70.1 | 46.1 | −0.1 | 36.9 | 0 | 0 | 0 |
| HA on cetuximab LC | 24 | 43.7 | 100 | 68.8 | 44.4 | −1.8 | 35.5 | 0 | 0 | 0 |
| HA on cetuximab LC | 27 | 41.2 | 100 | 67.6 | 40.7 | −5.5 | 32.6 | 0 | 0 | 0 |

| Tag | H2 + H2 + L1 + L1** | H2 + H2 + L1 + L2** | H2 + H2 + L2 + L2** | H1 + H2 + L1 + L1** | H1 + H2 + L2 + L2** | H1 + L1** | H1 + L2** | H2 + L1** | H2 + L2** |
|---|---|---|---|---|---|---|---|---|---|
| HA on D3H44 LC | 0 | 0 | 0 | 1.4 | 28 | 10.1 | 5 | 0 | 4.4 |
| HA on D3H44 LC | 0 | 0 | 0 | 1.2 | 27.9 | 9.3 | 5.3 | 0 | 5.1 |
| HA on D3H44 LC | 0 | 0 | 0 | 0 | 32.4 | 10.1 | 7.4 | 0 | 4.2 |
| None | 0 | 0 | 0 | 1.7 | 34 | 8.1 | 6.9 | 0 | 6.4 |
| FLAG on D3H44 LC | 0 | 0 | 0 | 1 | 38.9 | 5.8 | 5.4 | 0 | 4.9 |
| None | 0 | 0 | 0 | 1.7 | 34.9 | 8 | 7.2 | 0 | 4.8 |
| FLAG on D3H44 LC | 0 | 0 | 0 | 0 | 40.8 | 6.9 | 5.5 | 0 | 5.2 |
| FLAG on D3H44 LC | 0 | 0 | 0 | 1.2 | 40 | 6.4 | 5.6 | 0 | 4.9 |
| None | 0 | 0 | 0 | 1.7 | 37.1 | 7.5 | 7.2 | 0 | 5.4 |
| HA on cetuximab LC | 0 | 0 | 0 | 0 | 43.2 | 6.2 | 8.3 | 0 | 5.4 |
| HA on cetuximab LC | 0 | 0 | 0 | 0 | 44.5 | 6.1 | 9 | 0 | 4.9 |
| HA on cetuximab LC | 0 | 0 | 0 | 0 | 47.5 | 6.8 | 8.7 | 0 | 4.5 |

*% considering full Ab species only
**% considering all species

TABLE 33b

LC-MS pairing for the wild type antibody constructs from the D3H44 (H1L1)/trastuzumab (H2L2) bispecific system

| Tag | Post pA yield (mg/L A280) | % H1L1 Pairing (over all H1 species) | % H2L2 Pairing (over all H2 species) | % H1L1 and % H2L2 Pairing (over all species) | H1 + H2 + L1 + L2* | Change in % of H1:H2:L1:L2 with respect to median wild type* | H1 + H2 + L1 + L2** | H1 + H2 + L1 + L1** | H1 + H1 + L1 + L2** | H1 + H1 + L2 + L2** | H2 + H2 + L1 + L1** | H2 + H2 + L1 + L2** | H2 + H2 + L2 + L2** | H1 + H2 + L1 + L1** | H1 + H2 + L2 + L2** | H1 + L1** | H1 + L2** | H2 + L1** | H2 + L2** |
|---|---|---|---|---|---|---|---|---|---|---|---|---|---|---|---|---|---|---|---|
| FLAG on trastuzumab LC | 35 | 38.1 | 89.5 | 62.2 | 29 | −0.4 | 25 | 0 | 0 | 0 | 0 | 0 | 0 | 8.1 | 52.9 | 2.9 | 5.7 | 1.5 | 3.8 |
| FLAG on trastuzumab LC | 31 | 36.6 | 90.8 | 62.2 | 29.4 | 0 | 25.6 | 0 | 0 | 0 | 0 | 0 | 0 | 6.8 | 54.8 | 2.2 | 5.2 | 1.7 | 3.6 |
| FLAG on trastuzumab LC | 28 | 37.3 | 90.3 | 62 | 29.6 | 0.2 | 24.6 | 0 | 0 | 0 | 0 | 0 | 0 | 7 | 51.6 | 3.3 | 7.1 | 1.7 | 4.8 |
| FLAG on D3H44 LC | 36 | 37.3 | 94.1 | 64 | 33.2 | −3.1 | 29.3 | 0 | 0 | 0 | 0 | 0 | 0 | 4.3 | 54.6 | 2.1 | 5.4 | 1.2 | 3.1 |
| FLAG on D3H44 LC | 32 | 38.4 | 93.2 | 63.2 | 34.8 | −1.5 | 29 | 0 | 0 | 0 | 0 | 0 | 0 | 4.2 | 50.2 | 2.9 | 7.6 | 1.9 | 4.1 |
| FLAG on D3H44 LC | 31 | 38.1 | 94 | 64 | 34.7 | −1.6 | 30.3 | 0 | 0 | 0 | 0 | 0 | 0 | 4 | 53.1 | 2 | 5.9 | 1.5 | 3.2 |
| HA on trastuzumab LC; FLAG on D3H44 LC | 28 | 34.8 | 95 | 62.8 | 33.7 | 1.5 | 28.3 | 0 | 0 | 0 | 0 | 0 | 0 | 2.4 | 53.1 | 1.6 | 7.3 | 2.2 | 5.1 |
| HA on trastuzumab LC; FLAG on D3H44 LC | 33 | 31.9 | 94.7 | 60.9 | 30.6 | −1.6 | 25.7 | 0 | 0 | 0 | 0 | 0 | 0 | 2.3 | 55.8 | 1.7 | 7.6 | 2.5 | 4.4 |
| HA on trastuzumab LC; FLAG on D3H44 LC | 34 | 39.3 | 93.6 | 64.5 | 37 | 4.8 | 31.2 | 0 | 0 | 0 | 0 | 0 | 0 | 3.4 | 49.8 | 1.9 | 6.5 | 2.5 | 4.8 |

*% considering full Ab species only
**% considering all species

TABLE 33c

LC-MS pairing for the wild type antibody constructs from the trastuzumab (H1L1)/cetuximab (H2L2) bispecific system

| Tag | Post pA yield (mg/L A280) | % H1L1 Pairing (over all H1 species) | % H2L2 Pairing (over all H2 species) | % H1L1 and % H2L2 Pairing (over all species) | H1 + H2 + L1 + L2* | Change in % of H1:H2:L1:L2 with respect to median wild type* | H1 + H2 + L1 + L2** | H1 + H1 + L1 + L1** | H1 + H1 + L1 + L2** | H1 + H1 + L2 + L2** | H2 + H2 + L1 + L1** | H2 + H2 + L1 + L2** | H2 + H2 + L2 + L2** | H1 + H2 + L1 + L1** | H1 + H2 + L2 + L2** | H1 + L1** | H1 + L2** | H2 + L1** | H2 + L2** |
|---|---|---|---|---|---|---|---|---|---|---|---|---|---|---|---|---|---|---|---|
| FLAG on trastuzumab LC | 19 | 92.7 | 60.3 | 76.8 | 55.5 | 0 | 43.9 | 0 | 0 | 0 | 0 | 0 | 0 | 30.6 | 4.5 | 12 | 2.3 | 3.5 | 3.3 |
| FLAG on trastuzumab LC | 22 | 91.8 | 60.8 | 76.8 | 55.3 | −0.2 | 42.3 | 0 | 0 | 0 | 0 | 0 | 0 | 29.1 | 5.1 | 14.2 | 2.5 | 3.5 | 3.2 |
| FLAG on trastuzumab LC | 19 | 93.1 | 60.1 | 76.3 | 55.5 | 0 | 44.3 | 0 | 0 | 0 | 0 | 0 | 0 | 30.8 | 4.7 | 10.5 | 1.6 | 4.2 | 3.8 |
| FLAG on cetuximab LC | 19 | 92.2 | 29.6 | 61.3 | 25.8 | −0.6 | 20.8 | 0 | 0 | 0 | 0 | 0 | 0 | 56.6 | 3.2 | 8.8 | 4.1 | 4.8 | 1.8 |
| FLAG on cetuximab LC | 20 | 92.6 | 29.4 | 61 | 25.9 | −0.5 | 21.1 | 0 | 0 | 0 | 0 | 0 | 0 | 57.2 | 3.3 | 8 | 3.6 | 5.1 | 1.6 |
| FLAG on cetuximab LC | 15 | 94 | 24.6 | 60.9 | 23.9 | −2.5 | 19.4 | 0 | 0 | 0 | 0 | 0 | 0 | 60.4 | 1.6 | 10.5 | 4.2 | 3.9 | 0 |
| HA on cetuximab LC | 18 | 97.3 | 21.5 | 59.9 | 19.4 | −1.2 | 16.3 | 0 | 0 | 0 | 0 | 0 | 0 | 66.4 | 1.1 | 7.7 | 1.4 | 5 | 2.1 |
| HA on cetuximab LC | 22 | 97.3 | 22.5 | 59.8 | 20.2 | −0.4 | 16.9 | 0 | 0 | 0 | 0 | 0 | 0 | 65.4 | 1.2 | 7.1 | 1.3 | 5.7 | 2.5 |
| HA on cetuximab LC | 20 | 98.4 | 18.7 | 59.7 | 18 | −2.6 | 14.9 | 0 | 0 | 0 | 0 | 0 | 0 | 68.1 | 0 | 8.8 | 1.5 | 4.9 | 1.9 |

*% considering full Ab species only
**% considering all species

TABLE 34

Stabilizing mutations in Fab heterodimers

| Chain including the stabilizing mutation (H for heavy chain; L for light chain) | stabilizing mutation | dTm (° C., i.e. Tm of Fab with Stabilizing mutation-Tm of Fab lacking the stabilizing mutation) | H1L1 of LCCA Set # (including stabilizing mutation)** | H1 mutation (of Fab with stabilizing mutation) | L1 mutation (of Fab with stabilizing mutation)* | H1L1 of LCCA Set # (lacking stabilizing mutation)** | H1 (of Fab lacking stabilizing mutation)* | L1 (of Fab lacking stabilizing mutation)* |
|---|---|---|---|---|---|---|---|---|
| H | Q39R | 1.6 | 9824 | Q39R_H172R_S186R | Q38E_Q124E_Q160E_T180E | 9075 | H172R_S186R | Q38E_Q124E_Q160E_T180E |
| H | Q39R | 1.4 | 9822 | Q39R_D146G_Q179K | Q38E_Q124E_Q160E_T180E | 9065 | D146G_Q179K | Q38E_Q124E_Q160E_T180E |
| H | Q39R | 1.2 | 9828 | Q39R_S186R | Q38E_Q124E_Q160E_T180E | 9905 | S186R | Q38E_Q124E_Q160E_T180E |
| H | Q39R | 1.1 | 9821 | Q39R_D146G_H172R_Q179K | Q38E_Q124E_Q160E_T180E | 9064 | D146G_H172R_Q179K | Q38E_Q124E_Q160E_T180E |
| H | V190F | 1.0 | 9912 9913 9914 | S188L_V190F | WT | 9907 9909 9911 | S188L | WT |
| H | H172R | 2.1 | 9813 | Q39E_K145T_H172R_Q179E | Q38R_S131K | 9814 | Q39E_K145T_Q179E | Q38R_S131K |
| H | H172R | 2.0 | 9611 | L143E_K145T_H172R | Q124R_Q160K_T178R | 9590 9593 9594 9598 9602 9606 9609 9986 | L143E_K145T | Q124R_Q160K_T178R |
| H | H172R | 1.7 | 9824 | Q39R_H172R_S186R | Q38E_Q124E_Q160E_T180E | 9828 | Q39R_S186R | Q38E_Q124E_Q160E_T180E |
| H | H172R | 1.5 | NA | H172R | WT | 9045 9046 9047 9048 | WT | WT |
| H | H172R | 1.5 | 9111 | L124E_A125S_H172R_K228D | S121K_V133G_S176R | 9113 9114 | L124E_A125S_K228D | S121K_V133G_S176R |
| H | H172R | 1.3 | 9075 | H172R_S186R | Q38E_Q124E_Q160E_T180E | 9905 | S186R | Q38E_Q124E_Q160E_T180E |
| H | H172R | 1.3 | 10552 9752 | L45P_L143E_K145T_H172R | P44F_Q124R_Q160K_T178R | 10550 9751 | L45P_L143E_K145T | P44F_Q124R_Q160K_T178R |
| H | H172R | 1.3 | 9118 9119 | L124E_H172R | V133G_S176R | 9109 9110 | L124E | V133G_S176R |
| H | H172R | 1.3 | 9610 | L143E_K145T_H172R | Q124R | 9585 9587 9588 9589 | L143E_K145T | Q124R |
| H | H172R | 1.2 | NA | H172R | WT | 9045 9046 9047 9048 | WT | WT |
| H | H172R | 1.2 | 9074 | H172R_Q179K | Q124E_Q160E_T180E | 9759 9760 9761 9763 9766 9767 9769 9771 9772 9773 | Q179K | Q124E_Q160E_T180E |
| H | H172R | 1.2 | 9818 | Q39E_L143E_K145T_H172R | Q38R_Q124R_Q160K_T178R | 9817 | Q39E_L143E_K145T | Q38R_Q124R_Q160K_T178R |
| H | H172R | 1.1 | 9346 | L124R_A125R_H172R | V133G_S176D | 9342 | L124R_A125R | V133G_S176D |
| H | H172R | 1.1 | 9612 | L143E_K145T_H172R_Q179E | Q124R_T178R | 9663 9666 9667 9671 9675 9679 9682 9989 | L143E_K145T_Q179E | Q124R_T178R |
| H | H172R | 1.1 | 9819 | Q39E_L143E_K145T_H172R_Q179E | Q38R_Q124R_Q160K_T178R | 9820 | Q39E_L143E_K145T_Q179E | Q38R_Q124R_Q160K_T178R |
| H | H172R | 1.0 | 9117 | L124E_H172R | V133G_S176K | 9106 9107 9108 | L124E | V133G_S176K |
| H | H172R | 0.9 | 9064 | D146G_H172R_Q179K | Q38E_Q124E_Q160E_T180E | 9065 | D146G_Q179K | Q38E_Q124E_Q160E_T180E |
| H | H172R | 0.9 | 10551 9745 | L45P_K145T_H172R_Q179E | P44F_S131K | 10549 9746 | L45P_K145T_Q179E | P44F_S131K |
| H | H172R | 0.7 | 9753 | L45P_L143E_K145T_H172R_Q179E | P44F_Q124R_Q160K_T178R | 9754 | L45P_L143E_K145T_Q179E | P44F_Q124R_Q160K_T178R |
| H | H172R | 0.6 | 9821 | Q39R_D146G_H172R_Q179K | Q38E_Q124E_Q160E_T180E | 9822 | Q39R_D146G_Q179K | Q38E_Q124E_Q160E_T180E |
| H | H172R | 0.6 | 9826 | Q39R_L124R_H172R | Q38E_V133G_S176D | 9825 | Q39R_L124R | Q38E_V133G_S176D |
| H | H172R | 0.5 | 9816 | Q39E_L124E_H172R | Q38R_V133G_S176R | 9815 | Q39E_L124E | Q38R_V133G_S176R |
| H | H172R | 0.4 | 9749 9750 | L45P_L124E_H172R | P44F_V133G_S176R | 9747 9748 | L45P_L124E | P44F_V133G_S176R |
| H | Q179E | 0.8 | 9754 | L45P_L143E_K145T_Q179E | P44F_Q124R_Q160K_T178R | 10550 9751 | L45P_L143E_K145T | P44F_Q124R_Q160K_T178R |
| H | Q179E | 0.7 | 9820 | Q39E_L143E_K145T_Q179E | Q38R_Q124R_Q160K_T178R | 9817 | Q39E_L143E_K145T | Q38R_Q124R_Q160K_T178R |

TABLE 34-continued

Stabilizing mutations in Fab heterodimers

| Chain including the stabilizing mutation (H for heavy chain; L for light chain) | stabilizing mutation | dTm (° C., i.e. Tm of Fab with Stabilizing mutation- Tm of Fab lacking the stabilizing mutation) | H1L1 of LCCA Set # (including stabilizing mutation)** | H1 mutation (of Fab with stabilizing mutation) | L1 mutation (of Fab with stabilizing mutation)* | H1L1 of LCCA Set # (lacking stabilizing mutation)** | H1 (of Fab lacking stabilizing mutation)* | L1 (of Fab lacking stabilizing mutation)* |
|---|---|---|---|---|---|---|---|---|
| H | Q179E | 0.6 | 9819 | Q39E_L143E_K145T_H172R_Q179E | Q38R_Q124R_Q160K_T178R | 9818 | Q39E_L143E_K145T_H172R | Q38R_Q124R_Q160K_T178R |
| H | Q179E | 0.6 | 9651 9654 9988 | L143E_K145T_Q179E | Q124R_Q160K_T178R | 9590 9593 9594 9598 9602 9606 9609 9986 | L143E_K145T | Q124R_Q160K_T178R |
| H | Q179E | 0.5 | 9687 | L143E_K145T_Q179E_S188L | Q124R_Q160K_T178R | 9707 9708 9712 9716 9720 9721 9722 9723 9725 | L143E_K145T_S188L | Q124R_Q160K_T178R |
| H | Q179D | 0.6 | 9620 9623 | L143E_K145T_Q179D | Q124R_Q160K_T178R | 9590 9593 9594 9598 9602 9606 9609 9986 | L143E_K145T | Q124R_Q160K_T178R |
| H | Q179D | 0.5 | 9614 9617 | L143E_K145T_Q179D | Q124K_T178R | NA | L143E_K145T | Q124K_T178R |
| H | Q179D | 0.5 | 9632 9635 | L143E_K145T_Q179D | Q124R_T178R | 9987 | L143E_K145T | Q124R_T178R |
| H | S188L | 1.2 | 9688 9692 9696 9700 9702 | L143E_K145T_Q179E_S188L | Q124R_T178R | 9663 9666 9667 9671 9675 9679 9682 9989 | L143E_K145T_Q179E | Q124R_T178R |
| H | S188L | 1.0 | 9707 9708 9712 9716 9720 9721 9722 9723 9725 | L143E_K145T_S188L | Q124R_Q160K_T178R | 9590 9593 9594 9598 9602 9606 9609 9986 | L143E_K145T | Q124R_Q160K_T178R |
| H | S188L | 0.9 | 9687 | L143E_K145T_Q179E_S188L | Q124R_Q160K_T178R | 9651 9654 9988 | L143E_K145T_Q179E | Q124R_Q160K_T178R |
| H | S188L | 0.8 | 9703 9704 9705 9706 | L143E_K145T_S188L | Q124R | 9585 9587 9588 9589 | L143E_K145T | Q124R |
| H | S188L | 0.4 | 9644 | L143E_K145T_Q179D_S188L | Q124R_Q160K_T178R | 9620 9623 | L143E_K145T_Q179D | Q124R_Q160K_T178R |
| H | A125R | 0.6 | 9346 | L124R_A125R_H172R | V133G_S176D | 9369 9370 9371 | L124R_H172R | V133G_S176D |
| H | A125R | 0.4 | NA | A125R | WT | 9045 9046 9047 9048 | WT | WT |
| H | L143F | 0.4 | 9566 9567 | L124W_L143F | V133A | NA | L124W | V133A |
| L | Q124R | 0.9 | 9632 9635 | L143E_K145T_Q179D | Q124R_T178R | 9638 9641 | L143E_K145T_Q179D | T178R |
| L | Q124R | 0.8 | 9663 9666 9667 9671 9675 9679 9682 9989 | L143E_K145T_Q179E | Q124R_T178R | 9683 9684 | L143E_K145T_Q179E | T178R |
| L | Q160F | 0.6 | 9741 | L143R | Q124E_V133E_Q160F | 9735 9737 9740 | L143R | Q124E_V133E |
| L | S176L | 1.0 | 9055 9056 9057 | A139G_V190A | L135W_S176L | NA | A139G_V190A | L135W |
| L | S176L | 0.6 | 9885 9886 | S186R | Q124E_S176L_T180E | 9891 9893 9896 9898 9900 9901 | S186R | Q124E_T180E |
| L | S176L | 0.5 | 9847 9848 | S186K | Q124E_S176L_T180E | 9853 9855 9858 9860 9862 9863 | S186K | Q124E_T180E |
| L | S176L | 0.4 | 9781 9782 | Q179K | Q124E_S176L_T180E | 9787 9789 9792 9794 9796 9797 | Q179K | Q124E_T180E |
| L | Q124E | 0.5 | 9891 9893 9896 9898 9900 9901 | S186R | Q124E_T180E | NA | S186R | T180E |

TABLE 34-continued

Stabilizing mutations in Fab heterodimers

| Chain including the stabilizing mutation (H for heavy chain; L for light chain) | stabilizing mutation | dTm (° C., i.e. Tm of Fab with Stabilizing mutation-Tm of Fab lacking the stabilizing mutation) | H1L1 of LCCA Set # (including stabilizing mutation)** | H1 mutation (of Fab with stabilizing mutation) | L1 mutation (of Fab with stabilizing mutation)* | H1L1 of LCCA Set # (lacking stabilizing mutation)** | H1 (of Fab lacking stabilizing mutation)* | L1 (of Fab lacking stabilizing mutation)* |
|---|---|---|---|---|---|---|---|---|
| L | Q124E | 0.4 | 9869 9871 9874 9876 9878 9879 | S186R | Q124E_Q160E_T180E | NA | S186R | Q160E_T180E |
| L | T180E | 0.5 | 9785 9786 | Q179K | Q124E_T178E_T180E | 9783 9784 | Q179K | Q124E_T178E |

*WT refers to wild type
**NA refers to not applicable due to no corresponding LCCA set #.

TABLE 35a

Designs that exhibited transferability across all 3 bispecific systems (D3H44/cetuximab, D3H44/trastuzumab, and trastuzumab/cetuximab) in both orientations.

| Bispecific system | SMCA unique identifier | Cluster | Post pA yield (mg/LA280) | % H1L1 Pairing (over all H1 species) | Change in % H1L1 Pairing (over all H1 species) with respect to wild type | % H2L2 Pairing (over all H2 species) | Change in % H2L2 Pairing (over all H2 species) with respect to wild type | % H1L1 and % H2L2 Pairing (over all species) | H1 + H2 + L1 + L2* | Change in % of H1:H2:L1:L2 with respect to wild type | H1 + H2 + L1 + L2** | H1 + H1 + L1 + L1 ** |
|---|---|---|---|---|---|---|---|---|---|---|---|---|
| D3H44/cetuximab | 9561-9095_2 | 10 | 28 | 100.0 | 38.1 | 100.0 | 2.0 | 99.9 | 94.0 | 34.0 | 70.6 | 4.5 |
| D3H44/cetuximab | 9561-9095_1 | 10 | 41 | 98.5 | 40.4 | 100.0 | 1.7 | 99.2 | 79.4 | 22.7 | 34.6 | 7.4 |
| D3H44/trastuzumab | 9561-9095_1 | 10 | 41 | 47.7 | 7.1 | 100.0 | 7.0 | 73.6 | 47.9 | 11.6 | 44.4 | 0.0 |
| trastuzumab/cetuximab | 9561-9095_2 | 10 | 16 | 100.0 | 6.8 | 100.0 | 39.2 | 100.0 | 92.6 | 37.1 | 53.6 | 4.3 |
| trastuzumab/cetuximab | 9561-9095_1 | 10 | 52 | 100.0 | 2.7*** | 58.1 | 33.0** | 85.3 | 54.9 | 28.5*** | 40.8 | 4.0 |
| D3H44/cetuximab | 9121-9373_2 | 3 | 9 | 100.0 | 43.3*** | 100.0 | 1.6*** | 100.0 | 100.0 | 42.1*** | 82.7 | 0.0 |
| D3H44/cetuximab | 9121-9373_1 | 3 | 17 | 100.0 | 38.1 | 100.0 | 2.0 | 100.0 | 89.5 | 29.5 | 37.0 | 4.3 |
| D3H44/trastuzumab | 9121-9373_1 | 3 | 10 | 50.5 | 9.9 | 100.0 | 7.0 | 72.4 | 48.9 | 12.6 | 41.9 | 0.0 |
| trastuzumab/cetuximab | 9121-9373_2 | 3 | 8 | 100.0 | 2.7*** | 100.0 | 74.9*** | 100.0 | 76.5 | 50.1*** | 21.7 | 6.7 |
| trastuzumab/cetuximab | 9121-9373_1 | 3 | 2 | 100.0 | 6.0 | 44.0 | 14.4 | 76.2 | 42.1 | 15.7 | 34.6 | 0.0 |
| D3H44/cetuximab | 9116-9349_1 | 5 | 10 | 100.0 | 43.3*** | 100.0 | 1.6*** | 100.0 | 84.8 | 26.9*** | 22.2 | 4.0 |
| D3H44/cetuximab | 9116-9349_2 | 5 | 1 | 100.0 | 38.1 | 100.0 | 2.0 | 99.9 | 100.0 | 40.0 | 64.7 | 0.0 |
| D3H44/trastuzumab | 9116-9349_1 | 5 | 6 | 46.8 | 25.8*** | 100.0 | 4.7*** | 68.9 | 44.9 | 14.1*** | 34.4 | 0.0 |
| trastuzumab/cetuximab | 9116-9349_2 | 5 | 2 | 100.0 | 6.0 | 79.8 | 50.3 | 98.0 | 70.2 | 43.8 | 14.6 | 2.5 |
| trastuzumab/cetuximab | 9116-9349_1 | 5 | 1 | 100.0 | 2.7*** | 42.1 | 17.0*** | 89.4 | 40.5 | 14.1*** | 15.2 | 1.5 |
| D3H44/cetuximab | 9134-9521_2 | 1 | 15 | 100.0 | 38.1 | 100.0 | 2.0 | 100.0 | 44.8 | -15.3 | 15.7 | 19.3 |
| D3H44/cetuximab | 9134-9521_1 | 1 | 17 | 100.0 | 43.3*** | 100.0 | 1.6*** | 99.9 | 89.8 | 31.9*** | 36.3 | 0.0 |
| D3H44/trastuzumab | 9134-9521_1 | 1 | 26 | 100.0 | 62.7 | 100.0 | 9.2 | 100.0 | 79.1 | 49.7 | 25.3 | 0.0 |
| trastuzumab/cetuximab | 9134-9521_2 | 1 | 2 | 100.0 | 6.0 | 98.8 | 69.3 | 99.4 | 93.5 | 67.1 | 44.3 | 0.0 |
| trastuzumab/cetuximab | 9134-9521_1 | 1 | 35 | 100.0 | 2.7*** | 62.5 | 37.4*** | 99.3 | 9.7 | -16.7*** | 2.0 | 17.8 |

TABLE 35a-continued

Designs that exhibited transferability across all 3 bispecific systems
(D3H44/cetuximab, D3H44/trastuzumab, and trastuzumab/cetuximab) in both orientations.

| | | | | | | | | | | | | |
|---|---|---|---|---|---|---|---|---|---|---|---|---|
| D3H44/cetuximab | 9286-9402_2 | 2 | 12 | 100.0 | 43.3*** | 100.0 | 1.6*** | 100.0 | 89.9 | 32.0*** | 40.1 | 4.5 |
| D3H44/cetuximab | 9286-9402_1 | 2 | 16 | 100.0 | 38.1 | 98.4 | 0.0 | 99.1 | 98.2 | 38.2 | 89.3 | 0.0 |
| D3H44/trastuzumab | 9286-9402_1 | 2 | 16 | 92.0 | 51.4 | 100.0 | 7.0 | 98.3 | 83.1 | 46.8 | 37.9 | 0.0 |
| trastuzumab/cetuximab | 9286-9402_1 | 2 | 11 | 100.0 | 6.0 | 100.0 | 70.5 | 100.0 | 29.9 | 3.5 | 3.3 | 7.7 |
| trastuzumab/cetuximab | 9286-9402_2 | 2 | 8 | 100.0 | 6.8 | 97.3 | 36.5 | 98.7 | 92.8 | 37.3 | 61.8 | 0.0 |
| D3H44/cetuximab | 9667-9830_2 | 11 | 15 | 100.0 | 38.1 | 100.0 | 2.0 | 100.0 | 91.1 | 31.0 | 58.2 | 5.7 |
| D3H44/cetuximab | 9667-9830_1 | 11 | 35 | 100.0 | 43.3*** | 95.1 | -3.3*** | 96.8 | 98.1 | 40.2*** | 85.4 | 0.0 |
| D3H44/trastuzumab | 9667-9830_1 | 11 | 48 | 98.2 | 60.9 | 93.1 | 2.3 | 94.2 | 91.6 | 62.2 | 71.0 | 0.0 |
| trastuzumab/cetuximab | 9667-9830_1 | 11 | 20 | 98.5 | 5.3 | 100.0 | 39.2 | 99.1 | 87.0 | 31.5 | 41.9 | 4.6 |
| trastuzumab/cetuximab | 9667-9830_2 | 11 | 14 | 100.0 | 6.0 | 33.3 | 3.7 | 55.2 | 30.7 | 4.3 | 19.5 | 0.0 |
| D3H44/cetuximab | 9696-9848_1 | 12 | 43 | 100.0 | 52.5 | 98.8 | -1.2 | 99.4 | 98.7 | 52.5 | 90.4 | 0.0 |
| D3H44/cetuximab | 9696-9848_2 | 12 | 21 | 94.3 | 32.4 | 100.0 | 2.0 | 95.9 | 80.9 | 20.9 | 47.9 | 7.3 |
| trastuzumab/cetuximab | 9696-9848_1 | 12 | 40 | 88.3 | -4.9 | 100.0 | 39.2 | 91.8 | 76.4 | 20.9 | 42.8 | 4.6 |
| trastuzumab/cetuximab | 9696-9848_2 | 12 | 24 | 100.0 | 2.7 | 40.9 | 18.1 | 59.1 | 41.7 | 21.1 | 26.3 | 0.0 |
| D3H44/cetuximab | 9060-9756_2 | 7 | 29 | 100.0 | 38.1 | 100.0 | 2.0 | 100.0 | 96.2 | 36.2 | 77.6 | 3.1 |
| D3H44/cetuximab | 9060-9756_1 | 7 | 57 | 100.0 | 41.9 | 100.0 | 1.7 | 99.9 | 96.4 | 39.7 | 70.2 | 2.6 |
| D3H44/trastuzumab | 9060-9756_1 | 7 | 49 | 98.7 | 58.1 | 98.6 | 5.6 | 98.5 | 97.1 | 60.8 | 93.1 | 0.0 |
| trastuzumab/cetuximab | 9060-9756_2 | 7 | 15 | 100.0 | 6.8 | 100.0 | 39.2 | 99.9 | 100.0 | 44.5 | 84.7 | 0.0 |
| trastuzumab/cetuximab | 9060-9756_1 | 7 | 41 | 100.0 | 2.7*** | 96.7 | 71.6*** | 98.6 | 93.9 | 67.5*** | 77.2 | 2.4 |
| D3H44/cetuximab | 9682-9740_2 | 11 | 17 | 100.0 | 38.1 | 100.0 | 2.0 | 100.0 | 90.4 | 30.4 | 61.0 | 6.5 |
| D3H44/cetuximab | 9682-9740_1 | 11 | 34 | 100.0 | 43.3*** | 97.0 | -1.4*** | 98.5 | 96.2 | 38.3*** | 73.6 | 0.0 |
| D3H44/trastuzumab | 9682-9740_1 | 11 | 46 | 97.1 | 59.8 | 95.7 | 4.9 | 95.1 | 91.6 | 62.2 | 67.7 | 0.0 |
| trastuzumab/cetuximab | 9682-9740_1 | 11 | 31 | 100.0 | 6.8 | 100.0 | 39.2 | 100.0 | 79.1 | 23.6 | 36.5 | 9.7 |
| trastuzumab/cetuximab | 9682-9740_2 | 11 | 15 | 100.0 | 6.0 | 39.7 | 10.2 | 56.0 | 35.9 | 9.5 | 19.3 | 0.0 |
| D3H44/cetuximab | 9049-9759_1 | 11 | 51 | 100.0 | 52.5 | 100.0 | 0.0 | 100.0 | 92.8 | 46.6 | 60.6 | 4.7 |
| D3H44/cetuximab | 9049-9759_2 | 11 | 16 | 100.0 | 38.1 | 98.0 | 0.0 | 99.3 | 94.6 | 34.5 | 71.1 | 2.6 |
| D3H44/trastuzumab | 9049-9759_1 | 11 | 44 | 100.0 | 62.7 | 96.1 | 5.3 | 98.0 | 94.5 | 65.1 | 92.7 | 0.0 |
| trastuzumab/cetuximab | 9049-9759_1 | 11 | 24 | 100.0 | 6.8 | 100.0 | 39.2 | 100.0 | 100.0 | 44.5 | 84.2 | 0.0 |
| trastuzumab/cetuximab | 9049-9759_2 | 11 | 23 | 100.0 | 2.7 | 25.8 | 3.0 | 79.0 | 23.7 | 3.1 | 14.6 | 5.0 |
| D3H44/cetuximab | 9820-9823_2 | 8 | 24 | 100.0 | 43.3*** | 100.0 | 1.6*** | 100.0 | 98.5 | 40.6*** | 77.2 | 1.2 |
| D3H44/cetuximab | 9820-9823_1 | 8 | 27 | 100.0 | 38.1 | 98.6 | 0.6 | 99.4 | 97.2 | 37.2 | 81.8 | 1.1 |

TABLE 35a-continued

Designs that exhibited transferability across all 3 bispecific systems
(D3H44/cetuximab, D3H44/trastuzumab, and trastuzumab/cetuximab) in both orientations.

| D3H44/ trastuzumab | 9820-9823_1 | 8 | 54 | 86.6 | 46.0 | 100.0 | 7.0 | 93.6 | 86.4 | 50.1 | 81.3 | 0.0 |
| trastuzumab/ cetuximab | 9820-9823_2 | 8 | 12 | 100.0 | 2.7*** | 100.0 | 74.9*** | 100.0 | 100.0 | 73.6*** | 84.5 | 0.0 |
| trastuzumab/ cetuximab | 9820-9823-1 | 8 | 31 | 100.0 | 6.0 | 52.3 | 22.7 | 83.1 | 51.0 | 24.6 | 37.1 | 1.9 |

| Bispecific system | H1 + H1 + L1 + L2** | H1 + H1 + L2 + L2** | H1 + H2 + L2 + L1** | H2 + H2 + L1 + L2** | H2 + H2 + L2 + L2** | H1 + H2 + L2 + L1** | H1 + H2 + L2 + L2** | H1 + L1 ** | H1 + L2 ** | H2 + L1 ** | H2 + L2 ** |
|---|---|---|---|---|---|---|---|---|---|---|---|
| D3H44/ cetuximab | 0.0 | 0.0 | 0.0 | 0.0 | 0.0 | 0.0 | 0.0 | 23.1 | 0.0 | 0.0 | 1.7 |
| D3H44/ cetuximab | 0.0 | 0.0 | 0.0 | 0.0 | 0.0 | 0.0 | 1.6 | 56.4 | 0.0 | 0.0 | 0. |
| D3H44/ trastuzumab | 0.0 | 0.0 | 0.0 | 0.0 | 0.0 | 0.0 | 48.3 | 1.8 | 2.3 | 0.0 | 3.3 |
| trastuzumab/ cetuximab | 0.0 | 0.0 | 0.0 | 0.0 | 0.0 | 0.0 | 0.0 | 40.7 | 0.0 | 0.0 | 1.5 |
| trastuzumab/ cetuximab | 0.0 | 0.0 | 0.0 | 0.0 | 0.0 | 29.4 | 0.0 | 25.8 | 0.0 | 0.0 | 0.0 |
| D3H44/ cetuximab | 0.0 | 0.0 | 0.0 | 0.0 | 0.0 | 0.0 | 0.0 | 11.2 | 0.0 | 0.0 | 6.1 |
| D3H44/ cetuximab | 0.0 | 0.0 | 0.0 | 0.0 | 0.0 | 0.0 | 0.0 | 58.7 | 0.0 | 0.0 | 0.0 |
| D3H44/ trastuzumab | 0.0 | 0.0 | 0.0 | 0.0 | 0.0 | 0.0 | 43.8 | 8.6 | 5.7 | 0.0 | 0.0 |
| trastuzumab/ cetuximab | 0.0 | 0.0 | 0.0 | 0.0 | 0.0 | 0.0 | 0.0 | 71.6 | 0.0 | 0.0 | 0.0 |
| trastuzumab/ cetuximab | 0.0 | 0.0 | 0.0 | 0.0 | 0.0 | 47.6 | 0.0 | 15.0 | 0.0 | 0.0 | 2.8 |
| D3H44/ cetuximab | 0.0 | 0.0 | 0.0 | 0.0 | 0.0 | 0.0 | 0.0 | 73.8 | 0.0 | 0.0 | 0.0 |
| D3H44/ cetuximab | 0.0 | 0.0 | 0.0 | 0.0 | 0.0 | 0.0 | 0.0 | 28.4 | 0.0 | 0.0 | 6.8 |
| D3H44/ trastuzumab | 0.0 | 0.0 | 0.0 | 0.0 | 0.0 | 0.0 | 42.2 | 11.6 | 10.0 | 0.0 | 1.8 |
| trastuzumab/ cetuximab | 0.0 | 0.0 | 0.0 | 0.0 | 0.0 | 3.7 | 0.0 | 79.1 | 0.0 | 0.0 | 0.0 |
| trastuzumab/ cetuximab | 0.0 | 0.0 | 0.0 | 0.0 | 0.0 | 20.9 | 0.0 | 62.3 | 0.0 | 0.0 | 0.0 |
| D3H44/ cetuximab | 0.0 | 0.0 | 0.0 | 0.0 | 0.0 | 0.0 | 0.0 | 65.1 | 0.0 | 0.0 | 0.0 |
| D3H44/ cetuximab | 0.0 | 0.0 | 0.0 | 0.0 | 4.1 | 0.0 | 0.0 | 0.0 | 0.0 | 0.0 | 59.5 |
| D3H44/ trastuzumab | 0.0 | 0.0 | 0.0 | 0.0 | 6.7 | 0.0 | 0.0 | 0.0 | 0.0 | 0.0 | 68.0 |
| trastuzumab/ cetuximab | 0.0 | 0.0 | 0.0 | 0.0 | 1.9 | 1.2 | 0.0 | 2.0 | 0.0 | 0.0 | 50.6 |
| trastuzumab/ cetuximab | 0.0 | 0.0 | 0.0 | 0.0 | 0.0 | 1.2 | 0.0 | 78.9 | 0.0 | 0.0 | 0.0 |
| D3H44/ cetuximab | 0.0 | 0.0 | 0.0 | 0.0 | 0.0 | 0.0 | 0.0 | 55.4 | 0.0 | 0.0 | 0.0 |
| D3H44/ cetuximab | 0.0 | 0.0 | 0.0 | 0.0 | 0.0 | 1.6 | 0.0 | 1.9 | 0.0 | 0.0 | 7.1 |
| D3H44/ trastuzumab | 0.0 | 0.0 | 0.0 | 0.0 | 4.4 | 0.0 | 3.3 | 0.0 | 0.0 | 0.0 | 54.4 |
| trastuzumab/ cetuximab | 0.0 | 0.0 | 0.0 | 0.0 | 0.0 | 0.0 | 0.0 | 89.0 | 0.0 | 0.0 | 0.0 |
| trastuzumab/ cetuximab | 0.0 | 0.0 | 0.0 | 0.0 | 2.1 | 2.7 | 0.0 | 2.7 | 0.0 | 0.0 | 30.7 |
| D3H44/ cetuximab | 0.0 | 0.0 | 0.0 | 0.0 | 0.0 | 0.0 | 0.0 | 33.3 | 0.0 | 0.0 | 2.8 |
| D3H44/ cetuximab | 0.0 | 0.0 | 1.7 | 0.0 | 0.0 | 0.0 | 0.0 | 2.5 | 0.0 | 1.5 | 8.9 |
| D3H44/ trastuzumab | 0.0 | 0.0 | 0.0 | 0.0 | 1.8 | 4.8 | 0.0 | 2.1 | 1.4 | 2.0 | 16.9 |
| trastuzumab/ cetuximab | 0.0 | 0.0 | 0.0 | 0.0 | 0.0 | 0.0 | 1.6 | 51.8 | 0.0 | 0.0 | 0.0 |
| trastuzumab/ cetuximab | 0.0 | 0.0 | 1.1 | 0.0 | 0.0 | 42.9 | 0.0 | 0.0 | 0.0 | 22.3 | 14.2 |
| D3H44/ cetuximab | 0.0 | 0.0 | 0.0 | 0.0 | 0.0 | 1.2 | 0.0 | 3.8 | 0.0 | 0.0 | 4.6 |

TABLE 35a-continued

Designs that exhibited transferability across all 3 bispecific systems
(D3H44/cetuximab, D3H44/trastuzumab, and trastuzumab/cetuximab) in both orientations.

| | | | | | | | | | | | |
|---|---|---|---|---|---|---|---|---|---|---|---|
| D3H44/cetuximab | 0.0 | 0.0 | 0.0 | 0.0 | 0.0 | 0.0 | 4.0 | 37.5 | 2.1 | 0.0 | 1.2 |
| trastuzumab/cetuximab | 1.9 | 0.0 | 0.0 | 0.0 | 0.0 | 0.0 | 6.7 | 40.1 | 3.8 | 0.0 | 0.0 |
| trastuzumab/cetuximab | 0.0 | 0.0 | 1.1 | 0.0 | 0.0 | 35.6 | 0.0 | 0.0 | 0.0 | 22.0 | 15.0 |
| D3H44/cetuximab | 0.0 | 0.0 | 0.0 | 0.0 | 0.0 | 0.0 | 0.0 | 17.2 | 0.0 | 0.0 | 2.2 |
| D3H44/cetuximab | 0.0 | 0.0 | 0.0 | 0.0 | 0.0 | 0.0 | 0.0 | 27.1 | 0.0 | 0.0 | 0.0 |
| D3H44/trastuzumab | 0.0 | 0.0 | 0.0 | 0.0 | 0.0 | 1.4 | 1.3 | 1.9 | 0.0 | 0.0 | 2.2 |
| trastuzumab/cetuximab | 0.0 | 0.0 | 0.0 | 0.0 | 0.0 | 0.0 | 0.0 | 10.6 | 0.0 | 0.0 | 4.6 |
| trastuzumab/cetuximab | 0.0 | 0.0 | 0.0 | 0.0 | 0.0 | 2.6 | 0.0 | 17.7 | 0.0 | 0.0 | 0.0 |
| D3H44/cetuximab | 0.0 | 0.0 | 0.0 | 0.0 | 0.0 | 0.0 | 0.0 | 29.9 | 0.0 | 0.0 | 2.7 |
| D3H44/cetuximab | 0.0 | 0.0 | 1.5 | 0.0 | 1.4 | 0.0 | 0.0 | 1.7 | 0.0 | 0.0 | 21.8 |
| D3H44/trastuzumab | 0.0 | 0.0 | 0.0 | 1.3 | 3.1 | 1.8 | 0.0 | 1.8 | 2.7 | 1.2 | 21.0 |
| trastuzumab/cetuximab | 0.0 | 0.0 | 0.0 | 0.0 | 0.0 | 0.0 | 0.0 | 53.8 | 0.0 | 0.0 | 0.0 |
| trastuzumab/cetuximab | 0.0 | 0.0 | 1.6 | 1.5 | 0.0 | 31.4 | 0.0 | 0.0 | 0.0 | 26.1 | 20.2 |
| D3H44/cetuximab | 0.0 | 0.0 | 0.0 | 0.0 | 0.0 | 0.0 | 0.0 | 34.7 | 0.0 | 0.0 | 0.0 |
| D3H44/cetuximab | 0.0 | 0.0 | 0.0 | 0.0 | 0.0 | 1.5 | 0.0 | 22.5 | 0.0 | 0.0 | 2.4 |
| D3H44/trastuzumab | 0.0 | 0.0 | 0.0 | 0.0 | 1.4 | 4.0 | 0.0 | 0.0 | 0.0 | 0.0 | 1.9 |
| trastuzumab/cetuximab | 0.0 | 0.0 | 0.0 | 0.0 | 0.0 | 0.0 | 0.0 | 13.5 | 0.0 | 0.0 | 2.3 |
| trastuzumab/cetuximab | 0.0 | 0.0 | 0.0 | 0.0 | 0.0 | 42.0 | 0.0 | 38.4 | 0.0 | 0.0 | 0.0 |
| D3H44/cetuximab | 0.0 | 0.0 | 0.0 | 0.0 | 0.0 | 0.0 | 0.0 | 19.0 | 0.0 | 0.0 | 2.7 |
| D3H44/cetuximab | 0.0 | 0.0 | 0.0 | 0.0 | 0.0 | 1.2 | 0.0 | 14.2 | 0.0 | 0.0 | 1.7 |
| D3H44/trastuzumab | 0.0 | 0.0 | 0.0 | 0.0 | 0.0 | 0.0 | 12.8 | 1.7 | 0.0 | 0.0 | 4.2 |
| trastuzumab/cetuximab | 0.0 | 0.0 | 0.0 | 0.0 | 0.0 | 0.0 | 0.0 | 9.9 | 0.0 | 0.0 | 5.6 |
| trastuzumab/cetuximab | 0.0 | 0.0 | 0.0 | 0.0 | 0.0 | 33.8 | 0.0 | 27.2 | 0.0 | 0.0 | 0.0 |

\*% considering full Ab species only
\*\*% considering all species
\*\*\*estimated change with respect to wild type TABLE 35b Designs that exhibited transferability across all 3 bispecific systems (D3H44/cetuximab,
D3H44/trastuzumab, and trastuzumab/cetuximab) in one orientation, and transferred in the other
orientation for only one bispecific system, while also meeting the light chain utilization criteria of at least 10%.

| Bispecific system | SMCA unique identifier | Cluster | Post pA yield (mg/LA280) | % H1L1 Pairing (over all H1 species) | Change in % H1L1 Pairing (over all H1 species) with respect to wild type | % H2L2 Pairing (over all H2 species) | Change in % H2L2 Pairing (over all H2 species) with respect to wild type | % H1L1 and % H2L2 Pairing (over all species) | H1 + H2 + L1 + L2* | Change in % of H1:H2: L1:L2 with respect to wild type* | H1 + H2 + L1 + L2** | H1 + H1 + L1 + L1 ** |
|---|---|---|---|---|---|---|---|---|---|---|---|---|
| D3H44/cetuximab | 9327-6054_1 | 3 | 13 | 100.0 | 38.1 | 100.0 | 2.0 | 100.0 | 92.5 | 32.5 | 44.2 | 3.6 |
| D3H44/trastuzumab | 9327-6054_1 | 3 | 7 | 96.1 | 55.5 | 84.1 | −8.9 | 90.1 | 79.9 | 43.6 | 79.0 | 0.0 |
| trastuzumab/cetuximab | 9327-6054_1 | 3 | 2 | 98.3 | 1.0 | 91.3 | 68.5 | 95.4 | 89.1 | 68.5 | 74.8 | 0.0 |

TABLE 35b-continued

Designs that exhibited transferability across all 3 bispecific systems (D3H44/cetuximab, D3H44/trastuzumab, and trastuzumab/cetuximab) in one orientation, and transferred in the other orientation for only one bispecific system, while also meeting the light chain utilization criteria of at least 10%.

| | | | | | | | | | | | | |
|---|---|---|---|---|---|---|---|---|---|---|---|---|
| D3H44/cetuximab | 9815-9825_1 | 3 | 14 | 100.0 | 38.1 | 100.0 | 2.0 | 100.0 | 100.0 | 40.0 | 89.4 | 0.0 |
| D3H44/cetuximab | 9815-9825_2 | 3 | 7 | 100.0 | 43.3*** | 100.0 | 1.6*** | 100.0 | 100.0 | 42.1*** | 86.0 | 0.0 |
| D3H44/trastuzumab | 9815-9825_1 | 3 | 23 | 76.4 | 35.8 | 100.0 | 7.0 | 85.3 | 77.5 | 41.2 | 61.8 | 0.0 |
| trastuzumab/cetuximab | 9815-9825_1 | 3 | 4 | 100.0 | 6.0 | 41.5 | 11.9 | 68.2 | 39.8 | 13.4 | 34.4 | 0.0 |
| D3H44/cetuximab | 9587-9735_1 | 12 | 35 | 100.0 | 43.3*** | 100.0 | 1.6*** | 99.9 | 96.8 | 38.9*** | 71.2 | 0.0 |
| D3H44/cetuximab | 9587-9735_2 | 12 | 25 | 91.5 | 29.6 | 100.0 | 2.0 | 92.0 | 73.9 | 13.9 | 39.2 | 10.7 |
| D3H44/trastuzumab | 9587-9735_1 | 12 | 58 | 89.2 | 51.9 | 88.7 | -2.1 | 87.3 | 80.6 | 51.2 | 59.6 | 0.0 |
| trastuzumab/cetuximab | 9587-9735_1 | 12 | 38 | 93.9 | 0.7 | 95.2 | 34.4 | 94.7 | 69.3 | 13.8 | 34.2 | 8.6 |
| D3H44/cetuximab | 3522_1 | 9 | 38 | 100.0 | 43.3*** | 100.0 | 1.6*** | 100.0 | 89.6 | 31.7*** | 53.4 | 6.2 |
| D3H44/cetuximab | 3522_2 | 9 | 13 | 88.1 | 26.2 | 100.0 | 2.0 | 95.8 | 84.6 | 24.5 | 58.2 | 0.0 |
| D3H44/trastuzumab | 3522_1 | 9 | 61 | 100.0 | 62.7 | 94.8 | 4.0 | 98.0 | 91.6 | 62.2 | 74.0 | 2.8 |
| trastuzumab/cetuximab | 3522_1 | 9 | 37 | 100.0 | 6.8 | 100.0 | 39.2 | 100.0 | 97.7 | 42.2 | 79.7 | 1.9 |
| D3H44/cetuximab | 3519_1 | 6 | 45 | 100.0 | 43.3*** | 98.3 | -0.1*** | 99.2 | 96.6 | 38.7*** | 80.4 | 1.2 |
| D3H44/cetuximab | 3519_2 | 6 | 21 | 75.5 | 13.6 | 100.0 | 2.0 | 82.8 | 67.2 | 7.2 | 42.1 | 4.0 |
| D3H44/trastuzumab | 3519_1 | 6 | 53 | 100.0 | 62.7 | 96.3 | 5.5 | 97.2 | 92.9 | 63.5 | 65.1 | 0.0 |
| trastuzumab/cetuximab | 3519_1 | 6 | 25 | 99.0 | 1.7*** | 96.2 | 71.1*** | 98.3 | 87.4 | 61.0*** | 57.2 | 4.9 |

| Bispecific system | H1 + H1 + L1 + L2** | H1 + H1 + L1 + L2** | H2 + H2 + L1 + L1** | H2 + H2 + L1 + L2** | H2 + H2 + L2 + L1** | H1 + H2 + L1 + L1** | H1 + H2 + L2 + L2** | H1 + L1** | H1 + L2** | H2 + L1** | H2 + L2** |
|---|---|---|---|---|---|---|---|---|---|---|---|
| D3H44/cetuximab | 0.0 | 0.0 | 0.0 | 0.0 | 0.0 | 0.0 | 0.0 | 52.3 | 0.0 | 0.0 | 0.0 |
| D3H44/trastuzumab | 0.0 | 0.0 | 0.0 | 1.6 | 0.0 | 14.4 | 3.8 | 1.2 | 0.0 | 0.0 | 0.0 |
| trastuzumab/cetuximab | 0.0 | 0.0 | 0.0 | 0.0 | 0.0 | 7.6 | 1.6 | 12.7 | 0.0 | 0.0 | 3.3 |
| D3H44/cetuximab | 0.0 | 0.0 | 0.0 | 0.0 | 0.0 | 0.0 | 0.0 | 7.6 | 0.0 | 0.0 | 3.0 |
| D3H44/cetuximab | 0.0 | 0.0 | 0.0 | 0.0 | 0.0 | 0.0 | 0.0 | 7.4 | 0.0 | 0.0 | 6.6 |
| D3H44/trastuzumab | 0.0 | 0.0 | 0.0 | 0.0 | 0.0 | 0.0 | 17.9 | 14.6 | 5.7 | 0.0 | 0.0 |
| trastuzumab/cetuximab | 0.0 | 0.0 | 0.0 | 0.0 | 0.0 | 52.0 | 0.0 | 1.2 | 0.0 | 5.8 | 6.6 |
| D3H44/cetuximab | 0.0 | 0.0 | 0.0 | 0.0 | 2.3 | 0.0 | 0.0 | 0.0 | 0.0 | 0.0 | 26.4 |
| D3H44/cetuximab | 1.0 | 0.0 | 0.0 | 0.0 | 0.0 | 0.0 | 2.1 | 40.5 | 6.4 | 0.0 | 0.0 |
| D3H44/trastuzumab | 0.0 | 0.0 | 0.0 | 0.0 | 1.5 | 6.4 | 6.5 | 2.4 | 1.8 | 4.6 | 17.3 |
| trastuzumab/cetuximab | 1.5 | 0.0 | 0.0 | 0.0 | 0.0 | 1.9 | 3.2 | 48.6 | 2.0 | 0.0 | 0.0 |
| D3H44/cetuximab | 0.0 | 0.0 | 0.0 | 0.0 | 0.0 | 0.0 | 0.0 | 40.4 | 0.0 | 0.0 | 0.0 |
| D3H44/cetuximab | 0.0 | 0.0 | 0.0 | 0.0 | 2.5 | 0.0 | 8.1 | 1.8 | 0.0 | 0.0 | 29. |
| D3H44/trastuzumab | 0.0 | 0.0 | 0.0 | 1.1 | 0.0 | 3.0 | 0.0 | 19.2 | 0.0 | 0.0 | 0.0 |
| trastuzumab/cetuximab | 0.0 | 0.0 | 0.0 | 0.0 | 0.0 | 0.0 | 0.0 | 16.1 | 0.0 | 0.0 | 2.4 |
| D3H44/cetuximab | 0.0 | 0.0 | 0.0 | 1.6 | 0.0 | 0.0 | 0.0 | 8.4 | 0.0 | 0.0 | 8.4 |
| D3H44/cetuximab | 2.2 | 0.0 | 0.0 | 0.0 | 0.0 | 0.0 | 14.4 | 26.4 | 9.0 | 0.0 | 2.0 |

TABLE 35b-continued

Designs that exhibited transferability across all 3 bispecific systems (D3H44/cetuximab, D3H44/trastuzumab, and trastuzumab/cetuximab) in one orientation, and transferred in the other orientation for only one bispecific system, while also meeting the light chain utilization criteria of at least 10%.

| | | | | | | | | | | | |
|---|---|---|---|---|---|---|---|---|---|---|---|
| D3H44/trastuzumab | 0.0 | 0.0 | 0.0 | 0.0 | 3.3 | 1.7 | 0.0 | 2.1 | 0.0 | 2.0 | 25.8 |
| trastuzumab/cetuximab | 0.0 | 0.0 | 0.0 | 0.0 | 0.0 | 2.4 | 1.0 | 31.9 | 0.0 | 0.0 | 2.6 |

*% considering full Ab species only
**% considering all species
***estimated change with respect to wild type

The invention claimed is:

1. An antigen binding polypeptide construct comprising at least a first heterodimer and a second heterodimer, the first heterodimer comprising a first human or humanized immunoglobulin G (IgG) heavy chain polypeptide sequence (H1), and a first human or humanized immunoglobulin kappa light chain polypeptide sequence (L1), and binding to a first epitope; and the second heterodimer comprising a second human or humanized immunoglobulin G (IgG) heavy chain polypeptide sequence (H2), and a second human or humanized immunoglobulin kappa light chain polypeptide sequence (L2), and binding to a second epitope, wherein the H1 and L1 polypeptide sequences of the first heterodimer are different from the corresponding H2 and L2 polypeptide sequences of the second heterodimer, wherein H1 and H2 each comprise a heavy chain variable domain (VH domain) and a heavy chain constant domain (CH1 domain);

wherein L1 and L2 each comprise a light chain variable domain (VL domain) and a light chain constant domain (CL domain);

wherein H1, H2, L1, and L2 comprise the following amino acid substitutions that promote preferential pairing of H1 with L1 as compared to L2, and of H2 with L2 as compared to L1, at positions identified according to the Kabat numbering system:

a) H1 comprises amino acid substitutions 143E, 145T, and 179E, L1 comprises amino acid substitutions 124R and 178R, H2 comprises amino acid substitution 186K, and L2 comprises amino acid substitutions 124E, 160E and 178E;

b) H1 comprises amino acid substitutions 143E, 145T, and 179D, L1 comprises amino acid substitutions 124K and 178R, H2 comprises amino acid substitution 186K, and L2 comprises amino acid substitutions 124E and 180E;

c) H1 comprises amino acid substitutions 143E, 145T, and 179E, L1 comprises amino acid substitutions 124R and 178R, H2 comprises amino acid substitution 186K, and L2 comprises amino acid substitutions 124E, 178E and 180E;

d) H1 comprises amino acid substitutions 143E, 145T, and 179D, L1 comprises amino acid substitutions 124K and 178R, H2 comprises amino acid substitution 186R, and L2 comprises amino acid substitutions 124E and 180E;

e) H1 comprises amino acid substitutions 143E, 145T, and 179E, L1 comprises amino acid substitutions 124R and 178K, H2 comprises amino acid substitution 186K, and L2 comprises amino acid substitutions 124E and 180E;

f) H1 comprises amino acid substitutions 143E, 145T, and 179E, L1 comprises amino acid substitutions 124R and 178K, H2 comprises amino acid substitution 186R, and L2 comprises amino acid substitutions 124E and 180E;

g) H1 comprises amino acid substitutions 143E, 145T, and 179D, L1 comprises amino acid substitutions 124R and 178K, H2 comprises amino acid substitution 186K, and L2 comprises amino acid substitutions 124E and 180E;

h) H1 comprises amino acid substitutions 143E, 145T, and 179D, L1 comprises amino acid substitutions 124R and 178K, H2 comprises amino acid substitution 186R, and L2 comprises amino acid substitutions 124E and 180E;

i) H1 comprises amino acid substitutions 143E, 145T, and 179E, L1 comprises amino acid substitutions 124R and 178R, H2 comprises amino acid substitution 186R, and L2 comprises amino acid substitutions 124E and 180E;

j) H1 comprises amino acid substitutions 143E, 145T, and 179E, L1 comprises amino acid substitutions 124R and 178R, H2 comprises amino acid substitution 186R, and L2 comprises amino acid substitutions 124E, 160E and 178E;

k) H1 comprises amino acid substitutions 143E, 145T, and 179E, L1 comprises amino acid substitutions 124R and 178R, H2 comprises amino acid substitution 186K, and L2 comprises amino acid substitutions 124E, 160E and 180E;

l) H1 comprises amino acid substitutions 143E, 145T, and 179E, L1 comprises amino acid substitutions 124R and 178R, H2 comprises amino acid substitution 186R, and L2 comprises amino acid substitutions 124E, 178E and 180E;

m) H1 comprises amino acid substitutions 143E, 145T, and 179E, L1 comprises amino acid substitutions 124R and 178R, H2 comprises amino acid substitution 186R, and L2 comprises amino acid substitutions 124E and 178E;

n) H1 comprises amino acid substitutions 143E, 145T, and 179E, L1 comprises amino acid substitutions 124R, 160K and 178R, H2 comprises amino acid substitution 186R, and L2 comprises amino acid substitutions 124E and 180E;

o) H1 comprises amino acid substitutions 143E, 145T, and 179E, L1 comprises amino acid substitutions 124R and 178R, H2 comprises amino acid substitution 186K, and L2 comprises amino acid substitutions 124E and 178E;

p) H1 comprises amino acid substitutions 143E, 145T, and 179E, L1 comprises amino acid substitutions 124K and 178R, H2 comprises amino acid substitution 186K, and L2 comprises amino acid substitutions 124E and 180E;

q) H1 comprises amino acid substitutions 143E, 145T, and 179D, L1 comprises amino acid substitutions 124R, 160K and 178R, H2 comprises amino acid substitution 186R, and L2 comprises amino acid substitutions 124E and 180E;

r) H1 comprises amino acid substitutions 143E, 145T, and 179D, L1 comprises amino acid substitutions 124R and 178R, H2 comprises amino acid substitution 186K, and L2 comprises amino acid substitutions 124E, 160E and 180E;

s) H1 comprises amino acid substitutions 143E, 145T, and 179E, L1 comprises amino acid substitutions 124R, 160K and 178R, H2 comprises amino acid substitution 186K, and L2 comprises amino acid substitutions 124E and 180E;

t) H1 comprises amino acid substitutions 143E, 145T, and 179E, L1 comprises amino acid substitutions 124R and 178R, H2 comprises amino acid substitution 186K, and L2 comprises amino acid substitutions 124E and 180E;

u) H1 comprises amino acid substitutions 143E, 145T, and 179D, L1 comprises amino acid substitutions 124R and 178K, H2 comprises amino acid substitution 186K, and L2 comprises amino acid substitutions 124E, 160E and 180E;

v) H1 comprises amino acid substitutions 143E, 145T, and 179E, L1 comprises amino acid substitutions 124K and 178R, H2 comprises amino acid substitution 186R, and L2 comprises amino acid substitutions 124E and 180E;

w) H1 comprises amino acid substitutions 143D, 145T, and 179E, L1 comprises amino acid substitution 178R, H2 comprises amino acid substitution 186R, and L2 comprises amino acid substitutions 124E and 180E;

x) H1 comprises amino acid substitutions 143E, 145T, and 179D, L1 comprises amino acid substitutions 124R and 178R, H2 comprises amino acid substitution 186R, and L2 comprises amino acid substitutions 124E and 180E;

y) H1 comprises amino acid substitutions 143D, 145T, and 179E, L1 comprises amino acid substitution 178R, H2 comprises amino acid substitution 186K, and L2 comprises amino acid substitutions 124E and 180E;

z) H1 comprises amino acid substitutions 143E, 145T, and 179E, L1 comprises amino acid substitution 178R, H2 comprises amino acid substitution 186K, and L2 comprises amino acid substitutions 124E, 160E and 180E;

aa) H1 comprises amino acid substitutions 143D, 145T, and 179E, L1 comprises amino acid substitution 178R, H2 comprises amino acid substitution 186K, and L2 comprises amino acid substitutions 124E, 160E and 180E;

bb) H1 comprises amino acid substitutions 143E, 145T, and 179D, L1 comprises amino acid substitutions 124R, 160K and 178R, H2 comprises amino acid substitution 186K, and L2 comprises amino acid substitutions 124E and 180E;

cc) H1 comprises amino acid substitutions 143E and 145T, L1 comprises amino acid substitutions 124R, 160K and 178R, H2 comprises amino acid substitution 186R, and L2 comprises amino acid substitutions 124E and 180E;

dd) H1 comprises amino acid substitutions 143E, 145T, and 179E, L1 comprises amino acid substitutions 124R and 178K, H2 comprises amino acid substitution 186K, and L2 comprises amino acid substitutions 124E, 160E, 180E;

ee) H1 comprises amino acid substitutions 143E and 145T, L1 comprises amino acid substitutions 124R, 160K and 178R, H2 comprises amino acid substitution 186K, and L2 comprises amino acid substitutions 124E and 180E;

ff) H1 comprises amino acid substitutions 143E, 145T, and 179D, L1 comprises amino acid substitutions 124R and 178R, H2 comprises amino acid substitution 186K, and L2 comprises amino acid substitutions 124E and 180E;

gg) H1 comprises amino acid substitutions 143E, 145T, and 179D, L1 comprises amino acid substitution 178R, H2 comprises amino acid substitution 186R, and L2 comprises amino acid substitutions 124E and 180E;

hh) H1 comprises amino acid substitutions 143E, 145T, and 179E, L1 comprises amino acid substitutions 124R and 178R, H2 comprises amino acid substitution 186R, and L2 comprises amino acid substitutions 124E, 160E and 180E;

ii) H1 comprises amino acid substitutions 143E, 145T, and 179D, L1 comprises amino acid substitution 178R, H2 comprises amino acid substitution 186K, and L2 comprises amino acid substitutions 124E and 180E;

jj) H1 comprises amino acid substitutions 143E, 145T, and 179D, L1 comprises amino acid substitutions 124R and 178K, H2 comprises amino acid substitution 186R, and L2 comprises amino acid substitutions 124E, 160E and 180E;

kk) H1 comprises amino acid substitutions 143E, 145T, and 179E, L1 comprises amino acid substitutions 124R and 178R, H2 comprises amino acid substitution Q179R, and L2 comprises amino acid substitutions 124E and 178E;

ll) H1 comprises amino acid substitutions 143E, 145T, and 179E, L1 comprises amino acid substitutions 124R and 178R, H2 comprises amino acid substitution Q179R, and L2 comprises amino acid substitutions 124E, 160E and 178E;

mm) H1 comprises amino acid substitutions 143E, 145T, and 179E, L1 comprises amino acid substitutions 124R and 178R, H2 comprises amino acid substitution 179K, and L2 comprises amino acid substitutions 124E, 160E and 178E;

nn) H1 comprises amino acid substitutions 143E, 145T, and 179E, L1 comprises amino acid substitutions 124R and 178R, H2 comprises amino acid substitution 179R, and L2 comprises amino acid substitutions 124E, 178E and 180E;
oo) H1 comprises amino acid substitutions 143E, 145T, and 179E, L1 comprises amino acid substitutions 124R and 178R, H2 comprises amino acid substitution 179K, and L2 comprises amino acid substitutions 124E, 178E;
pp) H1 comprises amino acid substitutions 143E, 145T, and 179D, L1 comprises amino acid substitutions 124K and 178R, H2 comprises amino acid substitution 179K, and L2 comprises amino acid substitutions 124E, 180E;
qq) H1 comprises amino acid substitutions 143E, 145T, and 179E, L1 comprises amino acid substitutions 124R and 178R, H2 comprises amino acid substitution 179K, and L2 comprises amino acid substitutions 124E and 180E;
rr) H1 comprises amino acid substitutions 143E, 145T, and 179E, L1 comprises amino acid substitutions 124R and 178R, H2 comprises amino acid substitution 179K, and L2 comprises amino acid substitutions 124E, 178E and 180E;
ss) H1 comprises amino acid substitutions 143E, 145T, and 179E, L1 comprises amino acid substitutions 124R and 178K, H2 comprises amino acid substitution 179K, and L2 comprises amino acid substitutions 124E and 180E;
tt) H1 comprises amino acid substitutions 139C, 143E, 145T, and 179E, L1 comprises amino acid substitutions 116C, 124R and 178R, H2 comprises amino acid substitution 179K, and L2 comprises amino acid substitutions 124E, 160E and 180E;
uu) H1 comprises amino acid substitutions 143E, 145T, and 179D, L1 comprises amino acid substitutions 124R and 178K, H2 comprises amino acid substitution 179K, and L2 comprises amino acid substitutions 124E and 180E;
vv) H1 comprises amino acid substitutions 143E, 145T, and 179E, L1 comprises amino acid substitutions 124K and 178R, H2 comprises amino acid substitution 179K, and L2 comprises amino acid substitutions 124E, 160E and 180E;
ww) H1 comprises amino acid substitutions 143D, 145T, and 179E, L1 comprises amino acid substitution 178R, H2 comprises amino acid substitution 179K, and L2 comprises amino acid substitutions 124E and 180E;
xx) H1 comprises amino acid substitutions 143E, 145T, and 179D, L1 comprises amino acid substitutions 124R and 178R, H2 comprises amino acid substitution 179K, and L2 comprises amino acid substitutions 124E and 180E;
yy) H1 comprises amino acid substitutions 143E, 145T, and 179D, L1 comprises amino acid substitutions 124K and 178R, H2 comprises amino acid substitution 179K, and L2 comprises amino acid substitutions 124E, 160E and 180E;
zz) H1 comprises amino acid substitutions 143E, 145T, and 179E, L1 comprises amino acid substitutions 124R and 178R, H2 comprises amino acid substitution 179K, and L2 comprises amino acid substitutions 124E, 160E and 180E;
aaa) H1 comprises amino acid substitutions 143E, 145T, and 179E, L1 comprises amino acid substitutions 124R, 160K, and 178R, H2 comprises amino acid substitution 179K, and L2 comprises amino acid substitutions 124E and 180E;
bbb) H1 comprises amino acid substitutions 143E, 145T, and 179D, L1 comprises amino acid substitutions 124R and 178K, H2 comprises amino acid substitution 179K, and L2 comprises amino acid substitutions 124E, 160E and 180E;
ccc) H1 comprises amino acid substitutions 143E, 145T, and 179E, L1 comprises amino acid substitutions 124K and 178R, H2 comprises amino acid substitution 179K, and L2 comprises amino acid substitutions 124E and 180E;
ddd) H1 comprises amino acid substitutions 143E, 145T, and 179D, L1 comprises amino acid substitutions 124R, 160K, and 178R, H2 comprises amino acid substitution 179K, and L2 comprises amino acid substitutions 124E and 180E;
eee) H1 comprises amino acid substitutions 143E, 145T, and 179D, L1 comprises amino acid substitutions 124R and 178R, H2 comprises amino acid substitution 179K, and L2 comprises amino acid substitutions 124E, 160E and 180E;
fff) H1 comprises amino acid substitutions 143E, 145T, and 179D, L1 comprises amino acid substitution 178R, H2 comprises amino acid substitution 179K, and L2 comprises amino acid substitutions 124E and 180E;
ggg) H1 comprises amino acid substitutions 143E, 145T, and 179E, L1 comprises amino acid substitutions 124R and 178K, H2 comprises amino acid substitution 179K, and L2 comprises amino acid substitutions 124E, 160E and 180E;
hhh) H1 comprises amino acid substitutions 143E, 145T, and 179E, L1 comprises amino acid substitution 178R, H2 comprises amino acid substitution 179K, and L2 comprises amino acid substitutions 124E and 180E;
iii) H1 comprises amino acid substitutions 143E, 145T, and 179E, L1 comprises amino acid substitutions 124R and 178R, H2 comprises amino acid substitution 143K, and L2 comprises amino acid substitutions 124E and 133D; or
jjj) H1 comprises amino acid substitutions 143E, 145T, and 179E, L1 comprises amino acid substitutions 124R and 178R, H2 comprises amino acid substitution 143R, and L2 comprises amino acid substitutions 124E and 133E,
wherein when both L1 and L2 are co-expressed with at least one of H1 and H2, the amount of H1-L1 compared to H1-L2 and the amount of H2-L2 compared to H2-L1 is greater than the amount of H1-L1 compared to H1-L2 and the amount of H2-L2 compared to H2-L1 in the absence of the amino acid substitutions.

2. The antigen binding polypeptide construct of claim 1, wherein H1 comprises amino acid substitutions 143E, 145T, and 179E, L1 comprises amino acid substitutions 124R and 178R, H2 comprises amino acid substitution 179K, and L2 comprises amino acid substitutions 124E and 180E.

3. The antigen binding polypeptide construct of claim 2, wherein the antigen binding polypeptide construct further comprises an Fc comprising a first CH3 sequence and a second CH3 sequence, and a first CH2 sequence and a second CH2 sequence, wherein the Fc is coupled, with or without one or more linkers, to the first heterodimer and to the second heterodimer, and wherein the Fc is a human Fc.

4. The antigen binding polypeptide construct of claim 3, wherein the human Fc comprises one or more substitutions in at least one of the CH3 sequences that promote the formation of a heterodimeric Fc with stability comparable to a wild-type homodimeric Fc.

5. The antigen binding polypeptide construct of claim 4, wherein the human Fc comprises:
  i) a heterodimeric IgG1 Fc having the substitutions L351Y_F405A_Y407V in the first Fc polypeptide, and the substitutions T366L_K392M_T394W in the second Fc polypeptide;
  ii) a heterodimeric IgG1 Fc having the substitutions L351Y_F405A_Y407V in the first Fc polypeptide, and the substitutions T366L_K392L_T394W in the second Fc polypeptide;
  iii) a heterodimeric IgG1 Fc having the substitutions T350V_L351Y_F405A_Y407V in the first Fc polypeptide, and the substitutions T350V_T366L_K392L_T394W in the second Fc polypeptide;
  iv) a heterodimeric IgG1 Fc having the substitutions T350V_L351Y_F405A_Y407V in the first Fc polypeptide, and the substitutions T350V_T366L_K392M_T394W in the second Fc polypeptide; or
  v) a heterodimeric IgG1 Fc having the substitutions T350V_L351Y_S400E_F405A_Y407V in the first Fc polypeptide, and the substitutions T350V_T366L_N390R_K392M_T394W in the second Fc polypeptide;
  wherein the numbering of amino acid residues in the CH3 sequence is according to the EU numbering system.

6. The antigen binding polypeptide construct according to claim 2, wherein the antigen binding polypeptide construct is multispecific or bispecific.

7. The antigen binding polypeptide construct of claim 1, wherein H1 comprises amino acid substitutions 143E, 145T, and 179E, L1 comprises amino acid substitutions 124R and 178R, H2 comprises amino acid substitution 179R, and L2 comprises amino acid substitutions 124E, 178E and 180E.

8. The antigen binding polypeptide construct of claim 7, wherein the antigen binding polypeptide construct further comprises an Fc comprising a first CH3 sequence and a second CH3 sequence, and a first CH2 sequence and a second CH2 sequence, wherein the Fc is coupled, with or without one or more linkers, to the first heterodimer and to the second heterodimer, and wherein the Fc is a human Fc.

9. The antigen binding polypeptide construct of claim 8, wherein the human Fc comprises one or more substitutions in at least one of the CH3 sequences that promote the formation of a heterodimeric Fc with stability comparable to a wild-type homodimeric Fc.

10. The antigen binding polypeptide construct of claim 9, wherein the human Fc comprises:
  i) a heterodimeric IgG1 Fc having the substitutions L351Y_F405A_Y407V in the first Fc polypeptide, and the substitutions T366L_K392M_T394W in the second Fc polypeptide;
  ii) a heterodimeric IgG1 Fc having the substitutions L351Y_F405A_Y407V in the first Fc polypeptide, and the substitutions T366L_K392L_T394W in the second Fc polypeptide;
  iii) a heterodimeric IgG1 Fc having the substitutions T350V_L351Y_F405A_Y407V in the first Fc polypeptide, and the substitutions T350V_T366L_K392L_T394W in the second Fc polypeptide;
  iv) a heterodimeric IgG1 Fc having the substitutions T350V_L351Y_F405A_Y407V in the first Fc polypeptide, and the substitutions T350V_T366L_K392M_T394W in the second Fc polypeptide; or
  v) a heterodimeric IgG1 Fc having the substitutions T350V_L351Y_S400E_F405A_Y407V in the first Fc polypeptide, and the substitutions T350V_T366L_N390R_K392M_T394W in the second Fc polypeptide;
  wherein the numbering of amino acid residues in the CH3 sequence is according to the EU numbering system.

11. The antigen binding polypeptide construct according to claim 7, wherein the antigen binding polypeptide construct is multispecific or bispecific.

12. The antigen binding polypeptide construct of claim 1, wherein H1 comprises amino acid substitutions 143E, 145T, and 179E, L1 comprises amino acid substitutions 124R and 178R, H2 comprises amino acid substitution 143R, and L2 comprises amino acid substitutions 124E and 133E.

13. The antigen binding polypeptide construct of claim 12, wherein the antigen binding polypeptide construct further comprises an Fc comprising a first CH3 sequence and a second CH3 sequence, and a first CH2 sequence and a second CH2 sequence, wherein the Fc is coupled, with or without one or more linkers, to the first heterodimer and to the second heterodimer, and wherein the Fc is a human Fc.

14. The antigen binding polypeptide construct of claim 13, wherein the human Fc comprises one or more substitutions in at least one of the CH3 sequences that promote the formation of a heterodimeric Fc with stability comparable to a wild-type homodimeric Fc.

15. The antigen binding polypeptide construct of claim 14, wherein the human Fc comprises:
  i) a heterodimeric IgG1 Fc having the substitutions L351Y_F405A_Y407V in the first Fc polypeptide, and the substitutions T366L_K392M_T394W in the second Fc polypeptide;
  ii) a heterodimeric IgG1 Fc having the substitutions L351Y_F405A_Y407V in the first Fc polypeptide, and the substitutions T366L_K392L_T394W in the second Fc polypeptide;
  iii) a heterodimeric IgG1 Fc having the substitutions T350V_L351Y_F405A_Y407V in the first Fc polypeptide, and the substitutions T350V_T366L_K392L_T394W in the second Fc polypeptide;
  iv) a heterodimeric IgG1 Fc having the substitutions T350V_L351Y_F405A_Y407V in the first Fc polypeptide, and the substitutions T350V_T366L_K392M_T394W in the second Fc polypeptide; or
  v) a heterodimeric IgG1 Fc having the substitutions T350V_L351Y_S400E_F405A_Y407V in the first Fc polypeptide, and the substitutions T350V_T366L_N390R_K392M_T394W in the second Fc polypeptide;
  wherein the numbering of amino acid residues in the CH3 sequence is according to the EU numbering system.

16. The antigen binding polypeptide construct according to claim 12, wherein the antigen binding polypeptide construct is multispecific or bispecific.

17. The antigen binding polypeptide construct of claim 1, wherein H1 comprises amino acid substitutions 143E, 145T, and 179E, L1 comprises amino acid substitutions 124R and 178R, H2 comprises amino acid substitution 186K, and L2 comprises amino acid substitutions 124E, 160E and 178E.

18. The antigen binding polypeptide construct of claim 17, wherein the antigen binding polypeptide construct further comprises an Fc comprising a first CH3 sequence and a second CH3 sequence, and a first CH2 sequence and a second CH2 sequence, wherein the Fc is coupled, with or without one or more linkers, to the first heterodimer and to the second heterodimer, and wherein the Fc is a human Fc.

19. The antigen binding polypeptide construct of claim 18, wherein the human Fc comprises one or more substitutions in at least one of the CH3 sequences that promote the formation of a heterodimeric Fc with stability comparable to a wild-type homodimeric Fc.

20. The antigen binding polypeptide construct of claim 19, wherein the human Fc comprises:
   i) a heterodimeric IgG1 Fc having the substitutions L351Y_F405A_Y407V in the first Fc polypeptide, and the substitutions T366L_K392M_T394W in the second Fc polypeptide;
   ii) a heterodimeric IgG1 Fc having the substitutions L351Y_F405A_Y407V in the first Fc polypeptide, and the substitutions T366L_K392L_T394W in the second Fc polypeptide;
   iii) a heterodimeric IgG1 Fc having the substitutions T350V_L351Y_F405A_Y407V in the first Fc polypeptide, and the substitutions T350V_T366L_K392L_T394W in the second Fc polypeptide;
   iv) a heterodimeric IgG1 Fc having the substitutions T350V_L351Y_F405A_Y407V in the first Fc polypeptide, and the substitutions T350V_T366L_K392M_T394W in the second Fc polypeptide; or
   v) a heterodimeric IgG1 Fc having the substitutions T350V_L351Y_S400E_F405A_Y407V in the first Fc polypeptide, and the substitutions T350V_T366L_N390R_K392M_T394W in the second Fc polypeptide;
   wherein the numbering of amino acid residues in the CH3 sequence is according to the EU numbering system.

21. The antigen binding polypeptide construct according to claim 17, wherein the antigen binding polypeptide construct is multispecific or bispecific.

22. The antigen binding polypeptide construct of claim 1, wherein H1 comprises amino acid substitutions 139C, 143E, 145T, and 179E, L1 comprises amino acid substitutions 116C, 124R and 178R, H2 comprises amino acid substitution 179K, and L2 comprises amino acid substitutions 124E, 160E and 180E.

23. The antigen binding polypeptide construct of claim 22, wherein the antigen binding polypeptide construct further comprises an Fc comprising a first CH3 sequence and a second CH3 sequence, and a first CH2 sequence and a second CH2 sequence, wherein the Fc is coupled, with or without one or more linkers, to the first heterodimer and to the second heterodimer, and wherein the Fc is a human Fc.

24. The antigen binding polypeptide construct of claim 23, wherein the human Fc comprises one or more substitutions in at least one of the CH3 sequences that promote the formation of a heterodimeric Fc with stability comparable to a wild-type homodimeric Fc.

25. The antigen binding polypeptide construct of claim 24, wherein the human Fc comprises:
   i) a heterodimeric IgG1 Fc having the substitutions L351Y_F405A_Y407V in the first Fc polypeptide, and the substitutions T366L_K392M_T394W in the second Fc polypeptide;
   ii) a heterodimeric IgG1 Fc having the substitutions L351Y_F405A_Y407V in the first Fc polypeptide, and the substitutions T366L_K392L_T394W in the second Fc polypeptide;
   iii) a heterodimeric IgG1 Fc having the substitutions T350V_L351Y_F405A_Y407V in the first Fc polypeptide, and the substitutions T350V_T366L_K392L_T394W in the second Fc polypeptide;
   iv) a heterodimeric IgG1 Fc having the substitutions T350V_L351Y_F405A_Y407V in the first Fc polypeptide, and the substitutions T350V_T366L_K392M_T394W in the second Fc polypeptide; or
   v) a heterodimeric IgG1 Fc having the substitutions T350V_L351Y_S400E_F405A_Y407V in the first Fc polypeptide, and the substitutions T350V_T366L_N390R_K392M_T394W in the second Fc polypeptide;
   wherein the numbering of amino acid residues in the CH3 sequence is according to the EU numbering system.

26. The antigen binding polypeptide construct according to claim 22, wherein the antigen binding polypeptide construct is multispecific or bispecific.

27. The antigen binding polypeptide construct of claim 1, wherein the antigen binding polypeptide construct further comprises an Fc comprising a first CH3 sequence and a second CH3 sequence, and a first CH2 sequence and a second CH2 sequence, and wherein the Fc is coupled, with or without one or more linkers, to the first heterodimer and to the second heterodimer.

28. The antigen binding polypeptide construct of claim 27, wherein the Fc is a human Fc.

29. The antigen binding polypeptide construct of claim 28, wherein the human Fc is a heterodimeric Fc.

30. The antigen binding polypeptide construct of claim 29, wherein the human Fc comprises one or more substitutions in at least one of the CH3 sequences that promote the formation of a heterodimeric Fc with stability comparable to a wild-type homodimeric Fc.

31. The antigen binding polypeptide construct of claim 30, wherein the human Fc comprises:
   i) a heterodimeric IgG1 Fc having the substitutions L351Y_F405A_Y407V in the first Fc polypeptide, and the substitutions T366L_K392M_T394W in the second Fc polypeptide;
   ii) a heterodimeric IgG1 Fc having the substitutions L351Y_F405A_Y407V in the first Fc polypeptide, and the substitutions T366L_K392L_T394W in the second Fc polypeptide;
   iii) a heterodimeric IgG1 Fc having the substitutions T350V_L351Y_F405A_Y407V in the first Fc polypeptide, and the substitutions T350V_T366L_K392L_T394W in the second Fc polypeptide;
   iv) a heterodimeric IgG1 Fc having the substitutions T350V_L351Y_F405A_Y407V in the first Fc polypeptide, and the substitutions T350V_T366L_K392M_T394W in the second Fc polypeptide; or
   v) a heterodimeric IgG1 Fc having the substitutions T350V_L351Y_S400E_F405A_Y407V in the first Fc polypeptide, and the substitutions T350V_T366L_N390R_K392M_T394W in the second Fc polypeptide;
   wherein the numbering of amino acid residues in the CH3 sequence is according to the EU numbering system.

32. The antigen binding polypeptide construct of claim 27, wherein the first CH2 sequence and the second CH2 sequence comprise mutations that selectively alter the affinity of the Fc for Fcgamma receptors.

33. The antigen binding polypeptide construct of claim 27, wherein the Fc is coupled to H1 and H2 by one or more linkers.

34. The antigen binding polypeptide construct according to claim 1, wherein the antigen binding polypeptide construct is multispecific or bispecific.

35. The antigen binding polypeptide construct according to claim 27, wherein the antigen binding polypeptide construct is conjugated to a therapeutic agent.

36. A pharmaceutical composition comprising the antigen binding polypeptide construct of claim 1 and a pharmaceutically acceptable carrier.

37. An isolated polynucleotide or set of isolated polynucleotides comprising at least one sequence that encodes the antigen binding polypeptide construct according to claim 1.

38. A vector or set of vectors comprising one or more of the polynucleotides or sets of polynucleotides according to claim 37.

39. An isolated cell comprising the polynucleotide or set of polynucleotides according to claim 37.

40. A method of obtaining an antigen binding polypeptide construct from the isolated cell of claim 39, the method comprising the steps of:
   (a) obtaining a host cell culture comprising the isolated cell comprising one or more nucleic acid sequences encoding the antigen binding polypeptide construct; and
   (b) recovering the antigen binding polypeptide construct from the host cell culture.

* * * * *

UNITED STATES PATENT AND TRADEMARK OFFICE
CERTIFICATE OF CORRECTION

PATENT NO. : 12,286,489 B2  
APPLICATION NO. : 17/652557  
DATED : April 29, 2025  
INVENTOR(S) : Mario Sanches et al.

Page 1 of 1

It is certified that error appears in the above-identified patent and that said Letters Patent is hereby corrected as shown below:

On the Title Page

Item (73) Please replace "Zymeworks BC, Inc." with --Zymeworks BC Inc.--

Signed and Sealed this
Fifth Day of August, 2025

Coke Morgan Stewart
*Acting Director of the United States Patent and Trademark Office*

SEQUENCE LISTING

<160> NUMBER OF SEQ ID NOS: 79

<210> SEQ ID NO 1
<211> LENGTH: 214
<212> TYPE: PRT
<213> ORGANISM: Artificial Sequence
<220> FEATURE:
<223> OTHER INFORMATION: D3H44 light chain

<400> SEQUENCE: 1

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Asp Ile Lys Ser Tyr
            20                  25                  30

Leu Asn Trp Tyr Gln Gln Lys Pro Gly Lys Ala Pro Lys Val Leu Ile
        35                  40                  45

Tyr Tyr Ala Thr Ser Leu Ala Glu Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln His Gly Glu Ser Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 2
<211> LENGTH: 214
<212> TYPE: PRT
<213> ORGANISM: Artificial Sequence
<220> FEATURE:
<223> OTHER INFORMATION: Trastuzumab light chain

```
<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 214
<212> TYPE: PRT
<213> ORGANISM: Artificial Sequence
<220> FEATURE:
<223> OTHER INFORMATION: Cetuximab light chain

<400> SEQUENCE: 3

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
            130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 4
<211> LENGTH: 446
<212> TYPE: PRT
<213> ORGANISM: Artificial Sequence
<220> FEATURE:
<223> OTHER INFORMATION: D3H44 heavy chain

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Glu Tyr
                20                  25                  30

Tyr Met His Trp Val Arg Gln Ala Pro Gly Lys Gly Leu Glu Trp Val
                35                  40                  45

Gly Leu Ile Asp Pro Glu Gln Gly Asn Thr Ile Tyr Asp Pro Lys Phe
    50                  55                  60

Gln Asp Arg Ala Thr Ile Ser Ala Asp Asn Ser Lys Asn Thr Ala Tyr
65              70                  75                  80

Leu Gln Met Asn Ser Leu Arg Ala Glu Asp Thr Ala Val Tyr Tyr Cys
                85                  90                  95

Ala Arg Asp Thr Ala Ala Tyr Phe Asp Tyr Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
```

```
                   275                 280                 285
Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
                435                 440                 445

<210> SEQ ID NO 5
<211> LENGTH: 449
<212> TYPE: PRT
<213> ORGANISM: Artificial Sequence
<220> FEATURE:
<223> OTHER INFORMATION: Trastuzumab heavy chain

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
```

-continued

```
                195                 200                 205
Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 6
<211> LENGTH: 448
<212> TYPE: PRT
<213> ORGANISM: Artificial Sequence
<220> FEATURE:
<223> OTHER INFORMATION: Cetuximab heavy chain

<400> SEQUENCE: 6

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
                100                 105                 110
```

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 7
<211> LENGTH: 1347
<212> TYPE: DNA
<213> ORGANISM: Artificial Sequence
<220> FEATURE:
<223> OTHER INFORMATION: Trastuzumab_Heavy Chain

<400> SEQUENCE: 7
gaggtgcagc tggtggaaag cggaggagga ctggtgcagc caggaggatc tctgcgactg      60
agttgcgccg cttcaggatt caacatcaag gacacctaca ttcactgggt gcgacaggct     120
ccaggaaaag gactggagtg ggtggctcga atctatccca ctaatggata cacccggtat    180

```
gccgactccg tgaaggggag gtttactatt agcgccgata catccaaaaa cactgcttac        240
ctgcagatga acagcctgcg agccgaagat accgctgtgt actattgcag tcgatgggga        300
ggagacggat tctacgctat ggattattgg gacagggga ccctggtgac agtgagctcc         360
gcctctacca agggccccag tgtgtttccc ctggctcctt ctagtaaatc cacctctgga        420
gggacagccg ctctgggatg tctggtgaag gactatttcc ccgagcctgt gaccgtgagt        480
tggaactcag gcgccctgac aagcggagtg cacacttttc ctgctgtgct gcagtcaagc        540
gggctgtact ccctgtcctc tgtggtgaca gtgccaagtt caagcctggg cacacagact        600
tatatctgca acgtgaatca taagccctca aatacaaaag tggacaagaa agtggagccc        660
aagagctgtg ataagaccca cacctgccct ccctgtccag ctccagaact gctgggagga       720
cctagcgtgt tcctgtttcc ccctaagcca aaagacactc tgatgatttc aggactccc         780 gaggtgacct gcgtggtggt ggacgtgtct cacgaggacc ccgaagtgaa gttcaactgg        840
tacgtggatg gcgtggaagt gcataatgct aagacaaaac caagagagga acagtacaac        900
tccacttatc gcgtcgtgag cgtgctgacc gtgctgcacc aggactggct gaacgggaag        960
gagtataagt gcaaagtcag taataaggcc ctgcctgctc aatcgaaaa aaccatctct       1020 aaggccaaag gccagccaag ggagcccag tgtacacac tgccacccag cagagacgaa        1080
ctgaccaaga accaggtgtc cctgacatgt ctggtgaaag cttctatcc tagtgatatt       1140 gctgtggagt gggaatcaaa tggacagcca gagaacaatt acaagaccac acctccagtg       1200
ctggacagcg atggcagctt cttcctgtat tccaagctga cagtggataa atctcgatgg       1260
cagcagggga acgtgtttag ttgttcagtg atgcatgaag ccctgcacaa tcattacact       1320
cagaagagcc tgtccctgtc tcccggc                                            1347

<210> SEQ ID NO 8
<211> LENGTH: 642
<212> TYPE: DNA
<213> ORGANISM: Artificial Sequence
<220> FEATURE:
<223> OTHER INFORMATION: Trastuzumab_Light Chain

<400> SEQUENCE: 8
gacatccaga tgacccagtc tccatcctcc ctgtctgcat ctgtaggaga cagagtcacc         60
atcacttgcc gggcaagtca ggacgttaac accgctgtag cttggtatca gcagaaacca        120
gggaaagccc ctaagctcct gatctattct gcatcctttt tgtacagtgg ggtcccatca        180
aggttcagtg gcagtcgatc tgggacagat ttcactctca ccatcagcag tctgcaacct        240
gaagattttg caacttacta ctgtcaacag cattacacta ccccaccac tttcggccaa         300 gggaccaaag tggagatcaa acgaactgtg gctgcaccat ctgtcttcat cttcccgcca        360
tctgatgagc agttgaaatc tggaactgcc tctgttgtgt gcctgctgaa taacttctat        420
cccagagagg ccaaagtaca gtggaaggtg ataacgccc tccaatcggg taactcccaa         480
gagagtgtca cagagcagga cagcaaggac agcacctaca gcctcagcag caccctgacg        540
ctgagcaaag cagactacga gaaacacaaa gtctacgcct gcgaagtcac ccatcagggc        600
ctgagctcgc ccgtcacaaa gagcttcaac aggggagagt gt                           642

<210> SEQ ID NO 9
<211> LENGTH: 1344
<212> TYPE: DNA
<213> ORGANISM: Artificial Sequence
<220> FEATURE:
```

<223> OTHER INFORMATION: Cetuximab_Heavy Chain

<400> SEQUENCE: 9

| | | | | | |
|---|---|---|---|---|---|
| caggtgcagc | tgaaacagag | cggcccgggc | ctggtgcagc | cgagccagag | cctgagcatt | 60 |
| acctgcaccg | tgagcggctt | tagcctgacc | aactatggcg | tgcattgggt | gcgccagagc | 120 |
| ccgggcaaag | gcctggaatg | gctgggcgtg | atttggagcg | gcggcaacac | cgattataac | 180 |
| accccgttta | ccagccgcct | gagcattaac | aaagataaca | gcaaaagcca | ggtgtttttt | 240 |
| aaaatgaaca | gcctgcagag | caacgatacc | gcgatttatt | attgcgcgcg | cgcgctgacc | 300 |
| tattatgatt | atgaatttgc | gtattggggc | cagggcaccc | tggtgaccgt | gagcgcggcg | 360 |
| agcaccaaag | gcccgagcgt | gtttccgctg | gcgccagcag | caaaagcac | cagcggcggc | 420 |
| accgcggcgc | tgggctgcct | ggtgaaagat | tattttccgg | aaccggtgac | cgtgagctgg | 480 |
| aacagcggcg | cgctgaccag | cggcgtgcat | acctttccgg | cggtgctgca | gagcagcggc | 540 |
| ctgtatagcc | tgagcagcgt | ggtgaccgtg | ccgagcagca | gcctgggcac | ccagacctat | 600 |
| atttgcaacg | tgaaccataa | accgagcaac | accaaagtgg | ataaaaagt | ggaaccgaaa | 660 |
| agctgcgata | aaacccatac | ctgcccgccg | tgcccggcgc | cggaactgct | gggcggcccg | 720 |
| agcgtgtttc | tgtttccgcc | gaaaccgaaa | gatacccctga | tgattagccg | caccccggaa | 780 |
| gtgacctgcg | tggtggtgga | tgtgagccca | gaagatccgg | aagtgaaatt | taactggtat | 840 |
| gtggatggcg | tggaagtgca | taacgcgaaa | accaaaccgc | gcgaagaaca | gtataacagc | 900 |
| acctatcgcg | tggtgagcgt | gctgaccgtg | ctgcatcagg | attggctgaa | cggcaaagaa | 960 |
| tataaatgca | aagtgagcaa | caaagcgctg | ccggcgccga | ttgaaaaaac | cattagcaaa | 1020 |
| gcgaaaggcc | agccgcgcga | accgcaggtg | tatacctgc | cgccgagccg | cgatgaactg | 1080 |
| accaaaaacc | aggtgagcct | gacctgcctg | gtgaaaggct | tttatccgag | cgatattgcg | 1140 |
| gtggaatggg | aaagcaacgg | ccagccggaa | aacaactata | aaccaccc | gccggtgctg | 1200 |
| gatagcgatg | gcagcttttt | tctgtatagc | aaactgaccg | tggataaaag | ccgctggcag | 1260 |
| cagggcaacg | tgtttagctg | cagcgtgatg | catgaagcgc | tgcataacca | ttatacccag | 1320 |
| aaaagcctga | gcctgagccc | gggc | | | | 1344 |

<210> SEQ ID NO 10
<211> LENGTH: 642
<212> TYPE: DNA
<213> ORGANISM: Artificial Sequence
<220> FEATURE:
<223> OTHER INFORMATION: Cetuximab_Light Chain

<400> SEQUENCE: 10

| | | | | | |
|---|---|---|---|---|---|
| gacatcctgc | tgactcagag | cccagtgatc | ctgtcagtca | gcccaggaga | gcgggtgtcc | 60 |
| ttctcttgca | gagcaagtca | gtcaatcgga | acaaatattc | actggtacca | gcagaggact | 120 |
| aacggctccc | ctcgcctgct | gattaagtat | gctagcgaat | ccatctctgg | cattccatct | 180 |
| cggttcagtg | gctcagggag | cggaacagac | tttactctgt | ccatcaattc | tgtggagagt | 240 |
| gaagacattg | ccgattacta | ttgccagcag | aacaataact | ggcccaccac | attcggcgct | 300 |
| gggaccaagc | tggagctgaa | acgaacagtg | gccgctcctt | ctgtcttcat | cttccccct | 360 |
| agtgacgaac | agctgaaaag | cggcacagcc | tccgtggtct | gtctgctgaa | taacttttac | 420 |
| ccaagagagg | caaggtgca | gtggaaagtc | gataatgccc | tgcagtcagg | aacagccag | 480 |
| gagtccgtga | ctctaacagga | ctctaaggat | agtacctatt | cactgagctc | cactctgacc | 540 |
| ctgtccaaag | ctgattacga | gaagcacaaa | gtgtatgcat | gcgaagtcac | ccatcagggg | 600 | ctgtctagtc ccgtgacaaa gagctttaac cggggagagt gt                    642

<210> SEQ ID NO 11
<211> LENGTH: 1338
<212> TYPE: DNA
<213> ORGANISM: Artificial Sequence
<220> FEATURE:
<223> OTHER INFORMATION: D3H44_Heavy Chain

<400> SEQUENCE: 11
gaggtgcagc tggtcgaatc tggaggagga ctggtgcagc caggagggtc actgagactg    60
agctgcgccg cttccggctt caacatcaag gagtactata tgcactgggt gaggcaggca   120
cctggcaaag gactggagtg ggtgggactg atcgacccag aacagggaa ccatctac      180
gaccctaagt tcaggatag gcaaccatt tctgccgaca cagtaaaaa tacagcttat      240
ctgcagatga cagcctgag ggctgaagat actgcagtgt actattgcgc acgcgacacc    300
gcagcctact tcgattattg gggacagggc accctggtca cagtgagctc cgcatcaact   360
aagggaccca gcgtgtttcc actggccccc tctagtaaat ccacttctgg aggcaccgct   420
gcactgggct gtctggtgaa ggattacttc ccagagcccg tcacagtgag ctggaactcc   480
ggggccctga ccagcggagt ccatacattt cctgctgtgc tgcagtcaag cgggctgtac   540
tccctgtcct ctgtggtcac cgtgccaagt tcaagcctgg gaactcagac ctatatctgc   600
aacgtgaatc acaagccttc aaatacaaaa gtcgacaaga agtggaacc aaagagctgt    660
gataaaacac atacttgccc cccttgtcct gcaccagagc tgctgggagg accaagcgtg   720
ttcctgtttc cacccaagcc caaagacacc ctgatgattt cccgcacacc agaagtcact   780
tgcgtggtcg tggacgtgtc tcacgaggac cccgaagtca agttcaactg gtacgtggat   840
ggcgtcgagg tgcataatgc caagacaaaa ccccgggagg aacagtacaa ctccacatat   900
agagtcgtgt ctgtcctgac tgtgctgcac caggactggc tgaacgggaa ggagtataag   960
tgcaaagtga gtaataaggc cctgcccgct cctatcgaga aaacaattag caaggccaaa  1020
ggccagcctc gagaaccaca ggtgtacact ctgcctccat ctcgggacga gctgactaag  1080
aaccaggtca gtctgacctg tctggtgaaa ggattctatc ccagcgatat cgctgtggag  1140
tgggaatcca atggccagcc tgagaacaat tacaagacca cccccctgt gctggactct   1200
gatggcagtt tctttctgta tagtaagctg accgtcgata atcacgatg gcagcagggg   1260
aacgtgttca gctgttcagt gatgcacgaa gccctgcaca accattacac ccagaagagc  1320
ctgagcctgt ctcccggc                                              1338

<210> SEQ ID NO 12
<211> LENGTH: 642
<212> TYPE: DNA
<213> ORGANISM: Artificial Sequence
<220> FEATURE:
<223> OTHER INFORMATION: D3H44_Light Chain

<400> SEQUENCE: 12
gacatccaga tgacacagtc ccctagctcc ctgagtgcct cagtggggga cagagtcact    60
atcacctgcc gggcttccag agatattaag tcttacctga actggtatca gcagaagcca   120
ggcaaagcac ccaaggtgct gatctactat gccaccagtc tggctgaagg agtgccttca   180
cggttcagcg gctccgggtc tggaactgac tacacactga ctatttctag tctgcagcct   240
gaggatttcg ctacctacta ttgcctgcag cacggcgaat cccatggac ttttggccag   300

```
gggaccaaag tggagatcaa gaggacagtg gccgctccat ccgtcttcat tttccccct      360 tctgacgaac agctgaaatc aggaactgcc agcgtggtct gtctgctgaa caatttctac      420
ccccgcgagg caaaagtgca gtggaaggtc gataacgccc tgcagagtgg caattcacag      480
gagagcgtga cagaacagga ctccaaagat tctacttata gtctgtcaag caccctgaca      540
ctgtctaagg ctgattacga gaagcacaaa gtgtatgcat gcgaagtcac ccatcagggg      600
ctgtcctctc ccgtgacaaa gagctttaat cggggagagt gt                        642
```

<210> SEQ ID NO 13
<211> LENGTH: 217
<212> TYPE: PRT
<213> ORGANISM: Artificial Sequence
<220> FEATURE:
<223> OTHER INFORMATION: Human IgG1 Fc

<400> SEQUENCE: 13

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 14
<211> LENGTH: 117
<212> TYPE: PRT
<213> ORGANISM: Artificial Sequence
<220> FEATURE:
<223> OTHER INFORMATION: D3H44 VH

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Glu Tyr
            20                  25                  30
```

Tyr Met His Trp Val Arg Gln Ala Pro Gly Lys Gly Leu Glu Trp Val
            35                  40                  45

Gly Leu Ile Asp Pro Glu Gln Gly Asn Thr Ile Tyr Asp Pro Lys Phe
        50                  55                  60

Gln Asp Arg Ala Thr Ile Ser Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Thr Ala Ala Tyr Phe Asp Tyr Trp Gly Gln Gly Thr Leu
                    100                 105                 110

Val Thr Val Ser Ser
            115

<210> SEQ ID NO 15
<211> LENGTH: 98
<212> TYPE: PRT
<213> ORGANISM: Artificial Sequence
<220> FEATURE:
<223> OTHER INFORMATION: VH1

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 16
<211> LENGTH: 100
<212> TYPE: PRT
<213> ORGANISM: Artificial Sequence
<220> FEATURE:
<223> OTHER INFORMATION: VH2

<400> SEQUENCE: 16

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
            35                  40                  45

Trp Leu Ala Leu Ile Tyr Trp Asn Asp Asp Lys Arg Tyr Ser Pro Ser
        50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg
            100

```
<210> SEQ ID NO 17
<211> LENGTH: 98
<212> TYPE: PRT
<213> ORGANISM: Artificial Sequence
<220> FEATURE:
<223> OTHER INFORMATION: VH3

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 18
<211> LENGTH: 98
<212> TYPE: PRT
<213> ORGANISM: Artificial Sequence
<220> FEATURE:
<223> OTHER INFORMATION: VH4

<400> SEQUENCE: 18

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg

<210> SEQ ID NO 19
<211> LENGTH: 98
<212> TYPE: PRT
<213> ORGANISM: Artificial Sequence
<220> FEATURE:
<223> OTHER INFORMATION: VH5

<400> SEQUENCE: 19

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45
```

Gly Ile Ile Tyr Pro Gly Asp Ser Asp Thr Arg Tyr Ser Pro Ser Phe
            50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 20
<211> LENGTH: 101
<212> TYPE: PRT
<213> ORGANISM: Artificial Sequence
<220> FEATURE:
<223> OTHER INFORMATION: VH6

<400> SEQUENCE: 20

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg
            100

<210> SEQ ID NO 21
<211> LENGTH: 98
<212> TYPE: PRT
<213> ORGANISM: Artificial Sequence
<220> FEATURE:
<223> OTHER INFORMATION: VH7

<400> SEQUENCE: 21

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg

<210> SEQ ID NO 22
<211> LENGTH: 107
<212> TYPE: PRT
<213> ORGANISM: Artificial Sequence
<220> FEATURE:

<223> OTHER INFORMATION: D3H44 VL (kappa)

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Asp Ile Lys Ser Tyr
            20                  25                  30

Leu Asn Trp Tyr Gln Gln Lys Pro Gly Lys Ala Pro Lys Val Leu Ile
        35                  40                  45

Tyr Tyr Ala Thr Ser Leu Ala Glu Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln His Gly Glu Ser Pro Trp
            85                  90                  95

Thr Phe Gly Gln Gly Thr Lys Val Glu Ile Lys
            100                 105

<210> SEQ ID NO 23
<211> LENGTH: 95
<212> TYPE: PRT
<213> ORGANISM: Artificial Sequence
<220> FEATURE:
<223> OTHER INFORMATION: VKI

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
            85                  90                  95

<210> SEQ ID NO 24
<211> LENGTH: 101
<212> TYPE: PRT
<213> ORGANISM: Artificial Sequence
<220> FEATURE:
<223> OTHER INFORMATION: VKII

<400> SEQUENCE: 24

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln

```
                    85                  90                  95

Arg Ile Glu Phe Pro
            100

<210> SEQ ID NO 25
<211> LENGTH: 96
<212> TYPE: PRT
<213> ORGANISM: Artificial Sequence
<220> FEATURE:
<223> OTHER INFORMATION: VKIII

<400> SEQUENCE: 25

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 26
<211> LENGTH: 101
<212> TYPE: PRT
<213> ORGANISM: Artificial Sequence
<220> FEATURE:
<223> OTHER INFORMATION: VKIV

<400> SEQUENCE: 26

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100

<210> SEQ ID NO 27
<211> LENGTH: 95
<212> TYPE: PRT
<213> ORGANISM: Artificial Sequence
<220> FEATURE:
<223> OTHER INFORMATION: VKV

<400> SEQUENCE: 27

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30
```

```
Met Asn Trp Tyr Gln Gln Lys Pro Gly Glu Ala Ala Ile Phe Ile Ile
        35                  40                  45

Gln Glu Ala Thr Thr Leu Val Pro Gly Ile Pro Pro Arg Phe Ser Gly
 50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Leu Gln His Asp Asn Phe Pro
                 85                  90                  95
```

<210> SEQ ID NO 28
<211> LENGTH: 95
<212> TYPE: PRT
<213> ORGANISM: Artificial Sequence
<220> FEATURE:
<223> OTHER INFORMATION: VKVI

<400> SEQUENCE: 28

```
Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Gly Ser Ser
             20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys His Gln Ser Ser Ser Leu Pro
                 85                  90                  95
```

<210> SEQ ID NO 29
<211> LENGTH: 107
<212> TYPE: PRT
<213> ORGANISM: Artificial Sequence
<220> FEATURE:
<223> OTHER INFORMATION: D3H44 VL (lambda)

<400> SEQUENCE: 29

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Arg Asp Ile Lys Ser Tyr
             20                  25                  30

Leu Asn Trp Tyr Gln Gln Lys Pro Gly Lys Ala Pro Lys Val Leu Ile
        35                  40                  45

Tyr Tyr Ala Thr Ser Leu Ala Glu Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Leu Gln His Gly Glu Ser Pro Trp
                 85                  90                  95

Thr Phe Gly Gln Gly Thr Lys Val Glu Ile Lys
            100                 105
```

<210> SEQ ID NO 30
<211> LENGTH: 98
<212> TYPE: PRT
<213> ORGANISM: Artificial Sequence
<220> FEATURE:
<223> OTHER INFORMATION: VLI

<400> SEQUENCE: 30

Gln Ser Val Leu Thr Gln Pro Pro Ser Val Ser Glu Ala Pro Arg Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly

<210> SEQ ID NO 31
<211> LENGTH: 99
<212> TYPE: PRT
<213> ORGANISM: Artificial Sequence
<220> FEATURE:
<223> OTHER INFORMATION: VLII

<400> SEQUENCE: 31

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Phe

<210> SEQ ID NO 32
<211> LENGTH: 95
<212> TYPE: PRT
<213> ORGANISM: Artificial Sequence
<220> FEATURE:
<223> OTHER INFORMATION: VLIII

<400> SEQUENCE: 32

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala

```
                85                  90                  95

<210> SEQ ID NO 33
<211> LENGTH: 103
<212> TYPE: PRT
<213> ORGANISM: Artificial Sequence
<220> FEATURE:
<223> OTHER INFORMATION: VLIV

<400> SEQUENCE: 33

Leu Pro Val Leu Thr Gln Pro Pro Ser Ala Ser Ala Leu Leu Gly Ala
1               5                   10                  15

Ser Ile Lys Leu Thr Cys Thr Leu Ser Ser Glu His Ser Thr Tyr Thr
            20                  25                  30

Ile Glu Trp Tyr Gln Gln Arg Pro Gly Arg Ser Pro Gln Tyr Ile Met
        35                  40                  45

Lys Val Lys Ser Asp Gly Ser His Ser Lys Gly Asp Gly Ile Pro Asp
    50                  55                  60

Arg Phe Met Gly Ser Ser Ser Gly Ala Asp Arg Tyr Leu Thr Phe Ser
65                  70                  75                  80

Asn Leu Gln Ser Asp Asp Glu Ala Glu Tyr His Cys Gly Glu Ser His
                85                  90                  95

Thr Ile Asp Gly Gln Val Gly
            100

<210> SEQ ID NO 34
<211> LENGTH: 104
<212> TYPE: PRT
<213> ORGANISM: Artificial Sequence
<220> FEATURE:
<223> OTHER INFORMATION: VLV

<400> SEQUENCE: 34

Gln Pro Val Leu Thr Gln Pro Pro Ser Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser Asp Lys Gln Gly Ser Gly Val
    50                  55                  60

Pro Ser Arg Phe Ser Gly Ser Lys Asp Ala Ser Ala Asn Thr Gly Ile
65                  70                  75                  80

Leu Leu Ile Ser Gly Leu Gln Ser Glu Asp Glu Ala Asp Tyr Tyr Cys
                85                  90                  95

Met Ile Trp Pro Ser Asn Ala Ser
            100

<210> SEQ ID NO 35
<211> LENGTH: 98
<212> TYPE: PRT
<213> ORGANISM: Artificial Sequence
<220> FEATURE:
<223> OTHER INFORMATION: VLVI

<400> SEQUENCE: 35

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30
```

```
Tyr Val Gln Trp Tyr Gln Gln Arg Pro Gly Ser Ser Pro Thr Thr Val
            35                  40                  45

Ile Tyr Glu Asp Asn Gln Arg Pro Ser Gly Val Pro Asp Arg Phe Ser
 50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                85                  90                  95

Ser Asn

<210> SEQ ID NO 36
<211> LENGTH: 98
<212> TYPE: PRT
<213> ORGANISM: Artificial Sequence
<220> FEATURE:
<223> OTHER INFORMATION: VLVII

<400> SEQUENCE: 36

Gln Thr Val Val Thr Gln Glu Pro Ser Leu Thr Val Ser Pro Gly Gly
 1               5                  10                  15

Thr Val Thr Leu Thr Cys Ala Ser Ser Thr Gly Ala Val Thr Ser Gly
                20                  25                  30

Tyr Tyr Pro Asn Trp Phe Gln Gln Lys Pro Gly Gln Ala Pro Arg Ala
            35                  40                  45

Leu Ile Tyr Ser Thr Ser Asn Lys His Ser Trp Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Leu Leu Tyr Tyr Gly Gly
                85                  90                  95

Ala Gln

<210> SEQ ID NO 37
<211> LENGTH: 98
<212> TYPE: PRT
<213> ORGANISM: Artificial Sequence
<220> FEATURE:
<223> OTHER INFORMATION: VLVIII

<400> SEQUENCE: 37

Gln Thr Val Val Thr Gln Glu Pro Ser Phe Ser Val Ser Pro Gly Gly
 1               5                  10                  15

Thr Val Thr Leu Thr Cys Gly Leu Ser Ser Gly Ser Val Ser Thr Ser
                20                  25                  30

Tyr Tyr Pro Ser Trp Tyr Gln Gln Thr Pro Gly Gln Ala Pro Arg Thr
            35                  40                  45

Leu Ile Tyr Ser Thr Asn Thr Arg Ser Ser Gly Val Pro Asp Arg Phe
 50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Val Leu Tyr Met Gly Ser
                85                  90                  95

Gly Ile

<210> SEQ ID NO 38
<211> LENGTH: 104
<212> TYPE: PRT
```

```
<213> ORGANISM: Artificial Sequence
<220> FEATURE:
<223> OTHER INFORMATION: VLIX

<400> SEQUENCE: 38

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
                20                  25                  30

Val Asp Trp Tyr Gln Gln Arg Pro Gly Lys Gly Pro Arg Phe Val Met
            35                  40                  45

Arg Val Gly Thr Gly Gly Ile Val Gly Ser Lys Gly Asp Gly Ile Pro
        50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Ser Asn Phe Val
            100

<210> SEQ ID NO 39
<211> LENGTH: 98
<212> TYPE: PRT
<213> ORGANISM: Artificial Sequence
<220> FEATURE:
<223> OTHER INFORMATION: VLX

<400> SEQUENCE: 39

Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
                20                  25                  30

Gly Ala Ala Trp Leu Gln Gln His Gln Gly His Pro Pro Lys Leu Leu
            35                  40                  45

Ser Tyr Arg Asn Asn Asn Arg Pro Ser Gly Ile Ser Glu Arg Leu Ser
        50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95

Ser Ala

<210> SEQ ID NO 40
<211> LENGTH: 108
<212> TYPE: PRT
<213> ORGANISM: Artificial Sequence
<220> FEATURE:
<223> OTHER INFORMATION: D3H44 CH1
<220> FEATURE:
<221> NAME/KEY: MISC_FEATURE
<222> LOCATION: (99)..(108)
<223> OTHER INFORMATION: Upper hinge

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45
```

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr
            100                 105

<210> SEQ ID NO 41
<211> LENGTH: 98
<212> TYPE: PRT
<213> ORGANISM: Artificial Sequence
<220> FEATURE:
<223> OTHER INFORMATION: IGHG1*01

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 42
<211> LENGTH: 98
<212> TYPE: PRT
<213> ORGANISM: Artificial Sequence
<220> FEATURE:
<223> OTHER INFORMATION: IGHG1*03

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 43
<211> LENGTH: 98
<212> TYPE: PRT
<213> ORGANISM: Artificial Sequence
<220> FEATURE:

<223> OTHER INFORMATION: IGHG3*06

<400> SEQUENCE: 43

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 44
<211> LENGTH: 98
<212> TYPE: PRT
<213> ORGANISM: Artificial Sequence
<220> FEATURE:
<223> OTHER INFORMATION: IGHG3*18

<400> SEQUENCE: 44

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Tyr Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 45
<211> LENGTH: 98
<212> TYPE: PRT
<213> ORGANISM: Artificial Sequence
<220> FEATURE:
<223> OTHER INFORMATION: IGHG3*17

<400> SEQUENCE: 45

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Tyr Ser Gly Leu Tyr Ser
    50                  55                  60

Leu Ser Ser Val Val Thr Val Pro Ser Ser Asn Phe Gly Thr Gln Thr
65                  70                  75                  80

```
Tyr Thr Cys Asn Val Asn His Lys Pro Ser Asn Thr Lys Val Asp Lys
                85                  90                  95

Arg Val

<210> SEQ ID NO 46
<211> LENGTH: 98
<212> TYPE: PRT
<213> ORGANISM: Artificial Sequence
<220> FEATURE:
<223> OTHER INFORMATION: IGHG2*04

<400> SEQUENCE: 46

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Tyr Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 47
<211> LENGTH: 98
<212> TYPE: PRT
<213> ORGANISM: Artificial Sequence
<220> FEATURE:
<223> OTHER INFORMATION: IGHG4*01

<400> SEQUENCE: 47

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Tyr Ser Gly Leu Tyr Ser
        50                  55                  60

Leu Ser Ser Val Val Thr Val Pro Ser Ser Asn Phe Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 48
<211> LENGTH: 98
<212> TYPE: PRT
<213> ORGANISM: Artificial Sequence
<220> FEATURE:
<223> OTHER INFORMATION: IGHG2*03

<400> SEQUENCE: 48

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
```

```
                    20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Tyr Ser Gly Leu Tyr Ser
            50                  55                  60

Leu Ser Ser Val Val Thr Val Pro Ser Ser Asn Phe Gly Thr Lys Thr
65                  70                  75                  80

Tyr Thr Cys Asn Val Asp His Lys Pro Ser Asn Thr Lys Val Asp Lys
                85                  90                  95

Thr Val

<210> SEQ ID NO 49
<211> LENGTH: 98
<212> TYPE: PRT
<213> ORGANISM: Artificial Sequence
<220> FEATURE:
<223> OTHER INFORMATION: IGHG2*02

<400> SEQUENCE: 49

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Tyr Ser Gly Leu Tyr Ser
        50                  55                  60

Leu Ser Ser Val Val Thr Val Thr Ser Ser Asn Phe Gly Thr Lys Thr
65                  70                  75                  80

Tyr Thr Cys Asn Val Asp His Lys Pro Ser Asn Thr Lys Val Asp Lys
                85                  90                  95

Thr Val

<210> SEQ ID NO 50
<211> LENGTH: 107
<212> TYPE: PRT
<213> ORGANISM: Artificial Sequence
<220> FEATURE:
<223> OTHER INFORMATION: D3H44 CL (kappa)

<400> SEQUENCE: 50

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 51
```

```
<211> LENGTH: 107
<212> TYPE: PRT
<213> ORGANISM: Artificial Sequence
<220> FEATURE:
<223> OTHER INFORMATION: IGKC*01

<400> SEQUENCE: 51

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 52
<211> LENGTH: 107
<212> TYPE: PRT
<213> ORGANISM: Artificial Sequence
<220> FEATURE:
<223> OTHER INFORMATION: IGKC*04

<400> SEQUENCE: 52

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 53
<211> LENGTH: 107
<212> TYPE: PRT
<213> ORGANISM: Artificial Sequence
<220> FEATURE:
<223> OTHER INFORMATION: IGKC*05

<400> SEQUENCE: 53

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45
```

-continued

Ser Gly Asn Ser Gln Glu Ser Val Thr Glu Gln Asp Ser Lys Asp Ser
    50                  55                  60

Thr Tyr Ser Leu Ser Asn Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 54
<211> LENGTH: 107
<212> TYPE: PRT
<213> ORGANISM: Artificial Sequence
<220> FEATURE:
<223> OTHER INFORMATION: IGKC*02

<400> SEQUENCE: 54

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Gly Glu Val Thr His Gln Gly Leu Ser Ser
                85                  90                  95

Pro Val Thr Lys Ser Phe Asn Arg Gly Glu Cys
            100                 105

<210> SEQ ID NO 55
<211> LENGTH: 107
<212> TYPE: PRT
<213> ORGANISM: Artificial Sequence
<220> FEATURE:
<223> OTHER INFORMATION: IGKC*03

<400> SEQUENCE: 55

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Gly Glu Val Thr His Gln Gly Leu Ser Ser
                85                  90                  95

Pro Val Thr Lys Ser Phe Asn Arg Gly Glu Cys
            100                 105

<210> SEQ ID NO 56
<211> LENGTH: 107
<212> TYPE: PRT
<213> ORGANISM: Artificial Sequence

```
<220> FEATURE:
<223> OTHER INFORMATION: D3H44 CL (lambda)

<400> SEQUENCE: 56

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Arg Lys Val Asp Asn Ala Leu Gln
        35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 57
<211> LENGTH: 104
<212> TYPE: PRT
<213> ORGANISM: Artificial Sequence
<220> FEATURE:
<223> OTHER INFORMATION: IG(lambda)C1

<400> SEQUENCE: 57

Pro Lys Ala Asn Pro Thr Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Gly Ser Pro Val Lys
        35                  40                  45

Ala Gly Val Glu Thr Thr Lys Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 58
<211> LENGTH: 105
<212> TYPE: PRT
<213> ORGANISM: Artificial Sequence
<220> FEATURE:
<223> OTHER INFORMATION: IG(lambda)C7

<400> SEQUENCE: 58

Gln Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Gly Ser Pro Val
        35                  40                  45

Lys Ala Gly Val Glu Thr Thr Lys Pro Ser Lys Gln Ser Asn Asn Lys
    50                  55                  60
```

```
Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys Ser
            100                 105
```

<210> SEQ ID NO 59
<211> LENGTH: 105
<212> TYPE: PRT
<213> ORGANISM: Artificial Sequence
<220> FEATURE:
<223> OTHER INFORMATION: IG(lambda)C2

<400> SEQUENCE: 59

```
Gln Pro Lys Ala Ala Pro Ser Val Thr Leu Phe Pro Pro Ser Ser Glu
 1               5                   10                  15

Glu Leu Gln Ala Asn Lys Ala Thr Leu Val Cys Leu Ile Ser Asp Phe
                 20                  25                  30

Tyr Pro Gly Ala Val Thr Val Ala Trp Lys Ala Asp Ser Ser Pro Val
             35                  40                  45

Lys Ala Gly Val Glu Thr Thr Thr Pro Ser Lys Gln Ser Asn Asn Lys
 50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys Ser
            100                 105
```

<210> SEQ ID NO 60
<211> LENGTH: 104
<212> TYPE: PRT
<213> ORGANISM: Artificial Sequence
<220> FEATURE:
<223> OTHER INFORMATION: IG(lambda)C3

<400> SEQUENCE: 60

```
Pro Lys Ala Ala Pro Ser Val Thr Leu Phe Pro Pro Ser Ser Glu Glu
 1               5                   10                  15

Leu Gln Ala Asn Lys Ala Thr Leu Val Cys Leu Ile Ser Asp Phe Tyr
                 20                  25                  30

Pro Gly Ala Val Thr Val Ala Trp Lys Ala Asp Ser Ser Pro Val Lys
             35                  40                  45

Ala Gly Val Glu Thr Thr Thr Pro Ser Lys Gln Ser Asn Asn Lys Tyr
 50                  55                  60

Ala Ala Ser Ser Tyr Leu Ser Leu Thr Pro Glu Gln Trp Lys Ser His
 65                  70                  75                  80

Lys Ser Tyr Ser Cys Gln Val Thr His Glu Gly Ser Thr Val Glu Lys
                 85                  90                  95

Thr Val Ala Pro Thr Glu Cys Ser
            100
```

<210> SEQ ID NO 61
<211> LENGTH: 105
<212> TYPE: PRT
<213> ORGANISM: Artificial Sequence
<220> FEATURE:
<223> OTHER INFORMATION: IG(lambda)C6

```
<400> SEQUENCE: 61

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Lys Val Ala Trp Lys Ala Asp Ser Ser Pro Val
        35                  40                  45

Asn Thr Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Lys Ser Tyr Ser Cys Gln Val Thr His Glu Gly Ser Thr Val Glu
                85                  90                  95

Lys Thr Val Ala Pro Ala Glu Cys Ser
            100                 105

<210> SEQ ID NO 62
<211> LENGTH: 17
<212> TYPE: PRT
<213> ORGANISM: Artificial Sequence
<220> FEATURE:
<223> OTHER INFORMATION: IGHJ1*01

<400> SEQUENCE: 62

Ala Glu Tyr Phe Gln His Trp Gly Gln Gly Thr Leu Val Thr Val Ser
1               5                   10                  15

Ser

<210> SEQ ID NO 63
<211> LENGTH: 17
<212> TYPE: PRT
<213> ORGANISM: Artificial Sequence
<220> FEATURE:
<223> OTHER INFORMATION: IGHJ2*01

<400> SEQUENCE: 63

Tyr Trp Tyr Phe Asp Leu Trp Gly Arg Gly Thr Leu Val Thr Val Ser
1               5                   10                  15

Ser

<210> SEQ ID NO 64
<211> LENGTH: 16
<212> TYPE: PRT
<213> ORGANISM: Artificial Sequence
<220> FEATURE:
<223> OTHER INFORMATION: IGHJ3*02

<400> SEQUENCE: 64

Asp Ala Phe Asp Ile Trp Gly Gln Gly Thr Met Val Thr Val Ser Ser
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: IGHJ4*01

<400> SEQUENCE: 65

Tyr Phe Asp Tyr Trp Gly Gln Gly Thr Leu Val Thr Val Ser Ser
1               5                   10                  15
```

<210> SEQ ID NO 66
<211> LENGTH: 16
<212> TYPE: PRT
<213> ORGANISM: Artificial Sequence
<220> FEATURE:
<223> OTHER INFORMATION: IGHJ5*02

<400> SEQUENCE: 66

Asn Trp Phe Asp Pro Trp Gly Gln Gly Thr Leu Val Thr Val Ser Ser
1               5                   10                  15

<210> SEQ ID NO 67
<211> LENGTH: 20
<212> TYPE: PRT
<213> ORGANISM: Artificial Sequence
<220> FEATURE:
<223> OTHER INFORMATION: IGHJ6*01

<400> SEQUENCE: 67

Tyr Tyr Tyr Tyr Tyr Gly Met Asp Val Trp Gly Gln Gly Thr Thr Val
1               5                   10                  15

Thr Val Ser Ser
            20

<210> SEQ ID NO 68
<211> LENGTH: 12
<212> TYPE: PRT
<213> ORGANISM: Artificial Sequence
<220> FEATURE:
<223> OTHER INFORMATION: IGKJ1*01

<400> SEQUENCE: 68

Trp Thr Phe Gly Gln Gly Thr Lys Val Glu Ile Lys
1               5                   10

<210> SEQ ID NO 69
<211> LENGTH: 12
<212> TYPE: PRT
<213> ORGANISM: Artificial Sequence
<220> FEATURE:
<223> OTHER INFORMATION: IGKJ2*01

<400> SEQUENCE: 69

Tyr Thr Phe Gly Gln Gly Thr Lys Leu Glu Ile Lys
1               5                   10

<210> SEQ ID NO 70
<211> LENGTH: 12
<212> TYPE: PRT
<213> ORGANISM: Artificial Sequence
<220> FEATURE:
<223> OTHER INFORMATION: IGKJ2*01

<400> SEQUENCE: 70

Tyr Thr Phe Gly Gln Gly Thr Lys Leu Glu Ile Lys
1               5                   10

<210> SEQ ID NO 71
<211> LENGTH: 12
<212> TYPE: PRT
<213> ORGANISM: Artificial Sequence
<220> FEATURE:
<223> OTHER INFORMATION: IGKJ4*01

<400> SEQUENCE: 71

Leu Thr Phe Gly Gly Gly Thr Lys Val Glu Ile Lys

```
1               5                   10

<210> SEQ ID NO 72
<211> LENGTH: 12
<212> TYPE: PRT
<213> ORGANISM: Artificial Sequence
<220> FEATURE:
<223> OTHER INFORMATION: IGKJ5*01

<400> SEQUENCE: 72

Ile Thr Phe Gly Gln Gly Thr Arg Leu Glu Ile Lys
1               5                   10

<210> SEQ ID NO 73
<211> LENGTH: 12
<212> TYPE: PRT
<213> ORGANISM: Artificial Sequence
<220> FEATURE:
<223> OTHER INFORMATION: IGLJ1*01

<400> SEQUENCE: 73

Tyr Val Phe Gly Thr Gly Thr Lys Val Thr Val Leu
1               5                   10

<210> SEQ ID NO 74
<211> LENGTH: 12
<212> TYPE: PRT
<213> ORGANISM: Artificial Sequence
<220> FEATURE:
<223> OTHER INFORMATION: IGLJ2*01

<400> SEQUENCE: 74

Val Val Phe Gly Gly Gly Thr Lys Leu Thr Val Leu
1               5                   10

<210> SEQ ID NO 75
<211> LENGTH: 12
<212> TYPE: PRT
<213> ORGANISM: Artificial Sequence
<220> FEATURE:
<223> OTHER INFORMATION: IGLJ3*01

<400> SEQUENCE: 75

Val Val Phe Gly Gly Gly Thr Lys Leu Thr Val Leu
1               5                   10

<210> SEQ ID NO 76
<211> LENGTH: 12
<212> TYPE: PRT
<213> ORGANISM: Artificial Sequence
<220> FEATURE:
<223> OTHER INFORMATION: IGLJ4*01

<400> SEQUENCE: 76

Phe Val Phe Gly Gly Gly Thr Gln Leu Ile Ile Leu
1               5                   10

<210> SEQ ID NO 77
<211> LENGTH: 12
<212> TYPE: PRT
<213> ORGANISM: Artificial Sequence
<220> FEATURE:
<223> OTHER INFORMATION: IGLJ5*01

<400> SEQUENCE: 77

Trp Val Phe Gly Glu Gly Thr Glu Leu Thr Val Leu
1               5                   10
```

```
<210> SEQ ID NO 78
<211> LENGTH: 12
<212> TYPE: PRT
<213> ORGANISM: Artificial Sequence
<220> FEATURE:
<223> OTHER INFORMATION: IGLJ6*01

<400> SEQUENCE: 78

Asn Val Phe Gly Ser Gly Thr Lys Val Thr Val Leu
1               5                   10

<210> SEQ ID NO 79
<211> LENGTH: 12
<212> TYPE: PRT
<213> ORGANISM: Artificial Sequence
<220> FEATURE:
<223> OTHER INFORMATION: IGLJ7*01

<400> SEQUENCE: 79

Ala Val Phe Gly Gly Gly Thr Gln Leu Thr Val Leu
1               5                   10
```